US007629122B2

(12) United States Patent
Krantz et al.

(10) Patent No.: US 7,629,122 B2
(45) Date of Patent: Dec. 8, 2009

(54) METHODS AND COMPOSITIONS FOR THE DIAGNOSIS OF CORNELIA DE LANGE SYNDROME

(75) Inventors: Ian D. Krantz, Bala Cynwyd, PA (US); Laird G. Jackson, Philadelphia, PA (US)

(73) Assignee: The Children's Hospital of Philadelphia, Philadelphia, PA (US)

( * ) Notice: Subject to any disclaimer, the term of this patent is extended or adjusted under 35 U.S.C. 154(b) by 74 days.

(21) Appl. No.: 11/120,925

(22) Filed: May 3, 2005

(65) Prior Publication Data

US 2006/0003354 A1 Jan. 5, 2006

Related U.S. Application Data

(60) Provisional application No. 60/567,756, filed on May 3, 2004.

(51) Int. Cl.
*C12Q 1/68* (2006.01)
*C12P 19/34* (2006.01)

(52) U.S. Cl. .......................................... 435/6; 435/91.2

(58) Field of Classification Search ....................... None
See application file for complete search history.

(56) References Cited

OTHER PUBLICATIONS

Taylor MJ et al 'Multiple congenital anomalies, thymic dysplasia, severe congenital heart disease, and oligosyndactyly with a deletion of the short arm of chromosome 5.' Am J Med Genet. 1981;9(1):5-11.*

Bienvu t et al 'Unexpected inactivation of acceptor consensus splice sequence by a -3 C to T transition in intron 2 of the CFTR gene.' Hum Genet. Jul. 1994;94(1):65-8.*

Borck G NIPBL mutations and genetic heterogeneity in Cornelia de Lange syndrome. J Med Gener. Dec. 2004;41(12):pp. 1-6.*

Goldsby et al. Immunology, Fifth Edition, section "Cross-Reactivity," p. 141.*

DePalma A 'Capturing Proteins Using Antibody Arrays' from Genomics and Proteomics, available online from author at www.adeplama.com, pp. 1-5.*

Jupppner H 'Functional properties of the PTH/PTHrP receptor.' Bone. Aug. 1995;17(2 Suppl):39S-42S.*

Hacker UT et al 'Lack of association between an interleukin-1 receptor antagonist gene polymorphism and ulcerative colitis.' Gut. May 1997;40(5):623-7.*

Selicomi A et al 'Clinical score of 62 Italian patients with Cornelia de Lange syndrome and correlations with the presence and type of NIPBL mutation.' Clin Genet. Aug. 2007;72(2):98-108.*

Strachan T 'Cornelia de Lange Syndrome and the link between chromosomal function, DNA repair and developmental gene regulation.' Curr Opin Genet Dev. Jun. 2005;15(3):258-64.*

Tonkin ET et al 'NIPBL, encoding a homolog of fungal Scc2-type sister chromatid cohesion proteins and fly Nipped-B, is mutated in Cornelia de Lange syndrome.' Nat Genet. Jun. 2004;36(6):636-41.*

Goldsby et al. Immunology (2003), Fifth Edition, section "Cross-Reactivity," p. 141.*

Russell, K.L. et al. "Dominant Paternal Transmission of Cornelia de Lange Syndrome: A New Case and Review of 25 . . . "; Amer. Journal of Medical Gen., 104: 267-276 (2001).

Krantz, I.D. et al. "Exclusion of Linkage t the CDL1 Gene Region on Chromosome 3q26.3 in Some Familial Cases . . . "; Amer. Journal of Medical Gen., 101: 120-129 (2001).

* cited by examiner

*Primary Examiner*—Stephen Kapushoc
(74) *Attorney, Agent, or Firm*—Dann, Dorfman, Herrell & Skillman; Kathleen D. Rigaut; Robert C. Netter

(57) ABSTRACT

Compositions and methods for the diagnosis of Cornelia de Lange Syndrome are disclosed.

14 Claims, 66 Drawing Sheets

Figure 1 Facial features and limb findings in mutation-positive individuals with CdLS. Note the variability of features even among individuals with similar mutation types.

| | | |
|---|---|---|
| NIPBL | 1244 | ESAKI KAMGI MDKLSTDKTVKVLN - |
| Rat | 1311 | ESAKI KAMGI MDKLSTDKTVKVLN - |
| Mouse | 1184 | ESAKI KAMGI MDKLSTDKTVKVLN - |
| Drosophila | 718 | TLQFVCL ELVTT I FRKERYDK I RNS |
| | | A1246G |

| | | |
|---|---|---|
| NIPBL | 1302 | ERVTKSADACLTTINI MTS PNMPKA |
| Rat | 1369 | ERVTKSADACLTTINI MTS PNMPKA |
| Mouse | 1242 | ERVTKSADACLTTINI MTS PNMPKA |
| Drosophila | 776 | TALVLQLI QCATILPDS LCDNGKF S |
| | | L1312P |

| | | |
|---|---|---|
| NIPBL | 1792 | AMKC LSEVVAVDPS ILARLDMQ RGV |
| Rat | 1771 | AMKC LSEVVAVDPS ILARLDMQ RGV |
| Mouse | 1705 | AMKC LSEVVAVDPS ILARLDMQ RGV |
| Drosophila | 1149 | AMKC LANI VEVDPLVLKRKDMQMGV |
| | | D1803V |

| | | |
|---|---|---|
| NIPBL | 1779 | RVLGENAIAVRTKAMKCLSEVVAVD |
| Rat | 1758 | RVLGENAIAVRTKAMKCLSEVVAVD |
| Mouse | 1692 | RVLGENAIAVRTKAMKCLSEVVAVD |
| Drosophila | 1135 | LVVNEPSIAVRTRAMKCLANI VEVD |
| | | R1789L |

| | | |
|---|---|---|
| NIPBL | 1844 | QLAEQYYDMLI ERILDTG ISVRKRV |
| Rat | 1934 | QLAEQYYDMLI ERILDTG ISVRKRV |
| Mouse | 1758 | QLAEQYYDMLI ERILDTG ISVRKRV |
| Drosophila | 1202 | DL IDQYYDMLSTRILDTGVSVRKRV |
| | | R1856T |

| | | |
|---|---|---|
| NIPBL | 2295 | S SVRH FAL NVIALTLNQGL I H PVQ CV P |
| Rat | 2290 | S SVRH FAL NVIALTLNQGL I H PVQ CV P |
| Mouse | 2209 | S SVRH FAL NVIALTLNQGL I H PVQ CV P |
| Drosophila | 1663 | D TVR LWAVKVIQI VLRQGLVH PVR MV P |
| | | R2298H/C G2312R |

| | | |
|---|---|---|
| NIPBL | 2373 | TCLKDPVRGFR------QDES SSALCSHLY |
| Rat | 2367 | TCLKDPVRGFR------QDES SSALCSHLY |
| Mouse | 2286 | TCLKDPVRGFR------QDES SSALCSHLY |
| Drosophila | 1740 | INNRGKLE I IRGYASRGPDNTTTALNDFLY |
| | | G2381A A2390T |

| | | |
|---|---|---|
| NIPBL | 2420 | TAKTDVTMLLYI ADNLACFPYQTQEEPLF |
| Rat | 2414 | TAS ------------------------- |
| Mouse | 2333 | TAS ------------------------- |
| Drosophila | 1793 | QKTSLQQMLY IADN--------------- |
| | | Y2440H |

Figure 6

```
LOCUS       NIPBL GENOM 188056 BP DS-DNA          SYN       12-JAN-2004
DEFINITION  -
ACCESSION   -
KEYWORDS    -
SOURCE      -
FEATURES             Location/Qualifiers
     frag            1..107543
                     /note="1 to 9505 of CDLS gene  (BXIDN)"
     frag            3641..9505
                     /note="133 to 168 of Untitled5"
     frag            <3641..>3676
                     /note="19 to 48 of Untitled5 [Split]"
     frag            1..3640
                     /note="133 to 168 of Untitled5"
     frag            <1..>36
                     /note="19 to 48 of Untitled5 [Split]"
     frag            107544..188056
                     /note="1 to 9505 of CDLS gene  (BXIDN)"
     frag            111184..117048
                     /note="133 to 168 of Untitled5"
     frag            <111184..>111219
                     /note="19 to 48 of Untitled5 [Split]"
     frag            107544..111183
                     /note="133 to 168 of Untitled5"
     frag            <107544..>107579
                     /note="19 to 48 of Untitled5 [Split]"
BASE COUNT    58089 A  31468 C  34382 G  64117 T      0 OTHER
ORIGIN      -
        1 ACAGCGGCCT CGGCCTCCCC TTGGATTCAG ACGCCGATTC GCCCAGGTAA ATTCCTGCTC
       61 TTTATTTCGG CGGCGGCGGC GGCGGCGCCG GCGCCAGGTC CTCAGCGTCT CTCCTCCTCG
      121 CTCCCCTCCC CGCCGTTTCC TTAGCGGCCC CAGGTCTCTT CCACAGGCGA GTCTAGAGTT
      181 CGCTCCTCTC TGGTGGCAGC CGCCTTGGGT AGCGGTGGTT TTGTACCCTC TCCCGGCCGG
      241 CTCCGGTGGC GGGGACTGGG CTCCTGCTGG GCGGCCGGGG AGGCGTAGGC CCGGCGGAGA
      301 GTGCAGGCCG CGGGCCAGCG GAATCTACTT GAGCTCGGGG ATTAGGAGAG CTCCGGGCTG
      361 AGCGGAGCGA CTGCTGGTCG GTGACAGGCC TCGCCCGGGA GTGGAGCCGT AGCTAGTGGG
      421 GAGGCGGAAA CAATACAACT AACAGCAAAT GTGCCCTGAT CGTCCCCATA TTTACAACTT
      481 TCCCGGTCCG GGAGTGGGGA ACGTCCCAGT GAAACAAACA ACCTCCCTTC TTCCCCCTGT
      541 GACCCCATGA AGGGAGGAAG TAGTTTCAGT TAGTGAGACA AACGTAAATA CTCAGACGCG
      601 GATCCAGTGG TAATTCTTTC TCTTTCTAAA ACTTGTTTGG ACGTTGGAAA GTTCATAAAG
      661 ACTCATTTTC TTTTTTAAAG AATTAAATCG TCCACATGAA TATTTAATAC AGAAAAACAT
      721 ACTGTGGTAG ACACTGCACA TCTCCCCCTC CCCAAGAGCT TTTATCTTGT TGTTTTGACA
      781 GTGTGTTGTT GCACATGGAC TTTTTATTCA AAGACAAGTA TAAAGTACTT GACAGGTTTA
      841 CTCTGCCACT TTCTATTTGT ATGCGTTATG TAAGGGCAGT TTTAAGCGAC TATACGTAAA
      901 ACACTCAGGT ACTTCCTGAC CAAAACGTGT AGGAGCATAC AAAGAATTTT AAGTGTTCTG
      961 AGAATTGTGC TGAGATACGG GTAAAACCAC TTTTCTTTTC TTTTTCCAAA AAAGAAATTA
     1021 AGTTATACTT AAAATCCTTG GGAGGTTAAA AAATTGTAGA AGGTGCCATC CTTTTATGTC
     1081 AGGGCAGTTC TTCTTGAGGT CCCAGGATTG TCATTGGCTG TTTGTGCCAT GATGTTTGAC
     1141 TGTGTAATGA GAGAGGTGTC ATTTTAATAG GTTAAATGTA TCTGTAAATG CTGGAGAAAA
     1201 ATATCAGTTC TAACTTGACA AGTTCTAGTT CATGAGTAAG TTAAGTGTTT CGAGCTTGTT
     1261 TATGGAGGCG TTCATAATGT AGGTTGGTAT AAGGGGGAAA CACCAATTTA AAATTCCTCA
     1321 GTCAGGCAAA TTGCTAGAAA AGTGTACCTG GGTTACACGT TTTGATATTT TGTTTCATAT
     1381 TCGCTGAAGG AAAACTTTCA TTGGTTAAAA TGAAGCAGCA CTGCTCAGCG AAATCCCTTG
     1441 TTTTACTAGT GTTTGTTACA TTGGTTCATA TTTTTTGTGT CATTAAATTA TTGTCACTGT
     1501 AGAATAAGTT ATTTTGTGGA GGTTATTTTT GAGTTTAGCG TCCTGATTAC AATAAATTGT
     1561 TTCACATTTC CTGCAAACGT ACGGATAAAT GTTTAAAAGA ATGAAGTTAA TATAGCTGTC
     1621 ACGTACTAGG CATGTTTTTA ATGCTATAAA TCCGTGTAGT AGTCAGTAGC GTGTCCGTGA
     1681 TTTGTATTGG TCAGGGAGCA GTTTGAATTT TAAAAAGCCT GAAGCTCCTG CTGAGCCCCA
     1741 ATCCCGGCCT CCCTCCCTCC CACTAATCTC CCATTCCTGT CTTTGTGCTG CCTGCTCCTG
     1801 TTAGACACTG TTTGCTACGG GGCCTCAGGC CTACTGCGGG TGGGGGGGTG TGCGAGTGGG
     1861 GGGCATGCCA GGGAGGGAAT GCAGACGGGA GGAATACTTC ACATCTTAAG AAAGCAGAGG
     1921 GTTTGTTTTT TTGGGGATGG AGGTGGTAAG GGCTTCATTA TAAATGTTTA AAAGGCCTTC
```

Figure 7A1

```
1981 ATATATTCCT GTGATTGTCT CTACAACTTT TATTTCAAGG GATAAACATA TTTTTACTAA
2041 AGATAATAGA GGAGTTGTGC TTGCTTAATT TTCACGAACT GAAGCAACTT ATTTTTAGAG
2101 GTTGTCTTAT GCAGATGTTT GAATAAGTGT GTTAGAGATG GGTTTATGTG ATTGATTCTT
2161 TTTTTTCCTG AGACTTTGGA ATTGTTATAG TGAATTAGTT CTTCCCAACT TATTTTCCCA
2221 ATTCTACATA TTTAGTAATT TGTGAGTAAT ATAGGTTGTG TGATAGCTTT CATTATGATA
2281 GCATAAACAT TTCTTTAAAT TTAAAAATAT GTTTTGTTTG GTCCAAACCA ATTAAATACG
2341 TCATTTTTAA AGGAGAAAAC ATTGTGTAAA ATTCAAATTG TAAAATTTAA ACTTGAACTT
2401 TAAATCTCTG ATAACCTAGT TGGAGAGAAT AGTTTGTTTC CCTAAAGAGT GTAGAGTGTT
2461 CTGCTTCCCC TCTGTTGGTT GGAATATTCA CTAGTGGCTA ATCATCTATT TCCATTAAAA
2521 ATTAAAATTC AGTGAAAGGA GAAATCAGAA GTGTTCCAGT AACCTTATAA TCCTAGTTAT
2581 ATTATTTGGA GAAATATTTT CTCATACACC TAAAGGAAAT TTCAACAATG TCGCTTATTG
2641 TTTCTCTTAA CTCTGAAGAG TTGTCAATAA CTTTTGTTAC TTGAAAAGAG ATTTCAAGTA
2701 AATAATGAAA GTAAATCAGA GTTGAACATT AAATAGATAA TTTTCAATGT TTGAGAAGTG
2761 TATATAGGAT GCTTCCTTTT TAAAGTTATT CAACAATTTG TTTACTAAAG TTATCTGAGA
2821 ACATTTTTGA ACCTGTTCTA GAGATCATTA TAATATTTTC TGCTTTTAAG GAAAAGTTAT
2881 ACATTACTTG AAAAAAGAAA AACAGTCTAC TTGAGATTCT TTTTAGGGAT GTAAAGTGAA
2941 AGTTTTTACT ATGGCAGTAA ACTTGGTTCT TCATAGTAAT CATTATTAAA TTTCAAAAAT
3001 ATGAGCAAGC TATACCAATA CAAAATTTTC TTTACTTGCA GCCGAAAAAT GTATTTTCTA
3061 AGGCTTCTTC AACTAATTTC ATATTTAATT TTTTGGTACC AATCCATCAT CAAACTGTCA
3121 TAGAAATATT TGAACATATC TGTGTTACAT GTTTGAAATA CCCCATTGTG GTATTTTTAC
3181 TTTCTCAAAA TAAGATGTAG TAATTAATAA TATAAGAGTA AATAAAAACC AGGAGTTTGA
3241 GTTTTATTTA ATTTCATTTA ATCCTCCTTT CTGGTGCTTA TTAGGAAAAG CATAATTTGG
3301 AAGAAATTCT AAAATTTTAA ATTAAGATTT CAGTTTTATG TGAAGTGATT AGGGAGTGTG
3361 AGGTAAACAG TAATTCCTTT TAGAGAAATG TAACTTTAAT TCTGTTTATC ACATTTACTT
3421 GCCATAAAAA TGAATGGGAA ATAATTGACT AGGAACCTTT ATAGAAGGCT GACAACTAAC
3481 TGTTCAGTTG AACATGCTTA TTTTAATATC CTGAGCGTAC TAGGTTAGGT TTGGTGGTAA
3541 TTTATGGTCT TATATAGCCT TTAAAAATTG TTTTAAGATG GACTTTTTAA GCAAAGTTTT
3601 TCGTTTTTTC AGCAGTTGTC ATTTATAATA ATTCTTCGTA TTTTAAAACT AGTCCTTTTT
3661 CAAGGTGACC TGAGTTCATT TAAAAATATT CTGATATCCC TGTGAGAGAA GTGACCAGCT
3721 TTCCGTTTAA TGATGAAATA CTTGACACTT AAGAGACCAT ATGATTTGTG TAGATTCATG
3781 TAGTAAGTCA GCCGGAGGAT AAGGGATTCC CTGACACTAG TATTTTCTTA GATTATGTTG
3841 CTTTAAGAAA TGTGTGAGCT CTGGTCTTGA AGCTAGGTAT TGCTCAGTGC TGACACTGAC
3901 ACCATTTGTT ACTTTTTCAA TTATCTAAGT TCAAAGTGCA TTTTTCTTGT CTTTGAGAGA
3961 GAGGATACCT GTTTCTTGGT TGTATTTTCC TGGTATGAAA ATAGAGTGGG ATTTTAGTGT
4021 TTCTGGTTGA TTTAAAAGGA ATTTTAAACT CCATGTCTCT TAAGGCCATC ATTGTAATTT
4081 TAAAGGGTAT TTTATGTGCT TAGAATATTT TGCCCAAATA AATTAAGTAA TAAAAGTAAT
4141 TTTAGGTATT TGTCTTGTGT GTAATTTTTT TTTTTTGGTG TAAATCTGGA GTCAGTTTTG
4201 TTGAATTGAG TTTTGTCAAG TTGCATTATG TTTTAAGGCA TATTTTTTTC TATTCCCAAA
4261 GTTATATCAT TAGGAGAGAT CATTGCTTGA TGTAGCATTG CCAGCTAAGA TTTTGAGGAC
4321 TTATTTGCCA GGAGTTAAGT CTGTCCCCAT AATATCTCAT TTAATCTTTT AACATGCCCA
4381 AAAGTAGAAA CAATAATTAT CTACAATGTA CAGATGAGGA ACCTGAGGCT GGAAAGGTTT
4441 AGAAAACTGC CCATGGTCCT ACAATTAGTA AATGATCAGT CTGATTTACA TTTGTTCTTA
4501 TGGATTCAGG ATTCTATGTA TCTAGTTTCA ATGAAATTTT AATATTATCT TTTGGGTGTT
4561 AGTTGATGTG ATACTTGCCC AGTCACTTAG TCAAGAAAAT TGTGTACTTC AGGCAAAGAA
4621 GCTGAAATAG AATTCAGGCT ATATATTCTG TATTTATAAT ACTTTTAAAA ATCAATAACT
4681 CTTTACCATC TTGTGTTTAA AACAATTTTT GTTAAGCAGT CTGTGAAGCT TTTAGTTCTT
4741 TGAAGTATTT TATATTGAGT TGAAGATGTT TGTCAAAGCA TCTGTTGTTA GAAAGACAAA
4801 GTTCAGCTTT AGAGAGTCAT TTCATTCATA GAAATGTATA TGACCAATTG TAGGATAGTA
4861 GCTAGATCTA TAAATTAGTA TGACTGATCA TTTTGTAAAG TTTCAGTATT TTTATAGCCA
4921 GAGAATGTTG ATCATTATAG TCATCAACTT GGGAGGTTGT GCGCTTATTC CAGAACTGTT
4981 GCCAGTACAT ACAACCTTAT AGGAATTCCT TTTGTGAATA CCTTTAACAC ATTTGAAATA
5041 GTCTTTTTCT CATCTTTATG ACAAATCTTT ATTTTCTGGG GTGAATTTGA GTTTTAGATA
5101 CTGTACAACG TCACTTGAAA CTTAGTTTAG GGATTTTTTT TGTGTCTGGC ACTATGTTGA
5161 GTGCTTTATG TTTGTAATAT GTAGTATTAT TGAATGTTTC CATGTGACAG AAACTGTGCG
5221 AGGGAAAAGG TTTTTCAGTT CCTCAAGGTA TTGAAAAGTT GAATATGAAA TTGAAGTTAG
5281 TTGTATGAGA AAACTGAGAT ATAGAATGAT TACGTGACTA GCCCAAGGTC ACACAACTAA
5341 TAAGTTCAAG ACAGTGGAGA AAGGATTTCA GAGTTGATAC TTTACCCATA AGCCTTAACC
5401 ACGATACTGT GTATCATGAT TTGAACCACC CAACTACTCA GTGAAGTTAG TGATACTGTT
5461 CTCTTTTTAC AGAGGAAATT GAGGTTCATC ATGCTTAAGA AACTTATTCA GGGTAGCAAA
5521 CCTAGCAAGT GTTAGAAGTA GGATTCCAGC TAAAATGTAT CTAATTCTAA AACCTCTATT
```

Figure 7B1

5581 CTTTACATTC TACCACCCTG GCTCTTCAAA ATTTATAATA CAATTTTTGG TGAAAGGGTA
5641 GCCTTGATTA TGAAGTTAGT GACACTGTTT TTCTTGTGGA GCTTACAAGA GTAATTCTAA
5701 AATGTTTTGA TCAGTTATAG CTGATTCATT ATTTGATTAT AGTCTTTTTT TTTAAAAAAA
5761 AAACCCACCT TGTTACTTTA CTTCGTGTAT AGTACACAAA ATGTTTGTAT ATTCAAATAT
5821 GCATATAAAT AGGATATTGA TTTTTAAATG CAGGTACTGT GGAATATATT AAATGTAGGT
5881 ATCTGTGGAA TAAGTAGCTT TAGAAAATTT GGCAAAAGCT ATTCTCAGGC TATAACAATA
5941 CTGAAATTTT AAAAAAATGA TCAGTCATGC TAATTCATAG ATTAACTGTA TTTTTATGAT
6001 TTTATTGTGA CTCTTGTTAC TTTTAATAAT GTTAAGCATT AAAAAAATTC CCAAGAATGC
6061 ATTGAATTTT CAAAATAATT CATGTAGGTA AATTGCTTTG CCATCTTACA TGTGTGACAT
6121 ATCTCTTAAC ATGCATATAC CAATTTCCTT TGAGTTCTCT TTTGTACATA TTTCTCCTTT
6181 GACAGAAAAG AAAAACTTTT TCAGAAATTA GCAATATTAA TTTATTAAAA TAATTATATA
6241 TATACTTTTG CCTCTCCTGA GAAATGCAGA AGCTGTGACA TAATTTTAAA ATGCTGGATT
6301 TCCTTTTGTT AGAATTAACA TATTTGGGTC ACTTATGCAG GTGAAATGCA CAGTTATTTT
6361 TATATGAGCA CTATTGAAAA AATACTATTC TAGATACATT AAAACTAACA AATGTCTAAA
6421 ACACTAATTA TTAAATTCTG ACTATACTTT TAAAATATTA GTCTTTATGA TTGATATTTA
6481 TGATATTTAA TTTGGTATTT GTAAAGCAAA AATGTCCTTT AATCCTGGTG AGGAAATACA
6541 TTACAGAGTT TTCTCAACAC TGCTACTTGT CAACCCTTTC AGTATTTTAA AACCTGCCTT
6601 TAGTTGTCTT TATTTGAATC AGATTGTGGG TTGCCAGTTT TGAGCCAAAG ACATCGATCG
6661 TCTGAGTGTA TGCTCTATGT AATTCAGTTT TTTTTTTTGG TAATGACCAA GTTGAAGTTT
6721 TACATGGTTT TAAGTTGGGC ATAACTCCAT TTATTATTTA TTTATTTTTT ATTAATACTA
6781 TTCTTTAAAA TTGATGCACA TGAAAAAATT TCTTCCTAGG GTTCTGCGTA TACCTCAGAA
6841 AGCTCTAAGA TTGAAAGCTG AAATGTCATG ACCTGAAAAC TACTGATTCT TTCCCCTTTA
6901 AGAAAAGAAT TTGGAAACTA GTGTTTATTC CATAACGTTA CCTTCAAGTT ATCCTGAAAG
6961 ACACACATGA CATACGCTTT TATTTAACTC TACTAATCTT TTTACTATTT TCTCTTTCCC
7021 TTTTTTTATG TATCTCTTCC TTTCACTATC AATGTCCATT TCATCTCCCC CAAAGCAAAT
7081 TTTTACATAC TGTGGCTAAT ATAGGTATTT GTTGTTAATG TGGTTGATCT TGTAATGTGT
7141 TACTTTCCCT GATGAAACCC AGAGCAGTTT CAGAGGCCTC AAATTCTGAG ATCTTCCTAA
7201 GTTCAAAATA GATTGCTGGT AGAAAAGCAT TGACATTAAC CATGAAAATA TATATTTGTG
7261 TATTGTTCCC ACTTCTATAG ACATATATTA CTTTTCAAAA TGTCAGCTCA AGGACCAGAA
7321 ATTTTTTCTG AGGAGAAAGA GAAAGCATTG CCTTTACAAA AGTTTCCCTG ATCATTCCAT
7381 TTCATAGCAT TTGTACAGTT TTTTACTTGT ATCTCTTGAT AAAATAATTT GTTCCTATAT
7441 TCGTCAGCCA TACTCAACCA TCAGCTCTGT GAAAGCAAAG AGATTTTGTA TTATCTTCAT
7501 CTGTATGTCT ATAACATCAT CACAGTGCTG CTCCTGTTTT AGGTATTCAA TATATATTTG
7561 TTGTTTAGTT AGAATTGAGC CATGTGGTAT TTCTTAAAGG TATGTTTTTA AATCTAAGAT
7621 TAGTGAATGG CAAGTACATT TCTCTTAATT TCAAAATATA ATTTTCTTAG GTAGAGCTGT
7681 GTCCTTGAGG GCTTCTTGCT TTGGGGGTAG GAATATTTTA TTTACATATA TCCCTAACAA
7741 TACATACATA ACTTTATAAA GATAAAGAAA AATTTAAAGT TCCTTTTTAA GCTGTTAATG
7801 AGGATCGTGA AGTACAGGAA GGGTTTTTTG TTCTGATTCC TTAGGCAGTA TAATTGGAGT
7861 AAGATACTGG AGTATTGCAA GAAGTGAAAT ATCTAAATAC TTTCTTGTTT TAATCTTTGG
7921 ATTTATTGCA GTTTTAATTT TTTTTTTGCC AATTTAAGTA TTATATATAA TCAGATAAGT
7981 TAAATAATGA GAAATACGTT ACAGCACATA AAAAATGCTA TTCAGGGTCA GCAAAGCCTG
8041 AGTCCTGTCC TCTCGCTCTC CTCCCTGGAC AGCATGAGCT TCACCACTTG CTCCACCTTC
8101 TCCACCAACT ACTGGTTCCT GGGCTCTGTC CAGCCACCCA GCTATGGTGC CTGACTGGTC
8161 AGCAGTGCAG CCAGCGTCTA TGCAGGCGCC AGGGGCTCTG GTTCGCGGAT CTCCGTGTCC
8221 TGTTCCACCA GCTTCCGCGG CGGCTTGGGG TCCAGGGGCC TGGCCAAGTG GATGGCCCAG
8281 GGTCTGGCAG GAATGGGAGG CATCCAGAAC AAGGAGACCC TCCAAAGCCT GAACAACCAC
8341 CTGGCCTCCT ACCTGGACAG AGTGAGGAGC CTAGAGACCA AGAACCAGAG ACTGGAGAGC
8401 AACACCCGGG AGCACCTGGA GAAGAAGGGA CCCCAGGTCA GAGACTGGGG CCATTACTTC
8461 AAGACCATCG AGGATCTGAG GGCTCAGATC TTTGCAAATA CTGTGGACAA TGCCTGCATT
8521 GTTCTGCAGA TTGACAATGC CTACCTTGCT GCTGATGGCT TTAGAGTCAA GTGTGAGACA
8581 GAGCTGGCCA TGTGCCAGTC TGTAGAGAAC GACATCCGTG GGCTCTGCAA GGTCATTGAT
8641 GACACCAGTG TCACTTGGCT GTAGCTAGAG ACAGACATCG AGGCTCTCAG GGAGGAGCTG
8701 CTCTTAATGA AGGAGAACCA CGAAGAGGAA GTAAAAGGCC TACAAGCCCA GCTCACCAGC
8761 TCTGGGTTGA CCGTGAAGGT AGATGCTCCC AAATCTCAGG ACCTCGCCAA GATCATGGCA
8821 GACATACAGG CCCAATACGA CGAGCTAGCT CAGAAGAACC AAGAGGAGCT AGACAAGTAC
8881 TGGTCTCAGC AGATTGAGGA GAGCACCACA GTGGTCACCA CTCAGTCCGC GCAGGTCGGA
8941 GCTGCTGAGA TGACACTCAC GGAGCTGAGA CATACGGTCC AGTCCTTGGA GATCCATCTG
9001 GACTTGATAA GAAATCTGAA GGCCAGCTTC TGGAGAACAG CCTGAGGGAG GTGGAGACCT
9061 GCTATGCCCT GCAGGTAGAG CAGCTCAACA GAATCCTGCT GCACCTGGAG TCAGAGCTGG
9121 CACAGACCCA GGCAGAGGGG CAGCACCAGG CCCAGGAGTA CGAGACCATG CTGAACATCA
9181 AGGTCAAGCT GGAGGCTGAG AGCGCCACCT GCCACCGCCT GCTTGAAGAT GGCAAGAACT

Figure 7C1

9241 TCAGTCTTGA TGATGCCCTG GACAGCAGCA ACTCCATGCA AACTATCCAA AAGACCACCA
9301 CCCGCTGGAT AGTGGATGGC AGAGTGGTGT CTGAGACCAG TGACACCAAA GTTCTGAGAC
9361 ATTAAGTCAG CAGAAGCAGG GTACCCTTTG GGGAGCAGGA GGCCCATAAA ATGTTCAGAG
9421 GTCATTGGGG GAAAATAGGC TATTCAGTTA AAATAGTTAT CTGATGACTG AAATTTTTTT
9481 AATATGTCAG GTGTATTGAG GTATAATTTA TACAGTAAAA CTCAGTCTTT TGGGTGTGCA
9541 GTTTGATGAG TTTTGACAAA CATACACAGT CTTAAAACCA CCACCACAAT CAGAATATTT
9601 CCATTACCCC CAAAAGTTCC CATGTATCCC TTTGTAATCA GTTTCCTGCT CCTACTGCAG
9661 CCCGAGGCAA CTAGATCTGG TTTCTGTCTC TATAGTTTTT CCTTTTCTAG AACATAAAAA
9721 TGGAATCATA TATAGCCTTT TATGTCTTTT TTTTAAATTT AGCAGAAAGC TTCTGAGATT
9781 CATTCATGTT CTATGTATCA GTAGTTTGTC AATGACTGAA GTTTAAAATT GTTAACTTTG
9841 GTGAAGCTCT TACGAAAGAG TATTATCAAA AAATAGTACT TTGAACAGTG GTAGATATTT
9901 CTCTCAGATT TTGGCAGCTG CCTTATTATT GAACATTTTA CTTGCTCATT TTTACCCCTC
9961 GACCCCCAAA TTTTACTTAC CTGTTTAACC CTCAACCCCC AAATCTAGTC TAATAGACAT
10021 TATTATATGG CATTTATTTA TATTAGTAAA TGCTGTTTAA TTCTCTACCA AGCATGTGAA
10081 ATAGACCTAC TCTCTTTTTC ATAATTAAAA TAGGTAGCAT CTTGCATTTT GAACATACAG
10141 CACATAGAAA CTAGAATAAA AAATGAAGGA TGGTGCAGTA ACACCAAAAA CTTGAGTTTA
10201 CATTTGCTTT AGGTTTAGTG TTTGTAAGTT GGTGCTAAAA AAAGAGCATA GATTATAGTG
10261 AATAACAGTC ACAGCCTCTC TTCCAATGAT TAAAGTTAGA AAAGCAGTGC CCTTTACTGA
10321 AAATTGGGGG CAGATAATGA GAAAAGAGTA ATTTTCTGGA CATTTTATTC GACCACCTCT
10381 CCCCCGACCC TTTCCTTTTT GAAACAGCTT CATCTCTGGG ATATTCTCTT GTTGTTTGCT
10441 TATGTCTTTG ACCTCCCATT TTTTAAGTCT TTTGCTAGGT CTTGCTCCTC TACCTACCCC
10501 TTTAAATATT TGTATTCTCC AGGAGGTGCT TCAAACTTAT TTCTGTTCTT CCTGTTGATC
10561 TCATTTATTC ACATGACTTG TTACATGCTA CCTGTGTGCT GATGACTCAC AAATCTATCT
10621 CCAGAATATA TTTCTCTTCT GAGCCAGATC CAGCTGTCTA TCAGGTACCT CCTGATGTCC
10681 CATGAATAAC AGAAATTCCA TAGTATGTAA GTCTGAACTC ATCCCTTAAT TCTTCCTTAC
10741 TCTGACCTGT CACCCAAAGA AAGAAAACTA TTAAAAAATA CATGAAGTAG GTTAATGTTT
10801 TCACTATCAA CTCATTTACC TAAACTAGAA ATTTGGGATA ATCCTTGACA CTTCTTTACC
10861 ATACTTCCAG TTCAGTTATT CACCCAGTTC TGACATTTGT AACACTTCCC TGAATTATCA
10921 CTTGAATCTA CCCCTTCCCC AATGTTTTGA TTCTGTGAGA GGTCCTGAAC ATACAGTTTT
10981 CTCAGATTTA ATAACTTCTA GTATTTTAAG AAAGATTTAG CAGTAATTGT GAAAGTAATA
11041 TGTATTTAGT ATTGGATACT TTTTGCTTCT ATGCTTGGGC TCTGGTATTT AAAATTAAGG
11101 TGTAATCTTT AGTAACAGTG ATACTATATA GCCTAAATGT GACTGTGTTC TGTTATATCT
11161 AAAATTTAGG ACTTTTGACT TACAGCCCAG TTTATCAGCT GGAAGACTTG AACTCATTTT
11221 TTAACTCATT TTTTATCTTT TCATTCTTGC TTTTAGAATA CTGCATTTCA TGGAGTTGTA
11281 TATTCATTTC AATACTTTGT GTTTATGTGT TTTGGAGCAG GGTAGAGGAG AAAATGGGAA
11341 TGTATAAGGA AAGTTAAAGG AAGGACTTTT GAATTGACTT TCCTATACTG TGGAAACAAG
11401 TTTACTTAAA TAACATTTTC ACTTTTATTG CAAACAACAG AAAACTAAAG AAATGCTGTG
11461 GGATATGATA CCATTCAGGT GCTAAGCATG CACATATTTT TAATGACAGG AGTTAGATGT
11521 GTTGTAACAG TATTGCTTGT TTGTGAGTTT GGAAATTAAT GTTCATGGTT TTGTATAACT
11581 TTATGATATT TCTTCCTTAA AATAAGAAAT TACCCCTCCA GCCCACAGTT TGAGCCAAAG
11641 GGTCTGCTTG AAATTATTAG TTTAAATAAT CCTGAGCGCA TCTTTTGTAA AGGGCATTTT
11701 AAAATGTAAT GCTGCCTTGA AAAACAAAGC AAGCATTTTC TTCGTTATAT CTAGAGTTTA
11761 TAACTAAAGA AGTAATATGT GCTATATTTT GCTCTAGTGC CAAGTACCAT ATTTTGGAAT
11821 GAATAGAATC AATCTAAAGG CAGTTTACAA AGGCTGAAGG GAGACCCAGT TTGGTAGTCA
11881 TTGGATCCCT TTGGTGGCTT GCACATAGTA AGCACTCAAC AAACAATTGT TGAATAAATG
11941 AATTTGAATA TATTTTCAGT TTGGGGACAT AGGACTAATT AGAGTGACAG AAGATGGGTG
12001 GGGCTTGCTA AATACTGAGC AAGTTTTATA GAGGAAAGAA AACATGAAAC CCAGAAATGG
12061 TGGACAACAT TGACAGCAAA GAATTGGTGT AATTTAGTTA ACTATTTTTA TCTGGACAAT
12121 AAGGTTTGTT TAGTTGGATA AGAGAAAGAT CTATATACAG AAGTGTTTTG AGTTCTTTCT
12181 ACTCTTATTT CCACTCTGGC TCTACTTCTG AACCCCCATG TTCACTGCTA AAGAACTAAT
12241 TGTAGGCTTG GGGCTAAAAT GATCTGCATA ATCCAGATAC TCATATTAAG AACTGGGAGG
12301 AGGTGTTGGG AAAGAGGTAT TTCTTACAGT TCTTCAATCT TTCCAATTAC TCATGTTTCT
12361 TAGTATATGT CAGGGTGCCA CTGCACTGTC CTCCGTATTC ATATGAGGAT GTCTAAAAAC
12421 TAGAATTTAA AATCACATAT AATTTACAAT AAGCTTGTAA CTGTCCTAGT ATGAAGTTCA
12481 GTATCTGAAT CTCTAATAAT TAGTTACCTA GCTGTTGAGC CACATTGCCA TCTACTCTGA
12541 TTATCATATG TTTCTTATGA TTCTGATATT TTAAACTGGA AGATAAACAC CACAGTTTTA
12601 GTGTGTTTTA TAAAAATTTT ATAATTCAGT AACAATCCAT TCCTTTATTT TCTTGGAAGC
12661 CAAAACTACA TATAGTTTCC TGATATGTTA AGCTTAAACT GTGGAATTTA GAACTTAAAA
12721 ATTTTCAAGA GCTTCAAAGT TGAAGACTTT TCTTAATTTT TTTTCAATTG TAGAACCAAT
12781 GTGAAAAAAA AAACTACATG CTGTTTGGGA AATGGGAAAA ATATCAAATT TTATGTTTTT
12841 CCTACTAAGT TTCCTATTAA ATTTTTACAT AAAAATATTT ATGATGAATG TAATTATGGT

Figure 7D1

12901 TAAATACATA TATTAATGCT ATAAATTTAT TCCTCTTTTA ACGTTGGATC ATAAAGATTT
12961 TCCTAGTTTT CTATATAATG TTCATAATTC TTTAAAATGT TGCCCAGTAT TTTGTCAGTG
13021 GATGAACCAT AATTTATTCA TTCTATTCTT GCATACTTTT TGCTTTTACT TTTTTTCTAT
13081 ATAAATAATG AGGCAGTGAA CATCTTTATA TGTAGTTTTT TCCCCCTTTA GGGGCTTTAT
13141 TCGCTTAGAG TAGAATCTCT TAAGTGGAAG TAATCCTGTA AGTGGAAGTT GGGTCAAAAG
13201 GTTTGAACAT TTTTATGGCC TTTAATATAT ATTTCCAAAA CTAATTTTAT TCTGCTATAA
13261 TCTTTATTTT CATTCACATC TTAATTCATT CAGTAGATTC ATTGTGTTTT TCATATAGAA
13321 TACACACTTC CTATGAATAT TATTAGGTCA TTTAAATGCT CCCGTTTCCC ACTATTGTGC
13381 CTGTGGTCTC TTTTTACTAT ATATTTTTAA CCTCTTGATG ATAAACAGTT GTGGCTTTTC
13441 AAACGGTGTA TATCATTTCG AGGTATTATA TAGTAAAATT AGCATGGGAT CTAAACTGCT
13501 ATTAGCCAAG TGGCATTTAG GCCAATTCTT AACCCAAGCC CATGTCTTCA ACTGTAAACT
13561 GAAGAGGTTC TCAGCTTTTG AGATTTCATG GACTAGTCAG AACAAAGCAA GAAAGTGCTT
13621 TTCTGCAGAA ATAAAGTGGT AAGGATATTG TAGATTGGAA TGTAAAAAGA AAAGTAATGT
13681 CTAGGTAAGA CCCATTACTT AGTCTTAATA TTTGAAATGT GAAATACCCA GTGTGATGTG
13741 AACATGGTCA TGATCTCATA TTCATTCTCT TGTACATCAA ACACTGAGTG ATTCCTATGT
13801 CTTTTCTCAG GAGCTATTAA GGCATTGCAG ATGGTGAAAT AAAAGACTTC AGGCCGGGCA
13861 CGGTGGCTCA CGCTTGTAAT CCCAGCACTT TGGGAGGCCG AGGCGGGCGG ATCACGAAGT
13921 CAGGAGATGG AGACCATCCT AGCTAACACA GTGAAACCTC GTCTCTACTA AAAATACAAA
13981 AAATTAGCCA GGCACAGTGG CGGGCGCCTG TAGTTCCAGC TGCTTGGGAG GCTGAGGCAG
14041 GAGAACGGCA TGAACCCGGG AGGCAGAGCT TGCAGTGAGC CAAGATAGCA CCACTGCACT
14101 CTGGCCTGGG CAAAGAGCGA GACTCCATCT CAAAAAACAA AAAAAGAAAA AGAAATAAAA
14161 GACTTCAGCC CACCCATATT ATAGTCTAAT ACAGTTTATA GACAGGTAAA CAGAGATTAT
14221 GTTACAATAT CTAAGTGCTA TGATCAAGAT AAACAAGGTG CAGTTGGAGC ACTGGTGGTA
14281 GGGGTGGTCA CCTAATTTAG ACTAGTGTGG TGAGGCGCAG TAAGTCAGGA GCCCTCCTAG
14341 GTGTGATGGT TAGTAGATAT GCAAACTAAG TTTTGAAGGC TGTTAGTCAT ACTGTGGAGT
14401 CTGGGCCAAC AATTTGATTT TTGGAAACTG ATGATGGCTT AGATTATTAG AACATAGGCT
14461 GGAAAAGGGG CATGCCAAAA AGGTCTGAAG CTACAGAGAG GGGCAGGCTA CAGATTATGA
14521 AGGAGTGGAT ATGCCTTACT AAGAATTCTG TGTTTTATTT TAAAGACGAG AAGCCAGGAA
14581 GTTATTTAGT AATGGAGTAT GTTTTATGCA TATGTAAAAA AATTTTTGGA TAGTAGGCAT
14641 GAAAAGGGAG GCTCAGGAGG CCAGTAGGTG TTGAGGTCCT CAATTAAGAT GGGGGATTGT
14701 AGCGAAGGAA ACCCATAACA AATATTAAAG AGTTAATCTA GTTATAGTTT AGTGATTCTA
14761 TGTAGGTAGA TTGGGTAAGA GAGAATGAAA ACAGTCAAGG ATATATCCTT GATTCCCAAG
14821 TTTCATGTGG GCATATGAGA GTAGAATATA AGTTAAATCA GTTTTGGCTG CCTGTGAGTA
14881 AAAATATAGT GTACCAAAAC CTGTATCACC TTTCACATTT TAAAAGGAAT GGATATTGAA
14941 AAATTTAGTG GCTTGGTCAA ATTGTACTAA TGATTATTTG GAAATGACTT TTACAGCTGA
15001 CCTAGAAGAT CTCTCCAGTG TTAAATCAGG GTTAAAAGTA GTACAGTGGA TGAAAAAATG
15061 CTCATCACTG GCCATCAGAG AAATGCAAAT CAAAACTGCA ATAAGATACC ATCTCACACC
15121 AGTTAGAATG GCGATCATTA AAAAGTCAGG AAACAACAGG TGCTGGAGAG GATGTGGAGA
15181 AATAGGAACA CTTTTACATT GTTGTTGGGA CTGTAAACTA GTTCAACCAT TGTGGAAGTC
15241 AGTGTGGCGA TTCCTCAGGG ATCTAGAACT AGAAATACCA TTTGACCCAG CCATCCCATT
15301 ACTGGCTATA TACCCAAAGG ATTATAAATC ATGCTGCTAT AAAGACACAT GCACACGTAT
15361 GTTTATTGCG GCACTATTCA CAATAGCAAA GACTTGGAAC CAACCCAAAT ATCCAACAAC
15421 GATAGACTGG ATTAAGAAAA TGTGGCACAT ATACACCATG GAATACTATG CAGCCATAAA
15481 AAAGGATGAG TTCATGTCCT TTGTAGGGAC GTGGATGAAG CTGGAAACCA TCATTCTCAG
15541 GGAACTATTG CAAGGACAAA AAACCAAACA CCACATGTTC TCACTCATAG GTGGGAATTG
15601 AACAGTGAGA ACCCTTGGAC ACAGGAGGGG GAACATCACA CACCAGGGAC TGTTGTGGGG
15661 TGGGGGGAGT GGGGAGGGAT AGCATTAGGA GATATACCTA ATGCTAAATG ACAAGTTAAT
15721 GGGTGCAGCA CACCAACATG GCACATGTAT ACATATGTAA CAAACCTGCA CGTTGTGCAC
15781 GTGTACCCTA GAACTTTAAA GTATAATAAT AATAAAAAAG TAGCATGGTG GATTATAATC
15841 TTACTTGATT AAATTACTAG AAGATAATAC TATTTCTTTT TAATGCTTTG TTTTCTAGTA
15901 TATTGACTAT ATTCTTGTGA GCTTAGAATA ACATAATGAA TGTTCTTTAA TAACTATTTT
15961 CTATTGTGCA AAGTTCTCTT AGGGCCTTTC TGGTGTATTT GTTTATCCAG CCTCATCTGA
16021 AGACTGCCTC TTCAGTTAGT TTTATACTAA ATCCATACAT ACACTATAAT GAAATCTTGT
16081 AGTGAGAACT ATGTTACTTT GTTCATGAAG GGATTATCTT TACAAATATA ATTAAAGGGA
16141 TGCTTTTAAA ATAAATTTTA AAATGGCAGT AGCTTTTTAG AATTGTTACA TGTAGGAACA
16201 GTTATAAAGC AGTCAAACTG ATGTATCCAA AATAACTGAC CAGGTGACAT ACTGCCAAAA
16261 TGAAAATTAG TACTTTCCAA GGTTCTAAGT ATACTTAAAC AAATGTACTT CATTTTGTTT
16321 TTTGGCTTGA GAGGTAGCAT ATCAGAATCA CCTAGGGATT TTTTTTTTTC AAACTTTAAT
16381 CCTTTTTTGG AGATGTAAGT TTTTAAGTTT CTCTTTTAGC TGTGTTCCCT TAGACTTCTC
16441 AATCATTCAG TAAGAATTGA ATAACTGCAG TGTGTTCAGC AATGAATACT AGATATTTGA
16501 TATGGACTTT TTTTGAGTCT TCCTCCTGAA TTTTACATGG CTACCTAAAA GATCTCTCTC

Figure 7E1

16561 TTTTTTGTAT TCTATAAAAA CATCATCTGT GAGGCATAAA GGAGCAAGGA ATCATGTGAG
16621 CAGAGTTAGC GAATTAGATT TTTAAAAAAA TGAGAATGGT GAGATGTGTT TAGTTCTGAA
16681 GAATGGAGGA GGAGTTGCTG GATACTAGCG AGGACGTAGA ATTGAGGAAA GAAGTTAGGG
16741 TAGGAGATAG TGTAAATGAA TTTGGTAGAA AAAATTCAGT ACAGCCTACC AGCAGTACTT
16801 CAAGTAAAAT TAGAAATTGT GAACTGACCT ATCTGTTCCT AAAGGTGTCT TATATTTTAA
16861 AAGTTTGCTC AAAAGTCAAA TTGAATCTTG TTAGAAACAC ACTACTTAAA AATATAAACC
16921 ATGCCTATGT GTTCACACTA AGTCCTCAGC AAATACTTCT TCTTTATTAG TTCATAGTTG
16981 CCTTTCTACT GATTTGATGG AAAATATATC CTTCTCAAAT ATATTTCCAA ATGAAAATCT
17041 GCTAATTTGT GACATTTCTA ATGGATTATT AGGAAGGAAG GTATTTGATA AGAAGCAAAG
17101 AAAAAGTAAT CAAATTAGCT CAAGTTCATC TGATATTGAA ATATGATAAG TACTCCTTAG
17161 TAACACAGCT TAGCTAGAAA CCGCAGATAA AGTGAAGTAT CCAAAAAAAA ACTCTATTTA
17221 TATGAGAAGT TTGATTTAAC CTTTGTCTAA TATCTAAAGT TAATTATGTG TCCAAAGGTA
17281 TTGTACTATA CTATACTGTC ATGTATGTAC TTTCAAAAAT ACATGTATAT AAAAATACAT
17341 ATATACATAT AATATATTCG TATATACAAA TATATCCTAT GCACTTTGAT AGCTCTATTT
17401 TGATAACTTG TTTTGTATTT TCCTACCTCA CACCTTTTGA TCAAAACATT TACCTCCTTT
17461 TTTATCCATC TATCCAAATC ATACTTTCTT TCTATCATGA TCTTATGTTT TTTTCCCCCC
17521 ACTGCGGGGA GGTGGCATGT CAGAATCCTC TGTGGATTAT TTTCAAGCTT AAAATCCTTT
17581 CCACCTTTTC TCCTGCCCCA GTTCACTTGA TCTTTTCTAG CAGTACCTAT GTGTAGGAGT
17641 TATAGAAATT ATATGTTAGC TTGTCACATT TTCTTACTGT ATATCAAGCT AAAGTTTATT
17701 TTGTTTTATT TTTACCTTAT TTGTCTTCTC AGTCAGATTA TAAACTCTTA GAGGACACAG
17761 TCTGCCTGTG GTGCTTGGTG TCTTACCTGC AACAGGCTTG TAGCAAGTGT TTGCTGATAA
17821 CTGGTGTAGC TCATCTGGAC TGGTTTGAAG AGGTTTGGAA AATATCTCAC ACTCTTATAA
17881 ACTGTAAAAT TCACCCTTTT AAAGTGTAAA ACTCAGTGAT TTTTAGTATA TTCACAAAGT
17941 TATGCATTCA TCATTACTTT CTAGTTCCAG AGCATTTTCA TCACCCCCCA AAAAACCACG
18001 TTTCCATTAG TGGTCACACC CTGTTGTCTC CAGTCAGTCC TTGGCAACCA TTAATTTACC
18061 TTCTGTTGCT GTGGATTTCT GTATTCATAT AAGTGGAATC AAATAATGTG CCCTTTTGTG
18121 TCTGGCTTCT TTTAATTGCT CATCTATATT GCAGCATGGA TCAGTACTTC ATTTCTTTTT
18181 AGGACTGAAT ATACTCCATT GTATGGATAT ACCACATTTT ACTTTTGCTT TGTCGCTTGA
18241 TGGACGCATG GATTGTTTTC AACTTTTGAC TATTATGAAT AATGCTGTTA TAAGCATTCA
18301 TTTGTAAGTT TCTGTGTGGA TATGTTTTTA CTTCTCCTGA GTAGGTACAA AGGGGCAAAA
18361 TTTTTAGGTC ATGTGGTAAC TATGTTTAAC TCTGAGGAAC TGTCAGACTG TTTTCCAAAG
18421 AGGTGCATGA TTTTACATTT GTAGTAGCAA TGTATGAAGG TTAGACTGTC TTTACATCCT
18481 CACCAACACT TGTTATTGTC TGTCTGATTG TATTGGTCCT AGAGGGTGTG AAGTGGTATC
18541 TCTGTGTGGC TTTGATTTGC ATTTTCCTAA TGACTGATGA TATTAAACAC CTTTTTATGT
18601 GCTTATTGGT CATTTGTGTA TCTTCTTTGG AGCAACATTC ATCCAAATCT TTTGCCCATT
18661 TTTAAATTGG GTTATCTGCC TTTTTATTGT TGAATTATAA GTTGTTAGAC ATATTCTAGA
18721 TACAAGTTCC TTATCAGATA CGTGATTTGC AATATTTGCT CCCATTCTGT GGATTGTCTT
18781 TTCACTTTCT TGATAGTGTC CTTTGAAGCA CATACATTTT TAATTTTAAA GATCTCTATT
18841 GTTTTCCTTT GGTTGCTTAT GCTTTGGGTG TCATAAGAAA CTATTGCCTA ATCCAAGGAC
18901 AGGAAAAGTT ACACCCGTGT TTAGTTTTAG CACTTACATT TAATACTCTG ATCCATTTTG
18961 AGTTAATCTT TTTCATAAGG TATGAGGTAG GGATCCAACT TCATTATTAT GTACGTGTTT
19021 ATCCAATTTT CCATTACCAT TTGTTGAAAA GACTATTCTT TCCCATTGAA TGGTCTTGGC
19081 ATCCCTGTCA AAAATCAGTT GAATGTAAAT TTAAGAGTTT ATTTTTGGCT CTCAATTTTA
19141 TTCCATCAGT CCATATGTCT GTCCTTACGC CAGTACTACA CTGTCTTGAT TACTGTGGCT
19201 TTGTAGTAAG GTTTGAAAGT GAAATGTGTG AGTCCTCCAA CTTTGTTCTT TTTCAAGATT
19261 GTTTTGACTC TTCTGGATCT CTCATTTTCA TATGAAGTTT AGGATGTTTG TCATTTTCTG
19321 CAAAATAGGC AGCTGCAATT TTGATAGGGG TCGTATTAAA TCTGTAGATG AGTTTGGGGA
19381 GTATTGCCTT TACAATAATA TTAAATCTTA ACAATCCAAG GGCATGGGAA GACGTTCCAT
19441 TTTTTTAAAG CCCTAATTTC CTTTAGTGTT TTGTTTGTTT GTTTTGAGAC AAACTCTCGC
19501 TATATGGCCC AGGCTGGAGA GCAGTGGCAT GATCTTGGCT CACTGTAAAG TCCGCCTCCC
19561 TGGTTCAAGT GATTATTGTT CCTTAGCCTC CGAGTAGCTG GGATTACAGT CCTTTGCCAC
19621 CATGCCTGGC TAATTTTTGT ATTTTTAAGA GAAGGTGCGG TTTCGCCATG TTGGCCAGGC
19681 TTGTCTCGAA CTCCTGGCCT CAAGTGATCT GCCTGCCTTA GCCTCCCAAA GTGCTGGGAT
19741 TACAGGCTTG ACCCACCACA CCTGGCCAGT GTTTTGTAGA TTTAAATGTA CAAATATTGC
19801 ATTTCTTTTG TTAAATTTGT TCCTGTGCAT TGTGTTCTTT TTAATGCTAT TGTAAATGGA
19861 ATAGACTTTT ATATATTTTT TTTTTTTTGA GAAGGAGTCT TGCACTGTCA CCCGGGCTGC
19921 AGTGCAATGG CACGATCTTG GCTCACTGCA ACCTCCACTT CCCAGGTTCA GGCGATTCTC
19981 CTGCCTCAGC CTCCCGAGTA GCTGGGATTA CAGGTGCACA CCAGCACACC TGGCTAATTT
20041 TTTGTTTTTT TAGTAGAGAT GGGGTTTCAC TATGTTGGCC AGACTAGTCT TGAACTCCTG
20101 ACCTCGTGAT CCACCTGCTT TAGCCTCCCA AAGTGCTGGG ATTACAAGCA TGAGCCACCG
20161 CATCCGGCCT GGAATTGCTT TCTTAATTTT ACTTCCAGAT TGTTCACTGC TAGGGTATGG

Figure 7F1

```
20221 AAGTGCAGTT GATTTTTATA TATTGATCTT GTATCCTGCA ACCTTGCTGA ACTTGTTTAT
20281 TAATTGTAAC TCATGCTCTT CTTTCTAGGG ACAGTTTATG TTCTTTAGTT TGGTTCATTG
20341 TGCCCTCCTC CAGTTTTCCA AATAATACAT GTCAACAGTG TTATAAGAAA GAAATTTCTT
20401 ATTTTCTCAA TCCTGCTTTG TGACTTAAAC AAACTTACGC ACATATGAAA AGTAAGATCA
20461 GACAACTCAG AAGAAAAACG ATATCCACTA AAAACTATGT CAACATTTTC ATTTAGTGCT
20521 CTGGCTGTAA CATAGGATTA AAAATTTGAG GATTGTGGTT CAGTAGTTAA AGCAGTAAGC
20581 TTTGCCAATA GTGAGGCATC TTGAGTATTT GTTGCGGAAA TAAATAAATG CCTGCTAACA
20641 ATGTGTATAT AGGGATGCAA AATAAATTCT ATTGGTCAGT AATTTCTGAA GTCTTTACTC
20701 CACTAGTCAG TAAGTGATTT TCAGTAGTGC ATCTGGAAAG CTTGAGTCAT ACAGGGAAAA
20761 AAAAAAAAAA AAAGCAAGGA GGGAAGAAAC AAAAGGAAGT AAGATTAATA ATTTGAATTT
20821 TGTTAATACA GATAATATTG TGATTTAAAT AAATCTATTG ATTAGGAACA AAAGAGGAAA
20881 AAATAACAGA TTACAGTATT ATTCCTCAAG TTCAAACTTC TGTGTTTCTT AATGCCAGAA
20941 TCAAACCTAA AATGTCAAAC ACACATATAA AAAGATGCCC AAACTTACTA GCAGTTAGAG
21001 AAATAAAGAG TAAAAATCTA GCTAGCTTAT TATGTATTTT GTTGATCAGT AAGGATAAAG
21061 TGTTGAAAGT ATGCTTCATA TACTATAAAG TATGCTTGTT TAATAAGTTG TATCCTCTAT
21121 TATCATTAAT ATTGTTGTTC TTATCAGTGA CCTTTAGGTC TTAAAATAGA TGTAGAGAAG
21181 GGTAGTGTAA TCCTGCCTTT AAAAAAAAAT TCATCAAATG CTTTATGTCT TATTCATGGT
21241 CATATTTAAT ACTGTTGAAG AAACCCATGA GATAGATATT TTTGAGACAA TTGAGGCGTA
21301 GGAAGTTAAA TAATTTGCCC AAGCTTACAC AGCTTGAAAC AAGAGGAAGA AGAAATCAAA
21361 CCTATGTTTT TCTGATTCCT TTTTTTTTTT TTTTTTGAGA CGGAGTTTCG CTGTCATTGC
21421 CCAGGCTGGA GTGCAGTGGC ACGATCTCAG CTCACCACAA CCTCCGCCTC CCAGGTTCAA
21481 GTGATTCTCC TGTCTCAGCC TCCCGAATAG CTGGGATTAC AGGCATGCGC CATCACGCCC
21541 ACCCAATTTT GTATTTTTAG CAGAGATGGG GTTTCTCCAT GTTGGTCAGG CTGGTCTCGA
21601 ACTCCCGACC TCAGGCGATC CACCCACCTC ACCCTCCCAA AGTGCTGGGT ATAGGTGTGA
21661 ACCACCACAC CTGGCATGTT TTTCTGATTC TAAAACTTAG TTTTAAACTT TTTTTAAAAT
21721 TTAGTCTTTA ACTTTTAATT GGCATACTAT ATTGCTTCTC CACTACCTTT GAACTTATTC
21781 CTAGGTGGAT TATATAATAA ATAATATTCC TTGGAGTTTT AAATTGTATT AAATAAGATT
21841 TAAAGTAGAA TTTTAAAATT GGATTTTGAT TTTACTTCAG AAAACTCTCA AGTGTTTGCT
21901 TTGGGAAATC GAAGAAAACA TTTGCCCATT GTTGTAATGC TGCTGTATTT CCCAATTGTG
21961 ATTTCCAAAA TTTCTTTGAT TCTCACTTTG GGAAATGGGG TCTTGAAATT CATGAAATCC
22021 AGTTTTGGGT CCAGAAGCAA ATAGACTCAG TGAAAGAGAC AGTCATGGGA GAACCCCTTA
22081 AATAGTTTTA GGACAAAAAG TTACAGTTTA AAGAGAAGGA TGGGTAAATG TTGAAGAAAA
22141 CTTAATACCT CTTGTTTTCT CTATGTTGAA GACTTTTGGT TTTGCATTAA GTCTTGCCTG
22201 CATTAAAAAA AAAGTGTAAT GTGATTGTCT TATGTACTTA CAAATTAATA TGTATTGTAT
22261 CTTTAATTGC ATCTCTGTGG AATTTTTATA TCATTTGCTT TCTTTGTTTT ATACCTTTCT
22321 TTGGGAATCT CATATTCAGT GCAGACTGTT GTAATGAGTT TGGTTTGTTG ACCTGGTGAG
22381 CAGTAGGATT TTGTAAAAGG AAATTCAGCT TAAAGCATTC AGAACTTTGG CTGTTGTGCC
22441 CTTTCAAAAG TGAATTTTTA AATAGGTTTA AAATAAATGA CTGCCTCCAA AGGATTGCTT
22501 TCTAAATTTT GTGTTAGAGA CATGCTTGCC TCCTGATTTT GTATTTTAGC CCCAAAGTGA
22561 ATTAAGCTTT CCTGCTTGAG TTGGTGAATA TTACTTAAGT ACATGTATAT ACACAGAGTT
22621 AAAAACCTGC TAGTACTCAA AAATCAGTCC TGTATTGTAT AGAGATTTGC CTGCTGATGG
22681 ATCAGGTGTT GTTTTCAGTA TACTGTTCTT GGACTTTATG ACAGACTAGG GGTACTTAAT
22741 GCCTGAGTTG ATAATCACAT TATTACTTCT TACACTTTGT TTATAGAATC TAGAAGGAGT
22801 TAAACAGAAA AGTATTTTTC TGTTCCTTCC TTATGATTTA GAAAATAGAA AAAGTCTTCG
22861 CTAAAGCCTT TAATAGCCTT ATTCTTAGTG ATGATGATGA TTATATTAAT AGCAATGATG
22921 GCCAGTATTT GTCATGAGCT CACTGTTTTG AATATTTGAC TGGCATTATT TAATCTTCAC
22981 TACAGTTCTT GAGGTATAAT CAGCCCTTCA TATTTGAGAG TCACACATTT GCAGATTCAG
23041 CCAAGCACAG ATTGGAAATA TTCAGGAAAA GAAACCAATA AAAAAAATAC AAAAACATTT
23101 AAAGTGCAGT ATAAAAACTA TGTAGCATTT ACATTGTATT TGGTATTATA AGTATTCTAT
23161 TAATGATGTA AAGTATACAG GAAGGTGTGC ATTTTATATG CAAATACTAC ACCATTTTAA
23221 ATTAGAGACT TTAGCGTCCA TGAATTTCAT ATCTACAGGG ATCCTGGAAC CAGTCCCCTC
23281 AGGGCCAAAG GGGACTGTCT AGCTATAATA TCTCCACTTT CCAAATTAGG AAACTGATGC
23341 TTACAAAGAA TGTGACTTGC TCAAGAGATG AGAGAAGGAA GTCCCATGAG CAATTCAGTC
23401 AACATAATTA CAATGAATGT ATGCTCTCCT TAAGTTTAGT TAGACTCCTG ACCTCCTTGA
23461 GGTCAGGGAC TTAATATGTT TATTTCTTTA ATTCTAGTAC CAAGCACAGC ACCCAGCATA
23521 TGGCATATGC TCGGGTTTTT TTTGTTTTGT TTTGTTTTGT TTTTTTAATA AAGAAATGAA
23581 GTTGCGAGAG GCTGATTCAT TAGCTTTAGC TGTAAGTCTT CTGGAGGGAA TCCATACCAA
23641 TTTCATTTAC ATTGCATGAT TTTTTTTCCT TTGCCTTGGA ATACCGCTTG GCAGGGGACC
23701 TAGTAAGTTC CTGTTCATTC TTCAAGTTCC AGCGTAATTC CATCTTTTCT TTGATGCCTT
23761 CCTTGTCTCT TTTAGGCAGA ATTAATTGTT CCCTTTTCTA TCCACTCCCT TTTTTTCCCC
23821 AGCCTTTATT TTAGATTCCA GGGGGTACAT GTGCAGGTTT GTTACATGGG TAAATTGCGA
```

Figure 7G1

23881 GTCGCAGGGG GTTTGTTGTA TAGATTATTT TGTGACCCAG GTAATGAGCA TAGTACCTGA
23941 CAGGTAGTTT TTGATCTCCA CCCTTCTCCC ACCCTCAAGT AGGCTTTGGT GTCTCTTGTT
24001 TCCTTCTTTG TGTCCATCTG TGGTCTATGT TTAGCTCCCA CTTACAAGAG ATAACATGCA
24061 GTATTTGATT TTTTTGTTTC TGTATTAATT TGCTTAAGAT AATGGCCTCC AGCTGCCTCC
24121 ATGTTGCTGC AAAGGACATG ATTTCATCCT TTTTTATGGC TACATAGTAT TCCATGGTGT
24181 ATATGTACCA TATTTTCTTT ATCCAGTCCA CTGTTGGTGG GCATCTAGGT TGATTCCATG
24241 TCTTTGCTAT TGTGAATAGT GCTGTAGTGA ACATACACAT CCATGTGTCT TTATGGTAGA
24301 ATGATGTATA TTGCTTTGAG TATATACTCA GCAGTAGGAT TGCTGGGTTG CATGGTCCTT
24361 CTAAGTCCTT TTTTTTTTTT TTTTTTTTTT TTTTGAGTCG GAGATTTGCT CTTGTTGCCC
24421 AAGCTGGAGT GCAATGGCAC GATCTTGGCT CACTGCAACC TCTACCTCCC AGGTTCAAGT
24481 GATTGTCCTG CCTCAATCTC CCAAGTAGCG GGATTACAG GCGTGCACCA CCACACCCAA
24541 CTAATTTTGT ATTTTTAGTA GAGAGGGGGT TTCCCCATGT TGGTCAGGCT GGTCTCGAAC
24601 TCCTGACCTC AAGTGATCCA CCCCCCTCTG CCTCCCAAAG TGCTAGGATT ACAGGGGTGA
24661 GCCACTGCAC CCAGCCCTAA GTTCTTTGAG AAATTGCTGA ACTGTTTTCC ACAGTGGCTG
24721 AACTAGTTTA CATTCCCACC AGCAGTGTAT AAGCATTCCC TTTTCTCCAT TGCCTCACTA
24781 GCATCTGTTA TTTTTTGACT TTTTAGAATA GCCATTCTGA CTGGTGTGCA ATGGTGTCTC
24841 ATTGTGGTTT TGATTTGCAT TTCTCTAATG ATTAGTGATG TTGAACATTT TTTTGATATG
24901 CTTATTGGCG GTATGTATGT TTTCTTTTGA GAAGTGTCTG TTCATGTCCT TTGCCCGTTT
24961 TTTTTTTAAT AGAGTTGTTT TCTGCTTGTT ACTTTGTTTA GATTCCTTAC AGATTCTGGA
25021 TACTAGACCT TTGTTGGATG TATCGTTTGC AAACATGTTC TTCCATTCTG TAGGTTGTCT
25081 GTTCACTCTG TTGATAGTTT CTTTGGCTGT ACAGAACCTC TTTAGTTTAA TTAGATCCAG
25141 CTTGCCAATT TTTGTTTTTG TTGCAGTTGC TTTTGAAGTC TTCATCATGA AATCTTTGCC
25201 AGGGCTGATG TCCAGAAGAG TTTTTCCTAG GTTTTCTTCT AGGGTTTTTA TAGTTTAAAT
25261 TTTACATTTC AGTCTTTAAT CCATCTTGGG TTGATTTTTG CATGTGGTGA AAGGAAGAGG
25321 TCCAGTTTCA GTCTTGTGCA TATGGTTAGC CAGTTATTAT TGAATAGAGA GTCCTTTCCC
25381 CATTGCTTGT TATTTTCAGC TTTGTCAGAG ATTAGATGTT TTAGGTGTGT GGCTTTATTT
25441 CTGGGCTCTC ACCTGTTCCA TTTGTCTGTG TATCTGTTTT TGTACCAGTA CTGTGCTGTT
25501 TTGGTTACTG TAGCCTTTTA GTATAGTTTG AAGTTGGATG GTGTGATGCC TCTGGCTTTG
25561 TTCTTTTTGC TTAGGATTTC TTTGGCTATT CGGGCTCTTT TTTGGTTCCA TGTGAATTTT
25621 AGAAGTTTTT TGTTTGTTTG TTTTTTGGTT TTTTTTCCTA ATTCTGTGAA AACTGTCACT
25681 GGTAGTTTGA TAGGAACAGC AATGAATCTG TAAATTACTT TGGGCAGTAT GACCATTTTA
25741 ACAATATTGA TTCTTTCTAT CCATGATCAT GGAATGTTTT TCCACCTGTT TTTGTAAACT
25801 CTGATTTTTT TTTAGCAGTG TTTTCTAATT CTCATTGTAG AGATCTTTCA CATCCCTGGT
25861 TAGCTGTATT CCTAGGTATC TTATTCCTTT GTGGCTATTG TAAATGGGAT TACATTCTTG
25921 ATTTGACTCT CAGCTTGGAC GTCATTGGTT TATAGAAATG CTACTGATTT TTGCACTTCG
25981 TTTTGTATCC TGAAACTGTG CTGACGTGGT TTATCAGATC TAGGAGTTCT TGAATAGAGA
26041 CTGTGGGGTT TTCTAGGAAT AGGATCATTA TCATCTATGA GGAAAGATAG TTTGACTTTC
26101 TCTCTTCCTA TTCAGATGCC TTTTATTTCT TTCTCTTGCC TGATTGCTCT GGCTAGGGCT
26161 TCTAGTACTA TGTTGAGTAG GAATAGTGAG AGAGGGCATC CTTGTCTTGT TCCAGTTCTT
26221 AAGGGGAATG CTCCCAGCTT TTGCTCATTC AATATGATGT TGGCTGTGGG TTTGCTATAG
26281 ATGGCTCTTA CTATTTTGCC CCTCTTTTTA AACTTTAATA TATTAGTAAT ACCTATTATT
26341 TTCATATTGT AATTATCTAC TTCCTCTAGC CTGGGAATTC TTTATAGGTC GGGGAGGGGA
26401 CAGTGGTAGG CTTTATCTAA CTCATCTTAG TTATTGTCAG TCTCAAGTAT GATTTCTGGC
26461 ACTTGGTGGG TGCTCACTAA ATGTTTGGGC TGAATGAATT CATATAAACA AGCTAAAAAT
26521 AGACTTGTAG ATAAATGATG GAGAACTTTA TTTAAACTTT GTCTTCTCTG AATTACTGTC
26581 ATTTGCTTTG TGATTTTAGG CTACTTCTTA GTTTATGAGC ACCATTTCTC AAGGCTGCAT
26641 TCTTTAAGAA ATATTAATAT TTGAGGAGAT ACTACACCAT CCAAAGATTG CCGCTAGTAT
26701 TTTCTAAGAT GTTTTTTAGG GAAAAAATTT AAGAATGGAG GGAAGAACCT AATCAGTGAA
26761 AGATGTGATC ATAAATAAGC AGACAGATTT ATAGGAATAA ACAGGTTAAG AATTTGAATA
26821 TAGAAATATA GAAAGGAATA TATTAGATTA AATTATAGAG TCCTAAAGTA GAGTGTAAGC
26881 CAGAATTATA TGTGCTCTTA CACATACCAC ATACTGTATA GGATTGTTTA TGAGGTTCAG
26941 TTGAGATAAT ATAAATAGAA GTGCTCGTAA GTAGGATGTT TGTTTCTGCA AAATGAATTT
27001 TATTAAATAT TTAGTGTACT GTAGATAAAG TGATTCTTAA GAATTTTTAA AAACTGGGCC
27061 GGGTGCGGTG GCTCGCGCCT CTAATCCGAG CACTTTGGGA GGCCGAGTTG GGCTGATCAC
27121 AAGGTCAGGA GTTTGAGCCC AGCCTGGCCA ACGTGGTGAA ACCCTATCTC TGCTAAAAAT
27181 TCAAAAAATT AGCCGGGCAT GGTGGCGTGT GCCTGTAATC CCACTACTTG GGAGGCTGAG
27241 GCAGGAGAAT CACTTGAACC CGGGAGGCGG AGGTTGCAGT GAGTCAAGAT TGTGCCATTG
27301 CACTCCAGCC TGTGTGACAA GAGCAAGATT TCCTCTCAAA AACAAACAAG CAGTTATGTA
27361 TTGCCATGTA ACAAATTACA CCAAAATTTA GCAGTTTAGA GCAATAAATA TTTATTATCT
27421 TAGTATTCCT ATGGGCCAGG AATATGGCTA CAGCTTAGTT GAATGCCCTT TTACTCATGG
27481 TATCTCAGGA GGCTATAGTC TTCCTATAGT TAGGGTCAGT TGAAGCTGCA GTCATCACAA

Figure 7H1

27541 GGTTTGACTG GCAGAGAATC TGTTCCAAGC TTAATCACTT GGCTCTTGGT GAGCCATAGG
27601 TTGCCTATAG CTGTTGGCTG GATACCTCAG TTTCTTGCCA CCTGTGTCTC ACCTTAAAGC
27661 AGCTCACAAC ATGGCAGCTG ACTTCCCTTA AAGTGACTAA GAGAGGGTAC CACAACAGAA
27721 GCCAGTCTTT TTGTAACCTA ATCTCAGAAG TGACATGCCA TCCCTTTTGC CATATTCTAT
27781 ATTTGTTAGA AGTAAACACA CAATAGGAGG GAATTACACA AGGTGGATGG CGTAATTGAA
27841 GGCTGTCTTA AAGGCTGCCT ATCACAGTGC AATTAGTATG GCATTAGTAT GAGAATTCCA
27901 GTGATGCAAA AGTGAAAAAT TCGACAAAAA CAAGTACAGG AAGCAAGTTG AGGTTGGTTG
27961 GTTGGTTGGT TGGTTGGTTT TACAACTTTT AATGCATAGA GGGTAAATTG GCCAAAAAAA
28021 ATTAGTCAAG AACAGAAATA TGTAGCTTGT CAGCAGTTAG TTGGAAAGGG GTAATAAGCA
28081 ATGAATTTGA ATAATTTACT AAGAGATAAT ATTACTGTAA TGTGTGTGTT CATGGGATCA
28141 GTTCATCTCT TCCTATGTAT TTCTCATTTC TGTGTTGGTT CTGACGCAGG AGTTTTTTCC
28201 TGTTTGAGTG AGATCCACTA ATGGAGGATT GTTATTTGAT GCTTAGGACT TGGGATTGAG
28261 CAGAAAACAC TACTGTTGGC TTGTAAGATC ATAATCGGTG TTTTGAATAT GGAATATACT
28321 ACCTTCTTAA ATTTAGTTTT ACATGTGTGA GTGAGGCGGT TTCCCCTGTG CAGTTTTTCC
28381 TTGCACTTCT CCTTCCTGAA CCAATCTTAA TGAGGAATGT GTGTGACATG TACCAAAAAC
28441 TTCAAAACTT TAAGATAGAG AAAATATTTT GAAGATGCCT ATTCATAAAT TATTTATTGG
28501 TTTAATTTAT TTTCAATAAA AATTTCAGTG AGATGTTAGG TAGGCGCAAT ATTTCTGAAA
28561 TTTATCTAAA AAATAAGAAA GTCAAAGAAA ATTCTGAAAA CTATGTTTTT GTTTTTGTGT
28621 TTTTTTTTTG AGATGAAGTC TCACTCTGTC ACCCAGGCTG GAGTGCAGTG GTGCGATCTT
28681 GGCTCACTGC AAGCTCCGCC TCCCGGGTTC ACGCCATTCT CCTGCCTCAG CCTCCCAAGT
28741 AGCTGGACTA CAGGCACCCG CCACCACACC CAGCTAATTT TTTTTGTATT TTTAGTAGAG
28801 ATGGGGTTTC ACCGTGTTAG CCAGGATGGT CTCGATCTCC TGACCTCGTG ATCCGCCCAC
28861 CTTGGCCTCC CAAAGTGCTG GGATTACAGG CGTGAGCCAC TGCACCTGAC CCTGAAAAGT
28921 ATATTAATGG GGAAGGAAAA ACAGACATGC CTTACTACAT ATTAAAATGT CATTTCAAGC
28981 AGTAGTAGCT AAAACATCAA TACATCATGA TAAATCAGTG GATGAGAACA ACCCGAAAAT
29041 AAAACCCTAC CATTTCTGCG AATGAAGTAT ATAATCATTA TCTAATATAG CTAATATGTA
29101 ATATGTAGTA TATAACATGT AATGAATATA CATAAGATGT GTAAAGGAAT TCTGCATTTT
29161 TAGACCTCCC ACAACAATTT TAAATAGTGA CAGTGATACG AATAATATTA TGATTATTTT
29221 GGGACTCTTT TAACATTAAT TTTAACAAGA ATGTATTTTG TGTTAAGTAT AATCTTGGTT
29281 GCTGGGGTTA CATAATTTAT CATCCTGTTA AAATCATTTT GTTGTCTCTA TTAGTCTTTT
29341 CATTAAGAGT GATATGTCCT TTTTTCTATC AAACTACTAA TGTCTTTTAG AAATTATTTC
29401 TGCTACCAGG ACAGATTTTG TTTTACTTAT TGCTTAAGAT TGTTAACTTG CAAAACGAAG
29461 TGAAGTGAAA ATTTAATCAA CTGTGTAGAC TGTCCTAACT ACCTTAATCA AGTAAAAGAA
29521 TTTACTTGAC TTTGTTGCAA TCTGAGCTTT TATTTTGTCA AAGTCTAGTT ATCTTATTAA
29581 GTCTTCAGTA GAAGATATAA TTAATACTTG GTGATTTCTA AATCTGAATA TTGGAGAAAA
29641 GGGCACCAAA TTGAAGAATG CTAGATTTTA AATATTTTCT AGAACTTTAA TCTATATGTT
29701 CCTCAAGGGG AATTATTGTT AAGCACTGTC TTGATGTGGG AAAATAGATC CACAAGAAAC
29761 AGGAGTTTCT TCTTCCCAGC CCCTAAAGAT ACACTACATT GTAACTTTAG ACTTGACTGA
29821 ATTTTTCAAT GTAGTGCTGT CTTTGCATAG GTGTATGTCT TTGCACAGAT GGTGACTAGT
29881 AGAATGTGGA TTCCGCTTCT CATCCCATCA TACTTGTTTA GTTTTTCCGG GTGAATATAT
29941 AGCCAAGTTT TAAAAGCAAT GCTCTGAGAT TCTTACTCCA CATCTTGTTA AATGGCGATT
30001 GTGAACCAGT AGATCTGGAG TAGGGTTTGA GAGTCTGCAT TTCTAACAAA CCCAAAGGTG
30061 ATGTTATGCT CTCAGCAAGG TTCTAGACTG CTAAATTTCC TATATAGACT TAGTTGTTGC
30121 GATGTCTTTA TTCAAAAAGA ACTGCTTTGT TCTTGGTCTT ATAATTGTAA GATATTTTGT
30181 TAGGTGAGTC CCATATATTT TTTCTCACTT AATCTTCACA ACACCCCTGC AAGACTGTAA
30241 TACATGTTCA TTATGGAAAA TTCAGATAAG CAAAAAGAAG AAAAATAAAA GTTACGTAGA
30301 TACCAGAAAT TAAAATAATA TTTATTTATA AGTTTAAGAC TCCAAGTGAA GATTAAAGTT
30361 CTAAAAGGAA CTAAAGTTAT AGCTTCGGGA GTATTATATG CATTTTCCCA CCTTAAGTAA
30421 AGAAAACAAA ACATTGTGGG AGTAATATGA CTGAAACTAA AATGTATTTA CTTAGAAAAG
30481 ACCAGAAGAA AATGTCAGAG CATACAGTAG TTGCATTAGG GTGACAGGAT TATAACAGGC
30541 ACTTTTTCCT TTTATCTGCA GTCCACAATA TTTATAATGT GCATATGTTA CCTTTACAAT
30601 AAAAATTTAA AAACCTTAGT CTTCTCAGAA ATGCCACTGA GGAAAAGGTC TGAAAGTTAA
30661 TAATAACTAA ACTAAATAAA TACTTTACAA TTTAAATGAA AATCATCAAG ATGGACAAAG
30721 AATAATTCAC ACAAGTGAAA AATGGTAAAT GAACAACTGA AAAGAATAAA TCAAATACAG
30781 CTTTGGTAAA ATAGTAAACA GCTTTACACA ATAGTAAAAA AACATGCAGC TAAGCAGGTA
30841 TCTATCTTTT CCAAAAGGAA GTATTTTAGA GCTAACAACC AATGCTGACA AGGCACAGCA
30901 AAACCAATAT ATTTGTTCAT TTCTGGTAGT AGTATGCATC CTTTTGAAAG GTAATGTGAT
30961 TAACACAAAG ATTCATAAAT ATTTAATGGC AATAGAATAC AAAAATACTA TACACACTCC
31021 ATCTGTCACT ATGTAACATG TTTACATGCT GAAAGACAAT CTTTTGGGGA AAAAACTCTT
31081 TTTTGAGGAT AAAGAGATGA GATTACCGAG TGCTTTAGTG TTTGCTTAAA CATTCTTTAA
31141 GTCTTCTTAA CTTAAAAAAA GCAAATAACC AAAGTTAACT TTACATATGA TAGCCCTCTA

Figure 7I1

31201 TCAAGTAAGT AAACCACATT TTGCATATTA TGGATGTTTA TGCTTTTTTG TTTGTTTTTA
31261 GCCCTCTTTA GACAAATTCC TATAGAATTT TCCTAAATTA GAAACAAGTC TTGAGATTTG
31321 TTTTTAACTT TCCTAGTACT AAAGTCAACC ACTTATTCCA AATTTATTGA ATTCACCTGT
31381 ATGTGGTACA ATTATTATCT AGTTATCATA CAGGGAACGT AGAATTGGTA CCACAAGGAA
31441 ATAATGATTT TAAGAAATAG AAAGATTTAA AGGTATTATT TCAGAAATGA CTGGAGAACT
31501 TTAGGCATTA AAAAAAAATC TGTAAGTTCT GGTTTCAGTT TCTTCTCTTC AGTGTCCAAA
31561 ATTGCATCCA AAATAGCACA GCCACTGCCA AACATGTGCA TTAAATCTTG GAAAGCAAAA
31621 AGAGAAATGG TCTGTACCAG TAAGCCACAG TATTAAAAAG TTTAAGCAGA GACTTTCAGA
31681 AGTAATCGGT CAGGTGCAGG TTCTGTAGAA ACTTGAAGTC TTACCTAAGG AACAAGGTAA
31741 AGGAATGTAT AACATATACC ATGTTACATG AACATAACAT TTAATATTGC AAATACTTTA
31801 CAGAGCTATT ATTTTATGTA TATCCTTGTC TGAAATGATT TGTCTCCACT TGAACCTTGT
31861 TGACTGTTTT TCTAGACTTC TTAAAACTGA AACCAAATAG CATACCCTAA TTATCTAGTT
31921 GAGTATTTCC CAGCCATATG TTGGGTGAGA GCTGTTGGCA TTTTGGACAA GACACTTCTT
31981 GTGCTGGACT GCCCTGTGAT TTTGTGTCCC ACTCATTACT ACCAGTTGCA ACCCTCAGGA
32041 ATTGAGTACT AGAAACACCC TCACAGTTTT CATGGGGTTG GTGAGCAAGT ACCTTCTGTT
32101 GAGAATTGGT CTAGTCCTTT GAAGAATGCT AGGTAGCTCT TTCTAAAATA GGTTAATTTC
32161 ATGTCATAGT GTTTAGGTAA AAGCTTCACA TTGGACATGA ATAAAAAGGA TTAGAGTTCA
32221 GTGTATTCAG GAAACTAATA TAAGATCTTT GAATCTTCTT ATTTTGTTCC AAGATTGATG
32281 AAATTCAGGA GAGGACTTGC TACAGTGTTT TTGGAGGGTA ATTTTGCACT ACTGTTTGAA
32341 TCAAAATTTT AAATTACGCA TTTGTCATTA ACTCCACTTC TAGGAATCTA GCCTGTAGGA
32401 ATCTTGGAGG GCATAAAAAA TTATTTGCCA GGATGTTCAT TTGCAGTATT ATTGGTAATC
32461 ACAAAAATAG TAAAAACTAA AAAAAAGAAC GAAATAACCA ACAACAATAT AACCCCACCT
32521 ACCTGAATGA GTATTATAAA TAGAGAAAAG GTTAAATGGG CATATAGTAC ATGCTATACG
32581 TTTATTATTT AAAAGGAACC AGGACTCTAT ATCCTGAATA AATTTTTAAC AATGTATTAT
32641 TAAAGGAAAA AAAGAACAGT ATGGGCCATG CACAGTGGCT CACACCAGTG ATCCCAGCAC
32701 TTTGGGAGGC CAAGGTGGGC AGATCACAAG GTCAAGAGAT CGAGACTATC CTGGCCAACG
32761 TGGTGAAACC CCGCCTTTAC TCAAAATACA AAAATTAGTT GGGCATGGTG GTGCACACCT
32821 GTAGTCCCAG CTACTCGGGA GGCTGAGGCA GGAGAATCAC TTGAACCTGG GAGGCAGAGG
32881 GTGCAGTGAG CGGAGATCAC GCCACTGCAT TCCAGCCTGG TGACAGAGTG AGACTCAGTC
32941 TAAAAAAAAA AAAAAGAATG TTATGATTAG TATGATCTTC AGTTTTGAAA TAAAAATGTG
33001 TGTGTATGGA TAAGTAAGGC CTGGAAGGTG ACTTCTTATA TTGTTGAAAC AAATAAATAA
33061 AAAAGTAGAA CCAAGGCTTT CAAAGGTTGA GAAAGGGAAT AATACTTCCT TTGTTTTTCT
33121 AGAACATGAT TGGTCCTCCC ATCATTTTCC TTCATTTCTT CCTTTAGACT GCACAGTTGC
33181 ACTTGCAGTA AACCCTTCCT CTTGAATCCC TACCCAAAGA TATTTTGAAA AGGATCTAGT
33241 AACTAATGGG GCAATAAGCA GCACTATCAT CATGGGCACC TTAGGCTCAG AATTTGTCAT
33301 GTTTTAACTG TTTCTCTGTC TTTGCTCCCA TGTCATCTTC AGTTGTTGGG TCCAACTTGC
33361 ACATCTTTTC CATATACCTT TATTGTTCTT CCTGTCTTTA TCCTAGTTCA CTTCATACCT
33421 AGATTATTAT AGTAGCCTGT GAAGCTGGTC TCTTTTCGGC TTAAGTATTT CCAGCCGTGG
33481 AGAGTATACC TCAATGAAAA TATTGCTGTA GCAATTTGTA CCTCTTTACT CTATAATTTA
33541 TTTTTTATCT TACCTTTTTT TAGTGGTGGA GTAAGAAGGT AAAGGTAAAG GGAGATATAG
33601 GAGCTGATAC TATTGTGTTT CAGTACTGGT GATCTATTGC TAAATAATTA TATAAGCTTG
33661 CATACTGACC CAACTCTTCT AGAAGGGAGA GTGTTAACAA AACTAGGAGA GAGATTGTAG
33721 CCAAGGTTTA AAATGGATAT ATTTATGGGA GAAGCCTGCT TAGTGAATTG TGTTTTAGGG
33781 TAGGAATTCT GAATGAGTAA GCATGTCTGC TCTTTTTCTA ATATCTGTTA AGTTTGGGGC
33841 TATTTTATTC CATGTCTTTT ATCTTCCCTT TTAGAAATCC CTCAGTTGAA TTAAGAGGAA
33901 AAAAGATCAT TTAAAAAAAT ATCTAGACTA GCATTGTATG AATGAAGACT GCAGAAATCT
33961 GTAGAAACCC GCTAGAAATT GGTCAGTTAG TAAGGTGTAT CCCCTTGATA GCAATTTCTC
34021 ATATGGAGGA TGTAGTAGGG AGGTCATAGC ATCTGGAGAG CTTTTTCCTA AGTGACAGTC
34081 ATCACATTCT GAGATGGCAT CCCACTTATC ACCTTTCTCC CTTTGAGAAT CAGTTTTAAT
34141 GAGTCATTAT TACTAAGGGA ATGTGTTTTA TTTCTCATGT GCAGGGGCAG AAAATTAATT
34201 TGGAACAGTT ACCTTAAAGA AAGTGAGTTG GCAGTAACAG TGATTATTTC CTTCACTCCC
34261 ATGCCCAAAT CTTTCATACT CTTTAAGGCT GAAAACTGCC ACTTCCTGTA GGAAATATTC
34321 CCTGCTTTCC TTCTGGCCTT TCCTATTTAA TTTGTCCCTC TTCTGATCTT ACTTGAATCT
34381 TTTTTATGAC CCTTGTTATT TTCTACATTG TACTATAAAT TATGTGTGTG CTTATTAAAA
34441 AATCTATATT CTATACTAGA AACTCTTCCT AGAGCAGAGT ACATGTCTAA CGCCTCTTGT
34501 ATTCTCACAG TACTTAATAG AACATCTTGC ACATAATATA GAGGCTCAGC AAATATTTCC
34561 TGATCATATT ATTAATTGTG AAGTTTGCTA GGCAAAAGTT AATGAACTTC AAATGTCATT
34621 GCTCTTCTAC CCCTTTAAAA TGTCTTTTAC CACAGAGAAA AATTAGCAAA AATTATAAAG
34681 CTGATATCCA ATAACTGAAA TTAGGAAAGC AATGTATTGA AGAAGGAGCT AGTGTAAATC
34741 TAGAAGTGAG TAGAGATGTA GATAAGCAGT GAATTTTATA AAACCTTGTG GGTAATGCAA
34801 AGAGTTTGAC CTTTTTCCGT ACTTGAAGAG AGCCATTTGA AGACTTTTAA GAGGGGAGTC

Figure 7J1

```
34861 ATTTGATCAA ATTCGTGTTT TAAATAAATT AGTGTGATAC AATGAGGAAG CTAACTGTAC
34921 AGATAGTAAC ACCAGAAGAT GGGAACCCAA TTAGGTTATT GCAAGAATCT AGGAAAGAAT
34981 AAATCCTAAA ATCTTAGAGC AGAGGCAGTA TAGTAGGATA AAAGAGAATA GATTTAAGAA
35041 ATACAGATAA AATTGATAGG CTTGGTGCCT TATTTGATGT GAAGTAAGGC AGATGGAAGC
35101 ATCTTGATGA GGCTTTAGAG ATTGAAGTGC TGACACCTAA GTTAGAGAAG GAATATAGGG
35161 AGGAGGGAGA ATAGCAGTAA CTTTAGTGGC TGAGATGAGT TTTGAATGTG GCGATATTGG
35221 ATTGTCTGTA AGAGAGCCAG TTGAAGATGT CCAGCAGTCA GTTGGTTATA TAAGACTCAG
35281 GTTTATGGAG CGGTCAGTCT GAGAATCATC AGCATATAGA TTCAGAGTAA GAGTGGCTAG
35341 AGTTTGTCCT AGAGAACATG TATTACTGAT TTTTTTTTTT TTTTTTTGGG GATGGAATCT
35401 CACTGTCGCC CAGGCTGGAG TGCAGTGGCA GCAATCTTGG CTCACTGCAA GCTCCGCCTC
35461 CCGGATTCAA GCGATTCTCC TGCCTCAGCC TCCTGAGTAG CTGGGATTAC AGGCATGTGC
35521 CACCACTCCT GGCTAGTTTT GTATTTTTAG TAGAGATGGG GTTTCTCCAT TTTGTCGGGC
35581 TGGTCTCAAA CTCCTGACCT CAGGTGATCC ACCCGCCTCG GCCTCCCAGA GTGCTGGGAT
35641 TACAGATGTG AGCCACCGCG CCCGGTGTGT TGTTGATTTT TAGAACCTTT TTTTCACTGT
35701 TTTCTCTGGT GTTTCCATTA GCAAGTATTT GTTACGGTTT ACTTTCTATT ATTGTTTTTA
35761 TTATAGAAAC AGTGTCTTTC AACCTGAATT TAATCATGAG GGGAAAAAAA TCAAAGCAAT
35821 CCTAGTTGAG GAACACTGTG AAAAACAATT GGCGTTAAGT TTTCAACAAT GTGTGTCTTG
35881 AAATATTAAA AATATAGGTT GTGGAATTGT TCAACGTTAA AGGAGACTAA AAGAGACGTG
35941 ATAACCAAAT GCAACCTGAT TTGATTGATT GATTCCAGAT AATCTTTTTA GAGGACATTA
36001 TTGGAATAAT TGGAGAAATT TGAATATGGA TTGTATTTTA GATAATAGTA ACAATGTTAA
36061 AATGTGATAA TTTATTGTTG TATAGGAGAA TGTCCTTTTA CGTAGGGTAA AGTGCCATAA
36121 TGCAACAACT GCAGTGGTTC AGCACACACA AAAAAGTATG TGTAAAGTGA TAAAGCAAAT
36181 GTAGTTTGCA TTGTAAGTGC TTCTTATGTA AAAATGTATT TTTATAAAAG TGCCTAGTTT
36241 TCTTATTTCC TTCTTTTTTT TTTTTTTTTT TAAAAAGACA GACTGTCTTG CTCCGTCTCC
36301 CAGGCTGGAG TGCAGTGGCA TGATTACAGC TACTGCATCT TCTACTTCCT GGGCTCAAGC
36361 CATCCACCTG TCTCAGCCTC CTAAATACTT GGGACTACAG ATGTGTGCCA CCACAGCTGG
36421 CTAATTTTTC TGTAGAGAAA CTCCCAATTT TTCTGGTCTT GAACTCCTGG GCTCAAGCAG
36481 TCCTTCTGCC TCAGCCTCCC AAAGTGCTGG AATTTCAGGT GTGAGCCACT GTGCCCAGCT
36541 TAGTTTTCTT AATATATTTT TGCATGTGGT AGCATATTAG AGGTTGAATA CAATTGTATT
36601 TATTACATGT TTGTGCTTTT CTCTATTGAT TATGGGAAAT TGTTAAGACA AAAATCGCAT
36661 TCACTGTATA GCAGCTGGTT TATCCTGTGG TTCTTCTCTT TGCAGGCAAA CTTACTAAGT
36721 AAATGGACCA GAATAAATTA TTTTCATAAT CTATTATTAT TAAACCCTGT ATTAGTCAGA
36781 ATGGGATATA ATCTCAGTTA TTTAATACAA CTAGGGTTTA TTCTTGCTCA CATTACTTAT
36841 CCAACAGTTT GTCAGGAAAT AGATCTACTC CATACAGTAG CTCCAGAAAC CACACTGATG
36901 GAATTTCTGA CAGTGTATAT CTGTACACCT GGAACATTAG TCCTCCACGG TGACCACCAC
36961 ATGGAAATAA AGAGCTAGAA GGTCTTCTGT TGGCCGTTAA ATATTTCAGC CATGAAATGA
37021 CACCCAGGTC ATTCAGGCAC TCACAACCTA GTAACCAGAA CTAGTTACCT TACCCTACTG
37081 GTAAGTGTCT GGGACATGTG GGAAGCACAG GTTGTTTGGT GAACTGTAAA TGTGTCTGTC
37141 ACATATTGTA CTTCATCTCA AGAAATATGC GTAGCCTTTA AACCTATGGA TAATGGCCAT
37201 TGTTGCCATA ATTCTGCCTA TTAAATTGTA CTAAAAAAGT GTTACAGGCC GAGTATCTCT
37261 AATCCAAAAA TCTGAAATCC AAAATGATCC AAAATCCAAA ACTTTTTGAG TGCCTACGTG
37321 GTGCCACAAG TAGAAAATTC CACACCTGAC CTCATGACAG GTTGCAGTCA AAACTTTAAT
37381 GCGCAAAAGT ATTAGAGATA TTGTATAAAA TTACCTCTGG GCTATGTGTA TGGGGTGTAT
37441 ATGAAACATA AATGAATTTT GTGTTTAGAC TTGGGTCCCA TCTACAAGAT ATCTCATTAC
37501 GTATATGCAC ATGTGCCAAA ATTTGAAAAT CCGAAATTTG AAACACTTCT GGTTCCAAGA
37561 ATTGACACTC AACCTGAATC ACTTTCAGTG ACAAACAGTG GCTTTCCTCT TATATATTGA
37621 CTATTTCTCA CATAATCCAT TTTTATTTAT TACTTTCAAA ACTATATAAT AAATGTAAAC
37681 TGATTTTGAG AGTTTAGTGA TTTGCCCAGA GTTACAGAGT CTGTCACTTG GAGAGCTTGT
37741 AGAGTTTTGA GATTTTGCTT TGCCATTTAA ATTTAATGAT AGCTACATTT AAATACTATT
37801 TTAACCTGAA ACTTTTTAAA ATATTTTTAA AAAGGAGTTT TTTCCTCAGA TTTTTATTTT
37861 TCTTCTTAAA ATTTATATTA TTTACATTTA AAAAATAGCA TTAGATAGTG TTTTCAGAAT
37921 GAAGTCTATC AGCCCTGTAT ATAATCATCC TTTTTTCTTG GGCACTTAAT TAGTTAGACA
37981 TTTCTCAAAG GTATAAATTC TAATGTAGTT CTTAAAAAAT ATCCAAAATG TCCTATATTA
38041 TAGTTTATCT TAAACACATT TGAAATGTCT ACATATAATA GATTGATGAA ATCTATATAA
38101 ACTTTAGTAA CATGTCTCTA AGATATGGCA CTACAATTAA TTTCTAATAT TAAAAATTTT
38161 AATAGAACCA CAAACAATAG AAAACATTTT AAATTGTATT TAATTTTAGG ATGTTTATTT
38221 TAAATCTAGT TATAAACAAA GTCAGTTAAC CAGATTCTTC AATGGACTTG ATCCCTGTAC
38281 CACCCTTTCC TGCACACTTC TTTTTATTGA ATTAGGTAAA TTGTAAACCA AAAGCTCTTA
38341 CTAGATGAAG TTCTCAGGTC AGTACAGATT CAACAGTCTG TTATACCCCT GTAATTCCTG
38401 ATTGGAGTTT TGTTCTCAAA ATCATACTCT TATGAACAAA CGCCAAAGCT ATATCATAAC
38461 TATGGAATGA AGGGGAGAGA GTTACATTTT AATATTTAAA ATGTTTAAAG CTTTACATGT
```

Figure 7K1

38521 TTGAAGCAGG TTTATTAGCT TAGTAGTTTT AACTTTTGTT CAATTATAAT CAAAAAATAG
38581 CTTTCATGTT TAATCTCTGA CCTTTGGTTT GACATGTAAA AATGATAAAT TTTATCATAG
38641 TGATACATTG TAACACATGC CCAAGTATCT CCAAAACTGA CTTCATCTTT TGTGAAAGTG
38701 ATGCCAACTG AACATACCAG GAAGTCTTAG GCATTTGTAT CAAACTGCCT AAGAACCCAG
38761 CTGTTAGCTT ATAAGTCAGT GAAATTATAT TTTATCATTT ATTATCATTG ATAGAACACA
38821 GACTAAAAGG AAATACATCT GAAGTCCATT TCTTTAATTC ATCATTATCT TCAGTGGAAA
38881 AAGATATGAG GAACAACATC ACTCATTGGA AATGAACTGT CTTTGTCATT TCATTTGTGG
38941 TAGTTGTCCT TTCTTCAAAA AGCTATTTCT TGAAGAAAAG GAAAGTTAGT GAAATTTGTT
39001 TTCTCATTAT ACTTTATCCA AATTTGAAGT TTCCTAATAA AAGTAGATAA TTGCCTTTTG
39061 GCAAGTTTCC TCTTTATTAC AAGTTCATGT AGGTGTTTGA GTTTGTTTTT CTTATTTATA
39121 AGAGGCAGAA GATGATACCT ATTTTCACAG TTACTTACTA ACTTACTGCT TTAGTTTGAA
39181 AGAAACTGAC AATGTTTCTT CTGAAACTTT TTAACAATAC AATTAATTAG CATCTGACTA
39241 AAAGTATCTC TTTGGGTTTT TAAATTGGAC ATGTCAGGTT GTTTAGTATC AGTTGTTTTA
39301 CTAAAACCAC GGAAGTGCCC TCAATTTTTA CAGCATTTTG TTTTTTGAGT GAATTTTACC
39361 AACCATTTAC ATTTTTTTTA AATTATACTT TAAGTTCTAG GGTACATGTG CACAACGTGC
39421 AGTTTTGTTA CATATGTATA CATGTGCCAT GTTGGTGTGC TGCACCCATT AACTCGTCAT
39481 TTACATTAGG TATATCTCCT AATGCTATCC CTCCCCACTC CCCCCACCCC ACAACAGGCC
39541 CCAGTGTGTG ATGTTCCCCT TCCCGTGTCC AAGGGTTCCC ATTGTTCAAT TCCCACTTAT
39601 GAGTGAGAAC ATGCAGTGTT TGGTTTTTTG TCGTTGCAGT AGTTTGCTGA GAATGATGGT
39661 TTCCAGCTTC ATCCATGTCC CTACAAAGGA CATGAACTCA TCCTTTTTTA TGGCTGCATA
39721 GTATTCCATG GTGTATATGT GCCACATTTT CTTAATCCAG TCTATCATTG TTGGACACTT
39781 GGGTTGGTTC CAAGTCTTTG CTATTGTGAA TAGTGCCGCA ATAAACATAC GTGTGCATGT
39841 GTCTTTATAG CAGCATGATT TATAGTCCTT TGGGTATATA CCCAGTAATG GGATGGCTGG
39901 ATCCACTGGT ATTTCTAATT CTAGATCCTT GAAGAATTGC CACACTGTCT TCCACAATGA
39961 CTGAACTAGT TTACAGTCCC ACCAACAGTG TGAAAGTGTT CCTATTTCTC CACATCCTCT
40021 CTAGCACCTG TTGTCTCCTG ACTTTTTAGT GGATCGCCAT TCTAATTGGT ATCTCATTGT
40081 GGTTTTGATT TGCATTTCTC TGATGACCAG TGATGATGAG CATTTTTTCA TGTGTCTGTT
40141 GGCTGCATAA ATGTCTTCTT TTGAGAAGTG TCTGTTCATA TCCTTCGCCC CCTTTTTGAT
40201 GGGGTTGTTT TTTTCTTGTA AGTTTGTTTG AGTTCTTTGT AGATTCTGGA TATTAGCCCT
40261 TTGTCAGATG AGTGGATTGC AAAAATTTTC TCCCATTCTG TAGGTTGCCT CTTCACTCTG
40321 ATGGTAGTTT CTTTTGCTGT GCAGAAGCTC TTTAATTAGA TCCCATTTGT CAATTTTGGC
40381 TTTTGTTGCC ATTGCTAAAT GGCATTACTC ATCATTTACA TTCGGTAAAT GACATGTCAT
40441 TTAGTAATGA CATGAAGTCC TTGCCCATGC CTATGTCCTG AATGGTATTG CCTAGGTTTT
40501 CTTCTAGGGT TTTTATGGTT TTAGGTCTAA CATTTAAGTC TTTAATCCTT CTTGAATTAA
40561 TTTTTGTATA AGGTGTAAGG AAGGGATTCA GTTTCAACTT TCTACATATG GCTAGCCAGT
40621 TTTCCCAGCA CCATTTATTA AATAGGGAAT CCTTTCCCCA TTTCTTGTTT TTGTCAGGTT
40681 TGTCAAAAAT CAGATGGTTG TAGATGTGTG GTATTATTTC TGAGGGCTCT GTTCTGTTCC
40741 ATTGGTCTAT ATCTCTGTTT TGGTACCAGT ACCATGCTGT TTGGGTTACT GTAGCCTTGT
40801 AGTATAGTTT GAAGTCAGGT AGCATGATGC CTCCAGCTTT GTTCTTTTGG CTTAGGATTG
40861 TCTTGGCAAT GTGGGCTCTT TTTTGGTTCC ATGTGAACTT TAAAGTAGTT TTTTCCAATT
40921 CTGTGAAGAA AGTCATTGGT AGCTTGATGG AGATGGCATT GAATCTATAA ATTACCTTGG
40981 GCAGTATGGC CATTTTCACG ATATTGATTC TTCCTACCCA TGAGCATGGA ATGTTCTTCC
41041 ATTTGTTTGT ATCCTCTTTT ATTTCGTTGA GCAGTGGTAT GTAGTTCTCC TTGAAGAGGT
41101 CCTTCACATC CCTTTTAAGT TGGATTCCTA GGTATTTTAT TCTCTTTGAA GCAACTGTGA
41161 GTGGGAGTTC ACTCATGATT TGGCTCTCTG TTTGTCTGTT ATTGGTGTTT AAGAATGCTT
41221 GTGATTTTTG CACATTGATT TTGTATCCTG AGACTTTGCT GAAGTTGTTT ATCAGCCTAA
41281 GGAGATTTTG GTCTGAGATG ATGGGGTTTT CTAAATATAC AGTCATGTCA TCTGCAAACA
41341 GGGACAATTT GACTTCCTCT TTTCCTAATT GAATACCCTT TATTTTTTTC TCCTGCCTGA
41401 TTGCCCTGGC CAGAACTTCC AACACTATGT TGAATAGGAG TGGTGAGAGA GGGCGTCCCT
41461 GTCTTGTGCC AGTTTTCAAA AGGAATGCTT CCAGTTTTTG CCCATTCAGT ATGATATTGG
41521 CTGTGGGTTT GTCATAGATA GCTCTTGTTA CTTTGAGATA CGTTCCATCA ATACCTAATT
41581 TATTGAGAGT TTTTAGCATG AAGGGCTGTT GAATTTTGTC AAAGGCCTTT TCTGCATCTA
41641 CTGAGATAAT CATGTGGTTT TTGTCTTTGG TTCTGTTTAT ATGATGGATT ACGTTTATTG
41701 ATTTTTGTAT GTTGAACCAG TCTTGCATCC CAAGGATGAA ACCCACTTGA TCACGGTGGA
41761 TAAGCTTTTT GATGTGCTGC TGGATTCGCT TTGCCAATAT TTTATTGAGG ATTTTTGCAT
41821 CAATGTCCAT CAGGGGTATT GGTGTAAAAT TCTCTTTTTT TGTTGTGTCT CTGCCAGGCT
41881 TTGGTATCAG GATGATGCTG GCCTCCTAAA ATAAATTAGG GAGGAGTCCC TCTTTTTCTC
41941 TTGATTGGAA TAGTTTCAGA AGGAATGGTA CCAGCTCCTC CTTGTACCTC TGGTAGAATT
42001 CGAATCCATT TACATTTTAA TATAGGATTA CCAGGTTTTT ATGCTGCTAA GGACATTTTT
42061 GTAAAAATTA TTCCCCCAAA AAATTAGTTT AATAAAAGAG AGGGCATTTT ACTACCAAAA
42121 GGTAAAGTAG GAAAGGTGTA TCTTCAGAAT AAAAGACTGC CCTTCCATAT ATTTCAGTTG

Figure 7L1

42181 ACATTTTTAT GCTGATATAG TATGTCTCCC ATTATCTTTA TTTCTCTCCT ACCTCTCTTT
42241 TTTTTTTTAA GAGATAGGGT CTCATGAAAC TGCCCAGGCT GGCCTTGAAC ACCTGGGCTT
42301 GAGTGATCCT TCCACCTCAT CCTCCCTAGT GGCTGGGACT ACCGGCATGT ACCACTGCAC
42361 CGAGTATTAC TTTTTTTCTC TTTACCATGT GCTTCTGTGA ACTTTATTTT AATCCTTACT
42421 TGAAAAGCAT GATTTTGAAC ACACCCTGTG ATGAAGGTTA CAATGCTTAT TGCAATATTG
42481 CAATAGAAAA GGAGCTTTCA ATTTTGTAGG CAAAGTTTTT GTGTGCCAGA TCCCTGACTG
42541 AGAAAGAAGA TATTTTCATT TAAAAGTAAG CAAATAATCC TCTACTTTTT TTCTAACACA
42601 GCAAATTGAT CCATATGCAT AATGAAAAAC CTCTGATATT GAACATAGAG ATTCTTATTA
42661 ATTGCAGTGT TCACAGGATT AGAATTTAAA TACACAAATA GGTGTCTGCA GCTATCAATA
42721 CCAGATGACT CAGTAAGCTA AATACAGACT TTAATAGAAC TATCTTGGAT GCCTTTTAAA
42781 ATATCTTTTA AACTTGTTGT CAGGTATTCT GTTTTATCTT TTGATTTCTA AAATGGGTTG
42841 TAACATTTGA GATTCACTGA AGTTTCTTTT GTATTTTTTA TGGCAATAGT ATTTTGCCAT
42901 TTTCAGGATA GAAATACTCA TTTTTGAAGC TATTACAGTA GGCAGCTTTT TTGTAAGGTG
42961 ATATGAATAT CAGAGAAATA TAACTACATG TTATACTTCT GATTTCATGG GATTAAAAAA
43021 AGAAAAGGCT TCTCAAGTGA CACAAATGCA TATGTTTTCA GAGACTAAGA AAGCATAAAT
43081 TGATGATGAC AGAACTTGTA ACGCATTTAG ATTTGTGTCA CTTGAAAAAC ACTTGTTACA
43141 AGCATGTTGT CAATTTGTGT ATTTCAACAA ATAGCCATTT TAAAGAAAAA CATAAAGTAA
43201 ATAATAGTAC ACTGATGATA TTCAGATATG GTGAAATCAT ACAGGTAGAC CTTGAATGAA
43261 TAATGAGCAC ATTGCTTTAG GACAGATGTG ACTCTCAACT TTTGATATTT GACTGTGTGA
43321 GTTTAAAGTT GATGCTTTAA TTTTTTAATA GGTCAAACTT GGGAATCTAA TGACTGATAG
43381 TATTTTTGAT AAGAAAGCAC TAATATAGAA CAAGAAACAG TGTTCTGAAA TGAAAATTAT
43441 CAGACTTCCA CTTTCTGTTC ATATCTATTT CAAAAAATGT ACGTGGCATA TTATGTTCTT
43501 TGCTACTTAG TGGCTATTAA AATGGAATCA TTTTATAAAT GTCTTTCAGC AAAGAAAAAT
43561 GTTGTCTGCT GCTGTGATCA CCCGCCACTA AGTACTGTGC TCCTCCTCTC AGTAGCTTGA
43621 CCACCTTATA TACTTTATGT GGCATCTTTA ACCTGTATCT GTCACCTTAC ATATCTTCTT
43681 CTTTGTTCCT TAATTTTTTT TTTTTTTCAA AGACTGCCTG GACCTACTCT CTCATTCTCT
43741 CCTCTGTATT GCTGCTATAG TTGTCACTTT CTTCTACATT CCCATTCTCT GCTTTGGCTG
43801 CTGTAATTAT CTTTTGCTTT TACTATTTTG ATCTTGTCAT TCAGGACTGT ACTATAAATT
43861 ACATTTTACC ATGGGTTAGG TTTACCTATC TTCAAAAAAC TTCAGATTAC CTTATTCTCT
43921 CCTCAATACC AAATAATATA CTCTAGTTTT CTTAGCTAAT TTTTAAGCGT CTCCCCATTC
43981 CTCCAGATCC ACCAAGAAAA ATTCATCCTA CACCACATTT TTACCCCTGG ACCTAAAGTG
44041 TATTATATGT TCTTGAACAG GAAAATTTCA TCTCCTGAAA AAAAAAAAAT TACTGATATT
44101 TCCATGAGTA CATATTGATT CTGGTTTGAC TACTATTTTG AAATAGAGTG GATGTAAAAA
44161 TCTATGATGA AATCTTAAAA CTAGTAAAAT TATCATTAGA ACTAGTATTA TACATGGAAC
44221 TATTAGTCTG GTAGCATAGT CTGTTATACT ACTCACACTA AAGCAAAATA AAAAGTACTG
44281 TCTTCACTTG GAACTGTTGT CTTACAATTC TGTGCCTGTC TTCACCATTT CATGAAAATA
44341 TTAATTGTTC TTCTTGGCTT ACTTTTTCTT TAATTTATGT TCTTGCCAGG TCAAAATCAA
44401 AAGTGATGAT TTAGGACTTG GGCATTTGTC GAGATAAGTT CATATTGTCA CCACTTTCCC
44461 AATTTTGAAG CTTACAAAAA AAATAGGCAG GATTTTAGTT TGCCTTCAGT TAGGGAAAGG
44521 AGAATTCATT TGCCACAGGA GTAAAATCCT ACGTTTTATA AAGCTATTTT AATGAAAATA
44581 CCAGCTTTCC AAAATGAATG GGACAAACAC AGAATTGATT GTTGCTTAAA AACTTTAACT
44641 GTATTGAGTT TTGGTAAATC ATAATTCAAA AATAAAATGC AGGGGGACAA GAAATTATTA
44701 ACTTTTTATT GTTGAAATAC ATTTTCCTCA AAGTGTTTTT TTGGTTTTGG GTTTTTTTTG
44761 TTTTTTTTTT TTGAAACGAA GTCTTGCTCT GTCACCCAGG CTGGAGTTCA GTGGCGTGAT
44821 CTCAGCTCAC TGCAACCTCT GCCTCCCGGG TTCAAGTGGT TCTCCTGCCC CAGCCTCCCG
44881 AGTAGCTGGG ATTACAGGCT CCCACCACCA CGCCTGGTTA GTTTTTGTTA TTTTTAGTAG
44941 AGGCGGGGTT TCACCATGTT GGCCAGGCTG GTCTTGAACT CCTGACCTCA GGCGATCTGC
45001 CCGCCTCAGC CTCCCAAAGT GTTGAGATTA CAGGCATGAG CGACAGCACC TGGCCCCTTC
45061 AATGTTTTTC TTAAAAATAT GTTACCAGTT TCTATCACTG CCCATTTTCC ACCTCCTTAT
45121 TTTTTGTATA ATGACCTTGA ATTTTGACCC ATTTCTTAAA AATTGGATTT TTATCATAAT
45181 TTTTATACTC TTACCCTAAA CCTATTAGTT TGATTTTTCA ATAAGAAAAA TCATGCTATT
45241 CATAGTATAG GTGAAATCTC ATCTGAGGTT ACCCACTTGA GTAGTATATT CATAGAAAAA
45301 GTATTTTGAG TCCTTAAGAG CCATGAAGAA AACAAAACTG AGGGGTCAGT TTTCTTTTGG
45361 CCATTGTCGA GTATTATACT TTTAACTTAG TATGAAATGT AGGAAATGTC CAGCATACTG
45421 GATACTTATT TCTCTGGAAT CACTCTGGCT GTCTAATGGT GGTATTTGGT ATTACTGCAG
45481 AAAGCACAGG TTTTGTTTTA GAAAGTCCTG GATTTGACTA TCTTACTCAT TTTATGAAGT
45541 TGTGCAGTGA TGAACTCTGA GGTTCATGTA CTTATATTAC TTATAAAACA TTTAAATTGT
45601 TAGGGTTGTT ATGCCTAAAC TTGATGATTT TATGTACCAT CGCAATTTTG TTGAGAAGAT
45661 AAATGCCAAA AAGCAAACCC TTGGAAAATT AGTTTACCTT TCTTTACCTT ACCTTTGATA
45721 AAGGGAATGT TAAAGGGTAA CTGATTTGAA CTACAGATTT CTTTTCTACC ACCTTTAAGG
45781 TCCTTTCCAG TATTATCTCT GTAAACAAAG TTAAAGAAAA ATACATTTGA AAGAAAAGAT

Figure 7M1

45841 TTGTTGTAAC TAAACCAATT AAAGCTGGCT TCTAGGCCAG GGCTGGTGGC TCACACCTGT
45901 AATCCCAGAA CTTTGGGAGG CCGAGGCGGG CGGATCACGA GGTCAAGAGA TCAAAACCAT
45961 CCTGGCCAAC ATACAAAATT ACAAAATTTT TGTAATTTTG TACTAAAAAT ACAAAATACA
46021 AAAATTAGCT GGGTGTGGTG GCGTGCACCT GTAGTCCCAG CTACTTGGGA GGCTGAGGCA
46081 GGAGAATCGC TTGAACCCAG GAGGTGGAGG TTGCAGTGAG CCGAGATCAC ACCACTGCAC
46141 TCCAGCGTAG ATGACAGAGC GAGACTCCAT CTCAAAACAA AAAACAAAAA CAAACAACAA
46201 CAAAAAAATG CTGACTTCTC AGGGCCAATG ATGTTATTCT CTGAGATATA TATATATTTT
46261 TTCCTTTCAT GGATAAGTTG AGGACATTAT CTTGATATCT CTTGATCTGA TAACTAGAGT
46321 AATCTTTGAA TATTGTTGTT AGTTATTATT AAAAACACTT ATTAAGGTCC TTTATGGAAA
46381 GTGACCAGTT TCCTGCTTTT ATATACATTC TTCTTTCTGT GGCCTGAAAC ATTATGTGGT
46441 CTTTGGTTAT TTACTTTACA ATTTAGTTAT TCTGATAAAT ACTCTTACTT TAAAAATTTT
46501 ATATCCAGAA GAATCTTTTT CTGCAGTCAC AGAAGTAGTC TTGGTTGACC TGTTTTGGCT
46561 TTCTGTGTAA TGTCTGTATT AGATACCAAC TGATTGATAT AAATGAGACT CTAAGGGGAT
46621 AATAATAAGT GTTAAGGCCC AATCAACACC CTGAGGCTGT GAAAATGTTC ACTACTATTT
46681 GTAGAAAGTT CATATATAAT ATGATATAAA AATTGCAAAT TGAGTCCTGG CAATATCTAG
46741 TCTTATAAAT GGATAGAGCA AGATGCACTT TTGAGTGAAT GAATTCCTGT TTTAAAGTGG
46801 TTAAGGATTA TATTTGCAAG TTCCAAGTTA TCTGTATTCT ACTAATTGTC CTATAGATGA
46861 CATTGTTATA ATTTGTTCAC TCACATTGTT GCTTTCCACT AAGATCTGTT ATTATTATCT
46921 TTAGGATTTT CTTATTTGTT AACATGATTG CTTAAGTGAT TAATCAAACT AAATCAGATA
46981 ACATAGAACT CAATGAATAT AGCTCTTAAC TTTGGATAAC AGCTATTTTC CTCTTGAACT
47041 AATATCCAAA TTTTTGATCT TTAAATGTTA CAACTGCAGT AAGCATGGAA TATTATTGAA
47101 ATAAATTTAA ATATAACTGT TTAATAAATT ATTAATTATG GATGATTAAT AAAATGTTTA
47161 GTGTGTTACT GAATGTTTCT TGAGAAAATT TTATATCAGT TTAAATAGTT TTGTAGCTTG
47221 TCAGCATTAC AGAATTTTTT ATTTTTTTAT TGTGTCATTA AGTGTAGTGG TTAAGAACAT
47281 AGGCCTGGAG TAAGATTTGA ATTCATATTC TGATTGTGGT CTTTATTAGC TGTGTGAACT
47341 TAGGCAAATT ACTGTAACCT CTTTGAAAAG GCTTCCATTT CTATAATAGT TTGCCAGCTG
47401 GTTTGGTCAG GAACACTGTA TTGTCTTGTG TATAGGTGTA TCCACAATGT CTGGTACCTT
47461 GTAGGTACTC ACTAAATTTT TAATGAAATG AATGATAACT GCTTTGGATG ATTGCCATGA
47521 AAATTAAATG ATGATATGAA TGTAAAGCAG CTAGTAATGT ACATAGCTGA CACTAACTGC
47581 TGTTATTATC AACAGTGACA GAAAATCTCC AGTCTAGCTA ATACAAGAAA TAGATTTTTC
47641 CTCAGACTCT CATCTCACAT TCCCTTTTAA GATTTCCTTG TCCTATCCCC ACCCCAGACG
47701 TTTCCATTTT GCTTTTATTT TCTATAATAA TTCCTGGGGG CCTCTATTAA AGGCCTTTTT
47761 CTTTGACTAC TTACATCCAT TATACCAGTA TCTTTGTCAG TAAAATTTTA TATATCTTTT
47821 ATTCTGTCAT CAGGTTAAGA AACAATAATT GTATTTTTAA AGGAAAATAT TTTACGATGC
47881 TACTAAGCAG TTACTTTGTC CACTTATGCA GGTATTTCAT AAGTATGAAG TAGGGAGGTC
47941 AATATCTGTC TGACAGGAAT CTGCTGAAGA TTAATGTTAT CTAGCAGAAT GCTTGGCATA
48001 TAGAAGGTAC TCAAATAAGT GATGCTATCT ATTAATAGCA TTGATAGTAA TACTTTAAAA
48061 CACTCTTTTC TAGTATATCA TATCTCCAAA TTTAATATTT ATTGTCTTTT ACACTTATTT
48121 TACATACATT AATTCATTAC TTTTTTTTTT TTTGAGATGG ATTTTCACTC TTGTTGCCCA
48181 GGCTGGTGTG CAATGGCGTG ATCTCGGCGC ACTGCAACCT CCGCCTCCTG GGTTCAAGTG
48241 ATTCTCCTGC TTTTGCCTCC TGAGTAGCTG GGATTACAGG CATGTACCAC CACACCGGCT
48301 AATTTTGTAT TTTAGTAGAG ACGGGGTTTC ACCATGTTTG CCAGGTTGGT CTCGAACTCC
48361 CGACCTCAGG TGATCCATCC ACCTCGGCCT CCCAAAGTTC TGGTATTAAA GGCATGAGCC
48421 ACCGCGCCCA GCCAGTTCAT TAATTTTTAA AATAACTCTG AGGTAGGCAC TATTATCCTC
48481 ACTTTATATT TGAGGAAACC CTCAAAGAGA CTAAGTAAAT AACTTAAAGT CTTTCAACTA
48541 GTACGTGGCA GAATTATAAT TAAAAACCTG TTTTTGCCAC TATTGCATAT TGTTAGAAGG
48601 CTGTTTCTTC TTGAGGCTGA GCTAAGAGAA CATATATCCA TCCTACGTAA CTTACAGTTC
48661 CCATTGTCTG TTCATTTGCC TATATTCTAC TCACATTTCC TGCTTTCCAT TCTTACTTAT
48721 TTCTGTCCAA CTAGACCAAG AACATAATAT TCTATACCCT GTCTCCCAAA CTTCTAAGTC
48781 ATGGATTTGT TTTAACCTCC TGCTATGCTC ATTTAGCTAG GTATCATTTA TGAATATTTT
48841 CTTCTCATTT TCGTACCCAT TCTCAAGTCT AATTCATTGA TGACTCAGTC ACGTCAGTAG
48901 TTTCTCCATT ACCATGGCAA TACCTTCCTG AATATGAGAA TAAACATATA TCCTGACTTA
48961 ATTCCTTTGG CTCACTCTGT GAATTCTTTA CCACTTTTGA ACACTGTAAA TGTACCTTTG
49021 AGAACTTCTT TGTTGCCAGT TTGATTTAAA AACAAAACAA AAAAATGTTA CTGACTGTTC
49081 CAGTTATCTG TTGCTGTGTA ACAAACTACT CCCCATACTT AGTGTGGTTT TAAAATAACA
49141 GCCATTTTCC TATGTCTCAC GATTTTGTGG GTCAGGAATT TAGGCAGGGC TTGGCTTTGT
49201 TCATGTGGTG GTGATGGAGG TTACTTGGAG GTATTCAGCT GGTAGATGGG CTGGCCAGAA
49261 TAGTTCCAGA TGGCTTTACC CATATAAGTG CCGCCTTGGT AGAGACAGCC AAAAGGCTCG
49321 ATTCAGCGGA GACATCATGT GTAGCATCTG CATACAGCAT CATCAGCATG GCTTTTTCAT
49381 GGTCATGTGA TATTTAACAT AGTGGATCAG GGTTTCCAAA AAGTATTGTC AACATGCTTA
49441 TTTGAAAGCT GTAAGATTTC TTATCACCTA GCCCCTTTCT GCTGCATTTT ATTCACCATG

Figure 7N1

49501 CATGTCACAA AGGTCAGCCC AGATTCAAAG GAGAGGAATT AGCCATTACC TCAATATGAG
49561 GACTAGCAAA TAATTTGTGG TTTTTATTTT TTATTTTTGT GGGTACATAG TAAGTATATA
49621 TATTTATGGG GTATGTGAGA TATTTTGGTA TAGGCATGCC ATGAGTACTA ATCATGTGGT
49681 TTTTAATCTG CCACATTGAA TTAAACCAAT TATTTTAGAT TGTGTAAATT CAAGTTGAAA
49741 AAAATTGGTA ATAGGGCAAA TGGTTTCATG TATTTTTTTA CCGGGAACAA ATTTAAACAG
49801 TTATTAGAAT CAGAGCACCT ATAATGGGAG TCAATTTTTC CTGAAGCTGA ACCAAAATGT
49861 TTATTGGTTT GATTTGAAAG GAGAAGTTGG TTTTGTTGAC GTTAGAACTA TAAACACTTT
49921 TTCCTATAAA TATGTATATT CTCCCTCTAA TATTTGCTTT ATGATTAACA GTGTACTATC
49981 ATCTGCTTTT GTATCACGAC TTGAGTTCAA GAGTTGTAGG TGTATGAGAT CTGAGAAAAG
50041 AAAGAATCCT CCACTCCATT TCATTTAATG TTATATTCTC ACCAATTTAT ATAACACTTA
50101 CATATTATAA GTATTGTTTT CTCAAGGAGG ATACAGGCAT ATTTTACTGA GAGGAGAAAA
50161 GAATATCAAG GCGGATTTTT GGTTTAAAAT GTTATTCATA TTCTAAACTT GTAGATCATT
50221 ATAAGGATTT TGCCTTTGCT CTGAAAAAGT CATTGAAGGA TTTCAAAAAG AGTGACATGA
50281 TCCAACCTGT ATTTTAATAG AATCTCTGAT TGCTATGTTT AACTGCCAAG GAGTGCAAGA
50341 GTGAAAAAGA CCAATTAAGA GTCTGGGAAG GGAGCATGGT GGCTTGGAAA TGGTCGAATT
50401 TTGGATATAT TTTGAAGGTA GAGACTCACG ATCCAAAAGT TGTGTAAAAA AGATAGGAGT
50461 CAAGGATAAT AAGATTTTTG GCCAAAGGAA CTGGACAAAT GAGTTGTCTT TAATCAAAAT
50521 TAGGAGTATT GTAGAAGAAG CACGAAGAAC AGTATAAGGA ATTTATTTTG GAAGTAAGTT
50581 TGAGATGGTT GTTAGACATC CAAATGGAGA TATCAAATAG GCAGTTGGAT ATACCAGTCT
50641 GGAGTTCAGG AGAGAGGTCC AGGCTGGAGT CTTTAATATA TATAGTGTTT AAAATCCTTG
50701 AGACATGGAA ATCACCAAGG GAGAATAAAG TGGTAAAGGA GACGGGTTTC GCCATGTTGG
50761 CCAGGCTAGT CTCAAAATCC TGGCCTCAGG TGATCCACCT GCCTCAGCCT CCCGAAGTAG
50821 ATTACAGCCA TGAGCCACCA TGCCCGGCTG CAGTGATTTT TTTTTTTTAA ATTTTCTACC
50881 ACTTTCTTTC AATAAAACCA TACTCGATGC ACAAAAAGAG CAGGAAAGTC AGGAGACTGG
50941 GAAGCTTTGC AACTAACTTT GAATGTGTGG TCTTGAACAC GTAATTTCAT CTTTTTCTTA
51001 TCTGTAAAAC GAAGAGATTG GACTAGATTA TTTGTAAGAT GCCTTCCTAC TTTAATATAT
51061 CAGTGAATCT TTTCAAAACA GGGTAATTAT ATTGAATGTA ACTGTCATCC TAGGGTAAGT
51121 GAAGTAGTCT TTAACTACAT GCAGGTGACA GTTTGTAAGC TTGCTTAAAA ACATGATTGC
51181 TTTGCCTATT CTTCTCAAGA AATTTTAGTC AAGTGCAAGT TAGAGCTAAT TAATACAACC
51241 AAATCACAGT GTTTGTTTTT GCATTCCCAG AAATTGTTAG TACTGTATAT GATCAGTATG
51301 TACAATAAAT GTTTTTACTA ACTAAAAAAA TTTCTTAAGG AAAAATATAT TGACCTAAGG
51361 AGAAATGTTT AGAGCTAGAT AAAGGAGATT AATATCTCTA GATGCAATTT TACTTTACAA
51421 CGTTATTGAG GTATGATCCG CTTAATATAA AGTTCACCTG TTTAAGTATA CAATTTAATG
51481 GTTTCTAGTT TTAGAACCTT TTCATCAGTC CCCAAATTTT CCTCAAGCCT ATTTGCAGTG
51541 AGTTCCCAAC TCCCACAGCC CTCTCCAGTC CTGGCAACTA CTGATCTGCT CTTTGTTTCT
51601 ATAAATTTTT CTGGACATTT CATCTAAAAA GAATTATATG TAGTATTTTG CATCTGGCTT
51661 CTTTCACTTT GCATGTTTTG AGGTTCATTT ATGACATAAC GTATCAGTAT TTTGTTCTTT
51721 TTTATTGCTG AATGGTAGTT CATTGTATTA TGATATTTTG TTTGTCTATA CACTAGTTGG
51781 TAGATACTTA TATAATTTCC AGTTTTTTAC TTTTATGAGT AATACTTTTT TGAGCATTCA
51841 TGGAGAAATC TTTGTGTAGA CATACGTTTT TATTTATCTT GGATACATTC CTAAGAATGG
51901 AATTGCTGGG TCATATGATA ATTAACTTTT TAAGAAACAG CCAAACTGTA TTCCAGTGTG
51961 GCTGTATCAT TTTACATTTC TACCAGCAGT GTGTAAGGGT TCAAGTTTCT CTACATCTTC
52021 ACCAACAGTT AATAGTGTCT TTTTTTATAA CATTATGACA GTTTAATGGA TGTGTCATGG
52081 TATCATTGTG GTTTCAGTGA GAATATACCT AATGACTAAT GATACTGAGC ACTTTTTTTT
52141 ATATGTTTAT AAGCCATTCA CATGTGTTCT TTGGTGAAGT GATATTGAGC ACTTTTTTTT
52201 GTATATTTAT AAGCCATTCA TATGTGTTCT TTGGTGAAGT GTCTTAAGTA AGTTCTTTGC
52261 CCATTTTCAA AGTTGTGTTA TCTTCTTGTT CACTAGTGAG AGTTCATTTA AATTCTGAAT
52321 ACAAGAGCTT CATCAGATTT GTGATTTGGC AATATTTTCT CCCAGTCTAT GGCTTGTCTT
52381 TTCATTTTCT TATTGATATC ATTTGAACTA TGAAAATTGT TAACTTTAAT GAAATCCAGT
52441 TTATCAGTTT TATCTTTTAT GGCTCATGTT TTTGTTATCT AAGAACTCTG CCTTGTTTTT
52501 GTCATCTAAG AACTCTGCCT GACCTAAGGT CACAGATGTT TTCTCCTATA TTTTCCTTTA
52561 GATGGTTTAT AGTTTAAGCT CATACATTTA GGTATTTGAT CCATTTGAAT TAATTTTTGT
52621 GTATGGTATA AGTTAATGGT CTGTTTTTAA ATTTATTTTT GCATGTAAAT GTCCAGTTAT
52681 CTAAAAATCA TTTGTTGACA AGACTGTCTT TTATTCCATT GAATTTTGTG GGCATCTTTG
52741 TGAAAAATCT AACATAAATA CAAAGATTTA TTTCTGGACT CTAGATTCTC TTCATTGATC
52801 AATCCGTATA CCTGTCCTTA TATTAATAGC ACACAATCTT GATTACTGTA GCTTCATAGT
52861 AAGTTTTGAA ATTGGGTAGT ATAAGTTCTC CAACTTTTTT CTTCACTAAA TTATTTTGGC
52921 TATTCTAGAT CCTTTGTATT TTCCTATAAA GTTAGGATCA GCTTATTTCT ATGGAAAAAA
52981 AACAGCTGGG ATTTTGAAAA AGATTATGTT GAATCTATAG ATCAATTTGA AGAGAATTAC
53041 CATATTAACA ATTTTGAGTC TTCTAATTTA TGAGCATGGA ATGTTTTAGA TCTTTTTGGC
53101 TCAGCAGTGT CTTATAACAG TGTGCAAATA CAAATCTTAT ACTGATTTTT AAAAATTTAT

Figure 701

```
53161 TCCCAAATAT TCTTCATGGT CCTAGTTTGA ATGGAATTGT TTTCTTAATT TCATTTTTGC
53221 ATTTTTGCTA GAATATAGAA ATACAACTGA TTTTTGTATG TTGATTTTCT ATCTTGTGAT
53281 CTAGCTGAGC TTTTTTTTGA TTCTAGTTGT TCGTTGGTGG TTTCTTAGGA TTTTCTACAT
53341 ACTGGACAGT GTCATCTGAT AATGCAGTTT CATTTCTTCC TGTCTAATCT GAATGCATTT
53401 AATATCTTTT TAAGTTTTTT TCTTAAAATG TGTTACTTTT TGGTGTTTTG CTGTACTAAC
53461 TAAAACCTAC AGGACAATAT TCAGTGGAAG GAATAAGAAC AGGCATTTTT GTTTTTCTCC
53521 TGATAGGGAA GTTAGCTGTA GAATTTTCAT AGATGCTCTT TATTAGGTTG AAGAAGAGCC
53581 TTTTTATTTC TAATTTTTGA GAGTTTTAAA AAATAGTGGT TGTTGGATTT TGTCAAGTGT
53641 TTTTCTGTGT CTTTCAAAAT GGTCATGTAG CTTTAGTTGC TATTTCTATT AATAAGATGT
53701 TTTACATTAA TTTATTTTTA GATGGTTAAC CACCCTTGCA TTCACAGGAT AAATCCCATT
53761 TGGTCATAAT GTGTAGTCAT TTTTATATGT TGATGAATTT GGTTTGCCAG TTTTTAAAAA
53821 ATAATTTTTG TATGTGTGTT CATGAGGGAT ATTGGTCTGT AGTTTTCTTG CATTGTCTCT
53881 GTCTGGCTTT GGTGATACCA GACTCAGCTG GGAAATATTC TCTAGTTTAT AAAACAGTTT
53941 ATAAAAGTTT GCTATTCTTT CTTATATATT TCATAAAAAT CATTGGTGAG ATCGTCTGTG
54001 CCTAGGCTTT CTTAGTGTGA AGATTTTTAA TAAGTAGTTC AGTTTTCTTA TTTGTTAGGG
54061 ATCTATTCAG AGTTTCTATT TCTTGTTGAG TCTGTTCTGG TAATTTGTCT TTTGAAGAAT
54121 TTCCTTTTTT TTTAATATAA GTTGTGTAAT TTGTTGGCTT AAAGTTAATA TTCCCTTTTA
54181 ATTCTTTCTT TTTTTATTTT TTTGAAAAGG AGTCTCACTC TGTCACCCAG GCTGGAGTGC
54241 AGTGGTGTGA TCTCGGCTCA CTGCAGCCTC TGCCTCCTAG GCTCAAGTGA TCTTCCCACC
54301 TAACCCTCCT GAGAAACTAA GACCACAGGT GCATGCCACC ATGCCTGGCT AATTTTTGTA
54361 TTTTCTATAG AGACGAGGTT TTTCCTTGTT GCCCAGGTTG CTCTCGAACT CCTGGACTCA
54421 AATGATCTGC CCACCTTGGC CTGGAAAGTG CTGGGATTAT AGGCATGAGC CATCACACCG
54481 GGCCTTCCCT TTTAATTTCT AAAGTATTGG TAGTGATTTC CTCTCCTTCA TTTCTGATTT
54541 TGGTAATTTG TGTCTGTTCT CTCTTACTTT CCTGATCATT CTATTTAAGA CATTGTCAAT
54601 TTTGTTGATT ATTTTTTAAG AACTAATTTT TGAATTCATT CGTATGTCTC TGGTTTTTTT
54661 TTTTTTTGTT TATTTTTACT TTTATCTTTA TTTTTTTCTT CTTCCTGTTT TTGATTTTGT
54721 TTACACTTTT TCTAGTTTCT TAAGGTATGG AAGCATAAAT ACTGATTCGA GGCTGTTCTT
54781 TCTAATATGG GCATTTAAAG CTATAAATAT TCCTATAAAA CTGCTTTAGC TGTATCCCAT
54841 GAAGTTTAAT ATGTTGTGAT TTCATTTTCA TGCAGTTTTA AGTATTTAAT TTCTCTCATG
54901 ATTTCTTCTT TGACCCATTG ATTTTCTCAG ATTTCTTTCG GTTATGGGTT TTAATTTTAT
54961 TCTTTTGTTG TCAGGGAACA CCCTTTATAT GATTTGTTGT AAATTTAATG AGATTTATTT
55021 CATGGTCCAG CATGTGATCA ATTTTGGAGA ATGTTCTTGT ATGCTTAAAA GGCATTGAGT
55081 ATTCTGTGGT CTTTGGGTGG AGTGTTCTGT AAACTTAAGT TAGGTCATTT TGGCTGATAG
55141 TGTTGCTGAA GTTTTTTACA TCATTGTTAA TTTTCTCTCT AGTTATATTT ATCATTCAGT
55201 TCTGTCGGTT TGTGCTTCAT ATATGTGGCA ACTTCGTTGT TAGGTATGAA TACATGTATA
55261 AACGTTATAT CTTCCTTATG TACTGACTCT ATCATTATGA AATATCCCTC TTTTTCTTTA
55321 TTACTATTTA TCTTCAAGTC TGTTTCATCT GCTGTTAATA GCCATTCCAG CTTTTTTATT
55381 GTTTCTGTTT GTATGGAGTA TATTTTCTAT TATTTTACTT TCAACCTATT TGTATCTTTG
55441 AATCAAAGAG TGTCTTTTGT AGAAGTATAT AATTGGGTCT TGTTATTTGA ACCAATATGA
55501 TAGTTTTTGG CTTTTGATTG TCATATTTAG CCTATTCCCA TTTAATGTGA TTTTTGATAT
55561 GGGTGAATTT ACTTATGCCA TTCTTCCTTT ACTGCCTTCT TTTGTGTTAA ATATTCTTTT
55621 AGTGTACTAT TTAAATTCCT CTGCTGTTTT TTTTTTTTTT TTTTTTTTTT TAAAGAACAG
55681 GATCTCATTC TGTTGCCCAG GCTGAAGTGT ATTGGCTATT CACAACTGCC ATCATAGCAT
55741 ACTACAGACT CACACTCTCT GCTCAAGTGA TCCTTTCACT TCAGCCTTGT GAGTAGCTGG
55801 GAGTACAGGC ATATAGGAGT ACATTGGAGT ACAGGTGTAC GCTACTGCAT GCAGCTCTCT
55861 TGATTTTTTT TAAAACAACT TTTTAGAGTT ATTTCCTTGG AGGTTACTGT AGGGATTACA
55921 ATATGCTTCT TAATTTATCA CAATCTACTT GTATAGTTAA ATTTTTATTC CAGTATAGTA
55981 GTAGAAAAAC TCTTCCTTTA ATAAAGTTTA AAGTAGATAA GTTTTTAAAA ACATACTGTT
56041 TTTTAAAAAT GTACTGTTTT TAAAATCCTA ATTTTTATAC TTAGTTATTT TTAGCAGTGT
56101 CATATTGAAT TCTGTTACGA GTTTCATGGT TACTTATAAT AACCAGTTTC CTCATTACAT
56161 AGTAGAATGG TATTTTTCCA ATTTGAACTC TTAATTTTAA ATTTTCTTCT ACCTTTAAAA
56221 TTCTGTGATT CTGTTTGGTC AAAAGGGTCT GTGGAAATAA TACTTGATAT GTTTATATAG
56281 TGGTTATTCA AAACTTACTC ATATATTATT TGCTGACATC TGATGAGATA TAGTTCTAGA
56341 GACATTTTTT ATTTCTGGAC TTTAGTCTTG GATGGATGAA AATTTGATCC GATTTCAGGA
56401 AAGAAAAGGA TTATAAATTA GAATCCATAA CATGGTAAAA GAAGTTTGTT TTTAATGTCA
56461 ATCTAATGGT AATTTTTGAT CATTTAATTT TTTAATTTAA TTAAATCTAA GGCTGAGCAG
56521 ATTTTTCTGT ATGGTTTCAG ACACCAGTAG TGAAAATTAC CCAATTCCAT TTAATTCGGT
56581 AGCAGTAAGA TACCAGTTGG CTTTTATTGA TTAATCTTCC TTGCTCCTTC ATCAACTATA
56641 CCATATTTAT ATTTTATAAG TAAAAAGTTA CTCATATTGC TAGCTTTTTG TGGATCTGTT
56701 TTGGATTTTA TTCTCAATTT TCCCAAGGAT TTTTACATTT TCAGTCCATG TAAAACTTCA
56761 ACTCTTATTT TTCTTAATAA GAGTATGGGG GGGTGGGCAG TTTCTATAAT TAACTGATAG
```

Figure 7P1

56821 GTCTCTGTTA AAATGAGGTT CTCTTTCTAA TAAAAAACAA ATGTGACGTG GCTAATGTAA
56881 GTTTAACATG TAAAGATCAT GGTATTAAGA TCACTTGATT TATGTTTGTA TATGACCACC
56941 TGGTGTCATC ATTTTAACTA CATGAACTTG CTCAGCATCC AGATTTCACA CTCTTTAACT
57001 TAGTGTTTGA TTGTGTAAGA CGTTGTGTTT TTTATCTAAT ACATTCTCTA GCAGTGTTAT
57061 ATTTTATTTC AACCTGGTAA CCATATGACC AGCATTGTGC TAGGTATTAT GGAAAGATTT
57121 CAAAAATTAA TTTTTAAAAA TTAATGAGAC AAGATTCTGT ACCTAAGGTG CCAGTGAAAT
57181 GATTTGATAG AATGTAATTA TGCATGACTG GATGCTGACT TTGTGTGCAT CTAATACAGA
57241 AATTCATTAA AGGAAAAGAT TGTAAAGTAA AATGGTAGGT AGAGGATGGT TTCCAGGAAG
57301 AGTTGGAACT TGAAGGATGG TAAGTGAAAT GATAGAGGAA TAGAGGATAG ATAGATTTTT
57361 GTCTAGGTGT CATGATAAAA TAGTAACATA GACAGTCCTT GATTTACAGT GGGTCAACTT
57421 TACAGTTTAG ATTACTAATG AATGGGAGCA ATGGTAGAAA TTATAAGATT ACAGATAGTG
57481 GCTTTTCATT TTAGAAATAT TTGAGCACTA ACATTTTAAG GGGAAATGAT TGTCACATTG
57541 ACACATTCAT ACATTGGTAC TGTAAGAATT TGTAGTGCCA AAAAAGAATC ATGAATGAAT
57601 TCCCACATAA TGAAGCTATG AAGAACTTTC AGAGGCCATG GAAATAAATG AATTTTTGAA
57661 GAGCTATAGG TAGACCTAAG TAGCTAGAGT TAAGAAATTA TCAAAGATAA TGAACCACTG
57721 GAGAAAGTGG AGTCAGTAGA GTCAATCTAA GGTACAAGAA AGAAGATTGA GTCACAGAAA
57781 CCAAAGAATG AGTTACCAGA TAGAAGGACT CACACTCACC ATGCGCGTTG AATGTTGCAA
57841 TACTGTTTCT CTTCTCTTCA GTGTCCCTCT TTTCCTCCTT GTAGCTTAAA TTCAAAGGTC
57901 ATTTAATCAT TTCCTTGCAT ACAAATACCT TCAGTTCCTT CGCTCCTCTC TGTTTTGGCA
57961 AAACCACAGC TTTGGTTAAA TCTCACCCTT GCAGCTAAGT GGGACTGGAA AATAATTCAA
58021 AAAACATAAT GACTGGTCTC ACTTTAAAGG CAGTGGGCTC TTAATGTTAC CCAGCAATTG
58081 TACCACACTT CTTTGATCCA TTCACTCTCC TAGATGATTG TTTCATTCTT TTTCCTCTCC
58141 TGAAAACCTC CAACATCTCT TCTTCATCAA GGCAATCAGA AAAGTTTTCA CAAGTACCTG
58201 ACATCACATT TGTCCTCCTA TTCTTTGTTA AACCTACTCT AAACAGGTTT CTGCTCTTCT
58261 GTCCCACCGT TTTCAAAATG GGTCTTCTCT AAGTCACCAG TAACTTGCAT CAAGTCTAGT
58321 GATCAGTTCT CAGACTTCAA GATTCAGTGA CCAGTTGATG ACTCCTTTGG TATTGAGGGC
58381 TCTCTTCGTT GTGCTTCTAA GGTACCATAT TGTATTAGAA TTGCTGTATC AATACCAGTG
58441 CCAACACAGA ACACACAATA TCCAAGGTTT CTTTTCAGTT CTTTTTGTTC TTAGAATATA
58501 TTCCAGTATA TTAGTTTCCT AGGACTGCTA TAACAACTTA TAATACCATA AAGCTGGTGA
58561 CTTAAAACAA CAGAGATTTA TTCTCTCACA GTTCAAGGGG CCAGAAGTCC AAACCAAAAT
58621 GTCAGCATGC CTATTCACCT TCCAAAGGCT CTAGGAAAGA GTCTTTCCTT GCCTCTTCCA
58681 GCTATGGTAG TGGCTCCAGG GATTCCTTAA CTTGTGGCTA CCTAAAACCC CAGTCTCTGA
58741 CTCTATCCCT ACATGGCTCC CTTTGTGTGT CTGTCTCTTT CTTCTATCTT ATATAAGGAT
58801 GTGTGTCATT AGATTTAGGG ACCATCCAAA ATGATCTCAT CTTGAGATCC TTTATTACAT
58861 TGGCAAAGAC GCTTTTTCCA AATAAGGTGA CATTTATGGG CTCCCAGTGG ACTTATTTGC
58921 AGGGGGTTGA GGGTTTCACA TTTCAATAAA CTATTCAGTA ATTGCATAGT TATAGTCCTG
58981 TCATCAAAGT TACTTGAATT AAATTTTTCT GTGTGATTAT GGTATTATTT GATATATAGT
59041 TGGGTTTGTT TGTTGCTGTT TGTGTTCAGT TTTAGGATTT GCTTTTTCAT CCAATAATCA
59101 TAATACTGAT TTTTGAGTAT ATATAACATA CACAGTCATG CACCATATGA TGACATTTGG
59161 TCAACAACAG ACCATAATGA CCTACAGGTC CTACAGGATT TTAATACCAT ATTTTTACTG
59221 TACCTTTTCT ATGTTTAGAT ACACAAATAC TGTTGTGTTA CAGTTGGCTA CGTATACAGT
59281 ACAATAACAT GCTGTATAGG TTTGTAGCCT AGGAGCAATA GGCTATACCA GTAGCAATAG
59341 GTGCGTAGTA GGCTATAACA TCTAGGTTTG TGTAGGTACA TTCTGTTATA TTTGCACAGT
59401 GATGAAATTG CCTAATGGTA CATTTCTCAG AACGTTTGTC CCTGTCATTA TGTGACCCAT
59461 AACTGTGTGT AGCTCAGAGG TCAAAGTTAT ATTAGGAGGA TATGCCCAGA ATTCTCACTA
59521 CCATCCCATT TTACCTTCCT TGTGGATAAC CATTTCATGA CTACTTTCAA GTTTATCTTG
59581 ACCTAACAAG TAAGTCTGAT TGATTAACCT CATCTTAATC ATGGGACAAA AACAAGCAGA
59641 CTCCTCAAAG TTCCATATTT AAAATGGTGA TAACGAGACT TAACTCATTG GATTATATTG
59701 AAGATTAAAT GGAAAAAAAA AAAAGTAAAA CAACTAGCAC AGTGCCTGGC ACATAGTAGA
59761 TATAATTTCC TTTTTTCCCT TCTGTACCTC ATAATATAGG CTATGTATTG CCTACAATTA
59821 GGGAGGCTAA TCAGTTTGTT CACATATAGC CTTTTCTTTC TATAAAGGAG AATTTGTGAT
59881 ATATTAAACA GGCATTATAA AATATTACCC AGAAGTTTTA TCAATTTTTT GGCTTTCAGC
59941 TCCTGAAACT ATAGATAGCA TTTATCTATA GTTAGTAGCA CTAGTTTTAA AATTTGGAAT
60001 CTTGGTCCTC TCATTCATTT ATGTATTACA GCAGAGTCAG ACTTATTTTA AAAACAATTC
60061 TAACCTGCCT GAGGCTTCTG TCTAGAAGTG GAATGTATTT TGGGTAAGCT TCTTAAACTT
60121 CATAAAATCA CCTTCTCATT TATTCCTTGC CTTAATTAAT AAAACATGTA CTTCTGCTCT
60181 TAATGACCTT CAGCCATATA CTCTTGACAT TCTAAATTTT TCTAACACCC AATTTTGAGA
60241 AAATGTATTA ATAGAGGACT GACTAAAGGT TGGCATTCTC TGCATTCCTC TGAATATTTC
60301 AAATTTTACT TTTAGGTTAA ACCATACCGT TGGAGATCTG TGTGCATGGA TTGCATGATT
60361 TTGACCTCTT GTTAACTTTG CATTTGCTGG ATTGTACTTT CAGGATGTGA TTTTTTTTTT
60421 TCCCAAGAAA AGAGAAGAAA AGGAGAAGTT GCCTAAAACA GATCTTTAGT TTTTTTAGGA

Figure 7Q1

60481 ATGCTATTAA GGACCTTCTC CATTATGTCA TCCAACGTCT TTCTGAGGAC TTACTAGTGA
60541 AATTACTCTC AGATTTCTGC ATCTTGGAAA TGCTGTACTT CTGAACAACT ACTAATTCAC
60601 TTTTATTTTA TACACATATT TTCTTCTTTG CCTTACTAAC AAGGAGACTT AAGCCTTATT
60661 TTAGGACCAA CTCTTGGAGT TTGGAGAACA ATGTGTGTTT CTGTGTGCCA TTTTTATTTT
60721 CGATATCAAA ATGTATTGTT TGCCCTGAAT CTTTCCCCTG TTTATTTTTA GTCATATGTA
60781 TGCATCAGAA TTATCTGAAG CACTTATTAA ATACCAGCTC CCATCCCTGA AAACCTTGGG
60841 TTCAGCGGGT ATAATAGATT GCATTAATAG CACCGGTTGT TTGCCATGTG ACCACACCAT
60901 TTACCCCCTG CTCCTAAAGG GGCAGATTAT ATTTCCTTGC CCCCTGACTT TGGATTTGCT
60961 CATAGGACTT ACTTTGGTTT TAGTGGGCGT GACATGACCA AAGGCTTGAA TAGCACTGGC
61021 AGGATTAGGC TTGTACTTTT GTGCCTCTAT TGTCTCCAAA AGACCATGTC CAGCCTGGCC
61081 CACTGGTTCC GGGAGAAGGG TTGAGAGACT GTAGTTTTAG GCCAGTACGT ATTGAAGTAT
61141 TTAGGGGAAT GAACTTTGAT GTTGTCACCT CTTAAATGGT TCAGGGAGGC ACACACCACA
61201 CACACACACA CACCCCCGAC CACCACCACC ACACCACGAG TGAGAAAGGG AAAGACGAGG
61261 AAAGAGTGTG ATTATTTAAG CAGATGGAGC AAAATGTAAG CAACTGGTGA ATCTGGTTAA
61321 AGATTATGGT AGTTTCTTGA CTAATTATGT AATTTTTTGA GTTTGAAATT ATATCAAAAG
61381 TAAATGTTAT CTCTTCCACC TAAAAATGTA AAAACATTTA AAACCTTAAG AAAATTGTTC
61441 TGCAAAGTTT CTAAATCAGC TAGTTTGAAC ATTAAACTTT GTTCAGTGAT AAAAATCTAT
61501 ACTAATGAAC TAGGTACTGT CCAGAATACA CAGACTATTA CTGTTTTTTA AAATTTTTAA
61561 TTTTGAAATA ATGTAAATCC ATAGGAAGTT GGGAAAAAGT ATACAAGGAG GTCGTCACCC
61621 AGCTTCTCAC AATAATACAA TTTTACATAA CTGTATTACA GCTTCAAAAC CAGGAAACTG
61681 ACGTTGATAC AATCCGGGAG CTTGTTCATA TTTAACCAGC TGGATATGTA CTGTTGTGTG
61741 CGTGTACAGC AGGTGTGTGT GTGTACAGTT GTGTGTACAT ATAGTTATGT GTAACAGTAC
61801 CACACTCAAC TTACTATTCT ATCACTGTAA ACACTACTTC AGGTGGTATC TCTTCATAAC
61861 CACACCTGCG CTCTTGTTGT TTGTTTTTTT CACAGGGTCT TGCTCTGTCA CCCAGGCTGG
61921 AATACAGTAG TGTAGTCATA GCTTATTGCA CCCTCAACCT CCCTGGCTCA AGTGATCCTT
61981 ACACCTCAGC CTCCCAAATA GCTGGGACTA CAGGTGCATA CCACCACACT TGACTAATTT
62041 TTGTATTTTT TGTAGAGATG GGCTTTTGCC ATATTGCCCA GACTATTCTT GAACTCTTGG
62101 GCTCAAACTA TCCATCTGCC TCGGCCTCCT GAAGTTGGTA TTACAGGCTT GAGCCACTGC
62161 GTCTGGCCCA CTTGGGAGTT TTCAGCCCCT GGCAACCACT AATCTTTTCA CCATCTCTAC
62221 AATGTTATTA TTTCAAGAAT GTTACAAAAA TGGAATCATG TAGTTTGTAG GCTTTTGAAA
62281 TTGGTATTTT TTCTACTTAG TGTAATTTCC TTTATATCAT CCAAGTTGAT GTTTTTACCA
62341 ATAGTTTTTC CCTTTTATTG TTCTGGCAGT CTGTAGTATG GCTCTACCAT CGTTGGTTTA
62401 ACCATTCTGC ATTGAAGGAC ATTTGTTTCC AGCTTTTCGC TATTATGAAA TTGTCTTAGT
62461 CCATTTTGTG CTGCTATAAC AGAATATCTG AGACTGGGTA ATTTATAAAA AACAGAGATT
62521 TATTTCTTAT AGTTCTGGAG TCTGGAAAGT TCAAGATTGA GGGGCCCACA TCTGACGAGG
62581 ACCTTCTTGC TGTGTCATCC CATCATGGAA AGTGGAGGAG CAAGAGAGCA CAAGACATTA
62641 GTGGGGAGAA ATAGAAGGGG ACAGAACTCT TCTTTTTATC AGGAACCCAC TCCTGAGACA
62701 ACAACATTAA TCCATTTATG AGGGCAGAGT CCTTGTGAAC TAATCACCTC TTAAAGGTCC
62761 CATCTCTCAA CACTGTTGTA TTGGGGATTA AGTTTCCAAC AAATGAACTT TGGGGGACAC
62821 GGTCAAACCA TAGCACGAAT AAAGCAGCTA TGAACATTCA TTTGCAGGTT TTTGCATGAA
62881 CACAGTTTTC ATTTCATAAA TACCCAAGAA TGTACAATTG CCCTTTTACT TAGCATTTAG
62941 ATTTTTCCTT TAAAGTTTAT TCTGAGGCAA TTGTTTTCAT ACTCTGTTTG TGAGAAACTA
63001 TTGTTCTTTC CAAGGCCTTA AAGCTATGAC TAATTCTGTA AACACAGTTA TTGTAATTTC
63061 AGGTTAATAT TTTTAAGGAG TATATACAGC CTTGTGTGAA AAGAGAGAAA TGGATTCAAA
63121 ACTAAGCAAT TTTTAAGTGT GCCATGTTTA TTAACTAAGA TATGTATGTA AATAACCAGT
63181 AGATTATTTT TTGAAGTAGC ATGAGTCAAA ATAAATCAAA TTGAGAGCCC CTTCAGCTTG
63241 TCTGTCAGGT CAGGAATGAA CTAATTTGTA CGTACCTTTT CTCCCTCATC TTGTGTCAGT
63301 CCTTCACTAT GTACCAGTTA CATAATCTTC TTTCCTTAGC TAGGCTCTGT CCTTCTTCAG
63361 GGACTTGAGC ATGTTAATCA TTATGGATCC TCATTTCTTC TTCCGCCTTT GCCTGTTTAA
63421 CTCTTACTTA TGAGATTTCC TTAATGAGAC ATTTCCTCCC TCCCCAAACG TAAGTTTAGT
63481 TACCTTCTTT TTTTCTCTTG CAGCACTTTG TTTTGTTTTG TTTTTCATAT AAAAAAACAGC
63541 TAGGACTCTG GAATGTTAAG AGTGGGGATT CTGGAATCAG ACTTGGGCAA GTTACTTAAT
63601 CTTTATGTGC CTCTGTAATT ATTGTCTTAA AATGAACATA AAAGTAGTAC CTAATTCATA
63661 AGATAAGGAT TAAATGAATT AAAATATATA AATCCCTTAG ATAACAATGC TAGGCATATG
63721 TTAAGCACTA TGTTAGTATC ATCAAATGTT GTTGTTACTG TTATGGAATT TATCACAAAT
63781 ATGTAATTAT ATGTTTCGTA GTGATTATTC ATCACCCCTA CTGGACTCTA AGGTCTGTGA
63841 GGATATGTCT ATTTGGTTTA CCACTGTATC CTCAACAACT GCTGGTTGTC CCTATTGTAG
63901 GTGTTAGGTA TTAAGTGCAT GATAGTGAAT ACATAAAGGT TTACTTTTTT AAAAAAATTC
63961 AGGAAACCAG ATAATCAAAA AGAAAGAAAT TAATCACTTA ATAAGTTTCA TCTCCCAGGG
64021 ATAAGAAAAC ATAGGTAAAG AGAGATTAAA CTACTCCTTC AAGTTCAGGC AATTCAGTAT
64081 TCTAATTGAA AGTGTTGTGT TTCCTTTTTA AGTCTAGTTT TGCTTTTGTG TTTATATGTC

Figure 7R1

```
64141 ATAATTAATT GTGTTAAAAC ATAATTTTAG AAACCGATCT TTCTATATCC CTCTTTTCTA
64201 TACCCCCCAA TTTTACTTCA CTTTCTTAAA CAACAATAAA AGTCTCCTGT AACATAAGAA
64261 AGCTTTTCTT CCTAATTATC TTCTTTAGGT ACTTTAAAAA AAATCAATCA GCTATCACAT
64321 GTTATGGACA AGGGGAATCA CTATTGAGTT AATATCCTAA GACGTTCAAA ACCCAGAACC
64381 AAAAAAAAAA AAAAAACCAC CAAAAATGCT GTTTGGAGAG TTTCAGGTTT AATTAAAGAG
64441 TTTGTTCAGG TGTTTTTGCT GTTTGGAATC ATTATCTGAG AAATTATGCT ATAACACATG
64501 GTCATTTGAT TCTGTTTCCA TTAGCCTTCT ACTCTGGGAT ATATGGCTAC TACATTTTCT
64561 TTTTAATAAT CTGTGTTTCA CAGTAAGTTT ACTTTTGTGG AACTCTATTA TTAAATAAAT
64621 CAGAAATCTC ACTTAAAATT TAAAAAATTA TTTTTCTAAT GAAAAATTGA TATTACAGAA
64681 CTAAATTTTT AAAAGTTTAT GTACAGAAAG GATATAGTAT TTGATGTTAT CAAAACTTAC
64741 ATGTTATGAT TAGTTCATTG ACCATGAGTA TATTAATTTA GAAAAAAATA CATCCCTAAT
64801 TTACATCATC CTTAATTTGT ATACTTGTCA TGTAGTGCAG GGGTCCAGTG GAAATCATAG
64861 AAAGGTTGCT GTAGGTAATG AGTCACAAGT CACTTTTCTC CATTGATAGC TTCTTTTTCT
64921 GTAAATCGAA CTATTTAAAA TAATTTAAAA ACTTAGATCC TTAGTAAAAA GCTGTTTTTT
64981 ATTGGTCTAA GTTGACTTTT TAAAAATTTA TTTTCCCTGG CCAGGTGCAG TGGCTCATGC
65041 CTATAATCCC AGCTCTTTGG GAGGCGGAGT GGGGCGGATC ACCTCAGGTC AGGAGTTTGA
65101 GACCAGCCTG GCCAACATGG TAAAGCCCGT CTCTACTAAA AATACAAAAA TTAGCCAGGT
65161 GGGGTGGTGA ATGCCTGTAA TCCGAGCTAC TCAGGAGACT GAGGCACAAG AATGGCTTGA
65221 ACCCAGGAGT CGGAGGTTGC AGTGAGCTAA GATCGTGCCA CTGCATGCCA GCCTGGGTGA
65281 CAGAGTGAGA CTCTGTCTTT AAAAAAAAAA AAAAAAAAAA AAAAAGGCCA GGTGCGGTGG
65341 CTAACGCCTT GAAATCCAGC ACTTTGGGAG GCCAAAGCAG GCAGATCACT TGAGGTCAGG
65401 AGTTCGAGAC CAGTCTGGCC AAGATGGTGA AACCCCATCT CTACTAAAAA TAAAAAAATT
65461 AGCTGGGGGG TGGTGGTGCA CACCTGTAGC CCCAGCTACT TGGGGGGCTG AGGCACGAGA
65521 ATCACATGAA CCTTGGAGGC AGAGGCTGTA ATGAGCCGAG ATCGCACCAC TGCACTTCAG
65581 CCTGGGTGAC AGACTCTGTC TCAAAAAAAA AAAAAAAAAT TATCCTCCCT AAAAAGCTAT
65641 TCCAGTATCT TTTTTCACAT TCATTAGTTA TATTATTTAG TGGTTATATT TGGTTCTCTT
65701 GAACTGTTTT CTGAGTTTTT GAAACCAATT GCACAAATAC AGCGCAAGGG AAACATGGTT
65761 TAGCAGTAGT AGGACTGAAA AAAAGTTTTA ATTCTTGCTA ACCTCACTGT GAGACTGTAG
65821 TATTTTGTAC CTAACAAAAA ATTTTCCGCA GTAATCTTTA GTTAAAAAAA AACCCTTCTA
65881 TTACAGAAAA CTATATAGTT GTTATATTGT AACTTCAAAT TTTTGTTGTA TTTTTTATTG
65941 TCATATTGTT TTTTCTCAAA TATTTTCAGT CCACAATTTG TTGAATCCAT GGATGTGGAA
66001 CCTGTGAATA CGGAAGGCCA ACTGTACAAA AAAGATCCCA GAATTAATAA GTAAGGTTTA
66061 GTAAGCTTTC GGGATACAGA ATTAATATAC AATATTCTAT TGTATTTCTG CATCCTAACA
66121 ATTAACAATT GGAAATCAAA AATTTGTCAA TTATAATAAC ATCAAAAATG TGAACTACTT
66181 AGGAATGAAT CTGAAAAAGT ATGTGAAAGC ACCGTAGACC AAAAACTAGT AAACATTGCT
66241 GAGTGAAATT AAAGAATATC TAAATTAGTG GAGACATATA AATTGTTTGT AGATCATAAT
66301 GCTCAATATG GTTATCAGTT CTCAAATTGT TACATAGATT GAATGCTATA TCTATCATAT
66361 TCCAAGCAGC TTTGTAGAAA CTGACAAGAT GATTCTAAAA TCCATATGTA ACTATAAAAA
66421 AAAAACCCTA GCATCAGAAC AGTTTGGGAA GAGGGAATAA ATTTGTACTA AAGCAGAGAT
66481 ATTGATTAGA TAATTGGATA TGAGTCTAGT ATATGGGAGA AAAGTCAGAT TTAGAGATAC
66541 AAATTTGGGA GCCAGAAGCA CAGAAGCACT ATTTTAAAAT CATGCCACTG AATGAGTTCA
66601 ACAGTAGAGT ACGGAGAGGA AGATAAAAAG AACCAGAAGA GGATCCTGGA GTGGCCAGTT
66661 TAGTCAGCAG AAAAACTAGG AGAATGTGTT GTTCTGGAAG ACAAAGAATT ATTCAAGGAG
66721 GAGAGAATGA TCAACTTTGT TGATTTCTAG GTCAAATCAT ATGAGGTGAG AGGCTTGCCC
66781 ACTGAATCTA GCAATTTTAA TGTAATTGCT AACTGTGGCA AGATATTTGG TGGAATGGAG
66841 AATAAAAACA CATATGGTTG TGGGTTCCAA GAGAAAGTAG GAGAAGAATT AGGGATGAAT
66901 ATAAACAACT GAGGGAATTT TGCTGTGAAA GGGAACAGAA AAATTAAGCC ATTGTTGGAG
66961 AGAGATCATA GGGGTCAAGA TAAATGGTGG GGTTTTTTTG TGTTTTGTTT TTATTGGAAG
67021 TAGGGACAAT TATTTGCATA TATATGTTTT ATGCTGATTG GAATTATTCA ATATGTGGAA
67081 AAATTGATGA TGCAGGAGAG AGGAGAATTG CTGAAACGGT ATTTTTGAAT GAGTTAGAGC
67141 AGGATAGAGA TCAGTATGCA GATGACACAT AAGTGATCCA TGATTTTTTG CATCTCTTCC
67201 ACGTATACCT TTTCTTGATT GCTCTTTCAT GTGCTTTATT AATGATCTTA CCTATTGGGA
67261 GAGTTTCCTA AAGTATCTGA AGCATATTCC ATGTTTTCGT ACTAGATTGT CTTGAAGAAC
67321 TGAAGATCAA AAATCAAAGT AGCCAGAGTT TCTTGAAAAG ATTCTTAAGG CAGCCAGATT
67381 CCAAATGGCT AACAGAACCA AAATGGCAAA GACTATTACA TACTTTTATA ATTTAATATT
67441 AATATAGAAG TCTTGTTCAC AAATTTTTCT TATATTTCAC ATGTACATCT CAAAAAGTTT
67501 CCATTTCAGT ATTTAAACAA AAAACCACAC ACTTCAGGAT CTTTTGCTTT CTAATATTGT
67561 TGAATAATCA ATTCAGAAGA ATCTGGCCAA TCTTTGATGT GCTAGTAAAA AAAAAACCAA
67621 AGCTGAATTT TTAATTTTCT CACTTATTTA CATAAGTTGA AAGTGTGCCC TCTTGTGGAC
67681 TATTCAGTAA TTTTCACATA AAAGCCTTTT CCTTGTATAT TGCAGACTAA ATTAATTGTA
67741 TATCATCACA TATGTTTTGG TCAAACGTTG AGATCTAGAT CTTAATGTTA AGTTCTTTAA
```

Figure 7S1

```
67801 AACCTAAACC TCATTTGGAA ATAAACAGTC ATTGTTTGAT TTTGCATTTC TAATACAATT
67861 GTGTATGAAA CAGTCTTTTA ACAGTTTCAA CCTATATAAG GGACTTGGAG ACAGGCTATT
67921 TCTTTTGCAA TATAAAAGAA GATGAGAAAT AAATTTTGTT TTGGTGTGTT GGGAGTGGAC
67981 TAGGAATCCA AACAATTCAT AGACGCGCTT GGAAATTTCC TCCGTAGCCT CTATGTAAAA
68041 ATAAATTTTT AATAATCAAA TTCCAGGACA CAGGACTATT TTTTTCCTGA GGTAGTTTGT
68101 AGTTTTGTGT AGTTTGGTAC AATTAAACTT TGCATAACTA ACTACAGGCC TCTGCAAATC
68161 CATTTAACTG TATAACAAAC TGGGACTATT TAAAGTTATG TGAAGTTTTA TTAAAGTCAG
68221 TTCATAGATG TGTATAGTTT TGCTTATTGT TTTATTTCTC AGCAAACATA CACATATTTT
68281 ATAAACTGCT TTTGAGAAAC CCTAAATCTC AACTTTATTT ACTTAGTGGT AACTTTTCTT
68341 TCTCTGCATA ATAGTACTCA GTAGTGTAAA TATATCCTTC TAATACACGT TATAAATATG
68401 TGATATAGCT ACACTATTGG GACACGCATA TACATTATTG GTATCCAGCG GTGGCTGCAG
68461 AGAGCTCAGG GTTCCAGAAG CAAAGCAAGT GTCTGAAGAG AGTTTTAGAA CTTTGCTTTA
68521 TTTTGCATTT TAAAAATTTA TTGGAAGTAA TTTGAAACTT TAGAAAAGCA GAAATGTTTT
68581 AAAGAAAGTG AGAATTTTTA CAGTGCAGCT TATTGGGAAC TTTTTGTTTT TGAGGTAGGA
68641 TTTGAGGAAG ATCCTTTCAG AAGTATCTTA AATAGCATGT GAAAAATCTG TTCTTGAATA
68701 GCAGGCAGGG AAAAGGAATC TGAAGGTGGC TTGACTGAAG TGAAAGGATT CTGCTGGAGA
68761 GGTGCCACTC TCTAGGGACT CACTGACCTA TTTAAAATAG TAAGTAGTAC CACATAGATT
68821 TATTTATTTA TTTACTTAAC CTGTGTAGCT ATTTAGCATT TATATCCCAC CTATTTCCTA
68881 AAAGGATTTT AGGTGTTTTA TAATGTTAAA TGTAATATAA ACCAGGACAA TAAAAATATA
68941 CTAGTTTAAA CTTTTTAAAA AATTCTTTAA TGTGAGAAGG CTGAGCAAAG GGCAAGGAGA
69001 ACCTTTTCAT TCTCCCCCCA GAAATCTTGC TCCTCTTTTA CTAAAGCTTT CAATCATCTC
69061 TCCAAGTGGT GGCAGGGCAA TTCTAAGGTC TGACCTTAGT TCTTAGCATA GTATGTTAAC
69121 AGATTTACCC TTAGTTTTCT GGCCCACCAA GACTCCAGCA GACTTTCTGT TGCCCAACAG
69181 GCTGGGCTGC AGCCACACTA TAACAAGGTC TGAATCTCAG CCTTGTGAGA TGAGTATGCT
69241 TTTCCAAATT CTTATTTTCC TCAGATATTT TCCTCCCTTA AACATGTGGA TGGTAGCTGT
69301 TTCCTGTATT TGCCATTCCT GTATTTTGTA GAATCCTTTT TATACCTTCT AGTTAACCAT
69361 TTTTTTACTA CTTAATAATT CTATATATTA AATTTTTCTT GCTCAAAAAC AGTGTGTGTG
69421 TGTGTATATA TATGCATGTG TCTGTGTGTG TGTATATGTA TATATATACA CACACATATA
69481 TGTACTTAGT TTTAAGCCTT TCCCCCACCA CCAAAAAAAT TAACATTAGC AAAGGTGTTA
69541 ATTAGCTAAA TATTCCACAT ATATGAAATT TCAGTTTATT CAAAATAATG TTATAATCAC
69601 ACAAGGTGAC AATATAGTTT AAAGAATACT GACCTAGAGA TCAAACACTT ATATTCTAGT
69661 CTTGGCTAGT GAATTACTAG CTCAGAGACC TTGAACAGAC ACTTATGTTC TTTGAAGAAC
69721 TTTTACTGTT TGCTGTAGGT TTATCTTTTT TCCATAGCAG TGTAGATGTT TCTCAGTTTT
69781 ATGTCCTTTA GGCAAACATA AGAATATAAG ATTTGATTAG AAACACCTGA GTTCAAATCC
69841 TATTTCTGCT GCATGCTGCC TGTTTAGCTG TAGAGAGAGT ATTTACGCCC TGAAACTTAA
69901 TTTTTGCATC TGTGAAATAG TGATAATCTT TACAATCCTT TGATATTGGA ATGATTAAGG
69961 AAAGGAATAT ATAAATATCT GACACATAAG AAGTGCCAAA AAAAATTTCC CCTACAGCAT
70021 TACTTTATTT CTTGCCTATC TGATCTATTA TAATGTAACT GTTATCAACC CTCAATAAGT
70081 GGCTTCCATA ACTATAGCTA TAGTTCAGAC TACTTTTGTC AGATTGTGAA TTTCCAACTT
70141 CCTGCTTTAG ACATCTCCAA CTAGATATTA CACTGGCATT TTAATCTGAA CAAGTCCAAA
70201 ATCACACCAT GGTTACATGT AAGTACTGCA GTATTCTAAC AGAACTTTCT GCTTCCATCC
70261 TCTGTCTCTT TCTCCCCCAC CCTATCTTCC TTATCACTAT TAAATTAGTC TTAACTGAAA
70321 GCTTAAGGAT GTGGAAAAAG ATATCAACAT TATGTAAGAA ACTCCCTTGC AGGCTCCAAT
70381 TGACTTTTCT GGCCATATGC TCTGTCTAAA GTGTTTATGA ATATACCTTG CATATTATAT
70441 TAGTCTTTAG CACCTAGCTC AGTATACTTC ATAGAAGATG CTTAACATAG GTAATTATTT
70501 AAATATTCAG AGAAATCTAT GTACATATAG CAGCAACAGG AGACTTACTA ATTTTTTTAT
70561 TTTATCATAG TTTATATTAG TATTTTCCTG AATCATAAAG TAATATTCTA ATCATAATAA
70621 AAGTCCAAGG AGTACAGATA GAAATACCAC CAAAATAAGA ATTCCCCAGC ATCTCAGCAT
70681 ATACCCGACC CCTAATCATT GTTAAAGGTT TAATAATGTT CTTTTTTTTC ATGCCTAGAC
70741 CATCATTTTT ATGAAAATGT GTTTTAAGCA AAAGTATTTA GCTTGGTTGA TGAGCTTATG
70801 ATGTGCACAC TGATATTTTC AGTTAGCAAT ATATCTTTAA TATCTTTTCA TGAATTTTAA
70861 GAATCTTTGC CATTCTTCTT TATTTTAGTG CCAATTTGCT GAGAGATTAA AATATAGAAT
70921 CATCACTGTA AAGTTGGTTC AGGCTTTAAT TCAATGATTC TTTCTCTTTT CTCCCTCTGA
70981 AATATGTACC CCCCTTTACC ACATTCTTGT GGCCAAACTC AAATTTTAAA GGGCAGAGGA
71041 TGTTCCATCT TGTTAACCAT TGTACTTTGC TTGCCTAGCA TACATAGTGT CTGACACAGT
71101 AACATAAGAT AAATATTAAT TGGATGCCTC ATGAAGGACT AAATATTTTA GAAATAGTAT
71161 GTTGTGTTGG GTGCCACTTA TAACTCAGGA GGTACTTACA GGTTTGAATG AACTGTTATG
71221 TAACCTGATA CAGCATTTTA AACTGTTAAC TATTAAGCAT AGTAAAAGGA AAATGCTTTA
71281 GTTATGTTGA AGACAAGATG AAGCAGATTT TTCTGGAAAA CAACACAAAG TAGAGTTTAA
71341 AGCAATTTAT TAAATTGCTA AGACAGATTG AATAGTTATT ATGAGAAAAG TTACCAGAAT
71401 CGTATCTTAC ATCCATCATG TATTTAGCTC ATTTTTAGTG TATTCAAAGA TGGAGAAAAT
```

Figure 7T1

```
71461 AAGGGGTTTG TGCTTGGTAA GATTCATTTG CTAAAATGTC ATTGTACAAA TTTTGAAAAG
71521 AAAGGTTATG AACTTAACAT AAAAAATACC ATGGTGTTTA CTTACTCATT GTAATCTTGT
71581 ATCCAAAACT GTTTTTCCTC AAAGTGAATT TTGCTTTCTG CTCAATAGTT CAGATCAAGA
71641 AGAAAGTAAG AGTAATTGAA GTGCCATAGA AATGTGAATC ACATACTAAA TGTGGTTATA
71701 AAGTAAGGAT CCTAACTCCA TAAAGCCAGA GTCACCATAC TTCACTGTCA CATGGTGTAG
71761 TATACTGACT AACAGTCTTT TAAACTGGAT GTTTCAATCA ACCCGTAAAA TAATATTTAA
71821 AAAAGAATGA GACATCTGTA TAAATGAAAG ATTTCTAAGA TAATATACAT GGCAAAAGTA
71881 AGATGCAGAA GAATATATAA CAAATAACAT TTGTTGCATT TAACGAACAC TTAGTACATG
71941 CCCAGCACAG TTCTAAGAAC TTTACACATA TTATTTCATC CTCACAACAA AATTTAATAA
72001 TAATTACCTA CCTCATATAT CAGAGATGAG GAAACTGAGG TGCAGAGATT AAATAAGTTG
72061 TCCAAGGTTA TGTAGTAAGT GGGGGAGCTT GGATTCAAAC ACACAGCCTA ATTAATATTT
72121 TTCTTCTTGG CTATATATTT TGAGTACATT GATTGTGTAT GCATAGTAAT CTCTCATGGA
72181 TGTACCATCA TTTGTTATAC TAATAATATT GTTATACATT TTAGCTGTTA GTTTAAGTGT
72241 CCATGTGCCA GATAGCCTGA TCTTGACTCC AGCTGTATGG CCTTAGGCAA ATTATTTATC
72301 TTCTCTGTAC ATCACATTCT TCATCAAATA GAACTGTAAT ATTAGCACCT CAGGTTCATA
72361 TGAGGATTAA ATGAGGATTA AATTTATTAC ATAGTAAGTG CTGAGCAAAC ATGAGTTACC
72421 ATTTCTATTT TTTAATCACT AAAAGTAAAA ATATTGTGGG AATATCTACA TGTGTATGTT
72481 AACATGTATA TGATTATTTC TTTAGGATAT ATTTCTAAAA GTGAAATTGT TGAGAAAAAA
72541 TGATGCATTT TTTTAAGGCT TTGGTTATAG GGTGCAAAGT GGCCCGCCAG AAAGTTTATC
72601 TACCATCAGA TAATAAGAAT GCCTTTTATT CCAAATCTGT CCCAATTTTA GTAGTATTAT
72661 AATCCCTACT GATACTGTTT TATTTGCACT TCTTTTGTTT GCTTGAGGAA GTTGTAAATT
72721 TTGTTGTGAA ATTAAATGAA GAAGTGGAGT CTTTAAAAAT CTTGGCAAAT GCTTAAAAGT
72781 TCCCTTCAGA CTCATTAGAA TGGACTAAAT TGATAATTTA CTATAATATC TTCCCCTAAT
72841 TAAGCATTCT TTTAATTAAA CCTCAAGCCA TTCTTAAATT TAGTTTATAA ATGATTTCTC
72901 AATGTATTTT GTTCGATTTA GTTCTTAGTA TTACAACAGT TAAATTTTTT TCTGCTTTCT
72961 GTCGCCAGTA TTTATTTCTC CTACCTTATG ATTTAAATAA TTGTAGGTGA GCAGGCCCAA
73021 GACTATGACT TTTAATACTG TGGTGAAATA TATACTGGAA TGCCAAATAA TTATTTATAA
73081 TAGATCTTTT AGAAGTAGGA ATTATTTGTA TTGAAAAGAT GCCTTTCCCT CTATTTGTTT
73141 TGAAAAGACT CCTGTTCTTC ATCTGTTCTC CCGAATCTGT TTAGTAATGC TGTTAACTTT
73201 CTGGATCACT TACTATGTGC CAGGTGGTAT GTCAAATGAT ATATGTGCAT TATTTTATTT
73261 TATTCTCATC ACCACTTAGA GGTGGGCTAC TTTCCTCACT CTTCCATTTT TTCAAATCAG
73321 CAACTCTCAG ATGGCTTTGC CTGGTTTAAA ATTTACCCAC AATTTTAAAG ACATTTTACC
73381 TGAACTCACA AAGCACTGTG CAGTATACTC TTATAGTTCT ATTCCCTCCA TCCCTTTCAG
73441 TGTTCAACCC ACTAAATTTA TTTTATAATC TACTAATCAG TCACCAATCA CAGATTGTAA
73501 AGCACTACCT TAAGTGACAG TTTTAAAGCC CTCATTAAAA TCTTCTTTAC AGTTTGGTTG
73561 CAGTTTCATT CTAGACACAT GTCAGCTTCA GTTTTACGAA AAACAATATA CTTTCACAGA
73621 GCCAAGCAGT CCAAAACATT ATTCAATCCA GAGCCAAAAA TGTCATAGCT AGTTAGTTAG
73681 GGTTGTGTTT GTTCATGTTT AGAATCCTAG GAACGCTATT TCTTGATGGA CCCTGGTCAC
73741 CTTCCAACAT AAAGTAGCAA CATTTCCACA GATTACTTAC ATTTATTAAA AGCTGTGACT
73801 TTAGCTAAAA TTGTAACCTC ATTTCTACCA AATTCCTCTG CTGTTCTTCA AAATCTTGGA
73861 TTCCAGTGGA ATTAGCCATA GTTCAGCAGT GAAGATCAAA TATTTTTGTC AGTAATCATC
73921 AACGTGTAAT TAAAGCACTT TAAACCAAGT AAGTATTGTT GCTCTCCCGC CCTTTCCCCT
73981 TTACTCCCAG TGTTTACTTG ACATCATTTC AGTGCATTTT TATGTCACTG TGAAAAGCAC
74041 AATCTTGTGG TTAGGTTTAT TAATCTTCTA GTTCATACAT GGGTAACTAA ATACATAGTC
74101 ATTTTTAGGC TAAAAATCCT AGCCTGGGGT TGGATCTGCT CTATTTGTTA CTCACCTGGG
74161 ACTTAAGAAA ACAGTCAGGT AGCCCACAGT AGAATCCTCT AGCATATTAC TCTCTTTAGG
74221 TTCCTATTCT CTGAGTTAAA TAATTAAATA CAGTCATTTG TTACTTAATC TGCTTGAATA
74281 TGGCAGTGTA CGTGTACAAC AGTGAGTTGT ATATGAATAA CAAGATATTT TTGTGATCTG
74341 TAATTTTCAT TCAATGGTTT CTTTCCATTA ATTACTGAGC ATAAGTTGGA ACTTTCTTAT
74401 TAGCATAAAT TTAGGAAAAA TTCATTGTGT TTTGGTGACC TTTATCAGAT TTTAAATTCC
74461 AACCAACTTT TTAAAGTGCT TGATGTGACT ACTAACTATG CAGTGTTGCA TTAAATTTCT
74521 TTAGTAATTG TTAAATAATC AAATTAATAA TTTCAAAGAG TAGAAATTAG TAATTTCACA
74581 GTGTAGCAAA TGGACAAATA TAGAATAGCT AGTAGTGATT ATAGCTTTCC TATATTATTT
74641 CCTGTGCCTT TTCCTTTCAG TGGGCTTCTG CTAGAAATTT TGTCAGTCAT TCACCAAAGG
74701 AAAGTAATGT TTTTTCCCTT AGCTGGCAAT TAGTAAAGAA TGTACATATA AAGGTCTTTA
74761 AACTGTAAAG AAAAAAGAGG AAATGATTAC CACAAAGACA AGATAGTTAA TACCCCTAGA
74821 AGGAACCAGA ATGCTAGCCT TTTGGATGAT GATTCTATGG ATGCTTACTT TATAACTCTG
74881 TTAAACTGTG TGTGTGTGTG TGTGTGTGTG TGTGTGTGTG TGCGCGCGCG CGCGCGCGCG
74941 CATGTGTGTG TGTAGCAGTT TAATGTACCT TTGTGCAATA GGTCTTATAT TTATAATAAT
75001 AATGTTTGGG GTGAAGGAAA TTCTTAGTTT TAACTACCCG TATAATTATA CGTTAAATAA
75061 TTCTATTTGC AATGTTGCAT TCAGACATAA TGAGTAAGGG AAATTATCAG TATTATGTCA
```

Figure 7U1

```
75121 TTTGAATGTT TGACGTTTAC AACTCAAAAA CTTAAGAGGT TCTCTTAAAA GTGACTGACT
75181 AGCAAATACA ACCTTAAAAA GATAAATATT TAAGTTTTTT AAACTGGAAA TTACAATTCC
75241 GTTTTTAATC TTAGCTCTAT GGTTTAGTTG ATGTAGACTT CCATTTGCTG ATTAATTTAT
75301 AAAGTAAAAG TCACTTAATG AGAGCATATC TTTGATTAAT GCGTACATTG TTAAAATATT
75361 ATCTACTTAC AAAAAAGGAC TTACCAAGTA CTGTTAAAGG AAAGATAAAT GTTTTACAAG
75421 CCATATGTTG AAAATAAGAG AAAAATTTGG GGGCTTGGAA CAGAATAACA AAGTGTTCAG
75481 TTTTACAGAA TGTCTTCATA TATTTTTCTG TGTGTGAAGA GAGAGAGAAT TCCATCATGA
75541 TAAATACTGA ACATTAAAGT CAATTAAGTC ATTTGTATGG GGAACATTAA AAATGTTAAC
75601 ACGTCTTTGT CCTTTATGTG GTTGCATATT GATTATGTGA CTTGTAAGAA ACATGTAGTG
75661 ATAGTTGGAA AGACAAGCTA AGTACATGAA CATTAAGTAA TCGTGCAAGA TTGAAACAAG
75721 ACAAGTTTCA AAAGATGTCA CAAAGGAATA TATAATTATT TACCAAAATA ATATTGGGCA
75781 ATAAATGTCA TAAGTTCAGA GTAGATTAAG ATACTCATTT GGATGAATTT GAGGTTTCAT
75841 GAAATCGTGG GAACGTGCTT TGGATCTTGA AGAATTATAG GATTTGTTTG GACCAAAGTA
75901 GGAATGGGCT TCCTAGGTAG GAAGAATGTC TTAAGGAAAT GTATAAAGAT GGGAATACAC
75961 AAGGGAGATT TGGGAGAATC TGATTAGATC AGGTTGGTTG GAGAGGGTGG TTTATATAGG
76021 ATAATGATAA AAGACACAGC TAGAAAGGCA AGTTGAAGCT AGATTATGAG GTTAAATGTT
76081 TAACGTGCTT ATAATGTGGA AATGAATTGC AGTGCTTGTC GAGGTTGATC AAGTATTCCT
76141 TTCTAGCAAT CCAGCCTAGC AGTTAAGAAA CAAACTCTGG AACCAGATTG CTTTGGTTCT
76201 AATTCTTGCT CCACTAGTTA CTTTAAACTC ACTGTAAATT AATTTCCTCT TAGTAAAATG
76261 CAAAAAACAA TAGTAGCTAC TGTACTGGGT TGTTGTGAGA ACTGAATTAA TGTGTGCAAA
76321 GCACTTTGCA ATTGCTTAAC ATGTAATAAG TGGTATGTGA AAATGATTAT TATATAGGTT
76381 GAACAAACCA AAGCAGTAAC TTTTTTTTAT AGTGATTAAG CATTTTCCTG ATAGTAATAT
76441 ATCTGACATA TCTCTACAAA TAATTGTCTG TTTTGTGTGT TGCAGTGTTT GGGAAATGGG
76501 AAGTAATGAC AGCTGGCACC TGAACTAAGT ACTTTTATAG GCAACACCAT TCCAGAAATT
76561 CAGGATGAAT GGGGATATGC CCCATGTCCC CATTACTACT CTTGCGGGGA TTGCTAGTCT
76621 CACAGACCGT AAGTTTGGTT AATTTATCTA ATTTAAGTTC TACTGTGTGT TAACAATAAT
76681 TTTTACAGTG ACTGTTCTAA AAATTATTAT AGGTTCTTTA AAACACATTT ACAGAAATAG
76741 CAACTGAAAC TGCCCTTTAA AGAAAAAAAA AATTGATAGC CTAATTTATC TAACTTCTTA
76801 GTGATGTTTA TTTTGGTTGT CATGTTCAGT AATCTGTTGG AGCTTGTTGG AGGTATCAGC
76861 AGCCTATTTT ACTCTAAGGA CTTAAGAATT TTAAAGAACA TTGCCAGTCT TTTGAGATTT
76921 ATTTAATGTA ACTCAATTTT TCAGAGATTT ATTCTTTTGT TAGGCATTTG TAACTATAAT
76981 TCTTAGTCCT TGAATAATGA TACAAAAAGC TACCTACAAT TTTAGTTACT GTGTCATCCT
77041 ACCTGAATAA ATAAAAGGAA AAAGATATGA GAGGGAAGGG TAGAAAGTGA GAGGATGGCA
77101 TACTTTTCTT TGGATAGCAT TATGCAAGAT TTGGGACTTC ATAATAAGGG AGCTAGGAGA
77161 AAGTATCTTC AAGAAATGTT TTTGTCCATG TTCAGTATCC TCCAAATACA ACTTTTCTGG
77221 CTTTTGTTTT GTTTTGTGAA TTTCCAGTTG GTTTTAGTGG GGTAAAATAG ATAACAGCCT
77281 GTTAGCTTTG AGCTTAGGAA ATAAGCGTAA CTAGTTTATG AGGTCTAAAT TAACAGGAGA
77341 GTGCTGTAGG TGATTGGGTC AGCATTACTC AGGTAAGAAA ACTTTTTGAA ACTGGCATTA
77401 GTTTTTATTA TCACTTTGTT GTAGGTAAGG CATAAATAGG AGTTCAAAAT CAGATATACT
77461 GTCAGGAATT TCTTTTTGGT TTTTCTCCCC ATGATCTTTG CTATACCTAA ATATTTTGTC
77521 TTTCCAGGAA GCCCTGTTCA TTAAGTAATA ATTTATTTTC TGTGTTTTTA TTAATGAGAA
77581 TCCTGTTGGT ACCTATTGAG GCTGAGCACC ATGATAATTA TACTGTATAG GTGATTAGAA
77641 ATTAAGCCAA AAACAAAGAC ACCTGATATT TTAGTGAGCT TTCTTAACCT TTAGACAAAT
77701 GAACAAATTT GTTAGGTGAA CAGAGATTAA ACGGCTGAAT TTAAGCTACT ATAAAACATT
77761 TATGTTCTTT TGTTTGCTAT TAGAAGAGAA TAAGTAGGAG ACAACTAGGA ATTTGGAATT
77821 TAGAAGAATA TTTTAATATT CTTACAGAAT TCTATGCTAT GAATGCTTTC TTGCTAAAGT
77881 GAGGTATTTA TTTGTATATT CTTAAGCTTT TAAAAAACGT TACTTGTCTA CTTTATGAAG
77941 AGTCAGATAT TGTTATTTGT TTGTATGAGC GTACTATTGA TTCTGAAAAA TCTTATAAAC
78001 AAGAACAAAT GAGATTAATG AATTGCTACA TTGGAAGTTA GTTTGTAACC ATGCCTTTTT
78061 CGCTAGTCAT TTGTTAATAA AATTTAAGAA ATGAAAAGCA AGGATGAATA TAAGGGAGCT
78121 GAATTTTATT CCTAGAGACT AGTATAATCT ATTATGGTCC AAGTGATGTT TTGGAAGTTT
78181 TGTAGGGTTG ATTGAGGTTT GTTAGGAAGA GGAGGAATGC CTTTTAATAA TTTGTCACAT
78241 TGATATTTAT AACTTACTTT TAATCCCAAA ATACAGATAA GCACTAAAGA GACTTCTATA
78301 GTCACTCAAT TTCTAATAAT CTGATTTTAT TCCAAATAGT CCTGAACCAG CTGCCTCTTC
78361 CATCTCCTTT ACCTGCTACA ACTACAAAGA GCCTTCTCTT TAATGCACGA ATAGCAGAAG
78421 AGGTGAACTG CCTTTTGGCT TGTAGGGATG ACAATTTGGT TTCACAGCTT GTCCATAGCC
78481 TCAACCAGGT ATCAACAGAT CACATGTAAG TATGATCAAT TTTATATCTA CTATAAGTGA
78541 AAAGTTTTGG CCTTACTAAG AGAATCCGTA TTCCTGGTTT TATTTCAGAA ATTTTTAGAT
78601 ACATAGTTTA TTTTTTAAAA ATATCCATAT CCGAGGGAGA ATATAGTCTT ATTGCAATAA
78661 TAGATTAATG AGATTTAAGT AGGCAATATT TATTTTTAGA TAATAATTCT GACCCATGTA
78721 GCTCTATGGA TATTTTTTCA GCTCTTTTGA ACTTATCTTG GGGGATCCAT CATTTGTGCA
```

Figure 7V1

78781 GAGATCTGGT CATGAAACTA TATCCCTGTC TGGGCGCGGT GGCTTACACC TGTAATCCCA
78841 GCACTTTGGG AGGCCGAGGC AGGTGGATCA CGAGATCAAG AGATTGAGAC CATCCTGGCC
78901 AACATGGTGA AACCCCATCT CTACTAAAAA TACAAAAAAA AAAAAAAAAT TAGCCAGGCG
78961 TGGTGGCGGG CGCCTGTAGT CCCAGCTACT CGGGAGGCTG AGGCAGGAGA ATCACTTGAA
79021 CCCGGGAGGC AGAGGTTGCA GTGAGCCGAG ATCACGCCAC TGCACTCCAG CCTGGCAACA
79081 GAGTAAGACT CCGTCTGGGG AAAAAAAAAA TTATTTTTCA CTGCAAAACC AATACATATT
79141 TATACAAACA ACACAAAAAT GTGTAAAAAG TAAAATCTCT CATTCTTATC CCTTCATATT
79201 CCACCACACA ATGTTACTCA TGTAACCTCG CATTCTTTAT TTTTTTAATT TAAAAATTCA
79261 TCATGTAGGG GAATGAGGAT AAACACATTA TAATGGAGAG ATATCTACAT TAGATGCGGT
79321 ACATATTTTT GGGGCATTTT TAAAGCTGAT GACTCTAAGG TGAGATACTT ACTAAATGGA
79381 TTTTCTAATG GAGAAGCTAA GAAATGATTG GTTAAAATCA GAAAGAAGTA TAATACTACT
79441 AATATTTTGT CACTCCAAAA ATTCAGCAAT ATCTAAATCA CTTCTTTTTT TTTTTTTTTT
79501 TTTTTTTTTT GAGATGGAGT CTTGCTCTGT TGCCCAGGCT GGAGTGCAGT GGTGCGATCT
79561 CGGCTCACTG CAACCTCCAC CTCCTGGGTT CAAGTGATTG TTCTGTCTCA ACCTCCTGAG
79621 TAGCTGGGAT TACAGGCCCC CACCACCATG CCTGGCTAAT TTTTGTATTT TTAGTAGAGA
79681 CAGGTTTTCA CCATATTGGC CAGGCTGGTC TCAAATTCCC GACTTCAGGT GATCCACCCA
79741 CCTCGGCCTC CCAAAGTGCT AGGATTATAG GTGTGAGCCA CTGTGCCCAG CCTCTAAATC
79801 ACTTCTTATG CTTGTACATA CTTATTCAGT AGTTTTCACC AAATATTTAA AGATGTAAAG
79861 GAAATAGCAC ACGTAAAATA AGGACTTATT TTATGGAGAG CTCCTGTAAG ATTGCCCTGG
79921 AAATGTAGTG AGTCTTATCA TTGGACACCA TCTTTATAGG TCTTCATGGT TAGATCCAAT
79981 GAGTAGAACA TTGACATGTA TAATATAAAG TTAAAACACT GCCTATACTT AATTTTATCA
80041 TCATCTCCCA TGGTTATGAA TTTAATTTGC TACTTATATT GAAGTTTATT GAAAATTGCT
80101 GCTGTGAAGT GTATTGAAAT TTGCTGTTTG GTTTCCGCTT TTCCCGCACC ATGACATTAT
80161 TTGAGAAAGC AATGTAAGAT GGAAAAATTA CATAACCTCT GGGTCTTGTC TTAATCAGTG
80221 TGGCAACAGT ATCTTATTTG TAAGACATTC CCAGAAAGTC AGACTCACTC ATATTCAGGT
80281 GTAAGAAAAT ATATTCCAAT ACCAAATATC AACTTTTTGT GTAACTTTCA CTTGTCTACC
80341 CTTCCATTAT TTTGAATAGT TTAGAATAGA ATGTATTTCT TTTCTATTTT AGAACTACTT
80401 GGAAATTATT AAACTCATAG TTCAATAAAA TAGTGTTTTG GGCTTTTTTT CTCTTGACTG
80461 TGTAAAGTAA AATGAAGAAA AAGATTGTCC TTAGAAGAAT CCCTCTCTGT TATTTTTGAT
80521 AATTATATTT CTCCCAGGGA TAGCATATTT GAAAATTCAT AACTGTTGGG TCAGCCACAG
80581 TGGCTCACAC CTGTAATCCC AGCACTTTGG GAGGCCGAGG CGGGCAGACC ATCTGAGGTC
80641 AGGAGTTAGA GACCAGCCTG GCCAACATGG TGAAACCCTG TCTCTACTAA AAATACAAAA
80701 ATTAGCTGGG CGTGGTGGCA GGCACCTGTA ATCCCAGCTA CTCGGGAGGC TGAGGCAAGA
80761 GAATCACTTG AACCTGGGAG ACGGAGGTTG CAGTGAGCTG AGATTGTACC ATTGCACTCC
80821 AGCCTGGGGG ACAAGAGTGA GACTTCGTCT CAAAAAAAAA AAAAAAAAAT TCATATTGTT
80881 GGCCATACCA GTGTGATTTA CTTTTATATG ATAAGTCTTC TTAAGAATCA GTCACCATTT
80941 TAATTTTTGA TACTTATTTT CTCAATGCCA GAGAGTTGAA AGATAACCTT GGCAGTGATG
81001 ACCCAGAAGG TGACATACCA GTCTTGTTGC AGGCCGTCCT GGCAAGGAGT CCTAATGTTT
81061 TCAGGGAGAA AAGCATGCAG AACAGATATG TACAAAGTGG TGAGTTTCTT AATAACTGAA
81121 TTCCCATATC AAACTTGTTT TATACATATT TAAATCCAGG TGTCTTCTTT AACAAGCTGG
81181 CCTATCAGGA ATGCGATGTT TATGCCTTCA GTCAAGCCAA GAACAAGAAG GAAACTAAAC
81241 TGATAAGATT CTTGTAGTTT AATATGTAAC TAAATTCCTT GAGAATTAGA CAAAGCTTTA
81301 AGTGTATTTT GTTAAATATG TTGGAATATA TCAGTTTACT CAGCTTAAAA ATTTTTTTGT
81361 TTTAGAAAAT CAGAATTAAT TTGAAATAAG TCTTTCATTA ATTAAATAAA TATTTGCAAA
81421 GCTTTTGAAC ATGTACATTG TAGCAGGTAT ATAGAGTTTT AATACTGATT GTGATTATAT
81481 TCATGGTTTT CTAGTAATTG ATTTAATACT CCTGTTGCCT TAGCAACAGA AAAATTGGTT
81541 AAGTATTATT ATTAAAGAAA AATTGATTCA TGGTATTATA AAATAATAAA AATATTACAT
81601 CCAACACAGA TATAATTTTT ATGTAGTCAT GGAGTACCTT TGGGTTAAGA GCATTGTTCT
81661 GTTCAAGCTT ACTGAATTTG ACAAGCCCAA GTGCCTGTTT GGCTCTCAAG ATTAAAATAG
81721 GGCAGGAATA GCTTGGACAA CTTCAGAAAG TTCAACTTTG TTAATTAAAT AATTGTATTT
81781 AAGAATTTTA TCAGCCGGGC ATGGTGACTC ACGCCTGTAA TCCCAGCACT TTTGGAAGCT
81841 GAGGCAGGTG GATTGCCTCA GGCCAGGAGT TAAGACCAGC CTGGGCAACA TGGTGAAAAC
81901 CTGTCTCTAC AAAAAAATAC AACAACTAGC CAGGCATTAT GGTGTGCGCC TGTAGTCCCA
81961 GCTACTTGGG AGGTTGAAGT GGGAAGATCG CTTGAGCTCA GGAGGTCAAG GCTGCAGTGA
82021 GCTGAGATTG CACCACTGCC TTCCAGCCTG GGCGACAGAG CGAGACCCTG TCTCCAAACA
82081 AAAAGAAAAA ATAAATAAAA TAATTTTGCC AAATTCATTT TGGTTTTGGT TTACTTTGTT
82141 GGCAGCACTT CCATGATGCT TCCCATTCTG TTTCCTTTAA ATAATATTGC TTTGCTGATT
82201 CTGTGTACTT GTGTTGTTTG AATGGTATTT TGAAAGCAAT TGCATAGTTA CTATTGATTC
82261 CTCAAAATGC ATAATGGGGA TGCTTCTGAC CGACTTGCCT TTTAGCAAGT TGAAGGTAGG
82321 TATGCACGAC AGGGCTCTGA CTTCACCAGA ACTAATAAGT TAGATTGCAA TAGTAGGAGA
82381 CAGATATAAA TAATGAAGGA AGCTAGAGTT ATGACGGCTT TCTGGAAAAA TGTTGGAATT

Figure 7W1

82441 GAAAGAAAAT GTGGAAAGAG AGTTGAGTGG AAGAAAGACT AATAGAGTAG GAGTATTAGT
82501 TTTATGAGAA TGTGAGTAAA TCTAATATTG GATAAATGAA TCTAAGGCTA CTAATACTAC
82561 ATTTTTGCAA CTTACGTTTT TGAGTATTTG GGTAGTAAAT CACTCTGATA AAAACTTTTA
82621 GAGTGTTCAC CTCTCAGTCA CATATTTTGT GTTTTATACT ACATATACTT GTTTTTTAGT
82681 CCAAAATATT GTTTGATTTC TGTATACCCT ACTTTGTAAA AGCATAAACT AGCATTTAAA
82741 ATTAATCAAT TAATTGCATG TTATTTTTTT TTTTAAAGCA TTTTCCTGGT GATATATGGC
82801 TTTGAAATTT TAAAAGTTGG CTGGGCGTGG TGGCTCACGC CTGTAATCCT GGCACTTGGG
82861 AGGCCAAGGT AGGAGGATTG CTTGAGCCCA GGAGTTCAAG ACCAGCCTGG GCAATGCAGA
82921 GAGACCCTGT CTCATTGAAA AATAAAAAAT AAAAATAAAA TAGAAATTTA AAAAGTTGAT
82981 TTTGGGGTTG GTAAGTTTAA ATATGAGTCA TGCATGTGGA GAAAATTGTA ATAAAATGCA
83041 AATCACTTTA ATCATAGTTC TTTGGAACTT AGAATTAATT GAAAAGGACT GTTAGAATTT
83101 CATTTACCCG TTTTATTTAG AAAGCCATTG CTTTCAAACT AGTAATTCCA GTTTGTCCCA
83161 GTGATGGCTG TTAATTCAGG GGGGAAAAGC TTTTTAACTC CTGTCTCATT GAGTGTTCAT
83221 CTCCCTCCAA AAGAAAAAGA AAAAAAAAAA AACCTCCAGC AACAATAATT ATAGTAATTA
83281 AGCTATTAAA GCTATGGAGC AAAACAATTC TGTGCTGAGT TTGAGTTGGA AAAGAAAAGT
83341 CAGAAGTTGA AATTTAGACT ACATACTTAA GAAAACACCC TTCAATGGTA GACTTAGAGG
83401 CGATTTTGAA ACCTAATTTC ATTCAGCTAC AATCTCTTTT GTAGTACTCT TAGCAAATCA
83461 ACTTCTGTTT GAATATTTCT AGTGAAAGCC ACTTTTTATA ACAACAGCAG GAAATGAAAT
83521 TTGGAAATAC AATTTGATGC TTGCAGCTGC CAAAAAAGAG ATTGGCTATA GAAATCATAA
83581 GAAAATTCAG GGTGTTATTT GTAGATTTTT ATCTGATTTT GAAATGTCTA AATAAGTGAA
83641 TTTTTCTGTG TCTCCCATAT AATGAAATGT CATGTGAATA ATTGAGAAAT AATGTCTAGC
83701 TTGGAAATAA ATGTAAGAAC CAGAATGCTC TTCACAGGTT TTTATTTTTT AATAAAATAT
83761 TCCGTTAATC CCTACTATGT GACAAAGAGT TATTGTGAAA GAAGGAATAG GTACATTCTG
83821 TTTTGCTTCA GAAGACATTC AGGTGGAAAT TGCAGGAATT CAAACTTTCG GCCCATAAAT
83881 AAAGTACTTT TCAAAACCTG TGTCTGAACC ATGATAATAC AAATAGCTTT GTGAAATTAA
83941 GTTCCCAAGC ATGAGAGATG TATATGATAA AATATTCATG TAATAAAAAC TACCCTGAGT
84001 CCCGTTGTAG AAGGAAGTGT ATTGTGTTAG GTGCGAGGTT AGATAAGACA ACTTTTAAAA
84061 AAATCTTTTC AATTCTAAGG CTAAATAATA GAATATTGAG TAAGCAAGTA AATTTTTTTA
84121 AAATATTATA ATCTCTGTTT CTAGTCCTGG ATTAGTTTTA TGGAAAATGG TGTTGTAATA
84181 AAATTGTTCT TGAAATTTAC AGTTTTACAG CGTCTATATT TTGCTCTTTG AAATGAAAAC
84241 ATTGATCAAA AAAATCTCTG GAATGTTTGA AAGAATAACT GATTTCAGTT ATTTAAAGGA
84301 CACTTTACTG TTAGAAGAAA ATAACGTTCT GTATTTTTGT GTTTTGCATA GGAATGATGA
84361 TGTCTCAGTA TAAACTTTCT CAGAATTCCA TGCACAGTAG TCCTGCATCT TCCAATTATC
84421 AACAAACCAC TATCTCACAT AGCCCCTCCA GGTAATATAT GTATATATCG TTTATTAAAT
84481 ATTGTCTTGT ATGGTGAATA TGCTGGTGAA TATATGGTTC ATACATTTAG GTAATGGTGG
84541 ATTATTTAGA GTTTAAATAG TTGAAATACT TAAATAGTAA TCCACTTTGC ATTTGCCTTA
84601 AAATGTTGTA TATGGAAATA GTCTGATATG CTAATTGAAG TAGCTACCAT CTTAGTAATG
84661 TAATTTCATA CAGACAAAAA ATGTTAAAAT AACTAATGTG TTTGAGATAA GAAGATTTAC
84721 GGAGCATGGC TTTAAGTACC TTAAACAGAT TGGTACTTTT ATATAAGTAA ACAAATTACC
84781 TGTTTTTAAA AACTTTTTTA TTGTAACTCT TTGATTATGA ATTGTGAACA ATTTTTGTAT
84841 GTTATTTGAC TATTTTGCAA GATTCTTCTG TTTGCATAGA TTTTACATAT ATAAACTAAG
84901 AGATCAGAGG ACTTTGTGAC AGTCAGATTT CAAGGAATAG CGTGTTTATT TTATTTCCTT
84961 ATATTTTTTT ATTTGGGTTT TGGGTTTTAG CCGGTTTGTG CCACCACAGA CAAGCTCTGG
85021 GAACAGATTT ATGCCACAGC AAAATAGCCC AGTGCCTAGT CCATACGCCC CACAAAGCCC
85081 TGCAGGATAC ATGCCATATT CCCATCCTTC AAGTTACACA ACACATCCAC AGATGCAACA
85141 AGGTAAGAAA GTTGTTTGTA ACTTCACTGG GAATGTCTAA GTGCTTTAAT TCCAAGCAAA
85201 TTTGTTTTTT AAAATATAAT TATTAAACAC AAACTAAAAT ACTATACTGT ATACTTGTCA
85261 GTAAACCTTT TTAAAGATAT GGCTTAAATC ATTAAAACAA TGTTACACTT ACCATTTGAA
85321 AATTTGTCAT TTTAGGAGGT GAAAGGAGCA GTGTCATTTT GGCTTTTTGG ATTCAGTTAT
85381 TATATAACTA AGTATATTTA GGTGTGAAAT TAAGAAGAAC TGCGTTTTTA AAAATTGCTC
85441 CTTCTTCTTA CATTAGCACT AAGCCAAGGG ACAATTACAT TTTAATTGGT AAAGTAGATA
85501 CAGTCAGCCT TTCACATACA TGGTTTCTGC ATCATGGATT CAACCAAACA CGGAGTGAAA
85561 ATATTTGGAA AAAAAATTGA GTCTGTAGTG AACACGTACA GACATGTTTT CTTGTCGTTA
85621 TTACATAAAC AATATAGTAT AGCAACTGTT TACATAGCAC TTACATTGTA TAGGCATTGT
85681 AAGTAATCTA GAGATGATTT AAAGTACTGT ATAGTGCATA GGGCTATATG CAAGTACTAT
85741 GCATTTTATA TCAGGGACTT TTAAGCATTT GCAGATTTTG GTATCCACAG AAGGTATTGG
85801 AACCAATCCC TCATGGATAC TGAGGGATGA CTACTATGAA AAATTTACTA TACTGTAATA
85861 ATTTGTAGTA AAAATTTACT GTAGTACAGT AAAGGAAAAT TAATCTTAGA TGCAAAAATT
85921 TGAGATTAAA TTACCAGTTC TTACTTGATT ACTAGTTCTT AATGTCATAA TGTTGATATT
85981 ATGATGTCTT TTTAAGGTTA TATTGCCTGG AGATATATTT CATGGTTACT AAATAATTGA
86041 TTTATTATTA GTATAAATTG TATGTTTTAA AGAAATTTTT TAAAGCAGAA AAGTGCAAAG

Figure 7X1

86101 GATAATATAA AAAACATCTT TATTTTTGTC CTCCTTAATT AACAGCAAAT TTTAAAAACT
86161 TGCTTTCAGT CACTAGTTTC TACATGTGTA TTCTTGTTTA TTATGCATGA AGTTGAAACT
86221 TTATTCATTA ATAAACTTAT TAATGTATAA ACTTTTAACT TTGTCATCCA TCAAAACAGC
86281 TAACTCTGGT TTCCCAAAAC CAGATTATGA AATATTAGGT TGAGCTTTTT TACACACGAA
86341 CTCAAGGAGA AACTGGGAAG CAAATTTGAC ACATTTGAAA TAGACACAGC CAGGTGTGGT
86401 GGTATGCACT TGTAATCCCA GCACTGTAGG AGGCTGGGGC AGAGGAATCA TTTGAGCCCA
86461 GGAGCTCAAG ACCAGCCTGC GCAACATAGT GGGACCCTGT CTCTACAAAA AAAAAAAAAA
86521 TTAGCCAGGC ATGGTGGCAT TTACTTGTAG TCCCAGCTAC TCAGGAGGAT GGCTTGAACC
86581 CAGAAGGTCA AGACTGCAGT GAGTCATGAT CACACCATTG CAGTCCAGCC TGGGTGACAG
86641 ATTGAGACCT ATCTCAAAGA AAAGAAATAG ACACTTAGAA AATTACTGAA TTGAGTGTGA
86701 GTGCCAAACA TACATATCTA TGTGTATATG TAGATTCTTA ATATATGTAA AATACTATTA
86761 TACTCAAGTA CACAAAAGTC TGAGGGACAT TTTACATGTA ATGGAGGAAA AATGTCAAAA
86821 GAGCACATCC ATATACACAT GAATGTGTGT AAAACAGAAT GTAAATTTTA TCTCTAAGAA
86881 ATGTGATGTG TTTTCACAAA ATTAACTTAG GTTTTTAATG TAGTTTGAGG ACCTATTCAG
86941 TATTGTGTCA TTTCTTAGAA ATGCTCAGAT AAAGAACTAA AAACCATACT CAGGGATTAG
87001 CCTCACCCAG ATATTAAAGT TATTCTAAAT AAAAAAATTT AGTCAGTACT ACCCAAAACA
87061 GTTTCTATAT TCAACGTAAT CCCTATCAAA ATACCAATGA CATTCTTCAC ATAAACAGAA
87121 AAAATTTATA TGGAACCAAA AAAGACCCCA AATTTCCAAA GCAATCCTGA GGAAAAAGAA
87181 AAAAGCTGGA GGCATCACAC TACCTGACTT AAAAATACAT TACAAAGCTG TAGTAACCAA
87241 ATCAGCTTGA TACTAGCATA AAAACACATA GACCAATCCC AGAATAGAGA ATCCAGATAT
87301 AAATACAGAT ATTTACAGGC AACTTACTTT TGACAAAGGC ACCAAGAACA TAAAATGAGG
87361 AAAGGACAGT CTCTTCAATA AATAATGCTG TGAAAAATAA ACTCAAAATG GATTAAATAC
87421 TTAAATCTGA GACATGAAAC TACTAGAAGA AAACATTGAA GAAACACTCC AGGATGTTGG
87481 TCTGTGCAAA ATACTTTCTG TTTAAGATTT CAAAATATAG GCAACCAAAG GAAGAAATAG
87541 ACAAATGGGA TTACGTCAAG CTAAAAAGCT TCTGTACAGC AAAAGAAACA ATCAACAAAA
87601 TGAAGAGACA ACCTACAGAA TGGGAGAAAA TATTTGCAAA CTATCTGTTT GACAAGTGAT
87661 TAATAACTAG AATATCAGGA ATATATAAGG AACTCAATAG CAAAACAATA ACAACAGAAA
87721 CTGATTAAAA GCCAAAAGAT GTGAGTAGAC ATTCTCAAAT GAAGACATCA ATGGCCAGCA
87781 GATACAGCAA AAAATGCCGA ACATCACTCA TCATCAGAGA AATACAAACA AAAAGCACAG
87841 TGAAATATTA TCTTGCCTTA ATTAAAATGG CCTTTTTCAA AAAGACAGGT AATAGTGAAT
87901 ACTGGTGAGG ATGTGAAGAA AAGGGAATCC TCATATACTG TTGGTGGGAA TGTAAATTAG
87961 TACAGCCTTT ATGGAACACT GTATGGTGGT TTCTCAGAAT ACTAAAAATA GAGCTGCTGT
88021 ATGATCCAGC AATTCCACTA GTAGGTATGT ATCCAAAAGA AAGGGAATCA GTATACTGAA
88081 GAGATGCACG CCCATGTTTA TTGCAGTACT ATTCACAAAA TAGCCAAAAT ATGGAATCAA
88141 CCTAAGTCCC CCATCAGTGG ATGAATAGAG AAAAGGTGTA TGTATACACA ATGGAATATT
88201 ACTCAGCCAT AAAAAAGAAT AAAGTCCTGT CATTTTCAGC AACATAGAGG GAACTAGAGG
88261 TCATTATGTT AAGTGAAATA AGCAAAACAC AGACAAATAT TATATGTTCT CACTCATATG
88321 TGGCAATTAA AGTGGATTTT AAGAAGATAG AGAATAGATT GGTGGTTACC AGAGGCTGGG
88381 AAGGGTAGAG GAGGGAGGTG TTGAAGAGAG CTTGATTAAT GGGGACAAAT ATACTGTCTG
88441 ATAGGAGAAA TAACACACAG TGTTTAATAG CTCAGTAGGG TGACTGTAGT TGACAGCAAT
88501 CTATTTTATA TTTCAAAATA GCTGGAAGAA GATAATTTGA ATGTTTTTAC CATACAGAAA
88561 AGACAAATAT TAAGGTGGTG GATATCTGAA TTACACTGAT GCAATCTTTA CAAATTATAT
88621 GAATGTATTT ATCACATGTA TCCCAGAAAT ACGTGCCTCT ATTATCTGTC AATAATAAAA
88681 CATAATTTTA TTTGAAAAAG AAAAAAGTCT GGCAGGGAAA AAGTGGATAG GTCAGTAGGA
88741 CAGAGAGAAT GCAGACGTGA GACAGTTTAG ACTATTGAGA AAGGTTGCAT TTTTTTTCAA
88801 CTTTATATTA CAAAAATTTA ACCATGCAGA AAAGTTCTAA GATTAGCACA ATGAACCCCT
88861 TCACCAACAG GTATCCTGCC ACTTTGTCCT TAAGTACATC TGCTAAGAAT ATTCTCCTAT
88921 ATAAAAAATT AAGGTCAGTT CTGTGGTATC ATCTAATATC CAGAATACAT TTGACTTTTA
88981 CCAATCCAGT TGTCCTAAAT ATATTTTTAA TATCTTTTCA AAGCATGTTC AAATCTAGCT
89041 TTTCACACAT TGCATTTGAT TTTTACATCT CTTATGGAGG CTCTTTTAAT CTAAAGCAAT
89101 CTTACACCTT TTTCACCCCA TGACACTAAT TTTTGGTTTT TGAAGAGTTT GGCTACTTTT
89161 GTTGTAGAAT ATTTCATATT CTAAACTCCA CTCTTTTCTG CTGGTGTTGT TTAATTTGTT
89221 TTCTGTATTT CCTATCAAGT AGAAATTAGC TTTAAGGTTT TACTAGTTTC CAGTTACACA
89281 TTTTTGGCAA GAGTACTTGG TAAGCAGTGT TGTGCACTTT ACATTGTATC TTATCATTAT
89341 CATAAAATGG TCTCAGTATC AGTGGTGTTT AGGTGGTGAA CCTCTCTTTA TTGTAAAAGT
89401 ACATATTTTT CCCTTTGCAA TTAGTAAATA ATCTGTGGGA TGATACTTTG AGATCATGTA
89461 AATATACAAT TTCCCATTAA TCTTTTACTT AAAGGGGGTA GCATTCAGTG AATCTCATTT
89521 TATCAGTTTT TACAAAGTCA TTGGAAAAAC GATGATTTTT TAAAATTTTA TCATTCTAAA
89581 GATTACATTT TAAAATCAGC ATATAAGAAT GGATTGTTTA ATAAATGATG TTGGTGATTG
89641 TCTAGGTATT TTGCAATTTT AGCTGGATTC CTGGATCACT GAAAGCAAAA GTGTTCTAGA
89701 TTAATAAGCT GTTTGTATTT TTTAAGTCAT AAAATTATAA GAAAAACGTG GGCGAATTTT

Figure 7Y1

```
89761 TGGTATTCTA AGAGTTGAGA AGGCATTATT TCTAAGCAGA CCGAAAACCT CGATTGTAGA
89821 AATGAGAAAA AAAGATTAAT TATAAATTTG TATATAAGAG AACATAAATA TATAAATTAC
89881 ATAAATATAA AACAAATATG GGGGATATAT GCAACATTTA TTATAAACAC AAAGTATTGA
89941 TTTAATATAC CGAAATCTCA TACAGATCGA TAAGAACAAG ACAAAAATGA ACTAAAGAAG
90001 TAAACAGGCA ATTTACTGGA AAAGAATAGC CAAGTCGATA CAGAAAGATT TAATAAATAT
90061 ATGAAATTGT GGTCACCTTA GCTCATAGAG ATGCATTCAA AATTAAGATG AAATAAAATT
90121 TTATATCAGA TTGATAAACA TTTCAGTCTT CATAGTGATA TAAATTGGTG CAACTTTTTT
90181 AGAGAACCGT GTGTTTGACA GTATCTATCA TATAATTTAA AATTCATATA CCTCACTCAG
90241 TAGTCCAAAA TCTACCTCCC TTAAAAGAAG GGGAAAGGGA TAAAAACATA CTCAGACTGT
90301 TCTAACAAGT TCTACCAAAC ATTAAATGAA GAGATATGCT AATCTTAATC CATTCCAGAA
90361 AAAAGAAAAA CAGCAACACT TTCTTAACTC TTTTTATAAA GTTAAATTAC AATCTGGATA
90421 CCAAAATCAG GTGAAGTGAG GGGAGTATGA GAAAGGAAAA TTATAAATCA GTCATCACAT
90481 ATGAACATTC ATGTCCTGTT CCCGAATTGA AACAAAATGT TTCTAATTTT TTCTACCACT
90541 AGGTAAGATT AAATCAATCT CTTTTTCTTT TTTCCATACA GATGGGGTCT TGCTGTATTG
90601 CACAGGCTAG ACTCAAACTC CTGGGCTTAA GTGATCCTTA AGCCTTAAGG TGAAACAAAT
90661 TTTTTAAACA AATATTAAGA AACCAGGCCA GGCATGATTG CTCACTCTTG TAATCCTATC
90721 ACTTTGGGAG GCCAGAACGG GCAGATTGCT TGAAGCTTAG GAACTCAAGA CCAGCCTGGG
90781 CAACATGGTG AAACTCCATC TCTCTCCACA AAAAATTAGC CAGGCAAGGT GGTGTGTGCC
90841 TGTAGTCCCA GCTATTTGGA GGCTGAGGTG GGAGGATGGC TTGAGCCTGG GAGGCAGAGG
90901 TTGCAGTGAG CTGAGATCAC GCCACTGCAC TCTAGCCTGG ACAACAGAGT GAGACTCTGT
90961 CTCAAAAAAA AAAAAAAAAC AAAAAACAAA AAACGAATAA GCAGTGTTAT CAACCTATAT
91021 GACAAAATTG GATATATATA TGAATTGATT AGTAGAAGAC AATTAATATA ATTCAGATTA
91081 TGGGCCTGGG GTCCTGTGAG CCTTTTAATA GGTCTCAAAA GAGCATTCAG AAAGATTCAA
91141 CTTCCATTCA TGACATTTAA AACTTTTCAC TGAATAAAAA TACATTAAGC ACTTTGGGAG
91201 GCTGAGACTG GTGGATCACG AGGTCAGCAG ATTGAGACCA TCCTCGCTAA CACAGTGAAA
91261 CCCGTGTGTA CTAAAAATAC AAAAAAATTA GCTAGGCGTA GTGGCAGGCG CCTGTAGTCC
91321 CAGCTACTCC GAAGGCTGAG GCAGGAGAAT GGGGTTAGCC TGGGAGGCGG AGCTTGCAGT
91381 GAGCCGAGAT CGCCTGGGCA ACTGAGCAAG ACTCCGTCTC AAAAAAAAAA GAAGAAAAAT
91441 ACATTAAGCT GGGTGTGATG GTGCACATCT GTAGTCCCAG CTACTCAAGT GGCCAAGGCA
91501 GGAGGATCAC TTAAGCCCAG GAGTTTAAGT CTAGCCTGTG CAATACAGCA AGACCCCATC
91561 TGTATGGAAA AAAAAGGAGA AGAGGTTGAT TTAATGTTAC CTAGTGGTAG AAAAAATTAG
91621 AAACATTTTG TTTCAATTCA GGAACAGGCC ATGAATGCCT ATAATGACAT TTATTTAGTG
91681 GGTGTCCCAG CCAATACAGG AAGATAAGAA GCGTTAAACT ATGTATAATT ATTGGTAAGG
91741 AAGAAAAAAG TGTCATTTTC AGGTGACATA ATTGTCTTCA TAGAAAATCC AAGATAAGCT
91801 ACAGACAAGA TACTAGAATT AATAAAAGCA TTCCACTTAG TTACTGGACA CAGCATCATT
91861 ATAATGAAAT CAATTGCATT TTTATATACA GAAATAAGCA GTTATAATCT TTTTTGATAG
91921 CATTAACAGT TTAAAAGAGC ACCACAAGAT ACCTAGGAAT AAATTTAATG AAAGATGTAA
91981 AAGACTTTTG TGGAGCAAAT TACAAAACTT TTGAAAGAGA TAGAAGAAAA GAAAATGAAG
92041 AGTTATGCCA TCTTCATGGA TAGGAAGACT CAATAGGGTA AAGATTATTA TTACACCCGT
92101 ATCTATAAAT TCAGTATAAC ACTGATAAAA AATCTCAAGG AAGGTTTTTG TGGAATTTAA
92161 CCTGCTTCTA AAAATTCATA TAGAAGTTGT TCAAGAATAG ACAAAATAAT AAGGAATGAA
92221 GTGTAGCAGC TCAGTCTAAC AACAGTCAAG ATTTATTGTA ATATTGGTGC AGACATGGAA
92281 AAATAACATA TAGTGAAGTA GAACATGATG AAGAGCTTAG GAACATACCC ATGGACAAAT
92341 GTAAACTTGG TCCATATGGC ATTATATCTT AATGGGGGAA AGAATGATTT CTTTAATTAA
92401 TGATGCAGTT GTTCATATGG AAACAAGTAA CATTGGATCC CTATCTCACA CTTAAAAATA
92461 AGTTTTACAT GGGTTAAAGA CCTAACTGAA AAACCAAAAC TGTAAGGCTT TTAGAAGATA
92521 CAGGAGGCTG TCTTTTTATG ACTTTGTGTA AAGGAGGGGA TCTGAATGGC CAGTACACAA
92581 GAGAAGATGC TTGGCTTCAC TAGTAATCAA GGAAATCCAA AGTAAAGTGA CTGTCAGAAA
92641 CATTTCCTAC CCTTAGAATG ATAAAAATTA TTGGCAAGGA TATAGAACAG TGGGAACTCT
92701 CATACGCTAC CAATGAATAC AAATGGTCAT AAGTAATCTG TTATTTAGTA AGGTTAAAAT
92761 ATGCATATCT GGCAATTTCA CTCCTAGGTA TTGGCACCTA GAGCTCTTAC ACATTTATAA
92821 AAACAGTCCT TATGTACAAG AACATACATT GCAGCATTGT TTATGGCAGC AAGCATTTTA
92881 AGCGATTTGA ACATCCACAT AAGAATGAAC AAATAAATAG TGTACATCAT ACAGCAGAGT
92941 ATGTGTAATT ATTTAAAATA AATGAATTTA CACCAGGCAC AGTGGCTCAC ATCTACCTGT
93001 AATCCCAGTG CTTTGGGAGG CTAAGGCAGA AGGATCATTT GAAGCCAGGA GTTTGAGAGC
93061 AGCCTGGGCA ACATAGCAAG ACCCCATCTC TACCAAAAAA AGAAAAAGCC AGATGTGGTG
93121 GCAGTTTCCT GTAGTCCTAG CTACTCAGAA GGCTAAGGCA AGAGGATCAC TTGAACCCAG
93181 GAGTTTGAGG TTACAGTGAG CTATGATCAT GCCAGTGAAC TCCAGTCTAG GTAACAGAGC
93241 TGTCTGTAAA AAAAATAAAT AAATAAAAGA ATTTAAAACT ATATATATAT ATATATATAA
93301 AATCTCAGTA TAATATTAAA TGGAAAAACA AGTTATATAA GGATAGATAC ATATATCATC
93361 TATATAAAAT TATAATGTAA AAACAACACA ATGAATTACT TAGGAATATA TTCATGCATA
```

Figure 7Z1

```
93421 GCAAAGGTAT AAAGATAACA CATAGGCAGA ATAAACTCAG ATCAAAATAG TGGTTACCTC
93481 TAGGGAGTAA AAGGAAAGGA ATAGAGGAGA GAAATAACAG ATAAATGGAG ATCTTCAACT
93541 ATATTTGTAA TGTTTTAGTT CTTTTCAAAA ATAGATTGGA ATCTGGCAGA GTGTTAAGAT
93601 TTGATGAAAC TAGTCAGTAC ATGAGTATCT GTTATATTAT TCTCTGTAAT TTCTATATGC
93661 TTAAAATATT TGTGAATAAT TACTATTCTC CAAGAATGTT AAGAATCTTT TATTAAACCT
93721 TTTTTTATTC TTATTAATTT CAGCATCGGT ATCAAGTCCC ATTGTTGCAG GTGGTTTGAG
93781 AAACATACAT GATAATAAAG TTTCTGGTCC GTTGTCTGGC AATTCAGCTA ATCATCATGC
93841 TGATAATCCT AGACATGGTT CAAGTGAGGA CTACCTACAC ATGGTGCACA GGCTAAGTAG
93901 TGACGTATGT AATATATTAT CATTAAGGTG ATAAAATAGT TCTAATATTT GTCATATAAC
93961 CTAGTATTTC CATTTCAAAA TTTGAATGAT ACCTACCGTA TATCATTATA CTGGGTACTG
94021 AGTACAACAT GGCTCCTGCA CATACAGAGC TTAGTCTAGA GCAGGATTGG TCAAGTGTGA
94081 CCAGTAGCCT GAACCACAAA GTGAGAATGG TTTTTACATT TATAAAGAGT TATTTAAAAA
94141 AAAAAAAATG TGATAGAGAC TGTATGTGGC CCACAGAGCC TAAAATATTT ATTCTCTGTT
94201 CCTTTATAAT GAAAAGTTGG CTGACCCCTG ACCTTGAGGT TTAGGTTCTT AATGAAATAT
94261 TTCAGTTTTA GGTTAATACT GCTCACACTA AAATTTTTTT TTTTTTAGAT AATGAGCCTG
94321 TATTTATTAG TACTTGACTC TTTTTCCCTC TGATACTTGT ACAAAGTTTT GTGTCTGAAA
94381 TTTAATATTG CCTTGATGTT ATTAAAATAT TCCACATTCT GGAAATTTGC CTTGTTATTG
94441 ATTTGATTGT AATTTATGTA AGCTGCATGT GTCTAAGGAT AACACAGATG ACAATAAACT
94501 CTGCCCTCAA GTCATTTACC ACCTGGTAGA GTATTCATAG CTCCTTTTGT AGAAAAAAGC
94561 AAACAAAAAT GGAGCATACT AGTAATACAA ATTTTCTTAT TCATTGCCAT GCTTAGGCTG
94621 TTGATTCTTT TGGATACAAT TTCAATTCTT CTAAGATATA CCAAGAAGAA AACAGGAAAG
94681 TGCAGAAGAA TTATGCTTTT GAATTCCAAC ACTTTACCTG TCAGTAATTT ATGTCTCTTA
94741 TTGGTTCTCT TTTAAGATTT CTATAAAGCC TCTCCTGTCA TTCAAAAGAT AAATTGTATA
94801 CTCTATTTTT AGGATGGAGA TTCTTCAACA ATGAGGAATG CTGCATCTTT TCCCTTGAGA
94861 TCTCCACAGC CAGTATGCTC CCCTGCTGGA AGTGAAGGAA CTCCTAAAGG TACTACTGTA
94921 ACTAAAATTT CCTTCTGTAT ATTTTATATT TGAAGTTGAA TAAAGAACTC AGACTTCCTA
94981 AAGCAGATAT TAAAAAGTTA TTCTGTATTT TTTTTTCATT GTAGAAAAAA AAATAAACCT
95041 GTACAAGCAG GTCTGGATCA TGGGATTTAA ATCTGTCCCT ATTCATTGAT TCATTTATCT
95101 TCCACTTACC CAGTAATCTG TTGATAGTAT TCTCGGATAC ATCCAGTATC CATTCTCTTT
95161 AATAAATCCA GTGGTCTTTT CAAACCACAA CGTTCTTCTC TTAAACATTT GAAAATTTTG
95221 ATCAGCTTTC CTCTTTCCTC CAAAAAGACT TATTTCATAT GAGCCCATCT GTTTTTCTCC
95281 CACTTCTTTC ATTGATACTT TTTTTCTTCA TTAGCTCCTC TCCTTATTCT TATTCTTCTC
95341 AAGATTTCTA TTATTAGACC TTTTATCACT CATTGTACTT TTTTCCCTGG CCGTTTTATT
95401 AAGTTTCATT AACAGCATTG ATTATTTTCA TGCATAAGAC TCCTAAATCA ATCTTTGGCT
95461 CCAGTCTTGT CTCCCAAGTT CTAATTCTTC ATTTCCAGAC AAAACTTCCT TCATACCTAG
95521 CGGATATTTC CAATTCATCT TCAAAATGGT TTTCACTGTT CTTTCTACCA TCCCATCTGT
95581 CTTAATGCTA TTCCAGTCCT GAATCATTGT AACTTAAAAA TTTTAAGTTA TCATAAAGCC
95641 TCTTTTCAAC TATTTAGTCA TTTATCAAAT CTAACCTGTT CTGTTAATTT TTAAATCTCT
95701 CACGTCTACT TTTATCTCTG CCTTTTAAAA TTCTTTTATT CCAGATCTAA GTTAAATGGG
95761 TGATCTTCCA TGGGCCCTCC CCTAATCTCC TCAAGCTATT AGTTTATATT TTTTGTAAGA
95821 ACTTTTACTA CTTTATGCAC ACGAATTTCA GTTTATCTTT GAATTTTCAA AGAACCTTGC
95881 ATGGTCTTCT ATCTGTAACA GATTCACAAA ATTGTGAATT TAAGTCCAGG TTTGAGCCAG
95941 TTTTTAAAAT ACTTAAAATT GTAGTCAAAT AGCTTTAATT ATCAGTTTGT TGGAAGAGAA
96001 AACTGTCTTC TACTTTTTAA AATTAGCTTA TAATTAATTT TAACATAGCT GGTAATATAT
96061 TCTCTCAAGT AATGAGAATT TCTAATTATA GCCATCTGAA ACATAAAGAT ATTTTACCTC
96121 GTATCTGCTT CATATGGTAA AGATCTTTTT TTCACTGATT GTGTTCGTAC TATTTATCAA
96181 GGACATTTTT CTTTTTTTTT TTCAAAAATT TTTTAAAAAT TTTATTTTAT TTTACTTTAA
96241 GTTCTGGGAT ACATGTGCAG AATGTGCAGG TTTGTTACAT AGGTATACAT GTGCCATAGT
96301 GATTTGCTGC ACCTATCAAC CCGTCATCTA GGTTTTTTTT CTTTCTTTCT TTTGAGACAG
96361 AGTCTCGCAC TGTCACCCAG GCTGGAGTGC AGTGGCATGA TCTCGGCTCA CTGCAATCTC
96421 CACCTCCCGG GTTCAAACGA TTCTCCTGCC TCAGCCTCCT GAGTAGCTGG GATTACAGGC
96481 ACATGCCACC ACGCCCGGGT GATTTTTTTT GTATTTTTAG TAGAGACAGG GTTTCACCAT
96541 GTTGGTCAGG CTGGTCTCGA ACTCCTGACC TCGTGATCTG CCCGCCTCGG CCTCCCAAAG
96601 TGCTGGGATT ACAGGCGTGA GCCACCACAC CAGGCTTGTC GTCTAGGTTT TAAGCCCCGC
96661 CTGCATTATG TATTTGTCCT AATGCTCTCC CACTTCTTGC CCCCTACCCT CCAACAGGCC
96721 CTGGTGTGTG ATATTCCCCT CCCTGGGTCC ATGTGTTTTC ATTGTTCAGC TCCCACTTAA
96781 GAGTGAGAAC CTGCGGTGTT TGGTTTTCTA TCAAGGACAT TTTTCATAGA GTGAAAGTTG
96841 AGCTGTTATG AGCCATTTCA ATTCTGTAAA TTGTATGAAT TTTCAGGGAT AAAAACCCGG
96901 CTTCTGAAAG AGAGAAAAAC TTCCAGAGTA ACTATTTGTA GGTTAGATAC ATATCCCACA
96961 AGTGTTGTCA AGGTGAGAAG TTATTTAGAT TGCCGGGGAA AGAGAACAGG GAGATAGGTG
97021 ATTGATCTAG ATAACTAGCT TTTTTTCTTC TGACTCTTGA GATTAGATAG ATAAATAGTA
```

Figure 7A2

97081 GATGAACTTT AGATAGAAAT GGAAAACTTT AAAACAAATA ACCTCACTAA TATATTATTC
97141 ACCAAAAGCT TGAACTTCTG TCATGAAGTT GTTTTCTAAC TAGTTTTGAA GGGTAAGTGC
97201 ATTGTCAGTC TATCTTGATT TTTAGATTAA TTATTAGAAT TTGAAGTTTG TTCTAAAGTG
97261 TATATAATTT GCCACATAGA ATTTAAATAC AAAGGCATAA TGGTATATTA CAATTCAGAC
97321 TTAGACAAAT CTTGTTTTAA ATCTTCAGGT TTGTTAACTA CATAACCTTG GGCAAATTTC
97381 TTAACCTCTG TAGGCTTCAT GTTCCATTTC TGAAAAATTT TAAAGATAAT ACTCAAGAAT
97441 GTTGTAAAAA TCAAGTGAAT TGATATGTAA AGCACCTTTC ACAACTCTGA CACAAAATGT
97501 TAGACTAACA TTTATAGTTA ATTGCTCCCA TATCATCTTT ATCACACTAG AGTCAATAAA
97561 TAAAGTTGTA TGTTTATATA TAACATTTAA AATACATTAA CCTTGCTAAC TGAAAGTCCA
97621 GATTTATGTA TCATGGAAAA AGACTGAAAG CTTAATTGAA GGCAGTTCTA GGTTTAAGTT
97681 CTGTCTGTAA AAAAACTTTT ATCTTGACCA ATTTTTACAA TTTCTTACAA GTTTTTAAAT
97741 ATTTTATAGT TTAGTGATAA GAAATGTATA CATTATTCAG ATGCAGTTAT ACTATTATTT
97801 CTGAAGCATA TCAATGCACT TTTTCCTTCA TGTCTGAAGG AGAATTTTTG TCTGAAGGCT
97861 TATTAACTAG GATAATTTTT CCATCTGATT ATTTTTAACA CTTTCCTGTT TCATATAACA
97921 TTGGTTGATT TAATGGACTC TGGGCTCAAT ATATTTTATT GGGCCTTGAA ATTTACTGAA
97981 CTTATTTATT TTTCTAATAA AAAGAGGATT AGCAAGCTGA AGAGAGTATG TGAATGATGT
98041 TAAGGGAGAA AGAGAAGACC ACATAAAAGT ATAAATCAAT ATTTTACCAC CAGTTTTTGA
98101 AGTAAGTAAA GGCTCTAGTA ATTGTAAATT GACCACTTGC TTTTTGTTAT CATCCCAGTA
98161 GTATTCATGT AAGATAGTCT CTAGGATTAA ATTGTTATTT TTGTGTAATT TAACAAAAGC
98221 GTACTTATTC TTACTTTAAT CAGGATATAT CTGTTTTCCC AGATAGTCCA TGAAAGAACA
98281 GAGATGGTCA TACCCAAAAT ATTTGTGTTG TATCATCTTT AGAAGCAATG AACTTTTTAC
98341 CCCTATAAAG CTAAATATGT ATACTTTATA GGCACAAAAA TATAGAAATA ATACTGGTCT
98401 GAAAAATTGA ATACTCATAC TTAGATTCAA ACCTAGATTT TAGATTAACT ACTAGCAAGC
98461 TAAACAACTG TGTGGGACAA GTTTTTAAGC TTTCTTTTCA TCTTTCGTAA ATAAGTAGCT
98521 TGGATTATAT AATTTCTTAT TTTTTTCTAG TATTACTATA TTGTCACTTA TTAATATTTC
98581 TATCACATTG TAAGAAAATG TGAAACCACC ACAACTGTTA CTTCTATCGA ATTATTTTTC
98641 TAGGCTCAAG ACCACCTTTA ATCCTACAAT CTCAGTCTCT ACCTTGTTCA TCACCTCGAG
98701 ATGTTCCACC AGATATCTTG CTAGATTCTC CAGAAAGAAA ACAAAAGAAG CAGAAGAAAA
98761 TGAAATTAGG CAAGGATGAA AAAGAGCAGA GTGAGAAAGC GGCAATGTAT GATATAATTA
98821 GTTCTCCATC CAAGGACTCT ACTAAACTTA CATTAAGACT TTCTCGTGTA AGGTCTTCAG
98881 ACATGGACCA GCAAGAGGAT ATGATTTCTG GTGTGGAAAA TAGCAATGTT TCAGAAAATG
98941 ATATTCCTTT TAATGTGCAG TACCCAGGAC AGACTTCAAA AACACCCATT ACTCCACAAG
99001 ATATAAACCG CCCACTAAAT GCTGCTCAAT GTTTGTCGCA GCAAGAACAA ACAGCATTCC
99061 TTCCAGCAAA TCAAGTGCCT GTTTTACAAC AGAACACTTC AGTTGCTGCA AAACAACCCC
99121 AGACTTCTGT GGTACAGAAT CAACAACAGA TATCACAACA GGGACCTATA TATGATGAAG
99181 TGGAATTGGA TGCATTGGCT GAAATTGAGC GAATAGAGAG AGAATCAGCT ATTGAAAGGG
99241 AGCGCTTCTC AAAAGAAGTT CAAGATAAAG GTAAAATAAT CTCATTATTA CCACTTCATC
99301 ATCTGGGCAA ATATGTAATT ATAGTGTCAA AAATTTTTTT CACATTACTT TTTTCCCGAA
99361 TATTTTGTAT AATTTATGTC TACTCAAGTA CATATTTTTA TTACTAATAC TCATAATGCA
99421 GAAGTTAAAT TCGTAACAAT TTCATTTATT GTCTGAAACA ACTATATGAG ATTTGGTAAT
99481 TCTCTACTAC AGGTCTGTTA CTCATTATGT ACTATATGAT TTTACTTATT TGTGCTTTTC
99541 TGCTAAAATG AACATTAGCA TTTCTATATA ACATGTATAT TTCACAAGTT ACATTAATAT
99601 TGTTGTGCAC CTTCAAATTT TTTTCTGCTA AAACAAGGTT AACCACTGTA GAATTATTTT
99661 GAACAGGTAC ACTTAAGAAA AGCTCATGTG TATGCTTATT AGGCAGTTAG ATATTTCACT
99721 TGGTTTATGA TCCTACTGGC TTAATAATGT CAAATTTTTT TAGTAAACAA ATCATGGAAA
99781 GAGTTAATAT TAAATAGCAA ACCTTAGAAA TTAAGAGTCT TTTGGTGGTA ATTACAGTGA
99841 AGTGTTCCCT TTTGTCTGAC TAGTATGTTA GGATGGAGTT TCAAGACATA CCTGGTCTAT
99901 GAGTTTATGA GCTTTCCTTG CGCTTCATAA TCAAACAAAA ATAAATTCAT AGTAAGTTCT
99961 TAGTAATTTG GTATACACTG TATACAAAAT TTCTTTCATG TTTTAAGAGA CTGATGAATC
100021 AGTGATTCAA ATTAGCAATA TAATTGATGA ATTTGATTGC TATATAAATG CATATACACA
100081 TTTGATCAGA CCAAAAGCAT GCTTTATGAT TTAATTTTAT GATTAAAATA TTTTAGGTTG
100141 ATTTTCAGTT CTTATATTTT ATTTCTTGGT AATGATAAAA CTTCTTGATA TTGGGTAGAG
100201 CTGATTTTTA TATATGATGT GTTCAGTGTT TGACAGGATC ATGACAAGAT AATTGTGTTT
100261 CTATGCTAAG AAACATGCTG AAGATTAGTA TTATATTTCC TGTCTGTCAT GATGGCTCAT
100321 TTTAATGTTA TTGAAAAAAA ATGGACTGTA TTTAGTAATT GTTGTACTAC AATGTTTGCA
100381 ACATATGTAA ATCAGAAATA GATGCAAATA AAGAGATTGC TAGAAGTCTT CATTTTACTG
100441 GCTAGGGAGC TGGGTTTTTT TTTCTTTGTC TTTTTTTTTT TTTAATATAG ATTCAGGGGA
100501 TATATGTACA GGGGTTTGTT ACGTGGGTAT ATTGTGTGGT GGTGAGATTT GGGCTTGTAG
100561 TGAACCCGTC ACCCAAATAG TGATCATAGT ACCCATTAGA TAGTTTTTCA ACCTTGGCTT
100621 CGTCCCTTTT TCCCCCTTTT TGAGTCCCCT GTGTCTGTTG TTTCTAACTT TATGTCCGTG
100681 TGTACCCATT GTTGAATTCC CACTTATAAG TGAGAACCTG TAGTGTTTCA TTTTCTGTTT

Figure 7B2

100741 CTGCATTATT TCACTTAGGG TAGATAATGG CCTCAAACTG CATCCATGTT GCTGCAGAGG
100801 ACATGATTTC ATTCTTCTTT ATGATTGTGT ACCACGGTGT ATATATACCA CATTTTGTTT
100861 ATCCAGTCCA CTCCTGATGG ACGCTTAGGT TGATTCTGTA ACTTTGCTAT TGTAAATAGT
100921 GCTGTGATAA ACATATGAGT GCAGGTGTCT TTTTTATAAA GTAATTTTTT TCCCTATGGA
100981 TAGAAACCCA GTAGTGGGAT TACTAGGTCA AATGGTAGTT CTATTTTTTG TTCTTTGAGA
101041 AATCTCCATA CTGTTTTTCA TAAGGGTTGA ACTAATTTAC ATTCCCACCA ACAGTGTGTA
101101 AGTGTTCCCT TTTCTCTGCA GCCTCTGTTA TTTTTTGACT TTTTAGTAAT AGCCATTCTG
101161 ACTGGTGTAA GATTGTATCT CATTGTGGTT TAATTTGCAT TTCTCTGATG ATTAATGATA
101221 TTGAGCATTT TTTAAAATGT TTGTTGGCTG TGTGTACATC TTCTTTTGAG AAGTGTCTGT
101281 TCATGTCTTT TGCCCACTTT TTAGTGGGTT GTTTTTTTCT TGTTGATTTG AGTTCTTTAT
101341 AGATTCTCAG TATTAGACCT TTGTTGGATG CATAGTTTGT AAATACTTTC TCTCATTCTC
101401 TAGGTTGTCT GTTTACTCTG CTATGGTTTC TTTTGCTGTA CAGAAACTCT TTAGTTTAAT
101461 TAAGTCCCAT TTGTCAATTT TTCTTTGTGT TGTTTTTGCT TTTTAGGTCT TAGTCATAAA
101521 TTCTTTAATT AGGACAATGT CCCAAAAGAG TTTTTTGCAG GTTTTCTTCT AGGATTTTTA
101581 TTGTTTGAGG TCTTACAGTT ACATATTTAA TTCATCTTGA GTTAATTTTT GTATAGGTGA
101641 GAGGCAGGAG TCCCGTCTCG TTCTTCTGCT TATGGCTAGC CAGTTTTCCC AGCACCATTT
101701 ATTGAATAGC GTGTACTTTT TCCATTGTTT ATTTTTGTCA ACTTTGTTGG AGATCAGTTG
101761 TTTTTAGGTA TGTGGCTTTA TTTCTGGGTT CTCTATCCTG TTCCATTGAT CTGTGTGCCT
101821 ATTTTTATAC CAGTACCATG CTGTTTTGCT TACTCTAGTC TTGCAGTGTA GTTTGAAGTT
101881 TCCTAATATG ATGCCACCAG CTTTATTCTT TTTGCTGAGG ATTGCTTTGG CTATTCAGGT
101941 TCTTTGTTGG TTTTATATAA ATTTTAGGAT AGTTTTTCCA GTTCTTTGAA AAATTACGTT
102001 GGTAGTTTGA TAGGAATAGT GTTGAATCTG TAGATTACTT TGGGCAGTAT AGTCAGTTTT
102061 AACAATATTG ATTCTTCCTA TCCATGACCA TGGAATGTTT TTGATTTGTT TGTGTTATCT
102121 ATGATTTATT TTATCAGTGT TTTGTAGTTG TCCTTGTAAA GCTCTTGCAA CTCCTTGTTT
102181 AAATGTATTC CTAGGTATTT TATTTTGTGT GTGTGGCTAT TGTAAATGAG ATTGAGTTCT
102241 TGATTTGGTT CTCAGCTCGA ACGTTATTGG TGTATAGACA TGCTACTGAT TTTGGTACAA
102301 TTATTTTGTA TCCTAAAGCT TTATTGAAGT TATCAGGTCT ATGAATCTTT TGGAGGAATT
102361 TTTAGGGTTT TCTAAGTATG GGATCATGTC ATCAGTGAAC AGAGATAATT TGACTTCCTC
102421 TTTTCCTATT TGGATGCCTA ATATTCCTTT GTCCTGCCTG ATTGCTCTGG GTAGGACTTC
102481 TGGAATTTTT TTTTAAACTG GTAAAGTTTT GATATTAAGG GTGAAATGTT GCTTGTACCT
102541 CTTCTCTTTA GTTTGCAGTA TGAGGTTCAG GAAATAAATA TATAGGTTCC AAATTATATC
102601 TCTTCCTCTA ACCTGTTATA AAAGTATACG CATATCAAAT GAAAAAAGTA ATATTACTCA
102661 GCTTTTCTTA TTAACCTGTT CAAAATTCCT GAATCTTAGG ATAGCCAGTT TTGCAGGAAA
102721 CATACAATAT CACAATTCCC TGACCAAGAA ATATTAGTTG CCCTGATAAC TGAATTTTTT
102781 GCATGACGTT AAATCTGTAT TATGGAAAAA TGTGTTCTTG AAAAAGAATG TACTTTTTAA
102841 GTGAATTTTA ATAGATGTTG ATAGTAACAA AAACAGAGGA GGAATGGTGA CCTTTTTTTT
102901 ATGTATCATG TTTGTTGAAT CCAAAGTTTC TACTTATAAA AATGGAATTA AAATAAGGGT
102961 CATATATAGT TCTAATTGCA TATTAGCAAA CTTATTTTAT ACTGCGAACT TTCCTTTGGA
103021 AAAATAGAAC AAAGTCAACA GATACAACAT ACTGTTCTTG TAGAAACTTG TATATTTTAT
103081 TTTCAATTAT CTAAATAGTT TTTTCTGTAA TCTGTGATGG CATAGTTAAC AGATAACTGA
103141 AAAGTTGAAT GAGCAGAGTT GACATTCAAT TTTGGTGAAA ATACAGGTAT GCGGTGATAA
103201 CCTGAGGATT AAAGTAGGTT TTGCTGATTT CATATTATTG TTGTCATTTC TAACTTGTTT
103261 CCTGAAAGCC ACTTTCCTCT TATTTCGTGG ATTTATAGTC ACGTATCACA TAATGATGTT
103321 TCATTTCACA CCAGACTTTA TATACAATGG TGGTCCCATA AAAATATAAT ATTGTATATT
103381 TACTCTACCT TTTTTATGTT TAGATATGTT TTAGATACAC AGATGCTTAC CATTGTGTTA
103441 CAGTTGCCTA CAGTATTCAG TATAGTAACA TGCTGTACAG GTTTATAGCC TGGGAGCAAT
103501 AAGCTATACC ATATAGCCTA GGTACATAGT AGGCTATATC ATCTAGGTTT ATGTGAATAT
103561 ACTATATGAT GTTCACGTAA CAGAGACACC TCCTAACAAT GCATTTCGCA GAATGTATCC
103621 TGTTGTTAAG CAATACATGA AATACATGAC CGCATTTGAA AACTTTTGGA ACTTAGATGC
103681 CACCTAACCC TTTTGATTTG AACTTGGCAT ATTGCATTCA GTTTCTGCAT TGTGTGATGG
103741 GATGGTATTT GTTATATAAG AAGTTACCTT GAGATTTTGA GATGATTAAA GGTGTGTATA
103801 TTGGTCCAAG GGTGTAGGTG AGGTCATAAA TAAAAGCAAA ATTCTTCTGA AGTGGTGGTT
103861 TTAGAGCCCT TAAGAGATGA AATACTTCCT TGAAATTAAT TTGTCCCAGT TACCATTATT
103921 TTTACTTATT AAAGACTAAA TGTTAAAGTG GACATTTAAT ATATTCAAAC ATTTGGCACT
103981 GAGGACTTTT TTACAACTGT TGTATTACTA CTGGTGATAT GGAGCAGGCA GGACTATTTG
104041 TCTGGCCTAC TAGTTGCACT TTAGGATATG AGTTTGTTTG CCAATATATT CGTTTACTGT
104101 GAGAGAAATA TTCCACTCAA TAACCAGAAA TCAAAAACAC TGTACCTTAT AAGTAAGATT
104161 AGAAAGTTCA ACAAATGTAG AATATTTGTG GAATTCAAGT AAAGGGATAG AATAATCTTA
104221 AGAAATGTTT TACCTAGGCT GTGGTAGACC CTATTGTACC CTTGTTCCGC AGAAGAAAGA
104281 CATTTTTCTA GCCGCTAGGT ATTTATGTCC CTTTGTCCTG TTCTCTCTTC TTTGAGCAGT
104341 TCTGTATATA CGTTGATAAG GCAACTTTGT AACCTAATAT TTTATAATAT TCCAAAAGGA

Figure 7C2

```
104401 CCCTTTTCTC AATCTTTTTG CTCATACTTT TAGTGTCTCT AATTACATAA ATTAATTTTA
104461 AAAGGCTATT CATCTTTCTT TGCTTCTGGG ATGACCTGTC ATTAGATATT AATACCTTTT
104521 TCATGTGCTG AAAATTTCTG CTTTCTTTTG TCAAAGAGGG GGTTCCTTTG TTCATCTTTG
104581 CCTATTTCAT CTTTTCCCAA GGTCCACTTT CCATGTTAGC AAGTATAAGG AATGGCTCAG
104641 CTTCACTAAT GTTTTTATAA TGTTACAATA TTCTTGCACT ATAGCCCTTG TTAAAAGTCA
104701 ATGATTACCT ACTGTCATTT GGAATAAGAG ACCGGGATTT TGGTACAAGG AATAGGACAA
104761 TTAGCCACTC AGCCTGTATT GTGGTTGAGG GGTGGTGTGT TTTCATTTTA CATAATTGGC
104821 TACCATGTAT ACACAATTAT TGTGCTTTCT GCTTTAAGTG TTTTCATTTA TCACTTGTAG
104881 ATTTAAGTAA GTGGTATAGT TTGTTTTTCT TGTAAGCGTA ATTGAGTTTA GAATTTCTGT
104941 AAGGGCTGCA TCTTATTTTG AGAATATCAG CATCTGGATG ACAAGTGTTG GTTTTGAGAT
105001 TATGATAATC CTTTTGTATG CATTTTCTTT AGGAATATAT GTATTCTGAT AGCTAATCTT
105061 ATGGTTCCCA GTGCTGAAGA GGGCTTACAG GTAATCACTG TCCTAAATAC CAAAATGATT
105121 CTTCATAGAG ATGGCTTTCC ATGATTATTA GGTGGTTATG ATGTAATGAA GACTCATAAC
105181 AAAAGTGGGT GGACAAAAGT GACCTGTACA GATTCAGAGC TGCTTTATAA GGAGTAAGTT
105241 CATGGTGGAA TTGAATCAGA CCAAGTGAAT CAGAACATAC ATGCTCTTGA CATACCTAAG
105301 AATCCTTGTC ACAGTAATGA AAATTTTCCA GGTTTTACAG GAGTAAAGTA CTTTTCAGTA
105361 GTTGAACGAT TAAAATTTTG TATTTAACAG CATTTTGTAT ATACTGAAAA ACAATGGTAA
105421 GATGTTTCCC AATCTTAATT ACTTGTGTGC AAATACTTTC ATACATTTTT TATTATAAAT
105481 AATCATAGGA TTCATAGTTT AAATAAAATA TATCATTTCT TTGAAATTAA CTTACTGTAT
105541 TTGCTAAATT TTCATTTTAA TGTCTTTACG TAAATTGGAT TGAGGTTAAT AATATATAAA
105601 CTCTTGAGTA TTTTGTAATC CTTTAAAAAT CAGCCCTCTA AGCTATGTTA ATGTTTTTCT
105661 GAAGACTGTG CATAAAAGAG TCAGCCATAG ATATCTTAAA TCTTCAGATG CCTGAGACCT
105721 ATGTCGTTGT GTATCTTAAG TATGATTGAT TAGTCTACCA TTTTAATTAT TTTTACAAAG
105781 CATATTTCCT CAAAAATATA GAAATCTTAG GTTATATTTT TTGAATTTCT AGAGTCTTAT
105841 AAAAGTTTAA GGGATAAGCA TAAATTGATA AAGCATCTTA TTCATGAGAT ATCAATTGGT
105901 TTGCCCTGTG GCAGAACATA AAGATGATTT TTGAATGGCA GAACATTCTA AAAGAGGATT
105961 CTATAAACAT AAATTTAGTA TTCTGATTTC TTTTTTAAGG TATTGATGTA GAAAACTTCC
106021 TATAAATTCT TACCATGTTA GTTTTAACTG GTGGAAACAA TCTAATGATA ATATATTATA
106081 CTTTAGAATT AAAATGGTAG TGTTTTGCAA ATGGAGCATG TGTGGTGATA GATTTGACTG
106141 GACAACTGAA GGAGCAGAAG GACTTAGTTT TACAAAATAT AACTAACAAA TATCTTAAGT
106201 AAATTGCGGT TATATTTGAT TAGATTTTAA ACTGGCAAGA ACTGCTACTT CCCACTTTAA
106261 AAAGAAAACA GTGGAACTTT GCTATATAGA AGAAGCATTA CCATTAGGAA AAAAAAATCA
106321 CAACTTGGTT CTCTAACAAT AAGGAGCCAT TTTTCAGTTG TCAGTTTGAC TTTTAACCTT
106381 GTGATACCAT CTTCCTTATA TGATATATCA CATTAGTGAA TATTGCAAGA GAATCTAGAG
106441 ATTGCCTTGT TAAAATAAAT AACAGTGACT TTTAAAACAT ACTCAAGCAA TTCAGCAAAT
106501 AAACAAAAGG AAGCCAAACC TCAAGGTGCT ATAATGTAAC CATTCCCAAG ACCTAACTGG
106561 AGATTTAATT TATAGAAAAT GACTAGCTCC CTCTTAAGTC AGAAATGGAA TCATACACAG
106621 AAATATATAG ATGTTAAAAA TACCTTCACA TTTTATTGTA ATGGTGAATT TGTGTTTGTG
106681 TGTGTGTTTG TCTTTACATT TCATAATACT GTAAATTATT TCTTTCTGAG ACCAGAATGG
106741 ATCCCAGAAC ATTATAACTT TATATCGAAG AGTAGGAACT GTTTCCTTCA GTGGAAGTTG
106801 CTTAAGACAG GATTCTAATT TATACCTATT GCTCCCTGAT TTTAAATTTT CTATACCTAT
106861 GAAATCTGTT GCTTCCTTAT TTTAAATTTA CTTCTATCTA ACATTGTGGT TAACTTTTAA
106921 ACTCCTTTCA CACTTTTAAC ACTTCAAAGA ATTTGAATTA TTGATTAAAG TTAAATGACA
106981 AATTATTAAA TTCTTTTTTT AAATTCATTT TTTCCCAATG GCATGGTATA TATTTTCTTT
107041 CTTTTTTTTC CATACTTATC TTAGATACAG TAAAAACTTA TATTTCCTGT TTGGTATATT
107101 GGCAGATTTG GAGCTCTTTA TGGTTTTTGG CTAACAGTTA AAAGTAACCT GAGTGAGACT
107161 TTATGATTTG TAACTGGTTG CTTTATTATT AGGAAAAGAA TCTGATTTAT CCGTGACATC
107221 TATGAACATA AATATATGTT TGTATTTGGT ACATTATAAG TTCTATTCAT TTTATATTCT
107281 TACACTTATT TATATCCTTA AAGAGTATGC AGTTAAATTC TTTTTACTAT ATTTATTGAG
107341 ATCTCTCAAG CATATTTCTT CAAACCTTAC CTTTCAAAGT ATTGTGTCAT TCATGCTTAC
107401 TATTTTATGT GTACATATTT GCATTTGCAT TTTACTCCAT TTTAAAAACA TAACCTTAAA
107461 AAGATAAACA ACGTCCATAG GGTTTTTAAT AAGATAAGAA TACATGTCTA TTACTGATAT
107521 TGATATTTAT CTTTAAATTT CAGATAAGCC TTTGAAAAAA AGAAAACAAG ATTCTTACCC
107581 ACAGGAGGCT GGGGGTGCTA CAGGAGGTAA TAGACCAGCT TCTCAGGAGA CGGGTTCTAC
107641 GGGAAATGGG TCAAGGCCAG CATTAATGGT TAGCATTGAT CTTCATCAGG CAGGAAGAGT
107701 GGACTCTCAG GCTTCTATAA CTCAGGATTC AGACTCCATA AAAAAGCCTG AAGAAATCAA
107761 ACAATGTAAT GATGCACCTG TTTCTGTTCT TCAGGAAGAT ATTGTTGGAA GTCTTAAATC
107821 TACACCAGAA AACCATCCTG AGACACCTAA AAAAAAGTCT GATCCTGAGC TTTCAAAGAG
107881 TGAAATGAAA CAAAGTGAAA GTAGATTAGC AGAATCTAAA CCAAATGAAA ACCGATTGGT
107941 GGAGACAAAA TCAAGTGAAA ATAAGTTAGA AACTAAAGTT GAGACCCAAA CAGAAGAACT
108001 TAAACAGAAT GAGAGCAGAA CAACTGAATG CAAACAAAAC GAGAGCACCA TAGTTGAGCC
```

Figure 7D2

```
108061 TAAACAAAAT GAAAATAGAC TGTCTGACAC AAAACCAAAT GACAACAAAC AAAATAATGG
108121 CAGATCAGAA ACAACAAAAT CAAGGCCTGA AACCCCAAAG CAAAAGGGTG AAAGCCGGCC
108181 TGAGACTCCA AAACAAAAGA GTGATGGGCA TCCTGAAACC CCAAAACAGA AGGGTGATGG
108241 AAGGCCTGAA ACTCCAAAGC AAAAAGGTGA GAGCCGCCCT GAAACTCCAA AGCAAAAAAA
108301 TGAAGGGCGA CCTGAAACAC CAAAACACAG GCATGACAAT AGGAGGGATT CTGGAAAGCC
108361 ATCTACAGAG AAAAAACCTG AAGTGTCTAA ACATAAACAA GATACTAAAT CTGACTCACC
108421 TCGGTTAAAA TCAGAACGAG CTGAAGCCTT AAAGCAGAGA CCTGATGGGC GATCTGTTTC
108481 TGAGTCACTA AGACGTGACC ATGATAATAA ACAAAAATCA GATGACAGGG GTGAATCAGA
108541 GCGACATCGA GGGGATCAGT CTAGGGTTCG AAGACCAGAA ACATTGAGAT CCTCTAGTAG
108601 AAATGAACAT GGCATTAAAT CTGATAGTTC AAAAACTGAT AAACTAGAAC GAAAACACAG
108661 GCATGAATCA GGGGACTCAA GGGAAAGACC ATCTTCTGGG GAACAAAAAT CAAGACCTGA
108721 CAGTCCTCGT GTTAAACAAG GAGATTCTAA TAAATCAAGA TCTGATAAAC TTGGTTTTAA
108781 ATCACCAACT AGTAAAGATG ACAAAAGGAC AGAGGGTAAC AAGAGTAAAG TAGACACTAA
108841 TAAAGCACAC CCTGACAATA AGGCAGAATT TCCAAGTTAT TTGTTGGGGG GCAGGTCTGG
108901 TGCGTTGAAA AATTTTGTCA TTCCGAAAAT CAAGAGGGAT AAAGATGGCA ATGTTACTCA
108961 GGAGACAAAG AAAATGGAAA TGAAAGGAGA GCCGAAAGAC AAAGTAGAAA AAATAGGATT
109021 AGTTGAAGAT CTAAATAAAG GAGCTAAGCC TGTAGTTGTG CTACAAAAAC TGTCTTTGGA
109081 TGATGTTCAG AAACTTATTA AAGATAGAGA GGACAAATCA AGAAGTTCCC TTAAACCTAT
109141 CAAGAATAAA CCATCAAAGT CAAATAAAGG TAAGAATACT TCTACTGATG TCATTTATAA
109201 TATAATCGAT TTTAAGTGTT AAGATTACTA AGTTTTAAAA AGGAAATTTA CAAAAATTAG
109261 AAAGCTACTA CATGAAAATA TAACATTTAT GTCAAACAAC AGGAAATTTT TTTCAGGAGT
109321 ATAGATAAAA AGTTTCCAGT GAATTTTTTT TTCCCCACAG TTTTTTTCTT CCCACCCACT
109381 ACTCAAGGTA GTTATGAATG TTACTGCTAT TTGGTTACAC AGAGATAAGT TATTTTGCTG
109441 TTTAGTTATT TCTTATATTT CTGAAATATG CTTAAGTGAA TGTTGTATTA AAATAGCTGT
109501 CTTTAAAAAC TCTCTATTTA AAAATGTCTT ACAATACTAC ATTCTTACAG ACCTGTGTCT
109561 GAGCCAATTA TTGATGAATA ATTTGTATAG TTTAGAAAGT TATATAAAAG GTTATTTTTC
109621 ATTTTGTTGG GGAGATGGTT AGTTAAATAT GTTTTATATT TTTAAAACAT ATCTTTTTGT
109681 CCTTGTTTAT GCAAAGGTAA TAGGGAATGG TACTTACTTT TTAAATTTGG TTAAATTGTA
109741 AGTTTGTGGG AGGCGGGGGA CTGGTGTTAT TTTTGCATGG TTTCTGAATT CTCTGGTTAC
109801 TTGAGTAAAA TTATTTCCAA AGGGAGAAGA ATGTCTTAAG TGCCAAAAGA TAATGGCCAT
109861 TTGTGCAGAA GATATACTTC TGTATCCCTT TGTACACAAG TATTTAAAAT AACTTTTTTT
109921 ATTTTTAAAT AGAGATGGGG TCTTGCTTTG TTGACCAGGC TGGTTTCGAA CTCCTGGCCT
109981 CAAGTGATCC TCTCCTCTCA GCCTCCCAAA GTGCTGGGAT TACAGGCGTG AGCCACCGTG
110041 TCCATACAGT CTAAATATAC TGAGGTGTAG TGAAGGCAAT AGAACTGAGA GTTTATTTAA
110101 GTTTTCCTTC TGTGAAAGAG AATTATTAAG AATTTAGATT TATACTTATA TATAACCAAG
110161 TATATGAAAT CTGGAATTGC ATTGGCCAAG AGGGTAACCA TTGCCTTTTT TGGCTATTTA
110221 AATTTAAGTT AACTAAAATT GGAAGTTCAT TTCATTAGTA GTCACATGTG GCTGTTGGCT
110281 ACCATATTGG ACAAAACAGA ACATTTGCAT CATCACAAAG TTGTATAGCA CTGCAGTGTA
110341 TTAGGAGATA CAAAAAGTGT GTGGTTATTG TTTTTCATAA CATGCTGTTG TAGCTTGTCT
110401 ACCAAGAAAG CTCTTTGAAA ACATATTATA AAGAACTCTT TATTCAAAGA ATGACTTGTG
110461 GCTAATCTGT TGTTATTCTT GCTTGGTCTT CGTCAACATT CATTTTTTCA CTGTTAATTT
110521 ATTTCCTTTT GTCTTACAAT AATGAAAAAA GATTGCCTTC TGAGTCGCTA ATATTTGTGT
110581 TCTTTGAGTG AAGCTTTTAA ATTTTAAATT ATGGCAATTA GACTTACCAA AAGTCAGTTA
110641 AGACATCAGC CTTAATTAAT AAGTAGGCTT TTTTATTTAA CTTGAATGCA TCTTTTCAGA
110701 GTTACTTGTT AATATAAAAG AGGTTGTAGA ATGTGGGGGT TAACACCACA ATTGTTTTCT
110761 TTTAGGTAAA AATTTTCTTT AAAATTTTTT AGTGAAAGTT TGGGAGTAGC TTATATTTAT
110821 AAACTAAAGA GTATGGCTAT ACAATTTTAG AAGAGTCAGG TGAAAGATGG AAAGTGGTAC
110881 CCTCTTGTTC CTTTGATCTG GACCATCTTT CTCTCCCTCC CCTCTCAGCT TACCCTAGCC
110941 TTGCTTTCTA AACTCTGTTC TAACAAAGAG TCTTTTAAAA CTCCTTAAAG AACATCCAGA
111001 AGTGAATATA GCTTTTAGTT AGTAATTGGT ATATTATTTC ACCTGGGTTT TTCACATGCA
111061 ATAATATTGC CTATGAATAT GTTTTTAGCA CCAAAATGCG TTTCTGATAG TATACTTTTA
111121 ATGCAGATGT ATATACCTGA TATGGTCATG TTAGTATGTA AGTAAGCTAT CTGGGTGTCT
111181 GCCTATTAGA GTGATGTGTG TGTATGTGTA CATGTGCATG TTTGTGTATA TATACACATA
111241 TATTAATGTA ACTGCAATTA CAGTAACAGT CCTTTTCATC AAAAAATACT ATGTCAGTGC
111301 TTAGATGCAT TTCAGGATGC CGTGTAGCTA TCTTTTGGAT TAATTTATTT ATGTCTTAGG
111361 ATCCATATCT TTTTTTTTTA GTAATGATCC AATTTTGGTT TTGTTTTAGA TTTTTGCTAC
111421 TCAGTTTAAA TAGCAGAGTT GGGTAATTGT GGATTTTTTA AAATTGCATG TATATGAAGC
111481 ACAGTTGTAG ATTACTGACC CTTTGTAGTA TATACTGGGA TTTTCTTTGG AGATTCACAG
111541 AAAATCACAT TTTGATGTGT TGATGATTTT CTGAGTAAAG GAGTTAGTCT GAATACTGCT
111601 GGGATACTTG TATGGTTGGT TCCTAGGGCC AAAATTGAAG AGCCATAAAT TTCCATCTTT
111661 TAAATATTTT ACCTGATGTT CATATAGAAA ATATTCATTC TTTAGGATAT ATTTTAAGCT
```

Figure 7E2

```
111721 GATAAATTTT GATTGTGTGA TAGAGGTATA GATTTATTAC TCCTAATTTA GATTACTTAT
111781 TTTTGTCTTT TGTATGAGCA TGATAAATGT AAAGTGGCAT TGTTACATTT GATTTGATTT
111841 CTGTGGCACT ATATCTGTAT CCCTAGTACC TAACAAAATA CTTCATACAT AATAAATCAT
111901 ATTTAATGCC TATTGAATGG AGATGATGTT GCCACCATTT TCAGGAAAAG CTTTTGTGTA
111961 CAGATTAAAA TTAGATAATC GTCTTTTATG TTCCCATCAA TACACCCTAG CTCAAGAGCT
112021 ACTTATTTTT CAAATCCTGC TTCCTAAACA TTGTTAATAA CTCTTCACCC TGTCAACTAC
112081 CTAGTTTTTT TGTTAAGATC CAAAGAAAAC CTGCTTATAG TAATATGTGT TTAATTTTTC
112141 TGTCACACTT ATTTTGATCT ATACTGGGAT TAATATTATT CCCATTCTTA TCCTGCATTG
112201 TTAACTTCCC TATCTTTCCA TCACCATGTT TATTCCTTGC CTGGGAGGGG TGGAGGGGGC
112261 AGTCAGGCAG TGTAACTGTT TGTAGAATTC TTTTTAAGTT CTTCAAATAT CTTCTACTAA
112321 AATATACTTC AATCAGTATG TTACATGCCA AAAAATATGT TGTTAAAAAT TTTATTAGAC
112381 TATTACCCTA ATGTATAGTG TCTCTAAATT AAAATAATAA AGTTATGAGA TCCTTTAAGA
112441 TTGGCATAAT CTCCCAGCAT TTTGGGAGGC CAAGGTGGGT GGATCATTTG AGGTCAAGAG
112501 TTAGAGACCA GCCTGGCCAA CATGGTGAAA CCCCACCTCT ACTAAAAATA CAAAAATTAG
112561 TTAGGCACTG TGGCAGGCAC TTGGTAGCCC CAGCTACTCA GGAGGCTGAA GCAGGAGAAT
112621 CGCTTGAACC CAGGAGGAGG AGATTACAGT GAGCTGAGAT TGTGCCACTG CACTCCAGCC
112681 TGGGTGACAG AGCGAGACTC TGTCTCCAAA AAAAAAAAAA AAAAAAAAAA ATTGGCATAA
112741 TCATCAACTA ACACATGCCT TCAGTGTTAT TAACAGCTTA TTATCAGTAA TTACAAACAT
112801 ATTTGATTTT GTTGTTTTTT TTTTTAACTC CAGAGTGTCT CAAAATATCT TTGCTTTATG
112861 TCTAAGGAAA CCATTTTTTC TTCTCTCTCC CCCTACTTCT TTCCAACTAG TATATCATTC
112921 TCCATTGTGT GGACTCAGTG CTTTCAAGAA ATATCCGTAT TATTTGTTAT TTGACATCAT
112981 CCTTTAAACT GAAGAGTAAA GCAGTTTCTG AAAGTAGTCT TCACTGGGAA TGTATCTAGC
113041 AGCTTTAATA GTCAATAGCG ATTAGCCTAT ATTGCTCACT TGATGAGCTA ATGATTGCAG
113101 GCCTTACTAG CGACAGTGAT CGCACTTCAG TTATCTACTG TTACAGTTAC ACTACTAAAT
113161 GCTGATAACT ATCATCAGCT GGTTGCCTTT TACTTAGCAC TGAACCAGTC TAGTTAGATG
113221 GTGTTTAGGA TCCTCAGCTT CTGCAAGTCT GAAAGTATTG TTTCTGAGAG TGAATTTATA
113281 GCACAGTTTA TTAATTCCTA AATGAGGAAT TTTCGGTGTT TTCTTTAAAG TAGATTGTAA
113341 TATTGAATAA TATTTAATGA TGCAGTGGAA ATTTATTTTG TTTCATTTGT ACAGTTTTAT
113401 AAAATACCTT TCTTAAAAAC TCAAATTTTC AGTTTCTGTA AAGATTGATA TCAGTGATAT
113461 CTTTAGGAAA TGTTTGGAGA AAGTTTATTA CAGAAGTTGG CATAATCTGT ATCTAGCTCT
113521 TGTGACTTTA GAGCAGTATT TTGAAAATTT GTACTCATGA TTTCCATTTG TAGAAATTTT
113581 CCAAAGTATG CTTAATAGAT TGTTCATACA AATATTGCTT AAAAGAAATG CATTAAGTAG
113641 AAACCTTTTT ATAAAAACTA AAGTTTGCTG GAGGTATTCT CTCTCCTTTC CATTCTGTCT
113701 CTTAAGCCAG CCCAAAGACA TAGTTTCTAT AGGGTTCTTG TGTCTGTAGA AATAGGTATA
113761 TGATTTAACA GCTAAGGAGC TAGCAAATAT TAATTCTGTA AGACCCTGTG CCTATTTATG
113821 AAGAAATAAT CTTTGACATG CTAAATTCCC TTTTATATTC TAAAAAAAAA AAATTTAATG
113881 AAACCCTTCT TTACAAGGGC CTGATGTGAA ATTAAGAGTA TGAATACCTA CTAGTATTAC
113941 ACCACCAATA AAATGGGTTT TTTAATATGG ATCTCTCTGT CTTGCCTATA AAAATATTAG
114001 CGTTTTCTGG CTGTAATGTA TCAATTTTTA AAAATTCTCT TTTAAACTTA TTACAAATTA
114061 TAGTACAAAG AGAACTAATA TCAAAACCCT GAATAAGCCT TAACCTTTCA AAGCTTGGTT
114121 CATTCGCTTT TAAAATAAAG AAACCAATTT CCCTCCTACT TTATACAGTT ATAAAGACAA
114181 AAATGAATGT TGTTATAGTA AAAGCTAAAG TATGTCTGAT TTTTTTATAT AAAGGAAAGT
114241 ACAGTCATTC AATTTCTAAT TGAATTGAAT TTATCTAATG AAGAAAGTAA TTTTTTAAAA
114301 TAAATCTTTT TATGTATCTG TACTTTATAT TCAGTGTAGA TTTAAAGATA TTACTGCCAC
114361 AATTTATTTT TCTCACCGTG TATACATATC AAGGAAAGAA TCATTTGATC CCTGCCCCCT
114421 ACTTTTCTGT AATGAGTAGT AAGTTGTTAC TTACATAATG AGTAGTAAAT TGTCATTTAC
114481 ATGCAGTATT GAAAATTTTT TTTTGCCCCC ACTTACCTCT AATTGAAGTT GAAGATCCAT
114541 TTGGTGCTTC TGTGTTATAT GGGTAGGTTA GTGGAAGAAT TGTCACTGAA CTATTCCATT
114601 ATGCCTGCCC AAGTTTTTTT TTTTTTTTTT TTAGGATTTA TAAAATTTGG AGGTTTATGT
114661 GAGGCTCTTA GTTTTGTTTC TGAACGTGAC TTGTTTCCAT TGACCAAAGC TTCACTTCAG
114721 TCCCAAAGAT TTTATTAGTT TACGTGATTT ATTTCTATCT CAGAGTTGTT TTCCTGTTTT
114781 AAAAAGAAAA CAGAACACAT TGTTAGTTAT CAAATCAATG ATTCTTTTAA GTTTTTTGAT
114841 GATTTCTGGT TTTAATAATC TGGCAAGTGC TAATTTGAGT GATTTATAAT GGAAATCAAA
114901 GATTGCTTAA ATGTAGCATA TCTAGGAGTA AATGTATTCT TTAGCCATAT TAAAGCCAGA
114961 GTATAGAGTG CACTGTATCT AATGGAATAT ATGTACAGAA GCTGAAAATT TGATATCTCA
115021 CAAAATTGTG ACTAAATGAC ATTATTCATC AAGCCAGTAA CATAAAGTTT TATGGGAATT
115081 CAGACATGCT GATTTAAAGA ATAAAGTAGT TAGGACAAAA GAAATTAGGT GAGAGATAAT
115141 CATAAAGCAC TAGTAATCTG AAGTTTTAGG AACAAATAAC TTGGCAAGCA ACAATAATCC
115201 CTAAAATCAT CAATCCCTAA AATACATCAT CATATACTAA GAGATAGCAA GACTTTATGT
115261 TTGCATTTAA TGGATTATTA ACTAATTCAG GGGAAATAAC ATAACCAATT ATGTCATACA
115321 GATAATTTTA AGTACTTGCT GTTTATTCAT TTCTGTTAAA CTGAGTTAGT TATCCAGATC
```

Figure 7F2

```
115381 AGGATCCTTT TGTTTTTTTA AAGACAGGGT CTCATTCTCT TACCCAGGCT GAAGTACGGT
115441 GGTGCTAATA TAGCTCACTG CAACCTGGAA CTCCTGAGCT GAAATGATCC TCCCATCTCA
115501 GCCTCCAAAT GGCTGAGTTA TCCAGATCCT TGATGTCATA TTGAAGATCT CAGGCCTGAA
115561 TATGGGAAAG TCATGCATTT TATTTATTTA TTTATTTATT TATTTATTTA TTTATTTATT
115621 TATTTATTGA GATGGAGTCT CGCTGTGTTG CCCAGGCTGG AGTGCAGTGG CGTGATCTTG
115681 GCTCACTGCA GACTCCGCCT TCCGGGCTCA TGCCATTCTC CTGCCTCAGC CTCCCGAGTA
115741 GCTGGGACTA CAGGCACCCG CCACCATGCC TGGCTAATTT TTGTATTTTT AGTAGAGACG
115801 GGGTTTCACT GTGTTAGCCA GGATGGTCTC GATCTCCTGA CCTCGTGATC CACCCACCTC
115861 GGCCTCCCAA AGTGCTGGGA TTACAGGTGT GAGCCACTAC GCCTGGCCCC TTTATTTCTT
115921 ATCTTTGTAA TCAAGCAACC TGGCGGAGTC CATTTATAAA GAGCTTCATG AAATGGAAGA
115981 AAGGATGTGG TTAATTCAGA AAATGTGTGA AACCTGTGGA ATAGACAATT CTGTTCAAAA
116041 TGAAACAGCG TTCACTTTTG GAGGATGATA CATGTAGAGA CATTGATTCC TGGATTTTTT
116101 TTCTTTAAAG TTGGAGCACC TTCAGAAATA AAACATTTGG CCTTTGAATT ACATTGTTTA
116161 AACTTTCAAA GTTTTACAGA AGTTAAAATG ATCTAGAGGA TACTAGAGAG GTCTTAATTG
116221 ATAGTATTCT TGTTAATGTA GGGAATAAGA AAGGGTAAAC TACTGTTGAT AAATGTTGAT
116281 ACCTGCTTTA TTGGATATAA GGCATAGGTT ATCTGTGTTT GGCTATTGTG AGTAATTTTT
116341 TTAAAAAGAA GGAGCAGAGT CCTTGCTCTG GGAACATAAT CCATTGCAGA GAGAGCACAA
116401 GAACTAGTAC ATATTTTAAC CTTTGATTAT TGTGTTAATT AACAAGGAAA ATATTAATTC
116461 TGGGATATTA GTGTTGAGTC AGTGTGTCTG TGATGTGAAC TTAATCTAAG CAAAACACTT
116521 AGGTACATTT GCTTTAAAAA AAAAAATCCC GTGATGGATG AAAGGCCAAA TACTTTGGGT
116581 TATCTGTATT TATAAACCTA TGAAGATTAT AATGTTTCCA ATATACTGCA AAAAAAAAAA
116641 TTTGTATTCT TAGAAATTTT GGAAATGTAC TCATTTGTCT ATCAAATACA GCAACTCAGG
116701 AACTATCCAG GAAGTACATC TGTAAGTGGA CATGAGAAAT TGTGAACCAG AGTTAGGCAA
116761 TCAAGAAGCA TCTATTGACT ATCCATATAT ATGTACTCAA TATTATGTAG GTCATGTGGA
116821 AAAGGGAAGA TGTATACTCT AAAACATGAT TTTCCATCAA AAAGACACAT ATTAAAGTAG
116881 AGATATTCAA AGACTTTATA GTGAGGTGCA GAACGTGTTC AGTTTGGGGC TGAAAATATG
116941 CAATGCAAAG CTAAAGTTGA CTTCTTTTAC TTCTACCAGT ATTCTAAAAA AGAGGGCCCT
117001 CACTGATAAA ACTTAACTAG TTAAATTAAG AAAGCCAATA CAGAGAAATA TTACCTGATT
117061 TCAAAATGAC ACAGAAGTTA AACTCAACGT TAGTTAGAAT TCTTAGCAAT GAAGTCTTTG
117121 GGATATTACC AGTCATGAGT ATTTCATGTT TGTTGGGTAA AATTGTTCCT ATGCATGTCC
117181 TTAGAAGAAC AGAAGCCTAA AAGTTACTGA AATAACTCCT TTGTGATACT GAATAAAAGT
117241 TTCAGAAGAA TAAAAAAAGG GTTATTCTTT CATTAAGATT AATATTTTAT ATCTCCATCT
117301 TGAGTTATTT GATTGTATCG TCTTAATATT CTTGATAGCT ATTTACTTTT CTGTCATGAT
117361 TTTTATTCTT TACGTAAGCA CTATTATCAT TTGCATGTTA TAAAGGATAG TGTTAATGTT
117421 GATTGTAAGT TACTAATATT TCCTGCTATA AACCACAAAG GTACTCTTTG CTTCCAATTC
117481 ATAAAATTTA TCAGGTAAGA TTTTTCTTTT TATACTTCCA CTCAAAGTAA GTAAAGGAAG
117541 CTAAAATTGC CATCTTTAGT AATCATTAAG GACAAATTAT CCGAATAAGT AGCTTTTGCT
117601 ACTTCTACTT TATTTTTTAA ACTATCAGGA AGATAGTCCC AGTTTATTTC TTCATAAGAA
117661 CTATTTGTGT ATGTGTTTGT GTGTATGTGT GTAGGATTAA GTAGTATAAT GGCTCTTATT
117721 GTCTTGTCTT CTTTTTTATT GCCTTGACTC TTGTGGGAAG ATATGAACTT GAATTTCTAA
117781 CTTGAAATGT ACTTTTCAGT TACAGACATT TATATTTTAA AAGATTTGTC ATCTATTTAT
117841 CCTGTGTTAC ATGTTTCTCT CGTCTTCAGT TAAATTGTAT ATATTGATTT GTCTGTTTGA
117901 AGAAGTTCTC CGTAATGCTA AAGGCATTAC CATGCCCTCA AATAGACAGT AATAGGTAAA
117961 AGCATATGTA TAGCTCTTGT CTCAGCCACC ATACACAACT GCCAAGATCA TAGAGAAGGA
118021 GGAGGAGTGG TAAGTGTCTT CCAACACTTC TCACTTGTAT TGAGGGGTAA CATTAGATTC
118081 AAACTACTTC AGACCTACAC AAAACAAAAT TTATGTACTA CCAAGAATGT CAAGTGTACC
118141 TCTTACCACA AATCCACTTG CTAATGTCAG TGAATCTCTA GTTTCAGAAA GTTTTTAGTC
118201 AGTGCAAATT GAAGGCATTA TATCAAAAAT GTATTATATA ATTACCCTTC ATTTTTATGG
118261 TGGTGTCATG TTTTTAAAGT CATTACATAA TTATATGTAT ATATGTACAC ATACATATAT
118321 ATTAACTATA TTGTCACTTT AGGGTTAAGA GTATTATAGT TGTGTTTTAT TAAAATAAAC
118381 AGTTGATTTA GAAAACAAAT ACTAATATTT TTATTATGCT AACTTAGTTA AAATTTTCCT
118441 TTTATCTTCA GATTTACATT TTTTTTTTAA ATTTACCTTT CATTAATAGG TAGTATAGAT
118501 CAATCAGTGT TAAAAGAATT ACCCCCTGAA CTCCTGGCAG AAATTGAGTC CACCATGCCA
118561 CTTTGTGAAC GTGTGAAAAT GAACAAACGC AAGCGTAGCA CAGTTAATGA AAAGCCAAAA
118621 TATGCTGAAA TCAGTTCAGA TGAAGATAAT GATAGTGATG AAGCTTTTGA ATGTAAGTAT
118681 CACAGAACTC TTTGTTATTA TTTTAGAGTT TAAAAGCAGG TTGATGTGTT TTTCTCATTT
118741 ATAATTTGGG GGTTTAGCAA AAGCACAGTC ACCTTAATTC TTAATAACAC AGTATAGTAA
118801 GTTTTTTTCT CTATACTTTA AAAATGCGTG AAAGATGAGA TCAGTTGGCA CCAAGAAAAA
118861 AATATTAAAT AAGCTACAAT TAATTTTAAA ACACAGGTAG GTATGTGTCT GTATGCATTC
118921 AGCAAACATT TATTGAGCTC CTATTATATG CTAGACACTG AGAGTAAAAA TGCAAATAAG
118981 ATATGGCCCC TGTCTTCAAA GAGCCTTCAG TCTAATGGGG GAAATATGTA AATAAATAAT
```

Figure 7G2

119041 TGCAGTATGC TGATAAAAGT ACAATGATAA CAGTAAATCC AGGGTGCTAT GGGAACACAT
119101 TGGATTGGCA TCAAAATCAG AGTGGGGGCT CAGGGAATGC TTACTGGAAG AGGTGACACT
119161 TGAGTTGAGT CTTGAAGGAC ACGTAGGAGA TAGCCAGATG AAGAAATATT TAAAACCATA
119221 CTATCACTAA ATTATGAATG GATTAGCCAC ATTGCAGATT ATCTGTGTGG TTTGGACCTG
119281 GCTTCTCCTT TTTGCCCAGC TGTGTCCTGG AATTCCTCCC TTGTTTCACT GTTTTCCAGA
119341 GCTGGCTTCT TCACTACACA GCTACCTCTC TACAACACTG TGATCACCTG TCTTTGCACT
119401 AGACTTGCTA TACCTCGCCT GTCTTCCTAC TGGTCCACTG AAAAAGTTCT TCTCTTTTAT
119461 CCCTATCTTC CTTCTTCTGG AGCAAGAGAA TTGAGCCTAG CCAAGAGGGG TCAGCAACCT
119521 TGTTTGACTT AAACGGCATT CAGTGGAAAC AGACTATGGG AGATCTTCAC TTGTGTGCCA
119581 ACTGACTTAG TCATAATGAC CAAAAGAAGT GGGAAGACCA CCAGTGTTCT ACTTTTTCCA
119641 CCTAGTGTCC ATAGATTGAG GTGTGACAAG CAAGGGCAGG AAGGACAGAT GCATGCTGCC
119701 ATTTTTAAAT GTATATTGCT GATGGAAGCC CTTCACCTCC TCCAAAGTTT TTAATGTTAA
119761 TTTACTGATT TTTTTTTAAT TGTGAGCTCT TGAGCTATGA GCAGTAGACT ATGAATACTG
119821 AACAAATCTG AAAAAAGTTT TAAAATTGAA ATAAAATATA CAGCAAACTT AACATTTAAT
119881 CATGTATAAT TGTTATAATT GTATTATGAA ATGTATTGAC ACACAGTATA TTAAAATGGC
119941 TAAAGTTAAT TTTTTTTATT ACAATCAGAT ATTTTGGTCA TATGGGGACG TGGTTAGCTC
120001 TGGAAGATGA GAAGATAAAA GAAACATGGG GCCCAGGAAC TCATTCCCTT TAATATACAT
120061 GCCTTACCAC TCTGCCTCTT TCCCTCTAAT AAACATATCA CCCATATCTA GAACAGCCGA
120121 GAAGGAGGAG TCCCTGAATT CCAGTTTGAT TTCAAATGAC ATTTCAAATC CAGTTGACTG
120181 AAAGTGACTG CCTCCATTAC TAAATTGCAA AGATTTCTGA AGCTGTCTCA CAGTTAAGTG
120241 GAAAGGATAA CATAATCAAA AATTTCCACC AAGTGTAAAA TAGTGGAGAG TAGAGCCACA
120301 CATCCCTCAT GTTTGTCACC AATGCAGCCA CCATTCTTTT CCCCTTGCTT TCTATCATGA
120361 AAGCTATTGT CTCATCTTAT GGAGGCACAT AGCTTCGTTA TAAAGCCATG GACCCTGTTA
120421 TATCTATGCC CAACTATATC GAAAGGTAAT ATTTATTTTA AAGAACCTAA GCTTCACACA
120481 CTGCTAGAAG AAAGGAAAGT TTCTCTGGAT TTTTAAAGAG ATGTCAGGAG TAGCTTCCTG
120541 TTTTTCTTCA CTTATTTCTA TACAAGTAAC TATAGAAAAG TGGACACTGG AGGCACCGAT
120601 TTGAATGGTG AAAGAAGTCC AAATGATTGT TCACATAAAC AACCAAATGG TCACACCACA
120661 ACAGAAACAG TGTATTGAAA ATATAGCACA ATACAAAATG TGAAACTATT ATGAGAACGT
120721 TAAGTTGCAA GCATTATGCT GCTGAGAGAG AGAAAAAAAA ATTTTTGAAA CTTAGCAGTT
120781 TAATCAAATT GGTTTCTCAA AATCTAAAAC CAAGGAAATA GTTTTGTTGA AGGTTAGGGG
120841 AAAATGTTGA AGGATAATTT TGAAAGTTGG GGTACACAGA TTTGGATGGC CATAGCACAA
120901 ATATAAGGTC ACTGGGTGCC TGGGGAAAAT GGAGAGAGGG GTGATGTAAG AAGCTCAAGA
120961 GATACATAGG TGAAATTTGG AAAGAGAAGA TAGAGAACAC CCAAGTCATG TTTTACGTAC
121021 CTCTCTTTTG AGTCCTTTCC CCTCCCCTGC TTATTCCAGG GTAATGAGAG AAATGGAGAA
121081 AGAATAAGCT AACCACAATG AGTTGGTATC CTAATAACCT CATTATAACA CAATGTGTTA
121141 TGGAAGTTGT TTTTTTTTTA ATTTGTCACC CCATTTTTAT CTAAATTGTC TAAAATTTGA
121201 TGAATGTGAA ATAAAGATTT ACAAGATCTG TGGATAGTTA CCACCAATAC AGCATATTCT
121261 ATGTAATTAC AAACCACTAT AAGATTCTTC AAGCATTTTC TACTCATAGG ATTGAATGCT
121321 TGAAACAGAT TTGTTATGAA ATTAATTAAA ATGTACAAAG ACTAAAGCAG GTCATATTCA
121381 AGGTTGTAAA ATACTAATTT CTGGCGCAGT AGCTCATGCC TGTAATACCA ACACTTTGGG
121441 AGGCCGAGGT GGGAGGATTG TTTGAGCCCA GGAGTTTGAG ACCAGCCTGA GCAACATAGC
121501 AAGACCCCTT CTCTGCCCAC ATAAGAAAAT AGTGCTTTCT GAAGAAGTTT GCTTATTAGT
121561 TGTCATCCCT TGTAATGTAG GCATTTCAGT ACTTGTGAAA AAAACATCTA AGGAATTATA
121621 TATAGAAATG ACCTGTTTCT CTGTCACACA TACACACACC CTACTTATAT TAGTGTATGA
121681 AACAAGTTGT CACTAAAGGA ATGTACTAGA GCATACTGTA ATCATAAAAG AGGAACAGTC
121741 CTATCACTCT TCACATACGT CATAACCAAA TTCATACCTA ATTATGAAGA AAATCTCAGA
121801 TATTTATATC CATTTACATT TGTGCTTTAC ATGAACCTTT TTGCTATCCA AGCCTGTGAC
121861 TGTAAAGAAG AGGAAACAAA ATGACCTTTT CCTGCCATGT TGTCCATAGA TTAGCTAGAA
121921 GAGTCCAGAA CCAGAAACCA ACCTAGATTC TTGAACAGGA GTAGTTAGGG TAGCATTTAA
121981 GAATAAGATT AGACAGAGTA TAGACATTTA TTACCCACAC ATGAAGACAC TGGCACAAGC
122041 ATAGAGTGCC TGGGCCAGAG GTTGGCATCC TTACATCTAA GCCAAGTAGG GGACTTAAGC
122101 AAAACATTTG TCTTAAGTAT TTGTGTATTT ATCATAGTTA GGGATTCAGA AAAGAGCAGT
122161 TGCTAGTCAA ATAACAGACT AGAAAGTTTA TCATTGTCAG CAACAAGTGA TCACAACAAC
122221 AACCAGTATA TGATTTCAAG GTAGGACACA TCACTTCTCT GCCCTGGTTT TAACTTGGTG
122281 GTACCTACTG CATCCTAGAA CAGACATGGT AAATATTTGT CACTTATAGT GCCCCCCAGC
122341 TCTTACTGCA GACATTTCTA ATCAGTCTTT CTTGCTGAAC TATGATGCTT TCTCAGGGCT
122401 TGGGGTTATT TTCAGCATAA TGTTCTAGGC AGCTATTGCC AGTTGATGAG AGTTGATGTG
122461 TTAGATGAAA TCTGTTTGCC AGGTCTGCCT AAAGGCTCCT GTCAGTACGG GTGATTTTAG
122521 CAGAATGCTA AAATGATGGG GAAAAGATTG AAGGTAACAT ACATAATCAT GCTTATGAAG
122581 CGTGCATAAG CTTAGAAACT TTTCTTGGGT TTAAGCAAGA CTTTTGTTGA AGAACTGAAT
122641 TCATTATGTG AGTATTTACA ACTGTACAGG TTTTTTCTGT CTCAGTAGGC TTGTCATGTT

Figure 7H2

```
122701 AGGTCACCAG GGCTTATGGA ATTTATCGCT GAGTTGTGGG TTTAACTTAG CTATTAATTG
122761 ATGATGTACA TGGTTACCCA TATTCTGTAA CACTTTCTCA AAAGTTGACT TTTCCTCCAA
122821 ACCCTGCTCC CCATCAGTAA TCTAAGTGCT TTAAGGTGGT TCTGTTTTTC ATCTAATTCC
122881 TAAATATAGT TTGTTTTACA GCCTCAATTA ATCTTGAAGT TTAGGTATAA CCCTTACTGA
122941 CTTACTGAAT AACTGTCCTT GAAGTGAACA CTGTAGTTTA ATTTCAAGAA CCTTCCTCTC
123001 TGTATTTATT AGCAGTAAAC ACTGAGTTCA TGTAAAGATC TTTAAATCTG GGTAGATTGT
123061 GCTAAAATTA GTGATACTTT TTCTATATCA TAACTTAAAC TTCTGGATAG ACAAAATCAC
123121 TGAATTTCCT AGACCCTATG GAATGAAGAT TTTTTTCCCC ATGTGATTCA TTTGTAAAGT
123181 ACAAGTTTTA ATCATCTTTT TAAATGAGGT AAATTATTTG TCATGGGGAT TTGCTTCTAG
123241 CCTCTAGGAA ACGACATAAA AAAGATGATG ATAAAGCTTG GGAATATGAA GAGCGTGACA
123301 GAAGAAGCTC TGGGGATCAT AGGAGAAGTG GCCACTCTCA TGAAGGAAGA AGGAGTTCAG
123361 GTGGTGGTCG TTATCGAAAC CGAAGTCCGT CAGATTCTGA CATGGAAGAT TATTCTCCTC
123421 CTCCCAGCCT TAGTGAGGGT AATTCATCAG TGTCAACGGA TTTCTTACAT AAACCAATTT
123481 AAATTTAGGG CTTTAACTTT GAAGAATATT TTATATCTTT TTATGAGTTA ATAACTAATT
123541 TTCAATTAAG ACAAAAATAC TTAGTTTCTA TGTGCAGTGA TTATCGTTTA AGTCTTTAAC
123601 GTTCAGGAAA AAAACTAGAA ACAAAAATGG AATTATTTTA AGTTGTCAGT CCTGCATTTC
123661 AGTACTTCTT TTTGTTCGTT TTAGTTGCTA GGAAAATGAA GAAAAAAGAA AAACAGAAGA
123721 AAAGGAAAGC ATATGAACCA AAACTAACAC CTGAAGGTAA CACGTTAGTT TATTTAATTT
123781 GTCTTTATTC ATATTCTTCA GCTTCACATG TCTACTTGTA ATGTGAGAAT AATGAATATA
123841 TTTTTCTCTC TTGCAGAAAT GATGGACTCT TCAACTTTTA AGAGATTCAC AGCCTCAATA
123901 GAGAATATTT TGGATAATTT GGAAGATATG GATTTTTACTG CGTTTGGTAA AATCAACTTA
123961 AAATACATTT ACACATACTC TAAGTGTCTT AACTGTATCC TCTAGAGTAA CTCAGTTACT
124021 CTAGTGATGT GTCCTACCTT GAAATCATAT ACTGGTTGTT GTTGTGATCA CTTGTTGCTG
124081 ACAATGATAA ACTTTCTAGT CTGTTATTTG ACTAGCAACT GCTCTTTTCT GAATCCCTAA
124141 CTATGATAAA TACACAAATA CTTAAGGCTT AACTCAGTTA CTCTAGAGGA TACAGAGGCA
124201 TACTCTGTGC TATCAAGAAA CTTGAAATCT AGTTGTAAAG TCAAATCTAG TCTGTTACCA
124261 AGAAATTAAA AACTTTAGTA CAAAACTCAA GTATATATTA ATCAAGTCTG GATAGTATCT
124321 AAAGAATCAT GAGTAAGTGA GAGTAATTTA AAAAGTCTTT ATGCAGGTGA GGAGGCTTGA
124381 AAAGGCCCTG TATAATGAAG GTACTGATAG GAGCATATAT GCAGAAATAA GCATCTATTC
124441 TTCTGTTCAT TTATTCTAAT GACCAATATT TATTGAATAC TTACTGTATG CCAGTAGTAT
124501 GTTAAGTGCT GGAGATGTAA AAATAACTAA AACCCAAACA CCTGGCTTTA GGGAATACAG
124561 ATTCTAATAT GGAAAACAAA ATAGTAAACC AGTTAGAATA CAGTAGGATT AATGTTATAT
124621 TCATGTATTA CTTTTACAAT GACATAAAGA TTACATCTAT AAATATTAAA ATGTTTATAA
124681 AAACACTGCT TGCAATGTAT AGAGCTATTC TTAACAATCT TATGCCACCT TCAGCTGGTA
124741 AAGTAAGTAT TTGTTTTGTG AGAATTACTT GCCTGAGTAT CATTGTGTTT GCTGATTATT
124801 TAGAATGTCA GTTTCATCTT TTTTAAAACT TTACAGTTCT GTGCTGAGAA ATTGTCTTCT
124861 GTATCATTTA GGGTCCAAAA GTACAAAGGG CACTCTCAAA ATAGGATAAT ATGAGGAGGA
124921 GTTATTTACA AAGAGACCAG TTAAAAAGAT GGAGGCAAAA TAATACCAGA ACCCAGGGTT
124981 AACAGCCTTA AACCAAAAGA GTGAGGATAC AGAAAAGTCA CCAGAACTCA TTCTGCAGGA
125041 AAAAAAGTTG TAGAGTAGGC TGCCTTGAAA GAAGCAATAC CTTTTGGTCA GGGGACAGAG
125101 CCAGCCTGAG GAGACCTTGT AAGCAAAGAG TAAGAGATAT AAATACTTTG ACCTTACACT
125161 CCTCTTTGAT CTTCTAACAG GGCACCCTAC TGGCCAAACC CAAACAAAAG CCAGAGGGCA
125221 TGGGAGACTC TTGATGTAGT CCATTCAGGT CAGCCTCCTG AGGCAGAGAA TGTGGTTGAG
125281 AAAGAGTCAA GAGTATATCT AAAGTAGTAA AGATAAGATA TCTATCTCAT CTTCCCATTT
125341 CAGTCATAAA TCTGACTTCA ATTTCTGTCC TTTTTCATTC AGGGTTTACT TGAGGTTTAT
125401 ATATAGAGGC GTCTTAGGTT ATTTGTTTAG TTTGCATGTC TAAAAATTTT ATTAGAAAGT
125461 TAAGCTTGAC ATTTTGAACT ATTTTATTTA CCTAAACTTT GTTTGTGTTT GTTTGGCTTG
125521 ATTTTGCAGG TGATGATGAT GAAATTCCTC AGGAACTGCT CTTAGGAAAA CATCAGCTTA
125581 ATGAACTTGG CAGTGAATCT GCTAAAATAA AAGCAATGGG TATAATGGAT AAGGTATCTC
125641 ACCAAAGTAA AATTTATAAA TTTACTTCAT AGAAACATTT GAAATTAATT TAAGGTTTTC
125701 AGGGTAAATT ATAAAATTTA TGTAAAGTAA ATAGTAAAAA GAAAACTCAT TGTTGACTTC
125761 TGAGAGTCTA AATGAGTTTT TTTGTTTTTT TACAAAAGAA AAAAGTATTC TGCAGATTAT
125821 TCTAAAGAGA ATCATATTAC TGCATTGAAA GAGGCATGGA CTTTAATTTT TTCCAGAGTT
125881 TTTTTTTTTC ATTTTCTCAA ATATTTAGAT TATTTAAATG CAGAAATATA TTAAATTTTT
125941 CTTTGACATT TGCTTTAGTC ATTTAGGGTC GTTGAGTAGA AGTTCTAAGT GGGAAAGTTT
126001 TCTTACTCTT TAAGAGGGTG ACAATGCTAT TTCCTCCATA GCTCAAAGGG AATAATTGTA
126061 CAGATTGTTT CTTGAATAAT ATATAACTTT TACCAACGAT TGATAAAGAA TTTATATTGC
126121 TATTTTAGCT TTCAACTGAC AAAACTGTGA AAGTCTTAAA TATCTTGGAG AAGAATATTC
126181 AGGATGGGTC AAAGCTTTCC ACTTTGTTAA ATCATGTAAG TTTAAGATCC ATACTGTTAA
126241 TTTTACCCTT AATGTTATTA AGATCTATAG TAGTCCCCCA CTTCTCTATT GTTTCATTTT
126301 CCATTTTCTC AGTTACCTAC AGTCAACTGT GATCTGAAAG TAGGTGAATA ATTTTTATTA
```

Figure 7I2

```
126361 CAGTCTATTG TTCTGTTTTT TATTGTCATT AATCTCTTCC CATGCCTAAT TTATAAATTA
126421 AGTTTTATCT TAGGTATGTA TGTATAGGAA AAAACATAGT GTATATCGGG TTTGATAGTA
126481 TCCATGGCAT GCACTCGAGG TCTTGGAATC TATCATCTGT CCATTAGGGA GGGACTAATG
126541 TGAATTTTTT CACAAATGAC TCTCATGTGG GGGAAATTTC ACATTTCGTT AATTTGAGCA
126601 TGTTACCATG AATTACTAGT TACATTCATT AGCATTGCTA GTAGAACTTC ACTTTTAGTA
126661 ATTCAGAATT AATGTTACAC ATTGTCAATT CACAGCTTTG CCATAAAGTA AGAATAATAA
126721 AGACATGAAA ATGTTTGTCA ATTTAAGGGG CAGTTCTTTA GTTTATGCTC TTCCTTATGT
126781 AAGTATATGA ATGTTTAAAT TTTGTTTTTG AGTTATGAGA TGATAGTAGG TAGTAATTCT
126841 TTTTGTTGAG CTTCCCTGAA GAAATAACAT AGTTAGAAAC CTTATGATTT CCTAATATAT
126901 ACTAATTAAT ATACATTACT CCTTATATAC CGTTTTTATA CCTACCTCAA AGGGTTGTTC
126961 AAAGGATTAA AGAATTAATT CATGTAAAGC ACTTAGTGTC TGGCACACTT TAACTTCTCA
127021 GTAAATGTTA ACTCCAGCTG TTACTATATT TTAATATGCT TATATCAAAA GCAGTAGCAA
127081 CATGCTTGCA ATGGTTTATT AATTGAGTGA AGCAAATTTC CTGGGATTTG CCTTCCTAGC
127141 ATTGTAGTGG ACTATGAATT ATATGTGCAT TCAAATTGAT CTTGATATCT CTGACATTAA
127201 TGAATGCAAA CACTAATGCT TATAGGCATT TAGTAAGTTC TGAGTTGATA AATTTTCTTT
127261 CTCTCCCTTT TTTTTTTTTC TCCCCTGATA GAGCCAGGGT CTTGCTCTGT CCCCTGGGCT
127321 GGAGTGCAGT GCTACAGTCA TAGCTCATTG TAGTCTGGAA CTACTGGGCT CAGGTGATCC
127381 TCCCACCTCA GCCTCCCAAG CTGCTGGAAC TACAGGCATG CACCACAATG CCTGGCCAAT
127441 TATTTAAAAT GTTTTGTAGA GCCAAGCGCT CACTCTGTTG CTCAGACTGA TCTCAAACTG
127501 CTGGCAACAA ACAATCCTCC TGCCTTGTCC TCCCAAAGCT CTGGGACCAC AGATGTGAGG
127561 CACTACACCT GGCCAAATTT TCTTTATTTT TAAAAGCCTG ATTATAAAAG TAACATATTT
127621 ATTGTAGAAA ATTTCCAAAA CACAGAAAGC ACCAAAAAAG CTATATTCTA ATCCAGCAAT
127681 GACCATTTTG AACACTTTTG ATATATATAC TTCTCATGTA TACGTATGTA GTATATATAT
127741 TTAATATACA AGCACTAGAT TTTATTTTAT CTTATGAGGG AAATGCTCTT GGTGTTTAGA
127801 AAAGCCACAG GATTGCTAGG GGATCTACAT GGAATAAAAC AAGCTTGTCC AACCTGTGGC
127861 CCACTGGCCC GTGTGGCCCA GGACAGATTT GAATGCAGCC CAACACAAAT TCGTAAACTT
127921 TCTTGAAACA TGAGGATTTT TTGCAATTTC TTTTTACGCT CATCAGCTAT CGTAATTGTT
127981 AGTGTATTTT ATATGTAGTC CAAGACAATT CTTCTTCCAC TGTGGCCCAG GGAAGCCAAA
128041 AGATTGGACA CTTCTGGAAT AAAATATGTA GAAAAATAAT CTCAGGTGGT TGTTTTCTGG
128101 ATTATTAAAT ATATTTATAT TTTTAAGTGC CCTCTCTTTA CTTTTTGCAT CACAGAAACA
128161 AAGGCTTAGA GAAACCTAAA GTAACAATCT ACTCCATTGT TAGTCTACAA GTTACTTAAA
128221 TACTTCGCCA AGAAATTGTG ATAATCATCA TCAGAAATCT AGAGTTCTGG AGAGCTGGCT
128281 GACTCAGTCT TAAGGAAATT ACTTTCATCC CTAAAAACCG TAACAGTATT TAATATGTTG
128341 TGGATAGCCT TAACGTTTGG CATGAATCAT GAGCCTCCTT AACTGACTCT TCCAAACAAA
128401 CAGCAATGTT CGCATCAAAG ACAAGCTACT TTATCTTTCC TTTGTGAGGT TTTAGGCATT
128461 ACTGAACAGA AAGCCCTGTC TGCTTTACAT ATTATATATC GTGTTTTTGT TCGTTTTCCT
128521 AGGGTATAAG CTTTGAATTG GAAGTAGTCC TGTAATATAG TTTATATTTC ATAACTAAAG
128581 ATGTGATAGA AGGATTTTTA CTTTAACAGT GAGATTACTC CTAATTTGCA ATGTCAAGTT
128641 GCTGATGTGT AAATTAAAAT AAAGTCTTCT GTCAGTTCTT AAATTATCCA TTTAAAAAAA
128701 GTCTTCATTA GTCTGCATAT TACTACTTTT TAATCTCAGT TTCAGAAACT GTGTTGTCGA
128761 AAAGCAGGTG TTAGGAATGA TTGTCAATTT TAGTACTAAG TAAGATTTTA CCCTTTGTCA
128821 TTAATTTTTG CTTTGTTATC ACAGCAGCAA GCAGAATTTA TAAAGTCTTT AAACTATCAT
128881 AATGTTTATA CCCAAAACAC AAAATTAATT TATATGCAGT TAAAGTCATA AGCTAAATCT
128941 TAAATTCGGA TAAAGCACAC AAAGGATATA AAGATAATTA TAACTTTGTC AGTAGGGTGT
129001 CATCTAGTGG TGAAATGAGG TAGAGTATAT CACGTTTGAA AACATTGAAA CACAAATCGT
129061 GCTCAAAGTA GTATCAGTAT TTGTACCTCA TTCTGGATAT TCTTAAAAGA ATTAACACAC
129121 ATCATAACAC TTTTCCACCA GTGAAAATCA AATCATAATT TTAATGTATA TTTTAAACCT
129181 ATAAATGTGT TTATTTCCAT TTCATTAACA ATACTGTTTT ACAGAATAAC GATACTGAAG
129241 AAGAAGAAAG GTTATGGAGA GACCTTATTA TGGAGAGAGT TACAAAATCA GCGGATGCTT
129301 GTCTTACAAC TATCAACATT ATGACATCCC CTAACATGCC AAAAGCTGTG TACATTGAGG
129361 ATGTAATTGA AAGAGTTATA CAGTACACTA AATTTCATTT GCAGAATACA CTTTATCCTC
129421 AGTATGATCC TGTTTACAGA TTAGATCCTC ATGGAGGTTA GTTCGTATAA TATCAAAATT
129481 ATTGTAAATT TTTGCCATGT TAGATGAGTC AAAATAGGAC TTAAAATGGC ACCAAAATTT
129541 TTGAATCATA TAACTTGTAA TAAACACTGA TTTTGATTAT GGATTTGACT AGAATATAGT
129601 ACTTGTTCAA TTATAATTTC TTTAGGAACA TTTATATATA ATAGAAGTTA TTTCTACTTG
129661 TCAGGGAAAA TCTCAGAAAA TACTACCTTC TGGTTTCATT TATCACTTCG CCCTAATTTT
129721 ACCCAAAATA GCAGTTGTCT ACAAAATGGA TTGATTCAAG ATAAATACTC CTTTTCTTGT
129781 TCTTAACCTT TATAAATGAG CAATGAAATG TATACATTTG AAGGGAGTAA GGTCATACCT
129841 AAGTATAGTT CCTGAATAAT GAACTTGACG ATCTATTGTA TAACTGCAAA TTAATTTAAA
129901 GGGAAATATA ATCTTACTAT CCTGCTCCAA TGGAGAAAAG TAGAAATCAA GATAAAATAA
129961 TATTTTAGAT ACAGGGATTT AATAGCTGCT GAAGATTATC TGATGCAAGA ATGTTTCTAA
```

Figure 7J2

130021 TAGAATATCT CTAGAGAGTA ATTTTCTATT TTAATAAATA AAAAGCTTTA TCTTCCAGGT
130081 TCTGTAGCTA GAAAATTGTG TTCTCTTAAT TCAAAAAACA GTTTGAGTAC TGTTTATTAA
130141 AAATTATTAA AAGTTGATGT TTTCCTTATC TTGAATTTGT TTCATTTTAG GAGGCTTATT
130201 AAGTTCAAAA GCAAAACGGG CTAAATGTTC TACCCATAAG CAGAGAGTAA TAGTAATGCT
130261 TTATAACAAA GTTTGTGACA TTGTTAGCAG CTTATCAGAA TTGCTAGAGA TACAACTTCT
130321 TACAGACACA ACAATTCTTC AGGTAAGATT TTTTGGTAAG CATTTTGTAT ATTTCTAAAC
130381 TAAATGATTA AGTCTAGTAT AACCTAGCTC ACTCAATAAT AAGACCAGCA CTATATTATC
130441 AAGAATTTTT CCTGTTAAGA GTATGTTATA TCTAAATCGA AGAAATAAAA CTTCAGGAGT
130501 TTTAAAAAGA CATTTTATCA GGAGACAAAC AAATGTAGTG TAAATTCCAA ACTCTAAATT
130561 CTTTGAAAGA TGGGTTATAT TTTCATGCAG ATATTAAATG TTTGTTATTT CTTTATATTC
130621 CTGTGACATT TGTAAACTCA AAAAGTAGAG ATTAGAGGAC TGATAGCTAT GATACAATGT
130681 ACCTGTTGTA TATGCTAACG TGCTTTGAGG ATGAAGGGAA ACAGAGAAAA GAATAGATGC
130741 TGATTAGGTG GGGAAAAGAA AAAATGCTTT CTTAGTGTTT TCCAGTAAGC TTATGAATGT
130801 ATTGGAATTT AGTAAGATAG AATGTTACTG AAATCAACTA AAGGTGTATA CTACTTACTC
130861 TTCTTTTTTA AACAGGTTTC ATCTATGGGA ATAACACCAT TTTTTGTGGA AAATGTCAGT
130921 GAACTACAGT TGTGTGCCAT TAAGTTAGTC ACTGCAGTAA GTATAATCAA TTTGTATTTT
130981 TAGTTACCCC ACAAATAAAA CAATATTGAT GTCATTTAAT CCAAATTTCC AAAAAATAAT
131041 GAAGATACCT GGTTTTCAGT ACATTCATTT CAATCTAAGG ACTATTTTAC TAAGTCTTAT
131101 TAGACTTTAT TAATTGAGGA TTTATTTTTC TGTTTGGTTA ATTTGTTGGG TTATTCTGTT
131161 TTTGTCACAT TTAAAACACT TCCAAATATT TGCAAATATT TCAGCTAATA ATTCCTTGAT
131221 ATTTATAATA AAGTTAGAAT GGTTTAAAAT CATTTAAATT CTTGTCTGAC TGCCTATAGC
131281 CAAGATTTCA TAGTCCTTTA AATGAAACTA GTGTACTCTT TGACTTCTAT AAGAATGTTA
131341 TAATTAATGA TAGGAAAATA GAGCAGCTTA CCTTAGATAC TGAAAACATT TTCATTCTAA
131401 ATGGCAGGTA ATTTTTTAAA TCACATGATA TTATTTTTTG GTTTGTTTTC TATTATAAGT
131461 TTAACTTGGA ATCTTATAAT TACTAAACAG GTATTCTCAA GATATGAAAA ACATAGGCAG
131521 TTAATTTTGG AAGAAATTTT TACTTCACTT GCAAGATTAC CAACCAGCAA GAGGAGTTTA
131581 AGGAACTTCA GGTAATTAAT TATAACAGAG GTCAAGTTTA ATGAAGAACC ACCATTATAT
131641 TGAACCGTCA TACATTTATT CTTCATTTCT GTCTGATTTA TATTTTAATA ATTAAAAACT
131701 AGGCAGTTAC ATCAGAACAG CATGAAAAAT AGATGTGTGA AATAACATGG CATATTTAGG
131761 GGGCTTAGAA AACTTCACTG ATTCTCAAGG GTAAAGATCT GTGGCAGGGT TTTTCAGTGT
131821 TGGCACTGTT GACATTTTAG GCCATATAAC ACTTTGTTAT GCATAGCTGT CTAGTGGAAT
131881 ACAGCATGCT CAGCGGCATC CCTGACCTCT ACCCATTAGG TACCAATAGA CACCCTTCCT
131941 CCTTCCAGTT GTGACAACCA AAATTATTTC CAGGCACTGG AGAGCAAAAT CATTCCTTAA
132001 TATGAACCAC TAGTCAGTGA GAAGATCTTG TTCATCCTGT TGGAAATATG GCTCAAAATA
132061 ATCAGATCAG TTCAAAGAGG ATTTTATAAG ATTTTTGTGT CTCAAAAAAA AAAATAAAAA
132121 ACAGAAAGAT TAATGGCAGT ATGGAGAATA AACATGGGGA TTAAATGCTC TTTAATCACT
132181 AAGCACACTG TTAATAAGGA GTGTTACCCA CTGCTATGGT CAGCATTATT GTCTTTGCCA
132241 TCATAGATAA TCACCGGAAT TATCTTAATA TTCCTGAGTG ATTAAAAGTG TTGACGTGGC
132301 ATATAGGATT GTTTTTAAGA TTGCTTTGAA GGCTTCTTTC TTCTCTAAAA TAATTATTTT
132361 ATCTTAATCA TTTTTTGGAC TAATTGTATA CTGATAAACA TTTATTGTCT GTTAAACCTG
132421 AAGAAAAACT ATGAAGAAAA ACTATCAACA CATAAAAGAA TCCTTAGATT TTTTACAATA
132481 TCTATAGAAC AAAAGATGTG GAAATTGATT TTTTATAATC TGTGCTACCA ACACTAGCAT
132541 AGATGATCAA GAGCTGTGTA GCAGATTTTA ATACCAAATG AATAACAGAT TCAGCAGATG
132601 AATAGCAAAA TATATGGGCA TTTGGAAACT TTGAAGACTT TTATCATTTT CAAAATCATT
132661 TTGAGAAATG TTTAGTAGTA GTATGAATTT TTATCTGCAA TGTATGTAAA GCATACAAAT
132721 TTGTATTAAA TACTGTATTT TTCCTTTGAC TATTTTAATT ATCTCAGCAT GCATAGGCAT
132781 TTACTTGATG TTTTTGCTAA CTTACAACAA ATAATTACAC ATAAGAACAC AATAAGCACT
132841 AAGATCATGC CTAGAAATAT TGGCAAACAC AGTATCGTGA AACTTTCAGA CAATAGATGA
132901 CATTTAAATG AGATTATCTT GATACTCCAT ACAAATTTTT TTTCTTCATT AAAGGTTAAA
132961 CAGTAGTGAT ATGGATGGAG AACCTATGTA TATTCAGATG GTTACAGCAC TGGTTTTACA
133021 ACTTATTCAG TGTGTGGTAC ACTTACCATC ATCAGAGAAG GACTCTAATG CAGAAGAAGA
133081 TTCAAATAAA AAAGTAAGGA ATCTATTAAA GGTTTTACAA CTGTACTTTT ATTGAAGGAA
133141 ATACCTATAT TCTCTGTCAT TCTTATAAAA CTGAAGTTCT TTTTTTTTCT TTCTTTTTTT
133201 TGAGACGGAG TCTCGCTCTG TCACCCAGGC TGGAGTGCAG TGGCGCGATC TCGGCTCACT
133261 GCAACCTCTG CCTCCCGGGT TCAAGTGATT CTCCTGCCTC AGCCTGCTGA GTAGCTGGGA
133321 TTACAGGCAC GCACCACCAC GCCCGGCTAA TTTATGTATT TTTAGTAGAG ACGGGTTTTC
133381 GCCATGTTGG TCAGGCTGGT CTCGAACTCA TGATCCACCC TCCTCAGCCT CCCAAAGTGC
133441 TGGGGTTACA GGTGGGAGCC ACTGCGCCTG GCCAAAGCTG ATGTTCTTAA TTAGAGGTTC
133501 ATGGCTGGGC TTTAAGGTCC TTTTAGAGCA CTAGACATGG TGTTGGAAGA GTTGAGTTCT
133561 GGTTCTGTTG TATCTATCAG TCATAAAACA TATAAATCAT TTTAATCTTT CTGAGTTTAT
133621 TCTTCAGCTG TAAAATGGAG GTGATAATAC TTATCAAAAC TGCTATACCA GGTTGTAAGG

Figure 7K2

133681 GTCAGTGAGA TATTAAATGT GAAAGTGAAT AATACAATAT GTAATATATA TGCATGTTGA
133741 GTATCCCTGA TCCAAAAATC TAAAATCGGA AATGCTCTAA AATCTGAAAC TTTTTGAGTA
133801 CCAAAATGAT ATTCAAAGGA AATATTCATT AGGGCATTTT GCATTTCATA TTTTCAGATT
133861 AGGGGTACTA AACCCATATA TAAATACATA ACATAGGATT ATAATTAACA TTAAATTCAT
133921 GTGGAAAATG AGTTTATTCC CTCCCTAATA GGTAGCTCAT GCCGACGATT TGCGTTTGGT
133981 TTTACAGCTT TTGGAGATGT TTAGAATTTT TCCAAGTGTA TACTTTTATC TCAACAAAAG
134041 TTTAAGAGAA ACAAATAATT TTGTTTATCT ACTGTTAGAG CCAAGCATAT GTGTGTATCT
134101 TTTTGGGAAT AATAATAAAT ATGTAATAAT TATTAATAAC TGGACAGGCA CTTTGGCTCA
134161 TGCCCATAAT CCCAGCACTT TGCGAGGTCA AGGTGGGCAG ATTGCTTGAG GCCAGGAGTT
134221 CAAGACCAGT TGGGCAACAT GACAAAACTC TGTCTCTACA AAAAATACAC AAATTAGCTG
134281 GTCATGTTGT TGTGCACCTG TCATCCCAGC TACTCAGGAG GCTGAAACAG GAGGGTCGAT
134341 TGAGCCTTGA GAGATCGAGA CTCAGTGAGC CGAGATTGTG CCACTGCACC CTGGCCTGGA
134401 TGACAGAATG AGAACCTGTC TAAAAATGAA TGAATGAAAG AAAGAAAGTC AAATACTCTC
134461 TGAAAAGTTC AGATCCTCTT TATTTCTCCC ATCCCAATCC CATTGTTTGT CTCTAGTCTT
134521 CCTTTCCTAA CCATTGGTGA CAAGTATCAT GAATATGTTT CTTTCTTTCT TTTAATTATT
134581 TTTATGTAAA TTTGATATAC AATTATTTCA TTTTTACGTA AAGGACAGTG ACATATTTAC
134641 AGCTAATTTT TTCACTCAAC ATCGCTTTTA ATACATACAA CTCATACTAG ATTGTTTTTT
134701 ACTTGAGTTA AAAACACCAT ATCATAGAAT CACAACTTAA AGCAAAAGTT TCTGTAGATA
134761 CACTTAGAAG TAAAATTAAG ATAGTATACA TGCATTAAAT TTACTGGAAG TTGTCAATTT
134821 GCTTACTAAA GTGGTGTTTC AGTTTATAGC CCTACTTCTT ACTTAAAATT ATGGTCATTG
134881 AGAAATACCC ATCTTATTTT GCATTTTCCT GGTTATTAGT GAGCTTGAGC CCCTTTTCCT
134941 ATAGTTATTT GTCTGTTGTA TTTTTATAAC TGTGAATTGA CTGTTTATAT CTTAATCTTT
135001 AAATTTCTTT TTTTTTTTTT TCTTTTTGTT TTCTTTGAGA CAGGGTCTCA CTCTGTTGCC
135061 CAGGCTGGTT GCAGCAGCGT GATCACAGCT CACCACAGCC TCAACCGCCT AGGCTCAAGT
135121 GATCCTCCCA CCTCAGCCTT CCGAGTAGCT GGAACTACAG GCACGCGCCA CCATGCCGGG
135181 CTAATTTTTT TTTTTTTTTT ATCTTGGTGA TATTCTCTTT TTATTTATTT TGTCTTTATT
135241 CAGTAATCTG CTTTGATATC CTGAATCAGT ATTTCCTTAG GTGGAGAGAG TTTTCATATA
135301 TTGAATATTA GATTCTTTCT CCAATTTTTT TTTTTTTTTT TTTTTTTTTA TTCATTCTTG
135361 GGTGTTTCTC GCAGAGGGGG ATTTGGCAGG GTCACAGGAC AATAGTGGAG GGAAGGTCAG
135421 CAGATAAACA AGTGAACAAA GGTCTCTGGT TTTCCTAGGC AGAGGACCCT GCGGCCTTCC
135481 GGCCTTCCGC AGTGTTTGTG TCCCTGGGTA CTTGAGATTA GGGAGTGGTG ATGACTCTTA
135541 AGGAGCATGC TGCCTTCAAG CATCTGTTTA ACAAAGCACA TCTTGCACCG CCCTTAATTC
135601 ATTCAACCCT GAGTGGATAC AGCACGTTTC AGAGAGCACA GGGTTGGGGG TAAGGTCACA
135661 GATCAACAGG ATCCCAAGGC AGAAGAATTT TTCTTAGTAC AGAACAAAAT AAAAAGTCTC
135721 CCATGTCTAC CTCTTTCTAC ACAGACACGG CAACCATCCG ATTTCTCAAT CTTTTCCCCA
135781 CCTTTCCCCC TTTTCTATTC CACAAAACCG CCATTGTCAT CATGGCCCGT TCTCAATGAG
135841 CTGTTGGGTA CACTTCCCAG ACGGGGTGGT GGCCGGGCAG AGGCGCCCCT CACCTCCCGG
135901 ACGGGGGGCT GACCCCCCCC CACCTCCCTC CTGGACGGGG CAGCTGGCCG GGCAGAGGGG
135961 CTCCTCACTT CCCAGTAGGG GCGGCTGGGC AGAGGCGCCC CTCACCTCCC GGACGGGGCG
136021 GCTGGCCAGG CGGGGGGCTG ACCCCCCCAC CTCCCTCCCG GACGGGGCGG CTGGCCGGGC
136081 AGAGGGGCTC CTCACTTCCC AGTAGGCGCG GCCGGGCAGA GGCGCCCCTC ACCTCGCGGA
136141 TGGGGCGGCT GGCCAGGCGG GGGGCTGACC CCCCCACCTC CCTCCCGGAC GGGGCGGCTG
136201 GCCGGGCGGG GGGCTGACCC CCCCACCTCC CTTCCGGACG AGGTGGCTGC TGGGCGGAGA
136261 CGCTCCTCAC TTCCCAGACA GGGTGGCTGC TGGGCGGAGG GGCTCCTCAC TTCTCAGACG
136321 GGGCGGCTGC CGGGCGGAGG GGCTCCTCAC TTCTCAGACG GGGCGGTTGC CAGGCAGAGG
136381 GTCTCCTCAC TTCTCAGACG GGGCGGTCGG GCAGAGACGC TCCTCACATA CCGGACGGGG
136441 TGGCAGGGCA GAGGTGCTCC CCACATCTCA GACGATGGGT GGCCGGGCAG AGACGCTCCT
136501 CACTTCCCAG ATGTGATGGT GGCCGGGAAG AGGCGCTCCT CACTTCCTAG ATGGGATGGC
136561 GGCCGGGCAG AGATGCTCCT CACTTTCCAG ACTGGGCAGC CAGGCAGAGA GGCTCCTCAC
136621 ATCCCAGACG ATGGGCGGCC AGGCGGAGAT GCTCCTCACT TCCCAGACGG GTTGGCGGCC
136681 GGGCAGAGGC TGCAATCTCG GCACTTTGAG AGGCCAAGGC AGGCTGCTGG GAGGTGGAGG
136741 TTGTAGCCAG CCGAGATCAC GCCACTGCAC TCCAGCCTGG GCACCATTGA GCACTGAGTG
136801 AACGAGACTC CGTCTGCAAT CCCAGCACCT CGGGAGGCCG AGGCTGGCGG ATCACTCGCG
136861 GTTAGGAGCT GGAGACCAGC CCAGCCAACA CAGCGAAACC CCGTCTCCAC CAAAAAAATA
136921 CGAAAACCAG TCAGGCGTGG CGGTGCGCTC CTGCAATCGC AGCTCTCGGC AAGCTGAGGC
136981 AGGAGAATCA GGCAGGGAGG TTGCAGTGAG CCGAGATGGC AGCAGTACCG TCCAGCTTCG
137041 GCTCGGCATC AGAGGGAGAC CGTGGAAAGA GAGGGAGAGG GAGACCGTGG AGAGGGAGAG
137101 GGAGAGGGAG AAGGAGAGGG AGAGGGAGGG AGAGCTTAAT CTTTAAATTT CTGATGAAGG
137161 CTTTGAATTT TTTTTTTTGA TTGTATGGAT TATATGTTTC TTAAACTTTG AGGTTGACAT
137221 ATTTTTTCTA AATTCTTTTT TTATTTTCAA TCCATTTCTT TCTGTTCTGA CCAGGATTAT
137281 GATAAACAAC TATTGATATT AAATTTGTTA ACCACATATG TTACTCTTAC ATTATTTTAA

Figure 7L2

137341 TAACACTCTA TCTGTATTTT TATTTGTTTC TATAAAGTTT TAAAATATGC TTAGTGTGCT
137401 AATTTTGGCT TCTCTTATTA TATATAATGT AATAGTTTAA GCATTTTAGT ATTTAAATAT
137461 ATTACCCCTC TTCAGTAATA ACATGACAAT AGCAACAGGG CTAACTTATT ATTTCTTGTA
137521 TCTTTATAAA CTCACTTTTT TTCATTCTAG ATTGACCAGG ATGTTGTCAT TACTAACTCT
137581 TATGAAACAG CTATGCGAAC AGCCCAAAAC TTCCTCTCCA TCTTCCTTAA AAAGTGAGTA
137641 AAATTAATAT AAATCTGGTT TTTCTTTTCC ACAGTATAGA GAATAGTTCA TTTTTTTAAA
137701 AAGATGAATC CAATTTCCTG CCATAATCTG AACCTTGAAT ACATCTTCCT GACACTTGGT
137761 TTCTTGATCT TTAAAATGAG GCAATTGGAG TATTAAAAAT CTAAAATTGG GATGGGACTA
137821 CACGGGGGAA AAAAATCTAA AATTTTGTGA ATTTGCTTAT ATGTTAGACT CCAGAAATTA
137881 AAGTACTAGA TTGAAATTCT GTAATTTGTC TTCAGTAAAT TTTGGAGAAT TTTCCTAGTG
137941 TACCTGAATA GGAAAGTTTG TGAAGAGATG TTATTTAGCC TCCATATGAA TTTTTTTTTT
138001 TTTTTAATGA GACAGAGTTT CGCTCTTGTT GCCCAGGCTG GAGTGCAATG GCACGATCTC
138061 AGCTAACTGC AACCTCCGCC TCCCAGCTTC AAGCGATTCT CCTGCCTCAG CCTCCCAAGT
138121 AGCCGGGATT ACAGGCATGC ACCACCATGG CCAGCTAATT TTTGTATTTT CAGTAGAGAC
138181 GGGGTTTCCC CGTGTTGGTT AGGCTGGTCT CGAACTCCCA ACCTCCGGTG ATCTGCCTGC
138241 CCTGACCTCC CAAAGTGCTG GGATTACAGG CGTGAGCCAC TGCGCCCAGC CCAGCCTCCA
138301 TAAGAATTTA TGATGACCTT GGCCAGGTGT GGTGGCTCAC ACCTGTAATC CCAGCACTTT
138361 GGAAGACCAA GGCAGGTGGA TTACAAGGTC AGTTCGAGAC CAGCCTGACC AGCGTGGTGA
138421 AACCCTGTCT CTACTAAAAA TACAAAAATT AGCCAGGCAT GGTGGTGCAC GCCTGTAGTC
138481 CCAGCTACTT GAGAGGCTGA GGCAGGAGAA TCGCTGGAAC CCGGGAGGTG GAGGGTTGCC
138541 GTAAGCCAAG ATCATGCCAC TGCACTCCAG CCTGGGTGAC AGGGTGAGAC TCCATCTCAA
138601 AAAAATAAAG AATTTATGGT GATCTTTTAG GTAGAAAAAC AGTGATCATT TTTTTAAATG
138661 TGTTTCACTT GCGAGAAAGT AGTATTAGTA TTGCTTAATA AATGAATTCC CTATAATTAA
138721 GGAGAAAGTG GAGTTTGTGA AATAGACTCA TTTTAAACCA TATTTTATTT AATGTACATT
138781 TATATATTTT GTTACTAAAC ATAGAAAAAA GAAAACTTAG CTAACAATTT CAATCATGTT
138841 GGTAGACAGA TGACTGACAT GTGTCACCTA AATTGACATC CTTTTCATTA TTTGCCTTTG
138901 AACAGATGTG GTAGTAAGCA AGGTGAAGAA GATTACAGAC CACTGTTTGA AAATTTTGTT
138961 CAAGACCTTC TTTCAACAGT CAATAAGCCT GAATGGCCAG CTGCTGAACT ACTCCTTAGT
139021 TTGTTAGGGA GACTGTTGGT AAGAGTATAG CATTTAAAGA TTATTAGATT ACTAGAAGAC
139081 AACATAATGA GGATGTACTC TGATTCACAG ATGATGAATT CTTTAAAAAT GTGTAAGGAA
139141 ATATGAACAT TGCATCTCTT TTTGCATGTG CATAACTGTA CACAATATTG TCAGTACCTT
139201 GTAGAAAATT TTCAAATGTT GTGAAGTTTG GTGCTTTCAT TTCATTACAT AAGATAACAG
139261 TGCTTTAACA ATTTTTTTTT TTTTGGAAAT GTTATATTGT TAAAAGCATC TCAACACTGA
139321 GTCATAAGTT ACTCATTTCA AAGCAAGAAA ATGATTAATA TAGACTCCTT ATCATCTTTA
139381 AGAGTATTTC TACAAATGTA TGGCATTTTG TAGTCGTCAT GTAACACAGT AGGTAAATGC
139441 AAAGAAATGT TGTGACTCTA TTTTTAAACT ACATTTGAAC TTGCACAATA CACATTGTTA
139501 CAAAGCTTCT GGGACCTTTT TGTGAATGGG AAAATATGTT AATATTATTC GGAAACTATA
139561 ATAACTTTTC ATAGGCATCA GAATTCCACC CTAAGAAATT CTTACTCAGT AATACCACAT
139621 TTTGTGCAAA TAATACAGTT GAGCCTGCAT ATTTAATGAG TTGTGTTGTT CTTAAGGAAG
139681 TTTAATCTGT AATTTTTTTA GTCACATGAA AATGTTCAGA TTCCAGAAAA TCAAAAGGCA
139741 AAAATGACTT TATGGGACAA TATCACAGGA AAAAAAAAAG TTTAAATTTT AAATTATACA
139801 ATTTAGATTG GGAATTTATA TGATAAATTG CTATTTAAAA TATATTGTTA TAAATCTATT
139861 CAATCAAAAA CTATTTTGAT ATTTAGGTTC ATCAGTTCAG TAACAAGTCA ACAGAGATGG
139921 CTTTAAGAGT GGCATCTCTT GATTACCTTG GAACTGTTGC TGCACGGCTA AGAAAAGATG
139981 CTGTTACAAG CAAAATGGAT CAAGGATCTA TAGAACGCAT TTTAAAACAG GTACTAAGAT
140041 AAAAGATTAA AATTATGGGA ATGAATAATA GTTATTTTCT TTGCATGTCC TTACATTAGT
140101 TTTGCATTTC ATTTTGTGTG GATTCAAAAT AAGATTTTTA CTTCTAAAAG TGGGCTTTTC
140161 AAAGCCCCAG TGAGAAATTT TAAGACCTGA GAATGAATTA TTTAGTCTAA CAGGGACTTC
140221 TGAATGGTTC ATATAAATCA TTTACTTTCT TTTTGTGAAG TACTCTTAAT AATGTATAAT
140281 GCTGTTTTAT ATTTGATTTA ACATAAATTT TATTTAAGTT TTTAATTTAC TGAATGGTGA
140341 TTTAGCATAC ACAATAAGAT TGTTTTGTAC TTTTGAATGT TTTGTATCTT CTCATACCAA
140401 GGAGGTGTGA GGAGAGCTTT TTTATACTTT ATTACATTAG AGAGTTTTCA TCTTGGGGGA
140461 AAAAGTGTTT TATTGCTTTT TTTTTTTTAA TGTGGATGAA GTGGTAGTAA TAAAGTTACT
140521 TGAGAAAACT GGTGAAGAAA TGATTTCTAA TCCTACTATA TACAACTTCT GTTTTCATTT
140581 TTTTCTAGTC TTTTTTTATG CTCGTAATCA TATCCATGTT GGTAGAAATG CCTCTAATTT
140641 TTTTTTAGCT ATAGTTCGTG TTTTGAAATA ATCTCAACCT TAGAGAAAAA TTGTAGGAAT
140701 AGTACAAAGA ACTCCCATAA AAGCTTCTTG CAAATTCCTC AATTATTGAC AATTTACAAA
140761 ATTTCCTTTC TCATCTTTCA AAATATAGAT GTATGTGTGT CTGTATATGC ATTTTTTTTT
140821 AAATTTTGTT TCGAACCACT TGAAGTTAAG TTGCAGACAT GATTCCCTCA TTACCCCTGA
140881 ATTCTCTAAT GCAGTGATTT TCCAAGTATG ATCCCCTTGA CAAGTAACAC CAACATTGAA
140941 ATCATCTGGG AACTAACAAG TACATTTCTA ACAAAAGTAC AAATTCTTAG GACCCTCCCT

Figure 7M2

```
141001 GGACCTACTG AATCAAAAAC TCTTGGTTTA ACAAGCCCTC CAGGTGATTC TAATGAATGA
141061 ATGAATGCTG AAACTTGGGA ACCACTGCTT AGTGTATATT TCTGCAAACA AGAGCTCTCA
141121 CTTAAATATC TATAGTACAA TTATCAAAAG CAAAAAATTA TCATTAATAC AATATTAACA
141181 TCTGATGTAA TACAATACCT ACTCTGGTAA ATTATAATTT GTTGCCATCA TTATTTTAAT
141241 GCTCAAATCG TCCTAGATTT GATCAATGAG AACCCTTTGA AGCTGGCTTT TATATCATTT
141301 TGATATATTC CCATCATAAT TTGAGGGCTT TCTAGAACAA AAAGGTATTT CAGGCAGATC
141361 TTTTACCTTC CCTACCCCTG CCCTGGGATC AGTTGTTTCT CCTAGGAATC TTGGTTCCTT
141421 TTGTTGGTGA ATTGTAATGT AGAAACCAAG ATCTAGTTAC TGGATGACTT TCTGTATTTC
141481 TTAAAGTGGG CCTGGAACCT CTTATTGCCA TGTATGGCTA TGTTGATTAT ACATTGTGCA
141541 GCTCAAGGGG AAGGATCATT TGTAAATTTT TATGGCTCTC AACACATATT TCCAAAAGGA
141601 AATTCTTCCT ACCTCTGAAG ATTTAACACA TTTTTCTGAT CATTTTTATG TCAACTACCT
141661 ATGAGCTCTT TTTTTAAAAA ATGACATATG GTTCATAAAA ATAATGGCCG GGCGCAGTGG
141721 CTTACACCTG TAATCTCAGA AGGGTGGATT ATTTGAGGTC AGGAGTTCGA GATCAGCTTA
141781 GCCAACATGG TGAAACCCTG TCTCTACTAA AAATACAAAA ATTAGCCAGG CATGGTGGAC
141841 CATGCCTGTA GTCCCAGCTA CTAGGGAGGC TGAGGTAGGA GAATTGCTTG AACCCAGGAG
141901 GCAAAGATTG CAGTGAGCCG AGATAGTGCC ACTGGACTCC AGCCTGGGCG ACAGAGTGAA
141961 ACTCCATCTC AAAAAAAGTA AAACAAAAAA GGCAAACTTC AGCTATCAAT ATATAATATT
142021 TTTCGGAAAT AATATTTTTC TGTTTTTTCC TTTTAGTTAC TGTGGTTGTA TTTTCATTTT
142081 TAATATCAGT TTTTCCTTCA GATTTGTGTT TACAATTAGG TGATTTATTA AAGCACACCA
142141 GTAATATCTT TTTTGTTCTT ATTTGGTTTA TTCTATAGGT TTCAGGAGGG GAAGATGAAA
142201 TCCAACAATT ACAAAAAGCA TTGCTTGATT ACTTGGATGA AAACACTGAG ACTGATCCTT
142261 CACTAGTGGT AGGATTCTTT TCCCCTGTTT TGGAGATACT ACATGTTTAT TTAAATTGGG
142321 TTTAAGAAAA TTGGGAGGTA GCATGATGAA GAGGAAAACT TAAGTTGTTT GGAATATTGA
142381 TTTTCAAAAC AAAGGGATAC TTGATAATCT AAACAGAAAA GAATGCTTTG GGTTGATTTG
142441 TCTTATATGG AATTCTGGTT ACAGATACTG TACTGTACTA AAATTGTGTG ACAAGAGAAA
142501 TATTTGGAAG TCTCTCCGTA AGTGATCTTT GAGGCTAGGC TAGGTCATTG GTTCTCAGAG
142561 TGAGTATGGG CCGAGTGGTA CATGAGATGA TCTATAAGCC TGTAAAAATA AACTATTGGA
142621 TTTTTATATG TATATTTTTA AATATAATTT TACTTCTATT TCATGTATGT TACACAATGT
142681 AACCAAAATA TTAGTATAAG AGGTTCATGT ACAAAATTTA TAAACTATTA TTTGAGAACA
142741 TTATACATAG AGATATTTTA TTTTATTTTT TAACTGGTGG GATATGCAAT TGAAAGAAAT
142801 GGGATACTAC TAAGCTCTTC AGCCAAATAC TGTAGGTTTT CAGTTTGTAT TCAAAGGAAC
142861 AGATTTACAG GTGTGTCTCA GTGTTAAACT ATTTCAGTGA CAATTGTCTT GTGTGTTTCT
142921 TGGAGAACTA AGGCAAAATT TGAAAACAGA TGAAGTCTTC TACCTTCAGC ATTTTATCAA
142981 TTTGTTTTAA ACTTTCCTAG TTGACCCATC ATCTGTTTAA CTTTGTCATG ATGTTGTCCT
143041 TGATTAAGTA GTTGATAATA GTATTCTATA TTTAATACAG TTGTGTTTAT CAAATTATCT
143101 TGACTTCATT AATATAAGTA TTGGAACATA GTAAAATAAT AAGTTTTCTA ACATTTAGGA
143161 TATTCTATAT TTTCTGGCTT TCTTAAAATC TGTTTTTATC ACATGGAAGT TGTTTTAAAG
143221 TAAACTTTAA TATTTGTATT CCTGTAATGT GAGCACTCTA ACTTTATTAA CTTGGAAATC
143281 TTGTTGCTAA TTTCATCAAG CTCAAGTCTG TCTAATTTCT TTCCAGTTTT CTCGTAAATT
143341 CTATATAGCC CAGTGGTTTC GAGACACAAC TCTGGAAACA GAAAAAGCAA TGAAATCACA
143401 AAAAGATGAA GAATCATCTG AAGGAACACA TCATGCAAAG GAAATTGAGA CAACTGGCCA
143461 AATTATGCAT CGAGCTGAAA ACCGAAAAAA GTTTCTTAGA AGCATTATCA AAACCACACC
143521 TTCTCAGTTT AGCACATTAA AGTAAGATCC AAGGAGAAAA CAGTTTACAT TTATCTCCTT
143581 GATATCTATT TCCCTAAGTT ACAAAAAAAG AAAAATAAAT TTTTAATGAC TTTTTGTTGC
143641 AGGATGAACT CTGATACTGT GGACTATGAT GATGCTTGCT TGATTGTTCG ATACTTGGCC
143701 TCCATGAGGC CGTTTGCCCA GAGCTTTGAT ATTTATTTGA CACAGGTAAA CTGGATAAGA
143761 ATTCCTTATA CAGTGATATT GATTTTTCTG ATTCTGGATG CTTGTGAGCA GTATATAATA
143821 TCATTCATTG TTGAGTACAG ATACTTAAAA GATCATAGAT GTAGTATTTG TTTTTAGGTT
143881 CTCCGGCCGG GTGTAGTGGC TCACGCCTGT AATCCCAACA CTTTGGGAAG CCAAGGCAAG
143941 TGGATCACCT GAGGTCAAGA GTTCGAGACC AACCTGACCA ACATGGTGAA ACCCCGTCTC
144001 TACTAAAAAT ACAAAAATTA GCGGGGCGTG GTGGCACATG CCTGTAATCC CAGCTACTCG
144061 GGAGGCTGAG GCCGGAGAAT TGCTTGAACC TGGGAGGTGG AAGTTGCAGT GAGCCGAGAT
144121 CGTGCCATTG CACTCCAGCC TGGGCAACAA GAGGGAAACT CCATCTCAAA CAAAAAAAGA
144181 AAGTCCTTGT TCTACATCCC TTTTACATAT TCTTGTTTTA CAAATATATA TTTGTATGAA
144241 TGCACACACA TACAGTATCA GTAGAGTAAG TGACATTATA AAAACATCCA ACTAAATCCC
144301 AGCACTTTGG GAAGCCAAGG CGGGCAGATT ACGAGGTCAG GAGATCAAGA CCGTCCTGGC
144361 TAACACAGTG AAACCCCATC TCTACTAAAA ATACAAAAAA TTAGCTGCCA TGGTGGCATG
144421 TGCCTGTAGT CCCAGCTACT CAGGAGGCTG AGGCAGGAGA ATCGCTTGAA CCCGGGAGAT
144481 GGAGGTTGCA GGGAGCCGAG ATTGCGCCAC TGCACTCCAG CCTGGGCGAC AGAGCGAGAC
144541 TCCATCCCAA AAAATAAAGT AATAAAATAC AAAACATTCA ACTACCAAAT TATGATTTGA
144601 ATGATACTAA ATATCTTTGA TTCAAGTTAC ACATAGCAAG GTTTTAATGG GGCTACAGGT
```

Figure 7N2

144661 TCTGCAAATG AAGCAAAACA ATTAAAAAAC AGGTTTAATT GGATAAACGA AAGGCTCCAA
144721 AGTATGGACT ATACACTTAA CACCTGTACT GATTTTTAAG TTAAACTTTG AATCATTAGG
144781 AAAGATCCTT TACTCATTTA TATACAGATT AAAGAGAGGT AAATAATAGA TTTGTTTTCT
144841 TTTGCATGTT TTCATGCTAT TTTTAATTAA ATTTTATGTA TTCTAAAATT TACAAAAATG
144901 TCAATGTTTG CTTGGCAGAT CCTACGAGTT CTTGGTGAAA ATGCAATTGC TGTTCGAACA
144961 AAAGCCATGA AGTGTTTGTC TGAGGTTGTT GCTGTAGACC CCAGTATTCT AGCAAGGGTA
145021 AAGAGCAAAA ATGATTCTTT CTTTTCTACT CGAATTGGAA TATTCACTCT ATTTAGGTAT
145081 AAATTGTTTT TTTCTCTTCA TTTTTCTTTA GCTTGATATG CAACGAGGTG TTCATGGACG
145141 ATTGATGGAT AATTCGACTA GTGTCCGAGA AGCAGCAGTA GAATTACTAG GTCGATTTGT
145201 CCTTTGTCGA CCTCAGCTTG CTGAACAGTA TTATGATATG CTGATTGAAA GAATATTGGT
145261 ATGTTTGTCA TTTTTATAAT GATTCGTGAA TATAATTTTG CCTTTCAAGC ATCATGTTTT
145321 GTTTTAAAGT GTTAAGTTAG AAAAATAAAT GTACCAATTA TATATTTATA TTGTCAAATT
145381 TATGAACTAT TGCCACTTTC TAAACAAGTA CATATTTTCA AGAATAGCCC TTGCAATATC
145441 ATAAAACAAA TCATTGGTAA TAATTGGATT CCTTTTTTCA GTTGCTGTTT CTTTTTAATT
145501 ATACCAGTTT ACAATGAGTA GATGATAGGA ACCACATGGG GTAGTTAAAT GTTTTTGAAC
145561 AAGAATCTAG AGTGATTTTA TGTATATATT TATGTATGTA TATATATAAA CAGGAAGAAT
145621 TATTTCAGTG AGAGACACGT ACAGAACGTT GGTACCTGAC AATATTTTTG GATCCCTTAG
145681 GTGCATCTTC TTGTTTCCTT AAAGCTGATT AATGATAGCT CAGATACCTA CAAGTTAAGC
145741 CCAAAAGTCC ATTGAGGTTT AAGAGCAAAC TAAAGAGGTT CTACATACAT CATGGAATTC
145801 TCTGGCTCTG AAGCATTTTT CTGAAAAATG AAAGGAAACA TTGGCATTAG GAAATATCTG
145861 TGGAATCTCC ACACTACCCA TTGCAGGCAT ATTGACTTAT TGTAGAACTC AACATAGATG
145921 CACTAGTGCA CAAAATTAAG TATTACCTCA ATGACAAGAG TTTATTTTGT CACCCTTGGC
145981 CTAATATCAG AACATTGTGT GACAGAAGTA TAGAGTCATT TTTAGCTTCA ACTAGGCATA
146041 AATCTTGGTT GAGAAACAAA TAATTTAAAG AAAAGCTGGA AAAATTTTTT TCCTTCTTAG
146101 GGCTTCCATC TTTTGAAGGG TAAAATCAAC AGGATTCCCA CGTATCTGAT AAACTCTGAT
146161 ATTTGTAACC CTAGTAAAAT ATCCTAAAAT ATTTTGGGGA TTGCTAAAAT CACATAATGG
146221 AGATTAATAA TTTTGCACAC TTCATGTATG ATGCTTTTTA TTTTTAAAAC TCTTTAATAT
146281 GAAAGTTTGT TAAAGAAAAA TAGTACAGTG AACACCCTTG TACCTACCTC CATACTTCAT
146341 CTGTACTTTC TGCTAAATTA TTTTAAGTCA AACATTTTTT ACTTCTTTTC TTGTGAACAC
146401 TTCAGTTTGT AACACCAAAA AAAGATACTG TGCTATATAA ACAAAACCAT TATCTCACCC
146461 AAATTAGCAC TCTAGTATCA TCTGAATACT AGTTCTTAGA TCCTCCATTG TCCTAAAAAT
146521 GTTTTTTCAT TCTTCTTTTT TAAGAATCAG AATTCAGTCA AAGGTAATAC ATTGCATTTG
146581 GGGGTCATGT CTTAAAATTG AAGACTATTT TCTTATTCTT TTTTTTTTTT TTTTTTTTTT
146641 TTTACATCCC ATATGACATT GACGGATTAA AAAGGCCTGA TCGGTTTTGT TATCTTCCCA
146701 CACTTCGTTT AATTTAACTT GTGTTTTGTA TCTCTTATAA ACCATAAGAT AGGCCAGGCG
146761 CAGTGCCTCA TGCCTGTAAT TGCAGCACTT TGGGAGGCTG AGGCGGGTGA ATCACCCAAG
146821 GTCAGGAGTT CAAGACCAGC CTGACAACAT GGTGAAACAC TGTTTCTACT AAAAATACAA
146881 AAATTAGCCA GGCGTGGTGG TATGCACCTG TAATCCCAGC TACTCGGGAG GCTGAGACAG
146941 GAGAATCGCT TGAGCCTGGG AGGCAGAGGT TGCAGTGAGC TGAGATCGCA CCATTGTTAC
147001 CCCAGCCTGG GCGAGAAGAG CAAAACTCCA TCCCAAAAAA AAAAAAGAAG TAACCATAAG
147061 ATAGTGCCAA AGGTTTGATT AGATTCAGGT TAAACATTTT TATGAAGTCT ACTTTTAAGT
147121 GATACTTCAT GTGCTGTTTA AGTGCCAGAC ACTATTCTAA AGCTTATGTT TGTTTTCTCA
147181 TTTAATTTTG ACAAGCGTAT ACTTCTAGTC TTGTGTCCAG GGCTTAACTA TAAAATATGT
147241 TTCTATGTCT TAGATATCAT ACTTTAAAAG TAAAGACAAC ATAAAAAAAT AACACATTTA
147301 TAGTAGCAGA AAGCATGTAA AAAGCAAATA TGTCAAGTGT GTTTATCATG TTAACAAATA
147361 GTGAATATAC TGCGTATGGA TACTTATTTT CTAATTTCAT ACACTAGGCA TCTCAATTTT
147421 TCTGACTCTT AAAAATACCT TTCTGTTTTT AGGATACTGG TATCAGTGTC AGGAAAAGAG
147481 TAATAAAGAT TCTCAGAGAC ATTTGTATTG AACAACCAAC ATTTCCAAAA ATCACAGAAA
147541 TGTGTGTAAA AATGATTCGC AGAGTCAATG ATGAAGAGGG CATTAAGGTA GTGTTGACTG
147601 TTTTAAATTT ATTTTTCATT AATGTTTAAA ATAAGTTAAA TGTTTATTGC ACCTAAATGT
147661 TGATTTTAAA TATATCCAAA CACTTTACAA TGAATCGTTT ATAGTTTATA AACTTAAGAA
147721 AAATACATAC TTTAATTTTT TTTGTTTCTA GATTTTTATA TTAAGTATTA TAATCTGATT
147781 TTAACCAACC AATTCCTCAG TGGTAATATT TATTTAAGAC TGGCCATAGT AGCTCATGCC
147841 TATAATCCCA GCACTTTGGG AGGCCAAGGC AGGAGAATGG CTTGAGGCCA GGAGTTGGAG
147901 ATCAGCCTGG GCAACATAGT AAGAATCCTA TTTCTATAAA AAATAAAATG ATGAAAATAA
147961 TTTTTAAAAA TTTCACCAAA CATAGTAGAG CATGCCTATA GTTCCAGCTA CTCTAGAGAT
148021 TGACACAGGA AGATTACTTG AGCCCAGGAA TTCAAGGCTG CAGTGAGCTG TAATCTTGCC
148081 ACTGCACTCC TGCCTGGGCA AGGGTGAGAC TCCATCTCAA AAAATGTGCA TGTGTGTGTT
148141 GATTGATTTA TTGATTGTTA TTATAAGAGA TTGCATTATA TTCAAAGGTT TCTCATGGGA
148201 TTATTTTAAT TTTCAAATGA TTTTAGTTTT CTAAATTATT AAATAAATAC TTTGTTTCAT
148261 TATGTTAAGT GAAATAAGCC AGACACAGAA AATAGCACAT ATTTTCACTC ATGCGTGGAA

Figure 702

148321 GCTTAAAAAA AATTTATCTC ATAGAGATAG AGAATAGAAA GATGGTTAGC AGAGGGAGGG
148381 AAGGGTTGTG AGGGGTTGAA TAAAGAGGGG TTGGTTCACA GTTATCAAAA ATACACCCAG
148441 AAGGAATAAA ATTTAGTGTT CAGTAGCACA ATAGGGTGAC TATAGTTAAC AATAACTTAT
148501 TGTACATTTA AAAATAACTA GAAGAATGGA AATAGGATGT TCCTAACACA AAGAAATGGT
148561 AAGTGCTTGA GGCGATGGAT ACCCCAGTTA CCCTGATTTG ATCATTATAC ATTGTATGCT
148621 TGTATCAAAA GTTCAACTAT ACTTCATAAA TGTGTACAGC TATTATGTAT CCATAAAAAA
148681 AAAATTTTAA GTTTAGTCCT AAATTCATTA GTAAATTTAC ATTTATATAT AATAATATGT
148741 ATAATTGTCC CTTTTTTTTA AGTTTAGCAA ACACTGTAAC AACTTCTTCT CCAAAAGCAG
148801 TAAATATATT TTTTAGTTTG ATCATAAACA TTTGAGTGTA TAGTATGAAG AAGTTCTAGG
148861 CTAGGGATAG TATCACCCAT TCGTATTGTT TAAAATCTTT ACCAAATTGA AAATTTTTAT
148921 AGTTTTGAGA AATTAGTAGT TTTAGAAAAA ACTGAGGAAA TTAATACCAG AAATTCCTGG
148981 CAGTTTGTGT TTTGATTAGT TATTTATAGC TTTGTGTTGG GCCTAATGAG AATTTGGAAT
149041 TGTGAAATTG CCGTATTTGT TATAATTAGT TAATTTGAAA TTTCTCTTCC TTCTAGAAAT
149101 TAGTAAATGA AACATTCCAG AAACTCTGGT TTACTCCAAC TCCACACAAT GACAAAGAAG
149161 CAATGACAAG GAAAATTTTA AACATTACCG ATGTGGTAAG AAGGACTGGA ACAAGGGTGT
149221 GGTCACTGTT GATCCAGACC TAATTGAGGC CTACATGTCT TATGAAGGAA GAGACAATAA
149281 TGAGATATTT CATTAATCTT GACATTTCGT ACTGCTGCCT TTACTTTATA TTTCTGGAGA
149341 TGCTGAAGGG ATGCAAGTAA CATGTCGTTG ATGCTTCCAT ATAGCCCTAC TTCTTGGCAT
149401 TAATTGATGT AAACACTGAT ACTGAGATTT TCCTATTCCT CCAGCAATTA AAAACAGGGA
149461 GGGAAAGGAG AAATGGAAGA ACAGATACAA TCGCCCAAGG GTAATAATCT GCAAAGATAG
149521 TAATGCCTAC TTTTTTCAGA AATTATGAAT ATGGATTAGC TACATTTTTT ATTATGCATA
149581 AGCTATACAT TTTGTGTTTT TAATATAAGA AATTTTTGCC AGTCACAGCG CATATGCCTA
149641 TAATCCCAGC TGCTCAGGAG TCTGAGACGG GGGATCAAGA GATCTTTGAA CCAGGAGTTC
149701 AAAGCTGCAG TATACTGTAA TCATGCCTGT GAATAGGCAC TACACTCCAG CCTGGGCAAT
149761 ATAATAGCAA GATCCCTTCT CAAAAAAAAA AAAAGAAAAG AAAGAAAAAT TCTGTATATT
149821 CAATTACATC ATCTTCTACA TTTCTATTGA TGTCTTTAAA ATGTGCCATC TAGAAGCGTA
149881 ATAAGAAAAA TATTTTTGTT CTTAATGTTT AAGATATTAC AGATTTTCCT CACAGAGTGT
149941 AGTTCAAGTT ATTGTGCCAT TTTAAACTTA TGCCACTTTA AACATTTAGT GCCATATTAA
150001 ACCTCAATAC ATTAAACTAA TTTCTTCAAT GTTTTCCAAG ATATTTTTTA GAATAAAGTT
150061 CTGTAACGTT GGTAAATGGT TGTGTTACTG AAAAAATAGT TTACTTTAAA AATAAACTTT
150121 TGAATTGAGA AAATTGAAAC ATGTTTCAGG CTAAAGCATA ACAAAAGTAT ATTTTATTCA
150181 CATTTATAAA TATACTTCTA ACTTTGATTC TTTTCATCAC CCTTAGGTTG CAGCATGCAG
150241 AGATACTGGA TATGACTGGT TTGAGCAACT GCTTCAAAAC GTGAGTGTTC TTTTGACTCC
150301 TGATAACCTA AAATTTAATA GGTTAGTTTT TTGTTGTTGG TGTTTTTTTT TTTTTGGACT
150361 GTATGATTTA AAAGAACCTT TTTAGTTCTT TTGGTAGGGA AAATTTATTT CAATATGTTA
150421 GGCTGGATGA TTTTGTTAAT TTCTATAATT AATTCAGTTG CCTGGTTGTG GTTTTTTTTT
150481 TTTTTTTTTT TTTTTTGAGG TGGAGTCTCG CTCTCTCACT CTGTCGCCCA GGCTGGAGTG
150541 CAGTGGCACA ATCTTGGTTC ACTTCAACCT CTGCCTCCTG GGTTCAAGCA ATTCTCCTGC
150601 CTCAGCCTCC AGAGTAGCTA GGATTACAGG TGTCCACCAC CACACTCGGC TAATTTTTGT
150661 ATTTTTGGTA GAGACGGGGT TTTACTATGT TGGCCAGGCT GGTCTCAAAC TCCTGACCTC
150721 AGGTGACCTG CGTGCCTCGG CCTCCCAAAG TGCTGGGATT ATAGGCATGA GCCACTGCGC
150781 CTGGCCTTCA GTTGTCTATT GTACAAGTAA GTTTTCTGAA TCATTAACTA AAATTCTATC
150841 TTACTTTCTT TCCAGATAAT TTTTTTTCTT TAATCTCTGT GATTAATAGA TACAAGATTT
150901 ATAAATGGAT CAATATATTG CATTAAAAAT ATAATTACAT GATTTAGTAT GTTATGCATA
150961 GAATTTCCTT TAGTAGTACA GAGTCAAACC ACAACTAGTG GGTTTTTTTT AAGTTTCATA
151021 AATAGAAATG TTTATCTCCC TATGAATTGT TAAATTTTTT ATTTTAGAAA ATTTCACACA
151081 GGCAGAAATA TCCATCACCC AGCTTCAAAA ATTATCAGCA TTTTCCCAGT CTTGTTATAG
151141 CTATCCTTCC CCTATCTGGT TTTCTCCTTT TCTTTCTTTC TTCTTTTGTT TTCCATAATA
151201 CTTTTTTTTT TTTTTTTTTT TTGAGATAGA GTCTCACTCT GTTGCCCAAA CTGGAGTGCA
151261 GTGGCGCCAT CTTGGCCGGC TCACTGCAAC CTCCGCCTCC TGGGTTCAAG GGTTTCTCCT
151321 ACCTCAGCCT CCCAAGTAGC TGGGGTTACA GGCACTTGCC ACCACACCCA GCTAATTTTT
151381 GTATTTTTAG TAGAGATGAA GTTTCGCCAT GTTGGCCAGG CTGGTCTCAA ACTCCTGACC
151441 TCAGGTGATC TGCCCACCTC GGCCTCCCAA AGTGCTGAGA TACAGGTGTG GGCCACCATG
151501 CCCAGCCTGT AATACTTTTA AAACAAAGGC CAAACTTTAT ATTATCTCAT TCATAAATAC
151561 TTTAGCATCT ATCTATCTGT AGCAGATGAC TTTTTTAAAA AATTATCATT TATACCAAAA
151621 TAATAATGCA TTATTCCATA ACTAATACCT ATTCAGTGTT CATATTTTCC TGTCTCAAAA
151681 ATGTATTTTT ATAGTTGGTT TGCAGTTGCT TTGGTTGATA TACTCTTAAG TCTCTTATGT
151741 TAGTTTGCCC CTTACCTCCC TTTTCTCATG CGACTTGTAT GTTTTTCTGT AGAATCTCCC
151801 ACATTCTGGA TTTAATAGTC CACTTTTTTT CTGGTGTCAT TTAAGTTGTT CCTCTATCCA
151861 CCAGTTTTCA AGTAAACTCT TAGTGAAATC TAGAGGCTTA ATATGATTAA AGTTCAATTT
151921 TTAATCTAGG AGACAAATAC CTCATAGGTG GTGTTGAATA TTATTGCATC ACAGCAGGAA

Figure 7P2

151981 GCACATATCT AGTTGTCTCA TTTTCAGTGA TTGATCTTTG ATGAATTTAA GTGATGATAT
152041 ACAGTCATGT AACGTCCAAC ACAATGAACA TACAGGATTT CACCCTAAAA TGCCTTTTTG
152101 CAGTTGATCC TCTCTTCCTG GCCCTAGAAA ACTATTGATC TACTTTTTCT CACTGTAGTT
152161 GTACCTTTTC ATGTACATTG TTCCTATCAA TGGAGTCATA CAGTATGTAA TCTTGTGTTT
152221 GACTTTTTAA ACTTAGAATG TTGATTCATT CTTGTTGCTA ATATATTAAT ATATCTTTTT
152281 ATTACTGAGT AGTTTCAGTA GTGTGGATAT ATCATAATTT CTTTATCATT CACCATTTTG
152341 TGGACTTTGG GGTTCTTTCC AGTTTGGGGT GTTATGAATA ATGCTTCTGT GAATATTGGT
152401 GTGTAAGGTT TTGTGTAGAT GTATGTTTTC ATTTATCTTG GGTAAACTCC CAGGAATGTG
152461 ATTACAGGGT CATATGGTGA GTGAGAAACT GCCAAAATGT TTTTCCAAAA TTGCTAAACC
152521 ATTTTTCATT TCCACCATCA GTGTATGAAA GTTCCGGTTG CTCCACATCC TCACCAGTTC
152581 TCATTATTGT CACTTTTTTT AAAACTTTAG CCATTTTGGT GTGGTGGTAA AAGTAGTACA
152641 TTACTTTCTT AAGATGTCTT TTTTAAAAAA CCTTCATGGT GTTTTCAATG TGTAATCTTA
152701 GACTGTCTTC TTAAATCATC TTTCATTTCA TATTTTTACA TGATATATTT GGCATCATTT
152761 CTTTCCTAAA TCAAATAGTT AGCTCTATAT CATAGAACCT TATGACCACC TTAGTTAAGT
152821 TTATGTCAGC CATCCCAAAA GGTACATCAT GATTTCTAAA AGGCTCTAAA TCATATATTT
152881 CATTTGATAG TTATTATAAA TGATCAAGTA AGAATTCAAT GTAATTATCA GAAATGTCAC
152941 TATTTAGGAT TACTAAAAAG AATCTACAAT AATGTCATCT TGTATTAGCA AATTAGAAGC
153001 AGAAGGGACA TGACCAGATT TATACTCTCT TAACAATGAT AGTTTTACTT GTACATTCTT
153061 TGTATCTTTA TTCTCTAGTC CCATTTATTT AGTTAGTAAG TTAGTTTATC CATCCTATTC
153121 ATGCTCTCTA TTCTATGCTT TCCTACTTTA GTTTCTGCCA GCAACTTAGT TTACCAATGA
153181 TATTGTGACT TTGTGATATA TTTCCTTATA CTAGCAGAGT TTGGTTTAGT GAAAGAAAGC
153241 AAACTCATAT ATATATATAT GACAGAGACA TAACTACTCT GAGCAATTAT AACATATATG
153301 CATAAATGTT AAGAAAAGCT AGGAAGGATA TAAAGAATGG ACTGCTGGAG TTATTACAAA
153361 TTCTTGAGTC CAGAATAATT AACATGCTTA CTGTTTTTAC ATGAGCACAT ATGCATGCAT
153421 TGCATTCAGT CCAATTTCAG ATATTTCTAA TTTTTATTTT TGGATTGGGT TTTTGGGGTT
153481 TGTTGTTGTT GTTTGTTTTT TGTAGATCAT TGACTCTCCC CATTTATTGA ATTTTTTTTT
153541 AGGGAAACTT GAAGTACTAC TAAAATAGCT TCAAATTCCC ACATGTACTA AACTCTGTTC
153601 ATTGTCTAAA TAATTATGTT AGTATATCTT TTTTTTTTTG GAGACAGGGT CTCGCTGTGT
153661 CATGCAGGCT GGAGTGCAGT GGCACCATCA TGGCCCACTG TGGCCTCAAC CTCCCTGGCT
153721 CAAGCAGTCC TCTTTCCTCA GCCTCCCAAG TAGCTGGAAC CACAGGCATG CACCACCATG
153781 TTTAGCCTTT TTTTTTTTTT TTTTTTTTTT TGAGACAGGA TGTCACTATA TTACTCAAGC
153841 TTTTAGTATA TCTTTTGTTT TTGTTTTTGA GGCGGAGTTT CACTCTTGTC GCCCAGGGTG
153901 GAGTGCAGTG GCACGATCTC CGCTCACTGC AACCTCCGCC TCCTGGGTTC AAGTGATTCT
153961 CTTGCCTCAG CCTCCCGAGT AGCTGGAATT ACAGGCACCC ACCACCACGC CTGGCTAATT
154021 TTTTTATATC TTTAGTAGAG ACGGGGTTTC ACCATGTTGG CCAGGCTGGT CTTGAACTCC
154081 AGACCTCAGG TGATCTGCCC ACCTTGGCCT CCCAAAGTGC TGGGATTATA GGCGCAAGCC
154141 ACCGTGCCTG GCCAGTATGT CATTTTTAAA TGTATGGTGC TATCATTCCT TTATAACCTT
154201 TAACAATTCA TAGTTTTTTG GCATTTTTCA GTAGGATGTG GAAGATTAAC TTCTGTCCTG
154261 AAGGTCCTCA CATTTTTTTT ATTTCTAAAA TGTACTCCAG TTAGTTTAAA CCACTACCAT
154321 AAATTGAGTA GCCCTTTATG ACAGTCTTCT TCAAAAAACA CATTGATAGC CATGTGATGG
154381 GTACACAAAA ATTAAATAGA TTTTACAGTG CCATTCATTT TAATTACTTA AGATCTAAGA
154441 CTGACCATTT TCTAGTTTGT AAGGAAAATA CAGGCAATGA AAAACAGTTA AGAGTAACCT
154501 GTTTCATCTC TTCCTGTCCT TTGTAATCCA GAGCAAGATC TTTCCGAGTT TACAATAAAA
154561 TATTTTATCT CTATCAACCA GTGAATGGAT AAATAAACTA TGACAATCCC ATGCAATTTA
154621 ATAGTACTCC ACATCAAAAA GGAACAGGGT ATTAATACAT ACAGCAACAT AGATAAATAA
154681 TGAAAACATT GTGCAGAGTA AAAGAAGCCT TACGTAGAAG AGTACATATT ATAATTCCAT
154741 TTATACAAAA TTCTAGGAGA GGTAAAACTA ATCTATACTG GAAAAAATCA GAAGAGTGGC
154801 TGCAGGGAGC TGGGGATTGA CTGGGAAAGG ACATGAGGGA ACTTTCAGGG ATGATAGTTA
154861 TGGTCCCTAT CAGTGGTTCT AAAGGTTACC AGCATTACCT GGAGTTTTAT TAGAAATGCA
154921 AATTCTTAGG CCCTACTCCA GACTTAATTC ATCAGTAACT CTGAGGGTAG AGCCCATCAT
154981 TCTGTATTTT AACAGTCTCT CTCCAGATGA TTCAGATATA AGTTGACGAT TGAGAACAAC
155041 TGTTCTGTAT ATTGGTGTAG GGACTTGAGT TACAGTGGTG AATGCATTTG ACAAAACTGA
155101 GCAAATGTAC ACTAAAAATT TGTGCATTTT ATTGCATGTA CATTTTATCT CAAGGAAAAA
155161 ACGGGGAGTA TACTGAAGTC TCCAGTTTAC CTTGAAATGC ATTGAAAGTA AAATGGATAT
155221 AGGTGTGTGT GTATGCATAT GCATACATGT ATACGTGTGT GTGTGTGTGT GTGTGTGTGT
155281 GTGTGTGTGT GTGTGTGTGT GTGTGTAGTG TGTGTGTTCA TCCCAGCAGA AAAAATCTTA
155341 AAGGTAGGAT CCAGGAGCCA GGCTCAGTAG CTTGCACCCA GAATCCCAGC CTCTTAGAAG
155401 GTTGAGGCAG GAGGATCATT TGAAGCCTGG AGTTTTAGAC CAACCTGGAC AATGTACTGA
155461 GACCCCATCT CTGAAAAACA TAAATAAATA AAATTAACTG GGCATTGTGG CCTGTGCCTG
155521 TAAATTCAGC TACGTGGGAG GCAGAGGCAG GAGGATCACT TGAGCCCAGG AGTTTAGGC
155581 TGCAGTGAAC TATGATTGTG CCACTGCCCT TTCTTCTGGG GAACAGAGTG AGACTCTATC

Figure 7Q2

155641 TCACTCACCA AAAATGTTTT TAATGGTAGA ATCTAGATGA TGGTCGTTAG AGAGTGTTCA
155701 TGATAAAACT TTTTTCAACT CTTTTGTTTG GCTGAAATTT TTCGTAATAT TAAGATGGTG
155761 TAAAAAATAT ACCTGTATCA CTGAGAATGT TGGTACCTTT AAAAGATATT TTTTAAGTGA
155821 GCAAGCTAAA TTATACTTTA AAAAAATTTT ATGCACCTTG ATTACTTCTT ATTTATATTA
155881 TAAGTGCATG GCTAATATAT GTGTGTAGGT TAACATTAAA GTAGAAGAAA TCATTTCAGA
155941 GTGGGCAAGA AAAACTTTTG ATAAAATTCA ATATCCTTGA ATGATTACTT ATAATAAACA
156001 AGGATACAAT GTAAATTCCT TAATCTGACA GATAAAACTA CAAAACCTAA AATGAAAATA
156061 ATGCAAAATG GGAAACTGTG AGCTTTCTTC AAATCATGAA TAAAAAAATT TAAATATATC
156121 AAAGTGATTG TAAAATGTAT ATGGAAAAGC AGAGAAAAGG TAAAAATAAC TAATTTCTGA
156181 AAAAAGCTGA AGCACTGACT TGCCTTACAA AATATTGGGA CTTATTTTCA AAGATACATT
156241 ACATAATTAA GAGCAGTAAT AAGTAGATTA GTACGAAATA GAACAATGGA ACAGGATAGA
156301 GATCCCAGAA AACAGGCTTA CACATATAGA ATATGCTTGC TATAAAACAG AAGTGGCACT
156361 GCAGATGATG GAGAAAAGAT AGACTGTTTA GTAAATGGGG TTGGGATATT TGACTGTCCA
156421 TAAGAATTAA AAAAAAAAGA TTCCTACTTC AGCTCAAAAA TCAACTCCAT ATAGATTAAA
156481 GGAGAACTTT AAAACTTTTA GAAAATATAG GAGAAAAAAA TTTTTAATTA CATATGTGTG
156541 TGTATATGTA CATACACACA CACACACACA CACATATATA TATATATATA TATATATATT
156601 TTTTTTTTTT TTTTTTTTAA TGGCTTGGTC TTGCTGTGTT GCCCAGGCTG GACTCAAACT
156661 CCTAGGCTCA AGTGATCCTC CTACCTCAGC CTCTTGAGTA GCTGGGACTA CAAGCATGCA
156721 CCACCATGCC CAGCCTGAAT ATATTTTTGA TCTCTGAGTA GGAAAGGATG CCTTAAACAA
156781 GTCACAAAAA CCATTAACCT TAAAAGATTG AAGAAAGTGA AAATACAAGT CACAAAATGG
156841 GAAAAGATAT TTGGCACATA TATAACCAAC AATTAATACC GAGAATAAAT ACATAAGAAC
156901 TTCTCTCCTA CAAAACCAGT GTAAGTCAAG AGTCCCAGTA GAAAAATAGG TAAAGTTAAT
156961 TAATAGGCAT TTCATGGAGA AAATAGCATA TAGGACCTAT ACTGTGTTCA ACCCCATTAG
157021 TAAAGTAAGA AATACAAATC AAGACCACAT TCTACACCAT TTTATTGACA AAAATGGAGA
157081 AGTCAGACAA TCACAAGTAA TGGAAAAGAG GGATCAGGTA GTGTCTTTTA ATACAGATAA
157141 TAATTGAGAA AGTATTACAG CCACTTGAAA AATGATTTCA TAAAATTATC TCATAAAAGC
157201 ATTATCTTGT GAAGTTGAAC AATGCATGTA TCCAATGACC CAGCAATTCG ACTTCAAATA
157261 TATATACACA CAAAAGAATC TTGCATATTT GCATCAGGAG GCATATACAA GAGTGCTTAT
157321 TGTACTAAAA TTGGGATTAA CCTATCTACA AAAGAGTGGA TAAATGAATT AAGGTATAGG
157381 CACACAGTGG GGTGTTGTAC AGCAGAGAAA ATCAGTAAAA TACAGCTGTA TGCAGTAACC
157441 TAGATCATAG TGGCATAATG ATGAGTGAAA AAAGCAAATC TCAGAAGACT ACATCAAGTA
157501 TACTACCTTT TTAGAAAGTG GAAAATCAAA GAAAAATATA AATAGCATAC AGCTTATACT
157561 TTTTTTAAAA ACAAGGAGAT GGTAAATTTC TGATAGTGGT TATCTCAAGT GTGAAACAGG
157621 AAAATGGGAT AAGGGAAGGA GCACATTGGG AGCTACAAGA TATTAAAATT ATTCGTGTTC
157681 TTGATTTGGA TTCAAAGTAT GCCATTATTT ATTAGTAAAT TAGAAGGGCA TATACGAGTG
157741 GCAACAGTGT GTCATGAGTC AAAATTTATG ATTAATTCTT TTGTGTGTAC CTGAAGCCTT
157801 GGAAATGAAA AAGGAAAAAC CAAGGATGAG AGAGGATAGT TTTCTACTCC TGCCGTTAAA
157861 TAAAAGACCA AGCTAGGCCG GGCATGGTAG CTCATGCCTA TAATCCCAGC ACTATGGGAG
157921 GCTAAGGCAG GCGGATCACT TGAGCCCAAG AGTTTGAGAC CAGCTTGGGC AACATAGAGA
157981 ACCCCATCTC TACAAACTGT ACAAAAATAA GCTGGGCACG ATGGCTCACG CCTGTGGTCC
158041 CAGCTGTGTG GGAGGCTGAG CCTGGGAGGG CAAGGCTGCA GTGAGCTTTG ATTGTGCCAC
158101 TGCACTCCAG CCTGAGTGAC AATGAGACCC TGTCTCAGAA AAGACCAAAC TAGAATGTGA
158161 TATTAATAGC TGCTTTAAGG AAATTAGAGA ATGGGGCAGG AAGAATTTGC GGTTCATAGT
158221 TGAAACCTAG TACATTGAAG CTGTCTGCTT TATTTATTTC TTCAAATTGG AGGAAAAGGG
158281 GCAGTGTGTG TGTTATGTTA CTCTGGTTGC TGTCAGTTGT TTTAATCATT TATGCATCTT
158341 GTGGGGAAAG TTTAAGCTTG TGCTGCCCAA GCTTGTGCCC AACTGTAAGC CACATGCATT
158401 TTTTTAAATG TTAACTTAAT TTCAATTTTT ATTTTATTTA ATTTTAATTT CTCAGTCACA
158461 GTAGGTACAT TGCAAGTGCT TAATAACTGC ATGTGACTCT TGGAAACCAT ATTGGACAGC
158521 AAAGATATAG AATATTTCCA TTATTGCAGA GAAAGTTATA TTTAACAGCA GTGGAACTCT
158581 TCACAGAAAT CAAATACACA TTTAGATTCC TTCAATATCC CCAGAATTAG ATTAGCTAGC
158641 TTTTCTTAGG AAAACAGATA TACCTTATGA CTTTTCTGTT GACCTTTGAT TATGAAAGAT
158701 TAGATTGGTT TTACTTTTTA GCTATATTTA GAATGAGCTC TATCCTCATC TCATTATTCA
158761 TAACACTTTT CTAGCATTGT TTGTGATTTT GCAAAGGATA ATGCAGAAAA GAAATCTACC
158821 GTTATGTTTT ATAATTGCCT TTTAAGGTGC AATTCAGATG CAGTTATTAA TTATTTAAAA
158881 TAATTCAACT AGTATTATGT GATACTGTGT TTTTGATTGG AATAGGGAGA AAGGGAAGGT
158941 CATCTTTTCT ACATCTTTCA CGTATTACCT TAGGTCTTAC ACAGCAATTT AAGTACTTTG
159001 TAGTAAAATT GTTTGAAAGT ATTGGTAAAT TACTGGTTTA TAAGATATTT TTAAACATAT
159061 ATATTTTTGT TTTATTAATT TGCACTTTGA GTATTAAATT GTTAATGACA AATTGAAAAG
159121 TATGTTACTT ATGGACACTT TTAATGTGTT TATATTATTA TTGCCTAATG AATAATTATA
159181 CCGGGATTTT TTTTTCTTTT TTGTATATAT ATATGTATAT ATATATATAT ATATATGTAT
159241 ATATAGTTGT TGAAGTCCGA AGAGGATTCC TCATATAAAC CTGTGAAGAA AGCTTGTACT

Figure 7R2

159301 CAACTTGTTG ATAACCTAGT TGAGCACATT CTTAAATATG AGGAATCTCT AGCTGGTAAG
159361 ACATTTTATA TATATATTGA TCTTTAGTTG ATTTTATAAG ATATTTTTAA ATATTTTGAG
159421 TAAATTTCTC ATTTTTGCCT CTGGCTCTGC TTGTCTAATG ATTACTTCAC TTTTAAATGA
159481 AATACATTTT TGTTATATAG GTATCTGTTT GATGTTGCAT CCTAGATTAT ATTAAGATTG
159541 ACTAAGATTA TCTAGAGCAT TGTAATAAAA GCATGGGCCT CACCTCTTTC ACATATCTTT
159601 TAATAGCATA TTATAATTTT AGATGTCATA TTGAATAGGA GTAAAAATCC AGGGGCTAAT
159661 ATGTATCTAG CTAATGATAC TCATCACAAA ACTGATATCT CCTAAGTCAT ATAAAATTAT
159721 GTCTCAAAAT GAAATTGTTT TAGCTATTAT AAAAATGTTT TTTAAAGATT TATATTACAT
159781 TCCTAATATT TATTATTTAT AATTGTTACA TAAAGTTTGC TTAATCTTGA GCTAGAAATT
159841 TATTAAAATG TTTAAAATCA CAAATTATTT AAGTACTTAA TATTTTATAT TATCTCACAT
159901 TATTTACCAA TCACAAATCT GAAGTTTTTT AATCAATTAT AAATAAATGA TTACTTAAGA
159961 AATATAAAAA TTGGGCCAGG CGTGGTGGCT CACACCTGTA ATCCCAGCAC TTTGGGAGGC
160021 CAAGGCGGGC AGATCATGAG GTCAGGAGAT TGAGACCATC CTGGCTAACA CAATGAAACC
160081 CCGTCTCTAC TGAAAATACA AAAAAATTAA CCAGGCATGG TTTTGGGCGC CTGTAGTCCC
160141 AGCTACTTGG GAGGCTGAGG CAGGAGAATG GCATGAGCCC GGGAGGCAGA GCTTGCAGTG
160201 AGCCAAGATC ACGCCACTGC ACTCCAGCCT GGGTGACAGA GGGAGACTCC GTCTCAAAAA
160261 ATATATATAT ATATATGTAT ATATATATAT ATATGTATAT ATAGATACAT AGATAGATAT
160321 AGATACCCAT TGCTTGAAGC GCACAAAGAC TAGCATTACT TCCCATCTAA TGCACATTAA
160381 TGAGGAACAA CGTCAGCCTC AGTTGTTCTC CAAAATTGGG AGCCAATAGC CTCTAACAGC
160441 CGTCCATTTA TGGCACCTAC GGAAGTTGTT GATATGCTTT ATATTTTTTA TGCAGTCTTT
160501 TTTTTTTTTT TCCATGTGTA CCTCTTTTTT TTCTTTTTAT CTCCTTGTTC CGTTTTTTTA
160561 TTTTTCCCCA TCCTGGAATT TAGGGGTGAT ACTGATGTCC CTTAATGTTA AAAAGTTGCT
160621 AATTTCCTCT AAAAATTTGT TTCCTAAGAA CCAGTGTATT TCCTGATTAG CAACATTTTC
160681 TTCCCACCTG AACAGCATTT TGTTTAGAGC TGTCTTATAG CATTGTTCCA ATTTCTGTTT
160741 GTTGCTCCCA TTTTTTAACA TTCTTCTACT GCAACAACAT GTCTTTTTGT ACCAGTACCC
160801 TTAAACACAG TTTCACCTCA GCTAAATTGC TTTTTTTCCC ATATTCACTT CCTTTTTTTT
160861 TTTTTTTTTT TTTTAAAGAC AGGGTCTCAC TCTGTCACCC AGGCTGGGGT GTAGTGGCGC
160921 AATCATAGCT CAATGCAGCC TAGAACTCCT GGGCTGAAGC AATCCTCCCA CCTCGGCCTC
160981 CCGAGTAACT GAGACTACAA GTGCACATCA CCACACCGGG CTAATTTTTT ATTTTTCTGT
161041 AGAGATGCAG TTTTTGCGTG TTGTCCAGGC TGATCTCAGA TTCCTAGACT CAAACCTTCT
161101 TCCTGTGATG GCCTCCCAAA GTGCTGGGAT TACAGGTGTG AGCCATCACA CACAGCCCAT
161161 TGATTTTAGA TAAAACCAAT ACGACATTTA TTCCCAAAAG CCCATTCCTA AGCTTCCCAA
161221 TTTCCATTAG TATAAAACTT GCCTTCTATA GAGAGCATGG CCTCTTGTTC TTTATCTTGA
161281 GTATTATTTC TATATCAAAG AAAAAATGAG ATGGAGAAAG TCTAGTATCA TAAGAACTAC
161341 TAATTCATTA TATTGAGGCC TATACTGGAC CTATTTAGGG GATAATATTA AGTAATTTAA
161401 ATAATATTCT GTATAGTTTC CACTACCTTG TCATATTTTA GTGTCTTATT TCTCTGTTTG
161461 TTTTTCCAGA CTCTGACAAT AAAGGTGTGA ATTCTGGAAG ATTGGTAGCT TGCATAACCA
161521 CTTTGTTCTT ATTCAGCAAA ATAAGACCCC AGCTCATGGT TAAACATGCA ATGACTATGC
161581 AACCATACCT TACCACTAAA TGTAGTGTAA GTATAGAGCT GTCTTATTCT TGTATCTTAC
161641 ATAAAACATT AAGTGCTTTA AATTTAGAGT TCACATGCGT CAACCACATT CTCACTGACA
161701 GATCAACTGT GTCATTTACT TAGATATATG TACTATTTGT AGCAAGTGAT CTATAAACAT
161761 CAAGTCTGAC ATAAATAAAG TTCAGGTTCC ATTTTGCTGT AAACTCCTCA AGCCAAACCC
161821 TCAGTAGATG CTTACTAAAT GTTATAGCTA TTGTTAAGAT CTCAAAATGA ATGAAGCAGA
161881 GTTCCTCTCT TTGAGAAATT TACTATCTTT TGGGTCCTGA ATTTACTTTT CATTTGTCTG
161941 TCATTTATAA TATAATAAAT ATAAAAATTG ATACCCATTG CTTGAAGCAC ACAAAGACTA
162001 GCATTACTTC CCATCTAATG CACATTAATA AGGAACAGTA GTCAACCTCG GTCATTCTCC
162061 AAAATTGAGA GCCAGTAGCC TCTAACAGAG GTCCATTTAT GGCACCTAAG GAAATTGTTG
162121 ATATGCTTTA TATTTTTCAT ACAGTCTTTT TTAATTTTTT ATATTTTATA AATATATTTT
162181 ATTTTTATAA TAGAACAATA TATTAAATAT GGAAAATCTA TAATATCATA CCAGAGATGT
162241 TAGGCTGTTA ATATTAACAT ACACTATGTT TTTCTAAAAT AAGGTGTGAG TAGTAAGACA
162301 TTGCTTAAGT AAAATTATCC ATCAAATAAA GATTTTAAAG TATATATGAC AGCATAGTGA
162361 GTTACGTGGT TTACATGTAT AATGTCATTT GCTTTATGAA GTAGGTACTA TTATCTCTGT
162421 TTTACAGATA AGGAAACTGA AGCTTAAAGA GTATAAGTAA CTGCTAAAAA TTTGAAATTT
162481 TAAAATACTC TAAAAACTTA ACAAATATAA AGGTTTCTCA CATACTGTGT TCCTAATGTT
162541 CCTAAGGAGC TAATTTTAAC TGTTTCTCTG CTGCATTTGT TTTGCTGCTG TGGTCAGTTT
162601 TTTTGATTAT CCAAATTACA AGCTCTAGGT GAAAACCTCA GGACTTCCTG AGAAAACTTT
162661 AAGAACTGAG GAGAGTAGTA AAGGATAATA AATACCTAAA AACAACATGC ATTTACTTCT
162721 GAGACACTAA TTCTATCTTT AGGGTTCGTA TTAGATCCAG AAATAAATTG TTTAATAATT
162781 GTGGCTAATA ATAGCTAATA ATTTTTTAGC ACAGTACCAA GCACTGTGAA AATTTTACAT
162841 GTATTATCTC ATTAACTTTG TGAAGTAAGT ACTATTATGA TCTCAGTTTT ACAGATAAGG
162901 AAATGAAAGC TTAAAGAATA TAAATAACTG GCCCAATGTC ACAGAGCTAA GCAGTCCCAA

Figure 7S2

```
162961 AGTTAGAATT CAGCCCCATG TCTGCCAGTA GAGTCTGGAC TATAATGAAA CCTGTTATAT
163021 ATTATTTATA TCATAAATAG TCCTTGCATG ATTTTGAACC AGTGATTTTT TTAAAACAAA
163081 ATCACTTTTA AAATGTCTTG TGCATTTTTT ATGTATGTAT GTACACAAAT ATAAAGTTGT
163141 ATATAAATAA GAGTATCTCA TACATGGTAA ACTTTTTCTT AATGTTTTGT GGTTTTGATT
163201 TTTGTTTTTA TATCCTATCT CCATCTTTAT TCATCTTCCC TTCAGAATAA ACATCTTAGA
163261 GTATCCTTAA CATACTTTTA TAGTTGTGGA CACAGAGGTA TATATAAATG GTTGACCGGG
163321 TTTTGTAAAA ATTGAATCAT ATTATATAGA TATTTGTTAG GCATATTTGG TAATCTCACA
163381 TTACCTGGTA TATATCTAAT TCCTTGTTTT AGATGGCTAT ATATTATCCA TTTTATGGAT
163441 GTCCTATGAT TTATTTAATC ATTTCCCTAT TTGGCAGGTG TTTACATATT TCCTTTGGAT
163501 CACCACTACA AACAATTTTT AAATAAACAT TCCAATTTAA ATACCTAAGT ACTGGTGACT
163561 TTATTTTGTT GGAACAGTTT CTGAGAAGTG GACTTGCTAG GTTGAAACAA TGGTTATTTT
163621 GGTGTTCATT TTTAATTGAT CTTGCCATTT TGCAGTGGAT GTGTTTTATA CAACCTTTTG
163681 GAAAGCTGTA TGTGACAATC ATTGTCATTA TTTAGTATTC TTTGCCAGTC TAACAGGTGG
163741 TAAGGAATAA TTCATTATTG CTTCAGTTTC CTTCCCTGAC TGCAAAGAAG GTTGAGCATC
163801 TTTTCTTGGT ACTGACCAGT GGGGCTTGCT TTTCTGTTAA TTCACTATTT ATATCATTTT
163861 CATATCATTC GTTCATTTTA CCTTTGAATA ATAGGCTTTT TTTTTTAGGA GAGCTCTTTA
163921 TTTTAGATAT TAAACCATCT TATAGTATAT TCATTACAAA TATTTTTTCC TATTCTGTTC
163981 TGTTGCTCTT TTACTTAATG GTTTCCATCT TTCTTTAAAT TTTTCTTCTA GAATTTAAGA
164041 TATTTCTTTT ACTTGATTTT CCAGGCCAGG ATGTTAAGGG AAGGTTCAGA AAATGCTACT
164101 TTTTTGTTGT TATGTGGTGG TTTTTTTTTT TTTTTTTTTT TTTTTTTTTG AGACTGAGGC
164161 TCACACTGTC ACCCAGGCTG GAGTGCAATG GTGCAATCTT GGCTCACTGC AACCTCTGCC
164221 TCCTGGCTTC AAGCGATTCT CCTTCCTCAG CCTCCCAAGT AGCTGAGATT ACAGGTGCAC
164281 ACCACCACAC CTGGCTAATT TTTTGTATTT TTAGTAGAGA CGGGGTTTCA CTATGTTGGC
164341 CAGACTGGTC TTGAACTCCA GACCTTATTG ATCTGCCCCG CCTTGGCCTC CCAAAGTACT
164401 GGGATTACAG GCATGAGCCA CTGTGCCCGG CCTATTTCTT TTTTTTTTAA GACACAGTCT
164461 TGCTCTGTTG CCCAGGCTGG AGTACAGTCC TGCACTTCTG GCTGACTGCA ACCTTCGCCT
164521 CCCAGGTTCA AGCGATTCTC ATGCCTTAGC CACCCAAGTA GCTGGGATTT TACAGGTGTG
164581 CACCACCACA CCCGGCTAAT TTTTGTATTT TTAGTAGAGA CAGGGAATTG CCATGTTGGC
164641 CAGGCTGGTC TTGAACTCCG GGCCTCAAGT GATCTGCCTA CTGTGGCCTC CCAAAGAGCC
164701 GGGATTATAG GCGTGAGCCA CTGTGCCCAG CCACTACATT TTTTTTTTTT TTAAGTAAAA
164761 TGCTAGCACT GGTTCTCAAA TGAATATCTT ACCCAACAAA AATTCTTCTA TCCCTAGACC
164821 CACTTTAACT CATTATGGGA AACAACAGGA TTTCTATGCT ACTTAAAAAG AATTTATCTT
164881 TTCTTTTTAA TCCTGTGGGG ATCCTAAAAG GAAGGATGAA TATGATGTGG GAATTTCTTT
164941 TTTTTGTAAT TAATACTCCT ACAAGCCAAG TGGTGGGAAT GTTTTTAACT AGTGTGTTAA
165001 TGCACTCAAA AAGTCCAAAA TGGGCTGGGC ACGGTGGCTC ACGCCTGTAA TCCCAGCACT
165061 TTGGGAGGCC GAGGCAGGCG GATCACGAGG TCAGGAGTTC AAGACCAGCC TGGCCAGCAT
165121 GGTGAAACCC TGTCTCTACT AAAAATACAA AAATTAGCCA AGCATGGTGG TGCGCACCTA
165181 TAGTCCCAGC TCCTCGACAG GCTAAAGCAG GAGAATCGCT TGAACCTTGG AGGCGGAGGT
165241 TGCAGTGAGC CGAGACTGTG CTACTGCACT TCCGCCTGGG TGACAGAACG AGGCTCTGTG
165301 TCAAAAAAAA AAGTCCAAAA TCTATGCCGG TAATCCATTA CTAACAATGA GGATTAGTAG
165361 CTTAAAAACT AGATTAAGGC TGGACATGAT GGCTCACACC TGTAATCCCA GCACTTTGGG
165421 AGGCCGAGGC AGGCAGATCA CAAAGTGTGG AGTTTAAGAC CAGCCTGGCC AATATGGTGA
165481 AACCCCATCT CTACTAAAAA TACAAAAATT AGCCAGGCGT GGTGGCAGGC TAGTTGTCGA
165541 TCCATATTCC CGACATGCTG GTGCTTCTCC TTCCATGCCT CCAGCTACTC TGGAGGCTGA
165601 GGAGAATCAC TTGAACTCAG GAGGCGGAGG TTGCAGTGAG CCAAGATCGC GCCACTGCAT
165661 TCCAGCCTGG ATGACAGAGC GAGACTCCGT CTCAAAAAAA AAAAAGAAAG GAAAAAAAAA
165721 AACTAGATTA AAAACATGCA TTGAAAGCCT TACTACACAC ACGCGCGCAC ACACACACAC
165781 ACACACACAC ATATAACTTT GATTGCCTTT GGGGAAATGA ACTGGGTGGC TGGAGGATAG
165841 ATAGAAACAA GACTTTTTAT TGTAAATCCT TTTCTACCTT TTGGTTTTTT TTAAAAAGTC
165901 TCTACCTGTT TTTTTAAACA TGCTTATTAG TTTTTCTAAT CAAAGAAATA ACACATTTAA
165961 ATTTAAAATA AAGAAGTCCT AGGCTGAGCA TGGTGGCCCA CACCTGTAAT CCCAGTACTT
166021 TGGGTGGCCA AGGCAGGAGG ATCACTTGAG GCCAGGAATT CAAAACCAGC CTGCGCAACA
166081 TAGTGAGACC CTGTCTCTAC AAAAATGAAA ATTAAGGCCG GACGCAGTTT CTCACACCTG
166141 TAATCCCAGC ACTTTGGGAG GCCGAGGCAG GTGGATCACG AGGTCGTGAG TCCTAGACCA
166201 GCCTGGCCAA GATGGTGAAA CCCCGTCTCT ACTAAAAATA CAAAAATTAG CCAGGCATGG
166261 TGGTGGGCGC CTGTAATCCC AGCTACTCGG GTGGCTGAGT CAGGGGGTTG CTTGAACCCG
166321 GGAGGCAGAG GTTGCAGTGA GCCAAGATCA TGCCACTGCA CTCCAGCCTG GGCAACAGAG
166381 CAAGACTCTG TCTCAAAAAA AAAAAAAGAC AATTAAAAAA TTAACCGGGT GTGGTATTAT
166441 GCGCCTGTAG TCCTAGCTAC TCGAGAGACT GTCAGGAAAA TCGCTCAAGC TCAGGAGCAG
166501 GATTGCATTG AGCTGTGATT GTGCCACTGC ACTCCAACCT GGGCAATTGA GCAAGACTGT
166561 GTTTCTTAGA AGTAAAGAAG CCTTCTGCCT GGTTCTGGGA TTCTACATGT TTATCTGTCA
```

Figure 7T2

166621 TAGAAAATTT TAACACAGGG TTTCTCAACC TCAGCACTAT TGACAGGACT AGATGATTCT
166681 TTGTTGTCAA GGATTGTTCT GTGCATTGCA GGTTGTTAAG CAGCATCCCT GGCCTCTATC
166741 CACTAGATGC CAGTAGTGGC TCCCATTGTG ACAACCAAAA ATGTCTCCAG ATACTGCCAA
166801 ATACTCCTGT GTCAGGATAC GGGGGAAGAA GCTTATTCCT GATTGAGAAC TACTGGGTTA
166861 ACATACACAG TTTGGAAAAT ACTAATCGTA AAAACTGTAC CAGTCTTTGT ATAATGCTGT
166921 CAATATGTAA ATACCTTTGT TTAGAATTGA CTTGTGTTAC ATTTTAGGGA AAAAATATAA
166981 CATTGTGATT AAGTGACCCC AAAGTCACAT TTTGGTAAGT TAGTTGTCGG TACATATTCC
167041 TGACATGCTG GTGCTTCTCC TTCCATACCT TGAAAAAAAA ACTCTAACAG ACTTTTTTTT
167101 TTAACTGGAC CTTTACGTGC AAAATGCCCT ATTTCTGCCC CCAAATACGT AAAGCTGTAT
167161 ATAGTTTCTT TTCAGGTTTT GGATATTCAT AAAGCATTAA TTTTATTCTT ATAGACGCAA
167221 AATGATTTCA TGGTTATCTG CAATGTTGCA AAAATCCTAG AGCTAGTTGT ACCACTGATG
167281 GAGCATCCAA GTGAAACTTT TCTTGCCACT ATTGAGGAAG ATCTAATGAA GCTCATCATC
167341 AAATATGGCA TGACTGTAAG CACTCAGTTT ACCATTTCTT TATTCATTAG TGTAAAGTTC
167401 TAATGTATTT TATTAAAATT TTTAAAGCAA ATATTTGTAA AAAGCTAAGT TTTTAAAATA
167461 GTATATTTTT AACTTTTATC TAAACATTTT CTATATCTTT TAGGTAGTGC AACATTGTGT
167521 GAGCTGTCTT GGAGCTGTTG TAAATAAAGT GACACAAAAT TTTAAATTTG TGTGGGCTTG
167581 TTTCAATAGA TACTATGGTA AGTTCAATAC CAGGGTTTTA AAATTATTCT GCTAGGTCCT
167641 GCAGGGGGTC AGCTCATTTT AAACACATTT GATAAAAGGC TAGACTCGAG GAAATTATGA
167701 GGTGTGATTA TCCACCGTGG TCCTCTCAGA AACAATATTT TCTAGTGTCT TTTGTATTTC
167761 CTGAAGAACC CACTGTGATT ACTTCAGAAA TTTATCTCCT GATAAGTAAA GATTGGTAAA
167821 TTTTTTGCGC ACTGTGAAAA GTAAAATTTA AATTTTCTTA CATTAGTTTA GACTCTGAAG
167881 AGCACTCTCA TAATTCTAGA CATATTTAAT ATTTAGAACC ATTAGTAAAA ATTAATTGGC
167941 TGGGGACAGT GGCTCATGCC TGTAATCCCA GCACTTTGGG AGGCCACGGC GGGTGGATTA
168001 CCTGAGGTCG GGAGTTCGAG ATCAGCCTGG CCAACATGGT GAAACCCCGT CTCTCTACTA
168061 AAAATACAAA AATTTGCCAG GCGTGGTGGC ACACGACTGT AATCCCAGCT ACTTGGGAAG
168121 CTGAGGCAGG AGAATCACTT GAACACGGGA GGCGGAGGTT GCAGTGAGCC AAGATCATGT
168181 CACTGCACTC CAGCCTGGGT GACAGTGAGA CTCCATCTCA AAAAAAAAAT TGTAATTCAT
168241 TAGTAGTAAT TACTTGAACT TAGTAATTCA AAGATAAATA TTATAAGTAA ATATTACTTA
168301 TCTTTATTAG GTGCCATTTC AAAATTAAAA AGTCAACACC AAGAGGACCC AAATAACACT
168361 TCACTTCTAA CAAACAAACC AGCACTTCTT AGATCCCTTT TCACCGTTGG AGCACTATGT
168421 CGGCATTTTG ATTTTGATCT GGAAGATTTT AAAGGCAACA GCAAGGTAAA GGTAGTAATA
168481 CTTAAAATGC TATAAAACAT AGAGCTATAT GGCACTGTGA TCTGAGAATG ACAGTAGTGA
168541 CCCAGGATGA AGGCAACATT AGAGTAGTCT GGTTTAATGA AAATTCTGAA AACAGTGCTG
168601 CTCAAAACGT GGTCCTCAGA CTGGCTGCTA ATCCATCAAC TTTTTGTTAC TGGTGTGTAA
168661 CCAGATAATG AAATTTCCCT GACAAGTTAT ATCAGTTTTG TAACAGTAGC ACACTGTTGA
168721 CATCAACAGC TGACTTTTTA AAAAAAATTT TTTTCAATGA AGGAAACAAT GCACTGATTT
168781 ACATTCCGAA ACAAGCTTCT TTGTCACAGA CTGATACTTT GAATGCCACT GTTCTAAAAT
168841 AAATGGAATT GGTTACTTAT TTTTTTAATA AAGTTCACAC AAATTCTCAT TGTTTTAAGG
168901 TATTTTTTTC CTTTATAGTT GAAAATTAAT CTAAGTTACT GTTCATGAAC ACTTTAATGT
168961 GTTTTCCTCC CCTTAGGTTA ACATAAAAGA TAAAGTACTT GAACTATTGA TGTATTTTAC
169021 AAAACACTCA GATGAAGAAG TACAAACAAA AGCTATCATT GGTCTAGGTA AGTCTAAATT
169081 TCTTTATAAT TTGTAGCTAT TTGAGAGGGA TAGAGCATAT TTTTAAATAT TGTGAATCTA
169141 AATTGTTGAT TTACTTTAAT ATGTTTCTAT TAGCAGTAGG ATTTGGTGTA TAGAATGTAG
169201 GTCTGAGGAT TAAAACAACT GGGTTGCATT CTTGTCATGG CCATTGACTT CCTGGGTAAC
169261 CTTGAGCAAG CCATTTGTCT GTTCATCAGT TTCTTCATTA GTAAAATAGA GATAACAATA
169321 CTTTCTTCTA CCCCTCCTCC ATAGGGTATC TTAAGAACAT TTATTAAAGC CCTTTGATAA
169381 AGAAAAATAA TATAGAAGAA TTCTGTGCTC TTTGCATTTT TTTAATTGTT CTTTTTCATT
169441 GCAAAGCTTT GTCACTACAG GAAGCTGCCA CATCTGGTTA AAACAATGAT CAGTCTACAC
169501 TGACTTATTT ATATAAAAGC AAATAGTAAG CAACCCAGAA GGAACAATTT GGATATATAC
169561 CTGTTTTATA ATGTTTTTCC AGGAAGGATT GATGTAATAA AAACATGTTT TGCAATTGTT
169621 AGGCAGGTCT ATGTGGCTTA TATCTAGGAA GGAATTAGAA TATGAGGAAA TAGGAGGTGA
169681 ATGGCATTAA AGTACCTGAA TTGAATGCAC TTCAAAAAAA TACAAGAACA GTCTGTCCAG
169741 GTTTTTGGTT TTTGTTGTTG TTTTTTTTGG TACAAATACA GTTGGCCTTC CATATCCATG
169801 GGTTTCACAT CTGTGGATTT AACCACCAAG GATCAAAAAT ACTGAGAAAA AAAAATTACA
169861 CCTGTACTAA ATATGTACAG ACTTTTTTTG TTATTATTCT CTAAACAATA CAACAGCAAT
169921 TTACATAGCA TTTACATTGT ATTAGATATA AATAATCTAG AGAAGATTTA AAGTATACGA
169981 GAGGATATGA GTAGATTATA TGCAAATACT ACCCCATTTT ATATCAGGGA CTTGAGAATC
170041 CACGGATTTT GGTATCCCTG GGAGGTTCTG GAGCCAATCC CCCATGGATA CCGAGCAATG
170101 ACTGTACACG TAAAGCTACC CAATGAGATT AAAAACTTAT TTGGAAATTT TATTTTGGTG
170161 TTATGATTAA GGTTTATACT TTAATCTGCA TGAGTAGTTA TTTATATTAG TCTTTTGAAC
170221 AAAAATGAGT AAGAAAAGAT TCTAACTTAC CCATACCTTA TTAAATCATG TTTATGATTT

Figure 7U2

170281 CTGTAAATAA ATTGAAACCT TATCATTTTA TTCCTCCTCC ATCCCTTTTT GAAAATTACA
170341 TATAGCACAT AGAGTAAAAA TTCAGACATC ATTTACTAAG GAGTTAAATT GATGCAATAT
170401 TAACTTCAAG CCAATGTGTA CCTTCAGATA TTCAGTCTGG ACATAATTTA TACGGAGTGG
170461 CAAAACTAAT AGTGTTACAA GTATTTCAGA GTACAAAAAG ATGAAGTTTT AACTTAAGCA
170521 GCGCTATTCA GAAAATATTG CCTCTAGACC AGTTAATAAA AGACATCTTG CCTGGGCCAT
170581 AGTTATCCTG AGTGACCTTG GGCTAGTTAT CTGATCACTC TATGCTTTGA GTTTAGTTTG
170641 TTGTTTGTTA CCAATAATAC TTGCTATCAT CAGAGATCTT CATTTTTTCC TCAAATAAAC
170701 ATTATATACA AATAAACATG GATGATATAT TGCTACTTAT TAACCCGTGG TTATAGGATT
170761 CAGCATTGTG GCCTTATTAT AATGCCATAT GAAAAAGAAA TGGAAGATAT TTTTAGCTCT
170821 GGTTTATTAT ATTGTTTCAT CAAATGAATA TATTTTAATT TTTTTTTTAA AATAATGTCA
170881 ATGTAGTACC TTCTGCTGGG GATCTGAAAA ATGTTTGCAG ACATTATTTC TTAAATCCTG
170941 AAAACATCCC TGTGAGGTAG GTGGGTGGTA AATATTATTA TCCCCATTTT ACAGATGGAG
171001 AATTGAGGCA CAGAGAGATT ATGTGACTCA CCCAAGGTCA CACTACAAGT CAGTGGTGGA
171061 GCCAGGAATA GAACCCAAGA CTCCTGACTC CTAATCCACT CCCCTAGCCA CTAGGCCCTG
171121 CTCCCTCCTC AAGGTTTCCT CTTGTGTGAA ATTCTCCTTT GAAATGCAAT TTCTTGTTTT
171181 TAATTCATGG GGAAAGAAGT ACCTGCTCTA ATGCTTCTCT AGGTAAGGCC ACCAGCATAT
171241 TCTTCCAGTC ATTTTAAGTT TTAATTTTTT GAAATAAGGA GCCGTTTATA TAATTTATTA
171301 ACATATTTAT TAAATGTTTT ATTTAATTTT AATATGAATA TATGATGAGA TTTTTCCCCT
171361 CTCCCATAGG ATTTGCCTTT ATTCAGCATC CAAGTCTAAT GTTCGAGCAA GAAGTGAAGA
171421 ATCTATATAA TAATATTTTA TCTGATAAGA ACTCCTCAGT CAATTTAAAA ATACAAGTGT
171481 TAAAAAACCT CCAGACCTAC CTACAAGAAG AAGATACACG TATGCAGCAG GCAGATAGAG
171541 ACTGTAAGTG AAAATATATT TTTAAATTTC ATAGCTACAT TTATATTATA ATGGCTTTAT
171601 CTTCTTTAAT CTAAATATCT AAATTTCCTT ATTTGTTAGA TGAAGAAATT CAGTTAAATA
171661 GCAGTCCTTA TGCTGAGGTC TATAGCTGGG CTTTAGCATA TTCTTAAATT CTCTAAAATA
171721 GTTTTAAAAT TGTATATGTG TGTAAACATT AACATTTTGA GGGAGGAAAG AGATTATAGT
171781 TCTCACTGGG TTCTCAAAGG GGCCTCTGAC ACAGACACAC ACACACACAC ACACACACTC
171841 ACACACAGAT TAAGAACCAT TGAGCCAGAA CACTAGCTGT AACGTTTTGT GATTTTGGTT
171901 ATGGCCTAAT TTTGAAATAT TTAGTAAAGT TAGTATAGGT GCTCTTAATG TGTGTTTATC
171961 CTTTGCTTGC TTTTGTAGGG AAGAAAGTTG CAAAACAGGA AGACTTAAAA GAAATGGGTG
172021 ATGTTTCCTC AGGGATGAGT AGTTCCATCA TGCAGCTTTA TCTCAAACAG GTGCTTGAGG
172081 CATTTTTTCA CACCCAGTCA AGTGTACGCC ACTTTGCCCT AAATGTCATT GCATTGACTC
172141 TAAATCAAGG TCTTATTCAT CCAGTTCAGG TAAGCATGTT TTATGGCAGC AGCACTTACT
172201 AAAAGAGCAA GATTAGTTGT AATTTGATAC ATTGTGATTA TAGAGAATAA GTAGTTCTTC
172261 GTTCCTCTTA CTCTTCTTTG TACTAAACTC TTAAGAATCT GGCAGTTTTA GATAATCTCT
172321 TGGGTTATGA TTACTGCAAA ATACCCATAT ATTCATAATA TTGTCTCTGT TATAAACTTG
172381 TAATTTCTAT TGGCAGAACA TATACTCAAA TTATTTTTCT AAGTATGGGT GATATATTTG
172441 TTTTAATTCA TATTTACTTT TGTCCCTAAG ATCCAACAAT CTATAATGTG AAGAGAGTTA
172501 ACTGGGTTTA AAAGTATAAT CTGTTCAACA GGGTGGAGTC TTAGTCCACA GAAAAGTAAA
172561 TTATATAAAC TCAATTCCTT CATCTTTAAG TTGGGTATAA CACCAACTAC TCGACACCTC
172621 ATAGCATTAA TATGAGGACA CAACGACGTA ATAAAGACAT TAGTGTTACT GAAGATTGGC
172681 AGCCAATGCT GATGTAGTAG TATATACCAT CTGATGGTCA AGAGAGCACC ATAGGCTACA
172741 AAAGTGTATG TATTAAGTAA GCAGAGTCTA TACCCTTCAA GATTTTTATT TTGGGTATTT
172801 TTCATGGAAC GTTTTAAAAA TATGATTTAT TTAAACATAC TGTGGTCTTC CCTGTGTCCT
172861 GAAACAAAAC ATGTTAACAA ATATTTATCC TGTTCTTCAT GACTCCGGGC TATTATCATA
172921 AAGAATCATA CATTATAATG AAACAGTAGT ACATTGAGAC TGTCACCTTT TTAAACTACC
172981 GAGGGTTCTT TGTTGGGTGC TTTTTATTAT ATATGCCTTT TAAACTTTTT TTTTTAATTT
173041 CACACAAAGG AGTCAGGTGC AGTGGCTCAC ACATGTAATC CCAGCACTTT GGGAGGCAGA
173101 GGTGGGCGGA TCACTTGAGT CAGGAGTTCA AAACCAGCAT AGCCAACATG GCAAAACCCC
173161 GTCTCTACTA AAAATACAAA AATTAGCCAG GTGTGGTGGC ACATGCCTGT GGTCCCAGCT
173221 ACATGGGAGG CTGAGGCAGG AAAATTGCTT GAACCCAGGA AGCAGAGAAC CCAGGAAGCA
173281 GAGGTTGCAG TGAGCTGAGA CCGTGCCATT GCACTCCAGC CTGGCCAACA GAGGGAGACT
173341 CCATCTCAAA AAAAAAAAAA AAAAAATTCA CACAAAGAAA TTGCAAAAGT GATACGATGA
173401 ATTCCTTTAT TCTCTTCACC TCTATTCACC ATTTGTTGAC ATTTTGCCAC AATTGCTTTC
173461 TCTCTCTCCC TTTATACATC TGCTTTTTTC TGAATCATTT GGTAGGAAGT TTCAAGTAAT
173521 TATGATTCTT TACCACTAAA CACTTCAGCA TATATTTTCT AAGAACAAGG ACATTCTCTT
173581 ACAAAACCGT AATATAATCA TTAAATTTGG GAAGTTTAAC ACTGATACAA TATTATCTAA
173641 TATACAGTTC ATTTGCAGAT TCTGCTAGTT AACCAAGGGC GTTCTCTATA GCCTTTTTCC
173701 TCTTCTTTTT TTTTGAGGCA AGATCTTGCT CTGTTTCCCA GGCTGGAGTG CAGTGATGCA
173761 GTCTCAGCTT ACCTGCAGCC TCCGCCTCCT GGATTCAAGC ACTCTTCCCA CCTCTGCCTC
173821 CCAAGTAGCT GAGACTACAG GTGTGCGCCA CCACCTGGCT AATTTTTGTG TTTTTGTAGA
173881 GACGGGGTTT TACCATGTTG GCCAGGCTGG TCTCAAACTT CTGAGCTCAA GTAATCTGCC

Figure 7V2

173941 TGCCTCAGTG TCCCAAAGTG CTGGGATTAC AGGCATGAGC CACCGCACCC ACCTTACAGC
174001 CTTTTTTCTT TCCTGATTCG AGATTTAACA TGATCATTTC TTTCATTTAG TGCCATGTCT
174061 GTATTTTAAA GTTAGGTTTG TTGTTGTTTT TCTGGCCTTC ACATTGCTTT TTAATTCAGA
174121 CTCACTTAAC ATAGTAGTAC TGTTTTTTGA CTCTAGAAGT ACAGTGAATA TGACTGTTAT
174181 CAACTCTCTG TTCCTCAAAG CCACATCTGA AATCAACTTT GAAAAACAAT TATATTTTCG
174241 TAGCTTTGAG TATGGAAAAC AAATTACTGT TTGCCCTATA TTATCTTTAC AAGGCAAATT
174301 CAGTCAAGCT TTAAAAACTA CTGGATTATA CATTTGTAGT CTATATCATA ATCTTAAATA
174361 GATATTCTTA GTGTGAGAAT GCTTTATGTT TAAAGAACCT AAAATTTACA ATGAAATTGT
174421 TTAAATTTTA TCACGTCAGT ATTTTTGCTG GTGCTCCAGT GCTTTCTGGA TTTAAGCTGA
174481 ATCTCAAAAG ATCTGTCATT TTAAAAAGAA CACTAAAACA TAGACTTTAT AGGAAGGCCT
174541 ATAAGGTTAA ATTCATATAT CTCAGATATA TGAAAAGTTT TGACATATGT CTAAATAGAG
174601 AATTTTTACT ACCATGATAT CTCGTAATTT TTTTTTTTAT TTCCAGTGTG TGCCATATTT
174661 AATTGCTATG GGCACAGACC CAGAACCTGC TATGCGGAAC AAGGCTGATC AGCAACTTGT
174721 GGAAATAGAC AAAAAATATG CTGGATTCAT TCATGTATGT ATTTTAACAT TTTATAACCT
174781 AAATTTAAAC ATTTTTCTTG AGTAAAGCAT TTCTTTGATA AATGCTCTGC CCACATTCAT
174841 AATTGGAATA AAATGTCTTA CTTAGTACCT ATCTTCTAAA CATGCAACTA AGTTAGTCTT
174901 CCAAGGTGTT TATTCTAGTC TAAAGTTAAG GTTGGGCTAG AGGTGACAGT ACCAAGCACA
174961 CCAGACTAAA AATCAGGAAA CCTGGATTTT ATATCTTACT ATGTGAACTT GGCTGCAGTG
175021 ACTCTCCTGG GCCTCATTTT TTTTTTCTTC TTTGAAATGA GGGAATTGTA AGAGATAATC
175081 TCTAATGTTC CTTCTAGCAC TTCATTCTGT GATTCGTATT ATTTTAATTA AAAAAAAACA
175141 ATGAAGCTAG CCTCAGAATG TAATGCTCTA AGTATATTTT TAATTTGTGT CTTTTAATTT
175201 CCCTGACAAA AATGAGACTT TTATTGATTT CAGATGAAAG CAGTGGCTGG TATGAAGATG
175261 TCTTACCAGG TACAACAGGC AATCAACACA TGCCTAAAAG ATCCTGTAAG GGGTTTCAGA
175321 CAAGACGAGT CCTCTAGCGC TTTGTGTTCA CACCTTTACT CCATGATCCG TGGAAACCGC
175381 CAACACAGAC GAGCCTTTCT TATTTCTTTA CTCAACCTCT TTGATGACAC AGCAGTAAGC
175441 ACAAAAACTT ATTATTTTAA GAAAATAAGT GCTCTAGAAA TTTTATGGAT AAAGTAGTCA
175501 TTTTTTAAAT ATTACCATTT TATTAGTATA TGATAGTAAC TTCATTAAGT GTTTTCTTAA
175561 TCTTCTAAGT TATTTACAAA GTACACAGTC AGAAGTGAAG GGGAAATTTT GTATGAGAAT
175621 AAGTGTAATG AGGAATAATG TATAATTTTG CCTCCATACT GAATATCCTA TAAACTTTGA
175681 TAACAGTTTC TGTAAGCGTA TCTTTAAATA AGCAACATCA CTAAACTAAT CGCTTTGGGA
175741 ACCGATTACC TCAAATATTG TTAGAGAATA ACTGTTCTAG GTTTTTGGCT ATTGAGATCC
175801 CTAGTTGTTC AACTTGATTT CCCTTAATGA AGGGAAGTCA CTTTTCTGTA TAGTAGTCCA
175861 CTTTTGTGTA TAGTAGTCCT CCCTTATCAT TAAAGATACA TTTCATGACC CCCAGTGGAT
175921 GCATGAAACC ATGGATAGTA CTAATTATTA TATATACAGT CATGCATCAC TTAATGACAG
175981 GGATACATTT GGAGAAATGC ATAGTTAGGC GATTTCTTTG TGGGGTGAAC ATCTTACTTA
176041 CACAAACCTA GATGTTGTAG CCTACCTAGG CTATATTGTT CCTGGGCTAC AAACCTGTAC
176101 AGCATGTTAC TGTACTGAAT ACTGTAGATA ACTATAACAC AATGGTAAGT ATTCATGTAC
176161 CTAAACATAT CTAAACATAG AAAAGGTACA GTAAAAATAT GATAGGATAA TCTTATGGGA
176221 CCATCATCAT ATATATAGTT TGTAATTGAC TGAAACATGT TATGTGGCAC ATGACTGTAC
176281 TGGTTTTTCC AATACATACA AACCTATGTT AAAGTTTTAA TTTATAAATT AGTCACAGTA
176341 AGAGATTAAC ATAATAATAA AATAGAACAA TTAAAACAAT ATACTGTAAT AAAAGTTATG
176401 TGAATGGGAT CTTGCTTTTC TCTCTCTCTC AAAATACCCT GTTGTAGTTT ACTCACCTAT
176461 TTTTGGACTA TGGTTGACCA AGGGTAACTG AAACTATGGA AAGCAAAACA GCAATTGGGG
176521 AGATTACCAT AATTACAATT TTGACACTTC TGGCTGTTGC ACTAGTTGCA TTGGCCAGGA
176581 CCATAGGCCA AGAAAACTGA ATATTCTTTA AAGTTTACCT TTTAATTTAT TTATTTCACA
176641 CAGTATTTAT TCTGCATCTG CTATGTACCA GCCATTGCGC TAAGAAGTTT AACGAGCATA
176701 AAATAGTAAA AACAGATATG GTTTCTGCCC ACACAGAGCA CGCATGAACC TATGTGTATA
176761 GCAACTTTTA AAAGAACAAA AGAGGCCAGG AGTGGTGACT CACGCCTGTA ATCCCAGCGC
176821 TTTGGGAGGC CAAGGCAGGT GGATCACAAG GTCAGGAGTT CGAGACCAGC CTGACCAACA
176881 TGGTGAAACC CCATCTCTAC TAAAAATATA AAAATTAGCC GGGCGTGGTG GCACGCGCCT
176941 GTAATCCCAG CTACTCAGGA GGCTGAGGCA GGAGAATTGC TTGAACCCAG GAGGCAGAGG
177001 TTGCAGTGAG CTGAGATCAC GCCACTGCAT TCCAGCCTGG CCGACAGAGC GAGACTCCGT
177061 CTCAAAAAAA AAAAAAAAAA AAGAACAAAA GAAATACTTT AATTACTTGT TAGCCTGACA
177121 GCAGATTTTT GCAATAAAGC AAAATTATAA TTACCATAGT GCAGATATCT TACTAGACCT
177181 CTTCAAGTAC TACATGAAAT TTATCATCAA CATTATCATC ATATCATTAT CAGTATTAAG
177241 TTTGCATTGT GTATAGGACA CTATACGAGG AGTGCCAGAT GATATAATGT AGTGCTTTTG
177301 CCCTGAAAGG ATTTTCCCTC CAGCTGTGGG GATAGGATAC AAAATTAATA GTGATTACGG
177361 TTAGTATATC CTGAGTGCCC TGATGGTTTG TGTTGATAAT ATTGTTCCAG TCCTTGTTTC
177421 TGTCCAAAAG AACTTCATTT CTATGTGATT TCACTGCCTG CTTTATGTCA TTGACTAGAT
177481 GTTTTGTCAT CTCAGCATTT GAAATGCTAA ACTGGAAACC CAGCTCTCAC AATGCAATGC
177541 TTTCTTCTGA CTACCTCCAA CAAAGAATGT CAGAGAAGGA ACAAATGCCT GAAGGCCCAG

Figure 7W2

177601 AGGGATAGAA TGAGAGGGAT CTGCTATATA AACCAGGGAA GGAAGATGTT CCAGTCAGGG
177661 CCAAAAAATT AATTAAAAAT ACAAAGATAA GAATGTGTGG GAAATAATGA ATAGTTTGTT
177721 ATTTGACTGG GGCAGAAAGG TCATAATGAG GAATAATATA TAGAGGATCC TGTAGATGGC
177781 AAAAAAAAAA ACATTGTAAG TGTGTGAATA AAATAATGAG GACAATTGCC AAAGAGCAGT
177841 TTAGGAAGAT GAATTTTTTT AGCATTGTGG TCACACTGGA GGTAATAATA AATTACTATG
177901 ATAACAGTAG GGGAGAAAAA GAATGGATAG TAGAGGCTGG GTGTGGTGCC TCATGCCTGT
177961 AACCCCAGCA TTTGGGGAGG CCGAGGCAGA TGGATCACCT GAGGTCAGGA GTTCGAGAAC
178021 AGCCTGGCCA ACATGGCAAA ATCCTCTCTC TCCTGAAAAT ACAAAAAAAT TAGCCAGGCA
178081 TGATGGCGCG CACCTGTAGT CCCAGCTACT TGGGAGGCTG AGGCATGAGA ATCACTTGAA
178141 CCTGGGCAGC AGAGATTGGC AGTGAGCTGA GATCGCACCA CTGCACTCCA GCTGAGCGAC
178201 AGAGCGAGAC TCCATCTCAA CAGTAAAAAA AAAAAAAAAA AAGAATGGAT AGTAGAAAAG
178261 AAAAGAAAGT TGAGGAAAGA ATTAAATGAG ACTGTGTGAA AAGAATAGTT AGTGGACAAC
178321 TGGAATATTT TTATCTTGAG CACCTGAAAC AATAATAGGA TTGTTGCCAA AGTCAGATTG
178381 CAAAGGAGTT GGCTTGAGGA GTACATAAAA AGGGAGTAGT CAAAGAGGTA GGAAGAGAAA
178441 ACTTAGGAAG AAGATTTCAT GAAGGAAAGT GTGGGTAATA GTCAGATGCT ACTGAGAAGT
178501 CAAGGAGAGT AAGAAGTGAA AAATAGAGTA GAATGGTGAA CTTCGTGGAC AAAAACAGTC
178561 AAGCAGTGAG GGACAAAAGC AGATTGTAAT TGAAAAGGGA GGGCCAGGTG AGATGACTCA
178621 TGCTTGTAAT CCCAGCACCC AAGGCAGATG ATAGCTTGAG CCCAGGAGTT CCATACCAGC
178681 CTGGGCAACA TAGTGAGACC CTATCTCTAC AAAAATTAAA AAATAAAAAC TGGACAGGCC
178741 TGGTGGTATG CACCTATACT CCTAGCTACC TAGCTACTGA AGAGACCAAG GCAAAGGGAT
178801 TGCTTGAGCC CAGGAGTTCA AGGTGGCAGT GAGTGGTATC ATGTCTCCTT TAAAAAAAAA
178861 TAGTGGGGAA GACATGGGAG GAGCAGTCTA AACTATTCTT TGAAGAACTT TGAAAGGAAA
178921 GAGAAATACA GGGCTTTTAT GGATGTTGAA GAAAATATGT ATATTTTCTT CAATATTATA
178981 TGAGTTTTGA AAATATATGA ATTATAGTGT TAAAACTAAT AGATGAGGTA GGGTTTTATG
179041 TCTACATTTT TTCATCTGTA ACGTGGGTGT TGATACATAT TGTAAAGTAA AAATAGAGTG
179101 AGAGTGATAC TCTTATGAAT ATTAATAGCA AGGTTATTCC ATCTGTGCTA TGGGATCTTG
179161 CTGCTGCTGC TGTTGGGTTT TATGTTGTTT CCATGGCAGG GGAAGGTAGA TGGTAGGAGT
179221 GAGTGTTTTT TAGTTGTGAG CTTTTTTTTT CCTTGAGCTA TAAATATTTA AAAGAAATTT
179281 GAATATTAAT ATGCCTTTCT GTTTATGATC ATGAAATGCT TGAATTCTCT ATTACTTCTT
179341 TTTAAAGCAA GCAACTAAAT AATCATAATT TTTCTCTTAA ATTTTGCCTG CCTCACAGTT
179401 TTTACAGTGT GAAACTGATA GCATTGTCAA AACAACTCTG ACATTCTGAA TTACATATAC
179461 ACAGGAAACT GACAAATGTT TATGAGTACA TGGGATTTGG GTTTTTTCTT TTAACCTATG
179521 TATTAGTACT ATAATTACTA GTTATTTTGA GGGCAGAATA GTAACTGTGT GTAACTGATC
179581 TCCATATAGG TTAAACTCTT AGTAGCACAA TGATATAACT AGAACTTTCA TGTATACTTT
179641 CTGATATGGT ATGGATTTAT CATAAAGATT CCATATACTC TAAGAAAACT TCAAGGAATT
179701 TCACATGGAT GCAATAAAAA ATTTCACCTC TTCTCTTGAG ATAGCATAGT GTAAGTCATT
179761 ATAAAATTAA AAAAAATGGG CCTAAGATTA TTTTATAAAA TTCCATTTCT GTTCCCCCTT
179821 TTCCCTTTTT GTTACACCTG TCTCCCTTTC CCTTTTTCCC CCCTCTATAT TTCTCTCCCT
179881 CCTCCTCTCC CTCTGTCTCT CTGTGTCTCT CCCCACTCTC TCCGTGTGTG TCTGCTTATC
179941 TCTGTCTAAC ATTAAGTGAG GTGAAAGTGC CCTGTATTTT TTCTAAAAAA GGTTTTTTGG
180001 TTGGGTTTCT AGATTATCCG CTAAACATGT GTGCTTTTTC TTAAAATTTA CAGAAAACAG
180061 ACGTGACTAT GCTCTTGTAT ATAGCAGACA ATCTAGCCTG TTTTCCATAC CAGACACAGG
180121 AAGAGCCGTT GTTTATAATG CATCATATAG ACATTACACT CTCAGTTTCT GGTAGTAACC
180181 TACTGCAGTC ATTCAAGGAG GTAAGTTACA CACATTACTA TTCTTAATCC ATCTGTCAAA
180241 GTGCAGGCAT GCTGTTTTCA CTGTTTTGTT TCTCATTATT CTTTTTATCC TCTTCACGAG
180301 TATATAAAAT CTTTCTAAGT GAACTTAATG AAATCTGGGC AATACTTGAC TTGGGAGAGG
180361 ATGTACATTG CCACTTTACC TCTATTTAGA AACATCTAAA ATAGATATAT GGATTGTTCT
180421 GTTGATAAGC CATCACATTT ATTTCTCTCA CTTTAAGCAC TGACCTTAAG TGTTTGCATC
180481 CATTCATACA TTCATTTAAA CTCCATTTTA AAACATTATT CTGTAAATCT TGTAATGCTG
180541 TAATCACAAC ATTACACATG AAAATATATA GCTTATTTAC ACTTAAACAG AAAATTTATG
180601 ACACCATTGA CTTTCTTATC CCTCAACTAC AGCACCGTTA TAGAGTTTGC ATATGTGTGC
180661 CCAAAATCTT TGCTAAATTT CTTGTTGAAC CTTCCATTGT TTCTGTCATG ACTTTTAGGA
180721 GGAATGTAAT TTATTTAATT ATAAAAGTAC CTGGTGTAGC ACTAGGCATA TAGTAAGCAC
180781 TCAGTAAATT CTTTACAAAT TGAATATTCT CATGTATCTA ATGATCCAAG TAGATCTCAT
180841 TTTATAAAAT TGTATTGCTC ACAACTCAGC CTTGTCAGAC TAGTAAATCA GACAGATTAT
180901 TTTAGATGCC TCCTGAGGGC TGGAATTACA GAGGTGTCTT AAACCCTTAC TACTTGAAGT
180961 ATAGACCACA CACCAGCAGC AGTGGTTTCA CCTGAGAGCT TATTAAAGCT GTAGAACCTC
181021 AGGCCCCACC CAGATTTGCT GAAACAGAAT CTGCATCTTC AACAAAATCC ACAGATGTTA
181081 ATGTGCACAT TTAAGTTTGA GAAGTTAATA ATTTCCCAGG AGCTTTAGCC CTCATGTTCT
181141 CTTATTTTAC CTACTTACTG GTATGGCTAT CTTTGTAAAT GTTTCTTCCA CTTTTGAAGA
181201 AATGTTGTTA TAATGTGCCC CACACACACA CACCACACAA ACTGCTTAAG TCCAGTTGAC

Figure 7X2

181261 TTTGTTTCTA AGAGCTAACA TTTTCATAAA GTACAAAGAA ACAGGATTTA AGTCTTCAGA
181321 GAAAATTGCT TATTATCTTG CCGAAATGTT CTTGAAAAGG AGAGTTTGCT AGAAGCTGGG
181381 ATGTCCAAGA TTACTTTATT CTCCTCAGTT AAATTATAAT TACTGCTTTT CCTCATAATG
181441 ACTTACCTAT GCACCAAATT GATACTTTTA TAACTATCTT TTATTACTGT CCTTAGAAGA
181501 AAATTGTTTC CCTTTGAATG ATATTTCAGA AGGATTTTTT TGAAGGAGTG GTTGTAGGGG
181561 AGGGGGTGGA TATTATATAT AATTTTATTT AGTTTTAGAA ACTATCCCCT AAGATTACAT
181621 ATCCAGTTGT TGATATAAAG TCAAGAGGTT TATAAAATAT TAGTTTAAGG AAGCTTTTTC
181681 AAGCTGTTGA ATGGAGCATA CTTATATTTA CTAGTGGCAT TTTGTTTTTA TTGTTTATCA
181741 AACGATTTTT TCTTTCAGTC TATGGTAAAG GACAAAAGGA AAGAGAGAAA ATCATCACCT
181801 AGTAAGGAAA ATGAGTCAAG CGACAGTGAA GAAGAAGTTT CCAGGCCTCG GAAGTCACGG
181861 AAACGTGTAG ATTCAGATTC AGATTCAGAT TCAGAAGACG ATATAAATTC AGTGATGAAA
181921 TGTTTGCCAG AAAATTCAGC TCCTTTAATC GAATTTGCAA ATGTGTCCCA GGGTATTTTA
181981 TTACTTCTCA TGTTAAAACA ACATTTGAAG AATCTTTGTG GATTTTCTGA TAGGTAAGGT
182041 TACATAAGCA GTGAGAGAAA AAACTTCACT CTGTTCAAAT AATAAATATT TGGGCTGGGT
182101 GTGGTGGCTC ATGCCTGTAA TCCCAACATT TTGGGAGGCT GAGGCGGGCA GATCCCCTGA
182161 GGTCAGGAGT TCGAGACCAG CCTGGCCAAC ATGGTGAAAC GCCATCTCTA TTAAAAATAC
182221 AAAAATTAGC CTAGTGTGGT GGTGCACGCC TGTGACCCCA GCTACTCAGG AGACTGAGGC
182281 AGGAAAATCG CTTAAACCTG GGAGGCGGAG ATTGCAGTGA GCTGAGATTA CGCCACTGCA
182341 CTCCAGCCTG GGCAACAGAG CAAGACTCTG TCTAAAAAAA TAATAATAAA TATGAAACCC
182401 AGTTTTGTTT GCATGCTTAC TTTAATGTTA GAAATGTTCC TTTTTTAAAA AGGAGTTTAT
182461 TCTCTTCTAT TGCTGGATAG TATTCTATTG TGTAATATGC CATAATTTAT TTTTATTAAA
182521 GGGAAAAAAA CATATTCCTA TACTTGGTGA TAATGCATTA CAAATTGAAG GACTTATTTT
182581 GTTGATTTCC TTAAAAAGAC TCAAGCTAAC CTTAAAATAG ATTACAAGTT TAAGTTTTTA
182641 AAGAGCTCTG AAGTAACAGA TGTAAACCAA CTAAACAGAG CTCCAGTAGA ACTCAAATAG
182701 TATTTAAAGT ACTCTATAAA GTAAGAGAGA GAAAAGGTAC AGCTATTATA AACACCCTGT
182761 AGTTTTACCC ACCAGTAGTC ATTAAAGATA CCTCTTTTCT GCCTGTAACC ATGGAATTTT
182821 GGTCATTTTT TACATTCATT GAAATCTAAG ATTAGGAATC ACAAAATCAA ATGTTAATAG
182881 GCTACCTGGT CAATGGCCAA CTGGAAAGAG TGTGTTGCAT GTAAAGAGGT CATTTAAGTG
182941 GACCTGTCTC AAGTTTCCAT AAGCTTGTTG CCAAAGGAGA GGGTAGGCAT AATGTGGCTA
183001 GAGCTCCCAC TTTTTCAGGA GACACTAGAA ATCCAGATTT TTAAGAGGAA TATCTGTATT
183061 TGCAACAGGG TCTCGCTCTG ATGCCCAGGT GGAGTGCAGT TATGCAATCA TAAACTCCTG
183121 GGCTCAAGTA ATCCTCCTAC TTCAGCCACC TGAGTAGCTG GGAGTACAGA TGCATGCCAC
183181 CACACCCAGC TAATTTTTTT TATTTTTTAC TTGTAGAGAT GATGTCTAGT TGTGTTGCTC
183241 ATGGTAGTCT TGAACTCCTG GCCTCAAGTG ATCCTCCCAC ACTGGCCTCC CAAAACTCTG
183301 AGATTATAGG CATGAGCCAC TGCTCCTGGC CTTATAAGGA ATATCTTGAT GTTAAATGTT
183361 GGCAAGATGC AAAATAATTT AAAACCTTGT AAGGTTTTGA GGCAATGCTA AGGAGTTGGA
183421 AAGATTTTTA AGCAGAGTTG TTAATAACCT GAAACAGGTT TATAAACAAT CATTCTGGCC
183481 ACTATATAGA GGATGGATAG GTTGGGGGTG GGGGAGCAAC TAGTAGAAAG AGGTAAACCA
183541 GTTAGGTGGT ATTAAGTAAT TGTATTGAAG CTGTCCTAGG ATCACAATAG TATTAAAAAT
183601 AGACATGAGA AACTAATTTC ATTAATATGG TGCTTCCTAC CTATAATTGG ATTTCTCCAA
183661 ATACGTTGTT TCCATAGTTT TAAAGTTTTT GGTTTTGTTT TCCCAAAACA GTAAAATTCA
183721 GAAGTACTCT CCATCTGAAT CTGCAAAAGT ATATGATAAA GCGATAAACC GAAAAACAGG
183781 AGTTCATTTT CATCCAAAAC AAACACTGGA CTTCCTGCGG AGTGACATGG CTAATTCCAA
183841 AATCACAGAA GAGGTGAAAA GGAGTATAGT AAAACAGTAT CTAGATGTGA GTAGTAAAAC
183901 CAAAAGTTTT TACTTCTCAT AAGGGCTTTT TTGACAAGTA AATGTGGGGG GCCGGTGGGG
183961 AGATAACTAT CTCCTTCACA TTGAATATAA GCTTCATGAA CTATCAAGAT AATTTTTCTC
184021 TATCTTATTT TAATGAGTTA CTTTAAGCTT GTCTTTCCCA TTGCACCCAT GGCATCCTAA
184081 TTATTTTTTC TTAGGAAACA GCAGCCCACG AATAATTTTA TTTTAGCAAA AATGAAAGAT
184141 TATAGGAAAA CCTGTGTGTG TTTTGTAGTT GTCCCCTGGT ATCTGCGGGA AATTGGTTCC
184201 AGTCCCCCCA TGGATACCCA AATCCTCCGA TATTCAAGGG CCTGATAAAA AAATGGCGTA
184261 GTGGGCTGCG TGAGGTGGCT CACACCTGTC ATTCCAGTGC TTTGGGAGGC CATGGCAGGT
184321 GGATCACTTG AGCTCAGGAG TTTGAGACCA GCCTGGGCAA CATGGCAAAT CCCCGTATCT
184381 ATAAAAAATA CAAAAAATTA CCTGGGGGCA GTGGTGTGCA CCTGTAGTCC CAGCTACTCA
184441 GGAGGCTGAG GCAGGAGAAG TGCTTGAGCC TGAGAGGCAG AGGTTACAGT GACCTGAGAT
184501 TGCACCATTA CACCCCATAC TGGGTGACAG GAGTGAAACC CTGTCTCAAA AAAATTATTT
184561 AAAAAGCATA GTATTTGCAT ATAACCTACA TACATCCTCC CATATGCTTT AAGTCATTTC
184621 TAGATTACTT ATAATACCTA ATACAATGTA AATGCTATAT ACATAGTTGT TATACTGCAT
184681 TTTTTTTAAG TTGTATTTTT TATTGTAATG CTGTTTGTTT TGTTTTGAGA CGGAGTTTCA
184741 CTCTTGTTGC CCAGGCTGGA GTGCAATGGC GCGATCTCGG CTCACCGCAA CTTCTGCCTC
184801 CCAGGTTCAA GCAAGTCTCC TGCCTCAGCC TCCCGCATAG CTGGGATTAC AGGCGCCAGC
184861 CACCACGCCC GGCTAATTTT TGTATTTTTA GTAGAGATGG GGTTTCACCA TGTTGGCCAG

Figure 7Y2

184921 GCTGGTCTCA AACTCCTGAC CTCAGGTGAT CCGCCGGCCT CCCAAAGTGC TGGGATTACA
184981 GGCATGAGCC ACCATACCTG GCCAGTGCTG TTATTTTTTA TTGTGGCATT TTCCAAATAG
185041 TTTTTGATCC ACTGTGGGTT GAATCCGCAG GTGCGGAATC CGGGGATACA GAGGGCTATG
185101 TTTTTAATTC AGAAAAATAC ATGGCTTATA TGTCATAAAA GGTAAAACTG CAAGCAGTCA
185161 TTCTCTTACC GTGTTTGGCT ATTCTGTTCC TTTCTTTTCT GATAACCAAT ATTATTACTT
185221 TTTCGTATGT TCTTATATGA GTAATGCCAA TATATATATA TGTAGATTTT CTCACTTATC
185281 AAGTATGCAA ATGTATGTAT ATAAAATGTG CTTTAAAAAT AGAGACAGAT AATAGACTAG
185341 AGGTTACCAA GGACCGGGGA AGGAAAGAAC GGGGAGTTAT TGTTTAATGA GGACAGCTGT
185401 GGTTTCCAGT GATTAAAAAA AAAAAGAAAC AGCTCTGGAA ATGGACAGTG GTGATAGTTG
185461 TACAATATGC CAATGAATTA TACATTTAAA ATGGTTAAAC TGGTAGGCTG GACATGCTGG
185521 CTTATACCTG TAATCTTAGC ACCTTGGGAG GCCTATGTAG GAGGTTTGCT TGAGTCCAGG
185581 AAGTCCAGGC CAGCCTGAGC AACAGGGTGA GACCCTGTCT CTACAAAAAA TACAAACATT
185641 AGCCAGACAT GGCGGTGTGC ACCTGTAGTC CCAACTGCTG GGGAGGCTGA GGTGGGAGGA
185701 CCACCTAAGC CTGGGAGGTG GAGGCTACAG TGAGCCATGA TCGTGCCACT GCACTTCAGC
185761 CTGAGTGACA GAGTGAGACC CTGTCTCAAT TTAAAAAGAA AAAAAAAAAG GGTTAAGCTG
185821 GCAAATTTTA TGATATTTCT ATTTTATCAC AATATAAAAG TTTTTAAAAA TGTTTTTGAA
185881 ATTAGAGGAC TATCCTAAAA AATAAAAATA AAGTTTTATA TTTTAATCTA CTTAATTTCA
185941 GGTGTAGTGG CTCACAAGCA CTTTGGGAGG CTGAGGTGGG CAGATCACTC GAGGCCAGAG
186001 GTTTGACACC AGTTTGGCCA ACATTGCAAA ACCCCATTTC TATTTTTCTT AAAAAAATTT
186061 TTAAAAATCT ACTTTAAAGC AAGTAGCTGA ACATAAAATA AGGTTTTTTG AACTAAGAAT
186121 ATAATCTACA CAGTGGCTTT TCATATTATT CATTGACTGC AAACCTTACT CTAAAATTTA
186181 AAAATATTTT AGTTCTTATT TAAAATTTTT CAACATTCTT TGCTTTCTCT TGTATCGTCT
186241 TAGCAGAGAG CAAAGAGGGG AGATAACTAG AAAATGTCTA TCAGTAATTA TCACCTGATT
186301 GCTTGATGAC TTGGACCAAG GGTCTGAAAA CTCTGGCTGT TTTTGTATCT AACCCATTGC
186361 CTGTTTTTGC AAACAAAGTT TTATTGAAAA CATTCATGCC CACTCATTTA TTTGTCTGTA
186421 GCTGCTTTCA TACTACAGTG GCAGAGTTGG GTAGTTGTGA CAGACTATTT GACCTTCAAA
186481 ATGAAAAATA TTTACCACCT GGCTGTTTAC AGAAAATGTT TACTAGCCCC TAATTTAGAT
186541 GATGGCTAAC GTCTGTTTCA CCCACACCAA ACTACTGCCA TAGAAAACAT TTAGGAATTT
186601 GACAATCTTG CTTGAAATAT TTACTTAAAA TTCTGAAATA ATATCTGTTT TTTGTAGTTC
186661 AAACTTCTCA TGGAACATCT GGACCCTGAT GAAGAAGAAG AAGAAGGGGA GGTTTCAGCT
186721 AGCACAAATG CTCGGAACAA AGCAATTACC TCACTGCTTG GAGGAGGCAG CCCTAAAAAT
186781 AATACAGCAG CAGAGACAGA AGATGATGAA AGTGATGGGG AGGATAGAGG AGGAGGCACT
186841 TCAGGGGTGA GGCGGAGGAG GAGTCAACGT ATTTCGCAGC GTATTACGTA AAATGATTTT
186901 TATGTGCTTA TATATGTCAG TCTATTAAAT GTACACCAAG TAATGTAATA CTTAAAAGAG
186961 AAAACATTTT GTAGATAGAG ATTCTCTACT TACCCGTTTA TACATCCTTT TGTAGAAAGT
187021 TTAACATAAA AGACAATAAA AAAACAGAAA TGAGATTTAT CCAGCATAAA GGGTTAATTT
187081 TTCTTTGAAT TGTATTAATG TGTGTTATTT TTATTGTTGC TAAGTTTTAT GTAGCTATAT
187141 GGTTCATATG TATATATAAT TTTATATATC AATAAGAGTA AAGACACGGG TACAAATTAA
187201 GAGTTATATG GTTTTACAAG TATATGTTAA CCCCTTGGCG CTGGCGGTCA CGGTGCGTCT
187261 CATTGCCGGC AATGGAAGTG TGCCGGGAAA TCCCAACTCC CGGCGTCAAG GGATTAAAAG
187321 CAATAAAAAC AATAATTTCA CTAAAATTCT TTTGTGTAAC ACTTGGTCTT TTTTCCCCCC
187381 TCCCAATGTT TTAGTCATTG AGAAGGTCAA AACGAAATTC AGACTCTACG GAGTTGGCAG
187441 CACAGATGAA TGAAAGTGTT GACGTCATGG ATGTCATCGC TATTTGCTGT CCAAAGTACA
187501 AAGATCGACC ACAAATTGCA AGAGTAGTGC AGAAAACCAG CAGTGGCTTC AGTGTTCAGT
187561 GGATGGCAGG CTCCTACAGT GGCTCCTGGA CTGAGGCTAA GCGCCGTGAT GGCCGCAAAC
187621 TGGTGCCTTG GGTAGACACT ATTAAAGAGT CAGACATTAT TTACAAAAAA ATTGCTCTAA
187681 CGAGTGCTAA TAAGCTGACT AATAAAGTTG TTCAGACTTT ACGATCCCTG TATGCCGCCA
187741 AGGATGGGAC TTCCAGCTAA TGAATTTGTA CATGCAGCCA AATTTACAGG AATTTTTTTA
187801 AAAGGCAGAA AAACTTGAAA TACCAACATT CTGGCAAAAA AAAATCAGTT TTATGAAGAG
187861 TAAGTGGAAC CTGGGATGCA GGAACAAAAG AAGGAAATGT TGGGCAAACA TTTTTGTGGG
187921 AGCTCCCTTC GCTGTTGTGC AGCAGAAACA GATTCTCAGT TCATTTTTAC TCCCACTGTA
187981 TTATAGTTTA ACAAAAATTG TTTATATCTT GGAAAAAAAA CTTTCTGTTT AAAAAAAATA
188041 AACAAGTGAA TGTTGG

Figure 7Z2

□NIPBL cDNA
ORIGIN

```
1    GACAGCGGCC TCGGCCTCCC CTTGGATTCA GACGCCGATT CGCCCAGTGT TTGGGAAATG
61   GGAAGTAATG ACAGCTGGCA CCTGAACTAA GTACTTTTAT AGGCAACACC ATTCCAGAAA
121  TTCAGGATGA ATGGGGATAT GCCCCATGTC CCCATTACTA CTCTTGCGGG GATTGCTAGT
181  CTCACAGACC TCCTGAACCA GCTGCCTCTT CCATCTCCTT TACCTGCTAC AACTACAAAG
241  AGCCTTCTCT TTAATGCACG AATAGCAGAA GAGGTGAACT GCCTTTTGGC TTGTAGGGAT
301  GACAATTTGG TTTCACAGCT TGTCCATAGC CTCAACCAGG TATCAACAGA TCACATAGAG
361  TTGAAAGATA ACCTTGGCAG TGATGACCCA GAAGGTGACA TACCAGTCTT GTTGCAGGCC
421  GTCCTGGCAA GGAGTCCTAA TGTTTTCAGG GAGAAAAGCA TGCAGAACAG ATATGTACAA
481  AGTGGAATGA TGATGTCTCA GTATAAACTT TCTCAGAATT CCATGCACAG TAGTCCTGCA
541  TCTTCCAATT ATCAACAAAC CACTATCTCA CATAGCCCCT CCAGCCGGTT TGTGCCACCA
601  CAGACAAGCT CTGGGAACAG ATTTATGCCA CAGCAAAATA GCCCAGTGCC TAGTCCATAC
661  GCCCCACAAA GCCCTGCAGG ATACATGCCA TATTCCCATC CTTCAAGTTA CACAACACAT
721  CCACAGATGC AACAAGCATC GGTATCAAGT CCCATTGTTG CAGGTGGTTT GAGAAACATA
781  CATGATAATA AAGTTTCTGG TCCGTTGTCT GGCAATTCAG CTAATCATCA TGCTGATAAT
841  CCTAGACATG GTTCAAGTGA GGACTACCTA CACATGGTGC ACAGGCTAAG TAGTGACGAT
901  GGAGATTCTT CAACAATGAG GAATGCTGCA TCTTTTCCCT TGAGATCTCC ACAGCCAGTA
961  TGCTCCCCTG CTGGAAGTGA AGGAACTCCT AAAGGCTCAA GACCACCTTT AATCCTACAA
1021 TCTCAGTCTC TACCTTGTTC ATCACCTCGA GATGTTCCAC CAGATATCTT GCTAGATTCT
1081 CCAGAAAGAA AACAAAAGAA GCAGAAGAAA ATGAAATTAG GCAAGGATGA AAAAGAGCAG
1141 AGTGAGAAAG CGGCAATGTA TGATATAATT AGTTCTCCAT CCAAGGACTC TACTAAACTT
1201 ACATTAAGAC TTTCTCGTGT AAGGTCTTCA GACATGGACC AGCAAGAGGA TATGATTTCT
1261 GGTGTGGAAA ATAGCAATGT TTCAGAAAAT GATATTCCTT TTAATGTGCA GTACCCAGGA
1321 CAGACTTCAA AAACACCCAT TACTCCACAA GATATAAACC GCCCACTAAA TGCTGCTCAA
1381 TGTTTGTCGC AGCAAGAACA AACAGCATTC CTTCCAGCAA ATCAAGTGCC TGTTTTACAA
1441 CAGAACACTT CAGTTGCTGC AAAACAACCC CAGACTTCTG TGGTACAGAA TCAACAACAG
1501 ATATCACAAC AGGGACCTAT ATATGATGAA GTGGAATTGG ATGCATTGGC TGAAATTGAG
1561 CGAATAGAGA GAGAATCAGC TATTGAAAGG GAGCGCTTCT CAAAAGAAGT TCAAGATAAA
1621 GATAAGCCTT TGAAAAAAAG AAAACAAGAT TCTTACCCAC AGGAGGCTGG GGGTGCTACA
1681 GGAGGTAATA GACCAGCTTC TCAGGAGACG GGTTCTACGG GAAATGGGTC AAGGCCAGCA
1741 TTAATGGTTA GCATTGATCT TCATCAGACA GGAAGAGTGG ACTCTCAGGC TTCTATAACT
1801 CAGGATTCAG ACTCCATAAA AAAGCCTGAA GAAATCAAAC AATGTAGTGA TGCACCTGTT
1861 TCTGTTCTTC AGGAAGATAT TGTTGGAAGT CTTAAATCTA CACCAGAAAA CCATCCTGAG
1921 ACACCTAAAA AAAAGTCTGA TCCTGAGCTT TCAAAGAGTG AAATGAAACA AAGTGAAAGT
1981 AGATTAGCAG AATCTAAACC AAATGAAAAC CGATTGGTGG AGACAAAATC AAGTGAAAAT
2041 AAGTTAGAAA CTAAAGTTGA GACCCAAATA GAAGAACTTA AACAGAATGA GAGCAGAACA
2101 ACTGAATGCA AACAAAACGA GAGCACCATA GTTGAGCCTA AACAAAATGA AAATAGACTG
2161 TCTGACACAA AACCAAATGA CAACAAACAA AATAATGGCA GATCAGAAAC AACAAAATCA
2221 AGGCCTGAAA CCCCAAAGCA AAAGGGTGAA AGCCGGCCTG AGACTCCAAA ACAAAAGAGT
2281 GATGGGCATC CTGAAACCCC AAAACAGAAG GGTGATGGAA GGCCTGAAAC TCCAAAGCAA
2341 AAAGGTGAGA GCCGCCCTGA AACTCCAAAG CAAAAAAATG AAGGGCGACC TGAAACACCA
2401 AAACACAGGC ATGACAATAG GAGGGATTCT GGAAAGCCAT CTACAGAGAA AAAACCTGAA
2461 GTGTCTAAAC ATAAACAAGA TACTAAATCT GACTCACCTC GGTTAAAATC AGAACGAGCT
2521 GAAGCCTTAA AGCAGAGACC TGATGGGCGA TCTGTTTCTG AGTCACTAAG ACGTGACCAT
2581 GATAATAAAC AAAAATCAGA TGACAGGGGT GAATCAGAGC GACATCGAGG GGATCAGTCT
2641 AGGGTTCGAA GACCAGAAAC ATTGAGATCC TCTAGTAGAA ATGAACATGG CATTAAATCT
2701 GATAGTTCAA AAACTGATAA ACTAGAACGA AAACACAGGC ACGAATCAGG GGACTCAAGG
2761 GAAAGACCAT CTTCTGGGGA ACAAAAATCA AGACCTGACA GTCCTCGTGT TAAACAAGGA
2821 GATTCTAATA AATCAAGATC TGATAAACTT GGTTTTAAAT CACCAACTAG TAAAGATGAC
2881 AAAAGGACAG AGGGTAACAA GAGTAAAGTA GACACTAATA AAGCACACCC TGACAATAAG
2941 GCAGAATTTC CAAGTTATTT GTTGGGGGGC AGGTCTGGTG CGTTGAAAAA TTTTGTCATT
```

Figure 8A

```
3001 CCGAAAATCA AGAGGGATAA AGATGGCAAT GTTACTCAGG AGACAAAGAA AATGGAAATG
3061 AAAGGAGAGC CGAAAGACAA AGTAGAAAAA ATAGGATTAG TTGAAGATCT AAATAAAGGA
3121 GCTAAGCCTG TAGTTGTGCT ACAAAAACTG TCTTTGGATG ATGTTCAGAA ACTTATTAAA
3181 GATAGAGAGG ACAAATCGAG AAGTTCCCTT AAACCTATCA AGAATAAACC ATCAAAGTCA
3241 AATAAAGGTA GTATAGATCA ATCAGTGTTA AAAGAATTAC CCCCTGAACT CCTGGCAGAA
3301 ATTGAGTCCA CCATGCCACT TTGTGAACGT GTGAAAATGA ACAAACGCAA GCGTAGCACA
3361 GTTAATGAAA AGCCAAAATA TGCTGAAATC AGTTCAGATG AAGATAATGA TAGTGATGAA
3421 GCTTTTGAAT CCTCTAGGAA ACGACATAAA AAAGATGATG ATAAAGCTTG GGAATATGAA
3481 GAGCGTGACA GAAGAAGCTC TGGGGATCAT AGGAGAAGTG GCCACTCTCA TGAAGGAAGA
3541 AGGAGTTCAG GTGGTGGTCG TTATCGAAAC CGAAGTCCGT CAGATTCTGA CATGGAAGAT
3601 TATTCTCCTC CTCCCAGCCT TAGTGAGGTT GCTAGGAAAA TGAAGAAAAA AGAAAAACAG
3661 AAGAAAAGGA AAGCATATGA ACCAAAACTA ACACCTGAAG AAATGATGGA CTCTTCAACT
3721 TTTAAGAGAT TCACAGCCTC AATAGAGAAT ATTTTGGATA ATTTGGAAGA TATGGATTTT
3781 ACTGCGTTTG GTGATGATGA TGAAATTCCT CAGGAACTGC TCTTAGGAAA ACATCAGCTT
3841 AATGAACTTG GCAGTGAATC TGCTAAAATA AAAGCAATGG GTATAATGGA TAAGCTTTCA
3901 ACTGACAAAA CTGTGAAAGT CTTAAATATC TTGGAGAAGA ATATTCAGGA TGGGTCAAAG
3961 CTTTCCACTT TGTTAAATCA TAATAACGAT ACTGAAGAAG AAGAAAGGTT ATGGAGAGAC
4021 CTTATTATGG AGAGAGTTAC AAAATCAGCG GATGCTTGTC TTACAACTAT CAACATTATG
4081 ACATCCCCTA ACATGCCAAA AGCTGTGTAC ATTGAGGATG TAATTGAAAG AGTTATACAG
4141 TACACTAAAT TTCATTTGCA GAATACACTT TATCCTCAGT ATGATCCTGT TTACAGATTA
4201 GATCCTCATG GAGGAGGCTT ATTAAGTTCA AAAGCAAAAC GGGCTAAATG TTCTACCCAT
4261 AAGCAGAGAG TAATAGTAAT GCTTTATAAC AAAGTTTGTG ACATTGTTAG CAGCTTATCA
4321 GAATTGCTAG AGATACAACT TCTTACAGAC ACAACAATTC TTCAGGTTTC ATCTATGGGA
4381 ATAACACCAT TTTTTGTGGA AAATGTCAGT GAACTACAGT TGTGTGCCAT TAAGTTAGTC
4441 ACTGCAGTAT TCTCAAGATA TGAAAAACAT AGGCAGTTAA TTTTGGAAGA AATTTTTACT
4501 TCACTTGCAA GATTACCAAC CAGCAAGAGG AGTTTAAGGA ACTTCAGGTT AAACAGTAGT
4561 GATATGGATG GAGAACCTAT GTATATTCAG ATGGTTACAG CACTGGTTTT ACAACTTATT
4621 CAGTGTGTGG TACACTTACC ATCATCAGAG AAGGACTCTA ATGCAGAAGA AGATTCAAAT
4681 AAAAAAATTG ACCAGGATGT TGTCATTACT AACTCTTATG AAACAGCTAT GCGAACAGCC
4741 CAAAACTTCC TCTCCATCTT CCTTAAAAAA TGTGGTAGTA AGCAAGGTGA AGAAGATTAC
4801 AGACCACTGT TTGAAAATTT TGTTCAAGAC CTTCTTTCAA CAGTCAATAA GCCTGAATGG
4861 CCAGCTGCTG AACTACTCCT TAGTTTGTTA GGGAGACTGT TGGTTCATCA GTTCAGTAAC
4921 AAGTCAACAG AGATGGCTTT AAGAGTGGCA TCTCTTGATT ACCTTGGAAC TGTTGCTGCA
4981 CGGCTAAGAA AAGATGCTGT TACAAGCAAA ATGGATCAAG GATCTATAGA ACGCATTTTA
5041 AAACAGGTTT CAGGAGGGGA AGATGAAATC CAACAATTAC AAAAAGCATT GCTTGATTAC
5101 TTGGATGAAA ACACTGAGAC TGATCCTTCA CTAGTGTTTT CTCGTAAATT CTATATAGCC
5161 CAGTGGTTTC GAGACACAAC TCTGGAAACA GAAAAAGCAA TGAAATCACA AAAAGATGAA
5221 GAATCATCTG AAGGAACACA TCATGCAAAG GAAATTGAGA CAACTGGCCA AATTATGCAT
5281 CGAGCTGAAA ACCGAAAAAA GTTTCTTAGA AGCATTATCA AAACCACACC TTCTCAGTTT
5341 AGCACATTAA AGATGAACTC TGATACTGTG GACTATGATG ATGCTTGCTT GATTGTTCGA
5401 TACTTGGCCT CCATGAGGCC GTTTGCCCAG AGCTTTGATA TTTATTTGAC ACAGATCCTA
5461 CGAGTTCTTG GTGAAAATGC AATTGCTGTT CGAACAAAAG CCATGAAGTG TTTGTCTGAG
5521 GTTGTTGCTG TAGACCCCAG TATTCTAGCA AGGCTTGATA TGCAACGAGG TGTTCATGGA
5581 CGATTGATGG ATAATTCGAC TAGTGTCCGA GAAGCAGCAG TAGAATTACT AGGTCGATTT
5641 GTCCTTTGTC GACCTCAGCT TGCTGAACAG TATTATGATA TGCTGATTGA AAGAATATTG
5701 GATACTGGTA TCAGTGTCAG GAAAAGAGTA ATAAAGATTC TCAGAGACAT TTGTATTGAA
5761 CAACCAACAT TTCCAAAAAT CACAGAAATG TGTGTAAAAA TGATTCGCAG AGTCAATGAT
5821 GAAGAGGGCA TTAAGAAATT AGTAAATGAA ACATTCCAGA AACTCTGGTT TACTCCAACT
5881 CCACACAATG ACAAAGAAGC AATGACAAGG AAAATTTTAA ACATTACCGA TGTGGTTGCA
5941 GCATGCAGAG ATACTGGATA TGACTGGTTT GAGCAACTGC TTCAAAACTT GTTGAAGTCC
6001 GAAGAGGATT CCTCATATAA ACCTGTGAAG AAAGCTTGTA CTCAACTTGT TGATAACCTA
6061 GTTGAGCACA TTCTTAAATA TGAGGAATCT CTAGCTGACT CTGACAATAA AGGTGTGAAT
```

Figure 8B

6121 TCTGGAAGAT TGGTAGCTTG CATAACCACT TTGTTCTTAT TCAGCAAAAT AAGACCCCAG
6181 CTCATGGTTA AACATGCAAT GACTATGCAA CCATACCTTA CCACTAAATG TAGTACGCAA
6241 AATGATTTCA TGGTTATCTG CAATGTTGCA AAAATCCTAG AGCTAGTTGT ACCACTGATG
6301 GAGCATCCAA GTGAAACTTT TCTTGCCACT ATTGAGGAAG ATCTAATGAA GCTCATCATC
6361 AAATATGGCA TGACTGTAGT GCAACATTGT GTGAGCTGTC TTGGAGCTGT TGTAAATAAA
6421 GTGACACAAA ATTTTAAATT TGTGTGGGCT TGTTTCAATA GATACTATGG TGCCATTTCA
6481 AAATTAAAAA GTCAACACCA AGAGGACCCA AATAACACTT CACTTCTAAC AAACAAACCA
6541 GCACTTCTTA GATCCCTTTT CACCGTTGGA GCACTATGTC GGCATTTTGA TTTTGATCTG
6601 GAAGATTTTA AAGGCAACAG CAAGGTTAAC ATAAAAGATA AAGTACTTGA ACTATTGATG
6661 TATTTTACAA AACACTCAGA TGAAGAAGTA CAAACAAAAG CTATCATTGG TCTAGGATTT
6721 GCCTTTATTC AGCATCCAAG TCTAATGTTC GAGCAAGAAG TGAAGAATCT ATATAATAAT
6781 ATTTTATCTG ATAAGAACTC CTCAGTCAAT TTAAAAATAC AAGTGTTAAA AAACCTCCAG
6841 ACCTACCTAC AAGAAGAAGA TACACGTATG CAGCAGGCAG ATAGAGACTG GAAGAAAGTT
6901 GCAAAACAGG AAGACTTAAA AGAAATGGGT GATGTTTCCT CAGGGATGAG TAGTTCCATC
6961 ATGCAGCTTT ATCTCAAACA GGTGCTTGAG GCATTTTTTC ACACCCAGTC AAGTGTACGC
7021 CACTTTGCCC TAAATGTCAT TGCATTGACT CTAAATCAAG GTCTTATTCA TCCAGTTCAG
7081 TGTGTGCCAT ATTTAATTGC TATGGGCACA GACCCAGAAC CTGCTATGCG GAACAAGGCT
7141 GATCAGCAAC TTGTGGAAAT AGACAAAAAA TATGCTGGAT TCATTCATAT GAAAGCAGTG
7201 GCTGGTATGA AGATGTCTTA CCAGGTACAA CAGGCAATCA ACACATGCCT AAAAGATCCT
7261 GTAAGGGGTT TCAGACAAGA CGAGTCCTCT AGCGCTTTGT GTTCACACCT TTACTCCATG
7321 ATCCGTGGAA ACCGCCAACA CAGACGAGCC TTTCTTATTT CTTTACTCAA CCTCTTTGAT
7381 GACACAGCAA AAACAGACGT GACTATGCTC TTGTATATAG CAGACAATCT AGCCTGTTTT
7441 CCATACCAGA CACAGGAAGA GCCGTTGTTT ATAATGCATC ATATAGACAT TACACTCTCA
7501 GTTTCTGGTA GTAACCTACT GCAGTCATTC AAGGAGTCTA TGGTAAAGGA CAAAAGGAAA
7561 GAGAGAAAAT CATCACCTAG TAAGGAAAAT GAGTCAAGCG ACAGTGAAGA AGAAGTTTCC
7621 AGGCCTCGGA AGTCACGGAA ACGTGTAGAT TCAGATTCAG ATTCAGATTC AGAAGACGAT
7681 ATAAATTCAG TGATGAAATG TTTGCCAGAA AATTCAGCTC CTTTAATCGA ATTTGCAAAT
7741 GTGTCCCAGG GTATTTTATT ACTTCTCATG TTAAAACAAC ATTTGAAGAA TCTTTGTGGA
7801 TTTTCTGATA GTAAAATTCA GAAGTACTCT CCATCTGAAT CTGCAAAAGT ATATGATAAA
7861 GCGATAAACC GAAAAACAGG AGTTCATTTT CATCCAAAAC AAACACTGGA CTTCCTGCGG
7921 AGTGACATGG CTAATTCCAA AATCACAGAA GAGGTGAAAA GGAGTATAGT AAAACAGTAT
7981 CTAGATTTCA AACTTCTCAT GGAACATCTG GACCCTGATG AAGAAGAAGA AGAAGGGGAG
8041 GTTTCAGCTA GCACAAATGC TCGGAACAAA GCAATTACCT CACTGCTTGG AGGAGGCAGC
8101 CCTAAAAATA ATACAGCAGC AGAGACAGAA GATGATGAAA GTGATGGGGA GGATAGAGGA
8161 GGAGGCACTT CAGGGTCATT GAGAAGGTCA AAACGAAATT CAGACTCTAC GGAGTTGGCA
8221 GCACAGATGA ATGAAAGTGT TGACGTCATG GATGTCATCG CTATTTGCTG TCCAAAGTAC
8281 AAAGATCGAC CACAAATTGC AAGAGTAGTG CAGAAAACCA GCAGTGGCTT CAGTGTTCAG
8341 TGGATGGCAG GCTCCTACAG TGGCTCCTGG ACTGAGGCTA AGCGCCGTGA TGGCCGCAAA
8401 CTGGTGCCTT GGGTAGACAC TATTAAAGAG TCAGACATTA TTTACAAAAA AATTGCTCTA
8461 ACGAGTGCTA ATAAGCTGAC TAATAAAGTT GTTCAGACTT TACGATCCCT GTATGCCGCC
8521 AAGGATGGGA CTTCCAGCTA ATGAATTTGT ACATGCAGCC AAATTTACAG GAATTTTTTT
8581 TAAAAGGCAG AAAAACTTGA AATACCAACA TTCTGGCAAA AAAAAATCAG TTTTATGAAG
8641 AGTAAGTGGA ACCTGGGATG CAGGAACAAA AGAAGGAAAT GTTGGGCAAA CATTTTTGTG
8701 GGAGCTCCCT TCGCTGTTGT GCAGCAGAAA CAGATTCTCA GTTCATTTTT ACTCCCACTG
8761 TATTATAGTT TAACAAAAAT TGTTTATATC TTGGAAAAAA AACTTTCTGT TTAAAAAAAA
8821 TAAACAAGTG AATGTTGGAA ATTAGTCTGT TAATGTTCTT AATAAAGTGT TCTTGGAGTT
8881 TAACCTAGCA GCGGATGGCT TTCTTTAGCT TAGCCCAGTT TCCAGGGAAG CATTGTTTTT
8941 TCCAGGCTGT AAAATGGCAG AATCTCCTGG ATATATAATT TATTCTGTTG AAAAAAAAAA
9001 AAGCATGCAG TATCTATGAC CTATCTGCAG AAGGAGTTTT TGTAAATGTA GATTTTGATG
9061 TATTAGGTCA CCCTGAAAAC AATACAAGAA AAGGGATCCC CAGGTAATCT GGTGGAGCGA
9121 ATACTGCAAT AAATTTTTTT ACTTCTCTTT GTTACTTGTC TGTTTCCATT TGAATTTCTT
9181 ATTGTAAAAA TCTGTTTAAA TCCATTTATA TTATTTTACA GTCTTTTATG TAAAATTTAT

Figure 8C

```
9241 TATATCACTG GTTTTCAAAG CAAAACATAA AATATTGTTT ATACAGTTTG TATAGGCTGA
9301 CTTCTGAATA ATTGGTATCT ATTATTTTCA TTCCCATAAG AGGGTGTAAA CAATTAACTC
9361 CAGGGTTTTA TTGTATCCTG CAATATTTAG TATTAACTAT ATATGATTTA GCACTGTGCC
9421 AAACACATTT TCAAGAGTAC ATTTTGATAT AAAAAGAAAC TATAGTTTAA AAAAAAAAAA
9481 AAAAAAAAAA AAAAAAAAAA AAAAA//
```

Figure 8D

NIPBL protein

MNGDMPHVPITTLAGIASLTDLLNQLPLPSPLPATTTKSLLFNARIAEEVNCLLACRDDN
LVSQLVHSLNQVSTDHIELKDNLGSDDPEGDIPVLLQAVLARSPNVFREKSMQNRYVQS
GMMMSQYKLSQNSMHSSPASSNYQQTTISHSPSSRFVPPQTSSGNRFMPQQNSPVPSPY
APQSPAGYMPYSHPSSYTTHPQMQQASVSSPIVAGGLRNIHDNKVSGPLSGNSANHHAD
NPRHGSSEDYLHMVHRLSSDDGDSSTMRNAASFPLRSPQPVCSPAGSEGTPKGSRPPLIL
QSQSLPCSSPRDVPPDILLDSPERKQKKQKKMKLGKDEKEQSEKAAMYDIISSPSKDSTK
LTLRLSRVRSSDMDQQEDMISGVENSNVSENDIPFNVQYPGQTSKTPITPQDINRPLNAA
QCLSQQEQTAFLPANQVPVLQQNTSVAAKQPQTSVVQNQQQISQQGPIYDEVELDALAE
IERIERESAIERERFSKEVQDKDKPLKKRKQDSYPQEAGGATGGNRPASQETGSTGNGSR
PALMVSIDLHQAGRVDSQASITQDSDSIKKPEEIKQCNDAPVSVLQEDIVGSLKSTPENHP
ETPKKKSDPELSKSEMKQSESRLAESKPNENRLVETKSSENKLETKVETQTEELKQNESR
TTECKQNESTIVEPKQNENRLSDTKPNDNKQNNGRSETTKSRPETPKQKGESRPETPKQK
SDGHPETPKQKGDGRPETPKQKGESRPETPKQKNEGRPETPKHRHDNRRDSGKPSTEKK
PEVSKHKQDTKSDSPRLKSERAEALKQRPDGRSVSESLRRDHDNKQKSDDRGESERHR
GDQSRVRRPETLRSSSRNEHGIKSDSSKTDKLERKHRHESGDSRERPSSGEQKSRPDSPR
VKQGDSNKSRSDKLGFKSPTSKDDKRTEGNKSKVDTNKAHPDNKAEFPSYLLGGRSGA
LKNFVIPKIKRDKDGNVTQETKKMEMKGEPKDKVEKIGLVEDLNKGAKPVVVLQKLSL
DDVQKLIKDREDKSRSSLKPIKNKPSKSNKGSIDQSVLKELPPELLAEIESTMPLCERVKM
NKRKRSTVNEKPKYAEISSDEDNDSDEAFESSRKRHKKDDDKAWEYEERDRRSSGDHR
RSGHSHEGRRSSGGGRYRNRSPSDSDMEDYSPPPSLSEVARKMKKKEKQKKRKAYEPK
LTPEEMMDSSTFKRFTASIENILDNLEDMDFTAFGDDDEIPQELLLGKHQLNELGSESAKI
KAMGIMDKLSTDKTVKVLNILEKNIQDGSKLSTLLNHNNDTEEEERLWRDLIMERVTKS
ADACLTTINIMTSPNMPKAVYIEDVIERVIQYTKFHLQNTLYPQYDPVYRLDPHGGGLLS
SKAKRAKCSTHKQRVIVMLYNKVCDIVSSLSELLEIQLLTDTTILQVSSMGITPFFVENVS
ELQLCAIKLVTAVFSRYEKHRQLILEEIFTSLARLPTSKRSLRNFRLNSSDMDGEPMYIQM
VTALVLQLIQCVVHLPSSEKDSNAEEDSNKKIDQDVVITNSYETAMRTAQNFLSIFLKKC
GSKQGEEDYRPLFENFVQDLLSTVNKPEWPAAELLLSLLGRLLVHQFSNKSTEMALRVA
SLDYLGTVAARLRKDAVTSKMDQGSIERILKQVSGGEDEIQQLQKALLDYLDENTETDP
SLVFSRKFYIAQWFRDTTLETEKAMKSQKDEESSEGTHHAKEIETTGQIMHRAENRKKF
LRSIIKTTPSQFSTLKMNSDTVDYDDACLIVRYLASMRPFAQSFDIYLTQILRVLGENAIA
VRTKAMKCLSEVVAVDPSILARLDMQRGVHGRLMDNSTSVREAAVELLGRFVLCRPQL
AEQYYDMLIERILDTGISVRKRVIKILRDICIEQPTFPKITEMCVKMIRRVNDEEGIKKLVN
ETFQKLWFTPTPHNDKEAMTRKILNITDVVAACRDTGYDWFEQLLQNLLKSEEDSSYKP
VKKACTQLVDNLVEHILKYEESLADSDNKGVNSGRLVACITTLFLFSKIRPQLMVKHAM
TMQPYLTTKCSTQNDFMVICNVAKILELVVPLMEHPSETFLATIEEDLMKLIIKYGMTVV
QHCVSCLGAVVNKVTQNFKFVWACFNRYYGAISKLKSQHQEDPNNTSLLTNKPALLRS
LFTVGALCRHFDFDLEDFKGNSKVNIKDKVLELLMYFTKHSDEEVQTKAIIGLGFAFIQH
PSLMFEQEVKNLYNNILSDKNSSVNLKIQVLKNLQTYLQEEDTRMQQADRDWKKVAK
QEDLKEMGDVSSGMSSSIMQLYLKQVLEAFFHTQSSVRHFALNVIALTLNQGLIHPVQC
VPYLIAMGTDPEPAMRNKADQQLVEIDKKYAGFIHMKAVAGMKMSYQVQQAINTCLK
DPVRGFRQDESSSALCSHLYSMIRGNRQHRRAFLISLLNLFDDTAKTDVTMLLYIADNLA
CFPYQTQEEPLFIMHHIDITLSVSGSNLLQSFKESMVKDKRKERKSSPSKENESSDSEEEV
SRPRKSRKRVDSDSDSDSEDDINSVMKCLPENSAPLIEFANVSQGILLLLMLKQHLKNLC
GFSDSKIQKYSPSESAKVYDKAINRKTGVHFHPKQTLDFLRSDMANSKITEEVKRSIVKQ

Figure 9A

YLDFKLLMEHLDPDEEEEEGEVSASTNARNKAITSLLGGGSPKNNTAAETEDDESDGED
RGGGTSGSLRRSKRNSDSTELAAQMNESVDVMDVIAICCPKYKDRPQIARVVQKTSSGF
SVQWMAGSYSGSWTEAKRRDGRKLVPWVDTIKESDIIYKKIALTSANKLTNKVVQTLR
SLYAAKDGTSS

Figure 9B

METHODS AND COMPOSITIONS FOR THE DIAGNOSIS OF CORNELIA DE LANGE SYNDROME

This application claims priority under 35 U.S.C. §119(e) to U.S. provisional Application No. 60/567,756 filed May 3, 2004, the entire contents of which are incorporated by reference herein.

Pursuant to 35 U.S.C. §202(c) it is acknowledged that the U.S. Government has certain rights in the invention described, which was made in part with funds from the National Institutes of Health, Grant Numbers: 1 RO1 HD39323 and RO1 DK53104.

FIELD OF THE INVENTION

This invention relates to the fields of human genetics and molecular biology. More specifically, the invention provides compositions and methods useful for screening and diagnosing patients with Cornelia de Lange Syndrome.

BACKGROUND OF THE INVENTION

Several publications and patent documents are cited throughout the specification in order to describe the state of the art to which this invention pertains. Each of these citations is incorporated herein by reference as though set forth in full.

Cornelia de Lange syndrome (CdLS [OMIM #122470]), which was recognized as a distinct entity over 70 years ago, is a clinically heterogeneous developmental disorder characterized by facial dysmorphia, upper extremity malformations, hirsutism, cardiac defects, growth and cognitive retardation, and gastrointestinal abnormalities (Brachmann 1916; de Lange 1933). The distinctive facial features include synophrys, long eyelashes, depressed nasal bridge with an up-tilted nasal tip and anteverted nares, thin upper lip with down-turned corners of the mouth, and low-set, posteriorly-rotated ears. Abnormalities in the upper extremities range from subtle changes in the phalanges and metacarpal bones with small hands to oligodactyly and severe reduction defects. Gastrointestinal abnormalities include gastroesophageal reflux, intestinal malrotation, and pyloric stenosis. Additional relatively frequent features include hearing loss, ophthalmologic findings (ptosis, myopia), palatal abnormalities, genitourinary abnormalities (cryptorchidism, hypospadias), cardiac septal defects, and congenital diaphragmatic hernias. Growth retardation is an almost universal finding in CdLS and is typically of prenatal onset. Standard growth curves have been established for height, weight, and head circumference (Kline et al. 1993a). The mental retardation in CdLS is often severe, with a mean I.Q. of 53 (range 30-86) (Kline et al. 1993b). Many patients also demonstrate autistic-like behavior and self-injurious behavior (Jackson et al. 1993).

The clinical features seen in individuals with classic CdLS are striking and easily recognizable; however, there is marked variability and a milder phenotype has been consistently described (Ireland et al. 1993; Saul et al. 1993; Selicorni et al. 1993; Van Allen et al. 1993). Indeed, even the first reported descriptions of CdLS were markedly discrepant in phenotype: Brachmann described major upper limb reduction abnormalities (Brachmann 1916), while de Lange reported no limb reduction defects (de Lange 1933). This phenotypic variability and lack of a diagnostic marker have complicated the diagnosis and counseling for CdLS.

The prevalence of CdLS is estimated to be as high as 1 in 10,000 (Opitz 1985) and most cases appear to be sporadic. Pedigree analyses of several families demonstrate autosomal dominant inheritance with both maternal and paternal transmission (Robinson et al. 1985; Bankier et al. 1986; Halal and Silver 1992; Feingold and Lin 1993; Chodirker and Chudley 1994; Kozma 1996; Russell et al. 2001; McConnell et al. 2003). Assuming autosomal dominant inheritance, cases of apparently unaffected parents having multiple children with CdLS were hypothesized to be the result of germ line mosaicism (Beratis et al. 1971; Lieber et al. 1973; Fryns et al. 1987; Naguib et al. 1987; Krajewska-Walasek et al. 1995; Caksen et al. 2001). This hypothesis of germ line mosaicism was further supported by the identification of several families where an unaffected parent had multiple affected children through different partners (Krantz et al. 2001).

Due to the severity of the physical and cognitive impairment seen in CdLS, it has long been felt that an underlying chromosomal imbalance encompassing multiple genes may be etiologically responsible. Although several chromosomal rearrangements have been reported in the past in patients with CdLS, no consistent abnormalities have been identified (Kousseff et al. 1994). The identification of individuals with CdLS who carry de novo balanced translocations (Ireland et al. 1991) are of interest as they may be involved in disruption of the causative gene. The frequency of balanced translocations in the general population is estimated to be 1/500 (Bugge, M. 2000), so reports of a handful of apparently unrelated de novo translocations in children with CdLS, most of whom will have chromosomal analysis performed, may in fact be incidental.

Partial phenotypic overlap between individuals with CdLS and individuals with duplications of chromosome 3q (dup 3q syndrome) has been noted (Falek et al. 1966; Aqua M.S. et a. 1995; Ireland et al. 1995; Rizzu et al. 1997) and resulted in a locus assignment in OMIM for CdLS at 3q26 (See NCBI website at nlm. nih.gov/htbinpost/Omim/dispmim?122470). The identification of a de novo t(3;17)(q26.3;q23.1) translocation in a patient with a classic CdLS phenotype (Ireland et al. 1991) with the 3q breakpoint within the dup3q critical region further implicated this region. The 3q breakpoint has been cloned and a novel gene identified at the breakpoint however no mutations have been identified in this gene or in neighboring genes in individuals with CdLS (Smith et al. 1999; Tonkin et al., 2001). Linkage analysis to this region did not demonstrate cosegregation of chromosome 3q markers with the CdLS phenotype in all of the families studied (Krantz et al. 2001). These reports suggested that loci other than 3q26-27 may harbor a CdLS disease gene.

In light of all the foregoing, it is clear that a need exists for a new diagnostic marker for CdLS and methods of use thereof. Such a marker and methods can be used to advantage for genetic counseling and prenatal screening.

SUMMARY OF THE INVENTION

In accordance with the present invention, it has been discovered that NIPBL, when mutated, gives rise to Cornelia de Lange Syndrome (CdLS). Thus, NIPBL provides the first molecular diagnostic marker for this disorder. NIPBL is a large gene consisting of 47 exons spanning 188 kilobases of DNA with a transcript (mRNA) of 9505 base pairs. The gene was identified through a combination of genome-wide linkage analysis and fluorescence in situ hybridization (FISH) in families and individuals with CdLS. Mutations, (e.g., missense, splice site, frameshift and complex) are spread through out the gene, although there appears to be some clustering of mutations in exon 10. Most mutations identified are de novo, i.e., they occurred as a spontaneous event in the affected individual, although certain mutations have been found to run in families.

In one aspect of the invention, a method for diagnosing a patient as having an increased risk of developing Cornelia de Lange Syndrome (CdLS) is disclosed. An exemplary method entails providing a biological sample comprising DNA, or RNA from the individual and assessing the DNA or RNA for the presence or absence of a mutation in the NIPBL gene, wherein the presence of NIPBL gene mutation is correlated with the presence of CdLS in the individual being diagnosed. Suitable biological samples include, but are not limited to blood, saliva, amniotic fluid, and tissue.

In yet another embodiment of the invention, the protein product encoded by the NIPBL gene may be isolated and further assessed to determine whether the mutation, if present, results in an alteration in the amino acid sequence of the protein product. Accordingly, methods of expressing the nucleic acids encoding NIPBL mutated proteins in vitro and in host cells are provided herein. Such proteins and host cells are useful for screening test compounds which bind or modulate the activity of the mutated NIPBL molecules described herein.

A further aspect of the invention is based on the discovery that NIPBL plays a role in sister chromatid cohesion in humans. Accordingly, samples from patients suspected of having CdLS can be screened for precocious sister chromatid separation (PSCS) as described in Example 3. Such screening assays can be performed with or without the mutational screening described in Example 2. In yet another aspect of the invention, PSCS assays can be performed on cells isolated from CdLS patients in the presence and absence of a test compound to determine whether the test compound is capable of modulating the PSCS observed in CdLS patients. Agents which reduce PSCS may have efficacy in the treatment of CdLS.

Diagnostic probes useful in the methods of the invention are also disclosed herein. Suitable probes comprise about 10-200, more preferably about 10-100 and most preferably at least 10 contiguous bases from SEQ ID NOS: 1 or 2. Other exemplary probes suitable for identifying the mutations and polymorphisms described herein can be designed using the information provided in Tables 3, 4 and 5 are encompassed within the scope of the invention. Also provided herein is a kit for practicing the methods disclosed herein. An exemplary kit comprises the diagnostic probes described above useful for identifying alterations in the NIPBL gene, reagents useful for nucleic acid hybridization, polymerase chain reaction or in situ hybridization and suitable instructional materials.

BRIEF DESCRIPTION OF THE DRAWINGS

FIG. 3. Identifying NIPBL as the CdLS disease gene.

FIGS. 5*a-c*) Embryonic day 9.5, whole mount in situ hybridization; FIGS. 5*d-i*) Embryonic day 10.5, vibratome sections (200 μm) of embryos processed for whole mount in situ hybridization. FIGS. 5*a, d, g*) Sense control; FIGS. 5*b, e, h*) mNIPBL; FIGS. 5*c, f, i*) fgf8 (positive control). In FIG. 5*b*, mNIPBL expression is observed widely throughout the embryo, especially in the limb buds and branchial arches (arrow, fore limb bud; arrowhead, first branchial arch). In FIG. 5*c*, FGF8 expression marks a portion of the surface ectoderm of the same structures (arrow and arrowhead as in FIG. 5*b*). At E10.5, sections through the forelimb bud show that mNIPBL expression is concentrated in the mesenchyme (asterisk in FIG. 5*e* marks ventral limb bud mesenchyme; dorsal mesenchyme is also stained), whereas fgf8 expression marks the apical ectodermal ridge (arrow in FIG. 5*f*). No significant differences in intensity between fore- and hind-limb buds were observed (data not shown) Coronal sections at the level of the head show expression of mNIPBL in the mesenchyme of both the lateral and medial nasal processes (labeled L and M, respectively, in FIG. 5*h*). In contrast, fgf8 hybridization marks the ectoderm surrounding the developing nasal pit. Bar in FIG. 5*a*=0.5 mm for FIGS. 5*a-c*; bar in g=0.5 mm for FIGS. 5*d-i*.

FIG. 6. Evolutionary conservation of amino acid residues altered by missense mutations in NIPBL. A comparison of amino acids and the flanking sequences altered by 11 of the unique missense mutations in human (NIPBL) (SEQ ID NO: 118), rat (SEQ ID NO: 119), mouse (SEQ ID NO: 119) and *Drosophila* (SEQ ID NO: 120) is depicted. The mutated amino acid residue is shaded grey. Amino acid residue 2298 was mutated in three individuals- two had an R2298H change, and one had an R2298C change. The missense mutation M1K in the initation codon is not depicted since it is conserved in all species.

FIGS. 7A1-7Z2. The genomic sequence of the NIPBL gene. (SEQ ID NO: 1)

FIG. 8. The cDNA sequence encoded by the NIPBL gene. (SEQ ID NO: 2)

FIG. 9. The amino acid sequence of the protein encoded by the NIPBL gene. (SEQ ID NO: 3).

DETAILED DESCRIPTION OF THE INVENTION

Figure 1:
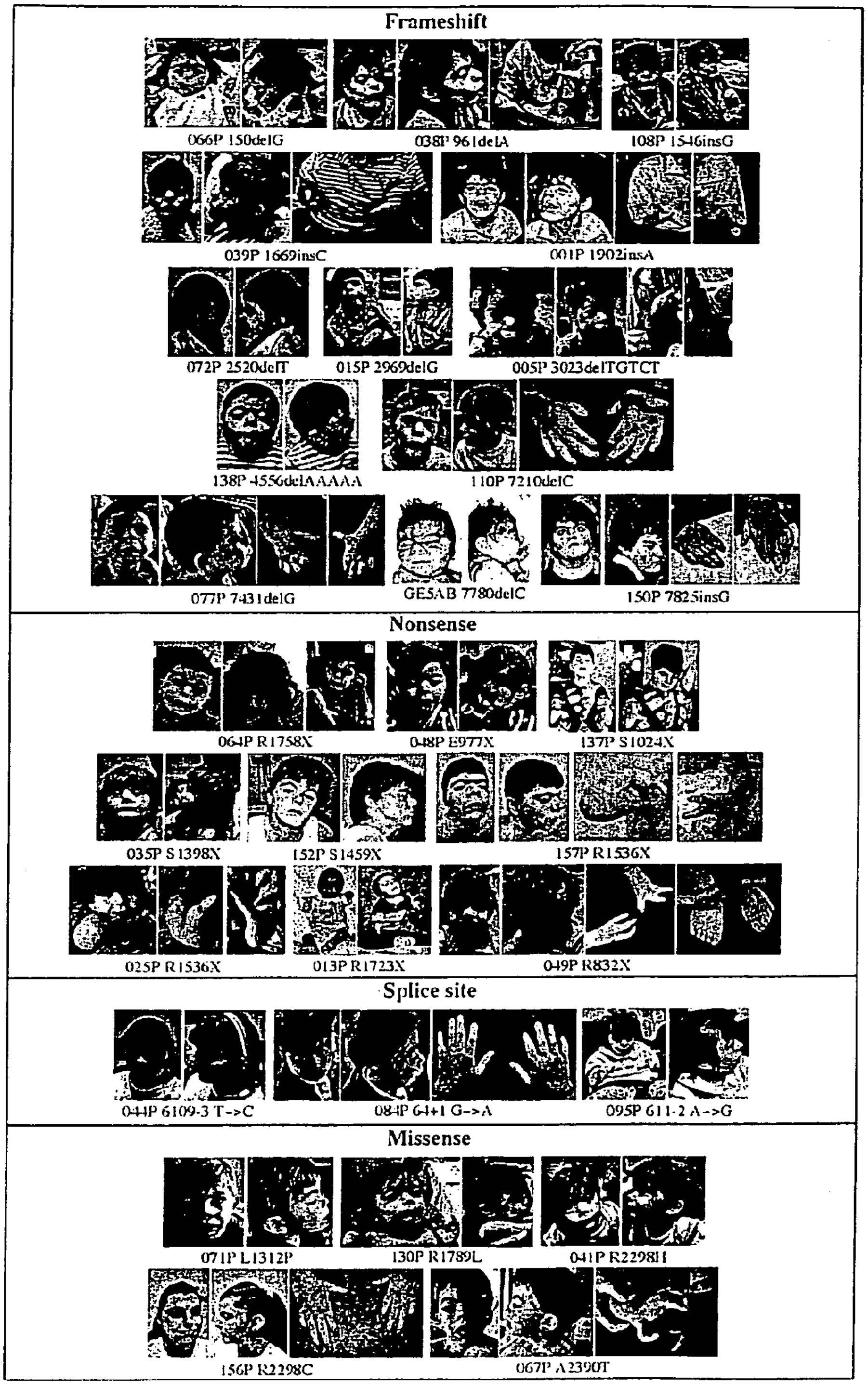
FIG. 1. Facial features and limb findings in mutation positive individuals with CdLS. Note the variability of features even among individuals with similar mutation types.

In accordance with the present invention, it has been discovered that mutations in NIPBL cause CdLS. Types of mutations identified in NIPBL include, missense, splice site, nonsense, and frameshift. Severe protein truncating mutations likely lead to haploinsufficiency of the NIPBL protein. Haploinsufficiency of NIPBL has been documented as a disease mechanism through the report of a child with classic features of CdLS who was stillborn but found prenatally to have a large cytogenetically visible deletion of chromosome 5p13.1-14.2 (Hulinsky et al. 2003). This deletion would be predicted to encompass the NIPBL gene. To our knowledge, there has not been any other reported cases of constitutional deletions of this region. The hypothesis of germ-line mosaicism was also validated by the identification of the same NIPBL mutation in affected siblings born to unaffected mutation-negative parents (Krantz et al. 2004).

The prevalence of NIPBL mutations in a large CdLS population and the correlation of specific mutations with phenotypic characteristics have not previously been formally addressed. The systematic molecular and cytogenetic evaluation of 120 individuals with CdLS for disruptions in the NIPBL gene is described herein. Mutations in 47% of tested probands have been identified and this cohort has been further assessed for genotype-phenotype correlations.

NIPBL is the human homolog of the *Drosophila* Nipped-B gene. Although its function in mammalian systems has not yet been elucidated, sequence homologs of Nipped-B in yeast (Scc2 and Mis4) are required for sister chromatid cohesion during mitosis, and a similar role was recently demonstrated for Nipped-B in *Drosophila*. In order to evaluate NIPBL's role in sister chromatid cohesion in humans, metaphase spreads on 90 probands (40 NIPBL mutation positive and 50 NIPBL mutation negative) with CdLS were evaluated for evidence of precocious sister chromatid separation (PSCS). We screened 50 metaphases from each proband and found evidence of PSCS in 41% (compared to 9% in control samples). These studies indicate that NIPBL may play a role in sister chromatid cohesion in humans as has been reported for its homologs in *Drosophila* and yeast.

I. Methods of Diagnosis

The present invention provides methods of identifying patients having a variant allele of a gene associated with the CdLS phenotype. The gene (NIPBL) is located in human chromosome 5 in the region conventionally designated p13.1 by reference to cytological markers and DNA. Specifically, the gene is within a segment of about 7.4 Mb spaning 5p13.1-13.3 and flanked by markers D5S477 distally and D5S1376 proximally and contained 58 putative genes. An allele of the gene present in persons not suffering from CdLS is arbitrarily designated as wildtype. A variant allele of the gene is associated with a phenotype of CdLS. Such genetic variants include, without limitation, nucleotide additions, deletions or substitutions relative to the wildtype allele. These genetic alterations are associated with a phenotype of CdLS, as defined above (see Example 1) in at least some individuals bearing the variant allele. The phenotype may result from a nucleotide change in the gene (addition, deletion or substitution) affecting expression of the gene by altering the kinetics of expression or the nature of the resulting expression product. For example, some genetic changes reduce transcription or translation of an expression product. Other changes result in a polypeptide having altered properties (cf. the sickle cell mutation). Still other changes introduce a premature stop codon thereby resulting in truncated expression product.

The genetic tests of the present invention provide a highly accurate assay for diagnosing CdLS. Physicians having the correct diagnosis in hand can then ensure that patients receive prophylactic or therapeutic treatment appropriate to the genetic and biochemical features of the disease.

The methods may also be used to advantage for in utero screening of fetuses for the presence of a variant NIPBL allele. Identification of such variations offers the possibility of gene therapy. For couples known to be at risk of giving rise to affected progeny, diagnosis can be combined with in vitro reproduction procedures to identify an embryo having wildtype NIPBL alleles before implantation. Screening children shortly after birth is also of value in identifying those having the variant gene. Early detection allows administration of appropriate treatment.

A. Mode of Inheritance

Evidence reveals that a CdLS susceptibility gene can be inherited in an autosomal dominant fashion. In 6 of the 7 familial cases, the NIPBL mutation appears to have resulted from germline mosaicism.

B. Diagnosis from Linked Polymorphic Markers

The invention further provides methods of diagnosing susceptibility to CdLS by detection of polymorphic markers linked to the NIPBL gene on human chromosome 5. Markers are linked if they occur within 50 cM from each other or the NIPBL gene. Preferably, markers occur within 15 cM and more preferably within 5 or 1 cM of the gene. The closer the polymorphic marker is to NIPBL locus, the less likely there is to be physical recombination between the two loci at meiosis. The polymorphic marker is usually outside the NIPBL gene, but also may occur within the gene. All human chromosomes are subdivided into regions by cytological and polymorphic markers. Example 1 shows that preferred markers include those mapped between D5S477 and D5S1376. Thus, these markers and other markers within about 5 cM are preferred for use in the methods of the present invention. Most preferred are markers which occur within the NIPBL gene itself. The claimed methods are utilized to determine which alleles of a linked polymorphic marker are present in the patient being diagnosed. For example, if the polymorphic marker is an RFLP, the alleles differ in the size of a restriction fragment. The determination is typically made by PCR amplification of a segment spanning the polymorphism and gel analysis of the amplification product. If one of the alleles present in the patient is known to be in phase with a variant NIPBL locus (i.e., present on the same chromosome), it is concluded with a high probability that the patient has a variant NIPBL gene and will have CdLS. The closer linked the polymorphic marker to NIPBL, the higher the probability that the patient has received the variant NIPBL gene. See Sutherland & Mulley, Clinical Genetics 37:2-11 (1990). Preferably, the methods analyze the presence of alleles of two polymorphic markers spaced on either side of the NIPBL gene and both in phase with the gene. Absent a rare double recombination event, the presence of both alleles signals the presence of the variant NIPBL gene.

The method described above requires knowledge that a particular allele of a marker is in phase with the variant form of the NIPBL gene. This information is acquired from analyzing the phenotype and polymorphic content of relatives of the patient in a family, some of whose members exhibit CdLS. The linkage and/or phase determinations are usually performed before analysis of DNA from the patient.

A phase determination requires at least two relatives of the patient who are of known phenotype for CdLS, at least one of the relatives having the disease and being informative for the marker. In practice, a relative having the disease is screened at several polymorphic markers to identify at least one marker in which the relative is heterozygous. The phase of this marker is then set by determining which alleles of the marker are present in a second relative of known phenotype. Strategies for setting phase in different families are described by Lazarou, Clinical Genetics 43:150-156 (1993). For example, consider two siblings, X (with disease) having alleles 1 and 2 of a marker linked to the disease, and Y (without disease) having alleles 3 and 4. It can be concluded that in this family, the 1 and 2 alleles are in phase with the variant NIPBL gene. As a further example, consider X (with disease) having alleles 1 and 2 and Y (with disease) having alleles 1 and 5. It is deduced that the 1, 2 and 5 alleles are in phase with the variant gene. Within a family, the allele of a closely linked marker that is in phase with the variant gene is usually the same in each affected family member because there is a low probability of recombination between the two loci. The more closely related the relatives to the patient, the more likely phase is to be conserved between the relatives and the patient. Thus, it is preferred that one of the relatives used in setting phase is a parent or sibling of the patient. Once phase has been determined for a family, multiple members of the family can be diagnosed without repeating the analysis. In general, the phase relationship between an allele of a polymorphic marker and a variant allele of the NIPBL gene is different in each family. However, certain alleles may be in linkage disequilibrium with the NIPBL gene. For such markers, the same allele is likely to be in phase with the variant allele of the NIPBL gene in any family. Thus, once such an allele is identified it is not necessary to set phase in every family to be tested.

C. Direct Assays for NIPBL Gene

Having localized the NIPBL gene as described infra, variations can be detected by more direct methods. These methods represent a special case of the methods described above in which the polymorphic marker being detected is a variation arising within the NIPBL gene.

1. Detection of Uncharacterized Variations

Hitherto uncharacterized variations in the NIPBL gene are identified and localized to specific nucleotides by comparison of nucleic acids from an individual with CdLS with an unaffected individual, preferably a relative of the affected individual. Comparison with a relative is preferred because the possibility of other polymorphic differences between the patient and person being compared, not related to the CdLS phenotype, is lower. Various screening methods are suitable for this comparison including, but not limited to, direct DNA sequencing, single strand conformation polymorphism analysis (SSCP), conformation shift gel electrophoresis (CSGE), heteroduplex analysis (HA), chemical cleavage of mismatched sequences (CCMS), denaturing gradient gel electrophoresis (DGGE), temperature gradient gel electrophoresis (TGGE), denaturing high performance liquid chromatography (dHPLC), ribonuclease cleavage, carbodiimide modification, and microarray analysis. See Cotton, Mutation Res. 285:125-144 (1993). Comparison can be initiated at either cDNA or genomic level. Initial comparison is often easier at the cDNA level because of its shorter size. Corresponding genomic changes are then identified by amplifying and sequencing a segment from the genomic exon including the site of change in the cDNA. In some instances, there is a simple relationship between genomic and cDNA changes. That is, a single base change in a coding region of genomic DNA gives rise to a corresponding changed codon in the cDNA. In other instances, the relationship between genomic and cDNA changes is more complex. Thus, for example, a single base change in genomic DNA creating an aberrant splice site can give rise to deletion of a substantial segment of cDNA.

2. Detection of Characterized Changes

The preceding methods serve to identify particular genetic changes responsible for CdLS. In a small number of families, affected members have the same change. However, individuals from different families appear to have different changes in the NIPBL gene. In contrast, in cystic fibrosis, about seventy percent of individuals have the same mutation in the CFTR gene. Once a change has been identified within a family, and/or as occurring within a population of affected individuals at a significant frequency, individuals can be tested for that change by various methods. A sample of such changes is provided in Tables 4 and 5. These methods include direct sequencing, allele-specific oligonucleotide hybridization, allele-specific amplification, ligation, primer extension and artificial introduction of extension sites (see Cotton, supra). For example, the allele-specific detection method uses one oligonucleotide exhibiting a perfect match to a target segment of the NIPBL gene having the change and a paired probe exhibiting a perfect match to the corresponding wildtype segment. If the individual is homozygous wildtype, only the wildtype probe binds. If the individual is a heterozygous variant, both probes bind. If the individual is a homozygous variant, only the variant probe binds. Paired probes for several variations can be immobilized as an array and the presence of several variations can thereby be analyzed simultaneously. Of course, the methods noted above, for analyzing uncharacterized variations can also be used for detecting characterized variations.

II. Identification of the NIPBL Gene

In accordance with the present invention, a human gene, NIPBL, has been discovered, which when mutated, gives rise to Cornelia de Lange syndrome. Genome-wide exclusion analysis was performed in 12 CdLS families resulting in the identification of 4 candidate regions, with chromosome 5p13.1 giving the highest multipoint LOD score of 2.7. Within this region, mutations in one gene, NIPBL, were identified in 4 sporadic and two familial CdLS cases. The gene is widely expressed in human tissues and is the human homolog of the *Drosphila* Nipped-B gene. The product of the Nipped-B gene is a facilitator of enhancer-promoter communication and plays a role in Notch signaling and other developmental pathways in *Drosophila.*

III. Expression Systems

Identification of the NIPBL gene facilitates the production of the gene product. The cDNA fragment or any other nucleic acid encoding the NIPBL gene can be used to make an expression construct for the NIPBL gene. The expression construct typically comprises one or more nucleic acid sequences encoding the NIPBL gene operably linked to a native or other promoter. Usually, the promoter is a eukaryotic promoter for expression in a mammalian cell. The transcription regulation sequences typically include a heterologous enhancer or promoter which is recognized by the host. The selection of an appropriate promoter, for example trp, lac, phage promoters, glycolytic enzyme promoters and tRNA promoters, depends on the host selected. Commercially available expression vectors can be used. Vectors can include host-recognized replication systems, amplifiable genes, selectable markers, host sequences useful for insertion into the host genome, and the like.

The means of introducing the expression construct into a host cell varies depending upon the particular vector and targeted host cell. Suitable means include fusion, conjugation, transfection, transduction, electroporation or injection, as described in Sambrook, supra. A wide variety of host cells can be employed for expression of the NIPBL gene, both prokaryotic and eukaryotic. Suitable host cells include bacteria such as *E. coli*, yeast, filamentous fungi, insect cells, mammalian cells, typically immortalized, e.g., mouse, CHO, human and monkey cell lines and derivatives thereof. Preferred host cells are able to process the NIPBL gene product to produce an appropriate mature polypeptide. Processing includes glycosylation, ubiquitination, disulfide bond formation, general post-translational modification, and the like.

The NIPBL protein may be isolated by conventional means of protein biochemistry and purification to obtain a substantially pure product, i.e., 80, 95 or 99% free of cell component contaminants, as described in Jacoby, Methods in Enzymology Volume 104, Academic Press, N.Y. (1984); Scopes, Protein Purification, Principles and Practice, 2nd Edition, Springer-Verlag, N.Y. (1987); and Deutscher (ed), Guide to Protein Purification, Methods in Enzymology, Vol. 182 (1990). If the protein is secreted, it can be isolated from the supernatant in which the host cell is grown. If not secreted, the protein can be isolated from a lysate of the host cells.

The invention further provides transgenic nonhuman animals capable of expressing an exogenous NIPBL gene and/or having one or both alleles of an endogenous NIPBL gene inactivated. Expression of an exogenous NIPBL gene is usually achieved by operably linking the gene to a promoter and optionally an enhancer, and microinjecting the construct into a zygote. See Hogan et al., "Manipulating the Mouse Embryo, A Laboratory Manual," Cold Spring Harbor Laboratory. Inactivation of endogenous NIPBL genes can be achieved by forming a transgene in which a cloned NIPBL gene is inactivated by insertion of a positive selection marker. See Capecchi, Science 244:1288-1292 (1989). The transgene is then introduced into an embryonic stem cell, where it undergoes homologous recombination with an endogenous NIPBL gene. Mice and other rodents are preferred animals. Such animals provide useful in vivo drug screening systems.

In addition to substantially full-length polypeptides expressed by the NIPBL gene, the present invention includes biologically active fragments of the polypeptides, or analogs thereof, including organic molecules which simulate the interactions of the peptides. Biologically active fragments include any portion of the full-length polypeptide which confers a biological function on the NIPBL gene product, including ligand binding, substrate for other molecules, dimer association, and the like. Ligand binding includes binding by nucleic acids, proteins or polypeptides, small biologically active molecules, or large cellular structures.

Polyclonal and/or monoclonal antibodies to the NIPBL gene product are also provided. Antibodies can be made by injecting mice or other animals with the NIPBL gene product or synthetic peptide fragments thereof. Monoclonal antibodies are screened by methods known in the art, as are described, for example, in Harlow & Lane, Antibodies, A Laboratory Manual, Cold Spring Harbor Press, N.Y. (1988), and Goding, Monoclonal antibodies, Principles and Practice (2d ed.) Academic Press, New York (1986). Monoclonal antibodies are tested for specific immunoreactivity with an epitope of the NIPBL gene product. These antibodies are useful in diagnostic assays for detection of the NIPBL gene product or a variant form thereof, or as an active ingredient in a pharmaceutical composition.

IV. Methods of Treatment

There are a number of drugs presently in use for treating the symptoms of CdLS. The present discovery that at least some subtypes of CdLS are associated with common genetic and presumably, biochemical features allows drug screening programs to be conducted in a group of patients having homogeneous disposition with respect to the NIPBL gene. Such a group is identified by the diagnostic methods discussed above. The provision of DNA encoding the NIPBL gene is also useful in developing new drugs and methods of treatment for CdLS. For example, variations in the NIPBL gene, including regulatory sequences, can be corrected by gene therapy. See Rosenberg, J. Clin. Oncol. 10:180-199 (1992). Gene therapy is preferably performed in utero rather than after birth, because of the undifferentiated nature of cells in a developing fetus. Exogenously supplied corrective genes integrate into the genomes of undifferentiated cells, and are subsequently distributed and expressed in entire tissues by the proliferation and differentiation of the ancestor cell.

The provision of the NIPBL gene product also allows screening for molecules that interact with the same and design of agents that agonize or antagonize this interaction. Such agents include monoclonal antibodies against the NIPBL gene product, fragments of the NIPBL gene product that compete with the full-length protein for binding, and synthetic peptides or analogs thereof selected from random combinatorial libraries. See, e.g., Ladner et al., U.S. Pat. No. 5,223,409 (1993) (incorporated by reference in its entirety herein). Therapeutic agents also includes transcription factors, and the like, which stimulate expression of the NIPBL gene.

V. Diagnostic Kits

The present invention also includes kits for the practice of the methods of the invention. The kits comprise a vial, tube, or any other container which contains one or more oligonucleotides or diagnostic probes, which hybridizes to a DNA segment within chromosome 5p13, which DNA segment is linked to the NIPBL gene. Preferably, the oligonucleotide hybridizes to a segment of chromosome 5 between markers D5S477 and D5S1376. Most preferably, the diagnostic probes will hybridize to at least one DNA molecule comprising an alteration as described in Table 4. Preferably, additional probes will be employed to identify a polymorphism set forth in Table 5. Some kits contain two such oligonucleotides, which serve as primers to amplify a segment of chromosome DNA. The segment selected for amplification can be a polymorphic marker linked to the NIPBL gene or a region from the NIPBL gene that includes a site at which a variation is known to occur. See Tables 3, 4 and 5. Some kits contain a pair of oligonucleotides for detecting precharacterized variations. For example, some kits contain oligonucleotides suitable for allele-specific oligonucleotide hybridization, or allele-specific amplification hybridization. The kits of the invention may also contain components of the amplification system, including PCR reaction materials such as buffers and a thermostable polymerase. In other embodiments, the kit of the present invention can be used in conjunction with commercially available amplification kits, such as may be obtained from GIBCO BRL (Gaithersburg, Md.) Stratagene (La Jolla, Calif.), Invitrogen (San Diego, Calif.), Schleicher & Schuell (Keene, N.H.), Boehringer Mannheim (Indianapolis, Ind.). The kits may optionally include positive or negative control reactions or markers, molecular weight size markers for gel electrophoresis, and the like. The kits usually include labelling or instructions indicating the suitability of the kits for diagnosing CdLS and indicating how the oligonucleotides are to be used for that purpose. The term "label" is used generically to encompass any written or recorded material that is attached to, or otherwise accompanies the diagnostic at any time during its manufacture, transport, sale or use.

Kits for performing PSCS assays may contain reagents suitable for isolating blood or lymphoblastoid cells from CdLS patients and culture media and reagents which promote the growth and viability of such cells. Such kits may also contain reagents (e.g., giemsa stain) for generating metaphase spreads from cells so cultured.

MODES OF PRACTICING THE INVENTION

1. Mutational Analysis/Conformation Sensitive Gel Electrophoresis (CSGE).

Conformation sensitive gel electrophoresis (CSGE) was carried out using standard protocols. See Examples I and II. Oligonucleotide primer sequences and PCR conditions used for amplification of all exons of the NIPBL gene are provided herein. PCR products corresponding to all altered migration patterns (shifts) were purified using QIAquick® PCR purification kit, QIAGEN Sciences) and sequenced on an ABI 377 sequencer.

2. Linkage Analysis

Determining linkage between a polymorphic marker and a locus associated with a particular phenotype is performed by mapping polymorphic markers and observing whether they co-segregate with the CdLS phenotype on a chromosome in an informative meiosis. See, e.g., Kerem et al., Science 245: 1073-1080 (1989); Monaco et al., Nature 316:842 (1985); Yamoka et al., Neurology 40:222-226 (1990), and as reviewed in Rossiter et al., FASEB Journal 5:21-27 (1991). A single pedigree rarely contains enough informative meioses to provide definitive linkage, because families are often small and markers may be not sufficiently informative. For example, a marker may not be polymorphic in a particular family.

Linkage may be established by an affected sib-pairs analysis as described in Terwilliger & Ott, Handbook of Human Genetic Linkage (Johns Hopkins, Md., 1994), Ch. 26. This approach requires no assumptions to be made concerning penetrance or variant frequency, but only takes into account the data of a relatively small proportion (i.e., the SIB pairs) of all the family members whose phenotype and polymorphic markers have been determined. Specifically, the affected SIB pairs analysis scores each pair of affected SIBS as sharing (concordant) or not sharing (discordant) the same allelic variant of each polymorphic marker. For each marker, a probability is then calculated that the observed ratio of concordant to discordant SIB pairs would arise without linkage of the marker.

As described in Thompson & Thompson, Genetics in Medicine, 5th ed, 1991, W.B. Saunders Company, Philadelphia, in linkage analysis, one calculates a series of likelihood ratios (relative odds) at various possible values of 0, ranging from $\theta$=0.0 (no recombination) to $\theta$=0.50 (random assortment). Thus, the likelihood ratio at a given value of $\theta$ is (likelihood of data if aloci are linked at $\theta$)/(likelihood of data if loci are unlinked). Evidence in support of linkage is usually expressed as the $\log_{10}$ of this ratio and called a "lod score" for "logarithm of the odds." For example, a lod score of 5 indicates 100,000:1 odds that the linkage being observed did not occur by chance. The use of logarithms allows data collected from different families to be combined by simple addition. Computer programs are available for the calculation of lod scores for differing values of $\theta$. Available programs include LIPED, and MLINK (Lathrop, Proc. Nat. Acad. Sci. 81:3443-3446 (1984).

For any particular lod score, a recombination fraction may be determined from mathematical tables. See Smith et al., Mathematical tables for research workers in human genetics (Churchill, London, 1961) and Smith, Ann. Hum. Genet. 32:127-150 (1968). The value of $\theta$ at which the lod score is the highest is considered to be the best estimate of the recombination fraction, the "maximum likelihood estimate".

Positive lod score values suggest that the two loci are linked, whereas negative values suggest that linkage is less likely (at that value of $\theta$) than the possibility that the two loci are unlinked. By convention, a combined lod score of +3 or greater (equivalent to greater than 1000:1 odds in favor of linkage) is considered definitive evidence that two loci are linked. Similarly, by convention, a negative lod score of −2 or less is taken as definitive evidence against linkage of the two loci being compared. If there are sufficient negative linkage data, a locus can be excluded from an entire chromosome, or a portion thereof, a process referred to as exclusion mapping. The search is then focused on the remaining non-excluded chromosomal locations. For a general discussion of lod scores and linkage analysis, see, e.g., T. Strachan, Chapter 4, "Mapping the human genome" in The Human Genome, 1992 BIOS Scientific Publishers Ltd. Oxford.

The data can also be subjected to haplotype analysis. This analysis assigns allelic markers between the chromosomes of an individual such that the number of recombinational events needed to account for segregation between generations is minimized. Linkage may also be established by determining the relative likelihood of obtaining observed segregation data for any two markers when the two markers are located at a recombination fraction $\theta$, versus the situation in which the two markers are not linked, and thus segregating independently.

3. Isolation and Amplification of DNA

Samples of patient, proband or family member genomic DNA is isolated from any convenient source including saliva, buccal cells, hair roots, blood, cord blood, amniotic fluid, interstitial fluid, peritoneal fluid, chorionic villus, and any other suitable cell or tissue sample with intact interphase nuclei or metaphase cells. The cells can be obtained from solid tissue as from a fresh or preserved organ or from a tissue sample or biopsy. The sample can contain compounds which are not naturally intermixed with the biological material such as preservatives, anticoagulants, buffers, fixatives, nutrients, antibiotics, or the like.

Methods for isolation of genomic DNA from these various sources are described in, for example, Kirby, DNA Fingerprinting, An Introduction, W.H. Freeman & Co. New York (1992). Genomic DNA can also be isolated from cultured primary or secondary cell cultures or from transformed cell lines derived from any of the aforementioned tissue samples.

Samples of patient, proband or family member RNA can also be used. RNA can be isolated from tissues expressing the NIPBL gene as described in Sambrook et al., supra. RNA can be total cellular RNA, mRNA, poly A+ RNA, or any combination thereof. For best results, the RNA is purified, but can also be unpurified cytoplasmic RNA. RNA can be reverse transcribed to form DNA which is then used as the amplification template, such that the PCR indirectly amplifies a specific population of RNA transcripts. See, e.g., Sambrook, supra, Kawasaki et al., Chapter 8 in PCR Technology, (1992) supra, and Berg et al., Hum. Genet. 85:655-658 (1990).

4. PCR Amplification

The most common means for amplification is polymerase chain reaction (PCR), as described in U.S. Pat. Nos. 4,683,195, 4,683,202, 4,965,188 each of which is hereby incorporated by reference. If PCR is used to amplify the target regions in blood cells, heparinized whole blood should be drawn in a sealed vacuum tube kept separated from other samples and handled with clean gloves. For best results, blood should be processed immediately after collection; if this is impossible, it should be kept in a sealed container at 4° C. until use. Cells in other physiological fluids may also be assayed. When using any of these fluids, the cells in the fluid should be separated from the fluid component by centrifugation.

Tissues should be roughly minced using a sterile, disposable scalpel and a sterile needle (or two scalpels) in a 5 mm Petri dish. Procedures for removing paraffin from tissue sections are described in a variety of specialized handbooks well known to those skilled in the art.

To amplify a target nucleic acid sequence in a sample by PCR, the sequence must be accessible to the components of the amplification system. One method of isolating target DNA is crude extraction which is useful for relatively large samples. Briefly, mononuclear cells from samples of blood, amniocytes from amniotic fluid, cultured chorionic villus cells, or the like are isolated by layering on sterile Ficoll-Hypaque gradient by standard procedures. Interphase cells are collected and washed three times in sterile phosphate buffered saline before DNA extraction. If testing DNA from peripheral blood lymphocytes, an osmotic shock (treatment of the pellet for 10 sec with distilled water) is suggested, followed by two additional washings if residual red blood cells are visible following the initial washes. This will prevent the inhibitory effect of the heme group carried by hemoglobin on the PCR reaction. If PCR testing is not performed immediately after sample collection, aliquots of $10^6$ cells can be pelleted in sterile Eppendorf tubes and the dry pellet frozen at −20° C. until use.

The cells are resuspended ($10^6$ nucleated cells per 100 μl) in a buffer of 50 mM Tris-HCl (pH 8.3), 50 mM KCl 1.5 mM $MgCl_2$, 0.5% Tween 20, 0.5% NP40 supplemented with 100 μg/ml of proteinase K. After incubating at 56° C. for 2 hr, the cells are heated to 95° C. for 10 min to inactivate the proteinase K and immediately moved to wet ice (snap-cool). If gross aggregates are present, another cycle of digestion in the same buffer should be undertaken. Ten μl of this extract is used for amplification. When extracting DNA from tissues, e.g., chorionic villus cells or confluent cultured cells, the amount of the above mentioned buffer with proteinase K may vary according to the size of the tissue sample. The extract is incubated for 4-10 hrs at 50°-60° C. and then at 95° C. for 10 minutes to inactivate the proteinase. During longer incubations, fresh proteinase K should be added after about 4 hr at the original concentration.

When the sample contains a small number of cells, extraction may be accomplished by methods as described in Higuchi, "Simple and Rapid Preparation of Samples for PCR", in PCR Technology, Ehrlich, H. A. (ed.), Stockton Press, N.Y., which is incorporated herein by reference. PCR can be employed to amplify target regions chromosome 1 in very small numbers of cells (1000-5000) derived from individual colonies from bone marrow and peripheral blood cultures. The cells in the sample are suspended in 20 μl of PCR lysis buffer (10 mM Tris-HCl (pH 8.3), 50 mM KCl, 2.5 mM $MgCl_2$, 0.1 mg/ml gelatin, 0.45% NP40, 0.45% Tween 20) and frozen until use. When PCR is to be performed, 0.6 μl of proteinase K (2 mg/ml) is added to the cells in the PCR lysis buffer. The sample is then heated to about 60° C. and incubated for 1 hr. Digestion is stopped through inactivation of the proteinase K by heating the samples to 95° C. for 10 min and then cooling on ice.

A relatively easy procedure for extracting DNA for PCR is a salting out procedure adapted from the method described by Miller et al., Nucleic Acids Res. 16:1215 (1988), which is incorporated herein by reference. Mononuclear cells are separated on a Ficoll-Hypaque gradient. The cells are resuspended in 3 ml of lysis buffer (10 mM Tris-HCl, 400 mM NaCl, 2 mM $Na_2$ EDTA, pH 8.2). Fifty μl of a 20 mg/ml solution of proteinase K and 150 μl of a 20% SDS solution are added to the cells and then incubated at 37° C. overnight. Rocking the tubes during incubation will improve the digestion of the sample. If the proteinase K digestion is incomplete after overnight incubation (fragments are still visible), an additional 50 μl of the 20 mg/ml proteinase K solution is mixed in the solution and incubated for another night at 37° C. on a gently rocking or rotating platform. Following adequate digestion, one ml of a 6M NaCl solution is added to the sample and vigorously mixed. The resulting solution is centrifuged for 15 minutes at 3000 rpm. The pellet contains the precipitated cellular proteins, while the supernatant contains the DNA. The supernatant is removed to a 15 ml tube that contains 4 ml of isopropanol. The contents of the tube are mixed gently until the water and the alcohol phases have mixed and a white DNA precipitate has formed. The DNA precipitate is removed and dipped in a solution of 70% ethanol and gently mixed. The DNA precipitate is removed from the ethanol and air-dried. The precipitate is placed in distilled water and dissolved.

Kits for the extraction of high-molecular weight DNA for PCR include a Genomic Isolation Kit A.S.A.P. (Boehringer Mannheim, Indianapolis, Ind.), Genomic DNA Isolation System (GIBCO BRL, Gaithersburg, Md.), Elu-Quik DNA Purification Kit (Schleicher & Schuell, Keene, N.H.), DNA Extraction Kit (Stratagene, La Jolla, Calif.), TurboGen Isolation Kit (Invitrogen, San Diego, Calif.), and the like. Use of these kits according to the manufacturer's instructions is generally acceptable for purification of DNA prior to practicing the methods of the present invention.

The concentration and purity of the extracted DNA can be determined by spectrophotometric analysis of the absorbance of a diluted aliquot at 260 nm and 280 nm. After extraction of the DNA, PCR amplification may proceed. The first step of each cycle of the PCR involves the separation of the nucleic acid duplex formed by the primer extension. Once the strands are separated, the next step in PCR involves hybridizing the separated strands with primers that flank the target sequence. The primers are then extended to form complementary copies of the target strands. For successful PCR amplification, the primers are designed so that the position at which each primer hybridizes along a duplex sequence is such that an extension product synthesized from one primer, when separated from the template (complement), serves as a template for the extension of the other primer. The cycle of denaturation, hybridization, and extension is repeated as many times as necessary to obtain the desired amount of amplified nucleic acid.

In a particularly useful embodiment of PCR amplification, strand separation is achieved by heating the reaction to a sufficiently high temperature for an sufficient time to cause the denaturation of the duplex but not to cause an irreversible denaturation of the polymerase (see U.S. Pat. No. 4,965,188, incorporated herein by reference). Typical heat denaturation involves temperatures ranging from about 80° C. to 105° C. for times ranging from seconds to minutes. Strand separation, however, can be accomplished by any suitable denaturing method including physical, chemical, or enzymatic means. Strand separation may be induced by a helicase, for example, or an enzyme capable of exhibiting helicase activity. For example, the enzyme RecA has helicase activity in the presence of ATP. The reaction conditions suitable for strand separation by helicases are known in the art (see Kuhn Hoffman-Berling, 1978, CSH-Quantitative Biology, 43:63-67; and Radding, 1982, Ann. Rev. Genetics 16:405-436, each of which is incorporated herein by reference).

Template-dependent extension of primers in PCR is catalyzed by a polymerizing agent in the presence of adequate amounts of four deoxyribonucleotide triphosphates (typically dATP, dGTP, dCTP, and dTTP) in a reaction medium comprised of the appropriate salts, metal cations, and pH buffering systems. Suitable polymerizing agents are enzymes known to catalyze template-dependent DNA synthesis.

In some cases, the target regions may encode at least a portion of a protein expressed by the cell. In this instance, mRNA may be used for amplification of the target region. Alternatively, PCR can be used to generate a cDNA library from RNA for further amplification, the initial template for primer extension is RNA. Polymerizing agents suitable for synthesizing a complementary, copy-DNA (cDNA) sequence from the RNA template are reverse transcriptase (RT), such as avian myeloblastosis virus RT, Moloney murine leukemia virus RT, or Thermus thermophilus (Tth) DNA polymerase, a thermostable DNA polymerase with reverse transcriptase activity marketed by Perkin Elmer Cetus, Inc. Typically, the genomic RNA template is heat degraded during the first denaturation step after the initial reverse transcription step leaving only DNA template. Suitable polymerases for use with a DNA template include, for example, *E. coli* DNA polymerase I or its Klenow fragment, T4 DNA polymerase, Tth polymerase, and Taq polymerase, a heat-stable DNA polymerase isolated from Thermus aquaticus and commercially available from Perkin Elmer Cetus, Inc. The latter enzyme is widely used in the amplification and sequencing of nucleic acids. The reaction conditions for using Taq polymerase are known in the art and are described in Gelfand, 1989, PCR Technology, supra.

5. Allele Specific PCR

Allele-specific PCR differentiates between chromosome 5 target regions differing in the presence or absence of a variation or polymorphism. PCR amplification primers are chosen which bind only to certain alleles of the target sequence. Thus, for example, amplification products are generated from those chromosome 5 sets which contain the primer binding sequence, and no amplification products are generated in chromosome 5 sets without the primer binding sequence. This method is described by Gibbs, Nucleic Acid Res. 17:12427-2448 (1989).

6. Allele Specific Oligonucleotide Screening Methods

Further diagnostic screening methods employ the allele-specific oligonucleotide (ASO) screening methods, as described by Saiki et al., Nature 324:163-166 (1986). Oligonucleotides with one or more base pair mismatches are generated for any particular allele. ASO screening methods detect mismatches between variant target genomic or PCR amplified DNA and non-mutant oligonucleotides, showing decreased binding of the oligonucleotide relative to a mutant oligonucleotide. Oligonucleotide probes can be designed that under low stringency will bind to both polymorphic forms of the allele, but which at higher stringency, bind to the allele to which they correspond. Alternatively, stringency conditions can be devised in which an essentially binary response is obtained, i.e., an ASO corresponding to a variant form of the NIPBL gene will hybridize to that allele, and not to the wildtype allele.

7. Ligase Mediated Allele Detection Method

Target regions of a patients can be compared with target regions in unaffected and affected family members by ligase-mediated allele detection. See Landegren et al., Science 241: 1077-1080 (1988). Ligase may also be used to detect point mutations in the ligation amplification reaction described in Wu et al., Genomics 4:560-569 (1989). The ligation amplification reaction (LAR) utilizes amplification of specific DNA sequence using sequential rounds of template dependent ligation as described in Wu, supra, and Barany, Proc. Nat. Acad. Sci. 88:189-193 (1990).

8. Denaturing Gradient Gel Electrophoresis

Amplification products generated using the polymerase chain reaction can be analyzed by the use of denaturing gradient gel electrophoresis. Different alleles can be identified based on the different sequence-dependent melting properties and electrophoretic migration of DNA in solution. DNA molecules melt in segments, termed melting domains, under conditions of increased temperature or denaturation. Each melting domain melts cooperatively at a distinct, base-specific melting temperature (Tm). Melting domains are at least 20 base pairs in length, and may be up to several hundred base pairs in length.

Differentiation between alleles based on sequence specific melting domain differences can be assessed using polyacrylamide gel electrophoresis, as described in Chapter 7 of Erlich, ed., PCR Technology, Principles and Applications for DNA Amplification, W.H. Freeman and Co, N.Y. (1992), the contents of which are hereby incorporated by reference.

Generally, a target region to be analyzed by denaturing gradient gel electrophoresis is amplified using PCR primers flanking the target region. The amplified PCR product is applied to a polyacrylamide gel with a linear denaturing gradient as described in Myers et al., Meth. Enzymol. 155:501-

527 (1986), and Myers et al., in Genomic Analysis, A Practical Approach, K. Davies Ed. IRL Press Limited, Oxford, pp. 95-139 (1988), the contents of which are hereby incorporated by reference. The electrophoresis system is maintained at a temperature slightly below the Tm of the melting domains of the target sequences.

In an alternative method of denaturing gradient gel electrophoresis, the target sequences may be initially attached to a stretch of GC nucleotides, termed a GC clamp, as described in Chapter 7 of Erlich, supra. Preferably, at least 80% of the nucleotides in the GC clamp are either guanine or cytosine. Preferably, the GC clamp is at least 30 bases long. This method is particularly suited to target sequences with high Tm's. Generally, the target region is amplified by the polymerase chain reaction as described above. One of the oligonucleotide PCR primers carries at its 5' end, the GC clamp region, at least 30 bases of the GC rich sequence, which is incorporated into the 5' end of the target region during amplification. The resulting amplified target region is run on an electrophoresis gel under denaturing gradient conditions as described above. DNA fragments differing by a single base change will migrate through the gel to different positions, which may be visualized by ethidium bromide staining.

9. Temperature Gradient Gel Electrophoresis

Temperature gradient gel electrophoresis (TGGE)is based on the same underlying principles as denaturing gradient gel electrophoresis, except the denaturing gradient is produced by differences in temperature instead of differences in the concentration of a chemical denaturant. Standard TGGE utilizes an electrophoresis apparatus with a temperature gradient running along the electrophoresis path. As samples migrate through a gel with a uniform concentration of a chemical denaturant, they encounter increasing temperatures. An alternative method of TGGE, temporal temperature gradient gel electrophoresis (TTGE or tTGGE) uses a steadily increasing temperature of the entire electrophoresis gel to achieve the same result. As the samples migrate through the gel the temperature of the entire gel increases, leading the samples to encounter increasing temperature as they migrate through the gel. Preparation of samples, including PCR amplification with incorporation of a GC clamp, and visualization of products are the same as for denaturing gradient gel electrophoresis.

10. Single-Strand Conformation Polymorphism Analysis

Target sequences or alleles at the NIPBL locus can be differentiated using single-strand conformation polymorphism analysis, which identifies base differences by alteration in electrophoretic migration of single stranded PCR products, as described in Orita et al., Proc. Nat. Acad. Sci. 86:2766-2770 (1989). Amplified PCR products can be generated as described above, and heated or otherwise denatured, to form single stranded amplification products. Single-stranded nucleic acids may refold or form secondary structures which are partially dependent on the base sequence. Thus, electrophoretic mobility of single-stranded amplification products can detect base-sequence difference between alleles or target sequences.

11. Chemical or Enzymatic Cleavage of Mismatches

Differences between target sequences can also be detected by differential chemical cleavage of mismatched base pairs, as described in Grompe et al., Am. J. Hum. Genet. 48:212-222 (1991). In another method, differences between target sequences can be detected by enzymatic cleavage of mismatched base pairs, as described in Nelson et al., Nature Genetics 4:11-18 (1993). Briefly, genetic material from a patient and an affected family member may be used to generate mismatch free heterohybrid DNA duplexes. As used herein, "heterohybrid" means a DNA duplex strand comprising one strand of DNA from one person, usually the patient, and a second DNA strand from another person, usually an affected or unaffected family member. Positive selection for heterohybrids free of mismatches allows determination of small insertions, deletions or other polymorphisms that may be associated with CdLS.

12. Non-PCR Based DNA Diagnostics

The identification of a DNA sequence linked to NIPBL can made without an amplification step, based on polymorphisms including restriction fragment length polymorphisms in a patient and a family member. Hybridization probes are generally oligonucleotides which bind through complementary base pairing to all or part of a target nucleic acid. Probes typically bind target sequences lacking complete complementarity with the probe sequence depending on the stringency of the hybridization conditions. The probes are preferably labeled directly or indirectly, such that by assaying for the presence or absence of the probe, one can detect the presence or absence of the target sequence. Direct labeling methods include radioisotope labeling, such as with 32p or 35S. Indirect labeling methods include fluorescent tags, biotin complexes which may be bound to avidin or streptavidin, or peptide or protein tags. Visual detection methods include photoluminescents, Texas red, rhodamine and its derivatives, red leuco dye and 3,3',5,5'-tetramethylbenzidine (TMB), fluorescein, and its derivatives, dansyl, umbelliferone and the like or with horse radish peroxidase, alkaline phosphatase and the like.

Hybridization probes include any nucleotide sequence capable of hybridizing to the 5p13 region of chromosome 5, and thus defining a genetic marker linked to NIPBL, including a restriction fragment length polymorphism, a hypervariable region, repetitive element, or a variable number tandem repeat. Hybridization probes can be any gene or a suitable analog. Further suitable hybridization probes include exon fragments or portions of cDNAs or genes known to map to the p13 region of chromosome 5. Other suitable probes include portions of introns or intron/exon spanning regions from genomic fragments of chromosome 5, or portions of spacer DNA, i.e., DNA between genes that is not intronic.

Preferred tandem repeat hybridization probes for use according to the present invention are those that recognize a small number of fragments at a specific locus at high stringency hybridization conditions, or that recognize a larger number of fragments at that locus when the stringency conditions are lowered.

The following definitions are provided to facilitate an understanding of the present invention:

Cornelia de Lange Syndrome refers to a dominantly inherited disorder with characteristic facial appearance, limb defects and growth and cognitive retardation.

The term "LOD score" refers to a number used in genetic linkage studies; logarithm (base 10) of the odds in favor of genetic linkage.

The term "corresponds to" is used herein to mean that a polynucleotide sequence is homologous to all or a portion of a reference polynucleotide sequence, or that a polypeptide sequence is identical to a reference polypeptide sequence. In contradistinction, the term "complementary to" is used herein to mean that the complementary sequences is homologous to all or a portion of a reference polynucleotide sequence. For illustration, the nucleotide sequence "TATAC" corresponds to a reference sequence "TATAC" and is complementary to a reference sequence "GTATA". Hybridization probes may be DNA or RNA, or any synthetic nucleotide structure capable of binding in a base-specific manner to a complementary strand of nucleic acid. For example, probes include peptide nucleic acids, as described in Nielsen et al., Science 254: 1497-1500 (1991).

"Linkage" describes the tendency of genes, alleles, loci or genetic markers to be inherited together as a result of their location on the same chromosome, and is measured by percent recombination (also called recombination fraction, or θ) between the two genes, alleles, loci or genetic markers.

"Centimorgan" is a unit of genetic distance signifying linkage between two genetic markers, alleles, genes or loci, corresponding to a probability of recombination between the two markers or loci of 1% for any meiotic event.

"Linkage disequilibrium" or "allelic association" means the preferential association of a particular allele, locus, gene or genetic marker with a specific allele, locus, gene or genetic marker at a nearby chromosomal location more frequently than expected by chance for any particular allele frequency in the population.

An "oligonucleotide" can be DNA or RNA, and single- or double-stranded. Oligonucleotides can be naturally occurring or synthetic, but are typically prepared by synthetic means.

The term "primer" refers to an oligonucleotide capable of acting as a point of initiation of DNA synthesis under conditions in which synthesis of a primer extension product complementary to a nucleic acid strand is induced, i.e., in the presence of four different nucleoside triphosphates and an agent for polymerization (i.e., DNA polymerase or reverse transcriptase) in an appropriate buffer and at a suitable temperature. A primer is preferably a single-stranded oligonucleotide. The appropriate length of a primer depends on the intended use of the primer but typically ranges from 15 to 30 nucleotides. Short primer molecules generally require cooler temperatures to form sufficiently stable hybrid complexes with the template. A primer need not reflect the exact sequence of the template but must be sufficiently complementary to hybridize with a template. The term "primer" may refer to more than one primer, particularly in the case where there is some ambiguity in the information regarding one or both ends of the target region to be amplified. For instance, if a region shows significant levels of polymorphism or mutation in a population, mixtures of primers can be prepared that will amplify alternate sequences. A primer can be labeled, if desired, by incorporating a label detectable by spectroscopic, photochemical, biochemical, immunochemical, or chemical means. For example, useful labels include $^{32}P$, fluorescent dyes, electron-dense reagents, enzymes (as commonly used in an ELISA), biotin, or haptens and proteins for which antisera or monoclonal antibodies are available. A label can also be used to "capture" the primer, so as to facilitate the immobilization of either the primer or a primer extension product, such as amplified DNA, on a solid support.

"Penetrance" is the percentage of individuals with a defective gene who show some symptoms of a trait resulting from that defect. Expressivity refers to the degree of expression of the trait (e.g., mild, moderate or severe).

"Polymorphism" refers to the occurrence of two or more genetically determined alternative sequences or alleles in a population. A polymorphic marker is the locus at which divergence occurs. Preferred markers have at least two alleles, each occurring at frequency of greater than 1%. A polymorphic locus may be as small as one base pair. Polymorphic markers suitable for use in the invention include restriction fragment length polymorphisms, variable number of tandem repeats (VNTR's), hypervariable regions, minisatellites, dinucleotide repeats, trinucleotide repeats, tetranucleotide repeats, and other microsatellite sequences.

"Restriction fragment length polymorphism" (RFLP) means a variation in DNA sequence that alters the length of a restriction fragment as described in Botstein et al., Am. J. Hum. Genet. 32:314-331 (1980). The restriction fragment length polymorphism may create or delete a restriction site, thus changing the length of the restriction fragment. For example, the DNA sequence GAATTC are the six bases, together with its complementary strand CTTAAG which comprises the recognition and cleavage site of the restriction enzyme EcoRI. Replacement of any of the six nucleotides on either strand of DNA to a different nucleotide destroys the EcoRI site. This RFLP can be detected by, for example, amplification of a target sequence including the polymorphism, digestion of the amplified sequence with EcoRI, and size fractionation of the reaction products on an agarose or acrylamide gel. If the only EcoRI restriction enzyme site within the amplified sequence is the polymorphic site, the target sequences comprising the restriction site will show two fragments of predetermined size, based on the length of the amplified sequence. Target sequences without the restriction enzyme site will only show one fragment, of the length of the amplified sequence. Similarly, the RFLP can be detected by probing an EcoRI digest of Southern blotted DNA with a probe from a nearby region such that the presence or absence of the appropriately sized EcoRI fragment may be observed. RFLP's may be caused by point mutations which create or destroy a restriction enzyme site, VNTR's, dinucleotide repeats, deletions, duplications, or any other sequence-based variation that creates or deletes a restriction enzyme site, or alters the size of a restriction fragment.

"Variable number of tandem repeats" (VNTR's) are short sequences of nucleic acids arranged in a head to tail fashion in a tandem array, and found in each individual, as described in Wyman et al., Proc. Nat. Acad. Sci. 77:6754-6758 (1980). Generally, the VNTR sequences are comprised of a core sequence of at least 16 base pairs, with a variable number of repeats of that sequence. Additionally, there may be variation within the core sequence, Jefferys et al., Nature 314:67-72 (1985). These sequences are highly individual, and perhaps unique to each individual. Thus, VNTR's may generate restriction fragment length polymorphisms, and may additionally serve as size-based amplification product differentiation markers. "Microsatellite sequences" comprise segments of at least about 10 base pairs of DNA consisting of a variable number of tandem repeats of short (1-6 base pairs) sequences of DNA(Clemens et al., Am. J. Hum. Genet. 49:951-960 1991). Microsatellite sequences are generally spread throughout the chromosomal DNA of an individual. The number of repeats in any particular tandem array varies greatly from individual to individual, and thus, microsatellite sequences may serve to generate restriction fragment length polymorphisms, and may additionally serve as size-based amplification product differentiation markers.

A "marker" is referred to as fully "informative" for a particular individual if the configuration of alleles observed in the family allow for the unambiguous determination of parental origin of the alleles of a child. For example, if the mother has a "1" and "2" allele, while the father has a "3" and "4" allele, then it is possible to unambiguously assign the parental origin of alleles in each of the four possible combinations in the children (1-3, 1-4, 2-3, 2-4). A marker is partially informative when unambiguous determination of parental origin is possible for only certain children. For example, if both parents have a "1" and "2" allele, then the parental origins of the alleles may be unambiguously determined for children with the genotypes 1-1 and 2-2, but not for the children with the genotype 1-2. If one parent is homozygous for a marker, the marker will be only partially informative, and the inheritance from that parent cannot be traced. If the marker is homozygous in both parents, the marker is fully uninformative for the transmission from them to their children, even though their children may be heterozygous and thus informative for the transmission of that marker to the next generation.

A "mutation" is any alteration in the NIPBL gene which alters the function or expression the NIPBL gene product.

The following examples are provided to illustrate embodiments of the present invention. They are not intended to limit the invention in any way.

EXAMPLE 1

Characterization of NIPBL Expression

As mentioned above, the Cornelia de Lange syndrome (CdLS [MIM #122470]) is a multisystem developmental disorder characterized by facial dysmorphia, upper extremity malformations, hirsutism, cardiac defects, growth and cognitive retardation, and gastrointestinal abnormalities. Both missense and protein truncating mutations in NIPBL, the human homolog of the *Drosophila* Nipped-B gene, have recently been reported to cause CdLS. See U.S. Provisional Application No. 60/567,756 incorporated by reference herein.

The *Drosophila* Nipped-B protein facilitates long-range enhancer-promoter interactions and plays a role in Notch signaling and other developmental pathways as well as being involved in mitotic sister chromatid cohesion. The present example describes the spectrum and distribution of NIPBL mutations in a large, well-characterized cohort of individuals with CdLS. Mutations were found in 56 of 120 (47%) unrelated individuals with sporadic or familial CdLS. Statistically significant phenotypic differences between mutation-positive and mutation-negative individuals were identified. Analysis also suggested a trend towards a milder phenotype in individuals with missense mutations as compared to other types of mutations.

The materials and methods set forth below are provided to facilitate the practice of Examples 1, 2 and 3.

Cornelia de Lange Syndrome Patients.

All patients and family members were enrolled in the study under an IRB-approved protocol of informed consent at The Children's Hospital of Philadelphia. Clinical dysmorphologists (I.D.K., A.D.K. and/or L.G.J.) with experience with CdLS evaluated all subjects. Clinical histories and photographs were obtained routinely for all probands, as well as for any other affected family members. Clinical records were reviewed for the presence of other CdLS-associated anomalies, such as: deafness, cleft palate, cardiac, ophthalmologic, gastrointestinal, genitourinary, and renal anomalies. For the purposes of the genotype-phenotype studies only probands were included and not affected family members. This may result in a bias towards the more severe phenotype, however as familial recurrences are extremely rare it was not possible to perform a separate analysis on the small number of affected family members. While all probands had characteristic facial features as part of their inclusion criteria into the study, we chose to further stratify the CdLS cohort based on the severity of three phenotypic parameters: limb differences, growth, and cognitive functioning (summarized in Table 1).

Limb malformations were classified by the presence or absence of reduction defects in the upper extremities as follows: Class I: mild, no reduction defect; Class II: moderate, partial reduction defect/oligodactyly (>2 digits on each hand); Class III: severe, reduction defect (≦2 digits on either hand). A score for severity of the physical growth parameters was calculated by averaging the percentiles for weight, height, and head circumference that were plotted on sex- and age-standardized growth curves for individuals with CdLS (Kline et al. 1993a). Growth parameters were classified as follows: Class I: mild, average growth parameters $>75^{th}$ centile on CdLS growth curves; Class II: moderate, average growth parameters $25^{th}$-$75^{th}$ centile on CdLS growth curves; Class III: severe, average growth parameters $<25^{th}$ centile on the CdLS growth curves. Cognitive functioning was the most difficult parameter to standardize as most individuals with CdLS enrolled in the study had not received formal developmental evaluations as well as the inherent difficulty of comparing developmental abilities in individuals of varying ages. We used a classification of developmental/cognitive abilities based on deviation from age-appropriate standards as follows: Class I: mild, motor milestones less than 2 years delayed from normal standards, development of speech and communication skills in older individuals; Class II: moderate, delay in reaching motor milestones greater than 2 years behind normal developmental standards, limited speech and communication; Class III: severe to profound delay in achieving motor milestones and without meaningful communication. Clinical stratification of all probands was performed without knowledge of mutational status.

TABLE 1

| | Phenotypic Classifications | | |
|---|---|---|---|
| | 1 (Mild) | 2 (Moderate) | 3 (Severe) |
| Limb Reduction | No reduction defect | Partial reduction defect, oligodactyly (>2 digits on each hand) | Severe reduction defect (≦2 digits on either hand) |
| Development and Cognitive Abilities | Motor milestones < 2 yrs delayed; speech and communication skills present | Motor milestones > 2 yrs delayed; limited speech and communication | Profound delay in achieving motor milestones and lack of meaningful communication |
| Growth (Average of Percentiles for Weight, Height, & Head Circumference Plotted on CdLS Standard Growth Curves) | $>75^{th}$ percentile | $>25^{th}$ and $<75^{th}$ percentile | $<25^{th}$ percentile |

Genome-Wide Linkage Analysis.

Linkage studies were performed using the ABI linkage mapping set version 2 consisting of 400 fluorescently-labeled polymorphic markers spaced at approximately 10 cM intervals throughout the genome. Marker allele frequencies used in the lod-score analysis were estimated based on alleles observed in the families' founders. Model based two point and multipoint linkage analysis on data from the whole genome scan and from the fine mapping of chromosomes 2, 5, 10, and 14 in all families were carried out by means of the GENEHUNTER computer program version 2.0 (GH2) (Kruglyak et al. 1996). For the purpose of lod-score analysis, we assumed the disease to follow an autosomal dominant mode of inheritance with disease allele frequency of 0.00001. In order to account for the possibility that the disease in families with unaffected parents was due to germline mosaicism in one of the parents, all unaffected individuals (parents and sibs) that were available for genotyping were coded as unknown at the disease phenotype. In this way, we did not have to make any assumption about the unknown penetrance of the putative CdLS gene mutation. However, marker genotype information from unaffected sibs was retained, when available, and used to reconstruct phase for haplotyping. Marker maps used in multipoint linkage analysis were sex averaged genetic maps from the Center for Medical Genetics of the Marshfield Clinic Research Foundation.

Fluorescence In Situ Hybridization (FISH) Analysis

Fluorescence in situ hybridization (FISH) studies were performed on metaphase chromosomes prepared from peripheral blood lymphocytes using standard techniques (Krantz et al. 1997). FISH was performed with the NIPBL-containing BAC RP1 1-14121 (ACO18853.3) (CHORI BAC-PAC Resources, Oakland, Calif.) on 28 mutation-negative individuals (4 familial, 24 sporadic) to evaluate for the possibility of a large but submicroscopic deletion encompassing the NIPBL gene. BAC DNA was isolated (Perfect Prep Plasmid XL, Eppendorf, Hamburg, Germany) and labeled by nick translation in the presence of Spectrum Red dUTP (Vysis, Downers Grove, Ill.). The labeled BAC probe was dissolved in LSI/WCP Hybridization Buffer (Vysis, Downers Grove, Ill.); 10 μg of Human Cot-I DNA® (Invitrogen Corp., Carlsbad, Calif.) was added per 1 μg of labeled BAC RP1 1-14121 probe. TelVysion® Probe 5p and/or 5q (Vysis, Downers Grove, Ill.) (as per manufacturer instructions) and 100 ng of labeled BAC probe per micoscope slide were co-denatured under a coverslip for 2 min on a 75° C. slide warmer and hybridized at 37° C. for ~16 hours in a humid chamber. Slides were subjected to two post hybridization washes; wash one (0.4×SSC, 0.3% NP-40) at 73° C. for 2 minutes and wash two (2×SSC, 0.1% NP-40) at room temperature for 1 minute, and counter stained with DAPI II (Vysis, Downers Grove, Ill.). A Nikon microscope, equipped with the appropriate filters, was used to visualize each slide. CytoVision® application software version 3.1 build 10 (Applied Imaging, Santa Clara, Calif.) and a CCD camera were used to capture FISH images.

In Situ Hybridization in the Developing Mouse

A probe to mouse NIPBL was generated by PCR from an EST clone using oligonucleotide primers 5'-CCGCTCGAGGATTCAAACGCTTCATCA-3'(SEQ ID NO: 4) and 5'-AGGATGGGAATATGGCATGTA-3' (SEQ ID NO:5), which yielded a 389 bp product corresponding to the mouse homologue of the last 190 bp of exon 10 and all of exon 11 of human NIPBL. This was subcloned into pCRII-TOPO (Invitrogen) for generation of antisense and sense digoxigenin-labeled cRNA probes. An Fgf8 probe (positive control) was generated from a 422bp NcoI-PstI fragment of the Fgf8 cDNA (bp 59-481 of GenBank Z48746) cloned into pBluescript. CD-1 (Charles River) mouse embryos were dissected at 9.5 and 10.5 days of gestation, and fixed and processed for whole mount in situ hybridization, with detection using alkaline phosphatase-conjugated, sheep-anti-digoxigenin antibodies, and BCIP-NBT as the chromagenic substrate (Kawauchi et al. 1999).

Northern Blot Analysis.

Poly A+ RNA Northern blots of multiple adult human tissues (Human 12-Lane Multiple Tissue Northern (MTN™) Blot BD Biosciences Clontech) and human fetal tissues (MessageMap™ Northern Blot, Stratagene) were hybridized with a 301 base pair probe from BX5381 78-specific cDNA sequence (NIPBL exon 2 and 3) (amplified from the following primers: forward: TGTTTGGGAAATGGGAAGTAA (SEQ ID NO: 6), reverse: TGTTGATACCTGGTTGAGGCTA (SEQ ID NO:7)) a 344 base pair probe from IDN3-specific cDNA sequence (NIPBL exon 46 and 47) (amplified from the following primers: forward: GAAGAAGGGGAGGTTTCAGC (SEQ ID NO: 8), reverse: GTCCAGGAGCCACTGTAGGA (SEQ ID NO:9)), and a 252 base pair probe from a region of overlap between the 2 putative transcripts (NIPBL exon 10) (amplified from the following primers: forward: TGAGAGCAGAACAACTGAATGC (SEQ ID NO:10), reverse: TGGCTTTCCAGAATCCCTCC (SEQ ID NO:11)). BD SpotLight™ Random Primer Labeling Kit (BD Bioscience Clontech) was used for labeling probes and SpotLight™ Chemiluminescent Hybridization & Detection Kit (BD Bioscience Clontech) was used for hybridization and visualization. Experiments were duplicated using Ready-to-go™ DNA labeling beads (−dCTP) (Amersham) with $P^{32}$ dCTP and purified on ProbeQuan™ G-50 microcolumns (Amersham), and blots were blocked with yeast tRNA and herring sperm DNA. Visualization of signal was carried out by exposure to autoradiograph film for 1-5 minutes (chemiluminescent) and 1-4 hours ($P^{32}$).

TABLE 2

Results of linkage analysis for markers with highest two point lod-scores from five positive regions after genome-wide scan

| | | Lod-scores by family | | | | | | | | | | | | Total lod-score | | | |
|---|---|---|---|---|---|---|---|---|---|---|---|---|---|---|---|---|---|
| Marker | cM | I | II | III | VI | VII | XIII | XIV | XV | XVII | XX | XXI | XXIV | 9 families | 12 families | Size of linked Region | ~# of genes |
| D2S125 | 260.6 | 0.30 | 0.60 | 0.30 | 0 | −0.03 | 0.30 | 0 | 0.30 | 0.30 | 0 | 0.30 | 0.18 | 2.08 | 2.55 | 11 Mb | 160 |
| D5S426 | 52.0 | 0 | 0 | 0.30 | 0.30 | 0.28 | 0.30 | −0.30 | 0.30 | 0.30 | 0 | 0.18 | 0 | 1.49 | 1.66 | 14 Mb | 55 |
| D10S1653 | 40.4 | 0 | 0.60 | 0.30 | 0 | 0.13 | 0.30 | 0.18 | 0.18 | 0.30 | 0 | 0 | −0.30 | 1.98 | 1.68 | 21 Mb | 100 |
| D14S74 | 87.4 | 0.30 | 0.60 | 0 | 0.30 | 0.26 | 0 | 0 | 0.18 | 0.30 | 0.18 | −.30 | 0 | 1.94 | 1.82 | 8 Mb | 90 |
| D17S938 | 14.7 | 0.60 | 0.60 | 0 | 0.18 | 0 | 0.30 | 0 | 0 | 0 | 0.18 | 0 | −4.40 | 1.08 | −3.14 | 9 Mb | 170 |

Mutational Analysis

Genomic DNA was isolated from peripheral blood lymphocytes (Gentra, Minneapolis, Minn.). Parental DNA was available for 41 of 48 (85%) patients with sporadic CdLS who had NIPBL mutations. DNA from both parents was available in 25/48 patients (52%), and DNA from only one parent was available in 16/48 patients (33%). The entire NIPBL coding region (exons 2-47) was screened for mutations. Primer sequences, annealing temperatures, and sizes of PCR products are listed in Supplementary table 1 (available online). Primer pairs were designed to amplify exons, exon/intron boundaries, and short flanking intronic sequences. Larger exons were subdivided to allow for optimal product lengths. All PCR reactions were performed in a 25-μl reaction volume containing 75 ng genomic DNA, 1 U AmpliTaq Gold (Applied Biosystems, Foster City, Calif.), 20 pmol each primer, 75 μM each dNTP, 10×PCR Buffer II (Applied Biosystems, Foster City, Calif.), and 1.0 mM or 1.5 mM MgCl2 (Applied Biosystems, Foster City, Calif.). Cycling parameters were as follows: 36 cycles of 94° C. for 30 s; 51-60° C. for 45 s, and 72° C. for 30 s; and 72° C. for 5 min (last ex Amplifications for exons 6, 11, 21, 26, 30, 44, and 45 were performed using 10 cycles of 95° C. for 30 s; 51-62° C. for 30 s, and 72° C. for 35 s followed by 25 cycles of s; 51-62° C. for 30 s, and 72° C. for 45 s increasing by 5 s for each cycle See Table 3. Mutational analysis of the amplimers was performed by means of conformation sensitive gel electrophoresis (CSGE), using standard protocols (Ganguly et al. 1993). PCR products corresponding to all altered migration patterns (shifts) on CSGE were purified using QIAquick™ PCR purification kit (QIAGEN Sciences, Valencia, Calif.) and sequenced bidirectionally on an ABI 377 sequencer.

TABLE 3

Primers and Conditions used to Amplify NIPBL Coding Sequence

| Exon | Forward | SEQ ID NO: | Reverse | SEQ ID NO: | Length (bp) | Conditions |
|---|---|---|---|---|---|---|
| 2 | ACTGGGTTGTTGTGAGAACTG | (12) | GCATTTCAGTTGCTATTTCTG | (13) | 470 | 1.5 mM $MgCl_2$ 55° C. |
| 3 | TTAGGAAGAGGAGGAATGCC | (14) | CTGAAATAAAACCAGGAATACGG | (15) | 387 | 1.5 mM $MgCl_2$ 55° C. |
| 4 | TGGGGGACAAGAGTGAGACTTC | (16) | GCATAAACATCGCATTCCTGATAG | (17) | 532 | 1.5 mM $MgCl_2$ 55° C. + DMSO |
| 5 | AAGGACACTTTACTGTTAGAAGAA | (18) | GCAAATGCAAAGTGGATTACT | (19) | 301 | 1.5 mM $MgCl_2$ 55° C. |
| 6 | CAGTCAGATTTCAAGGAATAGCG | (20) | CTCCTTTCACCTCCTAAAATGAC | (21) | 429 | * 1.5 mM $MgCl_2$ 58° C. |
| 7 | AACTAGTCAGTACATGAGTATCTG | (22) | GAAATGGAAATACTAGGTTATATG | (23) | 369 | 1.5 mM $MgCl_2$ 60° C. |
| 8 | CAAGAAGAAAACAGGAAAGTGC | (24) | CTGCTTTAGGAAGTCTGAGTTCT | (25) | 325 | 1.5 mM $MgCl_2$ 55° C. |
| 9A | GTGAAACCACCACAACTG | (26) | TGAGCAGCATTTAGTGGGC | (27) | 429 | 1.5 mM $MgCl_2$ 55° C. |
| 9B | CAGGACAGACTTCAAAAACACC | (28) | CCAAATCTCATATAGTTGTTTCAG | (29) | 512 | 1.5 mM $MgCl_2$ 55° C. |
| 10A | TTGCATTTGCATTTTACTCCA | (30) | GTGTCTCAGGATGGTTTTCTGG | (31) | 428 | 1.5 mM $MgCl_2$ 58° C. |
| 10B | TACGGGAAATGGGTCAAGGC | (32) | AGGCTCAACTATGGTGCTCTCG | (33) | 424 | 1.5 mM $MgCl_2$ 55° C. + DMSO |
| 10C | TGAGAGCAGAACAACTGAATGC | (34) | TGGCTTTCCAGGAATCCCTCC | (35) | 352 | 1.5 mM $MgCl_2$ 55° C. + DMSO |
| 10D | AGGTGAGAGCCGCCCTGAAACTC | (36) | CACGAGGACTGTCAGGTCTTGA | (37) | 467 | 1.5 mM $MgCl_2$ 55° C. + DMSO |
| 10E | TGAATCAGGGGACTCAAGGG | (38) | AGGGAACTTCTTGATTTGTCCTC | (39) | 468 | 1.5 mM $MgCl_2$ 55° C. + DMSO |
| 10F | AGGAGCTAAGCCTGTAGTTGTG | (40) | CTTGAGTAGTGGGTGGGGAAGA | (41) | 349 | 1.0 mM $MgCl_2$ 55° C. + DMSO |
| 11 | TGTCACTTTAGGGTTAAGAGT | (42) | GACTGTGCTTTTGCTAAACCC | (43) | 439 | * 1.5 mM $MgCl_2$ 52° C. |
| 12 | CACTGAATTTCCTAGACCCTATG | (44) | ATCACTGCACATAGAAACTAAG | (45) | 464 | 1.5 mM $MgCl_2$ 55° C. + DMSO |
| 13/14 | GTTTCTATGTGCAGTGATTATCG | (46) | GATTTCAAGGTAGGACACATCAC | (47) | 483 | 1.5 mM $MgCl_2$ 58° C. |
| 15 | ATTCAGGGTTTACTTGAGGTT | (48) | AGTCCATGCCTCTTTCAATGCAG | (49) | 486 | 1.5 mM $MgCl_2$ 58° C. |
| 16 | AGTCATTTAGGGTCGTTGAGT | (50) | GCATGGGAAGAGATTAATGAC | (51) | 449 | 1.5 mM $MgCl_2$ 58° C. |
| 17 | CATCATAACACTTTTCCACCAG | (52) | TGGTGCCATTTTAAGTCCTAT | (53) | 415 | 1.5 mM $MgCl_2$ 55° C. |
| 18 | CTTCCAGGTTCTGTAGCTAGA | (54) | GAGTTTGGAATTTACACTACATT | (55) | 483 | 1.5 mM $MgCl_2$ 55° C. |
| 19 | TGCTAACGTGCTTTGAGGATG | (56) | TAGTCCTTAGATTGAAATGAATG | (57) | 393 | 1.5 mM $MgCl_2$ 55° C. |
| 20 | GAGCAGCTTACCTTAGATACTGA | (58) | ATGCTGTTCTGATGTAACTGCC | (59) | 363 | 1.5 mM $MgCl_2$ 60° C. |
| 21 | GGCAAAACACAGTATCGTGAAAC | (60) | GATCGCGCCACTGCACTC | (61) | 389 | * 1.0 mM $MgCl_2$ 55° C. |
| 22 | TAGTGTGCTAATTTTGGCTTCT | (62) | ATTCAAGGTTCAGATTATGGC | (63) | 350 | 1.5 mM $MgCl_2$ 60° C. |
| 23 | CAATTTCAATCATGTTGGTAGAC | (64) | GTGTACAGTTATGCACATGC | (65) | 359 | 1.0 mM $MgCl_2$ 52° C. + DMSO |

TABLE 3-continued

Primers and Conditions used to Amplify NIPBL Coding Sequence

| Exon | Forward | SEQ ID NO: | Reverse | SEQ ID NO: | Length (bp) | Conditions |
|---|---|---|---|---|---|---|
| 24 | ACAGTTGAGCCTGCATATTTA | (66) | ACCATTCAGAAGTCCCTGTTA | (67) | 594 | 1.5 mM $MgCl_2$ 55° C. |
| 25 | AAGGCAAACTTCAGCTATCAA | (68) | CCTCTTCATCATGCTACCTCC | (69) | 366 | 1.5 mM $MgCl_2$ 58° C. |
| 26 | TGTATTCCTGTAATGTGAGCACTC | (70) | TCATCCTGCAACAAAAAGTCA | (71) | 413 | * 1.5 mM $MgCl_2$ 58° C. |
| 27 | ACCACACCTTCTCAGTTTAGCA | (72) | CTCACAAGCATCCAGAATCAG | (73) | 297 | 1.5 mM $MgCl_2$ 55° C. |
| 28/29A | ACGAAAGGCTCCAAAGTATG | (74) | ACTGCTGCTTCTCGGACAC | (75) | 473 | 1.5 mM $MgCl_2$ 52° C. + DMSO |
| 28/29B | GTCTGAGGTTGTTGCTGTAGA | (76) | ATGATATTGCAAGGGCTATTC | (77) | 423 | 1.5 mM $MgCl_2$ 55° C. |
| 30 | TTCTAGTCTTGTGTCCAGGGC | (78) | ATCAACATTTAGGTGCAATAA | (79) | 462 | * 1.5 mM $MgCl_2$ 55° C. |
| 31 | TCCTGGCAGTTTGTGTTTTG | (80) | CTGGAGGAATAGGAAAATCTCAG | (81) | 470 | 1.5 mM $MgCl_2$ 55° C. + DMSO |
| 32 | GTTCTGTAACGTTGGTAAATGGT | (82) | GGTTCTTTTAAATCATACAGTCCA | (83) | 321 | 1.5 mM $MgCl_2$ 58° C. |
| 33 | ACCTTAGGTCTTACACAGCAA | (84) | TGTGCTCAACTAGGTTATCAAC | (85) | 362 | 1.5 mM $MgCl_2$ 60° C. |
| 34 | TTGAGGCCTATACTGGACCTA | (86) | GGTTGACGCATGTGAACTCTA | (87) | 333 | 1.5 mM $MgCl_2$ 60° C. |
| 35 | TAACTGGACCTTTACGTGCAA | (88) | GCTCACACAATGTTGCACTAC | (89) | 423 | 1.5 mM $MgCl_2$ 55° C. |
| 36 | TGGCATGACTGTAAGCACTCA | (90) | AGAGGACCACGGTGGATAATC | (91) | 381 | 1.5 mM $MgCl_2$ 60° C. + DMSO |
| 37 | TGGTGGCACACGACTGTAATCC | (92) | TCATCCTGGGTCACTACTGTCAT | (93) | 467 | 1.5 mM $MgCl_2$ 60° C. |
| 38 | CTGATACTTTGAATGCCACTG | (94) | CACCAAATCCTACTGCTAATA | (95) | 378 | 1.5 mM $MgCl_2$ 55° C. |
| 39 | CTCTAGGTAAGGCCACCAGCAT | (96) | TAGACCTCAGCATAAGGACTGC | (97) | 466 | 1.5 mM $MgCl_2$ 55° C. |
| 40 | CAGATTAAGAACCATTGAGCC | (98) | GCAGTAATCATAACCCAAGAG | (99) | 492 | 1.5 mM $MgCl_2$ 58° C. |
| 41 | AGTGTGAGAATGCTTTATGTT | (100) | ATTATGAATGTGGGCAGAGCA | (101) | 474 | 1.5 mM $MgCl_2$ 55° C. |
| 42 | ATGAAGCTAGCCTCAGAATGT | (102) | CAAAATTTCCCCTTCACTTCTGA | (103) | 472 | 1.5 mM $MgCl_2$ 58° C. |
| 43 | GTGAGGTGAAAGTGCCCTGTA | (104) | TCCCAAGTCAAGTATTGCCCAG | (105) | 401 | 1.5 mM $MgCl_2$ 52° C. |
| 44 | CAAGCTGTTGAATGGAGCATAC | (106) | CATGAGCCACCACACCCAGC | (107) | 434 | * 1.0 mM $MgCl_2$ 58° C. |
| 45 | TCCAAATACGTTGTTTCCATAG | (108) | TCAATGTGAAGGAGATAGTTAT | (109) | 329 | * 1.5 mM $MgCl_2$ 51° C. |
| 46 | CCACACCAAACTACTGCCATAG | (110) | CATTTTACGTAATACGCTGCG | (111) | 334 | 1.0 mM $MgCl_2$ 60° C. |
| 47A | GTCACGGTGCGTCTCATTGC | (112) | TAGTGTCTACCCAAGGCACCA | (113) | 395 | 1.5 mM $MgCl_2$ 58° C. |
| 47B | GGCTTCAGTGTTCAGTGGATG | (114) | TTTGCCCAACATTTCCTTC | (115) | 364 | 1.5 mM $MgCl_2$ 58° C. |
| 47C | TGAAGAGTAAGTGGAACCTGG | (116) | GCTAAAGAAAGCCATCCGC | (117) | 274 | 1.5 mM $MgCl_2$ 55° C. |

* Denotes GC-rich PCR cycle.

Genotype-Phenotype Correlations

Genotype-phenotype correlations were assessed using contingency table analysis. This was performed for the three categories (mild, moderate, and severe) for each phenotypic parameter (limb defect, growth, and development) versus presence or absence of a mutation in NIPBL, and versus missense or other types of mutations. For the mutation-positive versus mutation-negative analysis the chi-square test with 2 degrees of freedom was used. For the missense versus other types of mutations analysis Fisher's exact test was used. The significance threshold was set at $P \leqq 0.05$.

Chromosomal Analysis and Evaluation for PSCS

Metaphase spreads were prepared for the 90 CDLS probands and 90 non-CdLS controls from either whole blood cultured in RPMI 1640 with 15% fetal bovine serum and phytohemagglutinin for 72 hours or lymphoblastoid cell lines transformed with Epstein-Barr Virus and harvested during the log phase. Metaphases were arrested with 0.8 ug/ml Colchicine (SIGMA-ALDRICH) for 20 minutes at 37° C., hypotonized with 0.075M KCL at room temperature and fixed with 3 parts methanol: 1 part acetic acid. The slides were stained with Wright's Stain (Fisher Scientific). Ten proband slides were C-banded. A minimum of 50 metaphases were microscopically examined and scored for PSCS. PSCS was diagnosed when the sister chromatids were completely separated and no connection at the Centromere was seen (Plaja et al., 2003). A metaphase was scored as positive for PSCS if all or the majority of sister chromatids in the metaphase spread demonstrated sister chromatid separation. A positive PSCS score was recorded for any individual with at least one metaphase per slide demonstrating PSCS.

GenBank Accession Numbers.

Human BX538178 (BX538178), Human IDN3 (NM_133433), *Saccharomyces cerevisiae* sister chromatid cohesion protein 2 (Q04002), Mouse IDN3 (BG070859; XM_127929), RatIDN3 (XM_238213). NIPBL (BKO05151).

Results

CdLS is a dominantly inherited disorder with characteristic facial appearance, limb defects, and growth/cognitive retardation. See FIG. 1. A genome-wide linkage analysis was initially carried out in 9 CdLS families with more than one affected family member. Under a model of genetic homogeneity, we used a linkage exclusion mapping approach, excluding all markers in which the affected individuals in one or more families demonstrated non-sharing of both parental alleles when both parents were unaffected, or of the allele transmitted by the affected parent. This analysis resulted in the identification of 5 regions containing one or more markers with positive lod-scores in the 9 families (chromosomes 2q37, 5p13, 10p13, 14q24, and 17p13) (Table 2). With the identification of 3 additional CdLS families, these 5 regions were analyzed in the initial cohort of 12 families. This resulted in negative lod-scores for D17S938 in one of the families and exclusion of chromosome 17. All other markers still gave positive total lod-scores (Table 2).

Figure 2:
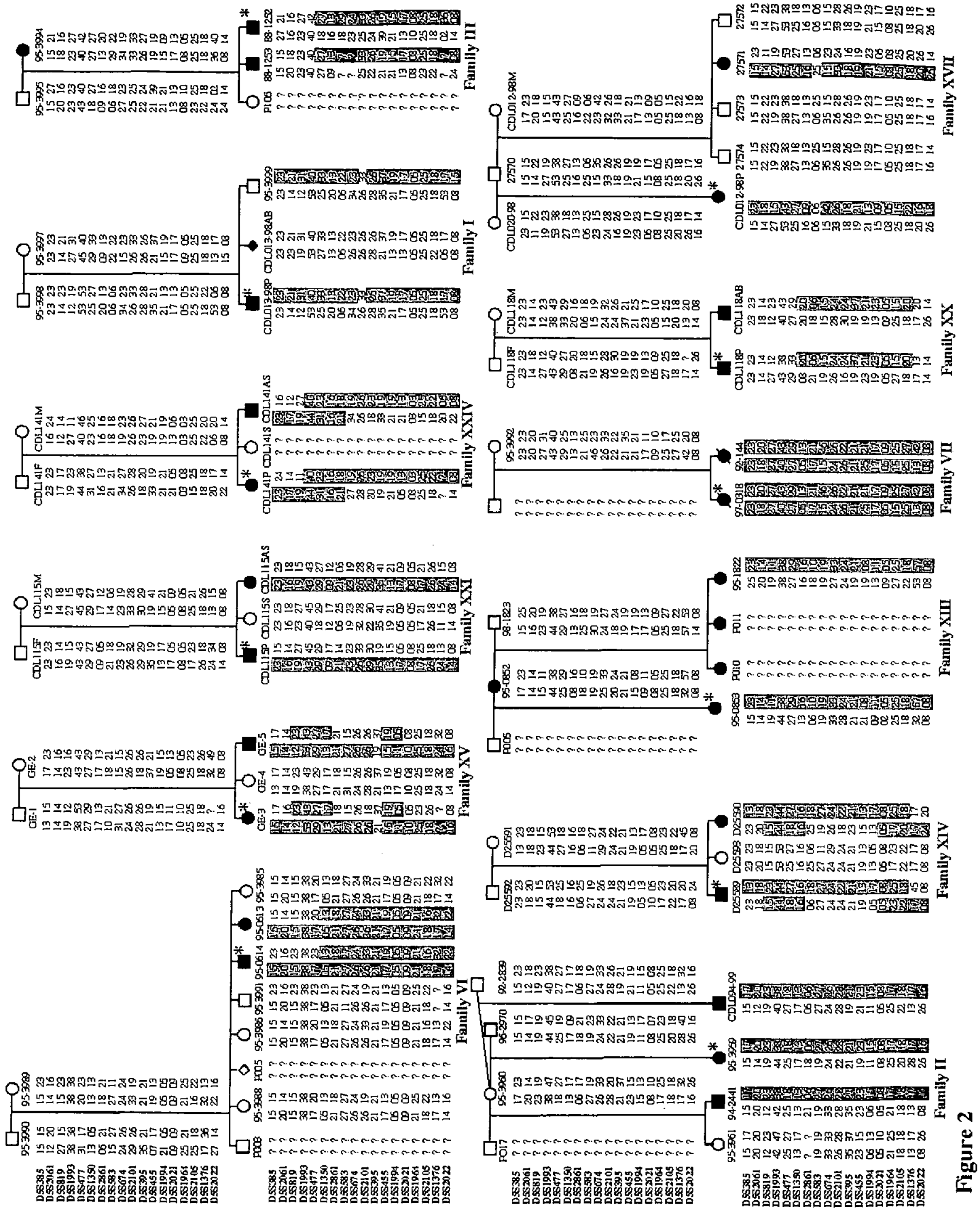
FIG. 2. High-resolution linkage analysis of 5p13 in the 12 CdLS families. All microsatellite markers used are indicated on the left (distances between markers are indicated in FIG. 3). Haplotypes for each individual are indicated below the individual identification numbers. Paternal alleles are on the left and maternal alleles are on the right. Alleles shared by affected individuals are indicated by gray shading. Family XX allowed for refinement of the distal boundary to marker D5S477 and of the proximal boundary to marker to D5S1376. Marker D5S426 which gave the initial positive LOD score in the genome-wide scan lies between markers D5S674 and D5S2101. The gene lies between markers D5S1994 and D5S 2021 (indicated in red).
Figure 3A:
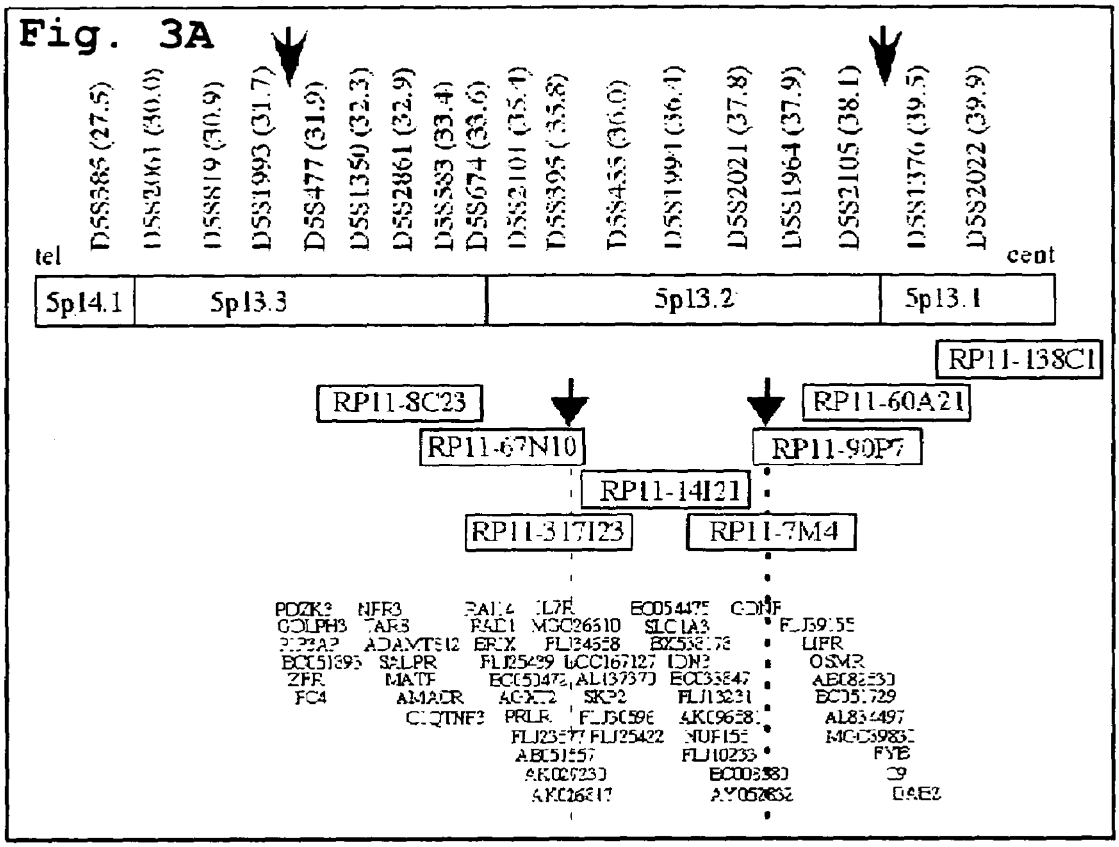
FIG. 3*a*) Chromosome 5p13 critical region. Ideogram of the 5p13 critical region with microsatellite markers indicated above the ideogram. Distance of markers from the p-terminal arm of chromosome 5, in megabases, are indicated in brackets. Arrows indicate refined critical region after high-resolution analysis and identification of obligate recombination events. BAC clones used for FISH analysis are indicated by their RP11 addresses. FISH analysis allowed for further narrowing of the critical region as indicated by arrows below the ideogram. An expanded view of the critical region is depicted. The genes contained within the defined critical region are indicated (from the July 2003 UCSC genome browser).

Fine mapping was performed in all families with additional markers at a 1-1.5 cM average density to the defined regions on chromosome 2, 5, 10, and 14. While multipoint linkage analysis did not improve the odds for linkage to chromosome 2, 10, or 14, it did result in a maximum LOD score of 2.7 for chromosome 5p13, which was the highest score for the entire genome analysis. The critical region on chromosome 5p13 was refined by obligate recombination events to an ~7.4 Mb region spanning 5p13.1-13.3 and flanked by markers D5S477 distally and D5S1376 proximally (FIG. 2) and contained 58 putative genes (FIG. 3*a*).

Based upon the results of this analysis, other corroborating evidence was sought to target one or more of the 4 candidate regions. A child with classic features of CdLS and a balanced de novo t(5;13)(p13.1;q12.1) had been identified by our group in the past and another child with classic features of CdLS and a de novo chromosome 5p13.1 -p14.2 deletion (the only reported case of a constitutional deletion of 5p13.2) was recently described. These cases supported the association of 5p13 with CdLS. Refinement of the 5p breakpoint in the translocation patient was undertaken (samples were not available on the 5p deleted child who died shortly after birth).

Figure 3B:
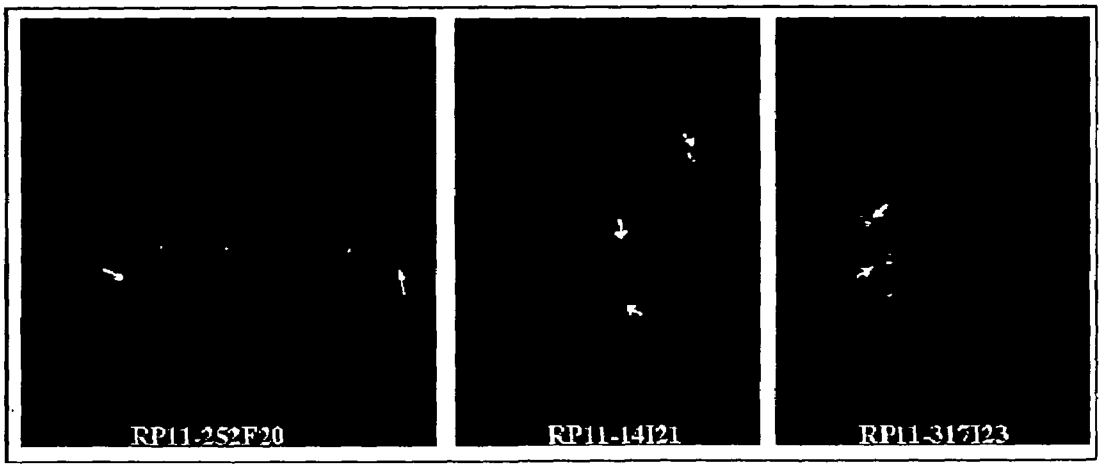
FIG. 3*b*) Fluorescence in situ hybridization (FISH) using BACs from within the linkage defined chromosome 5p13 critical region. In all panels the chromosome 5p telomeric control probe is labeled in green and the 5q telomeric control probe is labeled in red. In the first panel BAC RP11-252F20 is labeled in green. Both signals from BAC RP11-252F20 are on chromosome 5 p (arrows) indicating that it is proximal to the translocation breakpoint. In the middle panel BAC RP11-14121, that contains the NIPBL gene, is labeled in green. There is signal on both of the chromosome 5p arms as well as on chromosome 13q (arrows) indicating that the probe was split on the translocated chromosome. In the right hand panel BAC RP11-317123 is labeled in red. One signal is present on the normal chromosome 5p arm and the other is present on 13q indicating that this probe is distal to the translocation breakpoint.

Fluorescence in situ hybridization (FISH) using clones from within the minimal critical region on 5p13 was performed on the t(5;13)(p13.1;q12.1) child (FIG. 3*b*). Due to sample limitations we were initially unable to identify a clone that spanned the translocation breakpoint, however we were able to narrow the critical region to a 1.1 Mb interval containing 11 putative genes (FIG. 3*a*). Mutational analysis of the first 3 exons of all 11 genes was undertaken by conformation-sensitive gel electrophoresis (CSGE). Mutations in two overlapping transcripts BX538178 (3653 bp mRNA) and IDN3 (8124 bp mRNA) were identified (FIG. 3*a*). The identification of mutations in both of these transcripts (in BX5381 78-specific sequence, IDN3-specific sequence and in the overlap region), and their exact sequence identity over a 2259 bp region of overlap suggested that they were part of a larger transcript that we refer to as NIPBL.

Figure 4:
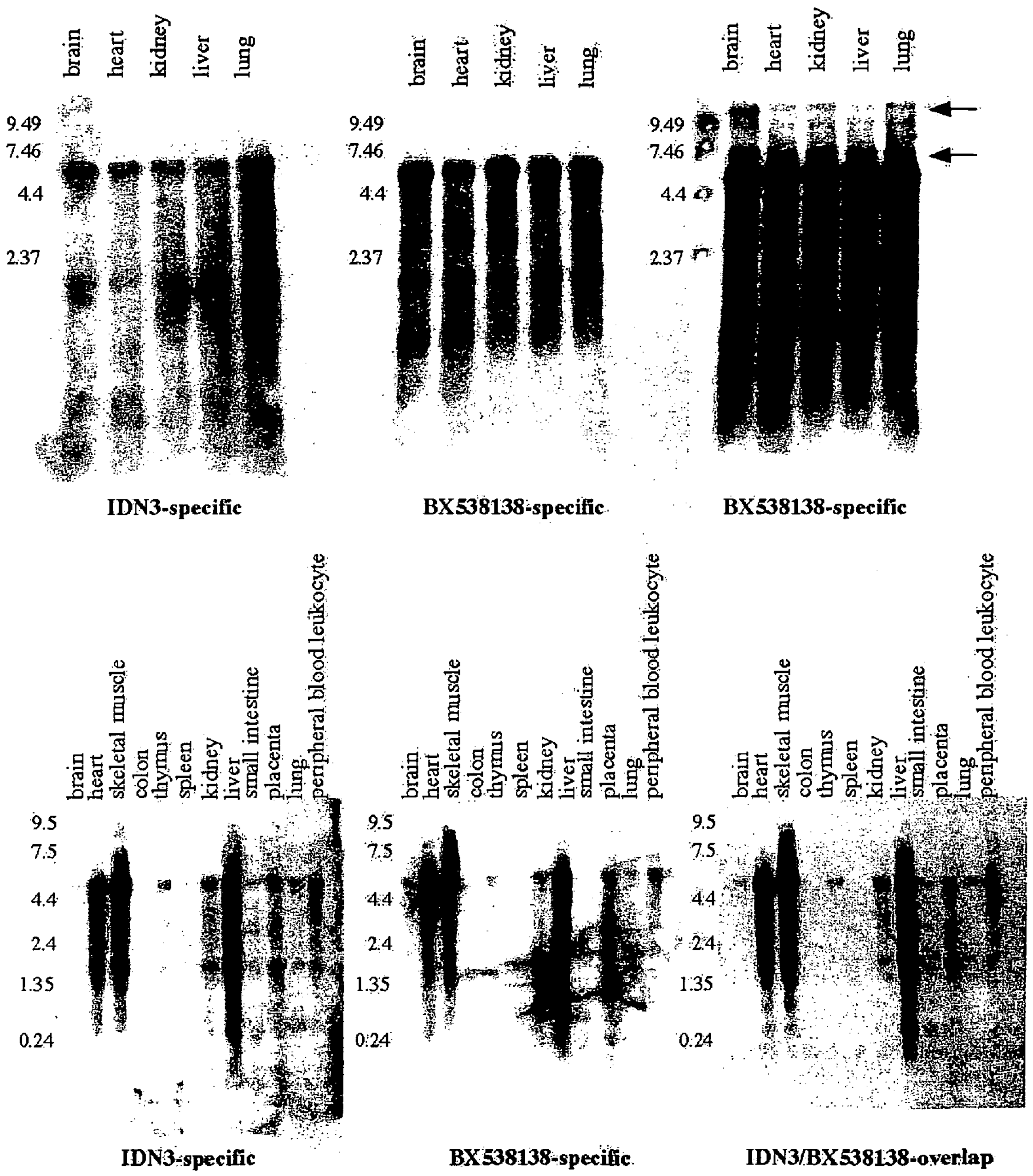
FIG. 4. Northern Blot Analysis of NIPBL. Analysis of NIPBL expression in adult and fetal tissues. Probes from BX5381 78-specific (NIPBL exons 2 and 3), IDN3 specific (NIPBL exons 46 and 47), and the overlap region of these 2 transcripts (NIPBL exon 10) were used giving identical results (not all data shown). An ~6 Kb and 1.9 Kb transcript were seen on all blots. Expression was ubiquitous however much lower levels of expression were seen in brain, colon and spleen, and high levels of expression seen in heart, skeletal muscle and liver.
Figure 5:
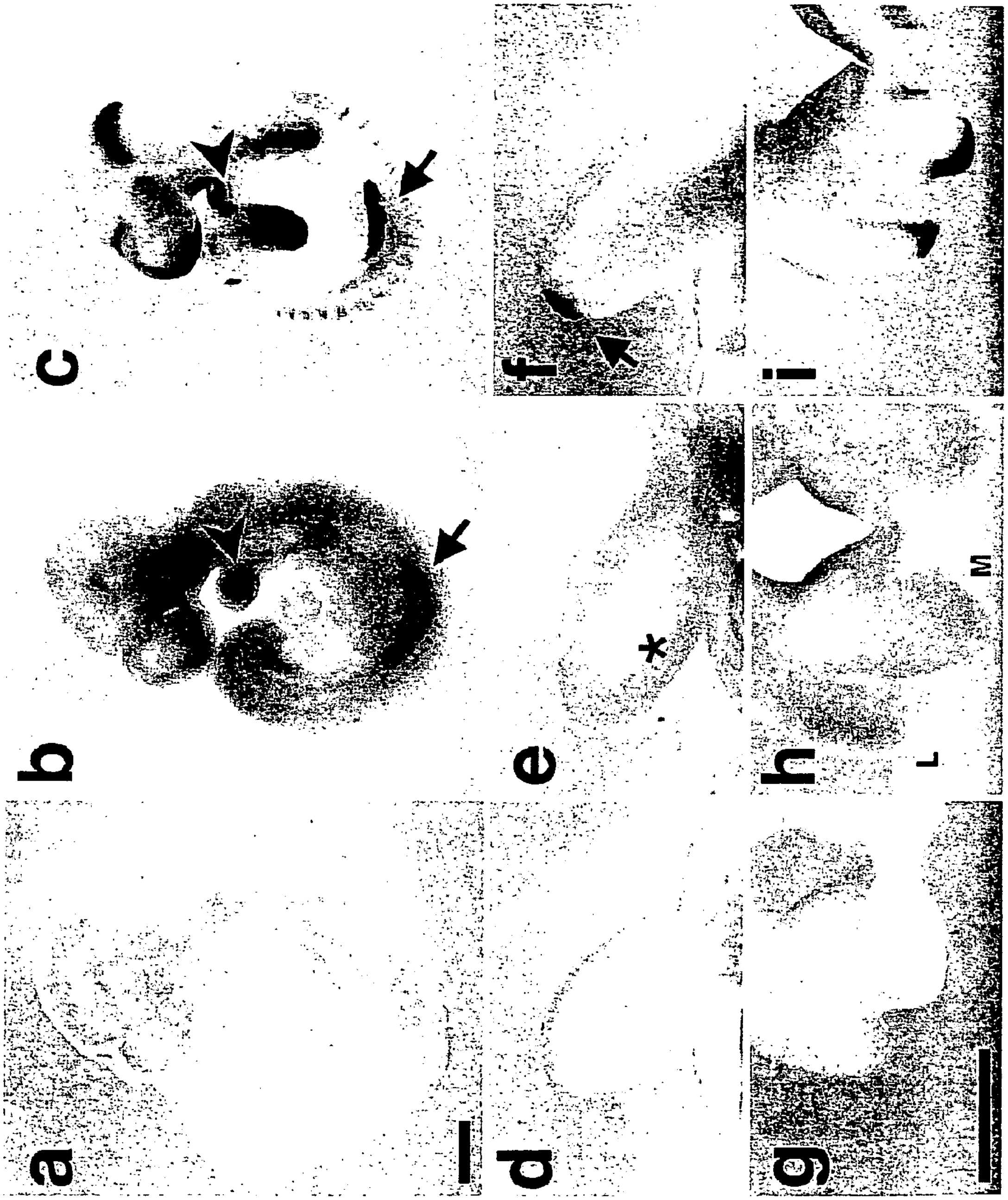
FIG. 5. Expression of NIPBL in the developing mouse.
Figure 10A:
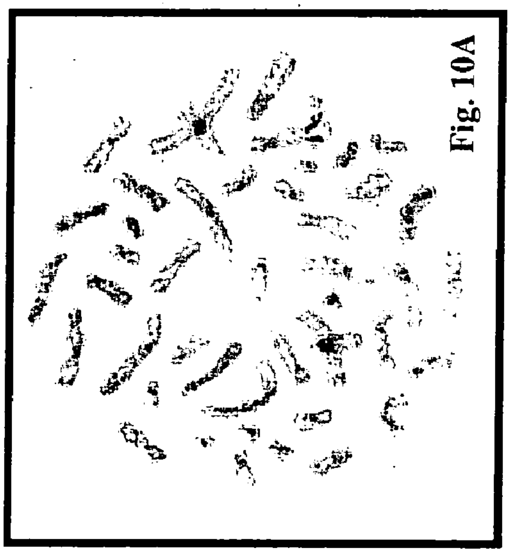
FIG. 10A. control metaphase spread stained with giemsa.
Figure 10B:
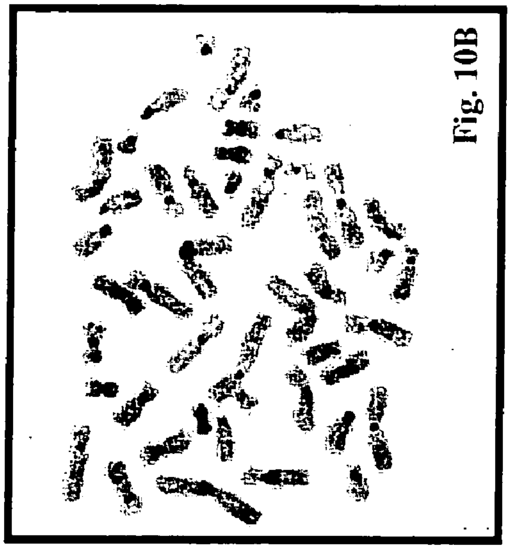
FIG. 10B. Control C-stained metaphase.
Figure 10C:
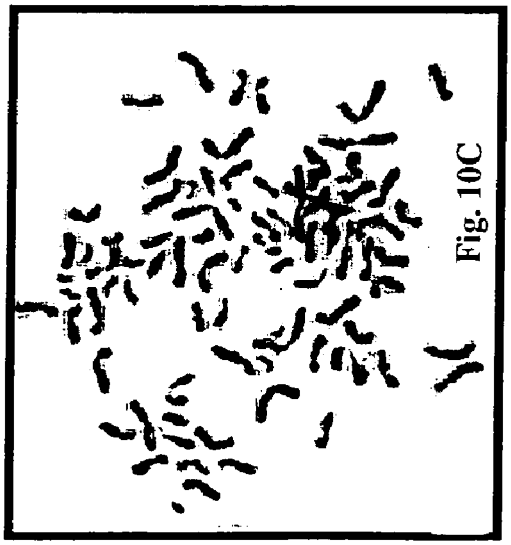
FIGS. 10C-E. Metaphase spread from 3 individuals with CdLS stained with giemsa demonstrating PSCS. Note separated sister chromatids and centromeres present in practically all sister chromatids.
Figure 10D:
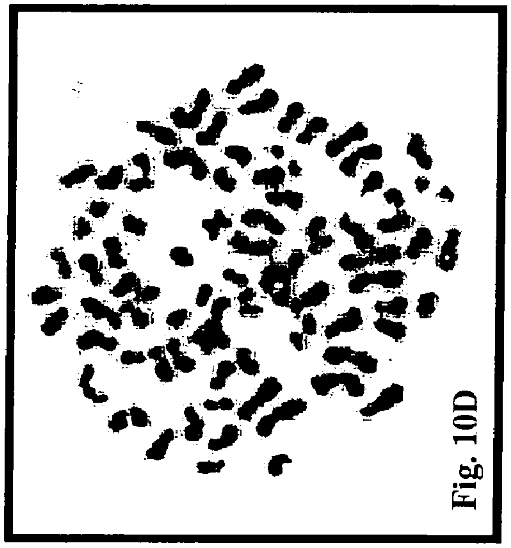
Figure 10E:
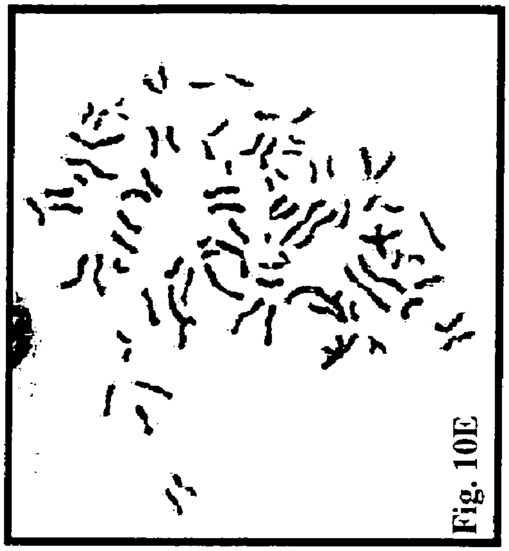
Figure 10H:
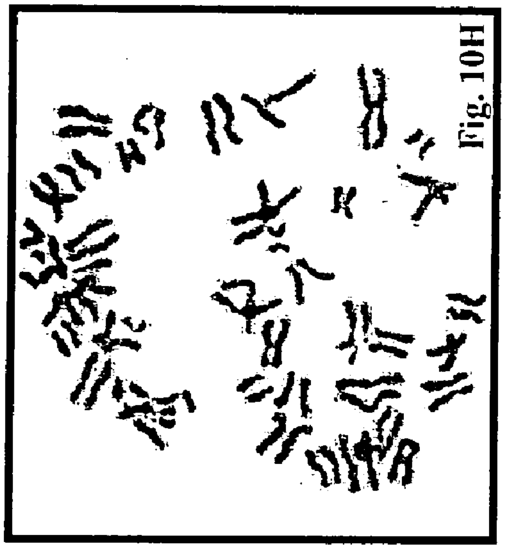
FIGS. 10F-H. C-stained metaphases from individuals with CdLS demonstrating the premature division and separation of the centromeres in the majority of sister chromatids. I. A metaphase form an individual with CdLS demonstrating apparent chromatid breaks (arrowheads).
Figure 10G:
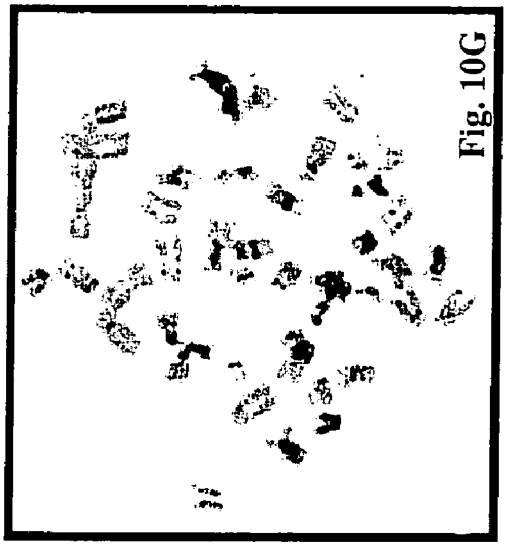
Figure 10I:
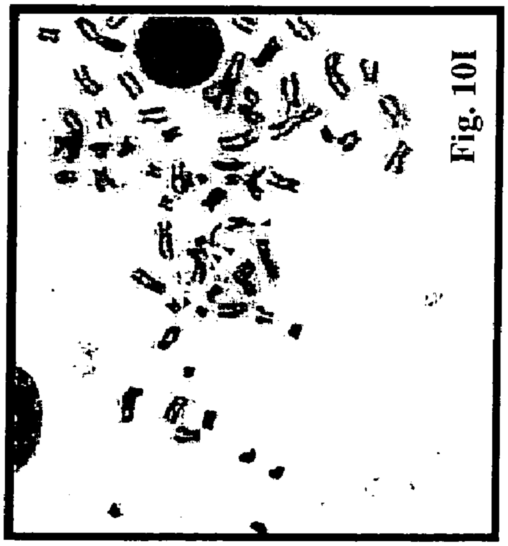
FIG. 10. Metaphase spreads in individuals with CdLS and unaffected controls.
Figure 10F:
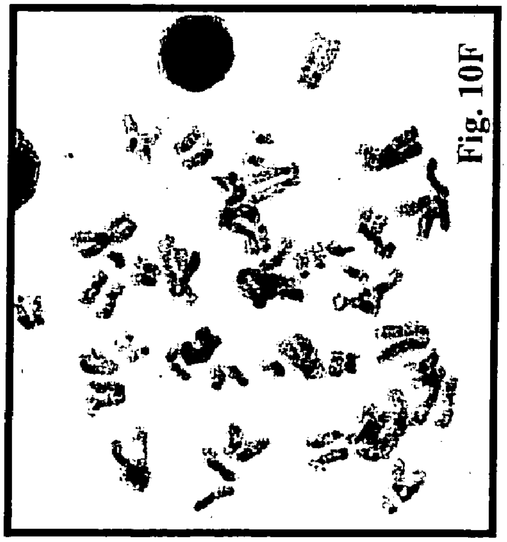

Expression patterns were studied by Northern blot and in situ analyses. Northern blots of both fetal and adult samples for multiple probes demonstrated ~6 Kb and 1.9 Kb transcripts and, in fetal samples, additional bands of 9.5 Kb and 7.2 Kb (FIG. 4). The presence of multiple transcripts suggests alternative splicing for this gene. Transcripts of the mouse homolog of NIPBL (mNIPBL) can be detected widely at days 9.5 and 10.5 of gestation (FIG. 5), with notable accumulations in limb bud, branchial arch and craniofacial mesenchyme. These data show that, in mouse, NIPBL is highly expressed in regions involved in patterning of, among other things, the skeleton and soft tissues of the limbs, jaw and face.

EXAMPLE 2

Mutational Analysis

The study population consisted of 120 propositi with CdLS, including 106 sporadic and 14 familial cases. Linkage to the NIPBL locus at 5p13.1 is described in the 12 families analyzed in Example I, with the identification of mutations in NIPBL in 2 of these families (Krantz et al. 2004). In one family, a missense mutation in the first codon (MIK) was identified in 3 affected half-siblings who each had a different father. The mutation was not present in DNA extracted from lymphocytes in their mother or in the 2 fathers on whom samples were available. In the second family, a splice site mutation (6763+5G>T) in the intron between exons 39 and 40 was identified in 2 affected siblings but not in DNA isolated from lymphocytes in either parent. The study population also included 4 previously reported, unrelated CdLS patients with unique, de novo mutations in NIPBL (Krantz et al. 2004).

Spectrum of NIPBL Mutations Detected

The 120 propositi with CdLS were screened for NIPBL coding-region mutations. Exons 2-47 and flanking intron sequences were PCR amplified and analyzed by means of CSGE. All products with variant migration profiles (band shifts) on CSGE were sequenced bidirectionally. NIPBL mutations were identified in 56 patients (7 familial; 49 sporadic) (47%) (Table 4, FIG. 1). Fifty-one different mutations were identified and comprised 21 frameshifts, 12 missense, 10 nonsense, and 9 splice site mutations. All but 4 (8%) mutations identified were private: a 2-bp deletion of exon 10 (2479delAG) in 2 unrelated patients; a nonsense mutation (R1536X) of exon 22 in 3 unrelated patients; a splice site mutation in the intron upstream of exon 35 (6109-3T>C) in 2 unrelated patients; and a missense mutation (R2298H) of exon 40 in 2 unrelated patients Forty-four different mutations were identified in 49 of the 106 individuals (46%) with sporadic CdLS. Fourteen (32%) of the 44 mutations were small deletions. Six (14%) of the mutations were insertions. Of these, five were single-base-pair insertions, and one was a complex deletion/insertion mutation with net insertion of 3 base pairs. All deletions and insertions led to frameshifts that resulted in a prematurely truncated protein product. The deletion, 2479delAG in exon 10, was seen in 2 unrelated sporadic cases. Nine (20%) of the different mutations had single-base-pair changes that led to immediate stop codons. Four (44%) of the nonsense mutations were found in exon 10. The nonsense mutation (RI 536X) of exon 22 was identified in 3 unrelated patients with sporadic CdLS. In one sporadic patient with a de novo t(14q;21q)(q32;q11) (Wilson et al. 1983), a nonsense mutation, S1459X in exon 20 of NIPBL was identified and was not present in either of her parents suggesting that the balanced de novo translocation may represent an unrelated event.

Seven patients (16%) with sporadic CdLS had different mutations predicted to lead to alterations in splicing. The six splice site mutations were not identified in available parental samples (6 mothers, 3 fathers), or in the 150 control patient samples.

Ten (23%) of the 44 mutations identified in patients with sporadic CdLS resulted in the substitution of a single amino acid. These substitutions were predicted to result in missense mutations by three criteria: absence in parental samples; absence in control samples; and evolutionary conservation of the altered amino acid. One missense mutation, R2298H in exon 40, was identified in 2 unrelated patients. The missense mutations identified included: A1246G (exon 15), L1312P (exon 17), R1789L (exon 28), D1803V (exon 28), R2298C (exon 40), R2298H (exon 40), G2312R (exon 40), G2381A (exon 42), A2390T (exon 42), and Y2440H (exon 43). These amino acids were, in general, highly conserved throughout evolution (FIG. 6). These mutations were not identified in available parental samples or in the 150 control patient samples.

In one apparent familial case of CdLS (previously reported as family XII) (Krantz et al. 2001), which was excluded from subsequent linkage analyses as it showed an atypical inheritance pattern with 2 affected first male cousins born to unaffected sisters, the two affected males were found to carry different de novo mutations in NIPBL. In one child an A1246G missense change in exon 15 was identified while in his affected cousin a 7861-1 G>C splice site change was identified in the intron upstream of exon 46. Neither mutation was identified in either of the two sets of parents nor in the other cousin. The maternal 5p13 regions flanking NIPBL (including intragenic SNP markers) in the affected individuals were not shared (data not shown). Paternity was confirmed in both cases.

TABLE 4

Summary of Mutations in NIPBL Identified in CdLS Probands

| Exon | Mutation | Type | Effect on Protein | Father | Mother | Number |
|---|---|---|---|---|---|---|
| 2 | 2 T > A; M1K | missense | no initiating methionine | negative | Negative | Familial |
| | 64 + 1A > G | Splice site | | NA | Negative | 1 |
| 3 | 150delG | frameshift | Truncates protein 27 aa downstream | negative | Negative | 1 |
| | 65 − 5A > G | Splice site | | negative | Negative | 1 |
| | 199del10; 199ins13 (atcaacaggtgac) = SEQ ID NO: 121 | complex | Truncates protein 9 aa into insertion | NA | NA | 1 |
| 7 | 611 − 2A > G | Splice site | | NA | Negative | 1 |
| | 742delCT | frameshift | Truncates protein 8 aa downstream | NA | NA | 1 |
| 9 | 961delA | frameshift | Truncates protein 7 aa downstream | NA | NA | 1 |
| | R479X | nonsense | Truncates protein | negative | Negative | 1 |
| 10 | 1546insG | frameshift | Truncates protein 5 aa downstream | negative | Negative | 1 |
| | 1669insC | frameshift | Truncates protein 11 aa downstream | NA | negative | 1 |
| | 1902insA | frameshift | Truncates protein 2 aa downstream | negative | negative | 1 |
| | 2479delAG | frameshift | Truncates protein 2 aa downstream | negative | negative | 2 |
| | 2520delT | frameshift | Truncates protein 6 aa downstream | negative | negative | 1 |
| | 2969delG | frameshift | Truncates protein 1 aa downstream | NA | NA | 1 |
| | 3023delTGTCT | frameshift | Truncates protein 2 aa downstream | NA | negative | 1 |
| | 3057delTAGA | frameshift | Truncates protein 23 aa downstream | negative | negative | 1 |
| | 3060delAGAG | frameshift | Truncates protein 22 aa downstream | negative | negative | 1 |
| | R797X | nonsense | Truncates protein | NA | negative | 1 |
| | R832X | nonsense | Truncates protein | negative | NA | 1 |
| | E977X | nonsense | Truncates protein | negative | negative | 1 |
| | S1024X | nonsense | Truncates protein | NA | negative | 1 |
| 15 | 3736C > G; A1246G | missense | | negative | negative | 1 |
| 17 | 3969insG | frameshift | Truncates protein 6 aa downstream | negative | negative | 1 |
| | 3935T > C; L1312P | missense | | NA | negative | 1 |
| 18 | S1398X | nonsense | Truncates protein | NA | negative | 1 |
| 20 | S1459X | nonsense | Truncates protein | negative | negative | 1 |
| 21 | 4556delAAAAA | frameshift | truncates protein 1 aa downstream | negative | negative | 1 |
| 22 | R1536X | nonsense | truncates protein | negative (1) NA (2) | negative (2) NA (1) | 3 |
| | 4567delC | frameshift | truncates protein 1 aa downstream | NA | NA | 1 |
| 26 | R1723X | nonsense | truncates protein | negative | negative | Familial |
| 27 | R1758X | nonsense | truncates protein | negative | negative | 1 |
| 28 | 5366G > T; R1789L | missense | | NA | NA | 1 |
| | 5408A > T; D1803V | missense | | NA | negative | 1 |
| 29 | 5567G > C; R1856T | missense | | negative | negative | Familial |
| | 5574 + 1G > T | Splice site | | negative | negative | 1 |
| 35 | 6109 − 3T > C | Splice site | | NA (2) | negative (1) | 2 |
| 39 | 6763 + 5G > T | Splice site | | negative | negative | Familial |
| 40 | 6892C > T; R2298C | missense | | NA | negative | 1 |
| | 6893G > A; R2298H | missense | | negative | negative | 2 |
| 42 | 6934G > C; G2312R | missense | | negative | negative | 1 |
| | 7151delAAGAC | frameshift | truncates protein 3 aa downstream | NA | negative | Familial |
| | 7210delC | frameshift | truncates protein 21 aa downstream | NA | negative | 1 |
| 43 | 7142G > C; G2381A | missense | | NA | negative | 1 |
| | 7168G > A; A2390T | missense | | negative | negative | 1 |

TABLE 4-continued

Summary of Mutations in NIPBL Identified in CdLS Probands

| Exon | Mutation | Type | Effect on Protein | Father | Mother | Number |
|---|---|---|---|---|---|---|
| | 7318T > C; Y2440H | missense | | negative | negative | 1 |
| | 7321 + 4 A > G | Splice site | | negative | positive | Familial |
| 44 | 7431delG | frameshift | truncates protein 30 aa downstream | NA | negative | 1 |
| 45 | 7780delC | frameshift | truncates protein 16 aa downstream | negative | negative | Familial |
| | 7825insG | frameshift | truncates protein 22 aa downstream | negative | negative | 1 |
| 46 | 7861 − 1G > C | Splice site | | negative | negative | 1 |

Mutations were identified in 7 of 14 (50%) familial cases of CdLS. Mutations in NIPBL were previously reported in 2 of these families: a missense mutation in the first codon (M1K) was identified in the 3 affected siblings, all of whom had different fathers, and was not present in the mother or two fathers available for testing (in all familial cases mutational analysis of parental samples was performed on DNA extracted from lymphocytes, and mosaicism in other tissues cannot be excluded); and a splice site mutation (6763+5G>T) segregated with the CdLS phenotype in a family with 2 affected siblings and not in either parent (Krantz et al. 2004). Four of the 5 remaining mutation-positive families had previously been linked to the NIPBL locus (Krantz et al. 2004). A nonsense mutation, R1723X, in exon 26 was identified in the first family with 2 affected brothers; neither of the parents nor the unaffected brother have the mutation. In the second family the two affected siblings share a unique 5-bp deletion, 7151delAAGAC in exon 42, resulting in protein truncation 3 amino acids downstream. The mother did not carry the change and there was no sample available for testing from the father. An affected brother and sister in the third family share a single base pair deletion, 7780delC of exon 45; this deletion results in premature protein truncation 16 amino acids downstream. Neither parent carried this mutation. In the fourth family with 4 affected siblings and a mildly affected mother a splice site mutation, 7321+4 A>G in exon 43, was identified in the 2 affected siblings from whom samples were available, as well as in the affected mother. In the final family, not included in the initial linkage studies as the affected female sibling of the proband was deceased and no sample was available, a missense mutation R1856T in exon 29, was identified in the affected male child, but was not present in either parent or in an unaffected sibling. Paternity was confirmed in all familial cases (as part of the genome-wide and high-resolution linkage analysis using multiple polymorphic markers) where a paternal sample was available.

None of the 51 different mutations were observed in 150 ethnically-matched control subjects.

Forty-two sequence variants that are likely to represent neutral polymorphisms were observed in subjects with CdLS, unaffected family members, and/or control individuals (Table 5). Three of the polymorphisms (N674S, N1994S, and 11206V) in the coding region of NIPBL led to an altered amino acid residue, while 3 (D817D, L1591L, and S1958S) were silent. Thirty-six polymorphisms were identified in intronic sequences flanking the exons.

TABLE 5

Polymorphisms in NIPBL Identified in Affected Individuals, Family Members and/or Controls

| Polymorphism | Exonic Localization |
|---|---|
| 230 + 61 C > A* | Exon 3 |
| 611 + 102 A > G# | Exon 6 |
| 2021 A > G; N674S* | Exon 10 |
| 2451 C > T; D817D# | Exon 10 |
| 3575 − 14 A > G* | Exon 14 |
| 3616 A > G; I1206V | Exon 14 |
| 3855 + 52 A > G* | Exon 16 |
| 4088 + 53 T > C# | Exon 17 |
| 3586 − 59 G > A | Exon 17 |
| 4239 + 53 T > C# | Exon 18 |
| 4239 + 152 C > G# | Exon 18 |
| 4240 − 48 C > T# | Exon 19 |
| 4321 − 96 C > T | Exon 20 |
| 4321 − 35 T > C# | Exon 20 |
| 4560 + 77 A > G* | Exon 21 |
| 4560 + 108 del T* | Exon 21 |
| 4561 − 9 T > A# | Exon 22 |
| 4561 − 106 C > T# | Exon 22 |
| 4634 + 24 G > A# | Exon 22 |
| 4773 G > T; L1591L# | Exon 23 |
| 4777 − 108 del A* | Exon 24 |
| 4921 − 58 G > A* | Exon 25 |
| 5575 − 193 T > C* | Exon 30 |
| 5575 − 92 G > C | Exon 30 |
| 5575 − 18 G > C# | Exon 30 |
| 5710 − 59 A > G# | Exon 31 |
| 5710 − 78 G > A# | Exon 31 |
| 5862 + 74 del TT* | Exon 32 |
| 5863 − 12 del AT* | Exon 33 |
| 5863 − 30 del AT* | Exon 33 |
| 5863 − 52 del T# | Exon 33 |
| 5874 C > T; S1958S* | Exon 33 |
| 5971 A > G; N1994S# | Exon 34 |
| 6109 − 54 ins A | Exon 35 |
| 6109 − 3 T > C # | Exon 35 |
| 6498 − 94 T > C# | Exon 38 |
| 6499 − 80 A > G# | Exon 39 |
| 6764 − 35 C > G* | Exon 40 |
| 6954 + 62 A > G# | Exon 40 |
| 6955 − 9 del T* | Exon 41 |
| 7861 + 39 G > A | Exon 45 |
| 8698 − 8701 del ACAA | Exon 47 (region of 3' UTR) |

*indicates found in patient samples, family members and/or normal controls.
#indicates found in patient samples and family members.
All other polymorphisms were identified in control samples only.

FISH Analysis

Twenty-eight probands (4 familial and 24 sporadic) in whom a NIPBL mutation was not identified were analyzed by FISH with a NIPBL-containing BAC probe (RP 11-14121) to evaluate the possibility of a submicroscopic deletion encompassing the NIPBL gene. RP11-14121 (AC018853.3) encompasses approximately 16 kb of sequence 5' of NIPBL gene through approximately exon 10 of NIPBL. No deletion of RP1 1-14121 was detected in any of the probands analyzed.

Genotype-Phenotype Correlation

Because of the clinical heterogeneity observed in CdLS (FIG. 1), we evaluated for possible associations between NIPBL genotype and the severity of the phenotype (severity of limb, growth and developmental involvement). The distribution of several major clinical features in our study cohort is shown in Table 6. The results of genotype-phenotype correlation analysis performed for each phenotypic parameter versus presence or absence of a mutation in NIPBL, and versus missense or other types of mutations, are also summarized in Table 6. Statistically significant ($P<0.05$) differences were observed in the distribution of severity of growth retardation and developmental delay between the mutation-positive and mutation-negative groups with the mutation-positive group displaying a more severe phenotype for these parameters. A similar trend was also observed in the severity of limb defects, although in this case the difference was not statistically significant. When comparing individuals with missense mutations versus all other mutation types, it appeared that the latter were associated with more severe phenotypes in all categories except possibly in growth retardation, although the number of missense mutations was small.

either the methods used for screening are not identifying all mutations in individuals with CdLS or that potentially additional genes in 5p13 may be responsible for the phenotype.

If NIPBL is the only CdLS disease gene then our mutation detection rate of only 47% may be partly due to the large size of the NIPBL gene and the use of CSGE for mutational analysis. Factors that may account for missed mutations in the gene include: 1) variations in sequence beyond the immediate intron/exon boundaries (such as regulatory regions or intronic sequence); 2) large intragenic deletions; 3) subtle sequence variations (such as point mutations); and 4) difficulty in amplifying and sequencing several NIPBL exons (e.g. exon 33) due to numerous polymorphisms. The multiple splice variants of this gene have made it difficult to screen cDNA accurately for mutations at this time, although this testing is currently being optimized and will allow for improved detection of intronic variations that lead to splice mutations as well as complete exonic deletions. Large-scale deletions of NIPBL were assayed for in those individuals in whom an NIPBL mutation was not identified, and in the 28 mutation-negative individuals studied by FISH no deletion of the region was seen.

Alternatively, it is possible that the linkage established in some of these small families was coincidental and that a second CdLS gene may yet be identified elsewhere in the genome to account for the phenotype in those individuals in whom mutations in NIPBL were not identified. In our initial genome-wide linkage exclusion analysis, 3 other regions were not excluded: chromosome 2q37; chromosome 10p13; and chromosome 14q24. These additional loci may contain a second CdLS gene (Krantz et al. 2004). Likewise several individuals with CdLS have been found to carry an apparently balanced de novo translocation suggesting possible additional loci for a CdLS disease gene. The child with the t(5;13)(p13.1;q12.1) was critical in the identification of NIPBL on chromosome 5p13 as the cause of CdLS when mutated (Hulinsky et al. 2003; Krantz et al. 2004; Tonkin et al. 2004). Two other de novo balanced translocations have been reported. A de novo t(3;17)(q26.3;q23.1) (Ireland et al. 1991) has been extensively evaluated in a child with sporadic CdLS,

TABLE 6

Distribution of Clinical Severity and Results of Genotype-Phenotype Correlation Analysis.

| PHENOTYPE | SCORE | MUTATION-POSITIVE (n = 56) Missense (%) | MUTATION-POSITIVE (n = 56) Frameshift, Splice Site, Nonsense (%) | MUTATION-NEGATIVE (n = 64) (%) | Mutation Positive versus Mutation Negative P value (Chi Square test) | Missense versus all other Mutations P value (Fisher's Exact Test) |
|---|---|---|---|---|---|---|
| Limb Reduction | 1 | 12 (0.92) | 25 (0.60) | 47 (0.75) | 0.085 | 0.029 |
| | 2 | 1 (0.08) | 3 (0.07) | 9 (0.14) | | |
| | 3 | 0 | 14 (0.33) | 7 (0.11) | | |
| | N/A | 0 | 1 | 1 | | |
| Developmental Delay | 1 | 3 (0.23) | 1 (0.03) | 12 (0.20) | 0.014 | 0.008 |
| | 2 | 6 (0.46) | 10 (0.25) | 27 (0.44) | | |
| | 3 | 4 (0.31) | 29 (0.73) | 22 (0.36) | | |
| | N/A | 0 | 3 | 3 | | |
| Growth Retardation | 1 | 3 (0.33) | 2 (0.07) | 17 (0.47) | 0.002 | 0.057 |
| | 2 | 4 (0.44) | 11 (0.38) | 13 (0.36) | | |
| | 3 | 2 (0.22) | 16 (0.55) | 6 (0.17) | | |
| | N/A | 4 | 14 | 28 | | |

n = 56 for mutation positive individuals, and n = 64 for mutation-negative individuals
NA = Not assessed.

Discussion

Through the combined use of genome-wide linkage exclusion analysis and mapping of a chromosomal rearrangement on chromosome 5p13, NIPBL was identified as a CdLS disease gene (Krantz et al. 2004; Tonkin et al. 2004). We have identified mutations in 47% of a well-characterized cohort of 120 unrelated probands with both sporadic and familial CdLS. Mutation detection rates were comparable between the sporadic and familial cases: 49 of 106 (46%) sporadic cases and 7 of 14 (50%) of familial cases had identifiable mutations. We expected to detect NIPBL mutations in all of the familial cases previously shown to be positively linked to the 5p13 region (Krantz et al. 2004); however, in our present analysis, we have identified mutations in only 6 of the 11 families available for mutational analysis. This indicates that and to date, no CdLS disease genes have been identified (Tonkin et al. 2001; Tonkin et al. 2004). In this report, a child with a previously described de novo t(14q;21q)(q32;q11) (Wilson et al. 1983) has been found to carry a de novo S1459X NIPBL mutation in exon 20. This may indicate that this translocation is an unrelated event. While not all breakpoints in these rare translocation cases have been completely evaluated, they do not appear to lend additional support to a potential second locus at this time.

Fifty-one different mutations in NIPBL have been identified in 56 patients (7 familial; 49 sporadic) and comprise frameshifts, missense, nonsense, and splice site mutations. Mutations were identified throughout the coding region of the gene (Krantz et al. 2004; Tonkin et al. 2004). To date, no mutations have been identified in exons 4-6, 8, 11-14, 16, 19, 23-25, 30-34, 36, 37 41 and 47. Several exons have been found to have multiple mutations including exons 2, 3, 7, 9, 10, 17, 22, 28, 29, 40, 42, 43 and 45. There is a preponderance of mutations identified in exon 10; however, this exon, at 1625 base pairs, is approximately 8 times the size of the average exon (~200 bp) in the NIPBL gene. Exon 42, at 200 base pairs, was found to contain 4 different mutations in this cohort. The majority of mutations identified are frameshift (22/56~39%) (16 deletions, 5 insertions, 1 complex), followed by missense mutations (13/56~23%), nonsense mutations (12/56~21%), and splice site mutations (9/56~16%). The frameshift, nonsense, and splice site mutations are likely to result in a prematurely truncated protein resulting in haploinsufficiency of NIPBL (a disease mechanism that has been documented in the report of a child with CdLS and a large cytogenetically visible deletion of chromosome 5p13.1-14.2 encompassing the NIPBL gene (Hulinsky et al. 2003)).

The missense mutations are important in that they may indicate residues of the NIPBL protein that are functionally important. Of the 12 unique missense mutations identified 8 are in amino acid residues that are evolutionarily conserved back to *Drosophila* (including the M1K change in the initiation codon), and 3 are evolutionarily conserved back to the mouse. One missense mutation, Y2440H, is present in an amino acid that is in a stretch of the human NIPBL protein not seen in rat, mouse or *Drosophila.*

Four mutations were identified in unrelated individuals: 2479delAG in exon 10 in 2 individuals; R1536X in exon 22 in 3 individuals; 6109-3T>C in the intronic sequence upstream of exon35 in 2 individuals; and R2298H in exon 40 in 2 individuals. An additional missense mutation in amino acid residue 2298 was also seen in another individual (R2298C). Even among individuals with the same mutation, the phenotype demonstrated some variability. The 3 individuals with the R1536X mutation are all severely affected in growth and development; however, 2 of the 3 have severe limb reduction defects while the third did not have reduction defects. The 2 children with the 2479delAG mutation are also similarly severely affected for growth and development, however one has significant limb reduction defects while the other does not have a reduction defect. The 2 children with the 6109-3T>C and the 2 children with the R2298H missense mutation are all moderately affected for growth and development and none have limb reduction defects. This variability in severity of the phenotypes associated with identical mutations indicates that mutations in NIPBL are not the sole determinants of phenotype and that other factors (genetic and/or environmental) can modify the clinical picture.

In 6 of the 7 familial cases in which an NIPBL mutation has been identified germ line mosaicism is the most likely mechanism. In 5 of these families, DNA from lymphocytes was available for testing from both parents and none carried the mutations identified in the affected siblings and paternity was confirmed in all cases. In one family with a 7151 delAGAC, the father was not available for testing, however he reportedly has no clinical features of CdLS and the mutation was not seen in the mother. Autosomal dominant transmission was demonstrated in the seventh family; a 7321+4 A>G mutation in exon 43 was identified in the mildly affected mother and in 2 of her 4 affected daughters in whom samples were available.

In the 25 sporadic cases in which both parents were available for screening, all mutations were found to have arisen de novo, and in the 17 sporadic cases in which only one parent was available for screening, none of these parents were found to carry the change seen in their child. This would indicate that the vast majority of mutations in individuals with CdLS arise as new events, and in the rare cases of familial recurrence where neither parent is affected germ line mosaicism is the likely explanation. In the family where two male first cousins have CdLS and their mothers, who are sisters, are unaffected, the 2 affected male cousins were each found to carry a different de novo mutation (neither mutation was seen in either set of parents and direct sequencing of the 2 cousins confirmed that they did not share the same mutation). None of the mutations identified in the individuals described here were seen in 300 ethnically matched normal control chromosomes.

A large number of polymorphisms also have been identified in NIPBL (Table 5). There were 3 polymorphisms (N674S, I1206V, and N1994S) that resulted in an amino acid substitution. All 3 of these were identified in probands who had mutations in other exons, and in the case of the N1994S it was present in one of the unaffected parents as well (both parents were not available for screening for the other 2 variants). One polymorphism, N674S, was seen in 25 unrelated probands, 11 of whom had identifiable NIPBL mutations, and in several controls. This amino acid residue is conserved back to the mouse, but is not conserved in *Drosophila*. If the polymorphism was on the non-mutant allele and had a mild functional effect on the protein, it is possible that it could be a modifier of the phenotype. In the cohort of 11 probands with a mutation and this polymorphism there did not appear to be a marked effect on phenotype. It is of interest that the one individual with a missense (A2390T) mutation who also had this polymorphism was the only one amongst the probands with missense mutations to have limb reduction defects. Further work is needed to evaluate this, and other polymorphisms, as potential modifiers of the phenotype through determining allelic localization of these changes in relation to the mutation as well as functional studies to assess their effects.

Genotype-phenotype correlations between mutation positive and mutation negative individuals as well as between those individuals with different types of mutations were investigated. Severity of limb defects, growth and cognitive development were evaluated (outlined in Tables 1 and 6). Mutations in NIPBL were found in mildly and severely affected individuals with CdLS. Similarly in the group of CdLS probands without identifiable mutations there are also severely and mildly affected individuals. In order to formally evaluate for genotype-phenotype associations between mutation-positive and mutation-negative individuals we performed a contingency table analysis for the three categories of each phenotype tested (limb, growth, and development) versus presence or absence of mutation (Table 6). This analysis demonstrated a trend towards a more severe phenotype in mutation-positive versus mutation-negative individuals. This may indicate that a subset of individuals with "mild" CdLS may either have a different genetic etiology causing their phenotypic findings or mutations in NIPBL that have not yet been detected using CSGE.

We hypothesized that the missense mutations identified in NIPBL may result in either a milder phenotype as a result of a less severe structural effect on the protein, or conversely, a more severe phenotype if they occurred in critical domains of the protein, causing a dominant-negative effect. For these reasons a similar analysis was performed to evaluate genotype-phenotype correlations between missense and all other types of mutations. This analysis suggests that individuals with missense mutations may have a milder phenotype; however, the numbers of individuals with missense mutations are too small to reach definite conclusions at this time.

The role of NIPBL in mammals has yet to be elucidated and what is known about its function has come from *Drosophila* studies. The *Drosophila* homolog of NIPBL, Nipped-B, was identified through a screen for mutations that reduce activation by the wing margin enhancer in the presence of a gypsy insertion (Rollins et al. 1999). Gypsy insertions in the cut gene in *Drosophila* are known to block a remote wing margin enhancer located 85 kb upstream of the promoter. This long range effect on transcription as well as its homology to chromosomal adherins (proteins that have a role in chromosome compaction and sister chromatid cohesion) suggest that the Nipped-B protein performs an architectural role in enhancer-promoter communication (Rollins et al. 1999). These interactions have been demonstrated to be involved in the regulation of multiple developmental pathways in *Drosophila* including the Notch signaling pathway (Rollins et al. 1999). Recently a role for the *Drosophila* Nipped-B protein in sister chromatid cohesion has also been demonstrated, and a model of how Nipped-B interacts with the cohesin protein complex to effect gene expression was proposed (Rollins et al. 2004). The ability of distal enhancers to activate promoters and initiate transcription relies on the coordinated interaction of multiple proteins and protein complexes. The large number of additional proteins that interact in these complexes suggest multiple possibilities for modifiers of NIPBL and/or potential additional CdLS disease genes.

We have shown that mutations in NIPBL are detected at present in 47% of individuals with both familial and sporadic CdLS. The mutations are spread throughout the gene, and frameshift, nonsense, splice site and missense mutations have been identified. The majority of mutations are protein truncating, likely leading to haploinsufficiency of the protein product. The 12 unique missense mutations identified in this screening will be important in characterizing functionally important domains of this novel protein. Furthermore, there appears to be a genotype-phenotype correlation between mutation positive and mutation-negative individuals as well as possibly between individuals with missense mutations when compared to all other mutation types.

EXAMPLE 3

Precocious Sister Chromatid Separation (PSCS) in Cornelia de Lange Syndrome

Mutations in NIPBL were identified in sporadic and familial CdLS cases. See Examples 1 and 2. NIPBL is the human homolog of the *Drosophila* Nipped-B gene. Although its function in mammalian systems has not been elucidated, Nipped-B has been shown to be an essential regulator of cut, *Ultrabithorax*, and Notch receptor signaling in *Drosophila*. Sequence homologs of Nipped-B in yeast (Scc2 and Mis4) are required for sister chromatid cohesion during mitosis, and a similar role was recently demonstrated for Nipped-B in *Drosophila* (Rollins et al., 2004). In order to evaluate NIPBL's role in sister chromatid cohesion in humans, metaphase spreads on a large cohort of mutation positive and mutation negative probands with CdLS were evaluated for evidence of precocious sister chromatid separation (PSCS). PSCS was seen in a significant number of CdLS probands when compared to unaffected matched controls. These studies indicate that NIPBL may play a role in sister chromatid cohesion in humans as has been reported for its homologs in *Drosophila* and yeast. The identification of PSCS in individuals with CdLS provides an additional diagnostic aid as NIPBL mutational analysis can be labor intensive and to date, mutations are identified in only 45% of affected probands.

Results

In order to evaluate NIPBL's role in sister chromatid cohesion in humans, metaphase spreads on 90 CdLS probands (40 NIPBL mutation positive and 50 NIPBL mutation negative) were evaluated for evidence of precocious sister chromatid separation (PSCS). We screened a minimum of 50 metaphases from each proband and found evidence of PSCS in 37 of 90 probands (41%) (FIG. 10). Of these, 37 probands with PSCS, 16 (43%) were mutation positive and 21 (57%) mutation negative. Of the 53 probands without evidence of PSCS, 24 (45%) were mutation positive and 29 (54%) were mutation negative. Ninety control slides were screened and 8 (9%) demonstrated evidence of PSCS. Both severe and mild CdLS phenotypes were seen in the PSCS positive and negative groups. Missense, frameshift and nonsense mutations have been seen in both groups. Two of the patients with PSCS have the same missense mutation: an R2298H in exon 40 in a highly conserved amino acid residue. An average of 2.05 metaphases (4%) (Range: 2-10%) were found to have PSCS in the CdLS probands. In the control samples that were positive for PSCS an average of 1.125 metaphases (2%) (Range 0-4%) were found to have PSCS. Additionally, several metaphase spreads from individuals with CdLS demonstrated some evidence of breakage. See FIG. 10-I.

Discussion

In eukaryotic cells, replicated DNA molecules remain physically connected from their synthesis in S phase until they are separated during anaphase. This phenomenon, called sister chromatid cohesion, is essential for the temporal separation of DNA replication and mitosis and for the equal separation of the duplicated genome. Sister chromatids in metaphase chromosomes are physically connected until their separation during anaphase (Nasmyth et al., 2000; Nasmyth et al., 2001). PSCS is a phenomenon whereby separate and splayed chromatids with discernible centromeres are seen and involves all or most chromosomes of a metaphase (Kajii and Asamoto 2004). It involves not only the centromere but also the entire sister chromatids of almost all mitotic chromosomes in a given metaphase (Kajii and Ikeuchi 2004). PSCS has been described in a number of conditions including Roberts Syndrome (German 1979), Fanconi Anemia and Ataxia Teleangiectasia (Mehes and Buhler 1995), Alzheimer disease (Moorhead and Heyman 1983; Spremo-Potparevic et al., 2004) Tuberous Sclerosis (Scappaticci et al., 1988), Variegated Aneuploidy (Kajii et al., 1998; Plajaet al., 2003; Plaja et al., 2001) and in normal individuals after exposure to genotoxic chemicals (Major et al., 1999) as well as in association with cancer such as Wilms tumor (Mehes et al., 2002) and breast cancer (Rao et al., 1996) and has been seen in spontaneous abortions (Keser et al., 1996). Recently mutations in the BUB1B gene were found to be a cause of multiple variegated aneuploidy (Hanks et al., 2004). BUB1B encodes BUBR1, a key protein in the mitotic spindle checkpoint. PSCS has also been reported to be present in a low percentage (less than 2-3%) of normal individuals (Dominguez and Rivera 1992; Kajii and Ikeuchi 2004).

Due to the role played by the yeast homologs of NIPBL (Scc2, Rad21, Mis4) in sister chromatid cohesion and the evidence that a similar cohesion abnormality is seen in *Drosophila* (Rollins et al., 2004), we hypothesized that a similar phenomenon may be present in individuals with CdLS. In studying a minimum of 50 metaphase spreads in 90 CdLS individuals and 90 matched control subjects we found a prevalence of PSCS of 41% in the CdLS samples and 9% in the control samples. The presence or absence of PSCS in CdLS did not appear to be influenced by the presence or absence of an identified mutation in NIPBL or by the age or sex of the individuals with CdLS.

The finding of several metaphases in some of the CdLS probands demonstrating apparently increased breakage (not observed in any of the controls) (FIG. 10-I) indicates that there may be some predisposition to chromosomal fragility in CdLS probands; however, this finding warrants further investigation.

The identification of PSCS in individuals with CdLS has diagnostic value. Presently mutations in NIPBL are identified in approximately 45% of individuals with a clear diagnosis of CdLS (Gillis et al., 2004; Krantz et al., 2004; Tonkin et al., 2004). There has not been any clear evidence that there are other loci for a CdLS gene at this time and it may be that the low mutation detection rate is complicated by the large size of the NIPBL gene and incomplete characterization of the entire coding region (Gillis et al., 2004). The development of an auxiliary test, such as screening for PSCS, provides another parameter to assess for supporting a diagnosis in individuals with CdLS in whom an NIPBL mutation has not been identified, or in whom testing was not performed.

REFERENCES

Bankier A, Haan E, Birrell R (1986) Familial occurrence of Brachmann-de Lange syndrome. Am J Med Genet 25:163-5

Beratis N G, Hsu L Y, Hirschhorn K (1971) Familial de Lange syndrome. Report of three cases in a sibship. Clin Genet 2:170-6

Brachmann W (1916) Ein fall von symmetrischer monodactylie durch ulnadefekt, mit symmetrischer flughautbildung in den ellenbeugen, sowie anderen abnormalitaten (zwerghaftigkeit, halsrippen, behaarung). Jahrbuch Kinderheilkd 84:225-235

Caksen H, Kurtoglu S, Cesur Y, Ozturk A (2001) An analysis of seven infants with Brachmann-de Lange syndrome, of whom two identical twin sisters. Genet Couns 12:373-7

Chodirker B N, Chudley A E (1994) Male-to-male transmission of mild Brachmann-de Lange syndrome. Am J Med Genet 52:331-3 de Lange C (1933) Sur un type nouveau de degeneratio (typus Amstelodamensis). Arch Med Enfants 36:713-719

Feingold M, Lin A E (1993) Familial Brachmann-de Lange syndrome: further evidence for autosomal dominant inheritance and review of the literature. Am J Med Genet 47:1064-7

Fryns J P, Dereymaeker A M, Hoefnagels M, D'Hondt F, Mertens G, van den Berghe H (1987) The Brachmann-de Lange syndrome in two siblings of normal parents. Clin Genet 31:413-5

Ganguly A, Rock M J, Prockop D J (1993) Conformation-sensitive gel electrophoresis for rapid detection of single-base differences in double-stranded PCR products and DNA fragments: evidence for solvent-induced bends in DNA heteroduplexes. Proc Natl Acad Sci U S A 90:10325-9

Halal F, Silver K (1992) Syndrome of microcephaly, Brachmann-de Lange-like facial changes, severe metatarsus adductus, and developmental delay: mild Brachmann-de Lange syndrome. Am J Med Genet 42:381-6

Hulinsky R, Winesette H, Dent K, Silver R, King J, Lowichik A, Chen Z, Viskochil D (2003) Prenatal diagnosis dilemma: fetus with del(5)(p13.1p14.2) diagnosed postnatally with Cornelia de Lange syndrome. Am J Hum Genet suppl. 73:602

Ireland M, Donnai D, Burn J (1993) Brachmann-de Lange syndrome. Delineation of the clinical phenotype. Am J Med Genet 47:959-64

Ireland M, English C, Cross I, Houlsby W T, Burn J (1991) A de novo translocation t(3;17)(q26.3;q23.1) in a child with Cornelia de Lange syndrome. J Med Genet 28:639-40

Jackson L, Kline A D, Barr M A, Koch S (1993) de Lange syndrome: a clinical review of 310 individuals. Am J Med Genet 47:940-6

Kline A D, Barr M, Jackson L G (1993a) Growth manifestations in the Brachmann-de Lange syndrome. Am J Med Genet 47:1042-9

Kline A D, Stanley C, Belevich J, Brodsky K, Barr M, Jackson L G (1993b) Developmental data on individuals with the Brachmann-de Lange syndrome. Am J Med Genet 47:1053-8

Kozma C (1996) Autosomal dominant inheritance of Brachmann-de Lange syndrome. Am J Med Genet 66:445-8

Krajewska-Walasek M, Chrzanowska K, Tylki-Szymanska A, Bialecka M (1995) A further report of Brachmann-de Lange syndrome in two sibs with normal parents. Clin Genet 47:324-7

Krantz I D, McCallum J, DeScipio C, Kaur M, Gillis L A, Yaeger D, Jukofsky L, Wasserman N, Bottani A, Morris C A, Nowaczyk M J, Toriello H, Bamshad M J, Carey J C, Rappaport E, Kawauchi S, Lander A D, Calof A L, Li H H, Devoto M, Jackson L G (2004) Cornelia de Lange syndrome is caused by mutations in NIPBL, the human homolog of *Drosophila* melanogaster Nipped-B. Nat Genet 36:631-5

Krantz I D, Tonkin E, Smith M, Devoto M, Bottani A, Simpson C, Hofreiter M, Abraham V, Jukofsky L, Conti B P, Strachan T, Jackson L (2001) Exclusion of linkage to the CDL1 gene region on chromosome 3q26.3 in some familial cases of Cornelia de Lange syndrome. Am J Med Genet 101:120-9

Krantz I D, Rand E B, Genin A, Hunt P, Jones M, Louis A A, Graham J M, Jr., Bhatt S, Piccoli D A, Spinner N B (1997) Deletions of 20p12 in Alagille syndrome: frequency and molecular characterization. Am J Med Genet 70:80-6

Lieber E, Glaser J H, Jhaveri R (1973) Brachmann-de Lange syndrome. Report of two cases in a sibship. Am J Dis Child 125:717-8

McConnell V, Brown T, Morrison PJ (2003) An Irish three-generation family of Cornelia de Lange syndrome displaying autosomal dominant inheritance. Clin Dysmorphol 12:241-4

Naguib K K, Teebi A S, Al-Awadi S A, Marafie M J (1987) Brachmann-de Lange syndrome in sibs. J Med Genet 24:627-9

Opitz J M (1985) The Brachmann-de Lange syndrome. Am J Med Genet 22:89-102

Robinson L K, Wolfsberg E, Jones K L (1985) Brachmann-de Lange syndrome: evidence for autosomal dominant inheritance. Am J Med Genet 22:109-15

Rollins R A, Korom M, Aulner N, Martens A, Dorsett D (2004) *Drosophila* nipped-B protein supports sister chromatid cohesion and opposes the stromalin/Scc3 cohesion factor to facilitate long-range activation of the cut gene. Mol Cell Biol 24:3100-11

Rollins R A, Morcillo P, Dorsett D (1999) Nipped-B, a *Drosophila* homologue of chromosomal adherins, participates in activation by remote enhancers in the cut and Ultrabithorax genes. Genetics 152:577-93

Russell K L, Ming J E, Patel K, Jukofsky L, Magnusson M, Krantz I D (2001) Dominant paternal transmission of Cornelia de Lange syndrome: a new case and review of 25 previously reported familial recurrences. Am J Med Genet 104:267-76

Saul R A, Rogers R C, Phelan M C, Stevenson R E (1993) Brachmann-de Lange syndrome: diagnostic difficulties posed by the mild phenotype. Am J Med Genet 47:999-1002

Selicorni A, Lalatta F, Livini E, Briscioli V, Piguzzi T, Bagozzi D C, Mastroiacovo P, Zampino G, Gaeta G, Pugliese A, Cerutti-Mainaroli P, Guala A, Zelante L, Stabile M, Belli S, Franceschini P, Gianotti A, Scarano G (1993) Variability of the Brachmann-de Lange syndrome. Am J Med Genet 47:977-82

Tonkin E, Smith M, Eichhorn P, Hagan D M, Herrell S, Lusher M, Ireland M, Burn J, Strachan T (2001) A novel gene is disrupted by a Cornelia de Lange-associated translocation breakpoint at 3q26.3. Am J Hum Genet 69:A618

Tonkin E T, Wang T J, Lisgo S, Bamshad M J, Strachan T (2004) NIPBL, encoding a homolog of fungal Scc2-type sister chromatid cohesion proteins and fly Nipped-B, is mutated in Cornelia de Lange syndrome. Nat Genet 36:636-41

Van Allen M I, Filippi G, Siegel-Bartelt J, Yong S L, McGillivray B, Zuker R M, Smith C R, Magee J F, Ritchie S, Toi A, Reynolds J F (1993) Clinical variability within Brachmann-de Lange syndrome: a proposed classification system. Am J Med Genet 47:947-58

Wilson W G, Kennaugh J M, Kugler J P, Wyandt H E (1983) Reciprocal translocation 14q;21q in a patient with the Brachmann-de Lange syndrome. J Med Genet 20:469-71

Dominguez M G, Rivera H. 1992. C-anaphases: a mitotic variant. Ann Genet 35(3):183-5.

German J. 1979. Roberts' syndrome. I. Cytological evidence for a disturbance in chromatid pairing. Clin Genet 16(6): 441-7.

Gillis L A, McCallum J, Kaur M, DeScipio C, Yaeger D, Mariani A, Kline A D, Li H H, Devoto M, Jackson L G, Krantz I D. 2004. NIPBL mutational analysis in 120 individuals with Cornelia de Lange syndrome and evaluation of genotype-phenotype correlations. Am J Hum Genet 75(4):610-23.

Hanks S, Coleman K, Reid S, Plaja A, Firth H, Fitzpatrick D, Kidd A, Mehes K, Nash R, Robin N, Shannon N, Tolmie J, Swansbury J, Irrthum A, Douglas J, Rahman N. 2004. Constitutional aneuploidy and cancer predisposition caused by biallelic mutations in BUBIB. Nat Genet 36(11): 1159-61.

Ireland M, Burn J. 1993. Cornelia de Lange syndrome—photo essay. Clin Dysmorphol 2(2):151-60.

Kajii T, Asamoto A. 2004. Prenatal diagnosis of a heterozygous carrier of premature chromatid separation (PCS) trait. Am J Med Genet A 126(4):432.

Kajii T, Ikeuchi T. 2004. Premature chromatid separation (PCS) vs. premature centromere division (PCD). Am J Med Genet A 126(4):433-4.

Kajii T, Kawai T, Takumi T, Misu H, Mabuchi O, Takahashi Y, Tachino M, Nihei F, Ikeuchi T. 1998. Mosaic variegated aneuploidy with multiple congenital abnormalities: homozygosity for total premature chromatid separation trait. Am J Med Genet 78(3):245-9.

Keser I, Luleci G, Gunduz G. 1996. Premature centromere division in three unrelated families. Ann Genet 39(2):87-90.

Major J, Jakab M G, Tompa A. 1999. The frequency of induced premature centromere division in human populations occupationally exposed to genotoxic chemicals. Mutat Res 445(2):241-9.

Mehes K, Buhler E M. 1995. Premature centromere division: a possible manifestation of chromosome instability. Am J Med Genet 56(1):76-9.

Mehes K, Kajtar P, Kosztolanyi G. 2002. Association of non-syndromic Wilms tumor with premature centromere division (PCD). Am J Med Genet 112(2):215-6.

Moorhead P S, Heyman A. 1983. Chromosome studies of patients with Alzheimer disease. Am J Med Genet 14(3): 545-56.

Nasmyth K, Peters J M, Uhlmann F. 2000. Splitting the chromosome: cutting the ties that bind sister chromatids. Science 288(5470): 1379-85.

Nasmyth K, Peters J M, Uhlmann F. 2001. Splitting the chromosome: cutting the ties that bind sister chromatids. Novartis Found Symp 237:113-33; discussion 133-8, 158-63.

Plaja A, Mediano C, Cano L, Vendrell T, Sarret E, Farran I, Sanchez M A. 2003. Prenatal diagnosis of a rare chromosomal instability syndrome: variegated aneuploidy related to premature centromere division (PCD). Am J Med Genet A 117(1):85-6.

Plaja A, Vendrell T, Smeets D, Sarret E, Gili T, Catala V, Mediano C, Scheres J M. 2001. Variegated aneuploidy related to premature centromere division (PCD) is expressed in vivo and is a cancer-prone disease. Am J Med Genet 98(3):216-23.

Rao N M, Joshi N N, Shined S R, Adjani S H, Gosh S N. 1996. Premature separation of centromere and aneuploidy: an indicator of high risk in unaffected individuals from familial breast cancer families? Euro J Cancer Prey 5(5):343-50.

Scappaticci S, Caramel D, Toni M, Vivarelli R, Fois A, Fraccaro M. 1988. Chromosome abnormalities in tuberous sclerosis. Hum Genet 79(2): 151-6.

Spremo-Potparevic B, Zivkovic L, Djelic N, Bajic V. 2004. Analysis of premature centromere division (PCD) of the X chromosome in Alzheimer patients through the cell cycle. Exp Gerontol 39(5):849-54.

Kousseff, B. G., Newkirk, P. & Root, A. W. Brachmann-de Lange syndrome. 1994 update. *Arch Pediatr Adolesc Med* 148, 749-55 (1994).

Bugge, M. et al. Disease associated balanced chromosome rearrangements: a resource for large scale genotype-phenotype delineation in man. *J Med Genet* 37, 858-65 (2000).

Falek, A., Schmidt, R. & Jervis, G. A. Familial de Lange syndrome with chromosome abnormalities. *Pediatrics* 37, 92-101 (1966).

Aqua, M. S. et al. Duplication 3q syndrome: molecular delineation of the critical region. *Am J Med Genet* 55, 33-7 (1995).

Ireland, M., English, C., Cross, I., Lindsay, S. & Strachan, T. Partial trisomy 3q and the mild Cornelia de Lange syndrome phenotype. *J Med Genet* 32, 837-8 (1995).

Rizzu, P. et al. Delineation of a duplication map of chromosome 3q: a new case confirms the exclusion of 3q25-q26.2 from the duplication 3q syndrome critical region. *Am J Med Genet* 68, 428-32 (1997).

Kruglyak, L., Daly, M. J., Reeve-Daly, M. P. & Lander, E. S. Parametric and nonparametric linkage analysis: a unified multipoint approach. *Am J Hum Genet* 58, 1347-63 (1996).

Kawauchi, S. et al. Regulation of lens fiber cell differentiation by transcription factor c-Maf. *J Biol Chem* 274, 19254-60 (1999).

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A method for diagnosing a human as having an increased risk of developing Cornelia de Lange Syndrome (CdLS) comprising:

a) providing a biological sample from said human comprising a nucleic acid molecule comprising an NIPBL (Nipped-B like) gene wherein said NIPBL gene encodes an NIPBL protein; and b) detecting in the NIPBL gene of step a) a genetic alteration which alters the length of the NIPBL protein encoded by the NTPBL gene of step a) such that the NIPBL protein encoded by the NIPBL gene of step a) is shorter than a protein consisting of SEQ ID NO: 3;

wherein said genetic alteration in the NIPBL gene of step a) corresponds to an alteration in SEQ ID NO: 2 selected from the group consisting of: deletion of G at position 276, replacement of the nucleotides at positions 325-334 with SEQ ID NO: 121, deletion of CT at positions 868-869, deletion of A at position 1087, insertion of G at position 1672, insertion of C at position 1795, insertion of A at position 2028, deletion of AG at positions 2605-2606, deletion of T at position 2646, deletion of G at position 3095, deletion of TGTCT at positions 3149-3153, deletion of TAGA at positions 3183-3186, deletion of AGAG at positions 3186-3189, insertion of G at position 4095, deletion of AAAAA at positions 4691-4695, deletion of C at position 4693, deletion of AAGAC at positions 7277-7281, deletion of C at position 7336, deletion of G at position 7557, deletion of C at position 7906, and insertion of G at position 7951;

or wherein said genetic alteration in the NIPBL gene of step a) is a nonsense mutation creating a stop codon at a position corresponding to the codon encoding an amino acid in the NIPBL protein of SEQ ID NO: 3 selected from the group consisting of: Arg at position 479, Arg at position 797, Arg at position 832, Glu at position 977, Ser at position 1024, Ser at position 1398, Ser at position 1459, Arg at position 1536, Arg at position 1723, and Arg at position 1758; and wherein said genetic alteration in the NIPBL gene of step a) is correlated with an increased risk of developing CdLS in said human.

2. The method according to claim 1, wherein said biological sample is selected from the group consisting of blood, saliva, amniotic fluid, embryonic tissue and tissue.

3. The method according to claim 2, wherein said biological sample is blood.

4. The method of claim 1, wherein the genetic alteration detected in step b) is in exon 10 of the NIPBL gene.

5. The method according to claim 1, wherein step b) is performed by a method selected from the group consisting of direct sequencing, conformation sensitive gel electrophoresis, single strand polymorphism assay, restriction fragment length polymorphism assay, ligase chain reaction, enzymatic cleavage and southern hybridization.

6. The method according to claim 5, wherein step b) is performed by direct sequencing.

7. The method according to claim 5, wherein step b) is performed by conformation sensitive gel electrophoresis.

8. The method according to claim 1, wherein said nucleic acid molecule comprising the NIPBL gene is a deoxyribonucleic acid.

9. The method according to claim 1, wherein said nucleic acid molecule comprising the NIPBL gene is a messenger ribonucleic acid.

10. The method according to claim 1, further comprising isolating the protein product encoded by said NIPBL gene of step a).

11. The method of claim 1, further comprising isolating cells from said human and assessing said cells for the presence or absence of precocious sister chromatid separation (PSOS).

12. The method as claimed in claim 1, wherein said genetic alteration has been previously identified in a patient having CdLS.

13. The method as claimed in claim 1, wherein said human is an infant, and said method further comprises performance of genotype-phenotype correlation analysis.

14. The method of claim 13, wherein the phenotype for the genotype-phenotype correlation is selected from the group consisting of limb reduction, developmental delay, and growth retardation.

* * * * *

SEQUENCE LISTING

```
<160> NUMBER OF SEQ ID NOS: 120

<210> SEQ ID NO 1
<211> LENGTH: 188056
<212> TYPE: DNA
<213> ORGANISM: Artificial Sequence
<220> FEATURE:
<223> OTHER INFORMATION: Synthetic Sequence

<400> SEQUENCE: 1

acagcggcct cggcctcccc ttggattcag acgccgattc gcccaggtaa attcctgctc     60

tttatttcgg cggcggcggc ggcggcgccg gcgccaggtc ctcagcgtct ctcctcctcg    120

ctcccctccc cgccgtttcc ttagcggccc caggtctctt ccacaggcga gtctagagtt    180

cgctcctctc tggtggcagc cgccttgggt agcggtggtt ttgtaccctc tcccggccgg    240

ctccggtggc ggggactggg ctcctgctgg gcggccgggg aggcgtaggc ccggcggaga    300

gtgcaggccg cgggccagcg gaatctactt gagctcgggg attaggagag ctccgggctg    360

agcggagcga ctgctggtcg gtgacaggcc tcgcccggga gtggagccgt agctagtggg    420

gaggcggaaa caatacaact aacagcaaat gtgccctgat cgtccccata tttacaactt    480

tcccggtccg ggagtgggga acgtcccagt gaaacaaaca acctcccttc ttccccctgt    540

gaccccatga agggaggaag tagtttcagt tagtgagaca aacgtaaata ctcagacgcg    600

gatccagtgg taattctttc tctttctaaa acttgtttgg acgttggaaa gttcataaag    660

actcattttc ttttttaaag aattaaatcg tccacatgaa tatttaatac agaaaaacat    720

actgtggtag acactgcaca tctccccctc cccaagagct tttatcttgt tgttttgaca    780

gtgtgttgtt gcacatggac tttttattca aagacaagta taaagtactt gacaggttta    840

ctctgccact ttctatttgt atgcgttatg taagggcagt tttaagcgac tatacgtaaa    900

acactcaggt acttcctgac caaaacgtgt aggagcatac aaagaatttt aagtgttctg    960

agaattgtgc tgagatacgg gtaaaaccac ttttcttttc tttttccaaa aaagaaatta   1020

agttatactt aaaatccttg ggaggttaaa aaattgtaga aggtgccatc cttttatgtc   1080

agggcagttc ttcttgaggt cccaggattg tcattggctg tttgtgccat gatgtttgac   1140

tgtgtaatga gagaggtgtc attttaatag gttaaatgta tctgtaaatg ctggagaaaa   1200

atatcagttc taacttgaca agttctagtt catgagtaag ttaagtgttt cgagcttgtt   1260

tatggaggcg ttcataatgt aggttggtat aagggggaaa caccaattta aaattcctca   1320

gtcaggcaaa ttgctagaaa agtgtacctg ggttacacgt tttgatattt tgtttcatat   1380

tcgctgaagg aaaactttca ttggttaaaa tgaagcagca ctgctcagcg aaatcccttg   1440
```

-continued

```
ttttactagt gtttgttaca ttggttcata ttttttgtgt cattaaatta ttgtcactgt   1500
agaataagtt attttgtgga ggttattttt gagtttagcg tcctgattac aataaattgt   1560
ttcacatttc ctgcaaacgt acggataaat gtttaaaaga atgaagttaa tatagctgtc   1620
acgtactagg catgttttta atgctataaa tccgtgtagt agtcagtagc gtgtccgtga   1680
tttgtattgg tcagggagca gtttgaattt taaaaagcct gaagctcctg ctgagcccca   1740
atcccggcct ccctccctcc cactaatctc ccattcctgt ctttgtgctg cctgctcctg   1800
ttagacactg tttgctacgg ggcctcaggc ctactgcggg tggggggtg tgcgagtggg   1860
gggcatgcca gggagggaat gcagacggga ggaatacttc acatcttaag aaagcagagg   1920
gtttgttttt ttggggatgg aggtggtaag ggcttcatta taaatgttta aaaggccttc   1980
atatattcct gtgattgtct ctacaacttt tatttcaagg gataaacata tttttactaa   2040
agataataga ggagttgtgc ttgcttaatt ttcacgaact gaagcaactt atttttagag   2100
gttgtcttat gcagatgttt gaataagtgt gttagagatg ggtttatgtg attgattctt   2160
tttttcctg agactttgga attgttatag tgaattagtt cttcccaact tattttccca   2220
attctacata tttagtaatt tgtgagtaat ataggttgtg tgatagcttt cattatgata   2280
gcataaacat ttctttaaat ttaaaaatat gttttgtttg gtccaaacca attaaatacg   2340
tcatttttaa aggagaaaac attgtgtaaa attcaaattg taaaatttaa acttgaactt   2400
taaatctctg ataacctagt tggagagaat agtttgtttc cctaaagagt gtagagtgtt   2460
ctgcttcccc tctgttggtt ggaatattca ctagtggcta atcatctatt tccattaaaa   2520
attaaaattc agtgaaagga gaaatcagaa gtgttccagt aaccttataa tcctagttat   2580
attatttgga gaaatatttt ctcatacacc taaaggaaat ttcaacaatg tcgcttattg   2640
tttctcttaa ctctgaagag ttgtcaataa cttttgttac ttgaaaagag atttcaagta   2700
aataatgaaa gtaaatcaga gttgaacatt aaatagataa ttttcaatgt ttgagaagtg   2760
tatataggat gcttcctttt taaagttatt caacaatttg tttactaaag ttatctgaga   2820
acatttttga acctgttcta gagatcatta taatattttc tgcttttaag gaaaagttat   2880
acattacttg aaaaaagaaa aacagtctac ttgagattct ttttagggat gtaaagtgaa   2940
agtttttact atggcagtaa acttggttct tcatagtaat cattattaaa tttcaaaaat   3000
atgagcaagc tataccaata caaaattttc tttacttgca gccgaaaaat gtattttcta   3060
aggcttcttc aactaatttc atatttaatt ttttggtacc aatccatcat caaactgtca   3120
tagaaatatt tgaacatatc tgtgttacat gtttgaaata ccccattgtg gtatttttac   3180
tttctcaaaa taagatgtag taattaataa tataagagta aataaaaacc aggagtttga   3240
gtttatttta atttcattta atcctccttt ctggtgctta ttaggaaaag cataatttgg   3300
aagaaattct aaaattttaa attaagattt cagttttatg tgaagtgatt agggagtgtg   3360
aggtaaacag taattccttt tagagaaatg taactttaat tctgtttatc acatttactt   3420
gccataaaaa tgaatgggaa ataattgact aggaaccttt atagaaggct gacaactaac   3480
tgttcagttg aacatgctta ttttaatatc ctgagcgtac taggttaggt ttggtggtaa   3540
tttatggtct tatatagcct ttaaaaattg ttttaagatg gactttttaa gcaaagtttt   3600
tcgtttttc agcagttgtc atttataata attcttcgta ttttaaaact agtccttttt   3660
caaggtgacc tgagttcatt taaaaatatt ctgatatccc tgtgagagaa gtgaccagct   3720
ttccgtttaa tgatgaaata cttgacactt aagagaccat atgatttgtg tagattcatg   3780
tagtaagtca gccggaggat aagggattcc ctgacactag tattttctta gattatgttg   3840
```

-continued

```
ctttaagaaa tgtgtgagct ctggtcttga agctaggtat tgctcagtgc tgacactgac   3900
accatttgtt actttttcaa ttatctaagt tcaaagtgca tttttcttgt ctttgagaga   3960
gaggatacct gtttcttggt tgtattttcc tggtatgaaa atagagtggg attttagtgt   4020
ttctggttga tttaaaagga attttaaact ccatgtctct taaggccatc attgtaattt   4080
taaagggtat tttatgtgct tagaatattt tgcccaaata aattaagtaa taaaagtaat   4140
tttaggtatt tgtcttgtgt gtaatttttt tttttggtg taaatctgga gtcagttttg   4200
ttgaattgag ttttgtcaag ttgcattatg ttttaaggca tatttttttc tattcccaaa   4260
gttatatcat taggagagat cattgcttga tgtagcattg ccagctaaga ttttgaggac   4320
ttatttgcca ggagttaagt ctgtccccat aatatctcat ttaatctttt aacatgccca   4380
aaagtagaaa caataattat ctacaatgta cagatgagga acctgaggct ggaaaggttt   4440
agaaaactgc ccatggtcct acaattagta aatgatcagt ctgatttaca tttgttctta   4500
tggattcagg attctatgta tctagtttca atgaaatttt aatattatct tttgggtgtt   4560
agttgatgtg atacttgccc agtcacttag tcaagaaaat tgtgtacttc aggcaaagaa   4620
gctgaaatag aattcaggct atatattctg tatttataat acttttaaaa atcaataact   4680
ctttaccatc ttgtgtttaa aacaattttt gttaagcagt ctgtgaagct tttagttctt   4740
tgaagtattt tatattgagt tgaagatgtt tgtcaaagca tctgttgtta gaaagacaaa   4800
gttcagcttt agagagtcat ttcattcata gaaatgtata tgaccaattg taggatagta   4860
gctagatcta taaattagta tgactgatca ttttgtaaag tttcagtatt tttatagcca   4920
gagaatgttg atcattatag tcatcaactt gggaggttgt gcgcttattc cagaactgtt   4980
gccagtacat acaaccttat aggaattcct tttgtgaata cctttaacac atttgaaata   5040
gtctttttct catctttatg acaaatcttt attttctggg gtgaatttga gttttagata   5100
ctgtacaacg tcacttgaaa cttagtttag ggattttttt tgtgtctggc actatgttga   5160
gtgctttatg tttgtaatat gtagtattat tgaatgtttc catgtgacag aaactgtgcg   5220
agggaaaagg tttttcagtt cctcaaggta ttgaaaagtt gaatatgaaa ttgaagttag   5280
ttgtatgaga aaactgagat atagaatgat tacgtgacta gcccaaggtc acacaactaa   5340
taagttcaag acagtggaga aaggatttca gagttgatac tttacccata agccttaacc   5400
acgatactgt gtatcatgat ttgaaccacc caactactca gtgaagttag tgatactgtt   5460
ctctttttac agaggaaatt gaggttcatc atgcttaaga aacttattca gggtagcaaa   5520
cctagcaagt gttagaagta ggattccagc taaaatgtat ctaattctaa aacctctatt   5580
ctttacattc taccaccctg gctcttcaaa atttataata caatttttgg tgaaagggta   5640
gccttgatta tgaagttagt gacactgttt ttcttgtgga gcttacaaga gtaattctaa   5700
aatgttttga tcagttatag ctgattcatt atttgattat agtctttttt tttaaaaaaa   5760
aaacccacct tgttacttta cttcgtgtat agtacacaaa atgtttgtat attcaaatat   5820
gcatataaat aggatattga tttttaaatg caggtactgt ggaatatatt aaatgtaggt   5880
atctgtggaa taagtagctt tagaaaattt ggcaaaagct attctcaggc tataacaata   5940
ctgaaatttt aaaaaaatga tcagtcatgc taattcatag attaactgta tttttatgat   6000
tttattgtga ctcttgttac ttttaataat gttaagcatt aaaaaaattc ccaagaatgc   6060
attgaatttt caaaataatt catgtaggta aattgctttg ccatcttaca tgtgtgacat   6120
atctcttaac atgcatatac caatttcctt tgagttctct tttgtacata tttctccttt   6180
```

-continued

```
gacagaaaag aaaaactttt tcagaaatta gcaatattaa tttattaaaa taattatata   6240
tatacttttg cctctcctga gaaatgcaga agctgtgaca taattttaaa atgctggatt   6300
tccttttgtt agaattaaca tatttgggtc acttatgcag gtgaaatgca cagttatttt   6360
tatatgagca ctattgaaaa aatactattc tagatacatt aaaactaaca aatgtctaaa   6420
acactaatta ttaaattctg actatacttt taaaatatta gtctttatga ttgatattta   6480
tgatatttaa tttggtattt gtaaagcaaa aatgtccttt aatcctggtg aggaaataca   6540
ttacagagtt ttctcaacac tgctacttgt caaccctttc agtattttaa aacctgcctt   6600
tagttgtctt tatttgaatc agattgtggg ttgccagttt tgagccaaag acatcgatcg   6660
tctgagtgta tgctctatgt aattcagttt tttttttgg taatgaccaa gttgaagttt   6720
tacatggttt taagttgggc ataactccat ttattattta tttatttttt attaatacta   6780
ttctttaaaa ttgatgcaca tgaaaaaatt tcttcctagg gttctgcgta tacctcagaa   6840
agctctaaga ttgaaagctg aaatgtcatg acctgaaaac tactgattct ttccccttta   6900
agaaaagaat ttggaaacta gtgtttattc cataacgtta ccttcaagtt atcctgaaag   6960
acacacatga catacgcttt tatttaactc tactaatctt tttactattt tctctttccc   7020
tttttttatg tatctcttcc tttcactatc aatgtccatt tcatctcccc caaagcaaat   7080
ttttacatac tgtggctaat ataggtattt gttgttaatg tggttgatct tgtaatgtgt   7140
tactttccct gatgaaaccc agagcagttt cagaggcctc aaattctgag atcttcctaa   7200
gttcaaaata gattgctggt agaaaagcat tgacattaac catgaaaata tatatttgtg   7260
tattgttccc acttctatag acatatatta cttttcaaaa tgtcagctca aggaccagaa   7320
attttttctg aggagaaaga gaaagcattg cctttacaaa agtttccctg atcattccat   7380
ttcatagcat ttgtacagtt ttttacttgt atctcttgat aaaataattt gttcctatat   7440
tcgtcagcca tactcaacca tcagctctgt gaaagcaaag agattttgta ttatcttcat   7500
ctgtatgtct ataacatcat cacagtgctg ctcctgtttt aggtattcaa tatatatttg   7560
ttgtttagtt agaattgagc catgtggtat ttcttaaagg tatgttttta aatctaagat   7620
tagtgaatgg caagtacatt tctcttaatt tcaaaatata attttcttag gtagagctgt   7680
gtccttgagg gcttcttgct ttgggggtag gaatatttta tttacatata tccctaacaa   7740
tacatacata actttataaa gataaagaaa aatttaaagt tccttttttaa gctgttaatg   7800
aggatcgtga agtacaggaa gggtttttttg ttctgattcc ttaggcagta taattggagt   7860
aagatactgg agtattgcaa gaagtgaaat atctaaatac tttcttgttt taatctttgg   7920
atttattgca gttttaattt tttttttgcc aatttaagta ttatatataa tcagataagt   7980
taaataatga gaaatacgtt acagcacata aaaaatgcta ttcagggtca gcaaagcctg   8040
agtcctgtcc tctcgctctc ctccctggac agcatgagct tcaccacttg ctccaccttc   8100
tccaccaact actggttcct gggctctgtc cagccaccca gctatggtgc ctgactggtc   8160
agcagtgcag ccagcgtcta tgcaggcgcc aggggctctg gttcgcggat ctccgtgtcc   8220
tgttccacca gcttccgcgg cggcttgggg tccaggggcc tggccaagtg gatggcccag   8280
ggtctggcag gaatgggagg catccagaac aaggagaccc tccaaagcct gaacaaccac   8340
ctggcctcct acctggacag agtgaggagc ctagagacca agaaccagag actggagagc   8400
aacacccggg agcacctgga gaagaaggga ccccaggtca gagactgggg ccattacttc   8460
aagaccatcg aggatctgag ggctcagatc tttgcaaata ctgtggacaa tgcctgcatt   8520
gttctgcaga ttgacaatgc ctaccttgct gctgatggct ttagagtcaa gtgtgagaca   8580
```

-continued

```
gagctggcca tgtgccagtc tgtagagaac gacatccgtg ggctctgcaa ggtcattgat   8640
gacaccagtg tcacttggct gtagctagag acagacatcg aggctctcag ggaggagctg   8700
ctcttaatga aggagaacca cgaagaggaa gtaaaaggcc tacaagccca gctcaccagc   8760
tctgggttga ccgtgaaggt agatgctccc aaatctcagg acctcgccaa gatcatggca   8820
gacatacagg cccaatacga cgagctagct cagaagaacc aagaggagct agacaagtac   8880
tggtctcagc agattgagga gagcaccaca gtggtcacca ctcagtccgc gcaggtcgga   8940
gctgctgaga tgacactcac ggagctgaga catacggtcc agtccttgga gatccatctg   9000
gacttgataa gaaatctgaa ggccagcttc tggagaacag cctgagggag gtggagacct   9060
gctatgccct gcaggtagag cagctcaaca gaatcctgct gcacctggag tcagagctgg   9120
cacagaccca ggcagagggg cagcaccagg cccaggagta cgagaccatg ctgaacatca   9180
aggtcaagct ggaggctgag agcgccacct gccaccgcct gcttgaagat ggcaagaact   9240
tcagtcttga tgatgccctg gacagcagca actccatgca aactatccaa aagaccacca   9300
cccgctggat agtggatggc agagtggtgt ctgagaccag tgacaccaaa gttctgagac   9360
attaagtcag cagaagcagg gtaccctttg gggagcagga ggcccataaa atgttcagag   9420
gtcattgggg gaaaataggc tattcagtta aaatagttat ctgatgactg aaattttttt   9480
aatatgtcag gtgtattgag gtataattta tacagtaaaa ctcagtcttt tgggtgtgca   9540
gtttgatgag ttttgacaaa catacacagt cttaaaacca ccaccacaat cagaatattt   9600
ccattacccc caaaagttcc catgtatccc tttgtaatca gtttcctgct cctactgcag   9660
cccgaggcaa ctagatctgg tttctgtctc tatagttttt ccttttctag aacataaaaa   9720
tggaatcata tatagccttt tatgtctttt ttttaaattt agcagaaagc ttctgagatt   9780
cattcatgtt ctatgtatca gtagtttgtc aatgactgaa gtttaaaatt gttaactttg   9840
gtgaagctct tacgaaagag tattatcaaa aaatagtact ttgaacagtg gtagatattt   9900
ctctcagatt ttggcagctg ccttattatt gaacatttta cttgctcatt tttacccctc   9960
gacccccaaa ttttacttac ctgtttaacc ctcaaccccc aaatctagtc taatagacat  10020
tattatatgg catttattta tattagtaaa tgctgtttaa ttctctacca agcatgtgaa  10080
atagacctac tctcttttc ataattaaaa taggtagcat cttgcatttt gaacatacag   10140
cacatagaaa ctagaataaa aaatgaagga tggtgcagta acaccaaaaa cttgagttta  10200
catttgcttt aggtttagtg tttgtaagtt ggtgctaaaa aaagagcata gattatagtg  10260
aataacagtc acagcctctc ttccaatgat taaagttaga aaagcagtgc cctttactga  10320
aaattggggg cagataatga gaaaagagta attttctgga cattttattc gaccacctct  10380
cccccgaccc tttccttttt gaaacagctt catctctggg atattctctt gttgtttgct  10440
tatgtctttg acctcccatt ttttaagtct tttgctaggt cttgctcctc tacctacccc  10500
tttaaatatt tgtattctcc aggaggtgct tcaaacttat ttctgttctt cctgttgatc  10560
tcatttattc acatgacttg ttacatgcta cctgtgtgct gatgactcac aaatctatct  10620
ccagaatata tttctcttct gagccagatc cagctgtcta tcaggtacct cctgatgtcc  10680
catgaataac agaaattcca tagtatgtaa gtctgaactc atcccttaat tcttccttac  10740
tctgacctgt cacccaaaga aagaaaacta ttaaaaaata catgaagtag gttaatgttt  10800
tcactatcaa ctcatttacc taaactagaa atttgggata atccttgaca cttctttacc  10860
atacttccag ttcagttatt cacccagttc tgacatttgt aacacttccc tgaattatca  10920
```

-continued

```
cttgaatcta ccccttcccc aatgttttga ttctgtgaga ggtcctgaac atacagtttt  10980
ctcagattta ataacttcta gtattttaag aaagatttag cagtaattgt gaaagtaata  11040
tgtatttagt attggatact ttttgcttct atgcttgggc tctggtattt aaaattaagg  11100
tgtaatcttt agtaacagtg atactatata gcctaaatgt gactgtgttc tgttatatct  11160
aaaatttagg acttttgact tacagcccag tttatcagct ggaagacttg aactcatttt  11220
ttaactcatt ttttatcttt tcattcttgc ttttagaata ctgcatttca tggagttgta  11280
tattcatttc aatactttgt gtttatgtgt tttggagcag ggtagaggag aaaatgggaa  11340
tgtataagga aagttaaagg aaggactttt gaattgactt tcctatactg tggaaacaag  11400
tttacttaaa taacattttc acttttattg caaacaacag aaaactaaag aaatgctgtg  11460
ggatatgata ccattcaggt gctaagcatg cacatatttt taatgacagg agttagatgt  11520
gttgtaacag tattgcttgt ttgtgagttt ggaaattaat gttcatggtt ttgtataact  11580
ttatgatatt tcttccttaa aataagaaat tacccctcca gcccacagtt tgagccaaag  11640
ggtctgcttg aaattattag tttaaataat cctgagcgca tcttttgtaa agggcatttt  11700
aaaatgtaat gctgccttga aaaacaaagc aagcattttc ttcgttatat ctagagttta  11760
taactaaaga agtaatatgt gctatatttt gctctagtgc caagtaccat attttggaat  11820
gaatagaatc aatctaaagg cagtttacaa aggctgaagg gagacccagt ttggtagtca  11880
ttggatccct ttggtggctt gcacatagta agcactcaac aaacaattgt tgaataaatg  11940
aatttgaata tattttcagt ttggggacat aggactaatt agagtgacag aagatgggtg  12000
gggcttgcta aatactgagc aagttttata gaggaaagaa aacatgaaac ccagaaatgg  12060
tggacaacat tgacagcaaa gaattggtgt aatttagtta actattttta tctggacaat  12120
aaggtttgtt tagttggata agagaaagat ctatatacag aagtgttttg agttctttct  12180
actcttattt ccactctggc tctacttctg aacccccatg ttcactgcta aagaactaat  12240
tgtaggcttg gggctaaaat gatctgcata atccagatac tcatattaag aactgggagg  12300
aggtgttggg aaagaggtat ttcttacagt tcttcaatct ttccaattac tcatgtttct  12360
tagtatatgt cagggtgcca ctgcactgtc ctccgtattc atatgaggat gtctaaaaac  12420
tagaatttaa aatcacatat aatttacaat aagcttgtaa ctgtcctagt atgaagttca  12480
gtatctgaat ctctaataat tagttaccta gctgttgagc cacattgcca tctactctga  12540
ttatcatatg tttcttatga ttctgatatt ttaaactgga agataaacac cacagtttta  12600
gtgtgtttta taaaaatttt ataattcagt aacaatccat tcctttattt tcttggaagc  12660
caaaactaca tatagtttcc tgatatgtta agcttaaact gtggaattta gaacttaaaa  12720
attttcaaga gcttcaaagt tgaagacttt tcttaatttt ttttcaattg tagaaccaat  12780
gtgaaaaaaa aaactacatg ctgtttggga aatgggaaaa atatcaaatt ttatgttttt  12840
cctactaagt ttcctattaa atttttacat aaaaatattt atgatgaatg taattatggt  12900
taaatacata tattaatgct ataaatttat tcctctttta acgttggatc ataaagattt  12960
tcctagtttt ctatataatg ttcataattc tttaaaatgt tgcccagtat tttgtcagtg  13020
gatgaaccat aatttattca ttctattctt gcatactttt tgcttttact ttttttctat  13080
ataaataatg aggcagtgaa catctttata tgtagttttt tcccccttta ggggctttat  13140
tcgcttagag tagaatctct taagtggaag taatcctgta agtggaagtt gggtcaaaag  13200
gtttgaacat ttttatggcc tttaatatat atttccaaaa ctaattttat tctgctataa  13260
tctttatttt cattcacatc ttaattcatt cagtagattc attgtgtttt tcatatagaa  13320
```

-continued

```
tacacacttc ctatgaatat tattaggtca tttaaatgct cccgtttccc actattgtgc  13380
ctgtggtctc tttttactat atatttttaa cctcttgatg ataaacagtt gtggcttttc  13440
aaacggtgta tatcatttcg aggtattata tagtaaaatt agcatgggat ctaaactgct  13500
attagccaag tggcatttag gccaattctt aacccaagcc catgtcttca actgtaaact  13560
gaagaggttc tcagcttttg agatttcatg gactagtcag aacaaagcaa gaaagtgctt  13620
ttctgcagaa ataaagtggt aaggatattg tagattggaa tgtaaaaaga aaagtaatgt  13680
ctaggtaaga cccattactt agtcttaata tttgaaatgt gaaataccca gtgtgatgtg  13740
aacatggtca tgatctcata ttcattctct tgtacatcaa acactgagtg attcctatgt  13800
cttttctcag gagctattaa ggcattgcag atggtgaaat aaaagacttc aggccgggca  13860
cggtggctca cgcttgtaat cccagcactt tgggaggccg aggcgggcgg atcacgaagt  13920
caggagatgg agaccatcct agctaacaca gtgaaacctc gtctctacta aaaatacaaa  13980
aaattagcca ggcacagtgg cgggcgcctg tagttccagc tgcttgggag gctgaggcag  14040
gagaacggca tgaacccggg aggcagagct tgcagtgagc caagatagca ccactgcact  14100
ctggcctggg caaagagcga gactccatct caaaaaacaa aaaaagaaaa agaaataaaa  14160
gacttcagcc cacccatatt atagtctaat acagtttata gacaggtaaa cagagattat  14220
gttacaatat ctaagtgcta tgatcaagat aaacaaggtg cagttggagc actggtggta  14280
ggggtggtca cctaatttag actagtgtgg tgaggcgcag taagtcagga gccctcctag  14340
gtgtgatggt tagtagatat gcaaactaag ttttgaaggc tgttagtcat actgtggagt  14400
ctgggccaac aatttgattt ttggaaactg atgatggctt agattattag aacataggct  14460
ggaaaagggg catgccaaaa aggtctgaag ctacagagag gggcaggcta cagattatga  14520
aggagtggat atgccttact aagaattctg tgttttattt taaagacgag aagccaggaa  14580
gttatttagt aatggagtat gttttatgca tatgtaaaaa aatttttgga tagtaggcat  14640
gaaaagggag gctcaggagg ccagtaggtg ttgaggtcct caattaagat gggggattgt  14700
agcgaaggaa acccataaca aatattaaag agttaatcta gttatagttt agtgattcta  14760
tgtaggtaga ttgggtaaga gagaatgaaa acagtcaagg atatatcctt gattcccaag  14820
tttcatgtgg gcatatgaga gtagaatata agttaaatca gttttggctg cctgtgagta  14880
aaaatatagt gtaccaaaac ctgtatcacc tttcacattt taaaaggaat ggatattgaa  14940
aaatttagtg gcttggtcaa attgtactaa tgattatttg gaaatgactt ttacagctga  15000
cctagaagat ctctccagtg ttaaatcagg gttaaaagta gtacagtgga tgaaaaaatg  15060
ctcatcactg gccatcagag aaatgcaaat caaaactgca ataagatacc atctcacacc  15120
agttagaatg gcgatcatta aaaagtcagg aaacaacagg tgctggagag gatgtggaga  15180
aataggaaca cttttacatt gttgttggga ctgtaaacta gttcaaccat tgtggaagtc  15240
agtgtggcga ttcctcaggg atctagaact agaaatacca tttgacccag ccatcccatt  15300
actggctata tacccaaagg attataaatc atgctgctat aaagacacat gcacacgtat  15360
gtttattgcg gcactattca caatagcaaa gacttggaac caacccaaat atccaacaac  15420
gatagactgg attaagaaaa tgtggcacat atacaccatg gaatactatg cagccataaa  15480
aaaggatgag ttcatgtcct ttgtagggac gtggatgaag ctggaaacca tcattctcag  15540
ggaactattg caaggacaaa aaaccaaaca ccacatgttc tcactcatag gtgggaattg  15600
aacagtgaga acccttggac acaggagggg gaacatcaca caccagggac tgttgtgggg  15660
```

-continued

```
tggggggagt ggggagggat agcattagga gatataccta atgctaaatg acaagttaat  15720
gggtgcagca caccaacatg gcacatgtat acatatgtaa caaacctgca cgttgtgcac  15780
gtgtacccta gaactttaaa gtataataat aataaaaaag tagcatggtg gattataatc  15840
ttacttgatt aaattactag aagataatac tatttctttt taatgctttg ttttctagta  15900
tattgactat attcttgtga gcttagaata acataatgaa tgttctttaa taactatttt  15960
ctattgtgca aagttctctt agggcctttc tggtgtattt gtttatccag cctcatctga  16020
agactgcctc ttcagttagt tttatactaa atccatacat acactataat gaaatcttgt  16080
agtgagaact atgttacttt gttcatgaag ggattatctt tacaaatata attaaaggga  16140
tgcttttaaa ataaatttta aaatggcagt agctttttag aattgttaca tgtaggaaca  16200
gttataaagc agtcaaactg atgtatccaa aataactgac caggtgacat actgccaaaa  16260
tgaaaattag tactttccaa ggttctaagt atacttaaac aaatgtactt cattttgttt  16320
tttggcttga gaggtagcat atcagaatca cctagggatt tttttttttc aaactttaat  16380
cctttttttgg agatgtaagt ttttaagttt ctcttttagc tgtgttccct tagacttctc  16440
aatcattcag taagaattga ataactgcag tgtgttcagc aatgaatact agatatttga  16500
tatggacttt ttttgagtct tcctcctgaa ttttacatgg ctacctaaaa gatctctctc  16560
ttttttgtat tctataaaaa catcatctgt gaggcataaa ggagcaagga atcatgtgag  16620
cagagttagc gaattagatt tttaaaaaaa tgagaatggt gagatgtgtt tagttctgaa  16680
gaatggagga ggagttgctg gatactagcg aggacgtaga attgaggaaa gaagttaggg  16740
taggagatag tgtaaatgaa tttggtagaa aaaattcagt acagcctacc agcagtactt  16800
caagtaaaat tagaaattgt gaactgacct atctgttcct aaaggtgtct tatattttaa  16860
aagtttgctc aaaagtcaaa ttgaatcttg ttagaaacac actacttaaa aatataaacc  16920
atgcctatgt gttcacacta agtcctcagc aaatacttct tctttattag ttcatagttg  16980
cctttctact gatttgatgg aaaatatatc cttctcaaat atatttccaa atgaaaatct  17040
gctaatttgt gacatttcta atggattatt aggaaggaag gtatttgata agaagcaaag  17100
aaaaagtaat caaattagct caagttcatc tgatattgaa atatgataag tactccttag  17160
taacacagct tagctagaaa ccgcagataa agtgaagtat ccaaaaaaaa actctattta  17220
tatgagaagt ttgatttaac ctttgtctaa tatctaaagt taattatgtg tccaaaggta  17280
ttgtactata ctatactgtc atgtatgtac tttcaaaaat acatgtatat aaaaatacat  17340
atatacatat aatatattcg tatatacaaa tatatcctat gcactttgat agctctattt  17400
tgataacttg ttttgtattt tcctacctca cacttttgga tcaaaacatt tacctccttt  17460
tttatccatc tatccaaatc atactttctt tctatcatga tcttatgttt ttttcccccc  17520
actgcgggga ggtggcatgt cagaatcctc tgtggattat tttcaagctt aaaatccttt  17580
ccaccttttc tcctgcccca gttcacttga tcttttctag cagtacctat gtgtaggagt  17640
tatagaaatt atatgttagc ttgtcacatt ttcttactgt atatcaagct aaagtttatt  17700
ttgttttatt tttaccttat ttgtcttctc agtcagatta taaactctta gaggacacag  17760
tctgcctgtg gtgcttggtg tcttacctgc aacaggcttg tagcaagtgt ttgctgataa  17820
ctggtgtagc tcatctggac tggtttgaag aggtttggaa aatatctcac actcttataa  17880
actgtaaaat tcaccctttt aaagtgtaaa actcagtgat ttttagtata ttcacaaagt  17940
tatgcattca tcattacttt ctagttccag agcattttca tcaccccccca aaaaaccacg  18000
tttccattag tggtcacacc ctgttgtctc cagtcagtcc ttggcaacca ttaatttacc  18060
```

-continued

```
ttctgttgct gtggatttct gtattcatat aagtggaatc aaataatgtg cccttttgtg  18120
tctggcttct tttaattgct catctatatt gcagcatgga tcagtacttc atttcttttt  18180
aggactgaat atactccatt gtatggatat accacatttt acttttgctt tgtcgcttga  18240
tggacgcatg gattgttttc aactttgac tattatgaat aatgctgtta taagcattca  18300
tttgtaagtt tctgtgtgga tatgttttta cttctcctga gtaggtacaa aggggcaaaa  18360
tttttaggtc atgtggtaac tatgtttaac tctgaggaac tgtcagactg ttttccaaag  18420
aggtgcatga ttttacattt gtagtagcaa tgtatgaagg ttagactgtc tttacatcct  18480
caccaacact tgttattgtc tgtctgattg tattggtcct agagggtgtg aagtggtatc  18540
tctgtgtggc tttgatttgc attttcctaa tgactgatga tattaaacac ctttttatgt  18600
gcttattggt catttgtgta tcttctttgg agcaacattc atccaaatct tttgcccatt  18660
tttaaattgg gttatctgcc tttttattgt tgaattataa gttgttagac atattctaga  18720
tacaagttcc ttatcagata cgtgatttgc aatatttgct cccattctgt ggattgtctt  18780
ttcactttct tgatagtgtc ctttgaagca catacatttt taattttaaa gatctctatt  18840
gttttccttt ggttgcttat gctttgggtg tcataagaaa ctattgccta atccaaggac  18900
aggaaaagtt acacccgtgt ttagttttag cacttacatt taatactctg atccattttg  18960
agttaatctt tttcataagg tatgaggtag ggatccaact tcattattat gtacgtgttt  19020
atccaatttt ccattaccat ttgttgaaaa gactattctt tcccattgaa tggtcttggc  19080
atccctgtca aaaatcagtt gaatgtaaat ttaagagttt atttttggct ctcaatttta  19140
ttccatcagt ccatatgtct gtccttacgc cagtactaca ctgtcttgat tactgtggct  19200
ttgtagtaag gtttgaaagt gaaatgtgtg agtcctccaa ctttgttctt tttcaagatt  19260
gttttgactc ttctggatct ctcattttca tatgaagttt aggatgtttg tcattttctg  19320
caaaataggc agctgcaatt ttgatagggg tcgtattaaa tctgtagatg agtttgggga  19380
gtattgcctt tacaataata ttaaatctta acaatccaag ggcatgggaa gacgttccat  19440
ttttttaaag ccctaatttc ctttagtgtt ttgtttgttt gttttgagac aaactctcgc  19500
tatatggccc aggctggaga gcagtggcat gatcttggct cactgtaaag tccgcctccc  19560
tggttcaagt gattattgtt ccttagcctc cgagtagctg ggattacagt cctttgccac  19620
catgcctggc taatttttgt atttttaaga gaaggtgcgg tttcgccatg ttggccaggc  19680
ttgtctcgaa ctcctggcct caagtgatct gcctgcctta gcctcccaaa gtgctgggat  19740
tacaggcttg acccaccaca cctggccagt gttttgtaga tttaaatgta caaatattgc  19800
atttcttttg ttaaatttgt tcctgtgcat tgtgttcttt ttaatgctat tgtaaatgga  19860
atagactttt atatattttt tttttttga gaaggagtct tgcactgtca cccgggctgc  19920
agtgcaatgg cacgatcttg gctcactgca acctccactt cccaggttca ggcgattctc  19980
ctgcctcagc ctcccgagta gctgggatta caggtgcaca ccagcacacc tggctaattt  20040
tttgtttttt tagtagagat ggggtttcac tatgttggcc agactagtct tgaactcctg  20100
acctcgtgat ccacctgctt tagcctccca aagtgctggg attacaagca tgagccaccg  20160
catccggcct ggaattgctt tcttaatttt acttccagat tgttcactgc tagggtatgg  20220
aagtgcagtt gatttttata tattgatctt gtatcctgca accttgctga acttgtttat  20280
taattgtaac tcatgctctt ctttctaggg acagtttatg ttctttagtt tggttcattg  20340
tgccctcctc cagttttcca aataatacat gtcaacagtg ttataagaaa gaaatttctt  20400
```

-continued

```
attttctcaa tcctgctttg tgacttaaac aaacttacgc acatatgaaa agtaagatca  20460
gacaactcag aagaaaaacg atatccacta aaaactatgt caacattttc atttagtgct  20520
ctggctgtaa cataggatta aaaatttgag gattgtggtt cagtagttaa agcagtaagc  20580
tttgccaata gtgaggcatc ttgagtattt gttgcggaaa taaataaatg cctgctaaca  20640
atgtgtatat agggatgcaa aataaattct attggtcagt aatttctgaa gtctttactc  20700
cactagtcag taagtgattt tcagtagtgc atctggaaag cttgagtcat acagggaaaa  20760
aaaaaaaaaa aaagcaagga gggaagaaac aaaaggaagt aagattaata atttgaattt  20820
tgttaataca gataatattg tgatttaaat aaatctattg attaggaaca aaagaggaaa  20880
aaataacaga ttacagtatt attcctcaag ttcaaacttc tgtgtttctt aatgccagaa  20940
tcaaacctaa aatgtcaaac acacatataa aaagatgccc aaacttacta gcagttagag  21000
aaataaagag taaaaatcta gctagcttat tatgtatttt gttgatcagt aaggataaag  21060
tgttgaaagt atgcttcata tactataaag tatgcttgtt taataagttg tatcctctat  21120
tatcattaat attgttgttc ttatcagtga cctttaggtc ttaaaataga tgtagagaag  21180
ggtagtgtaa tcctgccttt aaaaaaaaat tcatcaaatg ctttatgtct tattcatggt  21240
catatttaat actgttgaag aaacccatga gatagatatt tttgagacaa ttgaggcgta  21300
ggaagttaaa taatttgccc aagcttacac agcttgaaac aagaggaaga agaaatcaaa  21360
cctatgtttt tctgattcct tttttttttt tttttgaga cggagtttcg ctgtcattgc  21420
ccaggctgga gtgcagtggc acgatctcag ctcaccacaa cctccgcctc ccaggttcaa  21480
gtgattctcc tgtctcagcc tcccgaatag ctgggattac aggcatgcgc catcacgccc  21540
acccaatttt gtatttttag cagagatggg gtttctccat gttggtcagg ctggtctcga  21600
actcccgacc tcaggcgatc cacccacctc accctcccaa agtgctgggt ataggtgtga  21660
accaccacac ctggcatgtt tttctgattc taaaacttag ttttaaactt tttttaaaat  21720
ttagtcttta acttttaatt ggcatactat attgcttctc cactaccttt gaacttattc  21780
ctaggtggat tatataataa ataatattcc ttggagtttt aaattgtatt aaataagatt  21840
taaagtagaa ttttaaaatt ggattttgat tttacttcag aaaactctca agtgtttgct  21900
ttgggaaatc gaagaaaaca tttgcccatt gttgtaatgc tgctgtattt cccaattgtg  21960
atttccaaaa tttctttgat tctcactttg ggaaatgggg tcttgaaatt catgaaatcc  22020
agttttgggt ccagaagcaa atagactcag tgaaagagac agtcatggga gaacccctta  22080
aatagtttta ggacaaaaag ttacagttta aagagaagga tgggtaaatg ttgaagaaaa  22140
cttaatacct cttgttttct ctatgttgaa gacttttggt tttgcattaa gtcttgcctg  22200
cattaaaaaa aaagtgtaat gtgattgtct tatgtactta caaattaata tgtattgtat  22260
ctttaattgc atctctgtgg aatttttata tcatttgctt tctttgtttt ataccttttct  22320
ttgggaatct catattcagt gcagactgtt gtaatgagtt tggtttgttg acctggtgag  22380
cagtaggatt ttgtaaaagg aaattcagct taaagcattc agaactttgg ctgttgtgcc  22440
ctttcaaaag tgaattttta aataggttta aaataaatga ctgcctccaa aggattgctt  22500
tctaaatttt gtgttagaga catgcttgcc tcctgatttt gtattttagc cccaaagtga  22560
attaagcttt cctgcttgag ttggtgaata ttacttaagt acatgtatat acacagagtt  22620
aaaaacctgc tagtactcaa aaatcagtcc tgtattgtat agagatttgc ctgctgatgg  22680
atcaggtgtt gttttcagta tactgttctt ggactttatg acagactagg ggtacttaat  22740
gcctgagttg ataatcacat tattacttct tacactttgt ttatagaatc tagaaggagt  22800
```

-continued

```
taaacagaaa agtatttttc tgttccttcc ttatgattta gaaaatagaa aaagtcttcg  22860
ctaaagcctt taatagcctt attcttagtg atgatgatga ttatattaat agcaatgatg  22920
gccagtattt gtcatgagct cactgttttg aatatttgac tggcattatt taatcttcac  22980
tacagttctt gaggtataat cagcccttca tatttgagag tcacacattt gcagattcag  23040
ccaagcacag attggaaata ttcaggaaaa gaaaccaata aaaaaaatac aaaaacattt  23100
aaagtgcagt ataaaaacta tgtagcattt acattgtatt tggtattata agtattctat  23160
taatgatgta aagtatacag gaaggtgtgc attttatatg caaatactac accattttaa  23220
attagagact ttagcgtcca tgaatttcat atctacaggg atcctggaac cagtcccctc  23280
agggccaaag gggactgtct agctataata tctccacttt ccaaattagg aaactgatgc  23340
ttacaaagaa tgtgacttgc tcaagagatg agagaaggaa gtcccatgag caattcagtc  23400
aacataatta caatgaatgt atgctctcct taagtttagt tagactcctg acctccttga  23460
ggtcagggac ttaatatgtt tatttcttta attctagtac caagcacagc acccagcata  23520
tggcatatgc tcgggttttt tttgttttgt tttgttttgt ttttttaata aagaaatgaa  23580
gttgcgagag gctgattcat tagctttagc tgtaagtctt ctggagggaa tccataccaa  23640
tttcatttac attgcatgat tttttttcct ttgccttgga ataccgcttg gcaggggacc  23700
tagtaagttc ctgttcattc ttcaagttcc agcgtaattc catcttttct ttgatgcctt  23760
ccttgtctct tttaggcaga attaattgtt cccttttcta tccactccct tttttttcccc  23820
agcctttatt ttagattcca gggggtacat gtgcaggttt gttacatggg taaattgcga  23880
gtcgcagggg gtttgttgta tagattattt tgtgacccag gtaatgagca tagtacctga  23940
caggtagttt ttgatctcca cccttctccc accctcaagt aggctttggt gtctcttgtt  24000
tccttctttg tgtccatctg tggtctatgt ttagctccca cttacaagag ataacatgca  24060
gtatttgatt tttttgtttc tgtattaatt tgcttaagat aatggcctcc agctgcctcc  24120
atgttgctgc aaaggacatg atttcatcct tttttatggc tacatagtat tccatggtgt  24180
atatgtacca tattttcttt atccagtcca ctgttggtgg gcatctaggt tgattccatg  24240
tctttgctat tgtgaatagt gctgtagtga acatacacat ccatgtgtct ttatggtaga  24300
atgatgtata ttgctttgag tatatactca gcagtaggat tgctgggttg catggtcctt  24360
ctaagtcctt tttttttttt tttttttttt ttttgagtcg gagatttgct cttgttgccc  24420
aagctggagt gcaatggcac gatcttggct cactgcaacc tctacctccc aggttcaagt  24480
gattgtcctg cctcaatctc ccaagtagcg gggattacag gcgtgcacca ccacacccaa  24540
ctaattttgt atttttagta gagaggggggt ttccccatgt tggtcaggct ggtctcgaac  24600
tcctgacctc aagtgatcca cccccctctg cctcccaaag tgctaggatt acaggggtga  24660
gccactgcac ccagccctaa gttctttgag aaattgctga actgttttcc acagtggctg  24720
aactagttta cattcccacc agcagtgtat aagcattccc ttttctccat tgcctcacta  24780
gcatctgtta ttttttgact ttttagaata gccattctga ctggtgtgca atggtgtctc  24840
attgtggttt tgatttgcat ttctctaatg attagtgatg ttgaacattt ttttgatatg  24900
cttattggcg gtatgtatgt ttttcttttga gaagtgtctg ttcatgtcct ttgcccgttt  24960
tttttttaat agagttgttt tctgcttgtt actttgttta gattccttac agattctgga  25020
tactagacct ttgttggatg tatcgtttgc aaacatgttc ttccattctg taggttgtct  25080
gttcactctg ttgatagttt ctttggctgt acagaacctc tttagtttaa ttagatccag  25140
```

-continued

```
cttgccaatt tttgtttttg ttgcagttgc ttttgaagtc ttcatcatga aatctttgcc  25200
agggctgatg tccagaagag tttttcctag gttttcttct agggttttta tagtttaaat  25260
tttacatttc agtctttaat ccatcttggg ttgatttttg catgtggtga aaggaagagg  25320
tccagtttca gtcttgtgca tatggttagc cagttattat tgaatagaga gtcctttccc  25380
cattgcttgt tattttcagc tttgtcagag attagatgtt ttaggtgtgt ggctttattt  25440
ctgggctctc acctgttcca tttgtctgtg tatctgtttt tgtaccagta ctgtgctgtt  25500
ttggttactg tagcctttta gtatagtttg aagttggatg gtgtgatgcc tctggctttg  25560
ttctttttgc ttaggatttc tttggctatt cgggctcttt tttggttcca tgtgaatttt  25620
agaagttttt tgtttgtttg ttttttggtt ttttttccta attctgtgaa aactgtcact  25680
ggtagtttga taggaacagc aatgaatctg taaattactt tgggcagtat gaccatttta  25740
acaatattga ttctttctat ccatgatcat ggaatgtttt tccacctgtt tttgtaaact  25800
ctgatttttt tttagcagtg ttttctaatt ctcattgtag agatctttca catccctggt  25860
tagctgtatt cctaggtatc ttattccttt gtggctattg taaatgggat tacattcttg  25920
atttgactct cagcttggac gtcattggtt tatagaaatg ctactgattt ttgcacttcg  25980
ttttgtatcc tgaaactgtg ctgacgtggt ttatcagatc taggagttct tgaatagaga  26040
ctgtggggtt ttctaggaat aggatcatta tcatctatga ggaaagatag tttgactttc  26100
tctcttccta ttcagatgcc ttttatttct ttctcttgcc tgattgctct ggctagggct  26160
tctagtacta tgttgagtag gaatagtgag agagggcatc cttgtcttgt tccagttctt  26220
aaggggaatg ctcccagctt ttgctcattc aatatgatgt tggctgtggg tttgctatag  26280
atggctctta ctattttgcc cctcttttta aactttaata tattagtaat acctattatt  26340
ttcatattgt aattatctac ttcctctagc ctgggaattc tttataggtc ggggagggga  26400
cagtggtagg ctttatctaa ctcatcttag ttattgtcag tctcaagtat gatttctggc  26460
acttggtggg tgctcactaa atgtttgggc tgaatgaatt catataaaca agctaaaaat  26520
agacttgtag ataaatgatg gagaacttta tttaaacttt gtcttctctg aattactgtc  26580
atttgctttg tgattttagg ctacttctta gtttatgagc accatttctc aaggctgcat  26640
tctttaagaa atattaatat ttgaggagat actacaccat ccaaagattg ccgctagtat  26700
tttctaagat gtttttttagg gaaaaaattt aagaatggag ggaagaacct aatcagtgaa  26760
agatgtgatc ataaataagc agacagattt ataggaataa acaggttaag aatttgaata  26820
tagaaatata gaaaggaata tattagatta aattatagag tcctaaagta gagtgtaagc  26880
cagaattata tgtgctctta cacataccac atactgtata ggattgttta tgaggttcag  26940
ttgagataat ataaatagaa gtgctcgtaa gtaggatgtt tgtttctgca aaatgaattt  27000
tattaaatat ttagtgtact gtagataaag tgattcttaa gaatttttaa aaactgggcc  27060
gggtgcggtg gctcgcgcct ctaatcccag cactttggga ggccgagttg ggctgatcac  27120
aaggtcagga gtttgagccc agcctggcca acgtggtgaa accctatctc tgctaaaaat  27180
tcaaaaaatt agccgggcat ggtggcgtgt gcctgtaatc ccactacttg ggaggctgag  27240
gcaggagaat cacttgaacc cgggaggcgg aggttgcagt gagtcaagat tgtgccattg  27300
cactccagcc tgtgtgacaa gagcaagatt tcctctcaaa aacaaacaag cagttatgta  27360
ttgccatgta acaaattaca ccaaaattta gcagtttaga gcaataaata tttattatct  27420
tagtattcct atgggccagg aatatggcta cagcttagtt gaatgccctt ttactcatgg  27480
tatctcagga ggctatagtc ttcctatagt tagggtcagt tgaagctgca gtcatcacaa  27540
```

-continued

```
ggtttgactg gcagagaatc tgttccaagc ttaatcactt ggctcttggt gagccatagg  27600
ttgcctatag ctgttggctg gatacctcag tttcttgcca cctgtgtctc accttaaagc  27660
agctcacaac atggcagctg acttccctta aagtgactaa gagagggtac cacaacagaa  27720
gccagtcttt ttgtaaccta atctcagaag tgacatgcca tccctttgc catattctat  27780
atttgttaga agtaaacaca caataggagg gaattacaca aggtggatgg cgtaattgaa  27840
ggctgtctta aaggctgcct atcacagtgc aattagtatg gcattagtat gagaattcca  27900
gtgatgcaaa agtgaaaaat tcgacaaaaa caagtacagg aagcaagttg aggttggttg  27960
gttggttggt tggttggttt tacaactttt aatgcataga gggtaaattg gccaaaaaaa  28020
attagtcaag aacagaaata tgtagcttgt cagcagttag ttggaaaggg gtaataagca  28080
atgaatttga ataatttact aagagataat attactgtaa tgtgtgtgtt catgggatca  28140
gttcatctct tcctatgtat ttctcatttc tgtgttggtt ctgacgcagg agttttttcc  28200
tgtttgagtg agatccacta atggaggatt gttatttgat gcttaggact tgggattgag  28260
cagaaaacac tactgttggc ttgtaagatc ataatcggtg ttttgaatat ggaatatact  28320
accttcttaa atttagtttt acatgtgtga gtgaggcggt ttcccctgtg cagtttttcc  28380
ttgcacttct ccttcctgaa ccaatcttaa tgaggaatgt gtgtgacatg taccaaaaac  28440
ttcaaaactt taagatagag aaaatatttt gaagatgcct attcataaat tatttattgg  28500
tttaatttat tttcaataaa aatttcagtg agatgttagg taggcgcaat atttctgaaa  28560
tttatctaaa aaataagaaa gtcaaagaaa attctgaaaa ctatgttttt gtttttgtgt  28620
tttttttttg agatgaagtc tcactctgtc acccaggctg gagtgcagtg gtgcgatctt  28680
ggctcactgc aagctccgcc tcccgggttc acgccattct cctgcctcag cctcccaagt  28740
agctggacta caggcacccg ccaccacacc cagctaattt tttttgtatt tttagtagag  28800
atggggtttc accgtgttag ccaggatggt ctcgatctcc tgacctcgtg atccgcccac  28860
cttggcctcc caaagtgctg ggattacagg cgtgagccac tgcacctgac cctgaaaagt  28920
atattaatgg ggaaggaaaa acagacatgc cttactacat attaaaatgt catttcaagc  28980
agtagtagct aaaacatcaa tacatcatga taaatcagtg gatgagaaca acccgaaaat  29040
aaaaccctac catttctgcg aatgaagtat ataatcatta tctaatatag ctaatatgta  29100
atatgtagta tataacatgt aatgaatata cataagatgt gtaaaggaat tctgcatttt  29160
tagacctccc acaacaattt taaatagtga cagtgatacg aataatatta tgattatttt  29220
gggactcttt taacattaat tttaacaaga atgtattttg tgttaagtat aatcttggtt  29280
gctggggtta cataatttat catcctgtta aaatcatttt gttgtctcta ttagtctttt  29340
cattaagagt gatatgtcct tttttctatc aaactactaa tgtcttttag aaattatttc  29400
tgctaccagg acagattttg ttttacttat tgcttaagat tgttaacttg caaaacgaag  29460
tgaagtgaaa atttaatcaa ctgtgtagac tgtcctaact accttaatca agtaaaagaa  29520
tttacttgac tttgttgcaa tctgagcttt tattttgtca aagtctagtt atcttattaa  29580
gtcttcagta gaagatataa ttaatacttg gtgatttcta aatctgaata ttggagaaaa  29640
gggcaccaaa ttgaagaatg ctagatttta aatattttct agaactttaa tctatatgtt  29700
cctcaagggg aattattgtt aagcactgtc ttgatgtggg aaaatagatc cacaagaaac  29760
aggagtttct tcttcccagc ccctaaagat acactacatt gtaactttag acttgactga  29820
atttttcaat gtagtgctgt ctttgcatag gtgtatgtct ttgcacagat ggtgactagt  29880
```

-continued

```
agaatgtgga ttccgcttct catcccatca tacttgttta gtttttccgg gtgaatatat  29940
agccaagttt taaaagcaat gctctgagat tcttactcca catcttgtta aatggcgatt  30000
gtgaaccagt agatctggag tagggtttga gagtctgcat ttctaacaaa cccaaaggtg  30060
atgttatgct ctcagcaagg ttctagactg ctaaatttcc tatatagact tagttgttgc  30120
gatgtcttta ttcaaaaaga actgctttgt tcttggtctt ataattgtaa gatattttgt  30180
taggtgagtc ccatatattt tttctcactt aatcttcaca acacccctgc aagactgtaa  30240
tacatgttca ttatggaaaa ttcagataag caaaaagaag aaaaataaaa gttacgtaga  30300
taccagaaat taaaataata tttatttata agtttaagac tccaagtgaa gattaaagtt  30360
ctaaaaggaa ctaaagttat agcttcggga gtattatatg cattttccca ccttaagtaa  30420
agaaaacaaa acattgtggg agtaatatga ctgaaactaa aatgtattta cttagaaaag  30480
accagaagaa aatgtcagag catacagtag ttgcattagg gtgacaggat tataacaggc  30540
actttttcct tttatctgca gtccacaata tttataatgt gcatatgtta cctttacaat  30600
aaaaatttaa aaaccttagt cttctcagaa atgccactga ggaaaaggtc tgaaagttaa  30660
taataactaa actaaataaa tactttacaa tttaaatgaa aatcatcaag atggacaaag  30720
aataattcac acaagtgaaa aatggtaaat gaacaactga aaagaataaa tcaaatacag  30780
ctttggtaaa atagtaaaca gctttacaca atagtaaaaa aacatgcagc taagcaggta  30840
tctatctttt ccaaaaggaa gtattttaga gctaacaacc aatgctgaca aggcacagca  30900
aaaccaatat atttgttcat ttctggtagt agtatgcatc cttttgaaag gtaatgtgat  30960
taacacaaag attcataaat atttaatggc aatagaatac aaaaatacta tacacactcc  31020
atctgtcact atgtaacatg tttacatgct gaaagacaat cttttgggga aaaaactctt  31080
ttttgaggat aaagagatga gattaccgag tgctttagtg tttgcttaaa cattctttaa  31140
gtcttcttaa cttaaaaaaa gcaaataacc aaagttaact ttacatatga tagccctcta  31200
tcaagtaagt aaaccacatt ttgcatatta tggatgttta tgcttttttg tttgttttta  31260
gccctcttta gacaaattcc tatagaattt tcctaaatta gaaacaagtc ttgagatttg  31320
tttttaactt tcctagtact aaagtcaacc acttattcca aatttattga attcacctgt  31380
atgtggtaca attattatct agttatcata cagggaacgt agaattggta ccacaaggaa  31440
ataatgattt taagaaatag aaagatttaa aggtattatt tcagaaatga ctggagaact  31500
ttaggcatta aaaaaaaatc tgtaagttct ggtttcagtt tcttctcttc agtgtccaaa  31560
attgcatcca aaatagcaca gccactgcca aacatgtgca ttaaatcttg gaaagcaaaa  31620
agagaaatgg tctgtaccag taagccacag tattaaaaag tttaagcaga gactttcaga  31680
agtaatcggt caggtgcagg ttctgtagaa acttgaagtc ttacctaagg aacaaggtaa  31740
aggaatgtat aacatatacc atgttacatg aacataacat ttaatattgc aaatacttta  31800
cagagctatt attttatgta tatccttgtc tgaaatgatt tgtctccact tgaaccttgt  31860
tgactgtttt tctagacttc ttaaaactga aaccaaatag cataccctaa ttatctagtt  31920
gagtatttcc cagccatatg ttgggtgaga gctgttggca ttttggacaa gacacttctt  31980
gtgctggact gccctgtgat tttgtgtccc actcattact accagttgca accctcagga  32040
attgagtact agaaacaccc tcacagtttt catggggttg gtgagcaagt accttctgtt  32100
gagaattggt ctagtccttt gaagaatgct aggtagctct ttctaaaata ggttaatttc  32160
atgtcatagt gtttaggtaa aagcttcaca ttggacatga ataaaaagga ttagagttca  32220
gtgtattcag gaaactaata taagatcttt gaatcttctt attttgttcc aagattgatg  32280
```

-continued

```
aaattcagga gaggacttgc tacagtgttt ttggagggta attttgcact actgtttgaa  32340
tcaaaatttt aaattacgca tttgtcatta actccacttc taggaatcta gcctgtagga  32400
atcttggagg gcataaaaaa ttatttgcca ggatgttcat ttgcagtatt attggtaatc  32460
acaaaaatag taaaaactaa aaaaaagaac gaaataacca acaacaatat aaccccacct  32520
acctgaatga gtattataaa tagagaaaag gttaaatggg catatagtac atgctatacg  32580
tttattattt aaaaggaacc aggactctat atcctgaata aatttttaac aatgtattat  32640
taaaggaaaa aaagaacagt atgggccatg cacagtggct cacaccagtg atcccagcac  32700
tttgggaggc caaggtgggc agatcacaag gtcaagagat cgagactatc ctggccaacg  32760
tggtgaaacc ccgcctttac tcaaaataca aaaattagtt gggcatggtg gtgcacacct  32820
gtagtcccag ctactcggga ggctgaggca ggagaatcac ttgaacctgg gaggcagagg  32880
gtgcagtgag cggagatcac gccactgcat tccagcctgg tgacagagtg agactcagtc  32940
taaaaaaaaa aaaaagaatg ttatgattag tatgatcttc agttttgaaa taaaaatgtg  33000
tgtgtatgga taagtaaggc ctggaaggtg acttcttata ttgttgaaac aaataaataa  33060
aaaagtagaa ccaaggcttt caaaggttga gaaagggaat aatacttcct ttgtttttct  33120
agaacatgat tggtcctccc atcattttcc ttcatttctt cctttagact gcacagttgc  33180
acttgcagta aacccttcct cttgaatccc tacccaaaga tattttgaaa aggatctagt  33240
aactaatggg gcaataagca gcactatcat catgggcacc ttaggctcag aatttgtcat  33300
gttttaactg tttctctgtc tttgctccca tgtcatcttc agttgttggg tccaacttgc  33360
acatcttttc catatacctt tattgttctt cctgtcttta tcctagttca cttcatacct  33420
agattattat agtagcctgt gaagctggtc tcttttcggc ttaagtattt ccagccgtgg  33480
agagtatacc tcaatgaaaa tattgctgta gcaatttgta cctctttact ctataattta  33540
tttttatctt tacctttttt tagtggtgga gtaagaaggt aaaggtaaag ggagatatag  33600
gagctgatac tattgtgttt cagtactggt gatctattgc taaataatta tataagcttg  33660
catactgacc caactcttct agaagggaga gtgttaacaa aactaggaga gagattgtag  33720
ccaaggttta aaatggatat atttatggga gaagcctgct tagtgaattg tgttttaggg  33780
taggaattct gaatgagtaa gcatgtctgc tctttttcta atatctgtta agtttggggc  33840
tattttattc catgtctttt atcttccctt ttagaaatcc ctcagttgaa ttaagaggaa  33900
aaaagatcat ttaaaaaaat atctagacta gcattgtatg aatgaagact gcagaaatct  33960
gtagaaaccc gctagaaatt ggtcagttag taaggtgtat ccccttgata gcaatttctc  34020
atatggagga tgtagtaggg aggtcatagc atctggagag ctttttccta agtgacagtc  34080
atcacattct gagatggcat cccacttatc acctttctcc ctttgagaat cagttttaat  34140
gagtcattat tactaaggga atgtgtttta tttctcatgt gcaggggcag aaaattaatt  34200
tggaacagtt accttaaaga aagtgagttg gcagtaacag tgattatttc cttcactccc  34260
atgcccaaat ctttcatact ctttaaggct gaaaactgcc acttcctgta ggaaatattc  34320
cctgctttcc ttctggcctt tcctatttaa tttgtccctc ttctgatctt acttgaatct  34380
tttttatgac ccttgttatt ttctacattg tactataaat tatgtgtgtg cttattaaaa  34440
aatctatatt ctatactaga aactcttcct agagcagagt acatgtctaa cgcctcttgt  34500
attctcacag tacttaatag aacatcttgc acataatata gaggctcagc aaatatttcc  34560
tgatcatatt attaattgtg aagtttgcta ggcaaaagtt aatgaacttc aaatgtcatt  34620
```

-continued

```
gctcttctac ccctttaaaa tgtcttttac cacagagaaa aattagcaaa aattataaag  34680
ctgatatcca ataactgaaa ttaggaaagc aatgtattga agaaggagct agtgtaaatc  34740
tagaagtgag tagagatgta gataagcagt gaattttata aaaccttgtg ggtaatgcaa  34800
agagtttgac ctttttccgt acttgaagag agccatttga agacttttaa gaggggagtc  34860
atttgatcaa attcgtgttt taaataaatt agtgtgatac aatgaggaag ctaactgtac  34920
agatagtaac accagaagat gggaacccaa ttaggttatt gcaagaatct aggaaagaat  34980
aaatcctaaa atcttagagc agaggcagta tagtaggata aaagagaata gatttaagaa  35040
atacagataa aattgatagg cttggtgcct tatttgatgt gaagtaaggc agatggaagc  35100
atcttgatga ggctttagag attgaagtgc tgacacctaa gttagagaag gaatataggg  35160
aggagggaga atagcagtaa ctttagtggc tgagatgagt tttgaatgtg gcgatattgg  35220
attgtctgta agagagccag ttgaagatgt ccagcagtca gttggttata taagactcag  35280
gtttatggag cggtcagtct gagaatcatc agcatataga ttcagagtaa gagtggctag  35340
agtttgtcct agagaacatg tattactgat tttttttttt ttttttgggg gatggaatct  35400
cactgtcgcc caggctggag tgcagtggca gcaatcttgg ctcactgcaa gctccgcctc  35460
ccggattcaa gcgattctcc tgcctcagcc tcctgagtag ctgggattac aggcatgtgc  35520
caccactcct ggctagtttt gtatttttag tagagatggg gtttctccat tttgtcgggc  35580
tggtctcaaa ctcctgacct caggtgatcc acccgcctcg gcctcccaga gtgctgggat  35640
tacagatgtg agccaccgcg cccggtgtgt tgttgatttt tagaaccttt ttttcactgt  35700
tttctctggt gtttccatta gcaagtattt gttacggttt actttctatt attgttttta  35760
ttatagaaac agtgtctttc aacctgaatt taatcatgag gggaaaaaaa tcaaagcaat  35820
cctagttgag gaacactgtg aaaaacaatt ggcgttaagt tttcaacaat gtgtgtcttg  35880
aaatattaaa aatataggtt gtggaattgt tcaacgttaa aggagactaa aagagacgtg  35940
ataaccaaat gcaacctgat ttgattgatt gattccagat aatcttttta gaggacatta  36000
ttggaataat tggagaaatt tgaatatgga ttgtatttta gataatagta acaatgttaa  36060
aatgtgataa tttattgttg tataggagaa tgtcctttta cgtagggtaa agtgccataa  36120
tgcaacaact gcagtggttc agcacacaca aaaaagtatg tgtaaagtga taaagcaaat  36180
gtagtttgca ttgtaagtgc ttcttatgta aaaatgtatt tttataaaag tgcctagttt  36240
tcttatttcc ttcttttttt tttttttttt taaaaagaca gactgtcttg ctccgtctcc  36300
caggctggag tgcagtggca tgattacagc tactgcatct tctacttcct gggctcaagc  36360
catccacctg tctcagcctc ctaaatactt gggactacag atgtgtgcca ccacagctgg  36420
ctaatttttc tgtagagaaa ctcccaattt ttctggtctt gaactcctgg gctcaagcag  36480
tccttctgcc tcagcctccc aaagtgctgg aatttcaggt gtgagccact gtgcccagct  36540
tagttttctt aatatatttt tgcatgtggt agcatattag aggttgaata caattgtatt  36600
tattacatgt ttgtgctttt ctctattgat tatgggaaat tgttaagaca aaaatcgcat  36660
tcactgtata gcagctggtt tatcctgtgg ttcttctctt tgcaggcaaa cttactaagt  36720
aaatggacca gaataaatta ttttcataat ctattattat taaaccctgt attagtcaga  36780
atgggatata atctcagtta tttaatacaa ctagggttta ttcttgctca cattacttat  36840
ccaacagttt gtcaggaaat agatctactc catacagtag ctccagaaac cacactgatg  36900
gaatttctga cagtgtatat ctgtacacct ggaacattag tcctccacgg tgaccaccac  36960
atggaaataa agagctagaa ggtcttctgt tggccgttaa atatttcagc catgaaatga  37020
```

-continued

```
cacccaggtc attcaggcac tcacaaccta gtaaccagaa ctagttacct taccctactg  37080
gtaagtgtct gggacatgtg ggaagcacag gttgtttggt gaactgtaaa tgtgtctgtc  37140
acatattgta cttcatctca agaaatatgc gtagccttta aacctatgga taatggccat  37200
tgttgccata attctgccta ttaaattgta ctaaaaaagt gttacaggcc gagtatctct  37260
aatccaaaaa tctgaaatcc aaaatgatcc aaaatccaaa actttttgag tgcctacgtg  37320
gtgccacaag tagaaaattc cacacctgac ctcatgacag gttgcagtca aaactttaat  37380
gcgcaaaagt attagagata ttgtataaaa ttacctctgg gctatgtgta tggggtgtat  37440
atgaaacata aatgaatttt gtgtttagac ttgggtccca tctacaagat atctcattac  37500
gtatatgcac atgtgccaaa atttgaaaat ccgaaatttg aaacacttct ggttccaaga  37560
attgacactc aacctgaatc actttcagtg acaaacagtg gctttcctct tatatattga  37620
ctatttctca cataatccat ttttatttat tactttcaaa actatataat aaatgtaaac  37680
tgattttgag agtttagtga tttgcccaga gttacagagt ctgtcacttg gagagcttgt  37740
agagttttga gattttgctt tgccatttaa atttaatgat agctacattt aaatactatt  37800
ttaacctgaa actttttaaa atatttttaa aaaggagttt tttcctcaga tttttatttt  37860
tcttcttaaa atttatatta tttacattta aaaaatagca ttagatagtg ttttcagaat  37920
gaagtctatc agccctgtat ataatcatcc tttttttcttg ggcacttaat tagttagaca  37980
tttctcaaag gtataaattc taatgtagtt cttaaaaaat atccaaaatg tcctatatta  38040
tagtttatct taaacacatt tgaaatgtct acatataata gattgatgaa atctatataa  38100
actttagtaa catgtctcta agatatggca ctacaattaa tttctaatat taaaaatttt  38160
aatagaacca caaacaatag aaaacatttt aaattgtatt taattttagg atgtttattt  38220
taaatctagt tataaacaaa gtcagttaac cagattcttc aatggacttg atccctgtac  38280
cacccttcc tgcacacttc tttttattga attaggtaaa ttgtaaacca aaagctctta  38340
ctagatgaag ttctcaggtc agtacagatt caacagtctg ttataccccct gtaattcctg  38400
attggagttt tgttctcaaa atcatactct tatgaacaaa cgccaaagct atatcataac  38460
tatggaatga aggggagaga gttacatttt aatatttaaa atgtttaaag ctttacatgt  38520
ttgaagcagg tttattagct tagtagtttt aacttttgtt caattataat caaaaaatag  38580
ctttcatgtt taatctctga cctttggttt gacatgtaaa aatgataaat tttatcatag  38640
tgatacattg taacacatgc ccaagtatct ccaaaactga cttcatcttt tgtgaaagtg  38700
atgccaactg aacataccag gaagtcttag gcatttgtat caaactgcct aagaacccag  38760
ctgttagctt ataagtcagt gaaattatat tttatcattt attatcattg atagaacaca  38820
gactaaaagg aaatacatct gaagtccatt tctttaattc atcattatct tcagtggaaa  38880
aagatatgag gaacaacatc actcattgga aatgaactgt ctttgtcatt tcatttgtgg  38940
tagttgtcct ttcttcaaaa agctatttct tgaagaaaag gaaagttagt gaaatttgtt  39000
ttctcattat actttatcca aatttgaagt ttcctaataa aagtagataa ttgccttttg  39060
gcaagtttcc tctttattac aagttcatgt aggtgtttga gtttgttttt cttatttata  39120
agaggcagaa gatgatacct attttcacag ttacttacta acttactgct ttagtttgaa  39180
agaaactgac aatgtttctt ctgaaacttt ttaacaatac aattaattag catctgacta  39240
aaagtatctc tttgggtttt taaattggac atgtcaggtt gtttagtatc agttgtttta  39300
ctaaaaccac ggaagtgccc tcaattttta cagcattttg ttttttgagt gaattttacc  39360
```

-continued

```
aaccatttac atttttttta aattatactt taagttctag ggtacatgtg cacaacgtgc  39420
agttttgtta catatgtata catgtgccat gttggtgtgc tgcacccatt aactcgtcat  39480
ttacattagg tatatctcct aatgctatcc ctccccactc cccccacccc acaacaggcc  39540
ccagtgtgtg atgttcccct tcccgtgtcc aagggttccc attgttcaat tcccacttat  39600
gagtgagaac atgcagtgtt tggtttttttg tcgttgcagt agtttgctga gaatgatggt  39660
ttccagcttc atccatgtcc ctacaaagga catgaactca tcctttttta tggctgcata  39720
gtattccatg gtgtatatgt gccacatttt cttaatccag tctatcattg ttggacactt  39780
gggttggttc caagtctttg ctattgtgaa tagtgccgca ataaacatac gtgtgcatgt  39840
gtctttatag cagcatgatt tatagtcctt tgggtatata cccagtaatg ggatggctgg  39900
atccactggt atttctaatt ctagatcctt gaagaattgc cacactgtct tccacaatga  39960
ctgaactagt ttacagtccc accaacagtg tgaaagtgtt cctatttctc cacatcctct  40020
ctagcacctg ttgtctcctg actttttagt ggatcgccat tctaattggt atctcattgt  40080
ggttttgatt tgcatttctc tgatgaccag tgatgatgag cattttttca tgtgtctgtt  40140
ggctgcataa atgtcttctt ttgagaagtg tctgttcata tccttcgccc cctttttgat  40200
ggggttgttt ttttcttgta agtttgtttg agttctttgt agattctgga tattagccct  40260
ttgtcagatg agtggattgc aaaaattttc tcccattctg taggttgcct cttcactctg  40320
atggtagttt cttttgctgt gcagaagctc tttaattaga tcccatttgt caattttggc  40380
ttttgttgcc attgctaaat ggcattactc atcatttaca ttcggtaaat gacatgtcat  40440
ttagtaatga catgaagtcc ttgcccatgc ctatgtcctg aatggtattg cctaggtttt  40500
cttctagggt ttttatggtt ttaggtctaa catttaagtc tttaatcctt cttgaattaa  40560
tttttgtata aggtgtaagg aagggattca gtttcaactt tctacatatg gctagccagt  40620
tttcccagca ccatttatta aatagggaat cctttcccca tttcttgttt ttgtcaggtt  40680
tgtcaaaaat cagatggttg tagatgtgtg gtattatttc tgagggctct gttctgttcc  40740
attggtctat atctctgttt tggtaccagt accatgctgt ttgggttact gtagccttgt  40800
agtatagttt gaagtcaggt agcatgatgc ctccagcttt gttcttttgg cttaggattg  40860
tcttggcaat gtgggctctt ttttggttcc atgtgaactt taaagtagtt ttttccaatt  40920
ctgtgaagaa agtcattggt agcttgatgg agatggcatt gaatctataa attaccttgg  40980
gcagtatggc cattttcacg atattgattc ttcctaccca tgagcatgga atgttcttcc  41040
atttgtttgt atcctctttt atttcgttga gcagtggtat gtagttctcc ttgaagaggt  41100
ccttcacatc ccttttaagt tggattccta ggtattttat tctctttgaa gcaactgtga  41160
gtgggagttc actcatgatt tggctctctg tttgtctgtt attggtgttt aagaatgctt  41220
gtgatttttg cacattgatt ttgtatcctg agactttgct gaagttgttt atcagcctaa  41280
ggagattttg gtctgagatg atggggtttt ctaaatatac agtcatgtca tctgcaaaca  41340
gggacaattt gacttcctct tttcctaatt gaataccctt tatttttttc tcctgcctga  41400
ttgccctggc cagaacttcc aacactatgt tgaataggag tggtgagaga gggcgtccct  41460
gtcttgtgcc agttttcaaa aggaatgctt ccagtttttg cccattcagt atgatattgg  41520
ctgtgggttt gtcatagata gctcttgtta ctttgagata cgttccatca atacctaatt  41580
tattgagagt ttttagcatg aagggctgtt gaattttgtc aaaggccttt tctgcatcta  41640
ctgagataat catgtggttt ttgtctttgg ttctgtttat atgatggatt acgtttattg  41700
atttttgtat gttgaaccag tcttgcatcc caaggatgaa acccacttga tcacggtgga  41760
```

-continued

```
taagcttttt gatgtgctgc tggattcgct ttgccaatat tttattgagg atttttgcat  41820
caatgtccat caggggtatt ggtgtaaaat tctctttttt tgttgtgtct ctgccaggct  41880
ttggtatcag gatgatgctg gcctcctaaa ataaattagg gaggagtccc tctttttctc  41940
ttgattggaa tagtttcaga aggaatggta ccagctcctc cttgtacctc tggtagaatt  42000
cgaatccatt tacattttaa tataggatta ccaggttttt atgctgctaa ggacattttt  42060
gtaaaaatta ttcccccaaa aaattagttt aataaaagag agggcatttt actaccaaaa  42120
ggtaaagtag gaaaggtgta tcttcagaat aaaagactgc ccttccatat atttcagttg  42180
acatttttat gctgatatag tatgtctccc attatcttta tttctctcct acctctcttt  42240
ttttttttaa gagatagggt ctcatgaaac tgcccaggct ggccttgaac acctgggctt  42300
gagtgatcct tccacctcat cctccctagt ggctgggact accggcatgt accactgcac  42360
cgagtattac tttttttctc tttaccatgt gcttctgtga actttatttt aatccttact  42420
tgaaaagcat gattttgaac acaccctgtg atgaaggtta caatgcttat tgcaatattg  42480
caatagaaaa ggagctttca attttgtagg caaagttttt gtgtgccaga tccctgactg  42540
agaaagaaga tattttcatt taaaagtaag caaataatcc tctacttttt ttctaacaca  42600
gcaaattgat ccatatgcat aatgaaaaac ctctgatatt gaacatagag attcttatta  42660
attgcagtgt tcacaggatt agaatttaaa tacacaaata ggtgtctgca gctatcaata  42720
ccagatgact cagtaagcta aatacagact ttaatagaac tatcttggat gccttttaaa  42780
atatctttta aacttgttgt caggtattct gttttatctt ttgatttcta aaatgggttg  42840
taacatttga gattcactga agtttctttt gtatttttta tggcaatagt attttgccat  42900
tttcaggata gaaatactca tttttgaagc tattacagta ggcagctttt ttgtaaggtg  42960
atatgaatat cagagaaata taactacatg ttatacttct gatttcatgg gattaaaaaa  43020
agaaaaggct tctcaagtga cacaaatgca tatgttttca gagactaaga aagcataaat  43080
tgatgatgac agaacttgta acgcatttag atttgtgtca cttgaaaaac acttgttaca  43140
agcatgttgt caatttgtgt atttcaacaa atagccattt taaagaaaaa cataaagtaa  43200
ataatagtac actgatgata ttcagatatg gtgaaatcat acaggtagac cttgaatgaa  43260
taatgagcac attgctttag gacagatgtg actctcaact tttgatattt gactgtgtga  43320
gtttaaagtt gatgctttaa ttttttaata ggtcaaactt gggaatctaa tgactgatag  43380
tatttttgat aagaaagcac taatatagaa caagaaacag tgttctgaaa tgaaaattat  43440
cagacttcca ctttctgttc atatctattt caaaaaatgt acgtggcata ttatgttctt  43500
tgctacttag tggctattaa aatggaatca ttttataaat gtctttcagc aaagaaaaat  43560
gttgtctgct gctgtgatca cccgccacta agtactgtgc tcctcctctc agtagcttga  43620
ccaccttata tactttatgt ggcatcttta acctgtatct gtcaccttac atatcttctt  43680
ctttgttcct taattttttt tttttttcaa agactgcctg gacctactct ctcattctct  43740
cctctgtatt gctgctatag ttgtcacttt cttctacatt cccattctct gctttggctg  43800
ctgtaattat cttttgcttt tactattttg atcttgtcat tcaggactgt actataaatt  43860
acattttacc atgggttagg tttacctatc ttcaaaaaac ttcagattac cttattctct  43920
cctcaatacc aaataatata ctctagtttt cttagctaat ttttaagcgt ctccccattc  43980
ctccagatcc accaagaaaa attcatccta caccacattt ttacccctgg acctaaagtg  44040
tattatatgt tcttgaacag gaaaatttca tctcctgaaa aaaaaaaaat tactgatatt  44100
```

-continued tccatgagta catattgatt ctggtttgac tactattttg aaatagagtg gatgtaaaaa 44160
tctatgatga aatcttaaaa ctagtaaaat tatcattaga actagtatta tacatggaac 44220
tattagtctg gtagcatagt ctgttatact actcacacta aagcaaaata aaaagtactg 44280
tcttcacttg gaactgttgt cttacaattc tgtgcctgtc ttcaccattt catgaaaata 44340
ttaattgttc ttcttggctt actttttctt taatttatgt tcttgccagg tcaaaatcaa 44400
aagtgatgat ttaggacttg ggcatttgtc gagataagtt catattgtca ccactttccc 44460
aattttgaag cttacaaaaa aaataggcag gattttagtt tgccttcagt tagggaaagg 44520
agaattcatt tgccacagga gtaaaatcct acgttttata aagctatttt aatgaaaata 44580
ccagctttcc aaaatgaatg ggacaaacac agaattgatt gttgcttaaa aactttaact 44640
gtattgagtt ttggtaaatc ataattcaaa aataaaatgc agggggacaa gaaattatta 44700
actttttatt gttgaaatac attttcctca aagtgttttt ttggttttgg gttttttttg 44760
tttttttttt ttgaaacgaa gtcttgctct gtcacccagg ctggagttca gtggcgtgat 44820
ctcagctcac tgcaacctct gcctcccggg ttcaagtggt tctcctgccc cagcctcccg 44880
agtagctggg attacaggct cccaccacca cgcctggtta gtttttgtta tttttagtag 44940
aggcggggtt tcaccatgtt ggccaggctg gtcttgaact cctgacctca ggcgatctgc 45000
ccgcctcagc ctcccaaagt gttgagatta caggcatgag cgacagcacc tggccccttc 45060
aatgtttttc ttaaaaatat gttaccagtt tctatcactg cccattttcc acctccttat 45120
tttttgtata atgaccttga attttgaccc atttcttaaa aattggattt ttatcataat 45180
ttttatactc ttaccctaaa cctattagtt tgatttttca ataagaaaaa tcatgctatt 45240
catagtatag gtgaaatctc atctgaggtt acccacttga gtagtatatt catagaaaaa 45300
gtattttgag tccttaagag ccatgaagaa aacaaaactg aggggtcagt tttcttttgg 45360
ccattgtcga gtattatact tttaacttag tatgaaatgt aggaaatgtc cagcatactg 45420
gatacttatt tctctggaat cactctggct gtctaatggt ggtatttggt attactgcag 45480
aaagcacagg ttttgtttta gaaagtcctg gatttgacta tcttactcat tttatgaagt 45540
tgtgcagtga tgaactctga ggttcatgta cttatattac ttataaaaca tttaaattgt 45600
tagggttgtt atgcctaaac ttgatgattt tatgtaccat cgcaattttg ttgagaagat 45660
aaatgccaaa aagcaaaccc ttggaaaatt agtttacctt tctttacctt acctttgata 45720
aagggaatgt taaagggtaa ctgatttgaa ctacagattt cttttctacc acctttaagg 45780
tcctttccag tattatctct gtaaacaaag ttaaagaaaa atacatttga aagaaaagat 45840
ttgttgtaac taaaccaatt aaagctggct tctaggccag ggctggtggc tcacacctgt 45900
aatcccagaa ctttgggagg ccgaggcggg cggatcacga ggtcaagaga tcaaaaccat 45960
cctggccaac atacaaaatt acaaaatttt tgtaattttg tactaaaaat acaaaataca 46020
aaaattagct gggtgtggtg gcgtgcacct gtagtcccag ctacttggga ggctgaggca 46080
ggagaatcgc ttgaacccag gaggtggagg ttgcagtgag ccgagatcac accactgcac 46140
tccagcgtag atgacagagc gagactccat ctcaaaacaa aaaacaaaaa caaacaacaa 46200
caaaaaaatg ctgacttctc agggccaatg atgttattct ctgagatata tatatatttt 46260
ttcctttcat ggataagttg aggacattat cttgatatct cttgatctga taactagagt 46320
aatctttgaa tattgttgtt agttattatt aaaaacactt attaaggtcc tttatggaaa 46380
gtgaccagtt tcctgctttt atatacattc ttctttctgt ggcctgaaac attatgtggt 46440
ctttggttat ttactttaca atttagttat tctgataaat actcttactt taaaaatttt 46500

-continued

```
atatccagaa gaatcttttt ctgcagtcac agaagtagtc ttggttgacc tgttttggct  46560
ttctgtgtaa tgtctgtatt agataccaac tgattgatat aaatgagact ctaaggggat  46620
aataataagt gttaaggccc aatcaacacc ctgaggctgt gaaaatgttc actactattt  46680
gtagaaagtt catatataat atgatataaa aattgcaaat tgagtcctgg caatatctag  46740
tcttataaat ggatagagca agatgcactt ttgagtgaat gaattcctgt tttaaagtgg  46800
ttaaggatta tatttgcaag ttccaagtta tctgtattct actaattgtc ctatagatga  46860
cattgttata atttgttcac tcacattgtt gctttccact aagatctgtt attattatct  46920
ttaggatttt cttatttgtt aacatgattg cttaagtgat taatcaaact aaatcagata  46980
acatagaact caatgaatat agctcttaac tttggataac agctattttc ctcttgaact  47040
aatatccaaa tttttgatct ttaaatgtta caactgcagt aagcatggaa tattattgaa  47100
ataaatttaa atataactgt ttaataaatt attaattatg gatgattaat aaaatgttta  47160
gtgtgttact gaatgtttct tgagaaaatt ttatatcagt ttaaatagtt ttgtagcttg  47220
tcagcattac agaatttttt atttttttat tgtgtcatta agtgtagtgg ttaagaacat  47280
aggcctggag taagatttga attcatattc tgattgtggt ctttattagc tgtgtgaact  47340
taggcaaatt actgtaacct ctttgaaaag gcttccattt ctataatagt ttgccagctg  47400
gtttggtcag gaacactgta ttgtcttgtg tataggtgta tccacaatgt ctggtacctt  47460
gtaggtactc actaaatttt taatgaaatg aatgataact gctttggatg attgccatga  47520
aaattaaatg atgatatgaa tgtaaagcag ctagtaatgt acatagctga cactaactgc  47580
tgttattatc aacagtgaca gaaaatctcc agtctagcta atacaagaaa tagatttttc  47640
ctcagactct catctcacat tccctttttaa gatttccttg tcctatcccc accccagacg  47700
tttccatttt gcttttattt tctataataa ttcctggggg cctctattaa aggccttttt  47760
ctttgactac ttacatccat tataccagta tctttgtcag taaaatttta tatatctttt  47820
attctgtcat caggttaaga aacaataatt gtatttttaa aggaaaatat tttacgatgc  47880
tactaagcag ttactttgtc cacttatgca ggtatttcat aagtatgaag tagggaggtc  47940
aatatctgtc tgacaggaat ctgctgaaga ttaatgttat ctagcagaat gcttggcata  48000
tagaaggtac tcaaataagt gatgctatct attaatagca ttgatagtaa tactttaaaa  48060
cactcttttc tagtatatca tatctccaaa tttaatattt attgtctttt acacttattt  48120
tacatacatt aattcattac tttttttttt tttgagatgg attttcactc ttgttgccca  48180
ggctggtgtg caatggcgtg atctcggcgc actgcaacct ccgcctcctg ggttcaagtg  48240
attctcctgc ttttgcctcc tgagtagctg ggattacagg catgtaccac cacaccggct  48300
aattttgtat tttagtagag acggggtttc accatgtttg ccaggttggt ctcgaactcc  48360
cgacctcagg tgatccatcc acctcggcct cccaaagttc tggtattaaa ggcatgagcc  48420
accgcgccca gccagttcat taatttttaa aataactctg aggtaggcac tattatcctc  48480
actttatatt tgaggaaacc ctcaaagaga ctaagtaaat aacttaaagt ctttcaacta  48540
gtacgtggca gaattataat taaaaacctg tttttgccac tattgcatat tgttagaagg  48600
ctgtttcttc ttgaggctga gctaagagaa catatatcca tcctacgtaa cttacagttc  48660
ccattgtctg ttcatttgcc tatattctac tcacatttcc tgctttccat tcttacttat  48720
ttctgtccaa ctagaccaag aacataatat tctataccct gtctcccaaa cttctaagtc  48780
atggatttgt tttaacctcc tgctatgctc atttagctag gtatcattta tgaatatttt  48840
```

-continued

```
cttctcattt tcgtacccat tctcaagtct aattcattga tgactcagtc acgtcagtag  48900
tttctccatt accatggcaa taccttcctg aatatgagaa taaacatata tcctgactta  48960
attcctttgg ctcactctgt gaattcttta ccacttttga acactgtaaa tgtacctttg  49020
agaacttctt tgttgccagt ttgatttaaa aacaaaacaa aaaaatgtta ctgactgttc  49080
cagttatctg ttgctgtgta acaaactact ccccatactt agtgtggttt taaaataaca  49140
gccattttcc tatgtctcac gattttgtgg gtcaggaatt taggcagggc ttggctttgt  49200
tcatgtggtg gtgatggagg ttacttggag gtattcagct ggtagatggg ctggccagaa  49260
tagttccaga tggctttacc catataagtg ccgccttggt agagacagcc aaaaggctcg  49320
attcagcgga gacatcatgt gtagcatctg catacagcat catcagcatg gctttttcat  49380
ggtcatgtga tatttaacat agtggatcag ggtttccaaa aagtattgtc aacatgctta  49440
tttgaaagct gtaagatttc ttatcaccta gcccctttct gctgcatttt attcaccatg  49500
catgtcacaa aggtcagccc agattcaaag gagaggaatt agccattacc tcaatatgag  49560
gactagcaaa taatttgtgg tttttatttt ttatttttgt gggtacatag taagtatata  49620
tatttatggg gtatgtgaga tattttggta taggcatgcc atgagtacta atcatgtggt  49680
ttttaatctg ccacattgaa ttaaaccaat tattttagat tgtgtaaatt caagttgaaa  49740
aaaattggta atagggcaaa tggtttcatg tattttttta ccgggaacaa atttaaacag  49800
ttattagaat cagagcacct ataatgggag tcaatttttc ctgaagctga accaaaatgt  49860
ttattggttt gatttgaaag gagaagttgg ttttgttgac gttagaacta taaacacttt  49920
ttcctataaa tatgtatatt ctccctctaa tatttgcttt atgattaaca gtgtactatc  49980
atctgctttt gtatcacgac ttgagttcaa gagttgtagg tgtatgagat ctgagaaaag  50040
aaagaatcct ccactccatt tcatttaatg ttatattctc accaatttat ataacactta  50100
catattataa gtattgtttt ctcaaggagg atacaggcat attttactga gaggagaaaa  50160
gaatatcaag gcggattttt ggtttaaaat gttattcata ttctaaactt gtagatcatt  50220
ataaggattt tgcctttgct ctgaaaaagt cattgaagga tttcaaaaag agtgacatga  50280
tccaacctgt attttaatag aatctctgat tgctatgttt aactgccaag gagtgcaaga  50340
gtgaaaaaga ccaattaaga gtctgggaag ggagcatggt ggcttggaaa tggtcgaatt  50400
ttggatatat tttgaaggta gagactcacg atccaaaagt tgtgtaaaaa agataggagt  50460
caaggataat aagatttttg gccaaaggaa ctggacaaat gagttgtctt taatcaaaat  50520
taggagtatt gtagaagaag cacgaagaac agtataagga atttattttg gaagtaagtt  50580
tgagatggtt gttagacatc caaatggaga tatcaaatag gcagttggat ataccagtct  50640
ggagttcagg agagaggtcc aggctggagt ctttaatata tatagtgttt aaaatccttg  50700
agacatggaa atcaccaagg gagaataaag tggtaaagga gacgggtttc gccatgttgg  50760
ccaggctagt ctcaaaatcc tggcctcagg tgatccacct gcctcagcct cccgaagtag  50820
attacagcca tgagccacca tgcccggctg cagtgatttt ttttttttaa attttctacc  50880
actttctttc aataaaacca tactcgatgc acaaaaagag caggaaagtc aggagactgg  50940
gaagctttgc aactaacttt gaatgtgtgg tcttgaacac gtaatttcat ctttttctta  51000
tctgtaaaac gaagagattg gactagatta tttgtaagat gccttcctac tttaatatat  51060
cagtgaatct tttcaaaaca gggtaattat attgaatgta actgtcatcc tagggtaagt  51120
gaagtagtct ttaactacat gcaggtgaca gtttgtaagc ttgcttaaaa acatgattgc  51180
tttgcctatt cttctcaaga aattttagtc aagtgcaagt tagagctaat taatacaacc  51240
```

-continued

```
aaatcacagt gtttgttttt gcattcccag aaattgttag tactgtatat gatcagtatg  51300
tacaataaat gtttttacta actaaaaaaa tttcttaagg aaaaatatat tgacctaagg  51360
agaaatgttt agagctagat aaaggagatt aatatctcta gatgcaattt tactttacaa  51420
cgttattgag gtatgatccg cttaatataa agttcacctg tttaagtata caatttaatg  51480
gtttctagtt ttagaacctt ttcatcagtc cccaaatttt cctcaagcct atttgcagtg  51540
agttcccaac tcccacagcc ctctccagtc ctggcaacta ctgatctgct ctttgtttct  51600
ataaattttt ctggacattt catctaaaaa gaattatatg tagtattttg catctggctt  51660
ctttcacttt gcatgttttg aggttcattt atgacataac gtatcagtat tttgttcttt  51720
tttattgctg aatggtagtt cattgtatta tgatattttg tttgtctata cactagttgg  51780
tagatactta tataatttcc agttttttac ttttatgagt aatacttttt tgagcattca  51840
tggagaaatc tttgtgtaga catacgtttt tatttatctt ggatacattc ctaagaatgg  51900
aattgctggg tcatatgata attaactttt taagaaacag ccaaactgta ttccagtgtg  51960
gctgtatcat tttacatttc taccagcagt gtgtaagggt tcaagtttct ctacatcttc  52020
accaacagtt aatagtgtct ttttttataa cattatgaca gtttaatgga tgtgtcatgg  52080
tatcattgtg gtttcagtga gaatatacct aatgactaat gatactgagc actttttttt  52140
atatgtttat aagccattca catgtgttct ttggtgaagt gatattgagc actttttttt  52200
gtatatttat aagccattca tatgtgttct ttggtgaagt gtcttaagta agttctttgc  52260
ccattttcaa agttgtgtta tcttcttgtt cactagtgag agttcattta aattctgaat  52320
acaagagctt catcagattt gtgatttggc aatattttct cccagtctat ggcttgtctt  52380
ttcatttttct tattgatatc atttgaacta tgaaaattgt taactttaat gaaatccagt  52440
ttatcagttt tatcttttat ggctcatgtt tttgttatct aagaactctg ccttgttttt  52500
gtcatctaag aactctgcct gacctaaggt cacagatgtt ttctcctata ttttccttta  52560
gatggtttat agtttaagct catacattta ggtatttgat ccatttgaat taatttttgt  52620
gtatggtata agttaatggt ctgtttttaa atttattttt gcatgtaaat gtccagttat  52680
ctaaaaatca tttgttgaca agactgtctt ttattccatt gaattttgtg ggcatctttg  52740
tgaaaaatct aacataaata caaagattta tttctggact ctagattctc ttcattgatc  52800
aatccgtata cctgtcctta tattaatagc acacaatctt gattactgta gcttcatagt  52860
aagttttgaa attgggtagt ataagttctc caactttttt cttcactaaa ttattttggc  52920
tattctagat cctttgtatt ttcctataaa gttaggatca gcttatttct atggaaaaaa  52980
aacagctggg attttgaaaa agattatgtt gaatctatag atcaatttga agagaattac  53040
catattaaca attttgagtc ttctaattta tgagcatgga atgttttaga tctttttggc  53100
tcagcagtgt cttataacag tgtgcaaata caaatcttat actgattttt aaaaatttat  53160
tcccaaatat tcttcatggt cctagtttga atggaattgt tttcttaatt tcatttttgc  53220
atttttgcta gaatatagaa atacaactga tttttgtatg ttgattttct atcttgtgat  53280
ctagctgagc ttttttttga ttctagttgt tcgttggtgg tttcttagga ttttctacat  53340
actggacagt gtcatctgat aatgcagttt catttcttcc tgtctaatct gaatgcattt  53400
aatatctttt taagtttttt tcttaaaatg tgttactttt tggtgttttg ctgtactaac  53460
taaaacctac aggacaatat tcagtggaag gaataagaac aggcattttt gtttttctcc  53520
tgatagggaa gttagctgta gaattttcat agatgctctt tattaggttg aagaagagcc  53580
```

-continued

```
tttttatttc taatttttga gagttttaaa aaatagtggt tgttggattt tgtcaagtgt  53640
ttttctgtgt ctttcaaaat ggtcatgtag ctttagttgc tatttctatt aataagatgt  53700
tttacattaa tttattttta gatggttaac cacccttgca ttcacaggat aaatcccatt  53760
tggtcataat gtgtagtcat ttttatatgt tgatgaattt ggtttgccag tttttaaaaa  53820
ataatttttg tatgtgtgtt catgagggat attggtctgt agttttcttg cattgtctct  53880
gtctggcttt ggtgatacca gactcagctg ggaaatattc tctagtttat aaaacagttt  53940
ataaaagttt gctattcttt cttatatatt tcataaaaat cattggtgag atcgtctgtg  54000
cctaggcttt cttagtgtga agatttttaa taagtagttc agttttctta tttgttaggg  54060
atctattcag agtttctatt tcttgttgag tctgttctgg taatttgtct tttgaagaat  54120
ttcctttttt tttaatataa gttgtgtaat ttgttggctt aaagttaata ttccctttta  54180
attctttctt tttttatttt tttgaaaagg agtctcactc tgtcacccag gctggagtgc  54240
agtggtgtga tctcggctca ctgcagcctc tgcctcctag gctcaagtga tcttcccacc  54300
taaccctcct gagaaactaa gaccacaggt gcatgccacc atgcctggct aatttttgta  54360
ttttctatag agacgaggtt tttccttgtt gcccaggttg ctctcgaact cctggactca  54420
aatgatctgc ccaccttggc ctggaaagtg ctgggattat aggcatgagc catcacaccg  54480
ggccttccct tttaatttct aaagtattgg tagtgatttc ctctccttca tttctgattt  54540
tggtaatttg tgtctgttct ctcttacttt cctgatcatt ctatttaaga cattgtcaat  54600
tttgttgatt attttttaag aactaatttt tgaattcatt cgtatgtctc tggttttttt  54660
tttttttgtt tatttttact tttatcttta tttttttctt cttcctgttt ttgattttgt  54720
ttacactttt tctagtttct taaggtatgg aagcataaat actgattcga ggctgttctt  54780
tctaatatgg gcatttaaag ctataaatat tcctataaaa ctgctttagc tgtatcccat  54840
gaagtttaat atgttgtgat ttcattttca tgcagtttta agtatttaat ttctctcatg  54900
atttcttctt tgacccattg attttctcag atttctttcg gttatgggtt ttaattttat  54960
tcttttgttg tcagggaaca ccctttatat gatttgttgt aaatttaatg agatttattt  55020
catggtccag catgtgatca attttggaga atgttcttgt atgcttaaaa ggcattgagt  55080
attctgtggt ctttgggtgg agtgttctgt aaacttaagt taggtcattt tggctgatag  55140
tgttgctgaa gtttttttaca tcattgttaa ttttctctct agttatattt atcattcagt  55200
tctgtcggtt tgtgcttcat atatgtggca acttcgttgt taggtatgaa tacatgtata  55260
aacgttatat cttccttatg tactgactct atcattatga aatatccctc tttttcttta  55320
ttactattta tcttcaagtc tgtttcatct gctgttaata gccattccag ctttttttatt  55380
gtttctgttt gtatggagta tattttctat tatttttactt tcaacctatt tgtatctttg  55440
aatcaaagag tgtcttttgt agaagtatat aattgggtct tgttatttga accaatatga  55500
tagtttttgg cttttgattg tcatatttag cctattccca tttaatgtga tttttgatat  55560
gggtgaattt acttatgcca ttcttccttt actgccttct tttgtgttaa atattctttt  55620
agtgtactat ttaaattcct ctgctgtttt tttttttttt tttttttttt taaagaacag  55680
gatctcattc tgttgcccag gctgaagtgt attggctatt cacaactgcc atcatagcat  55740
actacagact cacactctct gctcaagtga tcctttcact tcagccttgt gagtagctgg  55800
gagtacaggc atataggagt acattggagt acaggtgtac gctactgcat gcagctctct  55860
tgattttttt taaaacaact ttttagagtt atttccttgg aggttactgt agggattaca  55920
atatgcttct taatttatca caatctactt gtatagttaa atttttattc cagtatagta  55980
```

-continued

```
gtagaaaaac tcttccttta ataaagttta aagtagataa gtttttaaaa acatactgtt  56040
ttttaaaaat gtactgtttt taaaatccta atttttatac ttagttattt ttagcagtgt  56100
catattgaat tctgttacga gtttcatggt tacttataat aaccagtttc ctcattacat  56160
agtagaatgg tatttttcca atttgaactc ttaattttaa attttcttct acctttaaaa  56220
ttctgtgatt ctgtttggtc aaaagggtct gtggaaataa tacttgatat gtttatatag  56280
tggttattca aaacttactc atatattatt tgctgacatc tgatgagata tagttctaga  56340
gacatttttt atttctggac tttagtcttg gatggatgaa aatttgatcc gatttcagga  56400
aagaaaagga ttataaatta gaatccataa catggtaaaa gaagtttgtt tttaatgtca  56460
atctaatggt aatttttgat catttaattt tttaatttaa ttaaatctaa ggctgagcag  56520
atttttctgt atggtttcag acaccagtag tgaaaattac ccaattccat ttaattcggt  56580
agcagtaaga taccagttgg cttttattga ttaatcttcc ttgctccttc atcaactata  56640
ccatatttat attttataag taaaaagtta ctcatattgc tagctttttg tggatctgtt  56700
ttggatttta ttctcaattt tcccaaggat ttttacattt tcagtccatg taaaacttca  56760
actcttattt ttcttaataa gagtatgggg gggtgggcag tttctataat taactgatag  56820
gtctctgtta aaatgaggtt ctctttctaa taaaaaacaa atgtgacgtg gctaatgtaa  56880
gtttaacatg taaagatcat ggtattaaga tcacttgatt tatgtttgta tatgaccacc  56940
tggtgtcatc attttaacta catgaacttg ctcagcatcc agatttcaca ctctttaact  57000
tagtgtttga ttgtgtaaga cgttgtgttt tttatctaat acattctcta gcagtgttat  57060
attttatttc aacctggtaa ccatatgacc agcattgtgc taggtattat ggaaagattt  57120
caaaaattaa tttttaaaaa ttaatgagac aagattctgt acctaaggtg ccagtgaaat  57180
gatttgatag aatgtaatta tgcatgactg gatgctgact ttgtgtgcat ctaatacaga  57240
aattcattaa aggaaaagat tgtaaagtaa aatggtaggt agaggatggt ttccaggaag  57300
agttggaact tgaaggatgg taagtgaaat gatagaggaa tagaggatag atagattttt  57360
gtctaggtgt catgataaaa tagtaacata gacagtcctt gatttacagt gggtcaactt  57420
tacagtttag attactaatg aatgggagca atggtagaaa ttataagatt acagatagtg  57480
gcttttcatt ttagaaatat ttgagcacta acattttaag gggaaatgat tgtcacattg  57540
acacattcat acattggtac tgtaagaatt tgtagtgcca aaaaagaatc atgaatgaat  57600
tcccacataa tgaagctatg aagaactttc agaggccatg gaaataaatg aatttttgaa  57660
gagctatagg tagacctaag tagctagagt taagaaatta tcaaagataa tgaaccactg  57720
gagaaagtgg agtcagtaga gtcaatctaa ggtacaagaa agaagattga gtcacagaaa  57780
ccaaagaatg agttaccaga tagaaggact cacactcacc atgcgcgttg aatgttgcaa  57840
tactgtttct cttctcttca gtgtccctct tttcctcctt gtagcttaaa ttcaaaggtc  57900
atttaatcat ttccttgcat acaaatacct tcagttcctt cgctcctctc tgttttggca  57960
aaaccacagc tttggttaaa tctcaccctt gcagctaagt gggactggaa aataattcaa  58020
aaaacataat gactggtctc actttaaagg cagtgggctc ttaatgttac ccagcaattg  58080
taccacactt ctttgatcca ttcactctcc tagatgattg tttcattctt tttcctctcc  58140
tgaaaacctc caacatctct tcttcatcaa ggcaatcaga aaagttttca caagtacctg  58200
acatcacatt tgtcctccta ttctttgtta aacctactct aaacaggttt ctgctcttct  58260
gtcccaccgt tttcaaaatg ggtcttctct aagtcaccag taacttgcat caagtctagt  58320
```

-continued

```
gatcagttct cagacttcaa gattcagtga ccagttgatg actcctttgg tattgagggc  58380
tctcttcgtt gtgcttctaa ggtaccatat tgtattagaa ttgctgtatc aataccagtg  58440
ccaacacaga acacacaata tccaaggttt cttttcagtt ctttttgttc ttagaatata  58500
ttccagtata ttagtttcct aggactgcta taacaactta taataccata aagctggtga  58560
cttaaaacaa cagagattta ttctctcaca gttcaagggg ccagaagtcc aaaccaaaat  58620
gtcagcatgc ctattcacct tccaaaggct ctaggaaaga gtctttcctt gcctcttcca  58680
gctatggtag tggctccagg gattccttaa cttgtggcta cctaaaaccc cagtctctga  58740
ctctatccct acatggctcc ctttgtgtgt ctgtctcttt cttctatctt atataaggat  58800
gtgtgtcatt agatttaggg accatccaaa atgatctcat cttgagatcc tttattacat  58860
tggcaaagac gctttttcca aataaggtga catttatggg ctcccagtgg acttatttgc  58920
agggggttga gggtttcaca tttcaataaa ctattcagta attgcatagt tatagtcctg  58980
tcatcaaagt tacttgaatt aaatttttct gtgtgattat ggtattattt gatatatagt  59040
tgggtttgtt tgttgctgtt tgtgttcagt tttaggattt gctttttcat ccaataatca  59100
taatactgat ttttgagtat atataacata cacagtcatg caccatatga tgacatttgg  59160
tcaacaacag accataatga cctacaggtc ctacaggatt ttaataccat atttttactg  59220
taccttttct atgtttagat acacaaatac tgttgtgtta cagttggcta cgtatacagt  59280
acaataacat gctgtatagg tttgtagcct aggagcaata ggctatacca gtagcaatag  59340
gtgcgtagta ggctataaca tctaggtttg tgtaggtaca ttctgttata tttgcacagt  59400
gatgaaattg cctaatggta catttctcag aacgtttgtc cctgtcatta tgtgacccat  59460
aactgtgtgt agctcagagg tcaaagttat attaggagga tatgcccaga attctcacta  59520
ccatcccatt ttaccttcct tgtggataac catttcatga ctactttcaa gtttatcttg  59580
acctaacaag taagtctgat tgattaacct catcttaatc atgggacaaa aacaagcaga  59640
ctcctcaaag ttccatattt aaaatggtga taacgagact taactcattg gattatattg  59700
aagattaaat ggaaaaaaaa aaaagtaaaa caactagcac agtgcctggc acatagtaga  59760
tataatttcc tttttccct tctgtacctc ataatatagg ctatgtattg cctacaatta  59820
gggaggctaa tcagtttgtt cacatatagc cttttctttc tataaaggag aatttgtgat  59880
atattaaaca ggcattataa aatattaccc agaagtttta tcaatttttt ggctttcagc  59940
tcctgaaact atagatagca tttatctata gttagtagca ctagttttaa aatttggaat  60000
cttggtcctc tcattcattt atgtattaca gcagagtcag acttatttta aaaacaattc  60060
taacctgcct gaggcttctg tctagaagtg gaatgtattt tgggtaagct tcttaaactt  60120
cataaaatca ccttctcatt tattccttgc cttaattaat aaaacatgta cttctgctct  60180
taatgacctt cagccatata ctcttgacat tctaaatttt tctaacaccc aattttgaga  60240
aaatgtatta atagaggact gactaaaggt tggcattctc tgcattcctc tgaatatttc  60300
aaattttact tttaggttaa accataccgt tggagatctg tgtgcatgga ttgcatgatt  60360
ttgacctctt gttaactttg catttgctgg attgtacttt caggatgtga tttttttttt  60420
tcccaagaaa agagaagaaa aggagaagtt gcctaaaaca gatctttagt ttttttagga  60480
atgctattaa ggaccttctc cattatgtca tccaacgtct ttctgaggac ttactagtga  60540
aattactctc agatttctgc atcttggaaa tgctgtactt ctgaacaact actaattcac  60600
ttttatttta tacacatatt ttcttctttg ccttactaac aaggagactt aagccttatt  60660
ttaggaccaa ctcttggagt ttggagaaca atgtgtgttt ctgtgtgcca tttttatttt  60720
```

-continued

```
cgatatcaaa atgtattgtt tgccctgaat ctttcccctg tttattttta gtcatatgta  60780
tgcatcagaa ttatctgaag cacttattaa ataccagctc ccatccctga aaaccttggg  60840
ttcagcgggt ataatagatt gcattaatag caccggttgt ttgccatgtg accacaccat  60900
ttaccccctg ctcctaaagg ggcagattat atttccttgc cccctgactt tggatttgct  60960
cataggactt actttggttt tagtgggcgt gacatgacca aaggcttgaa tagcactggc  61020
aggattaggc ttgtactttt gtgcctctat tgtctccaaa agaccatgtc cagcctggcc  61080
cactggttcc gggagaaggg ttgagagact gtagttttag gccagtacgt attgaagtat  61140
ttaggggaat gaactttgat gttgtcacct cttaaatggt tcagggaggc acacaccaca  61200
cacacacaca cacccccgac caccaccacc acaccacgag tgagaaaggg aaagacgagg  61260
aaagagtgtg attatttaag cagatggagc aaaatgtaag caactggtga atctggttaa  61320
agattatggt agtttcttga ctaattatgt aatttttga gtttgaaatt atatcaaaag  61380
taaatgttat ctcttccacc taaaaatgta aaaacattta aaaccttaag aaaattgttc  61440
tgcaaagttt ctaaatcagc tagtttgaac attaaacttt gttcagtgat aaaaatctat  61500
actaatgaac taggtactgt ccagaataca cagactatta ctgtttttta aaatttttaa  61560
ttttgaaata atgtaaatcc ataggaagtt gggaaaaagt atacaaggag gtcgtcaccc  61620
agcttctcac aataatacaa ttttacataa ctgtattaca gcttcaaaac caggaaactg  61680
acgttgatac aatccgggag cttgttcata tttaaccagc tggatatgta ctgttgtgtg  61740
cgtgtacagc aggtgtgtgt gtgtacagtt gtgtgtacat atagttatgt gtaacagtac  61800
cacactcaac ttactattct atcactgtaa acactacttc aggtggtatc tcttcataac  61860
cacacctgcg ctcttgttgt ttgttttttt cacagggtct tgctctgtca cccaggctgg  61920
aatacagtag tgtagtcata gcttattgca ccctcaacct ccctggctca agtgatcctt  61980
acacctcagc ctcccaaata gctgggacta caggtgcata ccaccacact tgactaattt  62040
ttgtattttt tgtagagatg ggcttttgcc atattgccca gactattctt gaactcttgg  62100
gctcaaacta tccatctgcc tcggcctcct gaagttggta ttacaggctt gagccactgc  62160
gtctggccca cttgggagtt ttcagcccct ggcaaccact aatcttttca ccatctctac  62220
aatgttatta tttcaagaat gttacaaaaa tggaatcatg tagtttgtag gcttttgaaa  62280
ttggtatttt ttctacttag tgtaatttcc tttatatcat ccaagttgat gtttttacca  62340
atagttttc cctttattg ttctggcagt ctgtagtatg gctctaccat cgttggttta  62400
accattctgc attgaaggac atttgtttcc agcttttcgc tattatgaaa ttgtcttagt  62460
ccattttgtg ctgctataac agaatatctg agactgggta atttataaaa aacagagatt  62520
tatttcttat agttctggag tctggaaagt tcaagattga ggggcccaca tctgacgagg  62580
accttcttgc tgtgtcatcc catcatggaa agtggaggag caagagagca caagacatta  62640
gtggggagaa atagaagggg acagaactct tctttttatc aggaacccac tcctgagaca  62700
acaacattaa tccatttatg agggcagagt ccttgtgaac taatcacctc ttaaaggtcc  62760
catctctcaa cactgttgta ttggggatta agtttccaac aaatgaactt tgggggacac  62820
ggtcaaacca tagcacgaat aaagcagcta tgaacattca tttgcaggtt tttgcatgaa  62880
cacagttttc atttcataaa tacccaagaa tgtacaattg ccctttact tagcatttag  62940
atttttcctt taaagtttat tctgaggcaa ttgttttcat actctgtttg tgagaaacta  63000
ttgttctttc caaggcctta aagctatgac taattctgta aacacagtta ttgtaatttc  63060
```

-continued

```
aggttaatat ttttaaggag tatatacagc cttgtgtgaa aagagagaaa tggattcaaa  63120
actaagcaat ttttaagtgt gccatgttta ttaactaaga tatgtatgta aataaccagt  63180
agattatttt ttgaagtagc atgagtcaaa ataaatcaaa ttgagagccc cttcagcttg  63240
tctgtcaggt caggaatgaa ctaatttgta cgtacctttt ctccctcatc ttgtgtcagt  63300
ccttcactat gtaccagtta cataatcttc tttccttagc taggctctgt ccttcttcag  63360
ggacttgagc atgttaatca ttatggatcc tcatttcttc ttccgccttt gcctgtttaa  63420
ctcttactta tgagatttcc ttaatgagac atttcctccc tccccaaacg taagtttagt  63480
taccttcttt ttttctcttg cagcactttg ttttgttttg tttttcatat aaaaaacagc  63540
taggactctg gaatgttaag agtggggatt ctggaatcag acttgggcaa gttacttaat  63600
ctttatgtgc ctctgtaatt attgtcttaa aatgaacata aaagtagtac ctaattcata  63660
agataaggat taaatgaatt aaaatatata aatcccttag ataacaatgc taggcatatg  63720
ttaagcacta tgttagtatc atcaaatgtt gttgttactg ttatggaatt tatcacaaat  63780
atgtaattat atgtttcgta gtgattattc atcaccccta ctggactcta aggtctgtga  63840
ggatatgtct atttggttta ccactgtatc ctcaacaact gctggttgtc cctattgtag  63900
gtgttaggta ttaagtgcat gatagtgaat acataaaggt ttactttttt aaaaaaattc  63960
aggaaaccag ataatcaaaa agaaagaaat taatcactta ataagtttca tctcccaggg  64020
ataagaaaac ataggtaaag agagattaaa ctactccttc aagttcaggc aattcagtat  64080
tctaattgaa agtgttgtgt ttccttttta agtctagttt tgcttttgtg tttatatgtc  64140
ataattaatt gtgttaaaac ataattttag aaaccgatct ttctatatcc ctcttttcta  64200
taccccccaa ttttacttca ctttcttaaa caacaataaa agtctcctgt aacataagaa  64260
agcttttctt cctaattatc ttctttaggt actttaaaaa aaatcaatca gctatcacat  64320
gttatggaca aggggaatca ctattgagtt aatatcctaa gacgttcaaa acccagaacc  64380
aaaaaaaaaa aaaaaaccac caaaaatgct gtttggagag tttcaggttt aattaaagag  64440
tttgttcagg tgtttttgct gtttggaatc attatctgag aaattatgct ataacacatg  64500
gtcatttgat tctgtttcca ttagccttct actctgggat atatggctac tacattttct  64560
ttttaataat ctgtgtttca cagtaagttt acttttgtgg aactctatta ttaaataaat  64620
cagaaatctc acttaaaatt taaaaaatta tttttctaat gaaaaattga tattacagaa  64680
ctaaattttt aaaagtttat gtacagaaag gatatagtat ttgatgttat caaaacttac  64740
atgttatgat tagttcattg accatgagta tattaattta gaaaaaaata catccctaat  64800
ttacatcatc cttaatttgt atacttgtca tgtagtgcag gggtccagtg gaaatcatag  64860
aaaggttgct gtaggtaatg agtcacaagt cacttttctc cattgatagc ttctttttct  64920
gtaaatcgaa ctatttaaaa taatttaaaa acttagatcc ttagtaaaaa gctgtttttt  64980
attggtctaa gttgactttt taaaaattta ttttccctgg ccaggtgcag tggctcatgc  65040
ctataatccc agctctttgg gaggcggagt ggggcggatc acctcaggtc aggagtttga  65100
gaccagcctg gccaacatgg taaagcccgt ctctactaaa aatacaaaaa ttagccaggt  65160
ggggtggtga atgcctgtaa tccgagctac tcaggagact gaggcacaag aatggcttga  65220
acccaggagt cggaggttgc agtgagctaa gatcgtgcca ctgcatgcca gcctgggtga  65280
cagagtgaga ctctgtcttt aaaaaaaaaa aaaaaaaaaa aaaaaggcca ggtgcggtgg  65340
ctaacgcctt gaaatccagc actttgggag gccaaagcag gcagatcact tgaggtcagg  65400
agttcgagac cagtctggcc aagatggtga aaccccatct ctactaaaaa taaaaaaatt  65460
```

-continued

```
agctgggggg tggtggtgca cacctgtagc cccagctact tggggggctg aggcacgaga  65520
atcacatgaa ccttggaggc agaggctgta atgagccgag atcgcaccac tgcacttcag  65580
cctgggtgac agactctgtc tcaaaaaaaa aaaaaaaaat tatcctccct aaaaagctat  65640
tccagtatct tttttcacat tcattagtta tattatttag tggttatatt tggttctctt  65700
gaactgtttt ctgagttttt gaaaccaatt gcacaaatac agcgcaaggg aaacatggtt  65760
tagcagtagt aggactgaaa aaaagtttta attcttgcta acctcactgt gagactgtag  65820
tattttgtac ctaacaaaaa attttccgca gtaatcttta gttaaaaaaa aacccttcta  65880
ttacagaaaa ctatatagtt gttatattgt aacttcaaat ttttgttgta ttttttattg  65940
tcatattgtt ttttctcaaa tattttcagt ccacaatttg ttgaatccat ggatgtggaa  66000
cctgtgaata cggaaggcca actgtacaaa aaagatccca gaattaataa gtaaggttta  66060
gtaagctttc gggatacaga attaatatac aatattctat tgtatttctg catcctaaca  66120
attaacaatt ggaaatcaaa aatttgtcaa ttataataac atcaaaaatg tgaactactt  66180
aggaatgaat ctgaaaaagt atgtgaaagc accgtagacc aaaaactagt aaacattgct  66240
gagtgaaatt aaagaatatc taaattagtg gagacatata aattgtttgt agatcataat  66300
gctcaatatg gttatcagtt ctcaaattgt tacatagatt gaatgctata tctatcatat  66360
tccaagcagc tttgtagaaa ctgacaagat gattctaaaa tccatatgta actataaaaa  66420
aaaaacccta gcatcagaac agtttgggaa gagggaataa atttgtacta aagcagagat  66480
attgattaga taattggata tgagtctagt atatgggaga aaagtcagat ttagagatac  66540
aaatttggga gccagaagca cagaagcact attttaaaat catgccactg aatgagttca  66600
acagtagagt acggagagga agataaaaag aaccagaaga ggatcctgga gtggccagtt  66660
tagtcagcag aaaaactagg agaatgtgtt gttctggaag acaaagaatt attcaaggag  66720
gagagaatga tcaactttgt tgatttctag gtcaaatcat atgaggtgag aggcttgccc  66780
actgaatcta gcaattttaa tgtaattgct aactgtggca agatatttgg tggaatggag  66840
aataaaaaca catatggttg tgggttccaa gagaaagtag gagaagaatt agggatgaat  66900
ataaacaact gagggaattt tgctgtgaaa gggaacagaa aaattaagcc attgttggag  66960
agagatcata ggggtcaaga taaatggtgg ggttttttttg tgttttgttt ttattggaag  67020
tagggacaat tatttgcata tatatgtttt atgctgattg gaattattca atatgtggaa  67080
aaattgatga tgcaggagag aggagaattg ctgaaacggt atttttgaat gagttagagc  67140
aggatagaga tcagtatgca gatgacacat aagtgatcca tgattttttg catctcttcc  67200
acgtatacct tttcttgatt gctctttcat gtgctttatt aatgatctta cctattggga  67260
gagtttccta aagtatctga agcatattcc atgttttcgt actagattgt cttgaagaac  67320
tgaagatcaa aaatcaaagt agccagagtt tcttgaaaag attcttaagg cagccagatt  67380
ccaaatggct aacagaacca aaatggcaaa gactattaca tacttttata atttaatatt  67440
aatatagaag tcttgttcac aaatttttct tatatttcac atgtacatct caaaaagttt  67500
ccatttcagt atttaaacaa aaaaccacac acttcaggat cttttgcttt ctaatattgt  67560
tgaataatca attcagaaga atctggccaa tctttgatgt gctagtaaaa aaaaaaccaa  67620
agctgaattt ttaattttct cacttattta cataagttga aagtgtgccc tcttgtggac  67680
tattcagtaa ttttcacata aaagcctttt ccttgtatat tgcagactaa attaattgta  67740
tatcatcaca tatgttttgg tcaaacgttg agatctagat cttaatgtta agttctttaa  67800
```

-continued aacctaaacc tcatttggaa ataaacagtc attgtttgat tttgcatttc taatacaatt 67860
gtgtatgaaa cagtctttta acagtttcaa cctatataag ggacttggag acaggctatt 67920
tcttttgcaa tataaaagaa gatgagaaat aaattttgtt ttggtgtgtt gggagtggac 67980
taggaatcca aacaattcat agacgcgctt ggaaatttcc tccgtagcct ctatgtaaaa 68040
ataaattttt aataatcaaa ttccaggaca caggactatt tttttcctga ggtagtttgt 68100
agttttgtgt agtttggtac aattaaactt tgcataacta actacaggcc tctgcaaatc 68160
catttaactg tataacaaac tgggactatt taaagttatg tgaagtttta ttaaagtcag 68220
ttcatagatg tgtatagttt tgcttattgt tttatttctc agcaaacata cacatatttt 68280
ataaactgct tttgagaaac cctaaatctc aactttattt acttagtggt aacttttctt 68340
tctctgcata atagtactca gtagtgtaaa tatatccttc taatacacgt tataaatatg 68400
tgatatagct acactattgg gacacgcata tacattattg gtatccagcg gtggctgcag 68460
agagctcagg gttccagaag caaagcaagt gtctgaagag agttttagaa ctttgcttta 68520
ttttgcattt taaaaattta ttggaagtaa tttgaaactt tagaaaagca gaaatgtttt 68580
aaagaaagtg agaattttta cagtgcagct tattgggaac tttttgtttt tgaggtagga 68640
tttgaggaag atcctttcag aagtatctta aatagcatgt gaaaaatctg ttcttgaata 68700
gcaggcaggg aaaaggaatc tgaaggtggc ttgactgaag tgaaaggatt ctgctggaga 68760
ggtgccactc tctagggact cactgaccta tttaaaatag taagtagtac cacatagatt 68820
tatttattta tttacttaac ctgtgtagct atttagcatt tatatcccac ctatttccta 68880
aaaggatttt aggtgtttta taatgttaaa tgtaatataa accaggacaa taaaaatata 68940
ctagtttaaa ctttttaaaa aattctttaa tgtgagaagg ctgagcaaag ggcaaggaga 69000
accttttcat tctcccccca gaaatcttgc tcctctttta ctaaagcttt caatcatctc 69060
tccaagtggt ggcagggcaa ttctaaggtc tgaccttagt tcttagcata gtatgttaac 69120
agatttaccc ttagttttct ggcccaccaa gactccagca gactttctgt tgcccaacag 69180
gctgggctgc agccacacta taacaaggtc tgaatctcag ccttgtgaga tgagtatgct 69240
tttccaaatt cttattttcc tcagatattt tcctccctta aacatgtgga tggtagctgt 69300
ttcctgtatt tgccattcct gtattttgta gaatcctttt tataccttct agttaaccat 69360
ttttttacta cttaataatt ctatatatta aatttttctt gctcaaaaac agtgtgtgtg 69420
tgtgtatata tatgcatgtg tctgtgtgtg tgtatatgta tatatataca cacacatata 69480
tgtacttagt tttaagcctt tcccccacca ccaaaaaaat taacattagc aaaggtgtta 69540
attagctaaa tattccacat atatgaaatt tcagtttatt caaaataatg ttataatcac 69600
acaaggtgac aatatagttt aaagaatact gacctagaga tcaaacactt atattctagt 69660
cttggctagt gaattactag ctcagagacc ttgaacagac acttatgttc tttgaagaac 69720
ttttactgtt tgctgtaggt ttatcttttt tccatagcag tgtagatgtt tctcagtttt 69780
atgtccttta ggcaaacata agaatataag atttgattag aaacacctga gttcaaatcc 69840
tatttctgct gcatgctgcc tgtttagctg tagagagagt atttacgccc tgaaacttaa 69900
tttttgcatc tgtgaaatag tgataatctt tacaatcctt tgatattgga atgattaagg 69960
aaaggaatat ataaatatct gacacataag aagtgccaaa aaaaatttcc cctacagcat 70020
tactttattt cttgcctatc tgatctatta taatgtaact gttatcaacc ctcaataagt 70080
ggcttccata actatagcta tagttcagac tacttttgtc agattgtgaa tttccaactt 70140
cctgctttag acatctccaa ctagatatta cactggcatt ttaatctgaa caagtccaaa 70200

-continued atcacaccat ggttacatgt aagtactgca gtattctaac agaactttct gcttccatcc 70260
tctgtctctt tctcccccac cctatcttcc ttatcactat taaattagtc ttaactgaaa 70320
gcttaaggat gtggaaaaag atatcaacat tatgtaagaa actcccttgc aggctccaat 70380
tgacttttct ggccatatgc tctgtctaaa gtgtttatga atataccttg catattatat 70440
tagtctttag cacctagctc agtatacttc atagaagatg cttaacatag gtaattattt 70500
aaatattcag agaaatctat gtacatatag cagcaacagg agacttacta atttttttat 70560
tttatcatag tttatattag tattttcctg aatcataaag taatattcta atcataataa 70620
aagtccaagg agtacagata gaaataccac caaaataaga attccccagc atctcagcat 70680
atacccgacc cctaatcatt gttaaaggtt taataatgtt ctttttttc atgcctagac 70740 catcattttt atgaaaatgt gttttaagca aaagtattta gcttggttga tgagcttatg 70800
atgtgcacac tgatattttc agttagcaat atatctttaa tatcttttca tgaattttaa 70860
gaatctttgc cattcttctt tattttagtg ccaatttgct gagagattaa aatatagaat 70920
catcactgta aagttggttc aggctttaat tcaatgattc tttctctttt ctccctctga 70980
aatatgtacc cccctttacc acattcttgt ggccaaactc aaattttaaa gggcagagga 71040
tgttccatct tgttaaccat tgtactttgc ttgcctagca tacatagtgt ctgacacagt 71100
aacataagat aaatattaat tggatgcctc atgaaggact aaatatttta gaaatagtat 71160
gttgtgttgg gtgccactta taactcagga ggtacttaca ggtttgaatg aactgttatg 71220
taacctgata cagcatttta aactgttaac tattaagcat agtaaaagga aaatgcttta 71280
gttatgttga agacaagatg aagcagattt ttctggaaaa caacacaaag tagagtttaa 71340
agcaatttat taaattgcta agacagattg aatagttatt atgagaaaag ttaccagaat 71400
cgtatcttac atccatcatg tatttagctc atttttagtg tattcaaaga tggagaaaat 71460
aaggggtttg tgcttggtaa gattcatttg ctaaaatgtc attgtacaaa ttttgaaaag 71520
aaaggttatg aacttaacat aaaaaatacc atggtgttta cttactcatt gtaatcttgt 71580
atccaaaact gtttttcctc aaagtgaatt ttgctttctg ctcaatagtt cagatcaaga 71640
agaaagtaag agtaattgaa gtgccataga aatgtgaatc acatactaaa tgtggttata 71700
aagtaaggat cctaactcca taaagccaga gtcaccatac ttcactgtca catggtgtag 71760
tatactgact aacagtcttt taaactggat gtttcaatca acccgtaaaa taatatttaa 71820
aaaagaatga gacatctgta taaatgaaag atttctaaga taatatacat ggcaaaagta 71880
agatgcagaa gaatatataa caaataacat ttgttgcatt taacgaacac ttagtacatg 71940
cccagcacag ttctaagaac tttacacata ttatttcatc ctcacaacaa aatttaataa 72000
taattaccta cctcatatat cagagatgag gaaactgagg tgcagagatt aaataagttg 72060
tccaaggtta tgtagtaagt gggggagctt ggattcaaac acacagccta attaatattt 72120
ttcttcttgg ctatatattt tgagtacatt gattgtgtat gcatagtaat ctctcatgga 72180
tgtaccatca tttgttatac taataatatt gttatacatt ttagctgtta gtttaagtgt 72240
ccatgtgcca gatagcctga tcttgactcc agctgtatgg ccttaggcaa attatttatc 72300
ttctctgtac atcacattct tcatcaaata gaactgtaat attagcacct caggttcata 72360
tgaggattaa atgaggatta aatttattac atagtaagtg ctgagcaaac atgagttacc 72420
atttctattt tttaatcact aaaagtaaaa atattgtggg aatatctaca tgtgtatgtt 72480
aacatgtata tgattatttc tttaggatat atttctaaaa gtgaaattgt tgagaaaaaa 72540

-continued

```
tgatgcattt ttttaaggct ttggttatag ggtgcaaagt ggcccgccag aaagtttatc  72600
taccatcaga taataagaat gccttttatt ccaaatctgt cccaatttta gtagtattat  72660
aatccctact gatactgttt tatttgcact tcttttgttt gcttgaggaa gttgtaaatt  72720
ttgttgtgaa attaaatgaa gaagtggagt ctttaaaaat cttggcaaat gcttaaaagt  72780
tcccttcaga ctcattagaa tggactaaat tgataattta ctataatatc ttcccctaat  72840
taagcattct tttaattaaa cctcaagcca ttcttaaatt tagtttataa atgatttctc  72900
aatgtatttt gttcgattta gttcttagta ttacaacagt taaatttttt tctgctttct  72960
gtcgccagta tttatttctc ctaccttatg atttaaataa ttgtaggtga gcaggcccaa  73020
gactatgact tttaatactg tggtgaaata tatactggaa tgccaaataa ttatttataa  73080
tagatctttt agaagtagga attatttgta ttgaaaagat gcctttccct ctatttgttt  73140
tgaaaagact cctgttcttc atctgttctc ccgaatctgt ttagtaatgc tgttaacttt  73200
ctggatcact tactatgtgc caggtggtat gtcaaatgat atatgtgcat tattttattt  73260
tattctcatc accacttaga ggtgggctac tttcctcact cttccatttt ttcaaatcag  73320
caactctcag atggctttgc ctggtttaaa atttacccac aattttaaag acattttacc  73380
tgaactcaca aagcactgtg cagtatactc ttatagttct attccctcca tccctttcag  73440
tgttcaaccc actaaattta ttttataatc tactaatcag tcaccaatca cagattgtaa  73500
agcactacct taagtgacag ttttaaagcc ctcattaaaa tcttctttac agtttggttg  73560
cagtttcatt ctagacacat gtcagcttca gttttacgaa aaacaatata ctttcacaga  73620
gccaagcagt ccaaaacatt attcaatcca gagccaaaaa tgtcatagct agttagttag  73680
ggttgtgttt gttcatgttt agaatcctag gaacgctatt tcttgatgga ccctggtcac  73740
cttccaacat aaagtagcaa catttccaca gattacttac atttattaaa agctgtgact  73800
ttagctaaaa ttgtaacctc atttctacca aattcctctg ctgttcttca aaatcttgga  73860
ttccagtgga attagccata gttcagcagt gaagatcaaa tatttttgtc agtaatcatc  73920
aacgtgtaat taaagcactt taaaccaagt aagtattgtt gctctcccgc cctttcccct  73980
ttactcccag tgtttacttg acatcatttc agtgcatttt tatgtcactg tgaaaagcac  74040
aatcttgtgg ttaggtttat taatcttcta gttcatacat gggtaactaa atacatagtc  74100
atttttaggc taaaaatcct agcctggggt tggatctgct ctatttgtta ctcacctggg  74160
acttaagaaa acagtcaggt agcccacagt agaatcctct agcatattac tctctttagg  74220
ttcctattct ctgagttaaa taattaaata cagtcatttg ttacttaatc tgcttgaata  74280
tggcagtgta cgtgtacaac agtgagttgt atatgaataa caagatattt ttgtgatctg  74340
taattttcat tcaatggttt ctttccatta attactgagc ataagttgga actttcttat  74400
tagcataaat ttaggaaaaa ttcattgtgt tttggtgacc tttatcagat tttaaattcc  74460
aaccaacttt ttaaagtgct tgatgtgact actaactatg cagtgttgca ttaaatttct  74520
ttagtaattg ttaaataatc aaattaataa tttcaaagag tagaaattag taatttcaca  74580
gtgtagcaaa tggacaaata tagaatagct agtagtgatt atagctttcc tatattattt  74640
cctgtgcctt ttcctttcag tgggcttctg ctagaaattt tgtcagtcat tcaccaaagg  74700
aaagtaatgt tttttccctt agctggcaat tagtaaagaa tgtacatata aaggtcttta  74760
aactgtaaag aaaaaagagg aaatgattac cacaaagaca agatagttaa taccccctaga  74820
aggaaccaga atgctagcct tttggatgat gattctatgg atgcttactt tataactctg  74880
ttaaactgtg tgtgtgtgtg tgtgtgtgtg tgtgtgtgtg tgcgcgcgcg cgcgcgcgcg  74940
```

-continued

```
catgtgtgtg tgtagcagtt taatgtacct ttgtgcaata ggtcttatat ttataataat  75000
aatgtttggg gtgaaggaaa ttcttagttt taactacccg tataattata cgttaaataa  75060
ttctatttgc aatgttgcat tcagacataa tgagtaaggg aaattatcag tattatgtca  75120
tttgaatgtt tgacgtttac aactcaaaaa cttaagaggt tctcttaaaa gtgactgact  75180
agcaaataca accttaaaaa gataaatatt taagtttttt aaactggaaa ttacaattcc  75240
gtttttaatc ttagctctat ggtttagttg atgtagactt ccatttgctg attaatttat  75300
aaagtaaaag tcacttaatg agagcatatc tttgattaat gcgtacattg ttaaaatatt  75360
atctacttac aaaaaaggac ttaccaagta ctgttaaagg aaagataaat gttttacaag  75420
ccatatgttg aaaataagag aaaaatttgg gggcttggaa cagaataaca aagtgttcag  75480
ttttacagaa tgtcttcata tatttttctg tgtgtgaaga gagagagaat tccatcatga  75540
taaatactga acattaaagt caattaagtc atttgtatgg ggaacattaa aaatgttaac  75600
acgtctttgt cctttatgtg gttgcatatt gattatgtga cttgtaagaa acatgtagtg  75660
atagttggaa agacaagcta agtacatgaa cattaagtaa tcgtgcaaga ttgaaacaag  75720
acaagtttca aaagatgtca caaaggaata tataattatt taccaaaata atattgggca  75780
ataaatgtca taagttcaga gtagattaag atactcattt ggatgaattt gaggtttcat  75840
gaaatcgtgg gaacgtgctt tggatcttga agaattatag gatttgtttg gaccaaagta  75900
ggaatgggct tcctaggtag gaagaatgtc ttaaggaaat gtataaagat gggaatacac  75960
aagggagatt tgggagaatc tgattagatc aggttggttg gagagggtgg tttatatagg  76020
ataatgataa aagacacagc tagaaaggca agttgaagct agattatgag gttaaatgtt  76080
taacgtgctt ataatgtgga aatgaattgc agtgcttgtc gaggttgatc aagtattcct  76140
ttctagcaat ccagcctagc agttaagaaa caaactctgg aaccagattg ctttggttct  76200
aattcttgct ccactagtta ctttaaactc actgtaaatt aatttcctct tagtaaaatg  76260
caaaaaacaa tagtagctac tgtactgggt tgttgtgaga actgaattaa tgtgtgcaaa  76320
gcactttgca attgcttaac atgtaataag tggtatgtga aaatgattat tatataggtt  76380
gaacaaacca aagcagtaac ttttttttat agtgattaag cattttcctg atagtaatat  76440
atctgacata tctctacaaa taattgtctg ttttgtgtgt tgcagtgttt gggaaatggg  76500
aagtaatgac agctggcacc tgaactaagt acttttatag gcaacaccat tccagaaatt  76560
caggatgaat ggggatatgc cccatgtccc cattactact cttgcgggga ttgctagtct  76620
cacagaccgt aagtttggtt aatttatcta atttaagttc tactgtgtgt taacaataat  76680
ttttacagtg actgttctaa aaattattat aggttcttta aaacacattt acagaaatag  76740
caactgaaac tgccctttaa agaaaaaaaa aattgatagc ctaatttatc taacttctta  76800
gtgatgttta ttttggttgt catgttcagt aatctgttgg agcttgttgg aggtatcagc  76860
agcctatttt actctaagga cttaagaatt ttaaagaaca ttgccagtct tttgagattt  76920
atttaatgta actcaatttt tcagagattt attcttttgt taggcatttg taactataat  76980
tcttagtcct tgaataatga tacaaaaagc tacctacaat tttagttact gtgtcatcct  77040
acctgaataa ataaaaggaa aaagatatga gagggaaggg tagaaagtga gaggatggca  77100
tacttttctt tggatagcat tatgcaagat ttgggacttc ataataaggg agctaggaga  77160
aagtatcttc aagaaatgtt tttgtccatg ttcagtatcc tccaaataca acttttctgg  77220
cttttgtttt gttttgtgaa tttccagttg gttttagtgg ggtaaaatag ataacagcct  77280
```

-continued

```
gttagctttg agcttaggaa ataagcgtaa ctagtttatg aggtctaaat taacaggaga  77340
gtgctgtagg tgattgggtc agcattactc aggtaagaaa actttttgaa actggcatta  77400
gtttttatta tcactttgtt gtaggtaagg cataaatagg agttcaaaat cagatatact  77460
gtcaggaatt tctttttggt ttttctcccc atgatctttg ctatacctaa atattttgtc  77520
tttccaggaa gccctgttca ttaagtaata atttattttc tgtgttttta ttaatgagaa  77580
tcctgttggt acctattgag gctgagcacc atgataatta tactgtatag gtgattagaa  77640
attaagccaa aaacaaagac acctgatatt ttagtgagct ttcttaacct ttagacaaat  77700
gaacaaattt gttaggtgaa cagagattaa acggctgaat ttaagctact ataaaacatt  77760
tatgttcttt tgtttgctat tagaagagaa taagtaggag acaactagga atttggaatt  77820
tagaagaata ttttaatatt cttacagaat tctatgctat gaatgctttc ttgctaaagt  77880
gaggtattta tttgtatatt cttaagcttt taaaaaacgt tacttgtcta ctttatgaag  77940
agtcagatat tgttatttgt ttgtatgagc gtactattga ttctgaaaaa tcttataaac  78000
aagaacaaat gagattaatg aattgctaca ttggaagtta gtttgtaacc atgccttttt  78060
cgctagtcat ttgttaataa aatttaagaa atgaaaagca aggatgaata taagggagct  78120
gaattttatt cctagagact agtataatct attatggtcc aagtgatgtt ttggaagttt  78180
tgtagggttg attgaggttt gttaggaaga ggaggaatgc cttttaataa tttgtcacat  78240
tgatatttat aacttacttt taatcccaaa atacagataa gcactaaaga gacttctata  78300
gtcactcaat ttctaataat ctgattttat tccaaatagt cctgaaccag ctgcctcttc  78360
catctccttt acctgctaca actacaaaga gccttctctt taatgcacga atagcagaag  78420
aggtgaactg ccttttggct tgtagggatg acaatttggt ttcacagctt gtccatagcc  78480
tcaaccaggt atcaacagat cacatgtaag tatgatcaat tttatatcta ctataagtga  78540
aaagttttgg ccttactaag agaatccgta ttcctggttt tatttcagaa atttttagat  78600
acatagttta ttttttaaaa atatccatat ccgagggaga atatagtctt attgcaataa  78660
tagattaatg agatttaagt aggcaatatt tatttttaga taataattct gacccatgta  78720
gctctatgga tattttttca gctcttttga acttatcttg ggggatccat catttgtgca  78780
gagatctggt catgaaacta tatccctgtc tgggcgcggt ggcttacacc tgtaatccca  78840
gcactttggg aggccgaggc aggtggatca cgagatcaag agattgagac catcctggcc  78900
aacatggtga aaccccatct ctactaaaaa tacaaaaaaa aaaaaaaaat tagccaggcg  78960
tggtggcggg cgcctgtagt cccagctact cgggaggctg aggcaggaga atcacttgaa  79020
cccgggaggc agaggttgca gtgagccgag atcacgccac tgcactccag cctggcaaca  79080
gagtaagact ccgtctgggg aaaaaaaaaa ttatttttca ctgcaaaacc aatacatatt  79140
tatacaaaca acacaaaaat gtgtaaaaag taaaatctct cattcttatc ccttcatatt  79200
ccaccacaca atgttactca tgtaacctcg cattctttat ttttttaatt taaaaattca  79260
tcatgtaggg gaatgaggat aaacacatta taatggagag atatctacat tagatgcggt  79320
acatattttt ggggcatttt taaagctgat gactctaagg tgagatactt actaaatgga  79380
ttttctaatg gagaagctaa gaaatgattg gttaaaatca gaaagaagta taatactact  79440
aatattttgt cactccaaaa attcagcaat atctaaatca cttctttttt tttttttttt  79500
tttttttttt gagatggagt cttgctctgt tgcccaggct ggagtgcagt ggtgcgatct  79560
cggctcactg caacctccac ctcctgggtt caagtgattg ttctgtctca acctcctgag  79620
tagctgggat tacaggcccc caccaccatg cctggctaat tttgtattt ttagtagaga  79680
```

-continued

```
caggttttca ccatattggc caggctggtc tcaaattccc gacttcaggt gatccaccca  79740
cctcggcctc ccaaagtgct aggattatag gtgtgagcca ctgtgcccag cctctaaatc  79800
acttcttatg cttgtacata cttattcagt agttttcacc aaatatttaa agatgtaaag  79860
gaaatagcac acgtaaaata aggacttatt ttatggagag ctcctgtaag attgccctgg  79920
aaatgtagtg agtcttatca ttggacacca tctttatagg tcttcatggt tagatccaat  79980
gagtagaaca ttgacatgta taatataaag ttaaaacact gcctatactt aattttatca  80040
tcatctccca tggttatgaa tttaatttgc tacttatatt gaagtttatt gaaaattgct  80100
gctgtgaagt gtattgaaat ttgctgtttg gtttccgctt ttcccgcacc atgacattat  80160
ttgagaaagc aatgtaagat ggaaaaatta cataacctct gggtcttgtc ttaatcagtg  80220
tggcaacagt atcttatttg taagacattc ccagaaagtc agactcactc atattcaggt  80280
gtaagaaaat atattccaat accaaatatc aactttttgt gtaactttca cttgtctacc  80340
cttccattat tttgaatagt ttagaataga atgtatttct tttctatttt agaactactt  80400
ggaaattatt aaactcatag ttcaataaaa tagtgttttg ggcttttttt ctcttgactg  80460
tgtaaagtaa aatgaagaaa aagattgtcc ttagaagaat ccctctctgt tatttttgat  80520
aattatattt ctcccaggga tagcatattt gaaaattcat aactgttggg tcagccacag  80580
tggctcacac ctgtaatccc agcactttgg gaggccgagg cgggcagacc atctgaggtc  80640
aggagttaga gaccagcctg gccaacatgg tgaaaccctg tctctactaa aaatacaaaa  80700
attagctggg cgtggtggca ggcacctgta atcccagcta ctcgggaggc tgaggcaaga  80760
gaatcacttg aacctgggag acggaggttg cagtgagctg agattgtacc attgcactcc  80820
agcctggggg acaagagtga gacttcgtct caaaaaaaaa aaaaaaaaat tcatattgtt  80880
ggccatacca gtgtgattta cttttatatg ataagtcttc ttaagaatca gtcaccattt  80940
taatttttga tacttatttt ctcaatgcca gagagttgaa agataacctt ggcagtgatg  81000
acccagaagg tgacatacca gtcttgttgc aggccgtcct ggcaaggagt cctaatgttt  81060
tcagggagaa aagcatgcag aacagatatg tacaaagtgg tgagtttctt aataactgaa  81120
ttcccatatc aaacttgttt tatacatatt taaatccagg tgtcttcttt aacaagctgg  81180
cctatcagga atgcgatgtt tatgccttca gtcaagccaa gaacaagaag gaaactaaac  81240
tgataagatt cttgtagttt aatatgtaac taaattcctt gagaattaga caaagcttta  81300
agtgtatttt gttaaatatg ttggaatata tcagtttact cagcttaaaa atttttttgt  81360
tttagaaaat cagaattaat ttgaaataag tctttcatta attaaataaa tatttgcaaa  81420
gcttttgaac atgtacattg tagcaggtat atagagtttt aatactgatt gtgattatat  81480
tcatggtttt ctagtaattg atttaatact cctgttgcct tagcaacaga aaaattggtt  81540
aagtattatt attaaagaaa aattgattca tggtattata aaataataaa aatattacat  81600
ccaacacaga tataattttt atgtagtcat ggagtacctt tgggttaaga gcattgttct  81660
gttcaagctt actgaatttg acaagcccaa gtgcctgttt ggctctcaag attaaaatag  81720
ggcaggaata gcttggacaa cttcagaaag ttcaactttg ttaattaaat aattgtattt  81780
aagaatttta tcagccgggc atggtgactc acgcctgtaa tcccagcact tttggaagct  81840
gaggcaggtg gattgcctca ggccaggagt taagaccagc ctgggcaaca tggtgaaaac  81900
ctgtctctac aaaaaaatac aacaactagc caggcattat ggtgtgcgcc tgtagtccca  81960
gctacttggg aggttgaagt gggaagatcg cttgagctca ggaggtcaag gctgcagtga  82020
```

-continued

```
gctgagattg caccactgcc ttccagcctg ggcgacagag cgagaccctg tctccaaaca  82080
aaaagaaaaa ataaataaaa taattttgcc aaattcattt tggttttggt ttactttgtt  82140
ggcagcactt ccatgatgct tcccattctg tttcctttaa ataatattgc tttgctgatt  82200
ctgtgtactt gtgttgtttg aatggtattt tgaaagcaat tgcatagtta ctattgattc  82260
ctcaaaatgc ataatgggga tgcttctgac cgacttgcct tttagcaagt tgaaggtagg  82320
tatgcacgac agggctctga cttcaccaga actaataagt tagattgcaa tagtaggaga  82380
cagatataaa taatgaagga agctagagtt atgacggctt tctggaaaaa tgttggaatt  82440
gaaagaaaat gtggaaagag agttgagtgg aagaaagact aatagagtag gagtattagt  82500
tttatgagaa tgtgagtaaa tctaatattg gataaatgaa tctaaggcta ctaatactac  82560
atttttgcaa cttacgtttt tgagtatttg ggtagtaaat cactctgata aaaactttta  82620
gagtgttcac ctctcagtca catattttgt gttttatact acatatactt gtttttttagt  82680
ccaaaatatt gtttgatttc tgtataccct actttgtaaa agcataaact agcatttaaa  82740
attaatcaat taattgcatg ttattttttt ttttaaagca ttttcctggt gatatatggc  82800
tttgaaattt taaaagttgg ctgggcgtgg tggctcacgc ctgtaatcct ggcacttggg  82860
aggccaaggt aggaggattg cttgagccca ggagttcaag accagcctgg gcaatgcaga  82920
gagaccctgt ctcattgaaa aataaaaaat aaaaataaaa tagaaattta aaaagttgat  82980
tttggggttg gtaagtttaa atatgagtca tgcatgtgga gaaaattgta ataaaatgca  83040
aatcacttta atcatagttc tttggaactt agaattaatt gaaaaggact gttagaattt  83100
catttacccg ttttatttag aaagccattg ctttcaaact agtaattcca gtttgtccca  83160
gtgatggctg ttaattcagg ggggaaaagc tttttaactc ctgtctcatt gagtgttcat  83220
ctccctccaa aagaaaaaga aaaaaaaaaa aacctccagc aacaataatt atagtaatta  83280
agctattaaa gctatggagc aaaacaattc tgtgctgagt ttgagttgga aaagaaaagt  83340
cagaagttga aatttagact acatacttaa gaaaacaccc ttcaatggta gacttagagg  83400
cgattttgaa acctaatttc attcagctac aatctctttt gtagtactct tagcaaatca  83460
acttctgttt gaatatttct agtgaaagcc actttttata acaacagcag gaaatgaaat  83520
ttggaaatac aatttgatgc ttgcagctgc caaaaaaagag attggctata gaaatcataa  83580
gaaaattcag ggtgttattt gtagattttt atctgatttt gaaatgtcta aataagtgaa  83640
tttttctgtg tctcccatat aatgaaatgt catgtgaata attgagaaat aatgtctagc  83700
ttggaaataa atgtaagaac cagaatgctc ttcacaggtt tttatttttt aataaaatat  83760
tccgttaatc cctactatgt gacaaagagt tattgtgaaa gaaggaatag gtacattctg  83820
ttttgcttca gaagacattc aggtggaaat tgcaggaatt caaactttcg gcccataaat  83880
aaagtacttt tcaaaacctg tgtctgaacc atgataatac aaatagcttt gtgaaattaa  83940
gttcccaagc atgagagatg tatatgataa aatattcatg taataaaaac taccctgagt  84000
cccgttgtag aaggaagtgt attgtgttag gtgcgaggtt agataagaca acttttaaaa  84060
aaatcttttc aattctaagg ctaaataata gaatattgag taagcaagta aattttttta  84120
aaatattata atctctgttt ctagtcctgg attagtttta tggaaaatgg tgttgtaata  84180
aaattgttct tgaaatttac agttttacag cgtctatatt ttgctctttg aaatgaaaac  84240
attgatcaaa aaaatctctg gaatgtttga aagaataact gatttcagtt atttaaagga  84300
cactttactg ttagaagaaa ataacgttct gtatttttgt gttttgcata ggaatgatga  84360
tgtctcagta taaactttct cagaattcca tgcacagtag tcctgcatct tccaattatc  84420
```

-continued

```
aacaaaccac tatctcacat agcccctcca ggtaatatat gtatatatcg tttattaaat  84480
attgtcttgt atggtgaata tgctggtgaa tatatggttc atacatttag gtaatggtgg  84540
attatttaga gtttaaatag ttgaaatact taaatagtaa tccactttgc atttgcctta  84600
aaatgttgta tatggaaata gtctgatatg ctaattgaag tagctaccat cttagtaatg  84660
taatttcata cagacaaaaa atgttaaaat aactaatgtg tttgagataa gaagatttac  84720
ggagcatggc tttaagtacc ttaaacagat tggtactttt atataagtaa acaaattacc  84780
tgtttttaaa aactttttta ttgtaactct ttgattatga attgtgaaca atttttgtat  84840
gttatttgac tattttgcaa gattcttctg tttgcataga ttttacatat ataaactaag  84900
agatcagagg actttgtgac agtcagattt caaggaatag cgtgtttatt ttatttcctt  84960
atattttttt atttgggttt tgggttttag ccggtttgtg ccaccacaga caagctctgg  85020
gaacagattt atgccacagc aaaatagccc agtgcctagt ccatacgccc cacaaagccc  85080
tgcaggatac atgccatatt cccatccttc aagttacaca acacatccac agatgcaaca  85140
aggtaagaaa gttgtttgta acttcactgg gaatgtctaa gtgctttaat tccaagcaaa  85200
tttgtttttt aaaatataat tattaaacac aaactaaaat actatactgt atacttgtca  85260
gtaaaccttt ttaaagatat ggcttaaatc attaaaacaa tgttacactt accatttgaa  85320
aatttgtcat tttaggaggt gaaaggagca gtgtcatttt ggctttttgg attcagttat  85380
tatataacta agtatattta ggtgtgaaat taagaagaac tgcgttttta aaaattgctc  85440
cttcttctta cattagcact aagccaaggg acaattacat tttaattggt aaagtagata  85500
cagtcagcct ttcacataca tggtttctgc atcatggatt caaccaaaca cggagtgaaa  85560
atatttggaa aaaaaattga gtctgtagtg aacacgtaca gacatgtttt cttgtcgtta  85620
ttacataaac aatatagtat agcaactgtt tacatagcac ttacattgta taggcattgt  85680
aagtaatcta gagatgattt aaagtactgt atagtgcata gggctatatg caagtactat  85740
gcattttata tcagggactt ttaagcattt gcagattttg gtatccacag aaggtattgg  85800
aaccaatccc tcatggatac tgagggatga ctactatgaa aaatttacta tactgtaata  85860
atttgtagta aaaatttact gtagtacagt aaaggaaaat taatcttaga tgcaaaaatt  85920
tgagattaaa ttaccagttc ttacttgatt actagttctt aatgtcataa tgttgatatt  85980
atgatgtctt tttaaggtta tattgcctgg agatatattt catggttact aaataattga  86040
tttattatta gtataaattg tatgttttaa agaaattttt taaagcagaa aagtgcaaag  86100
gataatataa aaaacatctt tatttttgtc ctccttaatt aacagcaaat tttaaaaact  86160
tgctttcagt cactagtttc tacatgtgta ttcttgttta ttatgcatga agttgaaact  86220
ttattcatta ataaacttat taatgtataa acttttaact ttgtcatcca tcaaaacagc  86280
taactctggt ttcccaaaac cagattatga aatattaggt tgagcttttt tacacacgaa  86340
ctcaaggaga aactgggaag caaatttgac acatttgaaa tagacacagc caggtgtggt  86400
ggtatgcact tgtaatccca gcactgtagg aggctggggc agaggaatca tttgagccca  86460
ggagctcaag accagcctgc gcaacatagt gggaccctgt ctctacaaaa aaaaaaaaaa  86520
ttagccaggc atggtggcat ttacttgtag tcccagctac tcaggaggat ggcttgaacc  86580
cagaaggtca agactgcagt gagtcatgat cacaccattg cagtccagcc tgggtgacag  86640
attgagacct atctcaaaga aaagaaatag acacttagaa aattactgaa ttgagtgtga  86700
gtgccaaaca tacatatcta tgtgtatatg tagattctta atatatgtaa aatactatta  86760
```

-continued

```
tactcaagta cacaaaagtc tgagggacat tttacatgta atggaggaaa aatgtcaaaa  86820
gagcacatcc atatacacat gaatgtgtgt aaaacagaat gtaaatttta tctctaagaa  86880
atgtgatgtg ttttcacaaa attaacttag gtttttaatg tagtttgagg acctattcag  86940
tattgtgtca tttcttagaa atgctcagat aaagaactaa aaaccatact cagggattag  87000
cctcacccag atattaaagt tattctaaat aaaaaaattt agtcagtact acccaaaaca  87060
gtttctatat tcaacgtaat ccctatcaaa ataccaatga cattcttcac ataaacagaa  87120
aaaatttata tggaaccaaa aaagacccca aatttccaaa gcaatcctga ggaaaaagaa  87180
aaaagctgga ggcatcacac tacctgactt aaaaatacat tacaaagctg tagtaaccaa  87240
atcagcttga tactagcata aaaacacata gaccaatccc agaatagaga atccagatat  87300
aaatacagat atttacaggc aacttacttt tgacaaaggc accaagaaca taaaatgagg  87360
aaaggacagt ctcttcaata aataatgctg tgaaaaataa actcaaaatg gattaaatac  87420
ttaaatctga gacatgaaac tactagaaga aaacattgaa gaaacactcc aggatgttgg  87480
tctgtgcaaa atactttctg tttaagattt caaaatatag gcaaccaaag gaagaaatag  87540
acaaatggga ttacgtcaag ctaaaaagct tctgtacagc aaaagaaaca atcaacaaaa  87600
tgaagagaca acctacagaa tgggagaaaa tatttgcaaa ctatctgttt gacaagtgat  87660
taataactag aatatcagga atatataagg aactcaatag caaaacaata acaacagaaa  87720
ctgattaaaa gccaaaagat gtgagtagac attctcaaat gaagacatca atggccagca  87780
gatacagcaa aaaatgccga acatcactca tcatcagaga aatacaaaca aaaagcacag  87840
tgaaatatta tcttgcctta attaaaatgg ccttttcaa aaagacaggt aatagtgaat  87900
actggtgagg atgtgaagaa aagggaatcc tcatatactg ttggtgggaa tgtaaattag  87960
tacagccttt atggaacact gtatggtggt ttctcagaat actaaaaata gagctgctgt  88020
atgatccagc aattccacta gtaggtatgt atccaaaaga aagggaatca gtatactgaa  88080
gagatgcacg cccatgttta ttgcagtact attcacaaaa tagccaaaat atggaatcaa  88140
cctaagtccc ccatcagtgg atgaatagag aaaaggtgta tgtatacaca atggaatatt  88200
actcagccat aaaaaagaat aaagtcctgt cattttcagc aacatagagg gaactagagg  88260
tcattatgtt aagtgaaata agcaaaacac agacaaatat tatatgttct cactcatatg  88320
tggcaattaa agtggatttt aagaagatag agaatagatt ggtggttacc agaggctggg  88380
aagggtagag gagggaggtg ttgaagagag cttgattaat ggggacaaat atactgtctg  88440
ataggagaaa taacacacag tgtttaatag ctcagtaggg tgactgtagt tgacagcaat  88500
ctattttata tttcaaaata gctggaagaa gataatttga atgtttttac catacagaaa  88560
agacaaatat taaggtggtg gatatctgaa ttacactgat gcaatcttta caaattatat  88620
gaatgtattt atcacatgta tcccagaaat acgtgcctct attatctgtc aataataaaa  88680
cataatttta tttgaaaaag aaaaaagtct ggcagggaaa aagtggatag gtcagtagga  88740
cagagagaat gcagacgtga gacagtttag actattgaga aaggttgcat ttttttttcaa  88800
ctttatatta caaaaattta accatgcaga aaagttctaa gattagcaca atgaacccct  88860
tcaccaacag gtatcctgcc actttgtcct taagtacatc tgctaagaat attctcctat  88920
ataaaaaatt aaggtcagtt ctgtggtatc atctaatatc cagaatacat ttgactttta  88980
ccaatccagt tgtcctaaat atatttttaa tatcttttca aagcatgttc aaatctagct  89040
tttcacacat tgcatttgat ttttacatct cttatggagg ctcttttaat ctaaagcaat  89100
cttacacctt tttcacccca tgacactaat ttttggtttt tgaagagttt ggctactttt  89160
```

-continued gttgtagaat atttcatatt ctaaactcca ctcttttctg ctggtgttgt ttaatttgtt 89220
ttctgtattt cctatcaagt agaaattagc tttaaggttt tactagtttc cagttacaca 89280
tttttggcaa gagtacttgg taagcagtgt tgtgcacttt acattgtatc ttatcattat 89340
cataaaatgg tctcagtatc agtggtgttt aggtggtgaa cctctcttta ttgtaaaagt 89400
acatattttt ccctttgcaa ttagtaaata atctgtggga tgatactttg agatcatgta 89460
aatatacaat ttcccattaa tcttttactt aaagggggta gcattcagtg aatctcattt 89520
tatcagtttt tacaaagtca ttggaaaaac gatgattttt taaaatttta tcattctaaa 89580
gattacattt taaaatcagc atataagaat ggattgttta ataaatgatg ttggtgattg 89640
tctaggtatt ttgcaatttt agctggattc ctggatcact gaaagcaaaa gtgttctaga 89700
ttaataagct gtttgtattt tttaagtcat aaaattataa gaaaaacgtg ggcgaatttt 89760
tggtattcta agagttgaga aggcattatt tctaagcaga ccgaaaacct cgattgtaga 89820
aatgagaaaa aaagattaat tataaatttg tatataagag aacataaata tataaattac 89880
ataaatataa aacaaatatg gggatatat gcaacattta ttataaacac aaagtattga 89940
tttaatatac cgaaatctca tacagatcga taagaacaag acaaaaatga actaaagaag 90000
taaacaggca atttactgga aaagaatagc caagtcgata cagaaagatt taataaatat 90060
atgaaattgt ggtcacctta gctcatagag atgcattcaa aattaagatg aaataaaatt 90120
ttatatcaga ttgataaaca tttcagtctt catagtgata taaattggtg caactttttt 90180
agagaaccgt gtgtttgaca gtatctatca tataatttaa aattcatata cctcactcag 90240
tagtccaaaa tctacctccc ttaaaagaag gggaaaggga taaaaacata ctcagactgt 90300
tctaacaagt tctaccaaac attaaatgaa gagatatgct aatcttaatc cattccagaa 90360
aaaagaaaaa cagcaacact ttcttaactc tttttataaa gttaaattac aatctggata 90420
ccaaaatcag gtgaagtgag gggagtatga gaaaggaaaa ttataaatca gtcatcacat 90480
atgaacattc atgtcctgtt cccgaattga aacaaaatgt ttctaatttt ttctaccact 90540
aggtaagatt aaatcaatct ctttttcttt tttccataca gatggggtct tgctgtattg 90600
cacaggctag actcaaactc ctgggcttaa gtgatcctta agccttaagg tgaaacaaat 90660
tttttaaaca aatattaaga aaccaggcca ggcatgattg ctcactcttg taatcctatc 90720
actttgggag gccagaacgg gcagattgct tgaagcttag gaactcaaga ccagcctggg 90780
caacatggtg aaactccatc tctctccaca aaaaattagc caggcaaggt ggtgtgtgcc 90840
tgtagtccca gctatttgga ggctgaggtg ggaggatggc ttgagcctgg gaggcagagg 90900
ttgcagtgag ctgagatcac gccactgcac tctagcctgg acaacagagt gagactctgt 90960
ctcaaaaaaa aaaaaaaaac aaaaaacaaa aaacgaataa gcagtgttat caacctatat 91020
gacaaaattg gatatatata tgaattgatt agtagaagac aattaatata attcagatta 91080
tgggcctggg gtcctgtgag ccttttaata ggtctcaaaa gagcattcag aaagattcaa 91140
cttccattca tgacatttaa aacttttcac tgaataaaaa tacattaagc actttgggag 91200
gctgagactg gtggatcacg aggtcagcag attgagacca tcctcgctaa cacagtgaaa 91260
cccgtgtgta ctaaaaatac aaaaaaatta gctaggcgta gtggcaggcg cctgtagtcc 91320
cagctactcc gaaggctgag gcaggagaat ggggttagcc tgggaggcgg agcttgcagt 91380
gagccgagat cgcctgggca actgagcaag actccgtctc aaaaaaaaaa gaagaaaaat 91440
acattaagct gggtgtgatg gtgcacatct gtagtcccag ctactcaagt ggccaaggca 91500

-continued

```
ggaggatcac ttaagcccag gagtttaagt ctagcctgtg caatacagca agaccccatc  91560
tgtatggaaa aaaaaggaga agaggttgat ttaatgttac ctagtggtag aaaaaattag  91620
aaacattttg tttcaattca ggaacaggcc atgaatgcct ataatgacat ttatttagtg  91680
ggtgtcccag ccaatacagg aagataagaa gcgttaaact atgtataatt attggtaagg  91740
aagaaaaaag tgtcattttc aggtgacata attgtcttca tagaaaatcc aagataagct  91800
acagacaaga tactagaatt aataaaagca ttccacttag ttactggaca cagcatcatt  91860
ataatgaaat caattgcatt tttatataca gaaataagca gttataatct tttttgatag  91920
cattaacagt ttaaaagagc accacaagat acctaggaat aaatttaatg aaagatgtaa  91980
aagactttg tggagcaaat tacaaaactt ttgaaagaga tagaagaaaa gaaaatgaag  92040
agttatgcca tcttcatgga taggaagact caatagggta aagattatta ttacacccgt  92100
atctataaat tcagtataac actgataaaa aatctcaagg aaggtttttg tggaatttaa  92160
cctgcttcta aaaattcata tagaagttgt tcaagaatag acaaaataat aaggaatgaa  92220
gtgtagcagc tcagtctaac aacagtcaag atttattgta atattggtgc agacatggaa  92280
aaataacata tagtgaagta gaacatgatg aagagcttag gaacataccc atggacaaat  92340
gtaaacttgg tccatatggc attatatctt aatgggggaa agaatgattt ctttaattaa  92400
tgatgcagtt gttcatatgg aaacaagtaa cattggatcc ctatctcaca cttaaaaata  92460
agttttacat gggttaaaga cctaactgaa aaaccaaaac tgtaaggctt ttagaagata  92520
caggaggctg tctttttatg actttgtgta aaggagggga tctgaatggc cagtacacaa  92580
gagaagatgc ttggcttcac tagtaatcaa ggaaatccaa agtaaagtga ctgtcagaaa  92640
catttcctac ccttagaatg ataaaaatta ttggcaagga tatagaacag tgggaactct  92700
catacgctac caatgaatac aaatggtcat aagtaatctg ttatttagta aggttaaaat  92760
atgcatatct ggcaatttca ctcctaggta ttggcaccta gagctcttac acatttataa  92820
aaacagtcct tatgtacaag aacatacatt gcagcattgt ttatggcagc aagcatttta  92880
agcgatttga acatccacat aagaatgaac aaataaatag tgtacatcat acagcagagt  92940
atgtgtaatt atttaaaata aatgaattta caccaggcac agtggctcac atctacctgt  93000
aatcccagtg ctttgggagg ctaaggcaga aggatcattt gaagccagga gtttgagagc  93060
agcctgggca acatagcaag accccatctc taccaaaaaa agaaaaagcc agatgtggtg  93120
gcagtttcct gtagtcctag ctactcagaa ggctaaggca agaggatcac ttgaacccag  93180
gagtttgagg ttacagtgag ctatgatcat gccagtgaac tccagtctag gtaacagagc  93240
tgtctgtaaa aaaaataaat aaataaaaga atttaaaact atatatatat atatatataa  93300
aatctcagta taatattaaa tggaaaaaca agttatataa ggatagatac atatatcatc  93360
tatataaaat tataatgtaa aaacaacaca atgaattact taggaatata ttcatgcata  93420
gcaaaggtat aaagataaca cataggcaga ataaactcag atcaaaatag tggttacctc  93480
tagggagtaa aaggaaagga atagaggaga gaaataacag ataaatggag atcttcaact  93540
atatttgtaa tgttttagtt cttttcaaaa atagattgga atctggcaga gtgttaagat  93600
ttgatgaaac tagtcagtac atgagtatct gttatattat tctctgtaat ttctatatgc  93660
ttaaaatatt tgtgaataat tactattctc caagaatgtt aagaatcttt tattaaacct  93720
tttttattc ttattaattt cagcatcggt atcaagtccc attgttgcag gtggtttgag  93780
aaacatacat gataataaag tttctggtcc gttgtctggc aattcagcta atcatcatgc  93840
tgataatcct agacatggtt caagtgagga ctacctacac atggtgcaca ggctaagtag  93900
```

-continued

```
tgacgtatgt aatatattat cattaaggtg ataaaatagt tctaatattt gtcatataac  93960
ctagtatttc catttcaaaa tttgaatgat acctaccgta tatcattata ctgggtactg  94020
agtacaacat ggctcctgca catacagagc ttagtctaga gcaggattgg tcaagtgtga  94080
ccagtagcct gaaccacaaa gtgagaatgg tttttacatt tataaagagt tatttaaaaa  94140
aaaaaaaatg tgatagagac tgtatgtggc ccacagagcc taaaatattt attctctgtt  94200
cctttataat gaaaagttgg ctgacccctg accttgaggt ttaggttctt aatgaaatat  94260
ttcagtttta ggttaatact gctcacacta aaattttttt ttttttagat aatgagcctg  94320
tatttattag tacttgactc tttttccctc tgatacttgt acaaagtttt gtgtctgaaa  94380
tttaatattg ccttgatgtt attaaaatat tccacattct ggaaatttgc cttgttattg  94440
atttgattgt aatttatgta agctgcatgt gtctaaggat aacacagatg acaataaact  94500
ctgccctcaa gtcatttacc acctggtaga gtattcatag ctccttttgt agaaaaaagc  94560
aaacaaaaat ggagcatact agtaatacaa atttcttat tcattgccat gcttaggctg  94620
ttgattcttt tggatacaat ttcaattctt ctaagatata ccaagaagaa aacaggaaag  94680
tgcagaagaa ttatgctttt gaattccaac actttacctg tcagtaattt atgtctctta  94740
ttggttctct tttaagattt ctataaagcc tctcctgtca ttcaaaagat aaattgtata  94800
ctctattttt aggatggaga ttcttcaaca atgaggaatg ctgcatcttt tcccttgaga  94860
tctccacagc cagtatgctc ccctgctgga agtgaaggaa ctcctaaagg tactactgta  94920
actaaaattt ccttctgtat attttatatt tgaagttgaa taaagaactc agacttccta  94980
aagcagatat taaaaagtta ttctgtattt ttttttcatt gtagaaaaaa aaataaacct  95040
gtacaagcag gtctggatca tgggatttaa atctgtccct attcattgat tcatttatct  95100
tccacttacc cagtaatctg ttgatagtat tctcggatac atccagtatc cattctcttt  95160
aataaatcca gtggtctttt caaaccacaa cgttcttctc ttaaacattt gaaaattttg  95220
atcagctttc ctctttcctc caaaaagact tatttcatat gagcccatct gtttttctcc  95280
cacttctttc attgatactt tttttcttca ttagctcctc tccttattct tattcttctc  95340
aagatttcta ttattagacc ttttatcact cattgtactt ttttccctgg ccgttttatt  95400
aagtttcatt aacagcattg attattttca tgcataagac tcctaaatca atctttggct  95460
ccagtcttgt ctcccaagtt ctaattcttc atttccagac aaaacttcct tcatacctag  95520
cggatatttc caattcatct tcaaaatggt tttcactgtt ctttctacca tcccatctgt  95580
cttaatgcta ttccagtcct gaatcattgt aacttaaaaa ttttaagtta tcataaagcc  95640
tcttttcaac tatttagtca tttatcaaat ctaacctgtt ctgttaattt ttaaatctct  95700
cacgtctact tttatctctg ccttttaaaa ttcttttatt ccagatctaa gttaaatggg  95760
tgatcttcca tgggccctcc cctaatctcc tcaagctatt agtttatatt ttttgtaaga  95820
acttttacta ctttatgcac acgaatttca gtttatcttt gaattttcaa agaaccttgc  95880
atggtcttct atctgtaaca gattcacaaa attgtgaatt taagtccagg tttgagccag  95940
tttttaaaat acttaaaatt gtagtcaaat agctttaatt atcagtttgt tggaagagaa  96000
aactgtcttc tactttttaa aattagctta taattaattt taacatagct ggtaatatat  96060
tctctcaagt aatgagaatt tctaattata gccatctgaa acataaagat attttacctc  96120
gtatctgctt catatggtaa agatcttttt ttcactgatt gtgttcgtac tatttatcaa  96180
ggacattttt cttttttttt ttcaaaaatt ttttaaaaat tttattttat tttactttaa  96240
```

-continued

```
gttctgggat acatgtgcag aatgtgcagg tttgttacat aggtatacat gtgccatagt  96300
gatttgctgc acctatcaac ccgtcatcta ggtttttttt ctttctttct tttgagacag  96360
agtctcgcac tgtcacccag gctggagtgc agtggcatga tctcggctca ctgcaatctc  96420
cacctcccgg gttcaaacga ttctcctgcc tcagcctcct gagtagctgg gattacaggc  96480
acatgccacc acgcccgggt gatttttttt gtatttttag tagagacagg gtttcaccat  96540
gttggtcagg ctggtctcga actcctgacc tcgtgatctg cccgcctcgg cctcccaaag  96600
tgctgggatt acaggcgtga gccaccacac caggcttgtc gtctaggttt taagccccgc  96660
ctgcattatg tatttgtcct aatgctctcc cacttcttgc cccctaccct ccaacaggcc  96720
ctggtgtgtg atattcccct ccctgggtcc atgtgttttc attgttcagc tcccacttaa  96780
gagtgagaac ctgcggtgtt tggttttcta tcaaggacat ttttcataga gtgaaagttg  96840
agctgttatg agccatttca attctgtaaa ttgtatgaat tttcagggat aaaaacccgg  96900
cttctgaaag agagaaaaac ttccagagta actatttgta ggttagatac atatcccaca  96960
agtgttgtca aggtgagaag ttatttagat tgccggggaa agagaacagg gagataggtg  97020
attgatctag ataactagct ttttttcttc tgactcttga gattagatag ataaatagta  97080
gatgaacttt agatagaaat ggaaaacttt aaaacaaata acctcactaa tatattattc  97140
accaaaagct tgaacttctg tcatgaagtt gttttctaac tagttttgaa gggtaagtgc  97200
attgtcagtc tatcttgatt tttagattaa ttattagaat ttgaagtttg ttctaaagtg  97260
tatataattt gccacataga atttaaatac aaaggcataa tggtatatta caattcagac  97320
ttagacaaat cttgttttaa atcttcaggt ttgttaacta cataaccttg ggcaaatttc  97380
ttaacctctg taggcttcat gttccatttc tgaaaaattt taaagataat actcaagaat  97440
gttgtaaaaa tcaagtgaat tgatatgtaa agcacctttc acaactctga cacaaaatgt  97500
tagactaaca tttatagtta attgctccca tatcatcttt atcacactag agtcaataaa  97560
taaagttgta tgtttatata taacatttaa aatacattaa ccttgctaac tgaaagtcca  97620
gatttatgta tcatggaaaa agactgaaag cttaattgaa ggcagttcta ggtttaagtt  97680
ctgtctgtaa aaaaactttt atcttgacca atttttacaa tttcttacaa gtttttaaat  97740
attttatagt ttagtgataa gaaatgtata cattattcag atgcagttat actattattt  97800
ctgaagcata tcaatgcact ttttccttca tgtctgaagg agaatttttg tctgaaggct  97860
tattaactag gataattttt ccatctgatt atttttaaca ctttcctgtt tcatataaca  97920
ttggttgatt taatggactc tgggctcaat atattttatt gggccttgaa atttactgaa  97980
cttatttatt tttctaataa aaagaggatt agcaagctga agagagtatg tgaatgatgt  98040
taagggagaa agagaagacc acataaaagt ataaatcaat attttaccac cagtttttga  98100
agtaagtaaa ggctctagta attgtaaatt gaccacttgc tttttgttat catcccagta  98160
gtattcatgt aagatagtct ctaggattaa attgttattt ttgtgtaatt taacaaaagc  98220
gtacttattc ttactttaat caggatatat ctgttttccc agatagtcca tgaaagaaca  98280
gagatggtca tacccaaaat atttgtgttg tatcatcttt agaagcaatg aactttttac  98340
ccctataaag ctaaatatgt atactttata ggcacaaaaa tatagaaata atactggtct  98400
gaaaaattga atactcatac ttagattcaa acctagattt tagattaact actagcaagc  98460
taaacaactg tgtgggacaa gtttttaagc tttcttttca tctttcgtaa ataagtagct  98520
tggattatat aatttcttat ttttttctag tattactata ttgtcactta ttaatatttc  98580
tatcacattg taagaaaatg tgaaaccacc acaactgtta cttctatcga attatttttc  98640
```

-continued

```
taggctcaag accaccttta atcctacaat ctcagtctct accttgttca tcacctcgag  98700
atgttccacc agatatcttg ctagattctc cagaaagaaa acaaaagaag cagaagaaaa  98760
tgaaattagg caaggatgaa aaagagcaga gtgagaaagc ggcaatgtat gatataatta  98820
gttctccatc caaggactct actaaactta cattaagact ttctcgtgta aggtcttcag  98880
acatggacca gcaagaggat atgatttctg gtgtggaaaa tagcaatgtt tcagaaaatg  98940
atattccttt taatgtgcag tacccaggac agacttcaaa aacacccatt actccacaag  99000
atataaaccg cccactaaat gctgctcaat gtttgtcgca gcaagaacaa acagcattcc  99060
ttccagcaaa tcaagtgcct gttttacaac agaacacttc agttgctgca aaacaacccc  99120
agacttctgt ggtacagaat caacaacaga tatcacaaca gggacctata tatgatgaag  99180
tggaattgga tgcattggct gaaattgagc gaatagagag agaatcagct attgaaaggg  99240
agcgcttctc aaaagaagtt caagataaag gtaaaataat ctcattatta ccacttcatc  99300
atctgggcaa atatgtaatt atagtgtcaa aaattttttt cacattactt ttttcccgaa  99360
tattttgtat aatttatgtc tactcaagta catattttta ttactaatac tcataatgca  99420
gaagttaaat tcgtaacaat ttcatttatt gtctgaaaca actatatgag atttggtaat  99480
tctctactac aggtctgtta ctcattatgt actatatgat tttacttatt tgtgcttttc  99540
tgctaaaatg aacattagca tttctatata acatgtatat ttcacaagtt acattaatat  99600
tgttgtgcac cttcaaattt ttttctgcta aaacaaggtt aaccactgta gaattatttt  99660
gaacaggtac acttaagaaa agctcatgtg tatgcttatt aggcagttag atatttcact  99720
tggtttatga tcctactggc ttaataatgt caaatttttt tagtaaacaa atcatggaaa  99780
gagttaatat taaatagcaa accttagaaa ttaagagtct tttggtggta attacagtga  99840
agtgttccct tttgtctgac tagtatgtta ggatggagtt tcaagacata cctggtctat  99900
gagtttatga gctttccttg cgcttcataa tcaaacaaaa ataaattcat agtaagttct  99960
tagtaatttg gtatacactg tatacaaaat ttctttcatg ttttaagaga ctgatgaatc 100020
agtgattcaa attagcaata taattgatga atttgattgc tatataaatg catatacaca 100080
tttgatcaga ccaaaagcat gctttatgat ttaattttat gattaaaata ttttaggttg 100140
attttcagtt cttatatttt atttcttggt aatgataaaa cttcttgata ttgggtagag 100200
ctgattttta tatatgatgt gttcagtgtt tgacaggatc atgacaagat aattgtgttt 100260
ctatgctaag aaacatgctg aagattagta ttatatttcc tgtctgtcat gatggctcat 100320
tttaatgtta ttgaaaaaaa atggactgta tttagtaatt gttgtactac aatgtttgca 100380
acatatgtaa atcagaaata gatgcaaata aagagattgc tagaagtctt cattttactg 100440
gctagggagc tgggtttttt tttctttgtc tttttttttt tttaatatag attcagggga 100500
tatatgtaca ggggtttgtt acgtgggtat attgtgtggt ggtgagattt gggcttgtag 100560
tgaacccgtc acccaaatag tgatcatagt acccattaga tagtttttca accttggctt 100620
cgtccctttt tccccctttt tgagtcccct gtgtctgttg tttctaactt tatgtccgtg 100680
tgtacccatt gttgaattcc cacttataag tgagaacctg tagtgtttca ttttctgttt 100740
ctgcattatt tcacttaggg tagataatgg cctcaaactg catccatgtt gctgcagagg 100800
acatgatttc attcttcttt atgattgtgt accacggtgt atatatacca cattttgttt 100860
atccagtcca ctcctgatgg acgcttaggt tgattctgta actttgctat tgtaaatagt 100920
gctgtgataa acatatgagt gcaggtgtct tttttataaa gtaatttttt tccctatgga 100980
```

-continued tagaaaccca gtagtgggat tactaggtca aatggtagtt ctatttttttg ttctttgaga 101040 aatctccata ctgtttttca taagggttga actaatttac attcccacca acagtgtgta 101100
agtgttccct tttctctgca gcctctgtta tttttgact ttttagtaat agccattctg 101160
actggtgtaa gattgtatct cattgtggtt taatttgcat ttctctgatg attaatgata 101220
ttgagcattt tttaaaatgt ttgttggctg tgtgtacatc ttcttttgag aagtgtctgt 101280
tcatgtcttt tgcccacttt ttagtgggtt gttttttttct tgttgatttg agttctttat 101340
agattctcag tattagacct ttgttggatg catagtttgt aaatactttc tctcattctc 101400
taggttgtct gtttactctg ctatggtttc ttttgctgta cagaaactct ttagtttaat 101460
taagtcccat ttgtcaattt ttctttgtgt tgtttttgct ttttaggtct tagtcataaa 101520
ttctttaatt aggacaatgt cccaaaagag tttttgcag gtttcttct aggatttttta 101580 ttgtttgagg tcttacagtt acatatttaa ttcatcttga gttaattttt gtataggtga 101640
gaggcaggag tcccgtctcg ttcttctgct tatggctagc cagttttccc agcaccattt 101700
attgaatagc gtgtactttt tccattgttt atttttgtca actttgttgg agatcagttg 101760
tttttaggta tgtggcttta tttctgggtt ctctatcctg ttccattgat ctgtgtgcct 101820
atttttatac cagtaccatg ctgttttgct tactctagtc ttgcagtgta gtttgaagtt 101880
tcctaatatg atgccaccag ctttattctt tttgctgagg attgctttgg ctattcaggt 101940
tctttgttgg ttttatataa atttaggat agtttttcca gttctttgaa aaattacgtt 102000
ggtagtttga taggaatagt gttgaatctg tagattactt tgggcagtat agtcagtttt 102060
aacaatattg attcttccta tccatgacca tggaatgttt ttgatttgtt tgtgttatct 102120
atgatttatt ttatcagtgt tttgtagttg tccttgtaaa gctcttgcaa ctccttgttt 102180
aaatgtattc ctaggtattt tattttgtgt gtgtggctat tgtaaatgag attgagttct 102240
tgatttggtt ctcagctcga acgttattgg tgtatagaca tgctactgat tttggtacaa 102300
ttattttgta tcctaaagct ttattgaagt tatcaggtct atgaatcttt tggaggaatt 102360
tttagggttt tctaagtatg ggatcatgtc atcagtgaac agagataatt tgacttcctc 102420
ttttcctatt tggatgccta atattccttt gtcctgcctg attgctctgg gtaggacttc 102480
tggaattttt ttttaaactg gtaaagtttt gatattaagg gtgaaatgtt gcttgtacct 102540
cttctcttta gtttgcagta tgaggttcag gaaataaata tataggttcc aaattatatc 102600
tcttcctcta acctgttata aaagtatacg catatcaaat gaaaaaagta atattactca 102660
gcttttctta ttaacctgtt caaaattcct gaatcttagg atagccagtt ttgcaggaaa 102720
catacaatat cacaattccc tgaccaagaa atattagttg ccctgataac tgaatttttt 102780
gcatgacgtt aaatctgtat tatggaaaaa tgtgttcttg aaaaagaatg tactttttaa 102840
gtgaatttta atagatgttg atagtaacaa aaacagagga ggaatggtga cctttttttt 102900
atgtatcatg tttgttgaat ccaaagtttc tacttataaa aatggaatta aaataagggt 102960
catatatagt tctaattgca tattagcaaa cttattttat actgcgaact ttcctttgga 103020
aaaatagaac aaagtcaaca gatacaacat actgttcttg tagaaacttg tatattttat 103080
tttcaattat ctaaatagtt ttttctgtaa tctgtgatgg catagttaac agataactga 103140
aaagttgaat gagcagagtt gacattcaat tttggtgaaa atacaggtat gcggtgataa 103200
cctgaggatt aaagtaggtt ttgctgattt catattattg ttgtcatttc taacttgttt 103260
cctgaaagcc actttcctct tatttcgtgg atttatagtc acgtatcaca taatgatgtt 103320
tcatttcaca ccagacttta tatacaatgg tggtcccata aaaatataat attgtatatt 103380

-continued tactctacct tttttatgtt tagatatgtt ttagatacac agatgcttac cattgtgtta 103440
cagttgccta cagtattcag tatagtaaca tgctgtacag gtttatagcc tgggagcaat 103500
aagctatacc atatagccta ggtacatagt aggctatatc atctaggttt atgtgaatat 103560
actatatgat gttcacgtaa cagagacacc tcctaacaat gcatttcgca gaatgtatcc 103620
tgttgttaag caatacatga aatacatgac cgcatttgaa aacttttgga acttagatgc 103680
cacctaaccc ttttgatttg aacttggcat attgcattca gtttctgcat tgtgtgatgg 103740
gatggtattt gttatataag aagttacctt gagattttga gatgattaaa ggtgtgtata 103800
ttggtccaag ggtgtaggtg aggtcataaa taaaagcaaa attcttctga agtggtggtt 103860
ttagagccct taagagatga aatacttcct tgaaattaat ttgtcccagt taccattatt 103920
tttacttatt aaagactaaa tgttaaagtg gacatttaat atattcaaac atttggcact 103980
gaggactttt ttacaactgt tgtattacta ctggtgatat ggagcaggca ggactatttg 104040
tctggcctac tagttgcact ttaggatatg agtttgtttg ccaatatatt cgtttactgt 104100
gagagaaata ttccactcaa taaccagaaa tcaaaaacac tgtaccttat aagtaagatt 104160
agaaagttca acaaatgtag aatatttgtg gaattcaagt aaagggatag aataatctta 104220
agaaatgttt tacctaggct gtggtagacc ctattgtacc cttgttccgc agaagaaaga 104280
catttttcta gccgctaggt atttatgtcc ctttgtcctg ttctctcttc tttgagcagt 104340
tctgtatata cgttgataag gcaactttgt aacctaatat tttataatat tccaaaagga 104400
cccttttctc aatcttttg ctcatacttt tagtgtctct aattacataa attaatttta 104460
aaaggctatt catctttctt tgcttctggg atgacctgtc attagatatt aatacctttt 104520
tcatgtgctg aaaatttctg ctttcttttg tcaaagaggg ggttcctttg ttcatctttg 104580
cctatttcat cttttcccaa ggtccacttt ccatgttagc aagtataagg aatggctcag 104640
cttcactaat gtttttataa tgttacaata ttcttgcact atagcccttg ttaaaagtca 104700
atgattacct actgtcattt ggaataagag accgggattt tggtacaagg aataggacaa 104760
ttagccactc agcctgtatt gtggttgagg ggtggtgtgt tttcatttta cataattggc 104820
taccatgtat acacaattat tgtgctttct gctttaagtg ttttcattta tcacttgtag 104880
atttaagtaa gtggtatagt ttgtttttct tgtaagcgta attgagttta gaatttctgt 104940
aagggctgca tcttattttg agaatatcag catctggatg acaagtgttg gttttgagat 105000
tatgataatc cttttgtatg cattttcttt aggaatatat gtattctgat agctaatctt 105060
atggttccca gtgctgaaga gggcttacag gtaatcactg tcctaaatac caaaatgatt 105120
cttcatagag atggctttcc atgattatta ggtggttatg atgtaatgaa gactcataac 105180
aaaagtgggt ggacaaaagt gacctgtaca gattcagagc tgctttataa ggagtaagtt 105240
catggtggaa ttgaatcaga ccaagtgaat cagaacatac atgctcttga catacctaag 105300
aatccttgtc acagtaatga aaattttcca ggttttacag gagtaaagta cttttcagta 105360
gttgaacgat taaaattttg tatttaacag cattttgtat atactgaaaa acaatggtaa 105420
gatgtttccc aatcttaatt acttgtgtgc aaatactttc atacattttt tattataaat 105480
aatcatagga ttcatagttt aaataaaata tatcatttct ttgaaattaa cttactgtat 105540
ttgctaaatt ttcattttaa tgtctttacg taaattggat tgaggttaat aatatataaa 105600
ctcttgagta ttttgtaatc ctttaaaaat cagccctcta agctatgtta atgtttttct 105660
gaagactgtg cataaaagag tcagccatag atatcttaaa tcttcagatg cctgagacct 105720

-continued

```
atgtcgttgt gtatcttaag tatgattgat tagtctacca ttttaattat ttttacaaag 105780
catatttcct caaaaatata gaaatcttag gttatatttt ttgaatttct agagtcttat 105840
aaaagtttaa gggataagca taaattgata aagcatctta ttcatgagat atcaattggt 105900
ttgccctgtg gcagaacata aagatgattt ttgaatggca gaacattcta aaagaggatt 105960
ctataaacat aaatttagta ttctgatttc ttttttaagg tattgatgta gaaaacttcc 106020
tataaattct taccatgtta gttttaactg gtggaaacaa tctaatgata atatattata 106080
ctttagaatt aaaatggtag tgttttgcaa atggagcatg tgtggtgata gatttgactg 106140
gacaactgaa ggagcagaag gacttagttt tacaaaatat aactaacaaa tatcttaagt 106200
aaattgcggt tatatttgat tagattttaa actggcaaga actgctactt cccactttaa 106260
aaagaaaaca gtggaacttt gctatataga agaagcatta ccattaggaa aaaaaaatca 106320
caacttggtt ctctaacaat aaggagccat ttttcagttg tcagtttgac ttttaacctt 106380
gtgataccat cttccttata tgatatatca cattagtgaa tattgcaaga gaatctagag 106440
attgccttgt taaaataaat aacagtgact tttaaaacat actcaagcaa ttcagcaaat 106500
aaacaaaagg aagccaaacc tcaaggtgct ataatgtaac cattcccaag acctaactgg 106560
agatttaatt tatagaaaat gactagctcc ctcttaagtc agaaatggaa tcatacacag 106620
aaatatatag atgttaaaaa taccttcaca ttttattgta atggtgaatt tgtgtttgtg 106680
tgtgtgtttg tctttacatt tcataatact gtaaattatt tctttctgag accagaatgg 106740
atcccagaac attataactt tatatcgaag agtaggaact gtttccttca gtggaagttg 106800
cttaagacag gattctaatt tatacctatt gctccctgat tttaaatttt ctatacctat 106860
gaaatctgtt gcttccttat tttaaattta cttctatcta acattgtggt taacttttaa 106920
actcctttca cacttttaac acttcaaaga atttgaatta ttgattaaag ttaaatgaca 106980
aattattaaa ttcttttttt aaattcattt tttcccaatg gcatggtata tattttcttt 107040
cttttttttc catacttatc ttagatacag taaaaactta tatttcctgt ttggtatatt 107100
ggcagatttg gagctcttta tggtttttgg ctaacagtta aaagtaacct gagtgagact 107160
ttatgatttg taactggttg ctttattatt aggaaaagaa tctgatttat ccgtgacatc 107220
tatgaacata aatatatgtt tgtatttggt acattataag ttctattcat tttatattct 107280
tacacttatt tatatcctta aagagtatgc agttaaattc tttttactat atttattgag 107340
atctctcaag catatttctt caaaccttac ctttcaaagt attgtgtcat tcatgcttac 107400
tattttatgt gtacatattt gcatttgcat tttactccat tttaaaaaca taaccttaaa 107460
aagataaaca acgtccatag ggtttttaat aagataagaa tacatgtcta ttactgatat 107520
tgatatttat ctttaaattt cagataagcc tttgaaaaaa agaaaacaag attcttaccc 107580
acaggaggct gggggtgcta caggaggtaa tagaccagct tctcaggaga cgggttctac 107640
gggaaatggg tcaaggccag cattaatggt tagcattgat cttcatcagg caggaagagt 107700
ggactctcag gcttctataa ctcaggattc agactccata aaaaagcctg aagaaatcaa 107760
acaatgtaat gatgcacctg tttctgttct tcaggaagat attgttggaa gtcttaaatc 107820
tacaccagaa aaccatcctg agacacctaa aaaaaagtct gatcctgagc tttcaaagag 107880
tgaaatgaaa caaagtgaaa gtagattagc agaatctaaa ccaaatgaaa accgattggt 107940
ggagacaaaa tcaagtgaaa ataagttaga aactaaagtt gagacccaaa cagaagaact 108000
taaacagaat gagagcagaa caactgaatg caaacaaaac gagagcacca tagttgagcc 108060
taaacaaaat gaaaatagac tgtctgacac aaaaccaaat gacaacaaac aaaataatgg 108120
```

-continued cagatcagaa acaacaaaat caaggcctga aaccccaaag caaaagggtg aaagccggcc 108180
tgagactcca aaacaaaaga gtgatgggca tcctgaaacc ccaaaacaga agggtgatgg 108240
aaggcctgaa actccaaagc aaaaaggtga gagccgccct gaaactccaa agcaaaaaaa 108300
tgaagggcga cctgaaacac caaaacacag gcatgacaat aggagggatt ctggaaagcc 108360
atctacagag aaaaaacctg aagtgtctaa acataaacaa gatactaaat ctgactcacc 108420
tcggttaaaa tcagaacgag ctgaagcctt aaagcagaga cctgatgggc gatctgtttc 108480
tgagtcacta agacgtgacc atgataataa acaaaaatca gatgacaggg gtgaatcaga 108540
gcgacatcga ggggatcagt ctagggttcg aagaccagaa acattgagat cctctagtag 108600
aaatgaacat ggcattaaat ctgatagttc aaaaactgat aaactagaac gaaaacacag 108660
gcatgaatca ggggactcaa gggaaagacc atcttctggg gaacaaaaat caagacctga 108720
cagtcctcgt gttaaacaag gagattctaa taaatcaaga tctgataaac ttggttttaa 108780
atcaccaact agtaaagatg acaaaaggac agagggtaac aagagtaaag tagacactaa 108840
taaagcacac cctgacaata aggcagaatt tccaagttat ttgttggggg gcaggtctgg 108900
tgcgttgaaa aattttgtca ttccgaaaat caagagggat aaagatggca atgttactca 108960
ggagacaaag aaaatggaaa tgaaaggaga gccgaaagac aaagtagaaa aaataggatt 109020
agttgaagat ctaaataaag gagctaagcc tgtagttgtg ctacaaaaac tgtctttgga 109080
tgatgttcag aaacttatta aagatagaga ggacaaatca agaagttccc ttaaacctat 109140
caagaataaa ccatcaaagt caaataaagg taagaatact tctactgatg tcatttataa 109200
tataatcgat tttaagtgtt aagattacta agttttaaaa aggaaattta caaaaattag 109260
aaagctacta catgaaaata taacatttat gtcaaacaac aggaaatttt tttcaggagt 109320
atagataaaa agtttccagt gaattttttt ttccccacag tttttttctt cccacccact 109380
actcaaggta gttatgaatg ttactgctat ttggttacac agagataagt tattttgctg 109440
tttagttatt tcttatattt ctgaaatatg cttaagtgaa tgttgtatta aaatagctgt 109500
ctttaaaaac tctctattta aaaatgtctt acaatactac attcttacag acctgtgtct 109560
gagccaatta ttgatgaata atttgtatag tttagaaagt tatataaaag gttatttttc 109620
attttgttgg ggagatggtt agttaaatat gttttatatt tttaaaacat atctttttgt 109680
ccttgtttat gcaaaggtaa tagggaatgg tacttacttt ttaaatttgg ttaaattgta 109740
agtttgtggg aggcggggga ctggtgttat ttttgcatgg tttctgaatt ctctggttac 109800
ttgagtaaaa ttatttccaa agggagaaga atgtcttaag tgccaaaaga taatggccat 109860
ttgtgcagaa gatatacttc tgtatccctt tgtacacaag tatttaaaat aactttttt 109920
atttttaaat agagatgggg tcttgctttg ttgaccaggc tggtttcgaa ctcctggcct 109980
caagtgatcc tctcctctca gcctcccaaa gtgctgggat tacaggcgtg agccaccgtg 110040
tccatacagt ctaaatatac tgaggtgtag tgaaggcaat agaactgaga gtttatttaa 110100
gttttccttc tgtgaaagag aattattaag aatttagatt tatacttata tataaccaag 110160
tatatgaaat ctggaattgc attggccaag agggtaacca ttgccttttt tggctattta 110220
aatttaagtt aactaaaatt ggaagttcat ttcattagta gtcacatgtg gctgttggct 110280
accatattgg acaaaacaga acatttgcat catcacaaag ttgtatagca ctgcagtgta 110340
ttaggagata caaaaagtgt gtggttattg tttttcataa catgctgttg tagcttgtct 110400
accaagaaag ctctttgaaa acatattata aagaactctt tattcaaaga atgacttgtg 110460

-continued gctaatctgt tgttattctt gcttggtctt cgtcaacatt catttttca ctgttaattt 110520 atttcctttt gtcttacaat aatgaaaaaa gattgccttc tgagtcgcta atatttgtgt 110580
tctttgagtg aagcttttaa attttaaatt atggcaatta gacttaccaa aagtcagtta 110640
agacatcagc cttaattaat aagtaggctt ttttatttaa cttgaatgca tcttttcaga 110700
gttacttgtt aatataaaag aggttgtaga atgtgggggt taacaccaca attgttttct 110760
tttaggtaaa aattttcttt aaaatttttt agtgaaagtt tgggagtagc ttatatttat 110820
aaactaaaga gtatggctat acaattttag aagagtcagg tgaaagatgg aaagtggtac 110880
cctcttgttc ctttgatctg gaccatcttt ctctccctcc cctctcagct taccctagcc 110940
ttgctttcta aactctgttc taacaaagag tcttttaaaa ctccttaaag aacatccaga 111000
agtgaatata gcttttagtt agtaattggt atattatttc acctgggttt ttcacatgca 111060
ataatattgc ctatgaatat gtttttagca ccaaaatgcg tttctgatag tatactttta 111120
atgcagatgt atatacctga tatggtcatg ttagtatgta agtaagctat ctgggtgtct 111180
gcctattaga gtgatgtgtg tgtatgtgta catgtgcatg tttgtgtata tatacacata 111240
tattaatgta actgcaatta cagtaacagt ccttttcatc aaaaaatact atgtcagtgc 111300
ttagatgcat ttcaggatgc cgtgtagcta tcttttggat taatttattt atgtcttagg 111360
atccatatct ttttttttta gtaatgatcc aattttggtt ttgttttaga tttttgctac 111420
tcagtttaaa tagcagagtt gggtaattgt ggatttttta aaattgcatg tatatgaagc 111480
acagttgtag attactgacc ctttgtagta tatactggga ttttctttgg agattcacag 111540
aaaatcacat tttgatgtgt tgatgatttt ctgagtaaag gagttagtct gaatactgct 111600
gggatacttg tatggttggt tcctagggcc aaaattgaag agccataaat ttccatcttt 111660
taaatatttt acctgatgtt catatagaaa atattcattc tttaggatat attttaagct 111720
gataaatttt gattgtgtga tagaggtata gatttattac tcctaattta gattacttat 111780
ttttgtcttt tgtatgagca tgataaatgt aaagtggcat tgttacattt gatttgattt 111840
ctgtggcact atatctgtat ccctagtacc taacaaaata cttcatacat aataaatcat 111900
atttaatgcc tattgaatgg agatgatgtt gccaccattt tcaggaaaag cttttgtgta 111960
cagattaaaa ttagataatc gtcttttatg ttcccatcaa tacaccctag ctcaagagct 112020
acttattttt caaatcctgc ttcctaaaca ttgttaataa ctcttcaccc tgtcaactac 112080
ctagtttttt tgttaagatc caaagaaaac ctgcttatag taatatgtgt ttaatttttc 112140
tgtcacactt attttgatct atactgggat taatattatt cccattctta tcctgcattg 112200
ttaacttccc tatctttcca tcaccatgtt tattccttgc ctgggagggg tggagggggc 112260
agtcaggcag tgtaactgtt tgtagaattc tttttaagtt cttcaaatat cttctactaa 112320
aatatacttc aatcagtatg ttacatgcca aaaaatatgt tgttaaaaat tttattagac 112380
tattacccta atgtatagtg tctctaaatt aaaataataa agttatgaga tcctttaaga 112440
ttggcataat ctcccagcat tttgggaggc caaggtgggt ggatcatttg aggtcaagag 112500
ttagagacca gcctggccaa catggtgaaa ccccacctct actaaaaata caaaaattag 112560
ttaggcactg tggcaggcac ttggtagccc cagctactca ggaggctgaa gcaggagaat 112620
cgcttgaacc caggaggagg agattacagt gagctgagat tgtgccactg cactccagcc 112680
tgggtgacag agcgagactc tgtctccaaa aaaaaaaaaa aaaaaaaaaa attggcataa 112740
tcatcaacta acacatgcct tcagtgttat taacagctta ttatcagtaa ttacaaacat 112800
atttgatttt gttgtttttt tttttaactc cagagtgtct caaaatatct ttgctttatg 112860

-continued tctaaggaaa ccattttttc ttctctctcc ccctacttct ttccaactag tatatcattc 112920
tccattgtgt ggactcagtg ctttcaagaa atatccgtat tatttgttat ttgacatcat 112980
cctttaaact gaagagtaaa gcagtttctg aaagtagtct tcactgggaa tgtatctagc 113040
agctttaata gtcaatagcg attagcctat attgctcact tgatgagcta atgattgcag 113100
gccttactag cgacagtgat cgcacttcag ttatctactg ttacagttac actactaaat 113160
gctgataact atcatcagct ggttgccttt tacttagcac tgaaccagtc tagttagatg 113220
gtgtttagga tcctcagctt ctgcaagtct gaaagtattg tttctgagag tgaatttata 113280
gcacagttta ttaattccta aatgaggaat tttcggtgtt ttctttaaag tagattgtaa 113340
tattgaataa tatttaatga tgcagtggaa atttattttg tttcatttgt acagttttat 113400
aaaatacctt tcttaaaaac tcaaattttc agtttctgta aagattgata tcagtgatat 113460
ctttaggaaa tgtttggaga aagtttatta cagaagttgg cataatctgt atctagctct 113520
tgtgacttta gagcagtatt ttgaaaattt gtactcatga tttccatttg tagaaatttt 113580
ccaaagtatg cttaatagat tgttcataca aatattgctt aaaagaaatg cattaagtag 113640
aaaccttttt ataaaaacta aagtttgctg gaggtattct ctctcctttc cattctgtct 113700
cttaagccag cccaaagaca tagtttctat agggttcttg tgtctgtaga aataggtata 113760
tgatttaaca gctaaggagc tagcaaatat taattctgta agaccctgtg cctatttatg 113820
aagaaataat ctttgacatg ctaaattccc ttttatattc taaaaaaaaa aaatttaatg 113880
aaacccttct ttacaagggc ctgatgtgaa attaagagta tgaataccta ctagtattac 113940
accaccaata aaatgggttt tttaatatgg atctctctgt cttgcctata aaaatattag 114000
cgttttctgg ctgtaatgta tcaattttta aaaattctct tttaaactta ttacaaatta 114060
tagtacaaag agaactaata tcaaaaccct gaataagcct taacctttca aagcttggtt 114120
cattcgcttt taaaataaag aaaccaattt ccctcctact ttatacagtt ataaagacaa 114180
aaatgaatgt tgttatagta aaagctaaag tatgtctgat ttttttatat aaaggaaagt 114240
acagtcattc aatttctaat tgaattgaat ttatctaatg aagaaagtaa ttttttaaaa 114300
taaatctttt tatgtatctg tactttatat tcagtgtaga tttaaagata ttactgccac 114360
aatttatttt tctcaccgtg tatacatatc aaggaaagaa tcatttgatc cctgcccccct 114420
acttttctgt aatgagtagt aagttgttac ttacataatg agtagtaaat tgtcatttac 114480
atgcagtatt gaaaattttt ttttgccccc acttacctct aattgaagtt gaagatccat 114540
ttggtgcttc tgtgttatat gggtaggtta gtggaagaat tgtcactgaa ctattccatt 114600
atgcctgccc aagttttttt tttttttttt ttaggattta taaaatttgg aggtttatgt 114660
gaggctctta gttttgtttc tgaacgtgac ttgtttccat tgaccaaagc ttcacttcag 114720
tcccaaagat tttattagtt tacgtgattt atttctatct cagagttgtt ttcctgtttt 114780
aaaaagaaaa cagaacacat tgttagttat caaatcaatg attcttttaa gtttttttgat 114840
gatttctggt tttaataatc tggcaagtgc taatttgagt gatttataat ggaaatcaaa 114900
gattgcttaa atgtagcata tctaggagta aatgtattct ttagccatat taaagccaga 114960
gtatagagtg cactgtatct aatggaatat atgtacagaa gctgaaaatt tgatatctca 115020
caaaattgtg actaaatgac attattcatc aagccagtaa cataaagttt tatgggaatt 115080
cagacatgct gatttaaaga ataaagtagt taggacaaaa gaaattaggt gagagataat 115140
cataaagcac tagtaatctg aagttttagg aacaaataac ttggcaagca acaataatcc 115200

-continued

```
ctaaaatcat caatccctaa aatacatcat catatactaa gagatagcaa gactttatgt 115260
ttgcatttaa tggattatta actaattcag gggaaataac ataaccaatt atgtcataca 115320
gataatttta agtacttgct gtttattcat ttctgttaaa ctgagttagt tatccagatc 115380
aggatccttt tgttttttta aagacagggt ctcattctct tacccaggct gaagtacggt 115440
ggtgctaata tagctcactg caacctggaa ctcctgagct gaaatgatcc tcccatctca 115500
gcctccaaat ggctgagtta tccagatcct tgatgtcata ttgaagatct caggcctgaa 115560
tatgggaaag tcatgcattt tatttattta tttatttatt tatttattta tttatttatt 115620
tatttattga gatggagtct cgctgtgttg cccaggctgg agtgcagtgg cgtgatcttg 115680
gctcactgca gactccgcct tccgggctca tgccattctc ctgcctcagc ctcccgagta 115740
gctgggacta caggcacccg ccaccatgcc tggctaattt ttgtattttt agtagagacg 115800
gggtttcact gtgttagcca ggatggtctc gatctcctga cctcgtgatc cacccacctc 115860
ggcctcccaa agtgctggga ttacaggtgt gagccactac gcctggcccc tttatttctt 115920
atctttgtaa tcaagcaacc tggcggagtc catttataaa gagcttcatg aaatggaaga 115980
aaggatgtgg ttaattcaga aaatgtgtga aacctgtgga atagacaatt ctgttcaaaa 116040
tgaaacagcg ttcacttttg gaggatgata catgtagaga cattgattcc tggatttttt 116100
ttctttaaag ttggagcacc ttcagaaata aaacatttgg cctttgaatt acattgttta 116160
aactttcaaa gttttacaga agttaaaatg atctagagga tactagagag gtcttaattg 116220
atagtattct tgttaatgta gggaataaga aagggtaaac tactgttgat aaatgttgat 116280
acctgcttta ttggatataa ggcataggtt atctgtgttt ggctattgtg agtaattttt 116340
ttaaaaagaa ggagcagagt ccttgctctg ggaacataat ccattgcaga gagagcacaa 116400
gaactagtac atattttaac ctttgattat tgtgttaatt aacaaggaaa atattaattc 116460
tgggatatta gtgttgagtc agtgtgtctg tgatgtgaac ttaatctaag caaaacactt 116520
aggtacattt gctttaaaaa aaaaaatccc gtgatggatg aaaggccaaa tactttgggt 116580
tatctgtatt tataaaccta tgaagattat aatgtttcca atatactgca aaaaaaaaaa 116640
tttgtattct tagaaatttt ggaaatgtac tcatttgtct atcaaataca gcaactcagg 116700
aactatccag gaagtacatc tgtaagtgga catgagaaat tgtgaaccag agttaggcaa 116760
tcaagaagca tctattgact atccatatat atgtactcaa tattatgtag gtcatgtgga 116820
aaagggaaga tgtatactct aaaacatgat tttccatcaa aaagacacat attaaagtag 116880
agatattcaa agactttata gtgaggtgca gaacgtgttc agtttggggc tgaaaatatg 116940
caatgcaaag ctaaagttga cttcttttac ttctaccagt attctaaaaa agagggccct 117000
cactgataaa acttaactag ttaaattaag aaagccaata cagagaaata ttacctgatt 117060
tcaaaatgac acagaagtta aactcaacgt tagttagaat tcttagcaat gaagtctttg 117120
ggatattacc agtcatgagt atttcatgtt tgttgggtaa aattgttcct atgcatgtcc 117180
ttagaagaac agaagcctaa aagttactga aataactcct ttgtgatact gaataaaagt 117240
ttcagaagaa taaaaaaagg gttattcttt cattaagatt aatattttat atctccatct 117300
tgagttattt gattgtatcg tcttaatatt cttgatagct atttactttt ctgtcatgat 117360
ttttattctt tacgtaagca ctattatcat ttgcatgtta taaaggatag tgttaatgtt 117420
gattgtaagt tactaatatt tcctgctata aaccacaaag gtactctttg cttccaattc 117480
ataaaattta tcaggtaaga tttttctttt tatacttcca ctcaaagtaa gtaaaggaag 117540
ctaaaattgc catctttagt aatcattaag gacaaattat ccgaataagt agcttttgct 117600
```

-continued acttctactt tattttttaa actatcagga agatagtccc agtttatttc ttcataagaa 117660
ctatttgtgt atgtgtttgt gtgtatgtgt gtaggattaa gtagtataat ggctcttatt 117720
gtcttgtctt ctttttattt gccttgactc ttgtgggaag atatgaactt gaatttctaa 117780
cttgaaatgt acttttcagt tacagacatt tatattttaa aagatttgtc atctatttat 117840
cctgtgttac atgtttctct cgtcttcagt taaattgtat atattgattt gtctgtttga 117900
agaagttctc cgtaatgcta aaggcattac catgccctca aatagacagt aataggtaaa 117960
agcatatgta tagctcttgt ctcagccacc atacacaact gccaagatca tagagaagga 118020
ggaggagtgg taagtgtctt ccaacacttc tcacttgtat tgaggggtaa cattagattc 118080
aaactacttc agacctacac aaaacaaaat ttatgtacta ccaagaatgt caagtgtacc 118140
tcttaccaca aatccacttg ctaatgtcag tgaatctcta gtttcagaaa gtttttagtc 118200
agtgcaaatt gaaggcatta tatcaaaaat gtattatata attacccttc atttttatgg 118260
tggtgtcatg tttttaaagt cattacataa ttatatgtat atatgtacac atacatatat 118320
attaactata ttgtcacttt agggttaaga gtattatagt tgtgttttat taaaataaac 118380
agttgattta gaaaacaaat actaatattt ttattatgct aacttagtta aaattttcct 118440
tttatcttca gatttacatt ttttttttaa atttaccttt cattaatagg tagtatagat 118500
caatcagtgt taaaagaatt accccctgaa ctcctggcag aaattgagtc caccatgcca 118560
ctttgtgaac gtgtgaaaat gaacaaacgc aagcgtagca cagttaatga aaagccaaaa 118620
tatgctgaaa tcagttcaga tgaagataat gatagtgatg aagcttttga atgtaagtat 118680
cacagaactc tttgttatta ttttagagtt taaaagcagg ttgatgtgtt tttctcattt 118740
ataatttggg ggtttagcaa aagcacagtc accttaattc ttaataacac agtatagtaa 118800 gttttttttct ctatacttta aaaatgcgtg aaagatgaga tcagttggca ccaagaaaaa 118860
aatattaaat aagctacaat taattttaaa acacaggtag gtatgtgtct gtatgcattc 118920
agcaaacatt tattgagctc ctattatatg ctagacactg agagtaaaaa tgcaaataag 118980
atatggcccc tgtcttcaaa gagccttcag tctaatgggg gaaatatgta aataaataat 119040
tgcagtatgc tgataaaagt acaatgataa cagtaaatcc agggtgctat gggaacacat 119100
tggattggca tcaaaatcag agtgggggct cagggaatgc ttactggaag aggtgacact 119160
tgagttgagt cttgaaggac acgtaggaga tagccagatg aagaaatatt taaaaccata 119220
ctatcactaa attatgaatg gattagccac attgcagatt atctgtgtgg tttggacctg 119280
gcttctcctt tttgcccagc tgtgtcctgg aattcctccc ttgtttcact gttttccaga 119340
gctggcttct tcactacaca gctacctctc tacaacactg tgatcacctg tctttgcact 119400
agacttgcta tacctcgcct gtcttcctac tggtccactg aaaaagttct tctcttttat 119460
ccctatcttc cttcttctgg agcaagagaa ttgagcctag ccaagagggg tcagcaacct 119520
tgtttgactt aaacggcatt cagtggaaac agactatggg agatcttcac ttgtgtgcca 119580
actgacttag tcataatgac caaaagaagt gggaagacca ccagtgttct actttttcca 119640
cctagtgtcc atagattgag gtgtgacaag caagggcagg aaggacagat gcatgctgcc 119700
atttttaaat gtatattgct gatggaagcc cttcacctcc tccaaagttt ttaatgttaa 119760
tttactgatt ttttttaat tgtgagctct tgagctatga gcagtagact atgaatactg 119820
aacaaatctg aaaaaagttt taaaattgaa ataaaatata cagcaaactt aacatttaat 119880
catgtataat tgttataatt gtattatgaa atgtattgac acacagtata ttaaaatggc 119940

-continued taaagttaat tttttttatt acaatcagat attttggtca tatggggacg tggttagctc 120000
tggaagatga gaagataaaa gaaacatggg gcccaggaac tcattccctt taatatacat 120060
gccttaccac tctgcctctt tccctctaat aaacatatca cccatatcta gaacagccga 120120
gaaggaggag tccctgaatt ccagtttgat ttcaaatgac atttcaaatc cagttgactg 120180
aaagtgactg cctccattac taaattgcaa agatttctga agctgtctca cagttaagtg 120240
gaaaggataa cataatcaaa aatttccacc aagtgtaaaa tagtggagag tagagccaca 120300
catccctcat gtttgtcacc aatgcagcca ccattctttt ccccttgctt tctatcatga 120360
aagctattgt ctcatcttat ggaggcacat agcttcgtta taaagccatg gaccctgtta 120420
tatctatgcc caactatatc gaaaggtaat atttatttta aagaacctaa gcttcacaca 120480
ctgctagaag aaaggaaagt ttctctggat ttttaaagag atgtcaggag tagcttcctg 120540
tttttcttca cttatttcta tacaagtaac tatagaaaag tggacactgg aggcaccgat 120600
ttgaatggtg aaagaagtcc aaatgattgt tcacataaac aaccaaatgg tcacaccaca 120660
acagaaacag tgtattgaaa atatagcaca atacaaaatg tgaaactatt atgagaacgt 120720
taagttgcaa gcattatgct gctgagagag agaaaaaaaa atttttgaaa cttagcagtt 120780
taatcaaatt ggtttctcaa aatctaaaac caaggaaata gttttgttga aggttagggg 120840
aaaatgttga aggataattt tgaaagttgg ggtacacaga tttggatggc catagcacaa 120900
atataaggtc actgggtgcc tggggaaaat ggagagaggg gtgatgtaag aagctcaaga 120960
gatacatagg tgaaatttgg aaagagaaga tagagaacac ccaagtcatg ttttacgtac 121020
ctctcttttg agtcctttcc cctcccctgc ttattccagg gtaatgagag aaatggagaa 121080
agaataagct aaccacaatg agttggtatc ctaataacct cattataaca caatgtgtta 121140
tggaagttgt ttttttttta atttgtcacc ccatttttat ctaaattgtc taaaatttga 121200
tgaatgtgaa ataaagattt acaagatctg tggatagtta ccaccaatac agcatattct 121260
atgtaattac aaaccactat aagattcttc aagcattttc tactcatagg attgaatgct 121320
tgaaacagat ttgttatgaa attaattaaa atgtacaaag actaaagcag gtcatattca 121380
aggttgtaaa atactaattt ctggcgcagt agctcatgcc tgtaatacca acactttggg 121440
aggccgaggt gggaggattg tttgagccca ggagtttgag accagcctga gcaacatagc 121500
aagacccctt ctctgcccac ataagaaaat agtgctttct gaagaagttt gcttattagt 121560
tgtcatccct tgtaatgtag gcatttcagt acttgtgaaa aaaacatcta aggaattata 121620
tatagaaatg acctgtttct ctgtcacaca tacacacacc ctacttatat tagtgtatga 121680
aacaagttgt cactaaagga atgtactaga gcatactgta atcataaaag aggaacagtc 121740
ctatcactct tcacatacgt cataaccaaa ttcataccta attatgaaga aaatctcaga 121800
tatttatatc catttacatt tgtgctttac atgaaccttt ttgctatcca agcctgtgac 121860
tgtaaagaag aggaaacaaa atgacctttt cctgccatgt tgtccataga ttagctagaa 121920
gagtccagaa ccagaaacca acctagattc ttgaacagga gtagttaggg tagcatttaa 121980
gaataagatt agacagagta tagacattta ttacccacac atgaagacac tggcacaagc 122040
atagagtgcc tgggccagag gttggcatcc ttacatctaa gccaagtagg ggacttaagc 122100
aaaacatttg tcttaagtat ttgtgtattt atcatagtta gggattcaga aaagagcagt 122160
tgctagtcaa ataacagact agaaagttta tcattgtcag caacaagtga tcacaacaac 122220
aaccagtata tgatttcaag gtaggacaca tcacttctct gccctggttt taacttggtg 122280
gtacctactg catcctagaa cagacatggt aaatatttgt cacttatagt gccccccagc 122340

-continued tcttactgca gacatttcta atcagtcttt cttgctgaac tatgatgctt tctcagggct 122400
tggggttatt ttcagcataa tgttctaggc agctattgcc agttgatgag agttgatgtg 122460
ttagatgaaa tctgtttgcc aggtctgcct aaaggctcct gtcagtacgg gtgattttag 122520
cagaatgcta aaatgatggg gaaaagattg aaggtaacat acataatcat gcttatgaag 122580
cgtgcataag cttagaaact tttcttgggt ttaagcaaga cttttgttga agaactgaat 122640
tcattatgtg agtatttaca actgtacagg tttttctgt ctcagtaggc ttgtcatgtt 122700
aggtcaccag ggcttatgga atttatcgct gagttgtggg tttaacttag ctattaattg 122760
atgatgtaca tggttaccca tattctgtaa cactttctca aaagttgact tttcctccaa 122820
accctgctcc ccatcagtaa tctaagtgct ttaaggtggt tctgtttttc atctaattcc 122880
taaatatagt ttgttttaca gcctcaatta atcttgaagt ttaggtataa cccttactga 122940
cttactgaat aactgtcctt gaagtgaaca ctgtagttta atttcaagaa ccttcctctc 123000
tgtatttatt agcagtaaac actgagttca tgtaaagatc tttaaatctg ggtagattgt 123060
gctaaaatta gtgatacttt ttctatatca taacttaaac ttctggatag acaaaatcac 123120
tgaatttcct agaccctatg gaatgaagat ttttttcccc atgtgattca tttgtaaagt 123180
acaagtttta atcatctttt taaatgaggt aaattatttg tcatggggat ttgcttctag 123240
cctctaggaa acgacataaa aaagatgatg ataaagcttg ggaatatgaa gagcgtgaca 123300
gaagaagctc tggggatcat aggagaagtg gccactctca tgaaggaaga aggagttcag 123360
gtggtggtcg ttatcgaaac cgaagtccgt cagattctga catggaagat tattctcctc 123420
ctcccagcct tagtgagggt aattcatcag tgtcaacgga tttcttacat aaaccaattt 123480
aaatttaggg ctttaacttt gaagaatatt ttatatcttt ttatgagtta ataactaatt 123540
ttcaattaag acaaaaatac ttagtttcta tgtgcagtga ttatcgttta agtctttaac 123600
gttcaggaaa aaaactagaa acaaaaatgg aattatttta agttgtcagt cctgcatttc 123660
agtacttctt tttgttcgtt ttagttgcta ggaaaatgaa gaaaaaagaa aaacagaaga 123720
aaaggaaagc atatgaacca aaactaacac ctgaaggtaa cacgttagtt tatttaattt 123780
gtctttattc atattcttca gcttcacatg tctacttgta atgtgagaat aatgaatata 123840
tttttctctc ttgcagaaat gatggactct tcaactttta agagattcac agcctcaata 123900
gagaatattt tggataattt ggaagatatg gattttactg cgtttggtaa aatcaactta 123960
aaatacattt acacatactc taagtgtctt aactgtatcc tctagagtaa ctcagttact 124020
ctagtgatgt gtcctacctt gaaatcatat actggttgtt gttgtgatca cttgttgctg 124080
acaatgataa actttctagt ctgttatttg actagcaact gctcttttct gaatccctaa 124140
ctatgataaa tacacaaata cttaaggctt aactcagtta ctctagagga tacagaggca 124200
tactctgtgc tatcaagaaa cttgaaatct agttgtaaag tcaaatctag tctgttacca 124260
agaaattaaa aactttagta caaaactcaa gtatatatta atcaagtctg gatagtatct 124320
aaagaatcat gagtaagtga gagtaattta aaaagtcttt atgcaggtga ggaggcttga 124380
aaaggccctg tataatgaag gtactgatag gagcatatat gcagaaataa gcatctattc 124440
ttctgttcat ttattctaat gaccaatatt tattgaatac ttactgtatg ccagtagtat 124500
gttaagtgct ggagatgtaa aaataactaa aacccaaaca cctggcttta gggaatacag 124560
attctaatat ggaaaacaaa atagtaaacc agttagaata cagtaggatt aatgttatat 124620
tcatgtatta cttttacaat gacataaaga ttacatctat aaatattaaa atgtttataa 124680

-continued aaacactgct tgcaatgtat agagctattc ttaacaatct tatgccacct tcagctggta 124740
aagtaagtat ttgttttgtg agaattactt gcctgagtat cattgtgttt gctgattatt 124800
tagaatgtca gtttcatctt ttttaaaact ttacagttct gtgctgagaa attgtcttct 124860
gtatcattta gggtccaaaa gtacaaaggg cactctcaaa ataggataat atgaggagga 124920
gttatttaca aagagaccag ttaaaaagat ggaggcaaaa taataccaga acccagggtt 124980
aacagcctta aaccaaaaga gtgaggatac agaaaagtca ccagaactca ttctgcagga 125040
aaaaaagttg tagagtaggc tgccttgaaa gaagcaatac cttttggtca ggggacagag 125100
ccagcctgag gagaccttgt aagcaaagag taagagatat aaatactttg accttacact 125160
cctctttgat cttctaacag ggcaccctac tggccaaacc caaacaaaag ccagagggca 125220
tgggagactc ttgatgtagt ccattcaggt cagcctcctg aggcagagaa tgtggttgag 125280
aaagagtcaa gagtatatct aaagtagtaa agataagata tctatctcat cttcccattt 125340
cagtcataaa tctgacttca atttctgtcc tttttcattc agggtttact tgaggtttat 125400
atatagaggc gtcttaggtt atttgtttag tttgcatgtc taaaaatttt attagaaagt 125460
taagcttgac attttgaact attttattta cctaaacttt gtttgtgttt gtttggcttg 125520
attttgcagg tgatgatgat gaaattcctc aggaactgct cttaggaaaa catcagctta 125580
atgaacttgg cagtgaatct gctaaaataa aagcaatggg tataatggat aaggtatctc 125640
accaaagtaa aatttataaa tttacttcat agaaacattt gaaattaatt taaggttttc 125700
agggtaaatt ataaaattta tgtaaagtaa atagtaaaaa gaaaactcat tgttgacttc 125760
tgagagtcta aatgagtttt tttgtttttt tacaaaagaa aaaagtattc tgcagattat 125820
tctaaagaga atcatattac tgcattgaaa gaggcatgga ctttaatttt ttccagagtt 125880
tttttttttc attttctcaa atatttagat tatttaaatg cagaaatata ttaaattttt 125940
ctttgacatt tgctttagtc atttagggtc gttgagtaga agttctaagt gggaaagttt 126000
tcttactctt taagagggtg acaatgctat ttcctccata gctcaaaggg aataattgta 126060
cagattgttt cttgaataat atataacttt taccaacgat tgataaagaa tttatattgc 126120
tattttagct ttcaactgac aaaactgtga aagtcttaaa tatcttggag aagaatattc 126180
aggatgggtc aaagctttcc actttgttaa atcatgtaag tttaagatcc atactgttaa 126240
ttttaccctt aatgttatta agatctatag tagtccccca cttctctatt gtttcatttt 126300
ccattttctc agttacctac agtcaactgt gatctgaaag taggtgaata atttttatta 126360
cagtctattg ttctgttttt tattgtcatt aatctcttcc catgcctaat tttataaatta 126420 agttttatct taggtatgta tgtataggaa aaaacatagt gtatatcggg tttgatagta 126480
tccatggcat gcactcgagg tcttggaatc tatcatctgt ccattaggga gggactaatg 126540
tgaatttttt cacaaatgac tctcatgtgg gggaaatttc acatttcgtt aatttgagca 126600
tgttaccatg aattactagt tacattcatt agcattgcta gtagaacttc acttttagta 126660
attcagaatt aatgttacac attgtcaatt cacagctttg ccataaagta agaataataa 126720
agacatgaaa atgtttgtca atttaagggg cagttcttta gtttatgctc ttccttatgt 126780
aagtatatga atgtttaaat tttgtttttg agttatgaga tgatagtagg tagtaattct 126840
ttttgttgag cttccctgaa gaaataacat agttagaaac cttatgattt cctaatatat 126900
actaattaat atacattact ccttatatac cgtttttata cctacctcaa agggttgttc 126960
aaaggattaa agaattaatt catgtaaagc acttagtgtc tggcacactt taacttctca 127020
gtaaatgtta actccagctg ttactatatt ttaatatgct tatatcaaaa gcagtagcaa 127080

-continued catgcttgca atggtttatt aattgagtga agcaaatttc ctgggatttg ccttcctagc 127140
attgtagtgg actatgaatt atatgtgcat tcaaattgat cttgatatct ctgacattaa 127200
tgaatgcaaa cactaatgct tataggcatt tagtaagttc tgagttgata aattttcttt 127260
ctctcccttt tttttttttc tcccctgata gagccagggt cttgctctgt cccctgggct 127320
ggagtgcagt gctacagtca tagctcattg tagtctggaa ctactgggct caggtgatcc 127380
tcccacctca gcctcccaag ctgctggaac tacaggcatg caccacaatg cctggccaat 127440
tatttaaaat gttttgtaga gccaagcgct cactctgttg ctcagactga tctcaaactg 127500
ctggcaacaa acaatcctcc tgccttgtcc tcccaaagct ctgggaccac agatgtgagg 127560
cactacacct ggccaaattt tctttatttt taaaagcctg attataaaag taacatattt 127620
attgtagaaa atttccaaaa cacagaaagc accaaaaaag ctatattcta atccagcaat 127680
gaccattttg aacacttttg atatatatac ttctcatgta tacgtatgta gtatatatat 127740
ttaatataca agcactagat tttattttat cttatgaggg aaatgctctt ggtgtttaca 127800
aaagccacag gattgctagg ggatctacat ggaataaaac aagcttgtcc aacctgtggc 127860
ccactggccc gtgtggccca ggacagattt gaatgcagcc caacacaaat tcgtaaactt 127920
tcttgaaaca tgaggatttt ttgcaatttc tttttacgct catcagctat cgtaattgtt 127980
agtgtatttt atatgtagtc caagacaatt cttcttccac tgtggcccag ggaagccaaa 128040
agattggaca cttctggaat aaaatatgta gaaaaataat ctcaggtggt tgttttctgg 128100
attattaaat atatttatat ttttaagtgc cctctcttta ctttttgcat cacagaaaca 128160
aaggcttaga gaaacctaaa gtaacaatct actccattgt tagtctacaa gttacttaaa 128220
tacttcgcca agaaattgtg ataatcatca tcagaaatct agagttctgg agagctggct 128280
gactcagtct taaggaaatt actttcatcc ctaaaaaccg taacagtatt taatatgttg 128340
tggatagcct taacgtttgg catgaatcat gagcctcctt aactgactct tccaaacaaa 128400
cagcaatgtt cgcatcaaag acaagctact ttatctttcc tttgtgaggt tttaggcatt 128460
actgaacaga aagccctgtc tgctttacat attatatatc gtgtttttgt tcgttttcct 128520
agggtataag ctttgaattg gaagtagtcc tgtaatatag tttatatttc ataactaaag 128580
atgtgataga aggattttta ctttaacagt gagattactc ctaatttgca atgtcaagtt 128640
gctgatgtgt aaattaaaat aaagtcttct gtcagttctt aaattatcca tttaaaaaaa 128700
gtcttcatta gtctgcatat tactactttt taatctcagt ttcagaaact gtgttgtcga 128760
aaagcaggtg ttaggaatga ttgtcaattt tagtactaag taagatttta ccctttgtca 128820
ttaatttttg ctttgttatc acagcagcaa gcagaattta taaagtcttt aaactatcat 128880
aatgtttata cccaaaacac aaaattaatt tatatgcagt taaagtcata agctaaatct 128940
taaattcgga taaagcacac aaaggatata aagataatta taactttgtc agtagggtgt 129000
catctagtgg tgaaatgagg tagagtatat cacgtttgaa aacattgaaa cacaaatcgt 129060
gctcaaagta gtatcagtat ttgtacctca ttctggatat tcttaaaaga attaacacac 129120
atcataacac ttttccacca gtgaaaatca aatcataatt ttaatgtata ttttaaacct 129180
ataaatgtgt ttatttccat ttcattaaca atactgtttt acagaataac gatactgaag 129240
aagaagaaag gttatggaga gaccttatta tggagagagt tacaaaatca gcggatgctt 129300
gtcttacaac tatcaacatt atgacatccc ctaacatgcc aaaagctgtg tacattgagg 129360
atgtaattga aagagttata cagtacacta aatttcattt gcagaataca ctttatcctc 129420

-continued agtatgatcc tgtttacaga ttagatcctc atggaggtta gttcgtataa tatcaaaatt 129480
attgtaaatt tttgccatgt tagatgagtc aaaataggac ttaaaatggc accaaaattt 129540
ttgaatcata taacttgtaa taaacactga ttttgattat ggatttgact agaatatagt 129600
acttgttcaa ttataatttc tttaggaaca tttatatata atagaagtta tttctacttg 129660
tcagggaaaa tctcagaaaa tactaccttc tggtttcatt tatcacttcg ccctaatttt 129720
acccaaaata gcagttgtct acaaaatgga ttgattcaag ataaatactc cttttcttgt 129780
tcttaacctt tataaatgag caatgaaatg tatacatttg aagggagtaa ggtcatacct 129840
aagtatagtt cctgaataat gaacttgacg atctattgta taactgcaaa ttaatttaaa 129900
gggaaatata atcttactat cctgctccaa tggagaaaag tagaaatcaa gataaaataa 129960
tattttagat acagggattt aatagctgct gaagattatc tgatgcaaga atgtttctaa 130020
tagaatatct ctagagagta attttctatt ttaataaata aaaagcttta tcttccaggt 130080
tctgtagcta gaaaattgtg ttctcttaat tcaaaaaaca gtttgagtac tgtttattaa 130140
aaattattaa aagttgatgt tttccttatc ttgaatttgt ttcattttag gaggcttatt 130200
aagttcaaaa gcaaaacggg ctaaatgttc tacccataag cagagagtaa tagtaatgct 130260
ttataacaaa gtttgtgaca ttgttagcag cttatcagaa ttgctagaga tacaacttct 130320
tacagacaca acaattcttc aggtaagatt ttttggtaag cattttgtat atttctaaac 130380
taaatgatta agtctagtat aacctagctc actcaataat aagaccagca ctatattatc 130440
aagaattttt cctgttaaga gtatgttata tctaaatcga agaaataaaa cttcaggagt 130500
tttaaaaaga cattttatca ggagacaaac aaatgtagtg taaattccaa actctaaatt 130560
ctttgaaaga tgggttatat tttcatgcag atattaaatg tttgttattt ctttatattc 130620
ctgtgacatt tgtaaactca aaaagtagag attagaggac tgatagctat gatacaatgt 130680
acctgttgta tatgctaacg tgctttgagg atgaagggaa acagagaaaa gaatagatgc 130740
tgattaggtg gggaaaagaa aaaatgcttt cttagtgttt tccagtaagc ttatgaatgt 130800
attggaattt agtaagatag aatgttactg aaatcaacta aaggtgtata ctacttactc 130860
ttctttttta aacaggtttc atctatggga ataacaccat tttttgtgga aaatgtcagt 130920
gaactacagt tgtgtgccat taagttagtc actgcagtaa gtataatcaa tttgtatttt 130980
tagttacccc acaaataaaa caatattgat gtcatttaat ccaaatttcc aaaaaataat 131040
gaagatacct ggttttcagt acattcattt caatctaagg actattttac taagtcttat 131100
tagactttat taattgagga tttatttttc tgtttggtta atttgttggg ttattctgtt 131160
tttgtcacat ttaaaacact tccaaatatt tgcaaatatt tcagctaata attccttgat 131220
atttataata aagttagaat ggtttaaaat catttaaatt cttgtctgac tgcctatagc 131280
caagatttca tagtccttta aatgaaacta gtgtactctt tgacttctat aagaatgtta 131340
taattaatga taggaaaata gagcagctta ccttagatac tgaaaacatt ttcattctaa 131400
atggcaggta attttttaaa tcacatgata ttattttttg gtttgttttc tattataagt 131460
ttaacttgga atcttataat tactaaacag gtattctcaa gatatgaaaa acataggcag 131520
ttaattttgg aagaaatttt tacttcactt gcaagattac caaccagcaa gaggagttta 131580
aggaacttca ggtaattaat tataacagag gtcaagttta atgaagaacc accattatat 131640
tgaaccgtca tacatttatt cttcatttct gtctgattta tattttaata attaaaaact 131700
aggcagttac atcagaacag catgaaaaat agatgtgtga aataacatgg catatttagg 131760
gggcttagaa aacttcactg attctcaagg gtaaagatct gtggcagggt ttttcagtgt 131820

-continued tggcactgtt gacattttag gccatataac actttgttat gcatagctgt ctagtggaat 131880
acagcatgct cagcggcatc cctgacctct acccattagg taccaataga cacccttcct 131940
ccttccagtt gtgacaacca aaattatttc caggcactgg agagcaaaat cattccttaa 132000
tatgaaccac tagtcagtga gaagatcttg ttcatcctgt tggaaatatg gctcaaaata 132060
atcagatcag ttcaaagagg attttataag atttttgtgt ctcaaaaaaa aaaataaaaa 132120
acagaaagat taatggcagt atggagaata aacatgggga ttaaatgctc tttaatcact 132180
aagcacactg ttaataagga gtgttaccca ctgctatggt cagcattatt gtctttgcca 132240
tcatagataa tcaccggaat tatcttaata ttcctgagtg attaaaagtg ttgacgtggc 132300
atataggatt gtttttaaga ttgctttgaa ggcttctttc ttctctaaaa taattatttt 132360
atcttaatca ttttttggac taattgtata ctgataaaca tttattgtct gttaaacctg 132420
aagaaaaact atgaagaaaa actatcaaca cataaaagaa tccttagatt ttttacaata 132480
tctatagaac aaaagatgtg gaaattgatt ttttataatc tgtgctacca acactagcat 132540
agatgatcaa gagctgtgta gcagatttta ataccaaatg aataacagat tcagcagatg 132600
aatagcaaaa tatatgggca tttggaaact ttgaagactt ttatcatttt caaaatcatt 132660
ttgagaaatg tttagtagta gtatgaattt ttatctgcaa tgtatgtaaa gcatacaaat 132720
ttgtattaaa tactgtattt ttcctttgac tattttaatt atctcagcat gcataggcat 132780
ttacttgatg tttttgctaa cttacaacaa ataattacac ataagaacac aataagcact 132840
aagatcatgc ctagaaatat tggcaaacac agtatcgtga aactttcaga caatagatga 132900
catttaaatg agattatctt gatactccat acaaattttt tttcttcatt aaaggttaaa 132960
cagtagtgat atggatggag aacctatgta tattcagatg gttacagcac tggttttaca 133020
acttattcag tgtgtggtac acttaccatc atcagagaag gactctaatg cagaagaaga 133080
ttcaaataaa aaagtaagga atctattaaa ggttttacaa ctgtactttt attgaaggaa 133140
atacctatat tctctgtcat tcttataaaa ctgaagttct tttttttct ttctttttt 133200
tgagacggag tctcgctctg tcacccaggc tggagtgcag tggcgcgatc tcggctcact 133260
gcaacctctg cctcccgggt tcaagtgatt ctcctgcctc agcctgctga gtagctggga 133320
ttacaggcac gcaccaccac gcccggctaa tttatgtatt tttagtagag acgggttttc 133380
gccatgttgg tcaggctggt ctcgaactca tgatccaccc tcctcagcct cccaaagtgc 133440
tggggttaca ggtgggagcc actgcgcctg gccaaagctg atgttcttaa ttagaggttc 133500
atggctgggc tttaaggtcc ttttagagca ctagacatgg tgttggaaga gttgagttct 133560
ggttctgttg tatctatcag tcataaaaca tataaatcat tttaatcttt ctgagtttat 133620
tcttcagctg taaaatggag gtgataatac ttatcaaaac tgctatacca ggttgtaagg 133680
gtcagtgaga tattaaatgt gaaagtgaat aatacaatat gtaatatata tgcatgttga 133740
gtatccctga tccaaaaatc taaaatcgga aatgctctaa aatctgaaac tttttgagta 133800
ccaaaatgat attcaaagga aatattcatt agggcatttt gcatttcata ttttcagatt 133860
aggggtacta aacccatata taaatacata acataggatt ataattaaca ttaaattcat 133920
gtggaaaatg agtttattcc ctccctaata ggtagctcat gccgacgatt tgcgtttggt 133980
tttacagctt ttggagatgt ttagaatttt tccaagtgta tacttttatc tcaacaaaag 134040
tttaagagaa acaaataatt ttgtttatct actgttagag ccaagcatat gtgtgtatct 134100
ttttgggaat aataataaat atgtaataat tattaataac tggacaggca ctttggctca 134160

-continued tgcccataat cccagcactt tgcgaggtca aggtgggcag attgcttgag gccaggagtt 134220
caagaccagt tgggcaacat gacaaaactc tgtctctaca aaaaatacac aaattagctg 134280
gtcatgttgt tgtgcacctg tcatcccagc tactcaggag gctgaaacag gagggtcgat 134340
tgagccttga gagatcgaga ctcagtgagc cgagattgtg ccactgcacc ctggcctgga 134400
tgacagaatg agaacctgtc taaaaatgaa tgaatgaaag aaagaaagtc aaatactctc 134460
tgaaaagttc agatcctctt tatttctccc atcccaatcc cattgtttgt ctctagtctt 134520
cctttcctaa ccattggtga caagtatcat gaatatgttt ctttctttct tttaattatt 134580
tttatgtaaa tttgatatac aattatttca tttttacgta aaggacagtg acatatttac 134640
agctaatttt ttcactcaac atcgctttta atacatacaa ctcatactag attgtttttt 134700
acttgagtta aaaacaccat atcatagaat cacaacttaa agcaaaagtt tctgtagata 134760
cacttagaag taaaattaag atagtataca tgcattaaat ttactggaag ttgtcaattt 134820
gcttactaaa gtggtgtttc agtttatagc cctacttctt acttaaaatt atggtcattg 134880
agaaataccc atcttatttt gcattttcct ggttattagt gagcttgagc cccttttcct 134940
atagttattt gtctgttgta tttttataac tgtgaattga ctgtttatat cttaatcttt 135000
aaatttcttt ttttttttt tctttttgtt ttctttgaga cagggtctca ctctgttgcc 135060
caggctggtt gcagcagcgt gatcacagct caccacagcc tcaaccgcct aggctcaagt 135120
gatcctccca cctcagcctt ccgagtagct ggaactacag gcacgcgcca ccatgccggg 135180
ctaatttttt ttttttttt atcttggtga tattctcttt ttatttattt tgtctttatt 135240
cagtaatctg ctttgatatc ctgaatcagt atttccttag gtggagagag ttttcatata 135300
ttgaatatta gattctttct ccaatttttt ttttttttt ttttttttta ttcattcttg 135360
ggtgtttctc gcagaggggg atttggcagg gtcacaggac aatagtggag ggaaggtcag 135420
cagataaaca agtgaacaaa ggtctctggt tttcctaggc agaggaccct gcggccttcc 135480
ggccttccgc agtgtttgtg tccctgggta cttgagatta gggagtggtg atgactctta 135540
aggagcatgc tgccttcaag catctgttta acaaagcaca tcttgcaccg cccttaattc 135600
attcaaccct gagtggatac agcacgtttc agagagcaca gggttggggg taaggtcaca 135660
gatcaacagg atcccaaggc agaagaattt ttcttagtac agaacaaaat aaaaagtctc 135720
ccatgtctac ctctttctac acagacacgg caaccatccg atttctcaat cttttcccca 135780
cctttccccc ttttctattc cacaaaaccg ccattgtcat catggcccgt tctcaatgag 135840
ctgttgggta cacttcccag acggggtggt ggccgggcag aggcgcccct cacctcccgg 135900
acgggggct gacccccccc cacctccctc ctggacgggg cagctggccg ggcagagggg 135960
ctcctcactt cccagtaggg gcggctgggc agaggcgccc ctcacctccc ggacggggcg 136020
gctggccagg cgggggctg acccccccac ctccctcccg gacggggcgg ctggccgggc 136080
agaggggctc ctcacttccc agtaggcgcg gccgggcaga ggcgcccctc acctcgcgga 136140
tggggcggct ggccaggcgg ggggctgacc cccccacctc cctcccggac ggggcggctg 136200
gccgggcggg gggctgaccc ccccacctcc cttccggacg aggtggctgc tgggcggaga 136260
cgctcctcac ttcccagaca gggtggctgc tgggcggagg ggctcctcac ttctcagacg 136320
gggcggctgc cgggcggagg ggctcctcac ttctcagacg gggcggttgc caggcagagg 136380
gtctcctcac ttctcagacg gggcggtcgg gcagagacgc tcctcacata ccggacgggg 136440
tggcagggca gaggtgctcc ccacatctca gacgatgggt ggccgggcag agacgctcct 136500
cacttcccag atgtgatggt ggccgggaag aggcgctcct cacttcctag atgggatggc 136560

-continued ggccgggcag agatgctcct cactttccag actgggcagc caggcagaga ggctcctcac 136620
atcccagacg atgggcggcc aggcggagat gctcctcact tcccagacgg gttggcggcc 136680
gggcagaggc tgcaatctcg gcactttgag aggccaaggc aggctgctgg gaggtggagg 136740
ttgtagccag ccgagatcac gccactgcac tccagcctgg gcaccattga gcactgagtg 136800
aacgagactc cgtctgcaat cccagcacct cgggaggccg aggctggcgg atcactcgcg 136860
gttaggagct ggagaccagc ccagccaaca cagcgaaacc ccgtctccac caaaaaaata 136920
cgaaaaccag tcaggcgtgg cggtgcgctc ctgcaatcgc agctctcggc aagctgaggc 136980
aggagaatca ggcagggagg ttgcagtgag ccgagatggc agcagtaccg tccagcttcg 137040
gctcggcatc agagggagac cgtggaaaga gagggagagg gagaccgtgg agagggagag 137100
ggagagggag aaggagaggg agagggaggg agagcttaat ctttaaattt ctgatgaagg 137160
ctttgaattt tttttttga ttgtatggat tatatgtttc ttaaactttg aggttgacat 137220
attttttcta aattcttttt ttattttcaa tccatttctt tctgttctga ccaggattat 137280
gataaacaac tattgatatt aaatttgtta accacatatg ttactcttac attattttaa 137340
taacactcta tctgtatttt tatttgtttc tataaagttt taaaatatgc ttagtgtgct 137400
aattttggct tctcttatta tatataatgt aatagtttaa gcattttagt atttaaatat 137460
attacccctc ttcagtaata acatgacaat agcaacaggg ctaacttatt atttcttgta 137520
tctttataaa ctcacttttt ttcattctag attgaccagg atgttgtcat tactaactct 137580
tatgaaacag ctatgcgaac agcccaaaac ttcctctcca tcttccttaa aaagtgagta 137640
aaattaatat aaatctggtt tttcttttcc acagtataga gaatagttca ttttttttaaa 137700
aagatgaatc caatttcctg ccataatctg aaccttgaat acatcttcct gacacttggt 137760
ttcttgatct ttaaaatgag gcaattggag tattaaaaat ctaaaattgg gatgggacta 137820
cacgggggaa aaaaatctaa aattttgtga atttgcttat atgttagact ccagaaatta 137880
aagtactaga ttgaaattct gtaatttgtc ttcagtaaat tttggagaat tttcctagtg 137940
tacctgaata ggaaagtttg tgaagagatg ttatttagcc tccatatgaa tttttttttt 138000
tttttaatga gacagagttt cgctcttgtt gcccaggctg gagtgcaatg gcacgatctc 138060
agctaactgc aacctccgcc tcccagcttc aagcgattct cctgcctcag cctcccaagt 138120
agccgggatt acaggcatgc accaccatgg ccagctaatt tttgtatttt cagtagagac 138180
ggggtttccc cgtgttggtt aggctggtct cgaactccca acctccggtg atctgcctgc 138240
cctgacctcc caaagtgctg ggattacagg cgtgagccac tgcgcccagc ccagcctcca 138300
taagaattta tgatgacctt ggccaggtgt ggtggctcac acctgtaatc ccagcacttt 138360
ggaagaccaa ggcaggtgga ttacaaggtc agttcgagac cagcctgacc agcgtggtga 138420
aaccctgtct ctactaaaaa tacaaaaatt agccaggcat ggtggtgcac gcctgtagtc 138480
ccagctactt gagaggctga ggcaggagaa tcgctggaac ccgggaggtg gagggttgcc 138540
gtaagccaag atcatgccac tgcactccag cctgggtgac agggtgagac tccatctcaa 138600
aaaaataaag aatttatggt gatcttttag gtagaaaaac agtgatcatt tttttaaatg 138660
tgtttcactt gcgagaaagt agtattagta ttgcttaata aatgaattcc ctataattaa 138720
ggagaaagtg gagtttgtga aatagactca ttttaaacca tattttattt aatgtacatt 138780
tatatatttt gttactaaac atagaaaaaa gaaaacttag ctaacaattt caatcatgtt 138840
ggtagacaga tgactgacat gtgtcaccta aattgacatc cttttcatta tttgcctttg 138900

-continued aacagatgtg gtagtaagca aggtgaagaa gattacagac cactgtttga aaattttgtt 138960
caagaccttc tttcaacagt caataagcct gaatggccag ctgctgaact actccttagt 139020
ttgttaggga gactgttggt aagagtatag catttaaaga ttattagatt actagaagac 139080
aacataatga ggatgtactc tgattcacag atgatgaatt ctttaaaaat gtgtaaggaa 139140
atatgaacat tgcatctctt tttgcatgtg cataactgta cacaatattg tcagtacctt 139200
gtagaaaatt ttcaaatgtt gtgaagtttg gtgctttcat ttcattacat aagataacag 139260
tgctttaaca attttttttt ttttggaaat gttatattgt taaaagcatc tcaacactga 139320
gtcataagtt actcatttca aagcaagaaa atgattaata tagactcctt atcatcttta 139380
agagtatttc tacaaatgta tggcattttg tagtcgtcat gtaacacagt aggtaaatgc 139440
aaagaaatgt tgtgactcta tttttaaact acatttgaac ttgcacaata cacattgtta 139500
caaagcttct gggacctttt tgtgaatggg aaaatatgtt aatattattc ggaaactata 139560 ataactttc ataggcatca gaattccacc ctaagaaatt cttactcagt aataccacat 139620
tttgtgcaaa taatacagtt gagcctgcat atttaatgag ttgtgttgtt cttaaggaag 139680
tttaatctgt aattttttta gtcacatgaa aatgttcaga ttccagaaaa tcaaaaggca 139740
aaaatgactt tatgggacaa tatcacagga aaaaaaaaag tttaaatttt aaattataca 139800
atttagattg ggaatttata tgataaattg ctatttaaaa tatattgtta taaatctatt 139860
caatcaaaaa ctattttgat atttaggttc atcagttcag taacaagtca acagagatgg 139920
ctttaagagt ggcatctctt gattaccttg gaactgttgc tgcacggcta agaaaagatg 139980
ctgttacaag caaaatggat caaggatcta tagaacgcat tttaaaacag gtactaagat 140040
aaaagattaa aattatggga atgaataata gttattttct ttgcatgtcc ttacattagt 140100
tttgcatttc attttgtgtg gattcaaaat aagattttta cttctaaaag tgggcttttc 140160
aaagccccag tgagaaattt taagacctga gaatgaatta tttagtctaa cagggacttc 140220
tgaatggttc atataaatca tttactttct ttttgtgaag tactcttaat aatgtataat 140280
gctgttttat atttgattta acataaattt tatttaagtt tttaatttac tgaatggtga 140340
tttagcatac acaataagat tgttttgtac ttttgaatgt tttgtatctt ctcataccaa 140400
ggaggtgtga ggagagcttt tttatacttt attacattag agagttttca tcttggggga 140460
aaaagtgttt tattgctttt ttttttttaa tgtggatgaa gtggtagtaa taaagttact 140520
tgagaaaact ggtgaagaaa tgatttctaa tcctactata tacaacttct gttttcattt 140580
ttttctagtc ttttttatg ctcgtaatca tatccatgtt ggtagaaatg cctctaattt 140640
ttttttagct atagttcgtg ttttgaaata atctcaacct tagagaaaaa ttgtaggaat 140700
agtacaaaga actcccataa aagcttcttg caaattcctc aattattgac aatttacaaa 140760
atttcctttc tcatctttca aaatatagat gtatgtgtgt ctgtatatgc attttttttt 140820
aaattttgtt tcgaaccact tgaagttaag ttgcagacat gattccctca ttacccctga 140880
attctctaat gcagtgattt tccaagtatg atccccttga caagtaacac caacattgaa 140940
atcatctggg aactaacaag tacatttcta acaaaagtac aaattcttag gaccctccct 141000
ggacctactg aatcaaaaac tcttggttta acaagccctc caggtgattc taatgaatga 141060
atgaatgctg aaacttggga accactgctt agtgtatatt tctgcaaaca agagctctca 141120
cttaaatatc tatagtacaa ttatcaaaag caaaaaatta tcattaatac aatattaaca 141180
tctgatgtaa tacaatacct actctggtaa attataattt gttgccatca ttattttaat 141240
gctcaaatcg tcctagattt gatcaatgag aaccctttga agctggcttt tatatcattt 141300

-continued tgatatattc ccatcataat ttgagggctt tctagaacaa aaaggtattt caggcagatc 141360
ttttaccttc cctacccctg ccctgggatc agttgtttct cctaggaatc ttggttcctt 141420
ttgttggtga attgtaatgt agaaaccaag atctagttac tggatgactt tctgtatttc 141480
ttaaagtggg cctggaacct cttattgcca tgtatggcta tgttgattat acattgtgca 141540
gctcaagggg aaggatcatt tgtaaatttt tatggctctc aacacatatt tccaaaagga 141600
aattcttcct acctctgaag atttaacaca tttttctgat catttttatg tcaactacct 141660
atgagctctt tttttaaaaa atgacatatg gttcataaaa ataatggccg ggcgcagtgg 141720
cttacacctg taatctcaga agggtggatt atttgaggtc aggagttcga gatcagctta 141780
gccaacatgg tgaaaccctg tctctactaa aaatacaaaa attagccagg catggtggac 141840
catgcctgta gtcccagcta ctagggaggc tgaggtagga gaattgcttg aacccaggag 141900
gcaaagattg cagtgagccg agatagtgcc actggactcc agcctgggcg acagagtgaa 141960
actccatctc aaaaaaagta aaacaaaaaa ggcaaacttc agctatcaat atataatatt 142020
tttcggaaat aatatttttc tgtttttttcc ttttagttac tgtggttgta ttttcatttt 142080
taatatcagt ttttccttca gatttgtgtt tacaattagg tgatttatta aagcacacca 142140
gtaatatctt ttttgttctt atttggttta ttctataggt ttcaggaggg gaagatgaaa 142200
tccaacaatt acaaaaagca ttgcttgatt acttggatga aaacactgag actgatcctt 142260
cactagtggt aggattcttt tcccctgttt tggagatact acatgtttat ttaaattggg 142320
tttaagaaaa ttgggaggta gcatgatgaa gaggaaaact taagttgttt ggaatattga 142380
ttttcaaaac aaagggatac ttgataatct aaacagaaaa gaatgctttg ggttgatttg 142440
tcttatatgg aattctggtt acagatactg tactgtacta aaattgtgtg acaagagaaa 142500
tatttggaag tctctccgta agtgatcttt gaggctaggc taggtcattg gttctcagag 142560
tgagtatggg ccgagtggta catgagatga tctataagcc tgtaaaaaata aactattgga 142620 tttttatatg tatattttta aatataattt tacttctatt tcatgtatgt tacacaatgt 142680
aaccaaaata ttagtataag aggttcatgt acaaaattta taaactatta tttgagaaca 142740
ttatacatag agatatttta ttttattttt taactggtgg gatatgcaat tgaaagaaat 142800
gggatactac taagctcttc agccaaatac tgtaggtttt cagtttgtat tcaaaggaac 142860
agatttacag gtgtgtctca gtgttaaact atttcagtga caattgtctt gtgtgtttct 142920
tggagaacta aggcaaaatt tgaaaacaga tgaagtcttc taccttcagc attttatcaa 142980
tttgttttaa actttcctag ttgacccatc atctgtttaa ctttgtcatg atgttgtcct 143040
tgattaagta gttgataata gtattctata tttaatacag ttgtgtttat caaattatct 143100
tgacttcatt aatataagta ttggaacata gtaaaataat aagttttcta acatttagga 143160
tattctatat tttctggctt tcttaaaatc tgttttttatc acatggaagt tgttttaaag 143220
taaactttaa tatttgtatt cctgtaatgt gagcactcta actttattaa cttggaaatc 143280
ttgttgctaa tttcatcaag ctcaagtctg tctaatttct ttccagtttt ctcgtaaatt 143340
ctatatagcc cagtggtttc gagacacaac tctggaaaca gaaaaagcaa tgaaatcaca 143400
aaaagatgaa gaatcatctg aaggaacaca tcatgcaaag gaaattgaga caactggcca 143460
aattatgcat cgagctgaaa accgaaaaaa gtttcttaga agcattatca aaaccacacc 143520
ttctcagttt agcacattaa agtaagatcc aaggagaaaa cagtttacat ttatctcctt 143580
gatatctatt tccctaagtt acaaaaaaag aaaaataaat ttttaatgac tttttgttgc 143640

-continued aggatgaact ctgatactgt ggactatgat gatgcttgct tgattgttcg atacttggcc 143700
tccatgaggc cgtttgccca gagctttgat atttatttga cacaggtaaa ctggataaga 143760
attccttata cagtgatatt gatttttctg attctggatg cttgtgagca gtatataata 143820
tcattcattg ttgagtacag atacttaaaa gatcatagat gtagtatttg tttttaggtt 143880
ctccggccgg gtgtagtggc tcacgcctgt aatcccaaca ctttgggaag ccaaggcaag 143940
tggatcacct gaggtcaaga gttcgagacc aacctgacca acatggtgaa accccgtctc 144000
tactaaaaat acaaaaatta gcggggcgtg gtggcacatg cctgtaatcc cagctactcg 144060
ggaggctgag gccggagaat tgcttgaacc tgggaggtgg aagttgcagt gagccgagat 144120
cgtgccattg cactccagcc tgggcaacaa gagggaaact ccatctcaaa caaaaaaaga 144180
aagtccttgt tctacatccc ttttacatat tcttgtttta caaatatata tttgtatgaa 144240
tgcacacaca tacagtatca gtagagtaag tgacattata aaaacatcca actaaatccc 144300
agcactttgg gaagccaagg cgggcagatt acgaggtcag gagatcaaga ccgtcctggc 144360
taacacagtg aaaccccatc tctactaaaa atacaaaaaa ttagctgcca tggtggcatg 144420
tgcctgtagt cccagctact caggaggctg aggcaggaga atcgcttgaa cccgggagat 144480
ggaggttgca gggagccgag attgcgccac tgcactccag cctgggcgac agagcgagac 144540
tccatcccaa aaaataaagt aataaaatac aaaacattca actaccaaat tatgatttga 144600
atgatactaa atatctttga ttcaagttac acatagcaag gttttaatgg ggctacaggt 144660
tctgcaaatg aagcaaaaca attaaaaaac aggtttaatt ggataaacga aaggctccaa 144720
agtatggact atacacttaa cacctgtact gatttttaag ttaaactttg aatcattagg 144780
aaagatcctt tactcattta tatacagatt aaagagaggt aaataataga tttgttttct 144840
tttgcatgtt ttcatgctat ttttaattaa attttatgta ttctaaaatt tacaaaaatg 144900
tcaatgtttg cttggcagat cctacgagtt cttggtgaaa atgcaattgc tgttcgaaca 144960
aaagccatga agtgtttgtc tgaggttgtt gctgtagacc ccagtattct agcaagggta 145020
aagagcaaaa atgattcttt cttttctact cgaattggaa tattcactct atttaggtat 145080
aaattgtttt tttctcttca tttttcttta gcttgatatg caacgaggtg ttcatggacg 145140
attgatggat aattcgacta gtgtccgaga agcagcagta gaattactag gtcgatttgt 145200
cctttgtcga cctcagcttg ctgaacagta ttatgatatg ctgattgaaa gaatattggt 145260
atgtttgtca tttttataat gattcgtgaa tataattttg cctttcaagc atcatgtttt 145320
gttttaaagt gttaagttag aaaaataaat gtaccaatta tatatttata ttgtcaaatt 145380
tatgaactat tgccactttc taaacaagta catattttca agaatagccc ttgcaatatc 145440
ataaaacaaa tcattggtaa taattggatt cctttttca gttgctgttt ctttttaatt 145500
ataccagttt acaatgagta gatgatagga accacatggg gtagttaaat gtttttgaac 145560
aagaatctag agtgatttta tgtatatatt tatgtatgta tatatataaa caggaagaat 145620
tatttcagtg agagacacgt acagaacgtt ggtacctgac aatatttttg gatcccttag 145680
gtgcatcttc ttgtttcctt aaagctgatt aatgatagct cagataccta caagttaagc 145740
ccaaaagtcc attgaggttt aagagcaaac taaagaggtt ctacatacat catggaattc 145800
tctggctctg aagcattttt ctgaaaaatg aaaggaaaca ttggcattag gaaatatctg 145860
tggaatctcc acactaccca ttgcaggcat attgacttat tgtagaactc aacatagatg 145920
cactagtgca caaaattaag tattacctca atgacaagag tttattttgt cacccttggc 145980
ctaatatcag aacattgtgt gacagaagta tagagtcatt tttagcttca actaggcata 146040

-continued

```
aatcttggtt gagaaacaaa taatttaaag aaaagctgga aaaatttttt tccttcttag 146100
ggcttccatc ttttgaaggg taaaatcaac aggattccca cgtatctgat aaactctgat 146160
atttgtaacc ctagtaaaat atcctaaaat attttgggga ttgctaaaat cacataatgg 146220
agattaataa ttttgcacac ttcatgtatg atgcttttta tttttaaaac tctttaatat 146280
gaaagtttgt taaagaaaaa tagtacagtg aacacccttg tacctacctc catacttcat 146340
ctgtactttc tgctaaatta ttttaagtca aacatttttt acttcttttc ttgtgaacac 146400
ttcagtttgt aacaccaaaa aaagatactg tgctatataa acaaaaccat tatctcaccc 146460
aaattagcac tctagtatca tctgaatact agttcttaga tcctccattg tcctaaaaat 146520
gttttttcat tcttcttttt taagaatcag aattcagtca aaggtaatac attgcatttg 146580
ggggtcatgt cttaaaattg aagactattt tcttattctt tttttttttt tttttttttt 146640
tttacatccc atatgacatt gacggattaa aaaggcctga tcggttttgt tatcttccca 146700
cacttcgttt aatttaactt gtgttttgta tctcttataa accataagat aggccaggcg 146760
cagtgcctca tgcctgtaat tgcagcactt tgggaggctg aggcgggtga atcacccaag 146820
gtcaggagtt caagaccagc ctgacaacat ggtgaaacac tgtttctact aaaaatacaa 146880
aaattagcca ggcgtggtgg tatgcacctg taatcccagc tactcgggag gctgagacag 146940
gagaatcgct tgagcctggg aggcagaggt tgcagtgagc tgagatcgca ccattgttac 147000
cccagcctgg gcgagaagag caaaactcca tcccaaaaaa aaaaaagaag taaccataag 147060
atagtgccaa aggtttgatt agattcaggt taaacatttt tatgaagtct acttttaagt 147120
gatacttcat gtgctgttta agtgccagac actattctaa agcttatgtt tgttttctca 147180
tttaattttg acaagcgtat acttctagtc ttgtgtccag ggcttaacta taaaatatgt 147240
ttctatgtct tagatatcat actttaaaag taaagacaac ataaaaaaat aacacattta 147300
tagtagcaga aagcatgtaa aaagcaaata tgtcaagtgt gtttatcatg ttaacaaata 147360
gtgaatatac tgcgtatgga tacttatttt ctaatttcat acactaggca tctcaatttt 147420
tctgactctt aaaaatacct ttctgttttt aggatactgg tatcagtgtc aggaaaagag 147480
taataaagat tctcagagac atttgtattg aacaaccaac atttccaaaa atcacagaaa 147540
tgtgtgtaaa aatgattcgc agagtcaatg atgaagaggg cattaaggta gtgttgactg 147600
ttttaaattt atttttcatt aatgtttaaa ataagttaaa tgtttattgc acctaaatgt 147660
tgattttaaa tatatccaaa cactttacaa tgaatcgttt atagtttata aacttaagaa 147720
aaatacatac tttaattttt tttgtttcta gatttttata ttaagtatta taatctgatt 147780
ttaaccaacc aattcctcag tggtaatatt tatttaagac tggccatagt agctcatgcc 147840
tataatccca gcactttggg aggccaaggc aggagaatgg cttgaggcca ggagttggag 147900
atcagcctgg gcaacatagt aagaatccta tttctataaa aaataaaatg atgaaaataa 147960
tttttaaaaa tttcaccaaa catagtagag catgcctata gttccagcta ctctagagat 148020
tgacacagga agattacttg agcccaggaa ttcaaggctg cagtgagctg taatcttgcc 148080
actgcactcc tgcctgggca agggtgagac tccatctcaa aaaatgtgca tgtgtgtgtt 148140
gattgattta ttgattgtta ttataagaga ttgcattata ttcaaaggtt tctcatggga 148200
ttattttaat tttcaaatga ttttagtttt ctaaattatt aaataaatac tttgtttcat 148260
tatgttaagt gaaataagcc agacacagaa aatagcacat attttcactc atgcgtggaa 148320
gcttaaaaaa aatttatctc atagagatag agaatagaaa gatggttagc agagggaggg 148380
```

-continued aagggttgtg aggggttgaa taaagagggg ttggttcaca gttatcaaaa atacacccag 148440
aaggaataaa atttagtgtt cagtagcaca atagggtgac tatagttaac aataacttat 148500
tgtacattta aaaataacta gaagaatgga aataggatgt tcctaacaca aagaaatggt 148560
aagtgcttga ggcgatggat accccagtta ccctgatttg atcattatac attgtatgct 148620
tgtatcaaaa gttcaactat acttcataaa tgtgtacagc tattatgtat ccataaaaaa 148680
aaaattttaa gtttagtcct aaattcatta gtaaatttac atttatatat aataatatgt 148740
ataattgtcc cttttttta agtttagcaa acactgtaac aacttcttct ccaaaagcag 148800
taaatatatt ttttagtttg atcataaaca tttgagtgta tagtatgaag aagttctagg 148860
ctagggatag tatcacccat tcgtattgtt taaaatcttt accaaattga aaatttttat 148920
agttttgaga aattagtagt tttagaaaaa actgaggaaa ttaataccag aaattcctgg 148980
cagtttgtgt tttgattagt tatttatagc tttgtgttgg gcctaatgag aatttggaat 149040
tgtgaaattg ccgtatttgt tataattagt taatttgaaa tttctcttcc ttctagaaat 149100
tagtaaatga aacattccag aaactctggt ttactccaac tccacacaat gacaaagaag 149160
caatgacaag gaaaatttta aacattaccg atgtggtaag aaggactgga acaagggtgt 149220
ggtcactgtt gatccagacc taattgaggc ctacatgtct tatgaaggaa gagacaataa 149280
tgagatattt cattaatctt gacatttcgt actgctgcct ttactttata tttctggaga 149340
tgctgaaggg atgcaagtaa catgtcgttg atgcttccat atagccctac ttcttggcat 149400
taattgatgt aaacactgat actgagattt tcctattcct ccagcaatta aaaacaggga 149460
gggaaaggag aaatggaaga acagatacaa tcgcccaagg gtaataatct gcaaagatag 149520
taatgcctac ttttttcaga aattatgaat atggattagc tacatttttt attatgcata 149580
agctatacat tttgtgtttt taatataaga aatttttgcc agtcacagcg catatgccta 149640
taatcccagc tgctcaggag tctgagacgg gggatcaaga gatctttgaa ccaggagttc 149700
aaagctgcag tatactgtaa tcatgcctgt gaataggcac tacactccag cctgggcaat 149760
ataatagcaa gatcccttct caaaaaaaaa aaaagaaaag aaagaaaaat tctgtatatt 149820
caattacatc atcttctaca tttctattga tgtctttaaa atgtgccatc tagaagcgta 149880
ataagaaaaa tatttttgtt cttaatgttt aagatattac agattttcct cacagagtgt 149940
agttcaagtt attgtgccat tttaaactta tgccacttta aacatttagt gccatattaa 150000
acctcaatac attaaactaa tttcttcaat gttttccaag atattttta gaataaagtt 150060 ctgtaacgtt ggtaaatggt tgtgttactg aaaaaatagt ttactttaaa aataaacttt 150120
tgaattgaga aaattgaaac atgtttcagg ctaaagcata acaaaagtat attttattca 150180
catttataaa tatacttcta actttgattc ttttcatcac ccttaggttg cagcatgcag 150240
agatactgga tatgactggt ttgagcaact gcttcaaaac gtgagtgttc ttttgactcc 150300
tgataaccta aaatttaata ggttagtttt ttgttgttgg tgttttttt tttttggact 150360 gtatgattta aaagaacctt tttagttctt ttggtaggga aaatttattt caatatgtta 150420
ggctggatga ttttgttaat ttctataatt aattcagttg cctggttgtg gtttttttt 150480 ttttttttt ttttttgagg tggagtctcg ctctctcact ctgtcgccca ggctggagtg 150540
cagtggcaca atcttggttc acttcaacct ctgcctcctg ggttcaagca attctcctgc 150600
ctcagcctcc agagtagcta ggattacagg tgtccaccac cacactcggc taatttttgt 150660
atttttggta gagacggggt tttactatgt tggccaggct ggtctcaaac tcctgacctc 150720
aggtgacctg cgtgcctcgg cctcccaaag tgctgggatt ataggcatga gccactgcgc 150780

-continued

```
ctggccttca gttgtctatt gtacaagtaa gttttctgaa tcattaacta aaattctatc 150840
ttactttctt tccagataat ttttttttct taatctctgt gattaataga tacaagattt 150900
ataaatggat caatatattg cattaaaaat ataattacat gatttagtat gttatgcata 150960
gaatttcctt tagtagtaca gagtcaaacc acaactagtg ggtttttttt aagtttcata 151020
aatagaaatg tttatctccc tatgaattgt taaatttttt attttagaaa atttcacaca 151080
ggcagaaata tccatcaccc agcttcaaaa attatcagca ttttcccagt cttgttatag 151140
ctatccttcc cctatctggt tttctccttt tctttctttc ttcttttgtt ttccataata 151200
cttttttttt tttttttttt ttgagataga gtctcactct gttgcccaaa ctggagtgca 151260
gtggcgccat cttggccggc tcactgcaac ctccgcctcc tgggttcaag ggtttctcct 151320
acctcagcct cccaagtagc tggggttaca ggcacttgcc accacaccca gctaattttt 151380
gtatttttag tagagatgaa gtttcgccat gttggccagg ctggtctcaa actcctgacc 151440
tcaggtgatc tgcccacctc ggcctcccaa agtgctgaga tacaggtgtg ggccaccatg 151500
cccagcctgt aatactttta aaacaaaggc caaactttat attatctcat tcataaatac 151560
tttagcatct atctatctgt agcagatgac ttttttaaaa aattatcatt tataccaaaa 151620
taataatgca ttattccata actaatacct attcagtgtt catattttcc tgtctcaaaa 151680
atgtattttt atagttggtt tgcagttgct ttggttgata tactcttaag tctcttatgt 151740
tagtttgccc cttacctccc ttttctcatg cgacttgtat gtttttctgt agaatctccc 151800
acattctgga tttaatagtc cacttttttt ctggtgtcat ttaagttgtt cctctatcca 151860
ccagttttca agtaaactct tagtgaaatc tagaggctta atatgattaa agttcaattt 151920
ttaatctagg agacaaatac ctcataggtg gtgttgaata ttattgcatc acagcaggaa 151980
gcacatatct agttgtctca ttttcagtga ttgatctttg atgaatttaa gtgatgatat 152040
acagtcatgt aacgtccaac acaatgaaca tacaggattt caccctaaaa tgccttttttg 152100
cagttgatcc tctcttcctg gccctagaaa actattgatc tactttttct cactgtagtt 152160
gtaccttttc atgtacattg ttcctatcaa tggagtcata cagtatgtaa tcttgtgttt 152220
gactttttaa acttagaatg ttgattcatt cttgttgcta atatattaat atatcttttt 152280
attactgagt agtttcagta gtgtggatat atcataattt ctttatcatt caccattttg 152340
tggactttgg ggttctttcc agtttggggt gttatgaata atgcttctgt gaatattggt 152400
gtgtaaggtt ttgtgtagat gtatgttttc atttatcttg ggtaaactcc caggaatgtg 152460
attacagggt catatggtga gtgagaaact gccaaaatgt ttttccaaaa ttgctaaacc 152520
atttttcatt tccaccatca gtgtatgaaa gttccggttg ctccacatcc tcaccagttc 152580
tcattattgt cacttttttt aaaactttag ccattttggt gtggtggtaa aagtagtaca 152640
ttactttctt aagatgtctt ttttaaaaaa ccttcatggt gttttcaatg tgtaatctta 152700
gactgtcttc ttaaatcatc tttcatttca tatttttaca tgatatattt ggcatcattt 152760
ctttcctaaa tcaaatagtt agctctatat catagaacct tatgaccacc ttagttaagt 152820
ttatgtcagc catcccaaaa ggtacatcat gatttctaaa aggctctaaa tcatatattt 152880
catttgatag ttattataaa tgatcaagta agaattcaat gtaattatca gaaatgtcac 152940
tatttaggat tactaaaaag aatctacaat aatgtcatct tgtattagca aattagaagc 153000
agaagggaca tgaccagatt tatactctct taacaatgat agttttactt gtacattctt 153060
tgtatcttta ttctctagtc ccatttattt agttagtaag ttagtttatc catcctattc 153120
```

-continued atgctctcta ttctatgctt tcctacttta gtttctgcca gcaacttagt ttaccaatga 153180
tattgtgact ttgtgatata tttccttata ctagcagagt ttggtttagt gaaagaaagc 153240
aaactcatat atatatatat gacagagaca taactactct gagcaattat aacatatatg 153300
cataaatgtt aagaaaagct aggaaggata taaagaatgg actgctggag ttattacaaa 153360
ttcttgagtc cagaataatt aacatgctta ctgtttttac atgagcacat atgcatgcat 153420
tgcattcagt ccaatttcag atatttctaa tttttatttt tggattgggt ttttggggtt 153480
tgttgttgtt gtttgttttt tgtagatcat tgactctccc catttattga attttttttt 153540
agggaaactt gaagtactac taaaatagct tcaaattccc acatgtacta aactctgttc 153600
attgtctaaa taattatgtt agtatatctt tttttttttg gagacagggt ctcgctgtgt 153660
catgcaggct ggagtgcagt ggcaccatca tggcccactg tggcctcaac ctccctggct 153720
caagcagtcc tctttcctca gcctcccaag tagctggaac cacaggcatg caccaccatg 153780
tttagccttt tttttttttt tttttttttt tgagacagga tgtcactata ttactcaagc 153840
ttttagtata tcttttgttt ttgtttttga ggcggagttt cactcttgtc gcccagggtg 153900
gagtgcagtg gcacgatctc cgctcactgc aacctccgcc tcctgggttc aagtgattct 153960
cttgcctcag cctcccgagt agctggaatt acaggcaccc accaccacgc ctggctaatt 154020
tttttatatc tttagtagag acggggtttc accatgttgg ccaggctggt cttgaactcc 154080
agacctcagg tgatctgccc accttggcct cccaaagtgc tgggattata ggcgcaagcc 154140
accgtgcctg gccagtatgt catttttaaa tgtatggtgc tatcattcct ttataacctt 154200
taacaattca tagtttttttg gcatttttca gtaggatgtg gaagattaac ttctgtcctg 154260
aaggtcctca cattttttttt atttctaaaa tgtactccag ttagtttaaa ccactaccat 154320
aaattgagta gccctttatg acagtcttct tcaaaaaaca cattgatagc catgtgatgg 154380
gtacacaaaa attaaataga ttttacagtg ccattcattt taattactta agatctaaga 154440
ctgaccattt tctagtttgt aaggaaaata caggcaatga aaaacagtta agagtaacct 154500
gtttcatctc ttcctgtcct ttgtaatcca gagcaagatc tttccgagtt tacaataaaa 154560
tattttatct ctatcaacca gtgaatggat aaataaacta tgacaatccc atgcaattta 154620
atagtactcc acatcaaaaa ggaacagggt attaatacat acagcaacat agataaataa 154680
tgaaaacatt gtgcagagta aaagaagcct tacgtagaag agtacatatt ataattccat 154740
ttatacaaaa ttctaggaga ggtaaaacta atctatactg gaaaaaatca gaagagtggc 154800
tgcagggagc tggggattga ctgggaaagg acatgaggga actttcaggg atgatagtta 154860
tggtccctat cagtggttct aaaggttacc agcattacct ggagttttat tagaaatgca 154920
aattcttagg ccctactcca gacttaattc atcagtaact ctgagggtag agcccatcat 154980
tctgtatttt aacagtctct ctccagatga ttcagatata agttgacgat tgagaacaac 155040
tgttctgtat attggtgtag ggacttgagt tacagtggtg aatgcatttg acaaaactga 155100
gcaaatgtac actaaaaatt tgtgcatttt attgcatgta cattttatct caaggaaaaa 155160
acggggagta tactgaagtc tccagtttac cttgaaatgc attgaaagta aaatggatat 155220
aggtgtgtgt gtatgcatat gcatacatgt atacgtgtgt gtgtgtgtgt gtgtgtgtgt 155280
gtgtgtgtgt gtgtgtgtgt gtgtgtagtg tgtgtgttca tcccagcaga aaaaatctta 155340
aaggtaggat ccaggagcca ggctcagtag cttgcaccca gaatcccagc ctcttagaag 155400
gttgaggcag gaggatcatt tgaagcctgg agttttagac caacctggac aatgtactga 155460
gaccccatct ctgaaaaaca taaataaata aaattaactg ggcattgtgg cctgtgcctg 155520

-continued taaattcagc tacgtgggag gcagaggcag gaggatcact tgagcccagg agttttaggc 155580
tgcagtgaac tatgattgtg ccactgccct ttcttctggg gaacagagtg agactctatc 155640
tcactcacca aaaatgtttt taatggtaga atctagatga tggtcgttag agagtgttca 155700
tgataaaact tttttcaact cttttgtttg gctgaaattt ttcgtaatat taagatggtg 155760
taaaaaatat acctgtatca ctgagaatgt tggtaccttt aaaagatatt ttttaagtga 155820
gcaagctaaa ttatacttta aaaaaatttt atgcaccttg attacttctt atttatatta 155880
taagtgcatg gctaatatat gtgtgtaggt taacattaaa gtagaagaaa tcatttcaga 155940
gtgggcaaga aaaacttttg ataaaattca atatccttga atgattactt ataataaaca 156000
aggatacaat gtaaattcct taatctgaca gataaaacta caaaacctaa aatgaaaata 156060
atgcaaaatg ggaaactgtg agctttcttc aaatcatgaa taaaaaaatt taaatatatc 156120
aaagtgattg taaaatgtat atggaaaagc agagaaaagg taaaaataac taatttctga 156180
aaaaagctga agcactgact tgccttacaa aatattggga cttattttca aagatacatt 156240
acataattaa gagcagtaat aagtagatta gtacgaaata gaacaatgga acaggataga 156300
gatcccagaa aacaggctta cacatataga atatgcttgc tataaaacag aagtggcact 156360
gcagatgatg gagaaaagat agactgttta gtaaatgggg ttgggatatt tgactgtcca 156420
taagaattaa aaaaaaaaga ttcctacttc agctcaaaaa tcaactccat atagattaaa 156480
ggagaacttt aaaactttta gaaaatatag gagaaaaaaa tttttaatta catatgtgtg 156540
tgtatatgta catacacaca cacacacaca cacatatata tatatatata tatatatatt 156600
ttttttttt tttttttaa tggcttggtc ttgctgtgtt gcccaggctg gactcaaact 156660
cctaggctca agtgatcctc ctacctcagc ctcttgagta gctgggacta caagcatgca 156720
ccaccatgcc cagcctgaat atatttttga tctctgagta ggaaaggatg ccttaaacaa 156780
gtcacaaaaa ccattaacct taaaagattg aagaaagtga aaatacaagt cacaaaatgg 156840
gaaaagatat ttggcacata tataaccaac aattaatacc gagaataaat acataagaac 156900
ttctctccta caaaaccagt gtaagtcaag agtcccagta gaaaaatagg taaagttaat 156960
taataggcat ttcatggaga aaatagcata taggacctat actgtgttca accccattag 157020
taaagtaaga aatacaaatc aagaccacat tctacaccat tttattgaca aaaatggaga 157080
agtcagacaa tcacaagtaa tggaaaagag ggatcaggta gtgtctttta atacagataa 157140
taattgagaa agtattacag ccacttgaaa aatgatttca taaaattatc tcataaaagc 157200
attatcttgt gaagttgaac aatgcatgta tccaatgacc cagcaattcg acttcaaata 157260
tatatacaca caaaagaatc ttgcatattt gcatcaggag gcatatacaa gagtgcttat 157320
tgtactaaaa ttgggattaa cctatctaca aaagagtgga taaatgaatt aaggtatagg 157380
cacacagtgg ggtgttgtac agcagagaaa atcagtaaaa tacagctgta tgcagtaacc 157440
tagatcatag tggcataatg atgagtgaaa aaagcaaatc tcagaagact acatcaagta 157500
tactaccttt ttagaaagtg gaaaatcaaa gaaaaatata aatagcatac agcttatact 157560
ttttttaaaa acaaggagat ggtaaatttc tgatagtggt tatctcaagt gtgaaacagg 157620
aaaatgggat aagggaagga gcacattggg agctacaaga tattaaaatt attcgtgttc 157680
ttgatttgga ttcaaagtat gccattattt attagtaaat tagaagggca tatacgagtg 157740
gcaacagtgt gtcatgagtc aaaatttatg attaattctt ttgtgtgtac ctgaagcctt 157800
ggaaatgaaa aaggaaaaac caaggatgag agaggatagt tttctactcc tgccgttaaa 157860

-continued taaaagacca agctaggccg ggcatggtag ctcatgccta taatcccagc actatgggag 157920
gctaaggcag gcggatcact tgagcccaag agtttgagac cagcttgggc aacatagaga 157980
accccatctc tacaaactgt acaaaaaataa gctgggcacg atggctcacg cctgtggtcc 158040
cagctgtgtg ggaggctgag cctgggaggg caaggctgca gtgagctttg attgtgccac 158100
tgcactccag cctgagtgac aatgagaccc tgtctcagaa aagaccaaac tagaatgtga 158160
tattaatagc tgctttaagg aaattagaga atggggcagg aagaatttgc ggttcatagt 158220
tgaaacctag tacattgaag ctgtctgctt tatttatttc ttcaaattgg aggaaaaggg 158280
gcagtgtgtg tgttatgtta ctctggttgc tgtcagttgt tttaatcatt tatgcatctt 158340
gtggggaaag tttaagcttg tgctgcccaa gcttgtgccc aactgtaagc cacatgcatt 158400
tttttaaatg ttaacttaat ttcaattttt attttattta attttaattt ctcagtcaca 158460
gtaggtacat tgcaagtgct taataactgc atgtgactct tggaaaccat attggacagc 158520
aaagatatag aatatttcca ttattgcaga gaaagttata tttaacagca gtggaactct 158580
tcacagaaat caaatacaca tttagattcc ttcaatatcc ccagaattag attagctagc 158640
ttttcttagg aaaacagata taccttatga cttttctgtt gacctttgat tatgaaagat 158700
tagattggtt ttacttttta gctatattta gaatgagctc tatcctcatc tcattattca 158760
taacactttt ctagcattgt ttgtgatttt gcaaaggata atgcagaaaa gaaatctacc 158820
gttatgtttt ataattgcct tttaaggtgc aattcagatg cagttattaa ttatttaaaa 158880
taattcaact agtattatgt gatactgtgt ttttgattgg aatagggaga aagggaaggt 158940
catcttttct acatctttca cgtattacct taggtcttac acagcaattt aagtactttg 159000
tagtaaaatt gtttgaaagt attggtaaat tactggttta taagatattt ttaaacatat 159060
atatttttgt tttattaatt tgcactttga gtattaaatt gttaatgaca aattgaaaag 159120
tatgttactt atggacactt ttaatgtgtt tatattatta ttgcctaatg aataattata 159180
ccgggatttt tttttctttt ttgtatatat atatgtatat atatatatat atatatgtat 159240
atatagttgt tgaagtccga agaggattcc tcatataaac ctgtgaagaa agcttgtact 159300
caacttgttg ataacctagt tgagcacatt cttaaatatg aggaatctct agctggtaag 159360
acattttata tatatattga tctttagttg attttataag atatttttaa atattttgag 159420
taaatttctc atttttgcct ctggctctgc ttgtctaatg attacttcac ttttaaatga 159480
aatacatttt tgttatatag gtatctgttt gatgttgcat cctagattat attaagattg 159540
actaagatta tctagagcat tgtaataaaa gcatgggcct cacctctttc acatatcttt 159600
taatagcata ttataatttt agatgtcata ttgaatagga gtaaaaatcc aggggctaat 159660
atgtatctag ctaatgatac tcatcacaaa actgatatct cctaagtcat ataaaattat 159720
gtctcaaaat gaaattgttt tagctattat aaaaatgttt tttaaagatt tatattacat 159780
tcctaatatt tattatttat aattgttaca taaagtttgc ttaatcttga gctagaaatt 159840
tattaaaatg tttaaaatca caaattattt aagtacttaa tattttatat tatctcacat 159900
tatttaccaa tcacaaatct gaagtttttt aatcaattat aaataaatga ttacttaaga 159960
aatataaaaa ttgggccagg cgtggtggct cacacctgta atcccagcac tttgggaggc 160020
caaggcgggc agatcatgag gtcaggagat tgagaccatc ctggctaaca caatgaaacc 160080
ccgtctctac tgaaaataca aaaaaattaa ccaggcatgg ttttgggcgc ctgtagtccc 160140
agctacttgg gaggctgagg caggagaatg gcatgagccc gggaggcaga gcttgcagtg 160200
agccaagatc acgccactgc actccagcct gggtgacaga gggagactcc gtctcaaaaa 160260

-continued atatatatat atatatgtat atatatatat atatgtatat atagatacat agatagatat 160320
agatacccat tgcttgaagc gcacaaagac tagcattact tcccatctaa tgcacattaa 160380
tgaggaacaa cgtcagcctc agttgttctc caaaattggg agccaatagc ctctaacagc 160440
cgtccattta tggcacctac ggaagttgtt gatatgcttt atattttta tgcagtcttt 160500
ttttttttt tccatgtgta cctctttttt ttctttttat ctccttgttc cgttttttta 160560
tttttcccca tcctggaatt taggggtgat actgatgtcc cttaatgtta aaaagttgct 160620
aatttcctct aaaaatttgt ttcctaagaa ccagtgtatt tcctgattag caacattttc 160680
ttcccacctg aacagcattt tgtttagagc tgtcttatag cattgttcca atttctgttt 160740
gttgctccca ttttttaaca ttcttctact gcaacaacat gtctttttgt accagtaccc 160800
ttaaacacag tttcacctca gctaaattgc tttttttccc atattcactt ccttttttttt 160860
ttttttttt ttttaaagac agggtctcac tctgtcaccc aggctggggt gtagtggcgc 160920
aatcatagct caatgcagcc tagaactcct gggctgaagc aatcctccca cctcggcctc 160980
ccgagtaact gagactacaa gtgcacatca ccacaccggg ctaatttttt atttttctgt 161040
agagatgcag tttttgcgtg ttgtccaggc tgatctcaga ttcctagact caaaccttct 161100
tcctgtgatg gcctcccaaa gtgctgggat tacaggtgtg agccatcaca cacagcccat 161160
tgattttaga taaaaccaat acgacattta ttcccaaaag cccattccta agcttcccaa 161220
tttccattag tataaaactt gccttctata gagagcatgg cctcttgttc tttatcttga 161280
gtattatttc tatatcaaag aaaaaatgag atggagaaag tctagtatca taagaactac 161340
taattcatta tattgaggcc tatactggac ctatttaggg gataatatta agtaatttaa 161400
ataatattct gtatagtttc cactaccttg tcatatttta gtgtcttatt tctctgtttg 161460
tttttccaga ctctgacaat aaaggtgtga attctggaag attggtagct tgcataacca 161520
ctttgttctt attcagcaaa ataagacccc agctcatggt taaacatgca atgactatgc 161580
aaccatacct taccactaaa tgtagtgtaa gtatagagct gtcttattct tgtatcttac 161640
ataaaacatt aagtgcttta aatttagagt tcacatgcgt caaccacatt ctcactgaca 161700
gatcaactgt gtcatttact tagatatatg tactatttgt agcaagtgat ctataaacat 161760
caagtctgac ataaataaag ttcaggttcc attttgctgt aaactcctca agccaaaccc 161820
tcagtagatg cttactaaat gttatagcta ttgttaagat ctcaaaatga atgaagcaga 161880
gttcctctct ttgagaaatt tactatcttt tgggtcctga atttactttt catttgtctg 161940
tcatttataa tataataaat ataaaaattg atacccattg cttgaagcac acaaagacta 162000
gcattacttc ccatctaatg cacattaata aggaacagta gtcaacctcg gtcattctcc 162060
aaaattgaga gccagtagcc tctaacagag gtccatttat ggcacctaag gaaattgttg 162120
atatgcttta tatttttcat acagtctttt ttaatttttt atattttata aatatatttt 162180
atttttataa tagaacaata tattaaatat ggaaaatcta taatatcata ccagagatgt 162240
taggctgtta atattaacat acactatgtt tttctaaaat aaggtgtgag tagtaagaca 162300
ttgcttaagt aaaattatcc atcaaataaa gattttaaag tatatatgac agcatagtga 162360
gttacgtggt ttacatgtat aatgtcattt gctttatgaa gtaggtacta ttatctctgt 162420
tttacagata aggaaactga agcttaaaga gtataagtaa ctgctaaaaa tttgaaattt 162480
taaaatactc taaaaactta acaaatataa aggtttctca catactgtgt tcctaatgtt 162540
cctaaggagc taattttaac tgtttctctg ctgcatttgt tttgctgctg tggtcagttt 162600

-continued ttttgattat ccaaattaca agctctaggt gaaaacctca ggacttcctg agaaaacttt 162660
aagaactgag gagagtagta aaggataata aatacctaaa aacaacatgc atttacttct 162720
gagacactaa ttctatcttt agggttcgta ttagatccag aaataaattg tttaataatt 162780
gtggctaata atagctaata attttttagc acagtaccaa gcactgtgaa aattttacat 162840
gtattatctc attaactttg tgaagtaagt actattatga tctcagtttt acagataagg 162900
aaatgaaagc ttaaagaata taaataactg gcccaatgtc acagagctaa gcagtcccaa 162960
agttagaatt cagccccatg tctgccagta gagtctggac tataatgaaa cctgttatat 163020
attatttata tcataaatag tccttgcatg attttgaacc agtgattttt ttaaaacaaa 163080
atcactttta aaatgtcttg tgcatttttt atgtatgtat gtacacaaat ataaagttgt 163140
atataaataa gagtatctca tacatggtaa actttttctt aatgttttgt ggttttgatt 163200
tttgttttta tatcctatct ccatctttat tcatcttccc ttcagaataa acatcttaga 163260
gtatccttaa catactttta tagttgtgga cacagaggta tatataaatg gttgaccggg 163320
ttttgtaaaa attgaatcat attatataga tatttgttag gcatatttgg taatctcaca 163380
ttacctggta tatatctaat tccttgtttt agatggctat atattatcca ttttatggat 163440
gtcctatgat ttatttaatc atttccctat ttggcaggtg tttacatatt tcctttggat 163500
caccactaca aacaattttt aaataaacat tccaatttaa atacctaagt actggtgact 163560
ttattttgtt ggaacagttt ctgagaagtg gacttgctag gttgaaacaa tggttatttt 163620
ggtgttcatt tttaattgat cttgccattt tgcagtggat gtgttttata caaccttttg 163680
gaaagctgta tgtgacaatc attgtcatta tttagtattc tttgccagtc taacaggtgg 163740
taaggaataa ttcattattg cttcagtttc cttccctgac tgcaaagaag gttgagcatc 163800
ttttcttggt actgaccagt ggggcttgct tttctgttaa ttcactattt atatcatttt 163860
catatcattc gttcatttta cctttgaata ataggctttt ttttttagga gagctcttta 163920
ttttagatat taaaccatct tatagtatat tcattacaaa tattttttcc tattctgttc 163980
tgttgctctt ttacttaatg gtttccatct ttctttaaat ttttcttcta gaatttaaga 164040
tatttctttt acttgatttt ccaggccagg atgttaaggg aaggttcaga aaatgctact 164100
tttttgttgt tatgtggtgg tttttttttt tttttttttt tttttttttg agactgaggc 164160
tcacactgtc acccaggctg gagtgcaatg gtgcaatctt ggctcactgc aacctctgcc 164220
tcctggcttc aagcgattct ccttcctcag cctcccaagt agctgagatt acaggtgcac 164280
accaccacac ctggctaatt ttttgtattt ttagtagaga cggggtttca ctatgttggc 164340
cagactggtc ttgaactcca gaccttattg atctgccccg ccttggcctc ccaaagtact 164400
gggattacag gcatgagcca ctgtgcccgg cctatttctt tttttttaa gacacagtct 164460
tgctctgttg cccaggctgg agtacagtcc tgcacttctg gctgactgca accttcgcct 164520
cccaggttca agcgattctc atgccttagc cacccaagta gctgggattt tacaggtgtg 164580
caccaccaca cccggctaat ttttgtattt ttagtagaga cagggaattg ccatgttggc 164640
caggctggtc ttgaactccg ggcctcaagt gatctgccta ctgtggcctc ccaaagagcc 164700
gggattatag gcgtgagcca ctgtgcccag ccactacatt tttttttttt ttaagtaaaa 164760
tgctagcact ggttctcaaa tgaatatctt acccaacaaa aattcttcta tccctagacc 164820
cactttaact cattatggga aacaacagga tttctatgct acttaaaaag aatttatctt 164880
ttctttttaa tcctgtgggg atcctaaaag gaaggatgaa tatgatgtgg gaatttcttt 164940
tttttgtaat taatactcct acaagccaag tggtgggaat gtttttaact agtgtgttaa 165000

-continued

```
tgcactcaaa aagtccaaaa tgggctgggc acggtggctc acgcctgtaa tcccagcact 165060
ttgggaggcc gaggcaggcg gatcacgagg tcaggagttc aagaccagcc tggccagcat 165120
ggtgaaaccc tgtctctact aaaaatacaa aaattagcca agcatggtgg tgcgcaccta 165180
tagtcccagc tcctcgacag gctaaagcag gagaatcgct tgaaccttgg aggcggaggt 165240
tgcagtgagc cgagactgtg ctactgcact tccgcctggg tgacagaacg aggctctgtg 165300
tcaaaaaaaa aagtccaaaa tctatgccgg taatccatta ctaacaatga ggattagtag 165360
cttaaaaact agattaaggc tggacatgat ggctcacacc tgtaatccca gcactttggg 165420
aggccgaggc aggcagatca caaagtgtgg agtttaagac cagcctggcc aatatggtga 165480
aaccccatct ctactaaaaa tacaaaaatt agccaggcgt ggtggcaggc tagttgtcga 165540
tccatattcc cgacatgctg gtgcttctcc ttccatgcct ccagctactc tggaggctga 165600
ggagaatcac ttgaactcag gaggcggagg ttgcagtgag ccaagatcgc gccactgcat 165660
tccagcctgg atgacagagc gagactccgt ctcaaaaaaa aaaaagaaag gaaaaaaaaa 165720
aactagatta aaaacatgca ttgaaagcct tactacacac acgcgcgcac acacacacac 165780
acacacacac atataacttt gattgccttt ggggaaatga actgggtggc tggaggatag 165840
atagaaacaa gactttttat tgtaaatcct tttctacctt ttggtttttt ttaaaaagtc 165900
tctacctgtt tttttaaaca tgcttattag tttttctaat caaagaaata acacatttaa 165960
atttaaaata aagaagtcct aggctgagca tggtggccca cacctgtaat cccagtactt 166020
tgggtggcca aggcaggagg atcacttgag gccaggaatt caaaaccagc ctgcgcaaca 166080
tagtgagacc ctgtctctac aaaaatgaaa attaaggccg gacgcagttt ctcacacctg 166140
taatcccagc actttgggag gccgaggcag gtggatcacg aggtcgtgag tcctagacca 166200
gcctggccaa gatggtgaaa ccccgtctct actaaaaata caaaaattag ccaggcatgg 166260
tggtgggcgc ctgtaatccc agctactcgg gtggctgagt caggggggttg cttgaacccg 166320
ggaggcagag gttgcagtga gccaagatca tgccactgca ctccagcctg ggcaacagag 166380
caagactctg tctcaaaaaa aaaaaaagac aattaaaaaa ttaaccgggt gtggtattat 166440
gcgcctgtag tcctagctac tcgagagact gtcaggaaaa tcgctcaagc tcaggagcag 166500
gattgcattg agctgtgatt gtgccactgc actccaacct gggcaattga gcaagactgt 166560
gtttcttaga agtaaagaag ccttctgcct ggttctggga ttctacatgt ttatctgtca 166620
tagaaaattt taacacaggg tttctcaacc tcagcactat tgacaggact agatgattct 166680
ttgttgtcaa ggattgttct gtgcattgca ggttgttaag cagcatccct ggcctctatc 166740
cactagatgc cagtagtggc tcccattgtg acaaccaaaa atgtctccag atactgccaa 166800
atactcctgt gtcaggatac gggggaagaa gcttattcct gattgagaac tactgggtta 166860
acatacacag tttggaaaat actaatcgta aaaactgtac cagtctttgt ataatgctgt 166920
caatatgtaa ataccttttgt ttagaattga cttgtgttac attttaggga aaaaatataa 166980
cattgtgatt aagtgacccc aaagtcacat tttggtaagt tagttgtcgg tacatattcc 167040
tgacatgctg gtgcttctcc ttccatacct tgaaaaaaaa actctaacag actttttttt 167100
ttaactggac ctttacgtgc aaaatgccct atttctgccc ccaaatacgt aaagctgtat 167160
atagtttctt ttcaggtttt ggatattcat aaagcattaa ttttattctt atagacgcaa 167220
aatgatttca tggttatctg caatgttgca aaaatcctag agctagttgt accactgatg 167280
gagcatccaa gtgaaacttt tcttgccact attgaggaag atctaatgaa gctcatcatc 167340
```

-continued

```
aaatatggca tgactgtaag cactcagttt accatttctt tattcattag tgtaaagttc 167400
taatgtattt tattaaaatt tttaaagcaa atatttgtaa aaagctaagt ttttaaaata 167460
gtatattttt aacttttatc taaacatttt ctatatcttt taggtagtgc aacattgtgt 167520
gagctgtctt ggagctgttg taaataaagt gacacaaaat tttaaatttg tgtgggcttg 167580
tttcaataga tactatggta agttcaatac cagggtttta aaattattct gctaggtcct 167640
gcagggggtc agctcatttt aaacacattt gataaaaggc tagactcgag gaaattatga 167700
ggtgtgatta tccaccgtgg tcctctcaga aacaatattt tctagtgtct tttgtatttc 167760
ctgaagaacc cactgtgatt acttcagaaa tttatctcct gataagtaaa gattggtaaa 167820
ttttttgcgc actgtgaaaa gtaaaattta aattttctta cattagttta gactctgaag 167880
agcactctca taattctaga catatttaat atttagaacc attagtaaaa attaattggc 167940
tggggacagt ggctcatgcc tgtaatccca gcactttggg aggccacggc gggtggatta 168000
cctgaggtcg ggagttcgag atcagcctgg ccaacatggt gaaaccccgt ctctctacta 168060
aaaatacaaa aatttgccag gcgtggtggc acacgactgt aatcccagct acttgggaag 168120
ctgaggcagg agaatcactt gaacacggga ggcggaggtt gcagtgagcc aagatcatgt 168180
cactgcactc cagcctgggt gacagtgaga ctccatctca aaaaaaaaat tgtaattcat 168240
tagtagtaat tacttgaact tagtaattca aagataaata ttataagtaa atattactta 168300
tctttattag gtgccatttc aaaattaaaa agtcaacacc aagaggaccc aaataacact 168360
tcacttctaa caaacaaacc agcacttctt agatcccttt tcaccgttgg agcactatgt 168420
cggcattttg attttgatct ggaagatttt aaaggcaaca gcaaggtaaa ggtagtaata 168480
cttaaaatgc tataaaacat agagctatat ggcactgtga tctgagaatg acagtagtga 168540
cccaggatga aggcaacatt agagtagtct ggtttaatga aaattctgaa aacagtgctg 168600
ctcaaaacgt ggtcctcaga ctggctgcta atccatcaac tttttgttac tggtgtgtaa 168660
ccagataatg aaatttccct gacaagttat atcagttttg taacagtagc acactgttga 168720
catcaacagc tgacttttta aaaaaaattt ttttcaatga aggaaacaat gcactgattt 168780
acattccgaa acaagcttct ttgtcacaga ctgatacttt gaatgccact gttctaaaat 168840
aaatggaatt ggttacttat ttttttaata aagttcacac aaattctcat tgttttaagg 168900
tatttttttc ctttatagtt gaaaattaat ctaagttact gttcatgaac actttaatgt 168960
gttttcctcc ccttaggtta acataaaaga taaagtactt gaactattga tgtattttac 169020
aaaacactca gatgaagaag tacaaacaaa agctatcatt ggtctaggta agtctaaatt 169080
tctttataat ttgtagctat ttgagaggga tagagcatat ttttaaatat tgtgaatcta 169140
aattgttgat ttactttaat atgtttctat tagcagtagg atttggtgta tagaatgtag 169200
gtctgaggat taaaacaact gggttgcatt cttgtcatgg ccattgactt cctgggtaac 169260
cttgagcaag ccatttgtct gttcatcagt ttcttcatta gtaaaataga gataacaata 169320
ctttcttcta cccctcctcc atagggtatc ttaagaacat ttattaaagc cctttgataa 169380
agaaaaataa tatagaagaa ttctgtgctc tttgcatttt tttaattgtt ctttttcatt 169440
gcaaagcttt gtcactacag gaagctgcca catctggtta aaacaatgat cagtctacac 169500
tgacttattt atataaaagc aaatagtaag caacccagaa ggaacaattt ggatatatac 169560
ctgttttata atgtttttcc aggaaggatt gatgtaataa aaacatgttt tgcaattgtt 169620
aggcaggtct atgtggctta tatctaggaa ggaattagaa tatgaggaaa taggaggtga 169680
atggcattaa agtacctgaa ttgaatgcac ttcaaaaaaa tacaagaaca gtctgtccag 169740
```

-continued

```
gtttttggtt tttgttgttg tttttttttgg tacaaataca gttggccttc catatccatg 169800
ggtttcacat ctgtggattt aaccaccaag gatcaaaaat actgagaaaa aaaaattaca 169860
cctgtactaa atatgtacag acttttttttg ttattattct ctaaacaata caacagcaat 169920
ttacatagca tttacattgt attagatata aataatctag agaagattta aagtatacga 169980
gaggatatga gtagattata tgcaaatact accccatttt atatcaggga cttgagaatc 170040
cacggatttt ggtatccctg ggaggttctg gagccaatcc cccatggata ccgagcaatg 170100
actgtacacg taaagctacc caatgagatt aaaaacttat ttggaaattt tattttggtg 170160
ttatgattaa ggtttatact ttaatctgca tgagtagtta tttatattag tcttttgaac 170220
aaaaatgagt aagaaaagat tctaacttac ccataccttta ttaaatcatg tttatgattt 170280
ctgtaaataa attgaaacct tatcatttta ttcctcctcc atcccttttt gaaaattaca 170340
tatagcacat agagtaaaaa ttcagacatc atttactaag gagttaaatt gatgcaatat 170400
taacttcaag ccaatgtgta ccttcagata ttcagtctgg acataattta tacggagtgg 170460
caaaactaat agtgttacaa gtatttcaga gtacaaaaag atgaagtttt aacttaagca 170520
gcgctattca gaaaatattg cctctagacc agttaataaa agacatcttg cctgggccat 170580
agttatcctg agtgaccttg ggctagttat ctgatcactc tatgctttga gtttagtttg 170640
ttgtttgtta ccaataatac ttgctatcat cagagatctt catttttttcc tcaaataaac 170700
attatataca aataaacatg gatgatatat tgctacttat taacccgtgg ttataggatt 170760
cagcattgtg gccttattat aatgccatat gaaaaagaaa tggaagatat ttttagctct 170820
ggtttattat attgtttcat caaatgaata tattttaatt ttttttttaa aataatgtca 170880
atgtagtacc ttctgctggg gatctgaaaa atgtttgcag acattatttc ttaaatcctg 170940
aaaacatccc tgtgaggtag gtgggtggta aatattatta tccccatttt acagatggag 171000
aattgaggca cagagagatt atgtgactca cccaaggtca cactacaagt cagtggtgga 171060
gccaggaata gaacccaaga ctcctgactc ctaatccact cccctagcca ctaggccctg 171120
ctccctcctc aaggtttcct cttgtgtgaa attctccttt gaaatgcaat ttcttgtttt 171180
taattcatgg ggaaagaagt acctgctcta atgcttctct aggtaaggcc accagcatat 171240
tcttccagtc attttaagtt ttaatttttt gaaataagga gccgtttata taatttatta 171300
acatatttat taaatgtttt atttaatttt aatatgaata tatgatgaga tttttcccct 171360
ctcccatagg atttgccttt attcagcatc caagtctaat gttcgagcaa gaagtgaaga 171420
atctatataa taatatttta tctgataaga actcctcagt caatttaaaa atacaagtgt 171480
taaaaaacct ccagacctac ctacaagaag aagatacacg tatgcagcag gcagatagag 171540
actgtaagtg aaaatatatt tttaaatttc atagctacat ttatattata atggctttat 171600
cttctttaat ctaaatatct aaatttcctt atttgttaga tgaagaaatt cagttaaata 171660
gcagtcctta tgctgaggtc tatagctggg ctttagcata ttcttaaatt ctctaaaata 171720
gttttaaaat tgtatatgtg tgtaaacatt aacattttga gggaggaaag agattatagt 171780
tctcactggg ttctcaaagg ggcctctgac acagacacac acacacacac acacacactc 171840
acacacagat taagaaccat tgagccagaa cactagctgt aacgttttgt gattttggtt 171900
atggcctaat tttgaaatat ttagtaaagt tagtataggt gctcttaatg tgtgtttatc 171960
ctttgcttgc ttttgtaggg aagaaagttg caaaacagga agacttaaaa gaaatgggtg 172020
atgtttcctc agggatgagt agttccatca tgcagcttta tctcaaacag gtgcttgagg 172080
```

-continued

```
catttttttca cacccagtca agtgtacgcc actttgccct aaatgtcatt gcattgactc 172140
taaatcaagg tcttattcat ccagttcagg taagcatgtt ttatggcagc agcacttact 172200
aaaagagcaa gattagttgt aatttgatac attgtgatta tagagaataa gtagttcttc 172260
gttcctctta ctcttctttg tactaaactc ttaagaatct ggcagtttta gataatctct 172320
tgggttatga ttactgcaaa atacccatat attcataata ttgtctctgt tataaacttg 172380
taatttctat tggcagaaca tatactcaaa ttatttttct aagtatgggt gatatatttg 172440
ttttaattca tatttacttt tgtccctaag atccaacaat ctataatgtg aagagagtta 172500
actgggttta aaagtataat ctgttcaaca gggtggagtc ttagtccaca gaaaagtaaa 172560
ttatataaac tcaattcctt catctttaag ttgggtataa caccaactac tcgacacctc 172620
atagcattaa tatgaggaca caacgacgta ataaagacat tagtgttact gaagattggc 172680
agccaatgct gatgtagtag tatataccat ctgatggtca agagagcacc ataggctaca 172740
aaagtgtatg tattaagtaa gcagagtcta tacccttcaa gatttttatt ttgggtattt 172800
ttcatggaac gttttaaaaa tatgatttat ttaaacatac tgtggtcttc cctgtgtcct 172860
gaaacaaaac atgttaacaa atatttatcc tgttcttcat gactccgggc tattatcata 172920
aagaatcata cattataatg aaacagtagt acattgagac tgtcaccttt ttaaactacc 172980
gagggttctt tgttgggtgc tttttattat atatgccttt taaacttttt tttttaattt 173040
cacacaaagg agtcaggtgc agtggctcac acatgtaatc ccagcacttt gggaggcaga 173100
ggtgggcgga tcacttgagt caggagttca aaaccagcat agccaacatg gcaaaacccc 173160
gtctctacta aaaatacaaa aattagccag gtgtggtggc acatgcctgt ggtcccagct 173220
acatgggagg ctgaggcagg aaaattgctt gaacccagga agcagagaac ccaggaagca 173280
gaggttgcag tgagctgaga ccgtgccatt gcactccagc ctggccaaca gagggagact 173340
ccatctcaaa aaaaaaaaaa aaaaaattca cacaaagaaa ttgcaaaagt gatacgatga 173400
attcctttat tctcttcacc tctattcacc atttgttgac attttgccac aattgctttc 173460
tctctctccc tttatacatc tgcttttttc tgaatcattt ggtaggaagt ttcaagtaat 173520
tatgattctt taccactaaa cacttcagca tatattttct aagaacaagg acattctctt 173580
acaaaaccgt aatataatca ttaaatttgg gaagtttaac actgatacaa tattatctaa 173640
tatacagttc atttgcagat tctgctagtt aaccaagggc gttctctata gccttttttcc 173700
tcttcttttt ttttgaggca agatcttgct ctgtttccca ggctggagtg cagtgatgca 173760
gtctcagctt acctgcagcc tccgcctcct ggattcaagc actcttccca cctctgcctc 173820
ccaagtagct gagactacag gtgtgcgcca ccacctggct aatttttgtg tttttgtaga 173880
gacggggttt taccatgttg gccaggctgg tctcaaactt ctgagctcaa gtaatctgcc 173940
tgcctcagtg tcccaaagtg ctgggattac aggcatgagc caccgcaccc accttacagc 174000
ctttttctt tcctgattcg agatttaaca tgatcatttc tttcatttag tgccatgtct 174060
gtattttaaa gttaggtttg ttgttgtttt tctggccttc acattgcttt ttaattcaga 174120
ctcacttaac atagtagtac tgttttttga ctctagaagt acagtgaata tgactgttat 174180
caactctctg ttcctcaaag ccacatctga aatcaacttt gaaaaacaat tatattttcg 174240
tagctttgag tatggaaaac aaattactgt ttgccctata ttatctttac aaggcaaatt 174300
cagtcaagct ttaaaaacta ctggattata catttgtagt ctatatcata atcttaaata 174360
gatattctta gtgtgagaat gctttatgtt taaagaacct aaaatttaca atgaaattgt 174420
ttaaatttta tcacgtcagt atttttgctg gtgctccagt gctttctgga tttaagctga 174480
```

-continued atctcaaaag atctgtcatt ttaaaaagaa cactaaaaca tagactttat aggaaggcct 174540
ataaggttaa attcatatat ctcagatata tgaaaagttt tgacatatgt ctaaatagag 174600
aatttttact accatgatat ctcgtaattt tttttttat ttccagtgtg tgccatattt 174660
aattgctatg ggcacagacc cagaacctgc tatgcggaac aaggctgatc agcaacttgt 174720
ggaaatagac aaaaaatatg ctggattcat tcatgtatgt attttaacat tttataacct 174780
aaatttaaac atttttcttg agtaaagcat ttctttgata aatgctctgc ccacattcat 174840
aattggaata aaatgtctta cttagtacct atcttctaaa catgcaacta agttagtctt 174900
ccaaggtgtt tattctagtc taaagttaag gttgggctag aggtgacagt accaagcaca 174960
ccagactaaa aatcaggaaa cctggatttt atatcttact atgtgaactt ggctgcagtg 175020
actctcctgg gcctcatttt ttttttcttc tttgaaatga gggaattgta agagataatc 175080
tctaatgttc cttctagcac ttcattctgt gattcgtatt attttaatta aaaaaaaaca 175140
atgaagctag cctcagaatg taatgctcta agtatatttt taatttgtgt cttttaattt 175200
ccctgacaaa aatgagactt ttattgattt cagatgaaag cagtggctgg tatgaagatg 175260
tcttaccagg tacaacaggc aatcaacaca tgcctaaaag atcctgtaag ggggtttcaga 175320
caagacgagt cctctagcgc tttgtgttca cacctttact ccatgatccg tggaaaccgc 175380
caacacagac gagcctttct tatttcttta ctcaacctct ttgatgacac agcagtaagc 175440
acaaaaaactt attattttaa gaaaataagt gctctagaaa ttttatggat aaagtagtca 175500
ttttttaaat attaccattt tattagtata tgatagtaac ttcattaagt gttttcttaa 175560
tcttctaagt tatttacaaa gtacacagtc agaagtgaag gggaaatttt gtatgagaat 175620
aagtgtaatg aggaataatg tataattttg cctccatact gaatatccta taaactttga 175680
taacagtttc tgtaagcgta tctttaaata agcaacatca ctaaactaat cgctttggga 175740
accgattacc tcaaatattg ttagagaata actgttctag gtttttggct attgagatcc 175800
ctagttgttc aacttgattt cccttaatga agggaagtca cttttctgta tagtagtcca 175860
cttttgtgta tagtagtcct ccccttatcat taaagataca tttcatgacc cccagtggat 175920
gcatgaaacc atggatagta ctaattatta tatatacagt catgcatcac ttaatgacag 175980
ggatacattt ggagaaatgc atagttaggc gatttctttg tggggtgaac atcttactta 176040
cacaaaccta gatgttgtag cctacctagg ctatattgtt cctgggctac aaacctgtac 176100
agcatgttac tgtactgaat actgtagata actataacac aatggtaagt attcatgtac 176160
ctaaacatat ctaaacatag aaaaggtaca gtaaaaatat gataggataa tcttatggga 176220
ccatcatcat atatatagtt tgtaattgac tgaaacatgt tatgtggcac atgactgtac 176280
tggtttttcc aatacataca aacctatgtt aaagttttaa tttataaatt agtcacagta 176340
agagattaac ataataataa aatagaacaa ttaaaacaat atactgtaat aaaagttatg 176400
tgaatgggat cttgcttttc tctctctctc aaaataccct gttgtagttt actcacctat 176460
ttttggacta tggttgacca agggtaactg aaactatgga aagcaaaaca gcaattgggg 176520
agattaccat aattacaatt ttgacacttc tggctgttgc actagttgca ttggccagga 176580
ccataggcca agaaaactga atattcttta aagtttacct tttaatttat ttatttcaca 176640
cagtatttat tctgcatctg ctatgtacca gccattgcgc taagaagttt aacgagcata 176700
aaatagtaaa aacagatatg gtttctgccc acacagagca cgcatgaacc tatgtgtata 176760
gcaactttta aaagaacaaa agaggccagg agtggtgact cacgcctgta atcccagcgc 176820

-continued

```
tttgggaggc caaggcaggt ggatcacaag gtcaggagtt cgagaccagc ctgaccaaca 176880
tggtgaaacc ccatctctac taaaaatata aaaattagcc gggcgtggtg gcacgcgcct 176940
gtaatcccag ctactcagga ggctgaggca ggagaattgc ttgaacccag gaggcagagg 177000
ttgcagtgag ctgagatcac gccactgcat tccagcctgg ccgacagagc gagactccgt 177060
ctcaaaaaaa aaaaaaaaaa aagaacaaaa gaaatacttt aattacttgt tagcctgaca 177120
gcagattttt gcaataaagc aaaattataa ttaccatagt gcagatatct tactagacct 177180
cttcaagtac tacatgaaat ttatcatcaa cattatcatc atatcattat cagtattaag 177240
tttgcattgt gtataggaca ctatacgagg agtgccagat gatataatgt agtgcttttg 177300
ccctgaaagg attttccctc cagctgtggg gataggatac aaaattaata gtgattacgg 177360
ttagtatatc ctgagtgccc tgatggtttg tgttgataat attgttccag tccttgtttc 177420
tgtccaaaag aacttcattt ctatgtgatt tcactgcctg ctttatgtca ttgactagat 177480
gttttgtcat ctcagcattt gaaatgctaa actggaaacc cagctctcac aatgcaatgc 177540
tttcttctga ctacctccaa caaagaatgt cagagaagga acaaatgcct gaaggcccag 177600
agggatagaa tgagagggat ctgctatata aaccagggaa ggaagatgtt ccagtcaggg 177660
ccaaaaaatt aattaaaaat acaaagataa gaatgtgtgg gaaataatga atagtttgtt 177720
atttgactgg ggcagaaagg tcataatgag gaataatata tagaggatcc tgtagatggc 177780
aaaaaaaaaa acattgtaag tgtgtgaata aaataatgag gacaattgcc aaagagcagt 177840
ttaggaagat gaattttttt agcattgtgg tcacactgga ggtaataata aattactatg 177900
ataacagtag gggagaaaaa gaatggatag tagaggctgg gtgtggtgcc tcatgcctgt 177960
aaccccagca tttggggagg ccgaggcaga tggatcacct gaggtcagga gttcgagaac 178020
agcctggcca acatggcaaa atcctctctc tcctgaaaat acaaaaaaat tagccaggca 178080
tgatggcgcg cacctgtagt cccagctact tgggaggctg aggcatgaga atcacttgaa 178140
cctgggcagc agagattggc agtgagctga gatcgcacca ctgcactcca gctgagcgac 178200
agagcgagac tccatctcaa cagtaaaaaa aaaaaaaaaa aagaatggat agtagaaaag 178260
aaaagaaagt tgaggaaaga attaaatgag actgtgtgaa aagaatagtt agtggacaac 178320
tggaatattt ttatcttgag cacctgaaac aataatagga ttgttgccaa agtcagattg 178380
caaaggagtt ggcttgagga gtacataaaa agggagtagt caaagaggta ggaagagaaa 178440
acttaggaag aagatttcat gaaggaaagt gtgggtaata gtcagatgct actgagaagt 178500
caaggagagt aagaagtgaa aaatagagta gaatggtgaa cttcgtggac aaaaacagtc 178560
aagcagtgag ggacaaaagc agattgtaat tgaaaaggga gggccaggtg agatgactca 178620
tgcttgtaat cccagcaccc aaggcagatg atagcttgag cccaggagtt ccataccagc 178680
ctgggcaaca tagtgagacc ctatctctac aaaaattaaa aaataaaaac tggacaggcc 178740
tggtggtatg cacctatact cctagctacc tagctactga agagaccaag gcaaagggat 178800
tgcttgagcc caggagttca aggtggcagt gagtggtatc atgtctcctt taaaaaaaaa 178860
tagtggggaa gacatgggag gagcagtcta aactattctt tgaagaactt tgaaaggaaa 178920
gagaaataca gggcttttat ggatgttgaa gaaaatatgt atattttctt caatattata 178980
tgagttttga aaatatatga attatagtgt taaaactaat agatgaggta gggttttatg 179040
tctacatttt ttcatctgta acgtgggtgt tgatacatat tgtaaagtaa aaatagagtg 179100
agagtgatac tcttatgaat attaatagca aggttattcc atctgtgcta tgggatcttg 179160
ctgctgctgc tgttgggttt tatgttgttt ccatggcagg ggaaggtaga tggtaggagt 179220
```

-continued gagtgttttt tagttgtgag cttttttttt ccttgagcta taaatattta aaagaaattt 179280
gaatattaat atgcctttct gtttatgatc atgaaatgct tgaattctct attacttctt 179340
tttaaagcaa gcaactaaat aatcataatt tttctcttaa attttgcctg cctcacagtt 179400
tttacagtgt gaaactgata gcattgtcaa aacaactctg acattctgaa ttacatatac 179460
acaggaaact gacaaatgtt tatgagtaca tgggatttgg gtttttttctt ttaacctatg 179520 tattagtact ataattacta gttattttga gggcagaata gtaactgtgt gtaactgatc 179580
tccatatagg ttaaactctt agtagcacaa tgatataact agaactttca tgtatacttt 179640
ctgatatggt atggatttat cataaagatt ccatatactc taagaaaact tcaaggaatt 179700
tcacatggat gcaataaaaa atttcacctc ttctcttgag atagcatagt gtaagtcatt 179760
ataaaattaa aaaaaatggg cctaagatta ttttataaaa ttccatttct gttccccctt 179820 ttccctttttt gttacacctg tctccctttc cctttttccc ccctctatat ttctctccct 179880
cctcctctcc ctctgtctct ctgtgtctct ccccactctc tccgtgtgtg tctgcttatc 179940
tctgtctaac attaagtgag gtgaaagtgc cctgtatttt ttctaaaaaa ggttttttgg 180000
ttgggtttct agattatccg ctaaacatgt gtgcttttttc ttaaaattta cagaaaacag 180060
acgtgactat gctcttgtat atagcagaca atctagcctg ttttccatac cagacacagg 180120
aagagccgtt gtttataatg catcatatag acattacact ctcagtttct ggtagtaacc 180180
tactgcagtc attcaaggag gtaagttaca cacattacta ttcttaatcc atctgtcaaa 180240
gtgcaggcat gctgttttca ctgttttgtt tctcattatt ctttttatcc tcttcacgag 180300
tatataaaat ctttctaagt gaacttaatg aaatctgggc aatacttgac ttgggagagg 180360
atgtacattg ccactttacc tctatttaga aacatctaaa atagatatat ggattgttct 180420
gttgataagc catcacattt atttctctca ctttaagcac tgaccttaag tgtttgcatc 180480
cattcataca ttcatttaaa ctccatttta aaacattatt ctgtaaatct tgtaatgctg 180540
taatcacaac attacacatg aaaatatata gcttatttac acttaaacag aaaatttatg 180600
acaccattga ctttcttatc cctcaactac agcaccgtta tagagtttgc atatgtgtgc 180660
ccaaaatctt tgctaaattt cttgttgaac cttccattgt ttctgtcatg acttttagga 180720
ggaatgtaat ttatttaatt ataaaagtac ctggtgtagc actaggcata tagtaagcac 180780
tcagtaaatt ctttacaaat tgaatattct catgtatcta atgatccaag tagatctcat 180840
tttataaaat tgtattgctc acaactcagc cttgtcagac tagtaaatca gacagattat 180900
tttagatgcc tcctgagggc tggaattaca gaggtgtctt aaacccttac tacttgaagt 180960
atagaccaca caccagcagc agtggtttca cctgagagct tattaaagct gtagaacctc 181020
aggccccacc cagatttgct gaaacagaat ctgcatcttc aacaaaatcc acagatgtta 181080
atgtgcacat ttaagtttga gaagttaata atttcccagg agctttagcc ctcatgttct 181140
cttattttac ctacttactg gtatggctat ctttgtaaat gtttcttcca cttttgaaga 181200
aatgttgtta taatgtgccc cacacacaca caccacacaa actgcttaag tccagttgac 181260
tttgtttcta agagctaaca ttttcataaa gtacaaagaa acaggattta agtcttcaga 181320
gaaaattgct tattatcttg ccgaaatgtt cttgaaaagg agagtttgct agaagctggg 181380
atgtccaaga ttactttatt ctcctcagtt aaattataat tactgctttt cctcataatg 181440
acttacctat gcaccaaatt gatactttta taactatctt ttattactgt ccttagaaga 181500
aaattgtttc cctttgaatg atatttcaga aggatttttt tgaaggagtg gttgtagggg 181560

-continued agggggtgga tattatatat aattttattt agttttagaa actatcccct aagattacat 181620
atccagttgt tgatataaag tcaagaggtt tataaaatat tagtttaagg aagctttttc 181680
aagctgttga atggagcata cttatattta ctagtggcat tttgttttta ttgtttatca 181740
aacgattttt tctttcagtc tatggtaaag gacaaaagga aagagagaaa atcatcacct 181800
agtaaggaaa atgagtcaag cgacagtgaa gaagaagttt ccaggcctcg gaagtcacgg 181860
aaacgtgtag attcagattc agattcagat tcagaagacg atataaattc agtgatgaaa 181920
tgtttgccag aaaattcagc tcctttaatc gaatttgcaa atgtgtccca gggtatttta 181980
ttacttctca tgttaaaaca acatttgaag aatctttgtg gattttctga taggtaaggt 182040
tacataagca gtgagagaaa aaacttcact ctgttcaaat aataaatatt tgggctgggt 182100
gtggtggctc atgcctgtaa tcccaacatt ttgggaggct gaggcgggca gatcccctga 182160
ggtcaggagt tcgagaccag cctggccaac atggtgaaac gccatctcta ttaaaaatac 182220
aaaaattagc ctagtgtggt ggtgcacgcc tgtgacccca gctactcagg agactgaggc 182280
aggaaaatcg cttaaacctg ggaggcggag attgcagtga gctgagatta cgccactgca 182340
ctccagcctg ggcaacagag caagactctg tctaaaaaaa taataataaa tatgaaaccc 182400
agttttgttt gcatgcttac tttaatgtta gaaatgttcc tttttaaaaa aggagtttat 182460
tctcttctat tgctggatag tattctattg tgtaatatgc cataatttat ttttattaaa 182520
gggaaaaaaa catattccta tacttggtga taatgcatta caaattgaag gacttatttt 182580
gttgatttcc ttaaaaagac tcaagctaac cttaaaatag attacaagtt taagttttta 182640
aagagctctg aagtaacaga tgtaaaccaa ctaaacagag ctccagtaga actcaaatag 182700
tatttaaagt actctataaa gtaagagaga gaaaaggtac agctattata aacaccctgt 182760
agttttaccc accagtagtc attaaagata cctcttttct gcctgtaacc atggaatttt 182820
ggtcattttt tacattcatt gaaatctaag attaggaatc acaaaatcaa atgttaatag 182880
gctacctggt caatggccaa ctggaaagag tgtgttgcat gtaaagaggt catttaagtg 182940
gacctgtctc aagtttccat aagcttgttg ccaaaggaga gggtaggcat aatgtggcta 183000
gagctcccac tttttcagga gacactagaa atccagattt ttaagaggaa tatctgtatt 183060
tgcaacaggg tctcgctctg atgcccaggt ggagtgcagt tatgcaatca taaactcctg 183120
ggctcaagta atcctcctac ttcagccacc tgagtagctg ggagtacaga tgcatgccac 183180
cacacccagc taattttttt tatttttttac ttgtagagat gatgtctagt tgtgttgctc 183240
atggtagtct tgaactcctg gcctcaagtg atcctcccac actggcctcc caaaactctg 183300
agattatagg catgagccac tgctcctggc cttataagga atatcttgat gttaaatgtt 183360
ggcaagatgc aaaataattt aaaaccttgt aaggttttga ggcaatgcta aggagttgga 183420
aagattttta agcagagttg ttaataacct gaaacaggtt tataaacaat cattctggcc 183480
actatataga ggatggatag gttgggggtg ggggagcaac tagtagaaag aggtaaacca 183540
gttaggtggt attaagtaat tgtattgaag ctgtcctagg atcacaatag tattaaaaat 183600
agacatgaga aactaatttc attaatatgg tgcttcctac ctataattgg atttctccaa 183660
atacgttgtt tccatagttt taaagttttt ggttttgttt tcccaaaaca gtaaaattca 183720
gaagtactct ccatctgaat ctgcaaaagt atatgataaa gcgataaacc gaaaaacagg 183780
agttcatttt catccaaaac aaacactgga cttcctgcgg agtgacatgg ctaattccaa 183840
aatcacagaa gaggtgaaaa ggagtatagt aaaacagtat ctagatgtga gtagtaaaac 183900
caaaagtttt tacttctcat aagggctttt ttgacaagta aatgtggggg gccggtgggg 183960

-continued agataactat ctccttcaca ttgaatataa gcttcatgaa ctatcaagat aatttttctc 184020
tatcttattt taatgagtta ctttaagctt gtctttccca ttgcacccat ggcatcctaa 184080
ttattttttc ttaggaaaca gcagcccacg aataatttta ttttagcaaa aatgaaagat 184140
tataggaaaa cctgtgtgtg ttttgtagtt gtcccctggt atctgcggga aattggttcc 184200
agtcccccca tggataccca aatcctccga tattcaaggg cctgataaaa aaatggcgta 184260
gtgggctgcg tgaggtggct cacacctgtc attccagtgc tttgggaggc catggcaggt 184320
ggatcacttg agctcaggag tttgagacca gcctgggcaa catggcaaat ccccgtatct 184380
ataaaaaata caaaaaatta cctggggggca gtggtgtgca cctgtagtcc cagctactca 184440
ggaggctgag gcaggagaag tgcttgagcc tgagaggcag aggttacagt gacctgagat 184500
tgcaccatta caccccatac tgggtgacag gagtgaaacc ctgtctcaaa aaaattattt 184560
aaaaagcata gtatttgcat ataacctaca tacatcctcc catatgcttt aagtcatttc 184620
tagattactt ataataccta atacaatgta aatgctatat acatagttgt tatactgcat 184680
ttttttaag ttgtattttt tattgtaatg ctgtttgttt tgttttgaga cggagtttca 184740
ctcttgttgc ccaggctgga gtgcaatggc gcgatctcgg ctcaccgcaa cttctgcctc 184800
ccaggttcaa gcaagtctcc tgcctcagcc tcccgcatag ctgggattac aggcgccagc 184860
caccacgccc ggctaatttt tgtattttta gtagagatgg ggtttcacca tgttggccag 184920
gctggtctca aactcctgac ctcaggtgat ccgccggcct cccaaagtgc tgggattaca 184980
ggcatgagcc accatacctg gccagtgctg ttattttttta ttgtggcatt ttccaaatag 185040
tttttgatcc actgtgggtt gaatccgcag gtgcggaatc cggggataca gagggctatg 185100
tttttaattc agaaaaatac atggcttata tgtcataaaa ggtaaaactg caagcagtca 185160
ttctcttacc gtgtttggct attctgttcc tttcttttct gataaccaat attattactt 185220
tttcgtatgt tcttatatga gtaatgccaa tatatatata tgtagatttt ctcacttatc 185280
aagtatgcaa atgtatgtat ataaaatgtg ctttaaaaat agagacagat aatagactag 185340
aggttaccaa ggaccgggga aggaaagaac ggggagttat tgtttaatga ggacagctgt 185400
ggtttccagt gattaaaaaa aaaaagaaac agctctggaa atggacagtg gtgatagttg 185460
tacaatatgc caatgaatta tacatttaaa atggttaaac tggtaggctg gacatgctgg 185520
cttatacctg taatcttagc accttgggag gcctatgtag gaggtttgct tgagtccagg 185580
aagtccaggc cagcctgagc aacagggtga gaccctgtct ctacaaaaaa tacaaacatt 185640
agccagacat ggcggtgtgc acctgtagtc ccaactgctg gggaggctga ggtgggagga 185700
ccacctaagc ctgggaggtg gaggctacag tgagccatga tcgtgccact gcacttcagc 185760
ctgagtgaca gagtgagacc ctgtctcaat ttaaaaagaa aaaaaaaaag ggttaagctg 185820
gcaaatttta tgatatttct attttatcac aatataaaag tttttaaaaa tgtttttgaa 185880
attagaggac tatcctaaaa aataaaaata aagttttata ttttaatcta cttaatttca 185940
ggtgtagtgg ctcacaagca ctttgggagg ctgaggtggg cagatcactc gaggccagag 186000
gtttgacacc agtttggcca acattgcaaa accccatttc tatttttctt aaaaaaattt 186060
ttaaaaatct actttaaagc aagtagctga acataaaata aggtttttttg aactaagaat 186120
ataatctaca cagtggcttt tcatattatt cattgactgc aaaccttact ctaaaattta 186180
aaaatatttt agttcttatt taaaattttt caacattctt tgctttctct tgtatcgtct 186240
tagcagagag caaagagggg agataactag aaaatgtcta tcagtaatta tcacctgatt 186300

-continued

```
gcttgatgac ttggaccaag ggtctgaaaa ctctggctgt ttttgtatct aacccattgc 186360
ctgtttttgc aaacaaagtt ttattgaaaa cattcatgcc cactcattta tttgtctgta 186420
gctgctttca tactacagtg gcagagttgg gtagttgtga cagactattt gaccttcaaa 186480
atgaaaaata tttaccacct ggctgtttac agaaaatgtt tactagcccc taatttagat 186540
gatggctaac gtctgtttca cccacaccaa actactgcca tagaaaacat ttaggaattt 186600
gacaatcttg cttgaaatat ttacttaaaa ttctgaaata atatctgttt tttgtagttc 186660
aaacttctca tggaacatct ggaccctgat gaagaagaag aagaagggga ggtttcagct 186720
agcacaaatg ctcggaacaa agcaattacc tcactgcttg gaggaggcag ccctaaaaat 186780
aatacagcag cagagacaga agatgatgaa agtgatgggg aggatagagg aggaggcact 186840
tcaggggtga ggcggaggag gagtcaacgt atttcgcagc gtattacgta aaatgatttt 186900
tatgtgctta tatatgtcag tctattaaat gtacaccaag taatgtaata cttaaaagag 186960
aaaacatttt gtagatagag attctctact tacccgttta tacatccttt tgtagaaagt 187020
ttaacataaa agacaataaa aaaacagaaa tgagatttat ccagcataaa gggttaattt 187080
ttctttgaat tgtattaatg tgtgttattt ttattgttgc taagttttat gtagctatat 187140
ggttcatatg tatatataat tttatatatc aataagagta aagacacggg tacaaattaa 187200
gagttatatg gttttacaag tatatgttaa ccccttggcg ctggcggtca cggtgcgtct 187260
cattgccggc aatggaagtg tgccgggaaa tcccaactcc cggcgtcaag ggattaaaag 187320
caataaaaac aataatttca ctaaaattct tttgtgtaac acttggtctt ttttcccccc 187380
tcccaatgtt ttagtcattg agaaggtcaa aacgaaattc agactctacg gagttggcag 187440
cacagatgaa tgaaagtgtt gacgtcatgg atgtcatcgc tatttgctgt ccaaagtaca 187500
aagatcgacc acaaattgca agagtagtgc agaaaaccag cagtggcttc agtgttcagt 187560
ggatggcagg ctcctacagt ggctcctgga ctgaggctaa gcgccgtgat ggccgcaaac 187620
tggtgccttg ggtagacact attaaagagt cagacattat ttacaaaaaa attgctctaa 187680
cgagtgctaa taagctgact aataaagttg ttcagacttt acgatccctg tatgccgcca 187740
aggatgggac ttccagctaa tgaatttgta catgcagcca aatttacagg aattttttta 187800
aaaggcagaa aaacttgaaa taccaacatt ctggcaaaaa aaaatcagtt ttatgaagag 187860
taagtggaac ctgggatgca ggaacaaaag aaggaaatgt tgggcaaaca tttttgtggg 187920
agctcccttc gctgttgtgc agcagaaaca gattctcagt tcatttttac tcccactgta 187980
ttatagttta acaaaaattg tttatatctt ggaaaaaaaa ctttctgttt aaaaaaaata 188040
aacaagtgaa tgttgg                                                 188056
```

<210> SEQ ID NO 2
<211> LENGTH: 9505
<212> TYPE: DNA
<213> ORGANISM: Artificial Sequence
<220> FEATURE:
<223> OTHER INFORMATION: Synthetic Sequence

<400> SEQUENCE: 2

```
gacagcggcc tcggcctccc cttggattca gacgccgatt cgcccagtgt ttgggaaatg     60
ggaagtaatg acagctggca cctgaactaa gtacttttat aggcaacacc attccagaaa    120
ttcaggatga atggggatat gccccatgtc cccattacta ctcttgcggg gattgctagt    180
ctcacagacc tcctgaacca gctgcctctt ccatctcctt tacctgctac aactacaaag    240
agccttctct ttaatgcacg aatagcagaa gaggtgaact gccttttggc ttgtagggat    300
```

-continued

```
gacaatttgg tttcacagct tgtccatagc ctcaaccagg tatcaacaga tcacatagag    360
ttgaaagata accttggcag tgatgaccca gaaggtgaca taccagtctt gttgcaggcc    420
gtcctggcaa ggagtcctaa tgttttcagg gagaaaagca tgcagaacag atatgtacaa    480
agtggaatga tgatgtctca gtataaactt tctcagaatt ccatgcacag tagtcctgca    540
tcttccaatt atcaacaaac cactatctca catagcccct ccagccggtt tgtgccacca    600
cagacaagct ctgggaacag atttatgcca cagcaaaata gcccagtgcc tagtccatac    660
gccccacaaa gccctgcagg atacatgcca tattcccatc cttcaagtta cacaacacat    720
ccacagatgc aacaagcatc ggtatcaagt cccattgttg caggtggttt gagaaacata    780
catgataata aagtttctgg tccgttgtct ggcaattcag ctaatcatca tgctgataat    840
cctagacatg gttcaagtga ggactaccta cacatggtgc acaggctaag tagtgacgat    900
ggagattctt caacaatgag gaatgctgca tcttttccct tgagatctcc acagccagta    960
tgctcccctg ctggaagtga aggaactcct aaaggctcaa gaccaccttt aatcctacaa   1020
tctcagtctc taccttgttc atcacctcga gatgttccac cagatatctt gctagattct   1080
ccagaaagaa aacaaaagaa gcagaagaaa atgaaattag gcaaggatga aaaagagcag   1140
agtgagaaag cggcaatgta tgatataatt agttctccat ccaaggactc tactaaactt   1200
acattaagac tttctcgtgt aaggtcttca gacatggacc agcaagagga tatgatttct   1260
ggtgtggaaa atagcaatgt ttcagaaaat gatattcctt ttaatgtgca gtacccagga   1320
cagacttcaa aaacacccat tactccacaa gatataaacc gcccactaaa tgctgctcaa   1380
tgtttgtcgc agcaagaaca aacagcattc cttccagcaa atcaagtgcc tgttttacaa   1440
cagaacactt cagttgctgc aaaacaaccc cagacttctg tggtacagaa tcaacaacag   1500
atatcacaac agggacctat atatgatgaa gtggaattgg atgcattggc tgaaattgag   1560
cgaatagaga gagaatcagc tattgaaagg gagcgcttct caaaagaagt tcaagataaa   1620
gataagcctt tgaaaaaaag aaaacaagat tcttacccac aggaggctgg gggtgctaca   1680
ggaggtaata gaccagcttc tcaggagacg ggttctacgg gaaatgggtc aaggccagca   1740
ttaatggtta gcattgatct tcatcagaca ggaagagtgg actctcaggc ttctataact   1800
caggattcag actccataaa aaagcctgaa gaaatcaaac aatgtagtga tgcacctgtt   1860
tctgttcttc aggaagatat tgttggaagt cttaaatcta caccagaaaa ccatcctgag   1920
acacctaaaa aaaagtctga tcctgagctt tcaaagagtg aaatgaaaca aagtgaaagt   1980
agattagcag aatctaaacc aaatgaaaac cgattggtgg agacaaaatc aagtgaaaat   2040
aagttagaaa ctaaagttga gacccaaata gaagaactta aacagaatga gagcagaaca   2100
actgaatgca aacaaaacga gagcaccata gttgagccta aacaaaatga aaatagactg   2160
tctgacacaa aaccaaatga caacaaacaa aataatggca gatcagaaac aacaaaatca   2220
aggcctgaaa ccccaaagca aaagggtgaa agccggcctg agactccaaa acaaaagagt   2280
gatgggcatc ctgaaacccc aaaacagaag ggtgatggaa ggcctgaaac tccaaagcaa   2340
aaaggtgaga gccgccctga aactccaaag caaaaaaatg aagggcgacc tgaaacacca   2400
aaacacaggc atgacaatag gagggattct ggaaagccat ctacagagaa aaaacctgaa   2460
gtgtctaaac ataaacaaga tactaaatct gactcacctc ggttaaaatc agaacgagct   2520
gaagccttaa agcagagacc tgatgggcga tctgtttctg agtcactaag acgtgaccat   2580
gataataaac aaaaatcaga tgacaggggt gaatcagagc gacatcgagg ggatcagtct   2640
```

-continued agggttcgaa gaccagaaac attgagatcc tctagtagaa atgaacatgg cattaaatct 2700
gatagttcaa aaactgataa actagaacga aaacacaggc acgaatcagg ggactcaagg 2760
gaaagaccat cttctgggga acaaaaatca agacctgaca gtcctcgtgt taaacaagga 2820
gattctaata aatcaagatc tgataaactt ggttttaaat caccaactag taaagatgac 2880
aaaaggacag agggtaacaa gagtaaagta gacactaata aagcacaccc tgacaataag 2940
gcagaatttc caagttattt gttgggggc aggtctggtg cgttgaaaaa ttttgtcatt 3000
ccgaaaatca agagggataa agatggcaat gttactcagg agacaaagaa aatggaaatg 3060
aaaggagagc cgaaagacaa agtagaaaaa ataggattag ttgaagatct aaataaagga 3120
gctaagcctg tagttgtgct acaaaaactg tctttggatg atgttcagaa acttattaaa 3180
gatagagagg acaaatcgag aagttccctt aaacctatca agaataaacc atcaaagtca 3240
aataaaggta gtatagatca atcagtgtta aaagaattac cccctgaact cctggcagaa 3300
attgagtcca ccatgccact ttgtgaacgt gtgaaaatga acaaacgcaa gcgtagcaca 3360
gttaatgaaa agccaaaata tgctgaaatc agttcagatg aagataatga tagtgatgaa 3420
gcttttgaat cctctaggaa acgacataaa aaagatgatg ataaagcttg ggaatatgaa 3480
gagcgtgaca gaagaagctc tggggatcat aggagaagtg gccactctca tgaaggaaga 3540
aggagttcag gtggtggtcg ttatcgaaac cgaagtccgt cagattctga catggaagat 3600
tattctcctc ctcccagcct tagtgaggtt gctaggaaaa tgaagaaaaa agaaaaacag 3660
aagaaaagga aagcatatga accaaaacta acacctgaag aaatgatgga ctcttcaact 3720
tttaagagat tcacagcctc aatagagaat attttggata atttggaaga tatggatttt 3780
actgcgtttg gtgatgatga tgaaattcct caggaactgc tcttaggaaa acatcagctt 3840
aatgaacttg gcagtgaatc tgctaaaata aaagcaatgg gtataatgga taagctttca 3900
actgacaaaa ctgtgaaagt cttaaatatc ttggagaaga atattcagga tgggtcaaag 3960
ctttccactt tgttaaatca taataacgat actgaagaag aagaaaggtt atggagagac 4020
cttattatgg agagagttac aaaatcagcg gatgcttgtc ttacaactat caacattatg 4080
acatccccta acatgccaaa agctgtgtac attgaggatg taattgaaag agttatacag 4140
tacactaaat ttcatttgca gaatacactt tatcctcagt atgatcctgt ttacagatta 4200
gatcctcatg gaggaggctt attaagttca aaagcaaaac gggctaaatg ttctacccat 4260
aagcagagag taatagtaat gctttataac aaagtttgtg acattgttag cagcttatca 4320
gaattgctag agatacaact tcttacagac acaacaattc ttcaggtttc atctatggga 4380
ataacaccat tttttgtgga aaatgtcagt gaactacagt tgtgtgccat taagttagtc 4440
actgcagtat tctcaagata tgaaaaacat aggcagttaa ttttggaaga aatttttact 4500
tcacttgcaa gattaccaac cagcaagagg agtttaagga acttcaggtt aaacagtagt 4560
gatatggatg gagaacctat gtatattcag atggttacag cactggtttt acaacttatt 4620
cagtgtgtgg tacacttacc atcatcagag aaggactcta atgcagaaga agattcaaat 4680
aaaaaaattg accaggatgt tgtcattact aactcttatg aaacagctat gcgaacagcc 4740
caaaacttcc tctccatctt ccttaaaaaa tgtggtagta agcaaggtga agaagattac 4800
agaccactgt ttgaaaattt tgttcaagac cttctttcaa cagtcaataa gcctgaatgg 4860
ccagctgctg aactactcct tagtttgtta gggagactgt tggttcatca gttcagtaac 4920
aagtcaacag agatggcttt aagagtggca tctcttgatt accttggaac tgttgctgca 4980
cggctaagaa aagatgctgt tacaagcaaa atggatcaag gatctataga acgcatttta 5040

-continued aaacaggttt caggagggga agatgaaatc caacaattac aaaaagcatt gcttgattac 5100
ttggatgaaa acactgagac tgatccttca ctagtgtttt ctcgtaaatt ctatatagcc 5160
cagtggtttc gagacacaac tctggaaaca gaaaaagcaa tgaaatcaca aaaagatgaa 5220
gaatcatctg aaggaacaca tcatgcaaag gaaattgaga caactggcca aattatgcat 5280
cgagctgaaa accgaaaaaa gtttcttaga agcattatca aaaccacacc ttctcagttt 5340
agcacattaa agatgaactc tgatactgtg gactatgatg atgcttgctt gattgttcga 5400
tacttggcct ccatgaggcc gtttgcccag agctttgata tttatttgac acagatccta 5460
cgagttcttg gtgaaaatgc aattgctgtt cgaacaaaag ccatgaagtg tttgtctgag 5520
gttgttgctg tagaccccag tattctagca aggcttgata tgcaacgagg tgttcatgga 5580
cgattgatgg ataattcgac tagtgtccga gaagcagcag tagaattact aggtcgattt 5640
gtcctttgtc gacctcagct tgctgaacag tattatgata tgctgattga aagaatattg 5700
gatactggta tcagtgtcag gaaaagagta ataaagattc tcagagacat ttgtattgaa 5760
caaccaacat ttccaaaaat cacagaaatg tgtgtaaaaa tgattcgcag agtcaatgat 5820
gaagagggca ttaagaaatt agtaaatgaa acattccaga aactctggtt tactccaact 5880
ccacacaatg acaaagaagc aatgacaagg aaaattttaa acattaccga tgtggttgca 5940
gcatgcagag atactggata tgactggttt gagcaactgc ttcaaaactt gttgaagtcc 6000
gaagaggatt cctcatataa acctgtgaag aaagcttgta ctcaacttgt tgataaccta 6060
gttgagcaca ttcttaaata tgaggaatct ctagctgact ctgacaataa aggtgtgaat 6120
tctggaagat tggtagcttg cataaccact ttgttcttat tcagcaaaat aagaccccag 6180
ctcatggtta aacatgcaat gactatgcaa ccatacctta ccactaaatg tagtacgcaa 6240
aatgatttca tggttatctg caatgttgca aaaatcctag agctagttgt accactgatg 6300
gagcatccaa gtgaaacttt tcttgccact attgaggaag atctaatgaa gctcatcatc 6360
aaatatggca tgactgtagt gcaacattgt gtgagctgtc ttggagctgt tgtaaataaa 6420
gtgacacaaa attttaaatt tgtgtgggct tgtttcaata gatactatgg tgccatttca 6480
aaattaaaaa gtcaacacca agaggaccca aataacactt cacttctaac aaacaaacca 6540
gcacttctta gatccctttt caccgttgga gcactatgtc ggcattttga ttttgatctg 6600
gaagatttta aaggcaacag caaggttaac ataaaagata aagtacttga actattgatg 6660
tattttacaa aacactcaga tgaagaagta caaacaaaag ctatcattgg tctaggattt 6720
gcctttattc agcatccaag tctaatgttc gagcaagaag tgaagaatct atataataat 6780
attttatctg ataagaactc ctcagtcaat ttaaaaatac aagtgttaaa aaacctccag 6840
acctacctac aagaagaaga tacacgtatg cagcaggcag atagagactg gaagaaagtt 6900
gcaaaacagg aagacttaaa agaaatgggt gatgtttcct cagggatgag tagttccatc 6960
atgcagcttt atctcaaaca ggtgcttgag gcatttttc acacccagtc aagtgtacgc 7020
cactttgccc taaatgtcat tgcattgact ctaaatcaag gtcttattca tccagttcag 7080
tgtgtgccat atttaattgc tatgggcaca gacccagaac ctgctatgcg gaacaaggct 7140
gatcagcaac ttgtggaaat agacaaaaaa tatgctggat tcattcatat gaaagcagtg 7200
gctggtatga agatgtctta ccaggtacaa caggcaatca acacatgcct aaaagatcct 7260
gtaaggggtt tcagacaaga cgagtcctct agcgctttgt gttcacacct ttactccatg 7320
atccgtggaa accgccaaca cagacgagcc tttcttattt ctttactcaa cctctttgat 7380

-continued

```
gacacagcaa aaacagacgt gactatgctc ttgtatatag cagacaatct agcctgtttt   7440

ccataccaga cacaggaaga gccgttgttt ataatgcatc atatagacat tacactctca   7500

gtttctggta gtaacctact gcagtcattc aaggagtcta tggtaaagga caaaaggaaa   7560

gagagaaaat catcacctag taaggaaaat gagtcaagcg acagtgaaga agaagtttcc   7620

aggcctcgga agtcacggaa acgtgtagat tcagattcag attcagattc agaagacgat   7680

ataaattcag tgatgaaatg tttgccagaa aattcagctc ctttaatcga atttgcaaat   7740

gtgtcccagg gtattttatt acttctcatg ttaaaacaac atttgaagaa tctttgtgga   7800

ttttctgata gtaaaattca gaagtactct ccatctgaat ctgcaaaagt atatgataaa   7860

gcgataaacc gaaaaacagg agttcatttt catccaaaac aaacactgga cttcctgcgg   7920

agtgacatgg ctaattccaa aatcacagaa gaggtgaaaa ggagtatagt aaaacagtat   7980

ctagatttca aacttctcat ggaacatctg gaccctgatg aagaagaaga agaaggggag   8040

gtttcagcta gcacaaatgc tcggaacaaa gcaattacct cactgcttgg aggaggcagc   8100

cctaaaaata atacagcagc agagacagaa gatgatgaaa gtgatgggga ggatagagga   8160

ggaggcactt cagggtcatt gagaaggtca aaacgaaatt cagactctac ggagttggca   8220

gcacagatga atgaaagtgt tgacgtcatg gatgtcatcg ctatttgctg tccaaagtac   8280

aaagatcgac cacaaattgc aagagtagtg cagaaaacca gcagtggctt cagtgttcag   8340

tggatggcag gctcctacag tggctcctgg actgaggcta agcgccgtga tggccgcaaa   8400

ctggtgcctt gggtagacac tattaaagag tcagacatta tttacaaaaa aattgctcta   8460

acgagtgcta ataagctgac taataaagtt gttcagactt tacgatccct gtatgccgcc   8520

aaggatggga cttccagcta atgaatttgt acatgcagcc aaatttacag gaattttttt   8580

taaaaggcag aaaaacttga aataccaaca ttctggcaaa aaaaaatcag ttttatgaag   8640

agtaagtgga acctgggatg caggaacaaa agaaggaaat gttgggcaaa catttttgtg   8700

ggagctccct tcgctgttgt gcagcagaaa cagattctca gttcattttt actcccactg   8760

tattatagtt taacaaaaat tgtttatatc ttggaaaaaa aactttctgt ttaaaaaaaa   8820

taaacaagtg aatgttggaa attagtctgt taatgttctt aataaagtgt tcttggagtt   8880

taacctagca gcggatggct ttctttagct tagcccagtt tccagggaag cattgttttt   8940

tccaggctgt aaaatggcag aatctcctgg atatataatt tattctgttg aaaaaaaaaa   9000

aagcatgcag tatctatgac ctatctgcag aaggagtttt tgtaaatgta gattttgatg   9060

tattaggtca ccctgaaaac aatacaagaa aagggatccc caggtaatct ggtggagcga   9120

atactgcaat aaattttttt acttctcttt gttacttgtc tgtttccatt tgaatttctt   9180

attgtaaaaa tctgtttaaa tccatttata ttattttaca gtcttttatg taaaatttat   9240

tatatcactg gttttcaaag caaaacataa aatattgttt atacagtttg tataggctga   9300

cttctgaata attggtatct attattttca ttcccataag agggtgtaaa caattaactc   9360

cagggtttta ttgtatcctg caatatttag tattaactat atatgattta gcactgtgcc   9420

aaacacattt tcaagagtac attttgatat aaaaagaaac tatagtttaa aaaaaaaaaa   9480

aaaaaaaaaa aaaaaaaaaa aaaaa                                         9505
```

<210> SEQ ID NO 3
<211> LENGTH: 2804
<212> TYPE: PRT
<213> ORGANISM: Artificial Sequence
<220> FEATURE:
<223> OTHER INFORMATION: Synthetic Sequence

<400> SEQUENCE: 3

```
Met Asn Gly Asp Met Pro His Val Pro Ile Thr Thr Leu Ala Gly Ile
 1               5                  10                  15

Ala Ser Leu Thr Asp Leu Leu Asn Gln Leu Pro Leu Pro Ser Pro Leu
            20                  25                  30

Pro Ala Thr Thr Thr Lys Ser Leu Leu Phe Asn Ala Arg Ile Ala Glu
        35                  40                  45

Glu Val Asn Cys Leu Leu Ala Cys Arg Asp Asp Asn Leu Val Ser Gln
    50                  55                  60

Leu Val His Ser Leu Asn Gln Val Ser Thr Asp His Ile Glu Leu Lys
65                  70                  75                  80

Asp Asn Leu Gly Ser Asp Asp Pro Glu Gly Asp Ile Pro Val Leu Leu
                85                  90                  95

Gln Ala Val Leu Ala Arg Ser Pro Asn Val Phe Arg Glu Lys Ser Met
            100                 105                 110

Gln Asn Arg Tyr Val Gln Ser Gly Met Met Met Ser Gln Tyr Lys Leu
        115                 120                 125

Ser Gln Asn Ser Met His Ser Ser Pro Ala Ser Ser Asn Tyr Gln Gln
    130                 135                 140

Thr Thr Ile Ser His Ser Pro Ser Ser Arg Phe Val Pro Pro Gln Thr
145                 150                 155                 160

Ser Ser Gly Asn Arg Phe Met Pro Gln Gln Asn Ser Pro Val Pro Ser
                165                 170                 175

Pro Tyr Ala Pro Gln Ser Pro Ala Gly Tyr Met Pro Tyr Ser His Pro
            180                 185                 190

Ser Ser Tyr Thr Thr His Pro Gln Met Gln Gln Ala Ser Val Ser Ser
        195                 200                 205

Pro Ile Val Ala Gly Gly Leu Arg Asn Ile His Asp Asn Lys Val Ser
    210                 215                 220

Gly Pro Leu Ser Gly Asn Ser Ala Asn His His Ala Asp Asn Pro Arg
225                 230                 235                 240

His Gly Ser Ser Glu Asp Tyr Leu His Met Val His Arg Leu Ser Ser
                245                 250                 255

Asp Asp Gly Asp Ser Ser Thr Met Arg Asn Ala Ala Ser Phe Pro Leu
            260                 265                 270

Arg Ser Pro Gln Pro Val Cys Ser Pro Ala Gly Ser Glu Gly Thr Pro
        275                 280                 285

Lys Gly Ser Arg Pro Pro Leu Ile Leu Gln Ser Gln Ser Leu Pro Cys
    290                 295                 300

Ser Ser Pro Arg Asp Val Pro Pro Asp Ile Leu Leu Asp Ser Pro Glu
305                 310                 315                 320

Arg Lys Gln Lys Lys Gln Lys Lys Met Lys Leu Gly Lys Asp Glu Lys
                325                 330                 335

Glu Gln Ser Glu Lys Ala Ala Met Tyr Asp Ile Ile Ser Ser Pro Ser
            340                 345                 350

Lys Asp Ser Thr Lys Leu Thr Leu Arg Leu Ser Arg Val Arg Ser Ser
        355                 360                 365

Asp Met Asp Gln Gln Glu Asp Met Ile Ser Gly Val Glu Asn Ser Asn
    370                 375                 380

Val Ser Glu Asn Asp Ile Pro Phe Asn Val Gln Tyr Pro Gly Gln Thr
385                 390                 395                 400

Ser Lys Thr Pro Ile Thr Pro Gln Asp Ile Asn Arg Pro Leu Asn Ala
```

-continued

```
                405                 410                 415

Ala Gln Cys Leu Ser Gln Gln Glu Gln Thr Ala Phe Leu Pro Ala Asn
            420                 425                 430

Gln Val Pro Val Leu Gln Gln Asn Thr Ser Val Ala Ala Lys Gln Pro
        435                 440                 445

Gln Thr Ser Val Val Gln Asn Gln Gln Gln Ile Ser Gln Gln Gly Pro
    450                 455                 460

Ile Tyr Asp Glu Val Glu Leu Asp Ala Leu Ala Glu Ile Glu Arg Ile
465                 470                 475                 480

Glu Arg Glu Ser Ala Ile Glu Arg Glu Arg Phe Ser Lys Glu Val Gln
                485                 490                 495

Asp Lys Asp Lys Pro Leu Lys Lys Arg Lys Gln Asp Ser Tyr Pro Gln
            500                 505                 510

Glu Ala Gly Gly Ala Thr Gly Gly Asn Arg Pro Ala Ser Gln Glu Thr
        515                 520                 525

Gly Ser Thr Gly Asn Gly Ser Arg Pro Ala Leu Met Val Ser Ile Asp
    530                 535                 540

Leu His Gln Ala Gly Arg Val Asp Ser Gln Ala Ser Ile Thr Gln Asp
545                 550                 555                 560

Ser Asp Ser Ile Lys Lys Pro Glu Glu Ile Lys Gln Cys Asn Asp Ala
                565                 570                 575

Pro Val Ser Val Leu Gln Glu Asp Ile Val Gly Ser Leu Lys Ser Thr
            580                 585                 590

Pro Glu Asn His Pro Glu Thr Pro Lys Lys Lys Ser Asp Pro Glu Leu
        595                 600                 605

Ser Lys Ser Glu Met Lys Gln Ser Glu Ser Arg Leu Ala Glu Ser Lys
    610                 615                 620

Pro Asn Glu Asn Arg Leu Val Glu Thr Lys Ser Ser Glu Asn Lys Leu
625                 630                 635                 640

Glu Thr Lys Val Glu Thr Gln Thr Glu Glu Leu Lys Gln Asn Glu Ser
                645                 650                 655

Arg Thr Thr Glu Cys Lys Gln Asn Glu Ser Thr Ile Val Glu Pro Lys
            660                 665                 670

Gln Asn Glu Asn Arg Leu Ser Asp Thr Lys Pro Asn Asp Asn Lys Gln
        675                 680                 685

Asn Asn Gly Arg Ser Glu Thr Thr Lys Ser Arg Pro Glu Thr Pro Lys
    690                 695                 700

Gln Lys Gly Glu Ser Arg Pro Glu Thr Pro Lys Gln Lys Ser Asp Gly
705                 710                 715                 720

His Pro Glu Thr Pro Lys Gln Lys Gly Asp Gly Arg Pro Glu Thr Pro
                725                 730                 735

Lys Gln Lys Gly Glu Ser Arg Pro Glu Thr Pro Lys Gln Lys Asn Glu
            740                 745                 750

Gly Arg Pro Glu Thr Pro Lys His Arg His Asp Asn Arg Arg Asp Ser
        755                 760                 765

Gly Lys Pro Ser Thr Glu Lys Lys Pro Glu Val Ser Lys His Lys Gln
    770                 775                 780

Asp Thr Lys Ser Asp Ser Pro Arg Leu Lys Ser Glu Arg Ala Glu Ala
785                 790                 795                 800

Leu Lys Gln Arg Pro Asp Gly Arg Ser Val Ser Glu Ser Leu Arg Arg
                805                 810                 815

Asp His Asp Asn Lys Gln Lys Ser Asp Asp Arg Gly Glu Ser Glu Arg
            820                 825                 830
```

-continued

```
His Arg Gly Asp Gln Ser Arg Val Arg Arg Pro Glu Thr Leu Arg Ser
        835                 840                 845

Ser Ser Arg Asn Glu His Gly Ile Lys Ser Asp Ser Ser Lys Thr Asp
    850                 855                 860

Lys Leu Glu Arg Lys His Arg His Glu Ser Gly Asp Ser Arg Glu Arg
865                 870                 875                 880

Pro Ser Ser Gly Glu Gln Lys Ser Arg Pro Asp Ser Pro Arg Val Lys
                885                 890                 895

Gln Gly Asp Ser Asn Lys Ser Arg Ser Asp Lys Leu Gly Phe Lys Ser
            900                 905                 910

Pro Thr Ser Lys Asp Asp Lys Arg Thr Glu Gly Asn Lys Ser Lys Val
        915                 920                 925

Asp Thr Asn Lys Ala His Pro Asp Asn Lys Ala Glu Phe Pro Ser Tyr
    930                 935                 940

Leu Leu Gly Gly Arg Ser Gly Ala Leu Lys Asn Phe Val Ile Pro Lys
945                 950                 955                 960

Ile Lys Arg Asp Lys Asp Gly Asn Val Thr Gln Glu Thr Lys Lys Met
                965                 970                 975

Glu Met Lys Gly Glu Pro Lys Asp Lys Val Glu Lys Ile Gly Leu Val
            980                 985                 990

Glu Asp Leu Asn Lys Gly Ala Lys Pro Val Val Val Leu Gln Lys Leu
        995                 1000                1005

Ser Leu Asp Asp Val Gln Lys Leu Ile Lys Asp Arg Glu Asp Lys Ser
    1010                1015                1020

Arg Ser Ser Leu Lys Pro Ile Lys Asn Lys Pro Ser Lys Ser Asn Lys
1025                1030                1035                1040

Gly Ser Ile Asp Gln Ser Val Leu Lys Glu Leu Pro Pro Glu Leu Leu
                1045                1050                1055

Ala Glu Ile Glu Ser Thr Met Pro Leu Cys Glu Arg Val Lys Met Asn
            1060                1065                1070

Lys Arg Lys Arg Ser Thr Val Asn Glu Lys Pro Lys Tyr Ala Glu Ile
        1075                1080                1085

Ser Ser Asp Glu Asp Asn Asp Ser Asp Glu Ala Phe Glu Ser Ser Arg
    1090                1095                1100

Lys Arg His Lys Lys Asp Asp Asp Lys Ala Trp Glu Tyr Glu Glu Arg
1105                1110                1115                1120

Asp Arg Arg Ser Ser Gly Asp His Arg Arg Ser Gly His Ser His Glu
                1125                1130                1135

Gly Arg Arg Ser Ser Gly Gly Gly Arg Tyr Arg Asn Arg Ser Pro Ser
            1140                1145                1150

Asp Ser Asp Met Glu Asp Tyr Ser Pro Pro Pro Ser Leu Ser Glu Val
        1155                1160                1165

Ala Arg Lys Met Lys Lys Lys Glu Lys Gln Lys Lys Arg Lys Ala Tyr
    1170                1175                1180

Glu Pro Lys Leu Thr Pro Glu Glu Met Met Asp Ser Ser Thr Phe Lys
1185                1190                1195                1200

Arg Phe Thr Ala Ser Ile Glu Asn Ile Leu Asp Asn Leu Glu Asp Met
                1205                1210                1215

Asp Phe Thr Ala Phe Gly Asp Asp Asp Glu Ile Pro Gln Glu Leu Leu
            1220                1225                1230

Leu Gly Lys His Gln Leu Asn Glu Leu Gly Ser Glu Ser Ala Lys Ile
        1235                1240                1245
```

-continued

```
Lys Ala Met Gly Ile Met Asp Lys Leu Ser Thr Asp Lys Thr Val Lys
    1250                1255                1260

Val Leu Asn Ile Leu Glu Lys Asn Ile Gln Asp Gly Ser Lys Leu Ser
1265                1270                1275                1280

Thr Leu Leu Asn His Asn Asn Asp Thr Glu Glu Glu Glu Arg Leu Trp
                1285                1290                1295

Arg Asp Leu Ile Met Glu Arg Val Thr Lys Ser Ala Asp Ala Cys Leu
            1300                1305                1310

Thr Thr Ile Asn Ile Met Thr Ser Pro Asn Met Pro Lys Ala Val Tyr
        1315                1320                1325

Ile Glu Asp Val Ile Glu Arg Val Ile Gln Tyr Thr Lys Phe His Leu
    1330                1335                1340

Gln Asn Thr Leu Tyr Pro Gln Tyr Asp Pro Val Tyr Arg Leu Asp Pro
1345                1350                1355                1360

His Gly Gly Gly Leu Leu Ser Ser Lys Ala Lys Arg Ala Lys Cys Ser
                1365                1370                1375

Thr His Lys Gln Arg Val Ile Val Met Leu Tyr Asn Lys Val Cys Asp
            1380                1385                1390

Ile Val Ser Ser Leu Ser Glu Leu Leu Glu Ile Gln Leu Leu Thr Asp
        1395                1400                1405

Thr Thr Ile Leu Gln Val Ser Ser Met Gly Ile Thr Pro Phe Phe Val
    1410                1415                1420

Glu Asn Val Ser Glu Leu Gln Leu Cys Ala Ile Lys Leu Val Thr Ala
1425                1430                1435                1440

Val Phe Ser Arg Tyr Glu Lys His Arg Gln Leu Ile Leu Glu Glu Ile
                1445                1450                1455

Phe Thr Ser Leu Ala Arg Leu Pro Thr Ser Lys Arg Ser Leu Arg Asn
            1460                1465                1470

Phe Arg Leu Asn Ser Ser Asp Met Asp Gly Glu Pro Met Tyr Ile Gln
        1475                1480                1485

Met Val Thr Ala Leu Val Leu Gln Leu Ile Gln Cys Val Val His Leu
    1490                1495                1500

Pro Ser Ser Glu Lys Asp Ser Asn Ala Glu Glu Asp Ser Asn Lys Lys
1505                1510                1515                1520

Ile Asp Gln Asp Val Val Ile Thr Asn Ser Tyr Glu Thr Ala Met Arg
                1525                1530                1535

Thr Ala Gln Asn Phe Leu Ser Ile Phe Leu Lys Lys Cys Gly Ser Lys
            1540                1545                1550

Gln Gly Glu Glu Asp Tyr Arg Pro Leu Phe Glu Asn Phe Val Gln Asp
        1555                1560                1565

Leu Leu Ser Thr Val Asn Lys Pro Glu Trp Pro Ala Ala Glu Leu Leu
    1570                1575                1580

Leu Ser Leu Leu Gly Arg Leu Leu Val His Gln Phe Ser Asn Lys Ser
1585                1590                1595                1600

Thr Glu Met Ala Leu Arg Val Ala Ser Leu Asp Tyr Leu Gly Thr Val
                1605                1610                1615

Ala Ala Arg Leu Arg Lys Asp Ala Val Thr Ser Lys Met Asp Gln Gly
            1620                1625                1630

Ser Ile Glu Arg Ile Leu Lys Gln Val Ser Gly Gly Glu Asp Glu Ile
        1635                1640                1645

Gln Gln Leu Gln Lys Ala Leu Leu Asp Tyr Leu Asp Glu Asn Thr Glu
    1650                1655                1660

Thr Asp Pro Ser Leu Val Phe Ser Arg Lys Phe Tyr Ile Ala Gln Trp
```

-continued

```
1665                1670                1675                1680

Phe Arg Asp Thr Thr Leu Glu Thr Glu Lys Ala Met Lys Ser Gln Lys
                1685                1690                1695

Asp Glu Glu Ser Ser Glu Gly Thr His His Ala Lys Glu Ile Glu Thr
            1700                1705                1710

Thr Gly Gln Ile Met His Arg Ala Glu Asn Arg Lys Lys Phe Leu Arg
        1715                1720                1725

Ser Ile Ile Lys Thr Thr Pro Ser Gln Phe Ser Thr Leu Lys Met Asn
    1730                1735                1740

Ser Asp Thr Val Asp Tyr Asp Asp Ala Cys Leu Ile Val Arg Tyr Leu
1745                1750                1755                1760

Ala Ser Met Arg Pro Phe Ala Gln Ser Phe Asp Ile Tyr Leu Thr Gln
                1765                1770                1775

Ile Leu Arg Val Leu Gly Glu Asn Ala Ile Ala Val Arg Thr Lys Ala
            1780                1785                1790

Met Lys Cys Leu Ser Glu Val Val Ala Val Asp Pro Ser Ile Leu Ala
        1795                1800                1805

Arg Leu Asp Met Gln Arg Gly Val His Gly Arg Leu Met Asp Asn Ser
    1810                1815                1820

Thr Ser Val Arg Glu Ala Ala Val Glu Leu Leu Gly Arg Phe Val Leu
1825                1830                1835                1840

Cys Arg Pro Gln Leu Ala Glu Gln Tyr Tyr Asp Met Leu Ile Glu Arg
                1845                1850                1855

Ile Leu Asp Thr Gly Ile Ser Val Arg Lys Arg Val Ile Lys Ile Leu
            1860                1865                1870

Arg Asp Ile Cys Ile Glu Gln Pro Thr Phe Pro Lys Ile Thr Glu Met
        1875                1880                1885

Cys Val Lys Met Ile Arg Arg Val Asn Asp Glu Glu Gly Ile Lys Lys
    1890                1895                1900

Leu Val Asn Glu Thr Phe Gln Lys Leu Trp Phe Thr Pro Thr Pro His
1905                1910                1915                1920

Asn Asp Lys Glu Ala Met Thr Arg Lys Ile Leu Asn Ile Thr Asp Val
                1925                1930                1935

Val Ala Ala Cys Arg Asp Thr Gly Tyr Asp Trp Phe Glu Gln Leu Leu
            1940                1945                1950

Gln Asn Leu Leu Lys Ser Glu Glu Asp Ser Ser Tyr Lys Pro Val Lys
        1955                1960                1965

Lys Ala Cys Thr Gln Leu Val Asp Asn Leu Val Glu His Ile Leu Lys
    1970                1975                1980

Tyr Glu Glu Ser Leu Ala Asp Ser Asp Asn Lys Gly Val Asn Ser Gly
1985                1990                1995                2000

Arg Leu Val Ala Cys Ile Thr Thr Leu Phe Leu Phe Ser Lys Ile Arg
                2005                2010                2015

Pro Gln Leu Met Val Lys His Ala Met Thr Met Gln Pro Tyr Leu Thr
            2020                2025                2030

Thr Lys Cys Ser Thr Gln Asn Asp Phe Met Val Ile Cys Asn Val Ala
        2035                2040                2045

Lys Ile Leu Glu Leu Val Val Pro Leu Met Glu His Pro Ser Glu Thr
    2050                2055                2060

Phe Leu Ala Thr Ile Glu Glu Asp Leu Met Lys Leu Ile Ile Lys Tyr
2065                2070                2075                2080

Gly Met Thr Val Val Gln His Cys Val Ser Cys Leu Gly Ala Val Val
                2085                2090                2095
```

-continued

Asn Lys Val Thr Gln Asn Phe Lys Phe Val Trp Ala Cys Phe Asn Arg
2100 2105 2110

Tyr Tyr Gly Ala Ile Ser Lys Leu Lys Ser Gln His Gln Glu Asp Pro
2115 2120 2125

Asn Asn Thr Ser Leu Leu Thr Asn Lys Pro Ala Leu Leu Arg Ser Leu
2130 2135 2140

Phe Thr Val Gly Ala Leu Cys Arg His Phe Asp Phe Asp Leu Glu Asp
2145 2150 2155 2160

Phe Lys Gly Asn Ser Lys Val Asn Ile Lys Asp Lys Val Leu Glu Leu
2165 2170 2175

Leu Met Tyr Phe Thr Lys His Ser Asp Glu Glu Val Gln Thr Lys Ala
2180 2185 2190

Ile Ile Gly Leu Gly Phe Ala Phe Ile Gln His Pro Ser Leu Met Phe
2195 2200 2205

Glu Gln Glu Val Lys Asn Leu Tyr Asn Asn Ile Leu Ser Asp Lys Asn
2210 2215 2220

Ser Ser Val Asn Leu Lys Ile Gln Val Leu Lys Asn Leu Gln Thr Tyr
2225 2230 2235 2240

Leu Gln Glu Glu Asp Thr Arg Met Gln Gln Ala Asp Arg Asp Trp Lys
2245 2250 2255

Lys Val Ala Lys Gln Glu Asp Leu Lys Glu Met Gly Asp Val Ser Ser
2260 2265 2270

Gly Met Ser Ser Ser Ile Met Gln Leu Tyr Leu Lys Gln Val Leu Glu
2275 2280 2285

Ala Phe Phe His Thr Gln Ser Ser Val Arg His Phe Ala Leu Asn Val
2290 2295 2300

Ile Ala Leu Thr Leu Asn Gln Gly Leu Ile His Pro Val Gln Cys Val
2305 2310 2315 2320

Pro Tyr Leu Ile Ala Met Gly Thr Asp Pro Glu Pro Ala Met Arg Asn
2325 2330 2335

Lys Ala Asp Gln Gln Leu Val Glu Ile Asp Lys Lys Tyr Ala Gly Phe
2340 2345 2350

Ile His Met Lys Ala Val Ala Gly Met Lys Met Ser Tyr Gln Val Gln
2355 2360 2365

Gln Ala Ile Asn Thr Cys Leu Lys Asp Pro Val Arg Gly Phe Arg Gln
2370 2375 2380

Asp Glu Ser Ser Ser Ala Leu Cys Ser His Leu Tyr Ser Met Ile Arg
2385 2390 2395 2400

Gly Asn Arg Gln His Arg Arg Ala Phe Leu Ile Ser Leu Leu Asn Leu
2405 2410 2415

Phe Asp Asp Thr Ala Lys Thr Asp Val Thr Met Leu Leu Tyr Ile Ala
2420 2425 2430

Asp Asn Leu Ala Cys Phe Pro Tyr Gln Thr Gln Glu Glu Pro Leu Phe
2435 2440 2445

Ile Met His His Ile Asp Ile Thr Leu Ser Val Ser Gly Ser Asn Leu
2450 2455 2460

Leu Gln Ser Phe Lys Glu Ser Met Val Lys Asp Lys Arg Lys Glu Arg
2465 2470 2475 2480

Lys Ser Ser Pro Ser Lys Glu Asn Glu Ser Ser Asp Ser Glu Glu Glu
2485 2490 2495

Val Ser Arg Pro Arg Lys Ser Arg Lys Arg Val Asp Ser Asp Ser Asp
2500 2505 2510

-continued

```
Ser Asp Ser Glu Asp Asp Ile Asn Ser Val Met Lys Cys Leu Pro Glu
        2515                2520                2525

Asn Ser Ala Pro Leu Ile Glu Phe Ala Asn Val Ser Gln Gly Ile Leu
    2530                2535                2540

Leu Leu Leu Met Leu Lys Gln His Leu Lys Asn Leu Cys Gly Phe Ser
2545                2550                2555                2560

Asp Ser Lys Ile Gln Lys Tyr Ser Pro Ser Glu Ser Ala Lys Val Tyr
                2565                2570                2575

Asp Lys Ala Ile Asn Arg Lys Thr Gly Val His Phe His Pro Lys Gln
            2580                2585                2590

Thr Leu Asp Phe Leu Arg Ser Asp Met Ala Asn Ser Lys Ile Thr Glu
        2595                2600                2605

Glu Val Lys Arg Ser Ile Val Lys Gln Tyr Leu Asp Phe Lys Leu Leu
    2610                2615                2620

Met Glu His Leu Asp Pro Asp Glu Glu Glu Glu Glu Gly Glu Val Ser
2625                2630                2635                2640

Ala Ser Thr Asn Ala Arg Asn Lys Ala Ile Thr Ser Leu Leu Gly Gly
                2645                2650                2655

Gly Ser Pro Lys Asn Asn Thr Ala Ala Glu Thr Glu Asp Asp Glu Ser
            2660                2665                2670

Asp Gly Glu Asp Arg Gly Gly Gly Thr Ser Gly Ser Leu Arg Arg Ser
        2675                2680                2685

Lys Arg Asn Ser Asp Ser Thr Glu Leu Ala Ala Gln Met Asn Glu Ser
    2690                2695                2700

Val Asp Val Met Asp Val Ile Ala Ile Cys Cys Pro Lys Tyr Lys Asp
2705                2710                2715                2720

Arg Pro Gln Ile Ala Arg Val Val Gln Lys Thr Ser Ser Gly Phe Ser
                2725                2730                2735

Val Gln Trp Met Ala Gly Ser Tyr Ser Gly Ser Trp Thr Glu Ala Lys
            2740                2745                2750

Arg Arg Asp Gly Arg Lys Leu Val Pro Trp Val Asp Thr Ile Lys Glu
        2755                2760                2765

Ser Asp Ile Ile Tyr Lys Lys Ile Ala Leu Thr Ser Ala Asn Lys Leu
    2770                2775                2780

Thr Asn Lys Val Val Gln Thr Leu Arg Ser Leu Tyr Ala Ala Lys Asp
2785                2790                2795                2800

Gly Thr Ser Ser
```

<210> SEQ ID NO 4
<211> LENGTH: 27
<212> TYPE: DNA
<213> ORGANISM: Artificial Sequence
<220> FEATURE:
<223> OTHER INFORMATION: primer

<400> SEQUENCE: 4
ccgctcgagg attcaaacgc ttcatca 27

<210> SEQ ID NO 5
<211> LENGTH: 21
<212> TYPE: DNA
<213> ORGANISM: Artificial Sequence
<220> FEATURE:
<223> OTHER INFORMATION: primer

<400> SEQUENCE: 5
aggatgggaa tatggcatgt a 21

-continued

<210> SEQ ID NO 6
<211> LENGTH: 21
<212> TYPE: DNA
<213> ORGANISM: Artificial Sequence
<220> FEATURE:
<223> OTHER INFORMATION: primer

<400> SEQUENCE: 6
tgtttgggaa atgggaagta a 21

<210> SEQ ID NO 7
<211> LENGTH: 22
<212> TYPE: DNA
<213> ORGANISM: Artificial Sequence
<220> FEATURE:
<223> OTHER INFORMATION: primer

<400> SEQUENCE: 7
tgttgatacc tggttgaggc ta 22

<210> SEQ ID NO 8
<211> LENGTH: 20
<212> TYPE: DNA
<213> ORGANISM: Artificial Sequence
<220> FEATURE:
<223> OTHER INFORMATION: primer

<400> SEQUENCE: 8
gaagaagggg aggtttcagc 20

<210> SEQ ID NO 9
<211> LENGTH: 20
<212> TYPE: DNA
<213> ORGANISM: Artificial Sequence
<220> FEATURE:
<223> OTHER INFORMATION: primer

<400> SEQUENCE: 9
gtccaggagc cactgtagga 20

<210> SEQ ID NO 10
<211> LENGTH: 22
<212> TYPE: DNA
<213> ORGANISM: Artificial Sequence
<220> FEATURE:
<223> OTHER INFORMATION: primer

<400> SEQUENCE: 10
tgagagcaga acaactgaat gc 22

<210> SEQ ID NO 11
<211> LENGTH: 20
<212> TYPE: DNA
<213> ORGANISM: Artificial Sequence
<220> FEATURE:
<223> OTHER INFORMATION: primer

<400> SEQUENCE: 11
tggctttcca gaatccctcc 20

<210> SEQ ID NO 12
<211> LENGTH: 21
<212> TYPE: DNA
<213> ORGANISM: Artificial Sequence
<220> FEATURE:

-continued

<223> OTHER INFORMATION: primer

<400> SEQUENCE: 12
actgggttgt tgtgagaact g 21

<210> SEQ ID NO 13
<211> LENGTH: 21
<212> TYPE: DNA
<213> ORGANISM: Artificial Sequence
<220> FEATURE:
<223> OTHER INFORMATION: primer

<400> SEQUENCE: 13
gcatttcagt tgctatttct g 21

<210> SEQ ID NO 14
<211> LENGTH: 20
<212> TYPE: DNA
<213> ORGANISM: Artificial Sequence
<220> FEATURE:
<223> OTHER INFORMATION: primer

<400> SEQUENCE: 14
ttaggaagag gaggaatgcc 20

<210> SEQ ID NO 15
<211> LENGTH: 23
<212> TYPE: DNA
<213> ORGANISM: Artificial Sequence
<220> FEATURE:
<223> OTHER INFORMATION: primer

<400> SEQUENCE: 15
ctgaaataaa accaggaata cgg 23

<210> SEQ ID NO 16
<211> LENGTH: 22
<212> TYPE: DNA
<213> ORGANISM: Artificial Sequence
<220> FEATURE:
<223> OTHER INFORMATION: primer

<400> SEQUENCE: 16
tgggggacaa gagtgagact tc 22

<210> SEQ ID NO 17
<211> LENGTH: 24
<212> TYPE: DNA
<213> ORGANISM: Artificial Sequence
<220> FEATURE:
<223> OTHER INFORMATION: primer

<400> SEQUENCE: 17
gcataaacat cgcattcctg atag 24

<210> SEQ ID NO 18
<211> LENGTH: 24
<212> TYPE: DNA
<213> ORGANISM: Artificial Sequence
<220> FEATURE:
<223> OTHER INFORMATION: primer

<400> SEQUENCE: 18
aaggacactt tactgttaga agaa 24

-continued

<210> SEQ ID NO 19
<211> LENGTH: 21
<212> TYPE: DNA
<213> ORGANISM: Artificial Sequence
<220> FEATURE:
<223> OTHER INFORMATION: primer

<400> SEQUENCE: 19
gcaaatgcaa agtggattac t 21

<210> SEQ ID NO 20
<211> LENGTH: 23
<212> TYPE: DNA
<213> ORGANISM: Artificial Sequence
<220> FEATURE:
<223> OTHER INFORMATION: primer

<400> SEQUENCE: 20
cagtcagatt tcaaggaata gcg 23

<210> SEQ ID NO 21
<211> LENGTH: 23
<212> TYPE: DNA
<213> ORGANISM: Artificial Sequence
<220> FEATURE:
<223> OTHER INFORMATION: primer

<400> SEQUENCE: 21
ctcctttcac ctcctaaaat gac 23

<210> SEQ ID NO 22
<211> LENGTH: 24
<212> TYPE: DNA
<213> ORGANISM: Artificial Sequence
<220> FEATURE:
<223> OTHER INFORMATION: primer

<400> SEQUENCE: 22
aactagtcag tacatgagta tctg 24

<210> SEQ ID NO 23
<211> LENGTH: 24
<212> TYPE: DNA
<213> ORGANISM: Artificial Sequence
<220> FEATURE:
<223> OTHER INFORMATION: primer

<400> SEQUENCE: 23
gaaatggaaa tactaggtta tatg 24

<210> SEQ ID NO 24
<211> LENGTH: 22
<212> TYPE: DNA
<213> ORGANISM: Artificial Sequence
<220> FEATURE:
<223> OTHER INFORMATION: primer

<400> SEQUENCE: 24
caagaagaaa acaggaaagt gc 22

<210> SEQ ID NO 25
<211> LENGTH: 23
<212> TYPE: DNA
<213> ORGANISM: Artificial Sequence
<220> FEATURE:
<223> OTHER INFORMATION: primer -continued

<400> SEQUENCE: 25
ctgctttagg aagtctgagt tct 23

<210> SEQ ID NO 26
<211> LENGTH: 18
<212> TYPE: DNA
<213> ORGANISM: Artificial Sequence
<220> FEATURE:
<223> OTHER INFORMATION: primer

<400> SEQUENCE: 26
gtgaaaccac cacaactg 18

<210> SEQ ID NO 27
<211> LENGTH: 19
<212> TYPE: DNA
<213> ORGANISM: Artificial Sequence
<220> FEATURE:
<223> OTHER INFORMATION: primer

<400> SEQUENCE: 27
tgagcagcat ttagtgggc 19

<210> SEQ ID NO 28
<211> LENGTH: 22
<212> TYPE: DNA
<213> ORGANISM: Artificial Sequence
<220> FEATURE:
<223> OTHER INFORMATION: primer

<400> SEQUENCE: 28
caggacagac ttcaaaaaca cc 22

<210> SEQ ID NO 29
<211> LENGTH: 24
<212> TYPE: DNA
<213> ORGANISM: Artificial Sequence
<220> FEATURE:
<223> OTHER INFORMATION: primer

<400> SEQUENCE: 29
ccaaatctca tatagttgtt tcag 24

<210> SEQ ID NO 30
<211> LENGTH: 21
<212> TYPE: DNA
<213> ORGANISM: Artificial Sequence
<220> FEATURE:
<223> OTHER INFORMATION: primer

<400> SEQUENCE: 30
ttgcatttgc attttactcc a 21

<210> SEQ ID NO 31
<211> LENGTH: 22
<212> TYPE: DNA
<213> ORGANISM: Artificial Sequence
<220> FEATURE:
<223> OTHER INFORMATION: primer

<400> SEQUENCE: 31
gtgtctcagg atggttttct gg 22

<210> SEQ ID NO 32
<211> LENGTH: 20

-continued

<212> TYPE: DNA
<213> ORGANISM: Artificial Sequence
<220> FEATURE:
<223> OTHER INFORMATION: primer

<400> SEQUENCE: 32
tacgggaaat gggtcaaggc 20

<210> SEQ ID NO 33
<211> LENGTH: 22
<212> TYPE: DNA
<213> ORGANISM: Artificial Sequence
<220> FEATURE:
<223> OTHER INFORMATION: primer

<400> SEQUENCE: 33
aggctcaact atggtgctct cg 22

<210> SEQ ID NO 34
<211> LENGTH: 22
<212> TYPE: DNA
<213> ORGANISM: Artificial Sequence
<220> FEATURE:
<223> OTHER INFORMATION: primer

<400> SEQUENCE: 34
tgagagcaga acaactgaat gc 22

<210> SEQ ID NO 35
<211> LENGTH: 21
<212> TYPE: DNA
<213> ORGANISM: Artificial Sequence
<220> FEATURE:
<223> OTHER INFORMATION: primer

<400> SEQUENCE: 35
tggctttcca ggaatccctc c 21

<210> SEQ ID NO 36
<211> LENGTH: 23
<212> TYPE: DNA
<213> ORGANISM: Artificial Sequence
<220> FEATURE:
<223> OTHER INFORMATION: primer

<400> SEQUENCE: 36
aggtgagagc cgccctgaaa ctc 23

<210> SEQ ID NO 37
<211> LENGTH: 22
<212> TYPE: DNA
<213> ORGANISM: Artificial Sequence
<220> FEATURE:
<223> OTHER INFORMATION: primer

<400> SEQUENCE: 37
cacgaggact gtcaggtctt ga 22

<210> SEQ ID NO 38
<211> LENGTH: 20
<212> TYPE: DNA
<213> ORGANISM: Artificial Sequence
<220> FEATURE:
<223> OTHER INFORMATION: primer

<400> SEQUENCE: 38

-continued tgaatcaggg gactcaaggg 20

<210> SEQ ID NO 39
<211> LENGTH: 23
<212> TYPE: DNA
<213> ORGANISM: Artificial Sequence
<220> FEATURE:
<223> OTHER INFORMATION: primer

<400> SEQUENCE: 39
agggaacttc ttgatttgtc ctc 23

<210> SEQ ID NO 40
<211> LENGTH: 22
<212> TYPE: DNA
<213> ORGANISM: Artificial Sequence
<220> FEATURE:
<223> OTHER INFORMATION: primer

<400> SEQUENCE: 40
aggagctaag cctgtagttg tg 22

<210> SEQ ID NO 41
<211> LENGTH: 22
<212> TYPE: DNA
<213> ORGANISM: Artificial Sequence
<220> FEATURE:
<223> OTHER INFORMATION: primer

<400> SEQUENCE: 41
cttgagtagt gggtggggaa ga 22

<210> SEQ ID NO 42
<211> LENGTH: 21
<212> TYPE: DNA
<213> ORGANISM: Artificial Sequence
<220> FEATURE:
<223> OTHER INFORMATION: primer

<400> SEQUENCE: 42
tgtcacttta gggttaagag t 21

<210> SEQ ID NO 43
<211> LENGTH: 21
<212> TYPE: DNA
<213> ORGANISM: Artificial Sequence
<220> FEATURE:
<223> OTHER INFORMATION: primer

<400> SEQUENCE: 43
gactgtgctt ttgctaaacc c 21

<210> SEQ ID NO 44
<211> LENGTH: 23
<212> TYPE: DNA
<213> ORGANISM: Artificial Sequence
<220> FEATURE:
<223> OTHER INFORMATION: primer

<400> SEQUENCE: 44
cactgaattt cctagaccct atg 23

<210> SEQ ID NO 45
<211> LENGTH: 22
<212> TYPE: DNA
<213> ORGANISM: Artificial Sequence -continued
<220> FEATURE:
<223> OTHER INFORMATION: primer

<400> SEQUENCE: 45
atcactgcac atagaaacta ag 22

<210> SEQ ID NO 46
<211> LENGTH: 23
<212> TYPE: DNA
<213> ORGANISM: Artificial Sequence
<220> FEATURE:
<223> OTHER INFORMATION: primer

<400> SEQUENCE: 46
gtttctatgt gcagtgatta tcg 23

<210> SEQ ID NO 47
<211> LENGTH: 23
<212> TYPE: DNA
<213> ORGANISM: Artificial Sequence
<220> FEATURE:
<223> OTHER INFORMATION: primer

<400> SEQUENCE: 47
gatttcaagg taggacacat cac 23

<210> SEQ ID NO 48
<211> LENGTH: 21
<212> TYPE: DNA
<213> ORGANISM: Artificial Sequence
<220> FEATURE:
<223> OTHER INFORMATION: primer

<400> SEQUENCE: 48
attcagggtt tacttgaggt t 21

<210> SEQ ID NO 49
<211> LENGTH: 23
<212> TYPE: DNA
<213> ORGANISM: Artificial Sequence
<220> FEATURE:
<223> OTHER INFORMATION: primer

<400> SEQUENCE: 49
agtccatgcc tctttcaatg cag 23

<210> SEQ ID NO 50
<211> LENGTH: 21
<212> TYPE: DNA
<213> ORGANISM: Artificial Sequence
<220> FEATURE:
<223> OTHER INFORMATION: primer

<400> SEQUENCE: 50
agtcatttag ggtcgttgag t 21

<210> SEQ ID NO 51
<211> LENGTH: 21
<212> TYPE: DNA
<213> ORGANISM: Artificial Sequence
<220> FEATURE:
<223> OTHER INFORMATION: primer

<400> SEQUENCE: 51
gcatgggaag agattaatga c 21

-continued

<210> SEQ ID NO 52
<211> LENGTH: 22
<212> TYPE: DNA
<213> ORGANISM: Artificial Sequence
<220> FEATURE:
<223> OTHER INFORMATION: primer

<400> SEQUENCE: 52
catcataaca cttttccacc ag 22

<210> SEQ ID NO 53
<211> LENGTH: 21
<212> TYPE: DNA
<213> ORGANISM: Artificial Sequence
<220> FEATURE:
<223> OTHER INFORMATION: primer

<400> SEQUENCE: 53
tggtgccatt ttaagtccta t 21

<210> SEQ ID NO 54
<211> LENGTH: 21
<212> TYPE: DNA
<213> ORGANISM: Artificial Sequence
<220> FEATURE:
<223> OTHER INFORMATION: primer

<400> SEQUENCE: 54
cttccaggtt ctgtagctag a 21

<210> SEQ ID NO 55
<211> LENGTH: 23
<212> TYPE: DNA
<213> ORGANISM: Artificial Sequence
<220> FEATURE:
<223> OTHER INFORMATION: primer

<400> SEQUENCE: 55
gagtttggaa tttacactac att 23

<210> SEQ ID NO 56
<211> LENGTH: 21
<212> TYPE: DNA
<213> ORGANISM: Artificial Sequence
<220> FEATURE:
<223> OTHER INFORMATION: primer

<400> SEQUENCE: 56
tgctaacgtg ctttgaggat g 21

<210> SEQ ID NO 57
<211> LENGTH: 23
<212> TYPE: DNA
<213> ORGANISM: Artificial Sequence
<220> FEATURE:
<223> OTHER INFORMATION: primer

<400> SEQUENCE: 57
tagtccttag attgaaatga atg 23

<210> SEQ ID NO 58
<211> LENGTH: 23
<212> TYPE: DNA
<213> ORGANISM: Artificial Sequence
<220> FEATURE:
<223> OTHER INFORMATION: primer -continued

<400> SEQUENCE: 58
gagcagctta ccttagatac tga 23

<210> SEQ ID NO 59
<211> LENGTH: 22
<212> TYPE: DNA
<213> ORGANISM: Artificial Sequence
<220> FEATURE:
<223> OTHER INFORMATION: primer

<400> SEQUENCE: 59
atgctgttct gatgtaactg cc 22

<210> SEQ ID NO 60
<211> LENGTH: 22
<212> TYPE: DNA
<213> ORGANISM: Artificial Sequence
<220> FEATURE:
<223> OTHER INFORMATION: primer

<400> SEQUENCE: 60
ggcaaacaca gtatcgtgaa ac 22

<210> SEQ ID NO 61
<211> LENGTH: 18
<212> TYPE: DNA
<213> ORGANISM: Artificial Sequence
<220> FEATURE:
<223> OTHER INFORMATION: primer

<400> SEQUENCE: 61
gatcgcgcca ctgcactc 18

<210> SEQ ID NO 62
<211> LENGTH: 22
<212> TYPE: DNA
<213> ORGANISM: Artificial Sequence
<220> FEATURE:
<223> OTHER INFORMATION: primer

<400> SEQUENCE: 62
tagtgtgcta attttggctt ct 22

<210> SEQ ID NO 63
<211> LENGTH: 21
<212> TYPE: DNA
<213> ORGANISM: Artificial Sequence
<220> FEATURE:
<223> OTHER INFORMATION: primer

<400> SEQUENCE: 63
attcaaggtt cagattatgg c 21

<210> SEQ ID NO 64
<211> LENGTH: 23
<212> TYPE: DNA
<213> ORGANISM: Artificial Sequence
<220> FEATURE:
<223> OTHER INFORMATION: primer

<400> SEQUENCE: 64
caatttcaat catgttggta gac 23

<210> SEQ ID NO 65

-continued

<211> LENGTH: 20
<212> TYPE: DNA
<213> ORGANISM: Artificial Sequence
<220> FEATURE:
<223> OTHER INFORMATION: primer

<400> SEQUENCE: 65
gtgtacagtt atgcacatgc 20

<210> SEQ ID NO 66
<211> LENGTH: 21
<212> TYPE: DNA
<213> ORGANISM: Artificial Sequence
<220> FEATURE:
<223> OTHER INFORMATION: primer

<400> SEQUENCE: 66
acagttgagc ctgcatattt a 21

<210> SEQ ID NO 67
<211> LENGTH: 21
<212> TYPE: DNA
<213> ORGANISM: Artificial Sequence
<220> FEATURE:
<223> OTHER INFORMATION: primer

<400> SEQUENCE: 67
accattcaga agtccctgtt a 21

<210> SEQ ID NO 68
<211> LENGTH: 21
<212> TYPE: DNA
<213> ORGANISM: Artificial Sequence
<220> FEATURE:
<223> OTHER INFORMATION: primer

<400> SEQUENCE: 68
aaggcaaact tcagctatca a 21

<210> SEQ ID NO 69
<211> LENGTH: 21
<212> TYPE: DNA
<213> ORGANISM: Artificial Sequence
<220> FEATURE:
<223> OTHER INFORMATION: primer

<400> SEQUENCE: 69
cctcttcatc atgctacctc c 21

<210> SEQ ID NO 70
<211> LENGTH: 24
<212> TYPE: DNA
<213> ORGANISM: Artificial Sequence
<220> FEATURE:
<223> OTHER INFORMATION: primer

<400> SEQUENCE: 70
tgtattcctg taatgtgagc actc 24

<210> SEQ ID NO 71
<211> LENGTH: 21
<212> TYPE: DNA
<213> ORGANISM: Artificial Sequence
<220> FEATURE:
<223> OTHER INFORMATION: primer

<400> SEQUENCE: 71

-continued tcatcctgca acaaaaagtc a 21

<210> SEQ ID NO 72
<211> LENGTH: 22
<212> TYPE: DNA
<213> ORGANISM: Artificial Sequence
<220> FEATURE:
<223> OTHER INFORMATION: primer

<400> SEQUENCE: 72
accacacctt ctcagtttag ca 22

<210> SEQ ID NO 73
<211> LENGTH: 21
<212> TYPE: DNA
<213> ORGANISM: Artificial Sequence
<220> FEATURE:
<223> OTHER INFORMATION: primer

<400> SEQUENCE: 73
ctcacaagca tccagaatca g 21

<210> SEQ ID NO 74
<211> LENGTH: 20
<212> TYPE: DNA
<213> ORGANISM: Artificial Sequence
<220> FEATURE:
<223> OTHER INFORMATION: primer

<400> SEQUENCE: 74
acgaaaggct ccaaagtatg 20

<210> SEQ ID NO 75
<211> LENGTH: 19
<212> TYPE: DNA
<213> ORGANISM: Artificial Sequence
<220> FEATURE:
<223> OTHER INFORMATION: primer

<400> SEQUENCE: 75
actgctgctt ctcggacac 19

<210> SEQ ID NO 76
<211> LENGTH: 21
<212> TYPE: DNA
<213> ORGANISM: Artificial Sequence
<220> FEATURE:
<223> OTHER INFORMATION: primer

<400> SEQUENCE: 76
gtctgaggtt gttgctgtag a 21

<210> SEQ ID NO 77
<211> LENGTH: 21
<212> TYPE: DNA
<213> ORGANISM: Artificial Sequence
<220> FEATURE:
<223> OTHER INFORMATION: primer

<400> SEQUENCE: 77
atgatattgc aagggctatt c 21

<210> SEQ ID NO 78
<211> LENGTH: 21
<212> TYPE: DNA

-continued

<213> ORGANISM: Artificial Sequence
<220> FEATURE:
<223> OTHER INFORMATION: primer

<400> SEQUENCE: 78
ttctagtctt gtgtccaggg c 21

<210> SEQ ID NO 79
<211> LENGTH: 21
<212> TYPE: DNA
<213> ORGANISM: Artificial Sequence
<220> FEATURE:
<223> OTHER INFORMATION: primer

<400> SEQUENCE: 79
atcaacattt aggtgcaata a 21

<210> SEQ ID NO 80
<211> LENGTH: 20
<212> TYPE: DNA
<213> ORGANISM: Artificial Sequence
<220> FEATURE:
<223> OTHER INFORMATION: primer

<400> SEQUENCE: 80
tcctggcagt ttgtgttttg 20

<210> SEQ ID NO 81
<211> LENGTH: 23
<212> TYPE: DNA
<213> ORGANISM: Artificial Sequence
<220> FEATURE:
<223> OTHER INFORMATION: primer

<400> SEQUENCE: 81
ctggaggaat aggaaaatct cag 23

<210> SEQ ID NO 82
<211> LENGTH: 23
<212> TYPE: DNA
<213> ORGANISM: Artificial Sequence
<220> FEATURE:
<223> OTHER INFORMATION: primer

<400> SEQUENCE: 82
gttctgtaac gttggtaaat ggt 23

<210> SEQ ID NO 83
<211> LENGTH: 24
<212> TYPE: DNA
<213> ORGANISM: Artificial Sequence
<220> FEATURE:
<223> OTHER INFORMATION: primer

<400> SEQUENCE: 83
ggttctttta aatcatacag tcca 24

<210> SEQ ID NO 84
<211> LENGTH: 21
<212> TYPE: DNA
<213> ORGANISM: Artificial Sequence
<220> FEATURE:
<223> OTHER INFORMATION: primer

<400> SEQUENCE: 84
accttaggtc ttacacagca a 21

<210> SEQ ID NO 85
<211> LENGTH: 22
<212> TYPE: DNA
<213> ORGANISM: Artificial Sequence
<220> FEATURE:
<223> OTHER INFORMATION: primer

<400> SEQUENCE: 85
tgtgctcaac taggttatca ac 22

<210> SEQ ID NO 86
<211> LENGTH: 21
<212> TYPE: DNA
<213> ORGANISM: Artificial Sequence
<220> FEATURE:
<223> OTHER INFORMATION: primer

<400> SEQUENCE: 86
ttgaggccta tactggacct a 21

<210> SEQ ID NO 87
<211> LENGTH: 21
<212> TYPE: DNA
<213> ORGANISM: Artificial Sequence
<220> FEATURE:
<223> OTHER INFORMATION: primer

<400> SEQUENCE: 87
ggttgacgca tgtgaactct a 21

<210> SEQ ID NO 88
<211> LENGTH: 21
<212> TYPE: DNA
<213> ORGANISM: Artificial Sequence
<220> FEATURE:
<223> OTHER INFORMATION: primer

<400> SEQUENCE: 88
taactggacc tttacgtgca a 21

<210> SEQ ID NO 89
<211> LENGTH: 21
<212> TYPE: DNA
<213> ORGANISM: Artificial Sequence
<220> FEATURE:
<223> OTHER INFORMATION: primer

<400> SEQUENCE: 89
gctcacacaa tgttgcacta c 21

<210> SEQ ID NO 90
<211> LENGTH: 21
<212> TYPE: DNA
<213> ORGANISM: Artificial Sequence
<220> FEATURE:
<223> OTHER INFORMATION: primer

<400> SEQUENCE: 90
tggcatgact gtaagcactc a 21

<210> SEQ ID NO 91
<211> LENGTH: 21
<212> TYPE: DNA
<213> ORGANISM: Artificial Sequence
<220> FEATURE:

-continued

<223> OTHER INFORMATION: primer

<400> SEQUENCE: 91
agaggaccac ggtggataat c 21

<210> SEQ ID NO 92
<211> LENGTH: 22
<212> TYPE: DNA
<213> ORGANISM: Artificial Sequence
<220> FEATURE:
<223> OTHER INFORMATION: primer

<400> SEQUENCE: 92
tggtggcaca cgactgtaat cc 22

<210> SEQ ID NO 93
<211> LENGTH: 23
<212> TYPE: DNA
<213> ORGANISM: Artificial Sequence
<220> FEATURE:
<223> OTHER INFORMATION: primer

<400> SEQUENCE: 93
tcatcctggg tcactactgt cat 23

<210> SEQ ID NO 94
<211> LENGTH: 21
<212> TYPE: DNA
<213> ORGANISM: Artificial Sequence
<220> FEATURE:
<223> OTHER INFORMATION: primer

<400> SEQUENCE: 94
ctgatacttt gaatgccact g 21

<210> SEQ ID NO 95
<211> LENGTH: 21
<212> TYPE: DNA
<213> ORGANISM: Artificial Sequence
<220> FEATURE:
<223> OTHER INFORMATION: primer

<400> SEQUENCE: 95
caccaaatcc tactgctaat a 21

<210> SEQ ID NO 96
<211> LENGTH: 22
<212> TYPE: DNA
<213> ORGANISM: Artificial Sequence
<220> FEATURE:
<223> OTHER INFORMATION: primer

<400> SEQUENCE: 96
ctctaggtaa ggccaccagc at 22

<210> SEQ ID NO 97
<211> LENGTH: 22
<212> TYPE: DNA
<213> ORGANISM: Artificial Sequence
<220> FEATURE:
<223> OTHER INFORMATION: primer

<400> SEQUENCE: 97
tagacctcag cataaggact gc 22

-continued

<210> SEQ ID NO 98
<211> LENGTH: 21
<212> TYPE: DNA
<213> ORGANISM: Artificial Sequence
<220> FEATURE:
<223> OTHER INFORMATION: primer

<400> SEQUENCE: 98
cagattaaga accattgagc c 21

<210> SEQ ID NO 99
<211> LENGTH: 21
<212> TYPE: DNA
<213> ORGANISM: Artificial Sequence
<220> FEATURE:
<223> OTHER INFORMATION: primer

<400> SEQUENCE: 99
gcagtaatca taacccaaga g 21

<210> SEQ ID NO 100
<211> LENGTH: 21
<212> TYPE: DNA
<213> ORGANISM: Artificial Sequence
<220> FEATURE:
<223> OTHER INFORMATION: primer

<400> SEQUENCE: 100
agtgtgagaa tgctttatgt t 21

<210> SEQ ID NO 101
<211> LENGTH: 21
<212> TYPE: DNA
<213> ORGANISM: Artificial Sequence
<220> FEATURE:
<223> OTHER INFORMATION: primer

<400> SEQUENCE: 101
attatgaatg tgggcagagc a 21

<210> SEQ ID NO 102
<211> LENGTH: 21
<212> TYPE: DNA
<213> ORGANISM: Artificial Sequence
<220> FEATURE:
<223> OTHER INFORMATION: primer

<400> SEQUENCE: 102
atgaagctag cctcagaatg t 21

<210> SEQ ID NO 103
<211> LENGTH: 23
<212> TYPE: DNA
<213> ORGANISM: Artificial Sequence
<220> FEATURE:
<223> OTHER INFORMATION: primer

<400> SEQUENCE: 103
caaaatttcc ccttcacttc tga 23

<210> SEQ ID NO 104
<211> LENGTH: 21
<212> TYPE: DNA
<213> ORGANISM: Artificial Sequence
<220> FEATURE:
<223> OTHER INFORMATION: primer

<400> SEQUENCE: 104
gtgaggtgaa agtgccctgt a 21

<210> SEQ ID NO 105
<211> LENGTH: 22
<212> TYPE: DNA
<213> ORGANISM: Artificial Sequence
<220> FEATURE:
<223> OTHER INFORMATION: primer

<400> SEQUENCE: 105
tcccaagtca agtattgccc ag 22

<210> SEQ ID NO 106
<211> LENGTH: 22
<212> TYPE: DNA
<213> ORGANISM: Artificial Sequence
<220> FEATURE:
<223> OTHER INFORMATION: primer

<400> SEQUENCE: 106
caagctgttg aatggagcat ac 22

<210> SEQ ID NO 107
<211> LENGTH: 20
<212> TYPE: DNA
<213> ORGANISM: Artificial Sequence
<220> FEATURE:
<223> OTHER INFORMATION: primer

<400> SEQUENCE: 107
catgagccac cacacccagc 20

<210> SEQ ID NO 108
<211> LENGTH: 22
<212> TYPE: DNA
<213> ORGANISM: Artificial Sequence
<220> FEATURE:
<223> OTHER INFORMATION: primer

<400> SEQUENCE: 108
tccaaatacg ttgtttccat ag 22

<210> SEQ ID NO 109
<211> LENGTH: 22
<212> TYPE: DNA
<213> ORGANISM: Artificial Sequence
<220> FEATURE:
<223> OTHER INFORMATION: primer

<400> SEQUENCE: 109
tcaatgtgaa ggagatagtt at 22

<210> SEQ ID NO 110
<211> LENGTH: 22
<212> TYPE: DNA
<213> ORGANISM: Artificial Sequence
<220> FEATURE:
<223> OTHER INFORMATION: primer

<400> SEQUENCE: 110
ccacaccaaa ctactgccat ag 22

<210> SEQ ID NO 111
<211> LENGTH: 21

-continued

<212> TYPE: DNA
<213> ORGANISM: Artificial Sequence
<220> FEATURE:
<223> OTHER INFORMATION: primer

<400> SEQUENCE: 111
cattttacgt aatacgctgc g 21

<210> SEQ ID NO 112
<211> LENGTH: 20
<212> TYPE: DNA
<213> ORGANISM: Artificial Sequence
<220> FEATURE:
<223> OTHER INFORMATION: primer

<400> SEQUENCE: 112
gtcacggtgc gtctcattgc 20

<210> SEQ ID NO 113
<211> LENGTH: 21
<212> TYPE: DNA
<213> ORGANISM: Artificial Sequence
<220> FEATURE:
<223> OTHER INFORMATION: primer

<400> SEQUENCE: 113
tagtgtctac ccaaggcacc a 21

<210> SEQ ID NO 114
<211> LENGTH: 21
<212> TYPE: DNA
<213> ORGANISM: Artificial Sequence
<220> FEATURE:
<223> OTHER INFORMATION: primer

<400> SEQUENCE: 114
ggcttcagtg ttcagtggat g 21

<210> SEQ ID NO 115
<211> LENGTH: 19
<212> TYPE: DNA
<213> ORGANISM: Artificial Sequence
<220> FEATURE:
<223> OTHER INFORMATION: primer

<400> SEQUENCE: 115
tttgcccaac atttccttc 19

<210> SEQ ID NO 116
<211> LENGTH: 21
<212> TYPE: DNA
<213> ORGANISM: Artificial Sequence
<220> FEATURE:
<223> OTHER INFORMATION: primer

<400> SEQUENCE: 116
tgaagagtaa gtggaacctg g 21

<210> SEQ ID NO 117
<211> LENGTH: 19
<212> TYPE: DNA
<213> ORGANISM: Artificial Sequence
<220> FEATURE:
<223> OTHER INFORMATION: primer

<400> SEQUENCE: 117

-continued gctaaagaaa gccatccgc 19

<210> SEQ ID NO 118
<211> LENGTH: 204
<212> TYPE: PRT
<213> ORGANISM: Artificial Sequence
<220> FEATURE:
<223> OTHER INFORMATION: Synthetic sequence

<400> SEQUENCE: 118

Glu Ser Ala Lys Ile Lys Ala Met Gly Ile Met Asp Lys Leu Ser Thr
1 5 10 15

Asp Lys Thr Val Lys Val Leu Asn Glu Arg Val Thr Lys Ser Ala Asp
20 25 30

Ala Cys Leu Thr Thr Ile Asn Ile Met Thr Ser Pro Asn Met Pro Lys
35 40 45

Ala Ala Met Lys Cys Leu Ser Glu Val Val Ala Val Asp Pro Ser Ile
50 55 60

Leu Ala Arg Leu Asp Met Gln Arg Gly Val Arg Val Leu Gly Glu Asn
65 70 75 80

Ala Ile Ala Val Arg Thr Lys Ala Met Lys Cys Leu Ser Glu Val Val
85 90 95

Ala Val Asp Gln Leu Ala Glu Gln Tyr Tyr Asp Met Leu Ile Glu Arg
100 105 110

Ile Leu Asp Thr Gly Ile Ser Val Arg Lys Arg Val Ser Ser Val Arg
115 120 125

His Phe Ala Leu Asn Val Ile Ala Leu Thr Leu Asn Gln Gly Leu Ile
130 135 140

His Pro Val Gln Cys Val Pro Thr Cys Leu Lys Asp Pro Val Arg Gly
145 150 155 160

Phe Arg Gln Asp Glu Ser Ser Ser Ala Leu Cys Ser His Leu Tyr Thr
165 170 175

Ala Lys Thr Asp Val Thr Met Leu Leu Tyr Ile Ala Asp Asn Leu Ala
180 185 190

Cys Phe Pro Tyr Gln Thr Gln Glu Glu Pro Leu Phe
195 200

<210> SEQ ID NO 119
<211> LENGTH: 178
<212> TYPE: PRT
<213> ORGANISM: Artificial Sequence
<220> FEATURE:
<223> OTHER INFORMATION: Synthetic Sequence

<400> SEQUENCE: 119

Glu Ser Ala Lys Ile Lys Ala Met Gly Ile Met Asp Lys Leu Ser Thr
1 5 10 15

Asp Lys Thr Val Lys Val Leu Asn Glu Arg Val Thr Lys Ser Ala Asp
20 25 30

Ala Cys Leu Thr Thr Ile Asn Ile Met Thr Ser Pro Asn Met Pro Lys
35 40 45

Ala Ala Met Lys Cys Leu Ser Glu Val Val Ala Val Asp Pro Ser Ile
50 55 60

Leu Ala Arg Leu Asp Met Gln Arg Gly Val Arg Val Leu Gly Glu Asn
65 70 75 80

Ala Ile Ala Val Arg Thr Lys Ala Met Lys Cys Leu Ser Glu Val Val
85 90 95

-continued

```
Ala Val Asp Gln Leu Ala Glu Gln Tyr Tyr Asp Met Leu Ile Glu Arg
            100                 105                 110

Ile Leu Asp Thr Gly Ile Ser Val Arg Lys Arg Val Ser Ser Val Arg
        115                 120                 125

His Phe Ala Leu Asn Val Ile Ala Leu Thr Leu Asn Gln Gly Leu Ile
    130                 135                 140

His Pro Val Gln Cys Val Pro Thr Cys Leu Lys Asp Pro Val Arg Gly
145                 150                 155                 160

Phe Arg Gln Asp Glu Ser Ser Ser Ala Leu Cys Ser His Leu Tyr Thr
                165                 170                 175

Ala Ser


<210> SEQ ID NO 120
<211> LENGTH: 196
<212> TYPE: PRT
<213> ORGANISM: Artificial Sequence
<220> FEATURE:
<223> OTHER INFORMATION: Synthetic Sequence

<400> SEQUENCE: 120

Thr Leu Gln Phe Val Cys Leu Glu Leu Val Thr Thr Ile Phe Arg Lys
 1               5                  10                  15

Glu Arg Tyr Asp Lys Ile Arg Asn Ser Thr Ala Leu Val Leu Gln Leu
            20                  25                  30

Ile Gln Cys Ala Thr Ile Leu Pro Asp Ser Leu Cys Asp Asn Gly Lys
        35                  40                  45

Phe Ser Ala Met Lys Cys Leu Ala Asn Ile Val Glu Val Asp Pro Leu
    50                  55                  60

Val Leu Lys Arg Lys Asp Met Gln Met Gly Val Leu Val Val Asn Glu
65                  70                  75                  80

Pro Ser Ile Ala Val Arg Thr Arg Ala Met Lys Cys Leu Ala Asn Ile
                85                  90                  95

Val Glu Val Asp Asp Leu Ile Asp Gln Tyr Tyr Asp Met Leu Ser Thr
            100                 105                 110

Arg Ile Leu Asp Thr Gly Val Ser Val Arg Lys Arg Val Asp Thr Val
        115                 120                 125

Arg Leu Trp Ala Val Lys Val Ile Gln Ile Val Leu Arg Gln Gly Leu
    130                 135                 140

Val His Pro Val Arg Met Val Pro Ile Asn Asn Arg Gly Lys Leu Glu
145                 150                 155                 160

Ile Ile Arg Gly Tyr Ala Ser Arg Gly Pro Asp Asn Thr Thr Thr Ala
                165                 170                 175

Leu Asn Asp Phe Leu Tyr Gln Lys Thr Ser Leu Gln Gln Met Leu Tyr
            180                 185                 190

Ile Ala Asp Asn
        195
```